(12) United States Patent
Martinez et al.

(10) Patent No.: US 11,974,574 B2
(45) Date of Patent: May 7, 2024

(54) COMPOSITIONS AND RELATED METHODS FOR MODULATING ENDOSYMBIONTS

(71) Applicant: Flagship Pioneering Innovations V, Inc., Cambridge, MA (US)

(72) Inventors: Ignacio Martinez, Lexington, MA (US); Zachary Garo Armen, Boston, MA (US); Barry Andrew Martin, Boston, MA (US); Maier Steve Avendano Amado, Cambridge, MA (US)

(73) Assignee: Flagship Pioneering Innovations V, Inc., Cambridge, MA (US)

( * ) Notice: Subject to any disclaimer, the term of this patent is extended or adjusted under 35 U.S.C. 154(b) by 649 days.

(21) Appl. No.: 16/487,661

(22) PCT Filed: Feb. 23, 2018

(86) PCT No.: PCT/US2018/019577
§ 371 (c)(1),
(2) Date: Aug. 21, 2019

(87) PCT Pub. No.: WO2018/156998
PCT Pub. Date: Aug. 30, 2018

(65) Prior Publication Data
US 2019/0367943 A1 Dec. 5, 2019

Related U.S. Application Data

(60) Provisional application No. 62/583,990, filed on Nov. 9, 2017, provisional application No. 62/463,451, filed on Feb. 24, 2017.

(51) Int. Cl.
| | |
|---|---|
| *C12N 15/82* | (2006.01) |
| *A01N 43/06* | (2006.01) |
| *A01N 43/14* | (2006.01) |
| *A01N 43/16* | (2006.01) |
| *A01N 57/16* | (2006.01) |
| *A01N 63/30* | (2020.01) |
| *A01N 63/32* | (2020.01) |
| *A01N 63/60* | (2020.01) |
| *A61K 31/557* | (2006.01) |
| *C12N 15/11* | (2006.01) |
| *C12N 15/113* | (2010.01) |
| *C12N 15/63* | (2006.01) |
| *C12N 15/74* | (2006.01) |

(52) U.S. Cl.
CPC ............ *A01N 57/16* (2013.01); *A01N 43/06* (2013.01); *A01N 43/14* (2013.01); *A01N 43/16* (2013.01); *A01N 63/30* (2020.01); *A01N 63/32* (2020.01); *A01N 63/60* (2020.01); *A61K 31/557* (2013.01); *C12N 15/111* (2013.01); *C12N 15/113* (2013.01); *C12N 15/63* (2013.01); *C12N 15/74* (2013.01); *C12N 15/82* (2013.01); *C12N 15/8218* (2013.01); *C12N 15/8286* (2013.01); *C12N 2310/14* (2013.01)

(58) Field of Classification Search
CPC ....................................................... A01N 57/16
USPC ....................................................... 800/302
See application file for complete search history.

(56) References Cited

U.S. PATENT DOCUMENTS

| | | | |
|---|---|---|---|
| 4,011,391 A | 3/1977 | Horii et al. | |
| 4,089,947 A | 5/1978 | Horii et al. | |
| 8,101,732 B2 | 1/2012 | Mahmud et al. | |
| 8,334,366 B1 | 12/2012 | Hughes et al. | |
| 10,051,860 B2 | 8/2018 | Kiguchi et al. | |
| 2006/0272049 A1* | 11/2006 | Waterhouse | C12N 15/8218 800/279 |
| 2009/0285937 A1 | 11/2009 | Vadis et al. | |
| 2009/0298787 A1 | 12/2009 | Raemaekers et al. | |
| 2011/0150780 A1 | 6/2011 | Krieger et al. | |
| 2011/0209228 A1 | 8/2011 | Cocks et al. | |
| 2011/0229937 A1 | 9/2011 | Pompejus et al. | |
| 2011/0263487 A1 | 10/2011 | Meagher | |
| 2011/0296555 A1* | 12/2011 | Ivashuta | C12N 15/8218 800/298 |
| 2014/0349917 A1 | 11/2014 | Eckert et al. | |
| 2017/0015716 A1 | 1/2017 | Walensky et al. | |

(Continued)

FOREIGN PATENT DOCUMENTS

| | | |
|---|---|---|
| CN | 101370940 A | 2/2009 |
| CN | 104109671 A | 10/2014 |
| CN | 105746585 A | 7/2016 |

(Continued)

OTHER PUBLICATIONS

Takeshita et al.(Research in Microbiology, 2017, 167:175-187, published online Dec. 10, 2016).*
Shigenobu et al.(Proc R Soc B, 2013, 280: 20121952).*
Thomas et al. , The Plant Journal 25(4):417-425 (Year: 2001).*
Price et al. , PNAS 111:320-325 (Year: 2014).*
"Chemical Summary for Validamycin," Pesticide Action Network North America, <http://pesticideinfo.org/Summary_Chemical.jsp?Rec_Id=PRI6495>, retrieved on Apr. 5, 2019 (1 page).
"Compound Summary: Validamycin," PubChem, <https://pubchem.ncbi.nlm.nih.gov/compound/Validamycin>, created on Jun. 24, 2005, modified on Mar. 30, 2019, retrieved on Apr. 5, 2019 (17 pages).

(Continued)

*Primary Examiner* — Li Zheng
(74) *Attorney, Agent, or Firm* — Clark & Elbing LLP

(57) ABSTRACT

Provided herein are methods and compositions for modulating the fitness of a host invertebrate (e.g., insect, mollusk, or nematode) by altering interactions between the host and one or more micoorganisms resident in the host. The invention features a composition including a modulating agent (e.g., a polypeptide, nucleic acid, small molecule, or combinations thereof) that can induce changes in the host's microbiota in a manner that modulates (e.g., increases or decreases) host fitness. The modulating agent described herein may modulate the fitness of a variety of invertebrates that are important for agriculture, commerce, and/or public health.

10 Claims, 20 Drawing Sheets

Specification includes a Sequence Listing.

(56) References Cited

U.S. PATENT DOCUMENTS

2019/0216093 A1 7/2019 Martinez et al.

FOREIGN PATENT DOCUMENTS

| CN | 107637597 A | 1/2018 |
|---|---|---|
| EP | 2438813 A1 | 4/2012 |
| JP | 2009-263362 A | 11/2009 |
| RU | 2267535 C2 | 1/2006 |
| RU | 2349642 C2 | 3/2009 |
| RU | 2503721 C2 | 1/2014 |
| TW | 201642741 A | 12/2016 |
| WO | WO-88/00976 A1 | 2/1988 |
| WO | WO-95/16776 A1 | 6/1995 |
| WO | WO-2005/034863 A2 | 4/2005 |
| WO | WO-2010/140675 A1 | 12/2010 |
| WO | WO-2015/100432 A2 | 7/2015 |

OTHER PUBLICATIONS

"General Information for Validamycin," BPDB: Bio-Pesticides DataBase, <https://sitem.herts.ac.uk/aeru/bpdb/Reports/677.htm>, updated on May 3, 2018, retrieved on Apr. 5, 2019 (9 pages).

"Validamycin," EXTOXNET: Extension Toxicology Network, <http://pmep.cce.cornell.edu/profiles/extoxnet/pyrethrins-ziram/validamycin-ext.html>, published in Sep. 1995, retrieved on Apr. 5, 2019 (4 pages).

Amos, "UBC students give bees a chance," University of British Columbia News, dated Sep. 18, 2015 (3 pages).

Asano et al., "Trehalase Inhibitors, Validoxylamine A and Related Compounds as Insecticides," J Antibiot (Tokyo). 43(6):722-26 (1990).

Bini et al., Trehalose mimetics as inhibitors of trehalose processing enzymes, Carbohydrate Chemistry: Chemical and Biological Approaches: vol. 37. A.P. Rauter and T.K. Lindhorst, 259- 302 (2012).

Chen et al., Validamycin and Its Derivatives: Discovery, Chemical Synthesis and Biological Activity. Elsevier (2017) (Table of Contents Only) (7 pages).

Gesellchen et al., "An RNA interference screen identifies Inhibitor of Apoptosis Protein 2 as a regulator of innate immune signalling in Drosophilia," EMBO Reports 6(10): 979-84 (2005).

International Search Report and Written Opinion for International Application No. PCT/US2018/015077, dated Apr. 23, 2018 (16 pages).

International Search Report and Written Opinion for International Application No. PCT/US2018/19577, mailed Jun. 4, 2018 (16 pages).

Jin et al., "Inhibitory effects of validamycin compounds on the termites trehalase," Pesticide Biochemistry and Physiology. 95(1):28-32 (2009).

Kameda et al., "Validoxylamines as Trehalase Inhibitors," J Antibiot (Tokyo). 40(4):563-5 (1987).

Kikuchi et al., "Symbiont-mediated insecticide resistance," Proc Natl Acad Sci U.S.A. 109(22):8618-22 (2012).

Knuesel et al., "Comparative studies of suidatrestin, a specific inhibitor of trehalases," Comp Biochem Physiol B Biochem Mol Biol. 120(4): 639-46 (1998).

Kono et al., "Inhibition of flight in Periplaneta americana (Linn.) by a trehalase inhibitor, validoxylamine A," Journal of Insect Physiology. 40(6):455-61 (1994).

Kono et al., "Lethal Activity of a Trehalase Inhibitor, Validoxylamine A, and its Influence on the Blood Sugar Level in Bombyx mori (Lepidoptera: Bombycidae)," Appl Entomol Zool. 28(3):379-86 (1993).

Liu et al., "Disruption of Methionine Metabolism in Drosophila melanogaster Impacts Histone Methylation and Results in Loss of Viability," G3 (Bethesda). 6(1):121-32 (2016).

Rai et al., "Role of nanotechnology in agriculture with special reference to management of insect pests," Appl Microbiol Biotechnol. 94(2):287-93 (2012).

Santo Domingo et al., "Characterization of the Cricket Hindgut Microbiota with Fluorescently Labeled rRNA-Targeted Oligonucleotide Probes," Appl Environ Microbiol. 64(2):752-5 (1998).

Sharma et al., "Metabolism of 1-naphthyl-N-methyl carbamate (carbaryl) by bacterial isolates from honey bees and the effect of bacterial inoculations on carbaryl tolerance in bees," Journal of Applied Bacteriology. 81(3):235-41 (1996).

Tang et al., "Suppressing the activity of trehalase with validamycin disrupts the trehalose and chitin biosynthesis pathways in the rice brown planthopper, Nilaparvata lugens," Pesticide Biochemistry and Physiology. <http://dx.doi.org/10.1016/j.pestbp.2016.10.003>, accepted Oct. 10, 2016 (2016) (10 pages).

Tatun et al., "Developmental and Lethal Effects of Trehalase Inhibitor (Validamycin) on the Tribolium castaneum(Coleoptera: Tenebrionidae)," Annals of the Entomological Society of America. doi: 10.1093/aesa/sav.111, Advance Access published Nov. 9, 2015 (2015) (8 pages).

Tatun et al., "Trehalase Activity in Fungus-Growing Termite, Odontotermes feae (Isoptera: Termitideae) and Inhibitory Effect of Validamycin," J Econ Entomol. 107(3):1224-32 (2014).

Trinder et al., "Probiotic Lactobacillus rhamnosus reduces organophosphate pesticide absorption and toxicity to Drosophila melanogaster," Applied and Environmental Microbiology (2016) vol. 82, No. 20, pp. 6204-6213.

Trötschel et al., "Characterization of methionine export in Corynebacterium glutamicum," J Bacteriol. 187(11):3786-94 (2005).

Vallier et al., "RNAi in the cereal weevil Sitophilus spp: Systemic gene knockdown in the bacteriome tissue," BMC Biotechnology. 9(44):10.1186/1472-6750-9-44 (2009) (7 pages).

Zhang et al., "Inhibitory effect of valienamine on the enzymatic activity of honeybee (Apis cerana Fabr.) alpha-glucosidase," Pesticide Biochemistry and Physiology. 87(1):73-7 (2007).

Extended European Search Report for European Patent Application No. 18758134.3, dated Jul. 28, 2020 (7 pages).

Xue et al., "New Approaches to Agricultural Insect Pest Control Based on RNA Interference," Adv Insect Physiol. 42:73-117 (2012).

International Preliminary Report on Patentability for International Application No. PCT/US2018/019577, dated Sep. 6, 2019 (8 pages).

Zhang et al., "Bacterial symbionts, Buchnera, and starvation on wing dimorphism in English grain aphid, Sitobion avenae (F.) (Homoptera: Aphididae)," Front Physiol. 6:155. doi: 10.3389/fphys.2015.00155 (2015) (9 Pages).

Zhang et al., "Differential temporal changes of primary and secondary bacterial symbionts and whitefly host fitness following antibiotic treatments," Sci Rep. 5:15898. doi: 10.1038 (2015) (12 pages).

Ishikawa et al., "Foliar spray of validamycin a or validoxylamine a controls tomato fusarium wilt," Pythopathology. 95(10):1209-16 (2005).

Cole et al., "Insects in Vegetables," Texas Agricultural Extension Service, <http://bio-nica.info/Biblioteca/Cole2004InsectsVegetables.pdf>, retrieved Feb. 3, 2004 (37 pages).

"Pentatomidae," NC State Agricultural and Life Sciences, <https://genent.cals.ncsu.edu/insect-identification/order-hemiptera-suborder-heteroptera/family-pentatomidae/>, retrieved Mar. 25, 2021 (2015) (4 pages).

Koga et al., "Selective elimination of aphid endosymbionts: effects of antibiotic dose and host genotype, and fitness consequences," FEMS Microbiol Ecol. 60(2):229-39 (2007).

Prado et al., "Host-Symbiont Interactions for Potentially Managing Heteropteran Pests, " Psyche. Article ID 269473, <https://downloads.hindawi.com/journals/psyche/2012/26>, (2012) (10 pages).

First Office Action for Chinese Patent Application No. 201880010183.1, dated Jan. 28, 2021 (28 pages).

Communication pursuant to Article 94(3) EPC for European Patent Application No. 18758134.3 dated Jul. 16, 2021 (4 pages).

Yu et al., "RNAi-mediated plant protection against aphids," Pest Manag Sci. 72(6):1090-8 (2016) (9 pages).

"RNA Interference and Plant Growth and Development," RNA interference in other applications (2013) (6 pages).

(56) References Cited

OTHER PUBLICATIONS

Xue et al., "Chapter 3: New Approaches to Agricultural Insect Pest Control Based on RNA Interference," *Advances in Insect Physiology*. 42:73-117 (2012).
Login et al., "Antimicrobial peptides keep insect endosymbionts under control," Science. 334(6054):362-5 (2011).
Falla et al., "Mode of action of the antimicrobial peptide indolicidin," J Biol Chem. 271(32):19298-303 (1996).
Walterson et al., "Pantoea: insights into a highly versatile and diverse genus within the Enterobacteriaceae," FEMS Microbiol Rev. 39(6):968-84 (2015).
Santos-Garcia et al., "No exception to the rule: Candidatus Portiera aleyrodidarum cell wall revisited," FEMS Microbiol Lett. 360(2):132-6 (2014).
Le-Feuvre et al., "Effect of the antimicrobial peptide indolicidin on the green peach aphid *Myzus persicae* (Sulzer)," J Appl Entomol 131(2):71-75 (2007).
Jiang et al., "Comparative analysis of genome sequences from four strains of the Buchnera aphidicola Mp endosymbion of the green peach aphid, Myzus persicae," BMC Genomics. 14:917 (2013) (12 pages).

\* cited by examiner

US 11,974,574 B2

COMPOSITIONS AND RELATED METHODS FOR MODULATING ENDOSYMBIONTS

CROSS-REFERENCE TO RELATED APPLICATIONS

This application claims priority to U.S. Provisional Application No. 62/463,451, filed on Feb. 24, 2017, and U.S. Provisional Application No. 62/583,990, filed on Nov. 9, 2017, the contents of which are hereby incorporated herein by reference in their entireties.

SEQUENCE LISTING

The instant application contains a Sequence Listing which has been submitted electronically in ASCII format and is hereby incorporated by reference in its entirety. Said ASCII copy, created May 28, 2019, is named 51215-008003_Sequence_Listing_5.28.19_ST25 and is 135,182 bytes in size.

BACKGROUND

Invertebrate organisms (e.g., insects, mollusks, or nematodes) are pervasive in the human environment. In some instances, invertebrates serve beneficial roles, such as nematodes or arthropods utilized in agriculture for pollination efforts and pest control or in commerce for the production of commercial products (e.g., honey or silk). In other instances, invertebrates can be detrimental, including some species of mollusks (e.g., snails and slugs), nematodes, or insects that can be serious crop pests or carriers of disease. Thus, there is need in the art for methods and compositions to modulate the fitness of invertebrates that are important in agriculture, commerce, or public health.

SUMMARY OF THE INVENTION

Disclosed herein are compositions and methods for modulating the fitness of invertebrates, including insects, nematodes, or mollusks, by altering the interactions between the host and one or more microorganisms resident in the host.

In one aspect, provided herein is a method for decreasing the fitness of an insect, the method including delivering to the insect an effective amount of a polynucleotide that includes a dsRNA that decreases expression of an insect bacteriocyte regulatory gene or an insect immunoregulatory gene in the insect relative to an insect that has not been administered the dsRNA.

In some embodiments, the gene encodes a protein from the bacteriocyte-specific cysteine rich proteins BCR family, a protein from the secreted proteins SP family, BicD (Protein bicaudal D), Cact (cactus), DIF (Dorsal related immunity factor), Toll (Toll Interacting Protein), or imd (immune deficiency protein). In some embodiments, the gene encodes a protein having at least 30%, 35%, 40%, 45%, 50%, 55%, 60%, 65%, 70%, 75%, 80%, 85%, 90%, 95%, or 100% amino acid sequence identity to a protein listed in Table 5, Table 8, or Table 9. In some embodiments, the gene encodes a functional homolog of a protein listed in Table 5, Table 8, or Table 9. For example, the gene may encode a cactus-like protein in aphids (e.g., any one of the proteins described by GenBank Accession Nos: XP_022175228.1, XP_016656687.1, NP_001156668.1, XP_008179071.1, or XP_016656686.1, the associated amino acid and nucleotide sequences of which are incorporated by reference).

In some embodiments, the dsRNA is complementary to 10 to 30 nucleotides of the gene in the insect (e.g., 10 to 30 nucleotides, 12 to 28 nucleotides, 14 to 26 nucleotides, 16 to 24 nucleotides, 14 to 22 nucleotides, or 18 to 20 nucleotides). In some embodiments, the dsRNA is complementary to 10, 11, 12, 13, 14, 15, 16, 17, 18, 19, 20, 21, 22, 23, 24, 25, 26, 27, 28, 29, or 30 nucleotides of the gene in the insect. In some embodiments, the entire length of the dsRNA is complementary to the gene. In alternative embodiments, only a portion of the dsRNA is complementary to the gene.

In some embodiments, the method is effective to decrease expression of the gene in the insect, e.g., by about 10%, 20%, 30%, 40%, 50%, 60%, 70%, 80%, 90%, 95%, 96%, 97%, 98%, or 99% or greater relative to an insect that has not been administered the polynucleotide. In some embodiments, the method is effective to decrease expression of the gene in the insect, e.g., by about 10%, 20%, 30%, 40%, 50%, 60%, 70%, 80%, 90%, 95%, 96%, 97%, 98%, or 99% or greater as compared to a reference level (e.g., as compared to expression of one or more control genes (e.g., a housekeeping gene), expression of the same gene in a different sample (e.g., one or more control samples), or expression of the same gene in the same sample at one or more earlier time points).

In some embodiments, the method is effective to decrease expression of the gene in the insect, e.g., by about 1.5×, 1.75×, 2×, 3×, 4×, 5×, 6×, 7×, 8×, 9×, 10×, 25×, 50×, 75×, or 100× fold less relative to an insect that has not been administered the polynucleotide. In some embodiments, the method is effective to decrease expression of the gene in the insect, e.g., by about 1.5×, 1.75×, 2×, 3×, 4×, 5×, 6×, 7×, 8×, 9×, 10×, 25×, 50×, 75×, or 100× fold less as compared to a reference level (e.g., as compared to expression of one or more control genes (e.g., a housekeeping gene), expression of the same gene in a different sample (e.g., one or more control samples), or expression of the same gene in the same sample at one or more earlier time points).

In some embodiments, the method is effective to inhibit expression of the gene in the insect or to decrease expression of the gene to an undetectable level.

In some embodiments, the method is effective to decrease the level, diversity, or metabolism of one or more microorganisms resident in the insect relative to an insect that has not been delivered the polynucleotide. In some embodiments, the method is effective to decrease the level, diversity, or metabolism of one or more microorganisms resident in the insect, e.g., by about 1.5×, 1.75×, 2×, 3×, 4×, 5×, 6×, 7×, 8×, 9×, 10×, 25×, 50×, 75×, or 100× fold less relative to an insect that has not been delivered the polynucleotide. In some embodiments, the method is effective to decrease the level, diversity, or metabolism of one or more microorganisms resident in the insect, e.g., by about 10%, 20%, 30%, 40%, 50%, 60%, 70%, 80%, 90%, 95%, 96%, 97%, 98%, 99%, or 100% less relative to an insect that has not been delivered the polynucleotide. In certain embodiments, the one or more microorganisms is a *Buchnera* spp.

In some embodiments, the method is effective to decrease the fitness of the insect relative to an insect that has not been delivered the polynucleotide. In some embodiments, the method is effective to decrease the fitness of the insect, e.g., by about 1.5×, 1.75×, 2×, 3×, 4×, 5×, 6×, 7×, 8×, 9×, 10×, 25×, 50×, 75×, or 100× fold less relative to an insect that has not been delivered the polynucleotide. In some embodiments, the method is effective to decrease the fitness of the insect, e.g., by about 10%, 20%, 30%, 40%, 50%, 60%, 70%, 80%, 90%, 95%, 96%, 97%, 98%, 99%, or 100% less relative to an insect that has not been delivered the polynucleotide.

In some embodiments, the polynucleotide is delivered in a composition formulated for delivery to insects. In some embodiments, the delivery includes delivering the polynucleotide to at least one habitat where the insect pest grows, lives, reproduces, feeds, or infests. In some embodiments, the delivery comprises spraying the antimicrobial peptide on an agricultural crop. In some embodiments, the polynucleotide is delivered as an insect comestible composition for ingestion by the insect.

In some embodiments, the polynucleotide is formulated with an agriculturally acceptable carrier as a liquid, a solid, an aerosol, a paste, a gel, or a gas composition.

In some embodiments, the insect is an aphid.

In another aspect, provided herein is a composition including a polynucleotide that includes a dsRNA formulated for delivery to an insect, wherein the dsRNA is complementary to 15 to 30 nucleotides of an insect bacteriocyte regulatory gene or an insect immunoregulatory gene. In some embodiments, the gene encodes a protein selected from the group consisting of a protein from the bacteriocyte-specific cysteine rich proteins BCR family, a protein from the secreted proteins SP family, BicD (Protein bicaudal D), Cact (cactus), DIF (Dorsal related immunity factor), Toll (Toll Interacting Protein), and imd (immune deficiency protein). In some embodiments, the gene encodes a protein having at least 30%, 35%, 40%, 45%, 50%, 55%, 60%, 65%, 70%, 75%, 80%, 85%, 90%, 95%, or 100% amino acid sequence identity to a protein listed in Table 5, Table 8, or Table 9. In some embodiments, the gene encodes a functional homolog of a protein listed in Table 5, Table 8, or Table 9. For example, the gene may encode a cactus-like protein in aphids (e.g., any one of the proteins described by GenBank Accession Nos: XP_022175228.1, XP_016656687.1, NP_001156668.1, XP_008179071.1, or XP_016656686.1, the associated amino acid and nucleotide sequences of which are incorporated by reference). In some embodiments, the dsRNA is complementary to 10 to 30 nucleotides of the gene in the insect (e.g., 10 to 30 nucleotides, 12 to 28 nucleotides, 14 to 26 nucleotides, 16 to 24 nucleotides, 14 to 22 nucleotides, or 18 to 20 nucleotides). In some embodiments, the dsRNA is complementary to 10, 11, 12, 13, 14, 15, 16, 17, 18, 19, 20, 21, 22, 23, 24, 25, 26, 27, 28, 29, or 30 nucleotides of the gene in the insect. In some embodiments, the entire length of the dsRNA is complementary to the gene. In alternative embodiments, only a portion of the dsRNA is complementary to the gene.

In a further aspect, provided herein is a plant comprising a topical application of the compositions described herein.

In yet another aspect, provided herein is a transgenic plant cell having in its genome a recombinant DNA construct, wherein the recombinant DNA construct includes a heterologous promoter operably linked to a DNA encoding a RNA including at least one double-stranded RNA region, at least one strand of which includes a nucleotide sequence that is complementary to 15 to 30 nucleotides of an insect bacteriocyte regulatory gene or an insect immunoregulatory gene. In some embodiments, the gene encodes a protein selected from the group consisting of a protein from the bacteriocyte-specific cysteine rich proteins BCR family, a protein from the secreted proteins SP family, BicD (Protein bicaudal D), Cact (cactus), DIF (Dorsal related immunity factor), Toll (Toll Interacting Protein), and imd (immune deficiency protein). In some embodiments, the gene encodes a protein having at least 30%, 35%, 40%, 45%, 50%, 55%, 60%, 65%, 70%, 75%, 80%, 85%, 90%, 95%, or 100% amino acid sequence identity to a protein listed in Table 5, Table 8, or Table 9. In some embodiments, the gene encodes a functional homolog of a protein listed in Table 5, Table 8, or Table 9. For example, the gene may encode a cactus-like protein in aphids (e.g., any one of the proteins described by GenBank Accession Nos: XP_022175228.1, XP_016656687.1, NP_001156668.1, XP_008179071.1, or XP_016656686.1, the associated amino acid and nucleotide sequences of which are incorporated by reference). In some embodiments, the dsRNA is complementary to 10 to 30 nucleotides of the gene in the insect (e.g., 10 to 30 nucleotides, 12 to 28 nucleotides, 14 to 26 nucleotides, 16 to 24 nucleotides, 14 to 22 nucleotides, or 18 to 20 nucleotides). In some embodiments, the dsRNA is complementary to 10, 11, 12, 13, 14, 15, 16, 17, 18, 19, 20, 21, 22, 23, 24, 25, 26, 27, 28, 29, or 30 nucleotides of the gene in the insect. In some embodiments, the entire length of the dsRNA is complementary to the gene. In alternative embodiments, only a portion of the dsRNA is complementary to the gene.

In yet another aspect, provided herein are compositions that include a modulating agent (e.g., a polypeptide (e.g., antibody, bacteriocin, antimicrobial peptide, or bacteriocyte regulatory peptide), a nucleic acid (e.g., DNA, RNA (e.g., mRNA, gRNA, or inhibitory RNA (e.g., RNAi, shRNA, miRNA)), CRISPR nucleic acid), a small molecule (e.g., prostaglandin), or a combination thereof) that modulates (e.g., increases or decreases) the fitness of an invertebrate host (e.g., insect, mollusk, or nematode), wherein the modulating agent alters interactions between the host and one or more microorganisms resident in the host.

In some embodiments, the modulating agent (e.g., a polypeptide (e.g., antibody, bacteriocin, antimicrobial peptide, or bacteriocyte regulatory peptide), a nucleic acid (e.g., DNA, RNA (e.g., mRNA, gRNA, or inhibitory RNA (e.g., RNAi, shRNA, miRNA)), CRISPR nucleic acid), a small molecule (e.g., prostaglandin), or a combination thereof) targets one or more host pathways that mediate interactions between the host and the one or more microorganisms resident in the host (e.g., host-microbiota interactions). In certain embodiments, the targeting (e.g., upregulation, downregulation, or inhibition) of the one or more host pathways alters the level, diversity, or function of the one or more microorganisms resident in the host in comparison to a host organism to which the modulating agent has not been administered. In certain embodiments, the targeting (e.g., upregulation, downregulation, or inhibition) of the one or more host pathways increases the level, diversity, or function of the one or more microorganisms resident in the host in comparison to a host organism to which the modulating agent has not been administered. In alternative embodiments, the targeting (e.g., upregulation, downregulation, or inhibition) of the one or more host pathways decreases the level, diversity, or function of the one or more microorganisms resident in the host in comparison to a host organism to which the modulating agent has not been administered.

In some embodiments, the host pathway is a pathway that regulates bacteriocyte function or development. In some embodiments, the targeting of bacteriocyte function or development may increase and/or decrease the level, diversity, and/or function of one or more microorganisms resident in the bacteriocyte in comparison to a host organism to which the modulating agent has not been administered. In certain embodiments, the targeting of bacteriocyte function or development decreases the level, diversity, or function of one or more microorganisms resident in the bacteriocyte (e.g., a bacteriocyte of an aphid) in comparison to a host organism to which the modulating agent has not been administered. In certain embodiments, the targeting of bacteriocyte function or development increases the level, diversity, or function of one or more microorganisms resident in the bacteriocyte (e.g., a bacteriocyte of an aphid) in comparison to a host organism to which the modulating agent has not been administered.

In some embodiments, the host pathway is a pathway that regulates the host's immune system. For example, in some embodiments, the modulating agent activates an immune response against the one or more microorganisms resident in the host, thereby decreasing the level, diversity, and/or function of the one or more microorganisms in comparison to a host organism to which the modulating agent has not been administered. Alternatively, in some embodiments, the modulating agent suppresses an immune response against the one or more microorganisms resident in the host, thereby increasing the level, diversity, and/or function of the one or more microorganisms in comparison to a host organism to which the modulating agent has not been administered.

In some embodiments, the modulating agent (e.g., a polypeptide (e.g., antibody, bacteriocin, antimicrobial peptide, or bacteriocyte regulatory peptide), a nucleic acid (e.g., DNA, RNA (e.g., mRNA, gRNA, or inhibitory RNA (e.g., RNAi, shRNA, miRNA)), CRISPR nucleic acid), a small molecule (e.g., prostaglandin), or a combination thereof) targets one or more host pathways by altering gene expression in the host in comparison to a host organism to which the modulating agent has not been administered. For example, the modulating agent may increase and/or decrease gene expression in the host in comparison to a host organism to which the modulating agent has not been administered. In some embodiments, the modulating agent alters expression of a gene that encodes a protein listed in Table 3, Table 4, Table 5, Table 7, Table 8, or Table 9 in comparison to a host organism to which the modulating agent has not been administered. In some embodiments, the modulating agent decreases expression of a gene that encodes a protein listed in Table 3, Table 4, Table 5, Table 7, Table 8, or Table 9 in comparison to a host organism to which the modulating agent has not been administered. In some embodiments, the modulating agent decreases expression of a gene that encodes a protein listed in Table 3, Table 4, Table 5, Table 7, Table 8, or Table 9 in comparison to a host organism to which the modulating agent has not been administered. In some embodiments, the gene encodes a bacteriocyte regulatory peptide. For example, the bacteriocyte regulatory peptide may be one listed in Table 5 or Table 8 (e.g., BCR1). In some embodiments, the gene encodes an immune system component. For example, the immune system component may be one listed in Table 9. In some embodiments, the modulating agent targets a polypeptide in the host. In some embodiments, the polypeptide is an enzyme or cell receptor. In some embodiments, the modulating agent increases and/or decreases enzyme activity in comparison to a host organism to which the modulating agent has not been administered. In some embodiments, the modulating agent increases and/or decreases cell receptor signaling in comparison to a host organism to which the modulating agent has not been administered. In some embodiments, the host protein is one listed in Table 4, Table 5, Table 8, or Table 9.

The modulating agent (e.g., a polypeptide (e.g., antibody, bacteriocin, antimicrobial peptide, or bacteriocyte regulatory peptide), a nucleic acid (e.g., DNA, RNA (e.g., mRNA, gRNA, or inhibitory RNA (e.g., RNAi, shRNA, miRNA)), CRISPR nucleic acid), a small molecule (e.g., prostaglandin), or a combination thereof) may additionally or alternatively target one or more microbial pathways that mediate interactions between the host and one or more microorganisms resident in the host. In some embodiments, the modulating agent alters gene expression in one or more microorganisms resident in the host in comparison to a host organism to which the modulating agent has not been administered. For example, the modulating agent may increase and/or decrease gene expression in the one or more microorganisms in comparison to a host organism to which the modulating agent has not been administered. In some embodiments, the modulating agent alters (e.g., increases or decreases) the expression of a gene that encodes a protein listed in Table 3 or Table 7 in comparison to a host organism to which the modulating agent has not been administered. In some embodiments, the modulating agent targets (e.g., binds, antagonizes, and/or agonizes) a polypeptide in one or more microorganisms resident in the host (e.g., a protein listed in Table 3 or Table 7).

In some embodiments, the one or more microorganisms resident in the host is an endosymbiotic microorganism. In some embodiments, the one or more microorganisms is resident in the host's gut. In some embodiments, the one or more microorganisms is resident in a bacteriocyte in the host. In some embodiments, the one or more microorganisms resident in the host is a fungus or bacterium. In some embodiments, the bacterium resident in the host is at least one selected from the group consisting of *Candidatus* spp, *Buchenera* spp, *Blattabacterium* spp, *Baumania* spp, *Wigglesworthia* spp, *Wolbachia* spp, *Rickettsia* spp, *Orientia* spp, *Sodalis* spp, *Burkholderia* spp, *Cupriavidus* spp, *Frankia* spp, *Snirhizobium* spp, *Streptococcus* spp, *Wolinella* spp, *Xylella* spp, *Erwinia* spp, *Agrobacterium* spp, *Bacillus* spp, *Paenibacillus* spp, *Streptomyces* spp, *Micrococcus* spp, *Corynebacterium* spp, *Acetobacter* spp, *Cyanobacteria* spp, *Salmonella* spp, *Rhodococcus* spp, *Pseudomonas* spp, *Lactobacillus* spp, *Enterococcus* spp, *Alcaligenes* spp, *Klebsiella* spp, *Paenibacillus* spp, *Arthrobacter* spp, *Corynebacterium* spp, *Brevibacterium* spp, *Thermus* spp, *Pseudomonas* spp, *Clostridium* spp, and *Escherichia* spp. In some embodiments, the fungus resident in the host is at least one selected from the group consisting of *Candida*, *Metschnikowia*, *Debaromyces*, *Starmerella*, *Pichia*, *Cryptococcus*, *Pseudozyma*, *Symbiotaphrina bucneri*, *Symbiotaphrina Scheffersomyces shehatae*, *Scheffersomyces stipites*, *Cryptococcus*, *Trichosporon*, *Amylostereum areolatum*, *Epichloe* spp, *Pichia pinus*, *Hansenula capsulate*, *Daldinia decipien*, *Ceratocytis* spp, *Ophiostoma* spp, and *Attamyces bromatificus*. In some embodiments, the modulating agent alters the growth, division, viability, metabolism, and/or longevity of the microorganism resident in the host. In some embodiments, the modulating agent decreases the growth, division, viability, metabolism, and/or longevity of the one or more microorganisms. In some embodiments, the modulating agent increases the growth, division, viability, metabolism, and/or longevity of the one or more microorganisms.

In some embodiments, the modulating agent is a polypeptide (e.g., antibody, bacteriocin, antimicrobial peptide, or bacteriocyte regulatory peptide), a nucleic acid (e.g., DNA, RNA (e.g., mRNA, gRNA, or inhibitory RNA (e.g., RNAi, shRNA, miRNA)), CRISPR nucleic acid), a small molecule (e.g., prostaglandin), or any combination thereof.

In some embodiments, the modulating agent is a nucleic acid. The nucleic acid may be a DNA molecule, a RNA molecule (e.g., double-stranded RNA (dsRNA) or single-stranded RNA (ssRNA)), or a hybrid DNA-RNA molecule. In some embodiments, the RNA is a messenger RNA (mRNA), a guide RNA (gRNA), or an inhibitory RNA. In some embodiments, the inhibitory RNA is RNAi, shRNA, or miRNA. In some embodiments, the nucleic acid encodes a polypeptide. In some embodiments, the nucleic acid is an expression vector encoding a polypeptide. In some embodiments, the nucleic acid is a CRISPR nucleic acid.

In some embodiments, the modulating agent is a small molecule. In some embodiments, the small molecule is an agonist, antagonist, inhibitor, or an activator of a component of a host immune system pathway or bacteriocyte regulatory pathway. In some embodiments, the small molecule is prostaglandin.

In some embodiments, the modulating agent is a polypeptide. In some embodiments, the polypeptide is an antibody or an antibody fragment. For example, the antibody or antibody fragment may be an agonist or antagonist of an enzyme in the host (e.g., an immune system or bacteriocyte-regulatory enzyme) or in the microorganism resident in the host, including any of the proteins listed in Table 5, Table 7, Table 8, or Table 9.

In some embodiments, the modulating agent (e.g., a polypeptide (e.g., antibody, bacteriocin, antimicrobial peptide, or bacteriocyte regulatory peptide), a nucleic acid (e.g., DNA, RNA (e.g., mRNA, gRNA, or inhibitory RNA (e.g., RNAi, shRNA, miRNA)), CRISPR nucleic acid), a small molecule (e.g., prostaglandin), or a combination thereof) modulates the host's fitness by increasing or decreasing the host's susceptibility to a pesticide (e.g., a pesticide listed in Table 11). In some embodiments, the pesticide is a bactericide or fungicide. In some embodiments, the pesticide is an insecticide, molluscicide, or nematicide.

In some embodiments, the composition includes a plurality (e.g., 2, 3, 4, 5, 6, 7, 8, 9, 10, or more than 10) of different modulating agents (e.g., a polypeptide (e.g., antibody, bacteriocin, antimicrobial peptide, or bacteriocyte regulatory peptide), a nucleic acid (e.g., DNA, RNA (e.g., mRNA, gRNA, or inhibitory RNA (e.g., RNAi, shRNA, miRNA)), CRISPR nucleic acid), a small molecule (e.g., prostaglandin), or a combination thereof). In some embodiments, the composition includes a modulating agent and a pesticide (e.g., a pesticide listed in Table 11). In some embodiments, the pesticide is a bactericide or fungicide. In some embodiments, the pesticide is an insecticide, molluscicide, or nematicide. In some embodiments, the composition includes a modulating agent and an agent that increases crop growth.

In some embodiments, the modulating agent (e.g., a polypeptide (e.g., antibody, bacteriocin, antimicrobial peptide, or bacteriocyte regulatory peptide), a nucleic acid (e.g., DNA, RNA (e.g., mRNA, gRNA, or inhibitory RNA (e.g., RNAi, shRNA, miRNA)), CRISPR nucleic acid), a small molecule (e.g., prostaglandin), or a combination thereof) is linked to a second moiety. In some embodiments, the second moiety is selected from the group consisting of a modulating agent, peptide nucleic acid, cell penetrating peptide (CPP), and targeting domain. In some embodiments, the modulating agent includes a linker. In some embodiments, the linker is a cleavable linker. In some embodiments, the CPP is any one listed in Table 10.

In some embodiments, the composition further includes a carrier. In some embodiments, the carrier is an agriculturally acceptable carrier. In some embodiments, the composition further includes a host bait, a sticky agent, or a combination thereof. In some embodiments, the host bait is a comestible agent. In some embodiments, the host bait is a chemoattractant.

In some embodiments, the composition is at a dose effective to modulate host fitness. In some embodiments, the composition is at a dose effective to increase host fitness. In alternative embodiments, the composition is at a dose effective to decrease host fitness. In some embodiments, host fitness is measured by survival, lifespan, reproduction, or metabolism of the host.

In some embodiments, the composition is formulated for delivery to a microorganism inhabiting the gut of the host. In some embodiments, the composition is formulated for delivery to a microorganism inhabiting a bacteriocyte of the host. In some embodiments, the composition is formulated for delivery to a plant. In some embodiments, the composition is formulated for use in a host feeding station. In some embodiments, the composition is formulated as a liquid, a powder, granules, or nanoparticles. In some embodiments, the composition is formulated as one selected from the group consisting of a liposome, polymer, bacteria secreting peptide, and synthetic nanocapsule. In some embodiments, the synthetic nanocapsule delivers the composition to a target site in the host. In some embodiments, the target site is the gut of the host. In some embodiments, the target site is a bacteriocyte in the host.

In another aspect, provided herein are plants including any of the previous compositions (e.g., a modulating agent (e.g., a polypeptide (e.g., antibody, bacteriocin, antimicrobial peptide, or bacteriocyte regulatory peptide), a nucleic acid (e.g., DNA, RNA (e.g., mRNA, gRNA, or inhibitory RNA (e.g., RNAi, shRNA, miRNA)), CRISPR nucleic acid), a small molecule (e.g., prostaglandin), or a combination thereof)). In some embodiments, the plant includes a nucleic acid integrated into the plant genome, wherein the nucleic acid encodes any of the previous modulating agents (e.g., a polypeptide (e.g., an antibody, a bacteriocin (e.g., colA), an antimicrobial peptide, a bacteriocyte regulatory peptide, a nucleic acid, or a small molecule). The modulating agent may be non-endogenous to the plant. In some embodiments, the plant further includes a comestible agent for invertebrates (e.g., insect, mollusk, or nematode), wherein the comestible agent produces and/or carries the modulating agent. In some embodiments, the comestible agent includes one or more components of the plant. In some embodiments, the one or more components of the plant includes a root, stem, leaf, flower, sap, bark, wood, spine, pollen, nectar, seed, fruit, or any combination thereof. For example, in some embodiments, the plant produces a modulating agent that the insect ingests by eating one or more components of the plant.

In yet another aspect, provided herein are hosts including any of the previous compositions (e.g., a modulating agent (e.g., a polypeptide (e.g., antibody, bacteriocin, antimicrobial peptide, or bacteriocyte regulatory peptide), a nucleic acid (e.g., DNA, RNA (e.g., mRNA, gRNA, or inhibitory RNA (e.g., RNAi, shRNA, miRNA)), CRISPR nucleic acid), a small molecule (e.g., prostaglandin), or a combination thereof)). The host may be an invertebrate (e.g., insect, mollusk, or nematode). In some embodiments, the invertebrate is an insect. In some embodiments, the insect is a bacteriocyte-containing insect. For example, in certain embodiments, the bacteriocyte-containing insect may be an aphid (e.g., a corn leaf aphid or green peach aphid). In further embodiments, the insect is a beetle, weevil, fly, aphid, whitefly, leafhopper, scale, moth, butterfly, grasshopper, cricket, thrip, or mite. In other embodiments, the invertebrate is a mollusk. In some embodiments, the mollusk is a species belonging to Veronicellidae, Ampullariidae, Achatinidae, Helicidae, Hydromiidae, Planobidae, Lymnaeidae, Urocyclidae, Bradybaenidae, Agriolimacidae, Arionidae, or Milacidae. In another embodiment, the invertebrate may be a nematode. In some embodiments, the nematode is a species belonging to Criconematidae, Belonolaimidae, Hoplolaimidae, Heteroderidae, Longidoridae, Pratylenchidae, Trichodoridae, or Anguinidae.

In another aspect, provided herein is a system for modulating (e.g., increasing or decreasing) a host's fitness. The system includes a modulating agent (e.g., a polypeptide (e.g., antibody, bacteriocin, antimicrobial peptide, or bacteriocyte regulatory peptide), a nucleic acid (e.g., DNA, RNA (e.g., mRNA, gRNA, or inhibitory RNA (e.g., RNAi, shRNA, miRNA)), CRISPR nucleic acid), a small molecule (e.g., prostaglandin), or a combination thereof) that alters interactions between the host and one or more microorganisms resident in the host, wherein the system is effective to modulate (e.g., increasing or decreasing) the host's fitness, and wherein the host is an invertebrate (e.g., insect (e.g., an aphid), mollusk, or nematode). In some embodiments, the modulating agent of the system is any of the previous compositions. In some embodiments, the modulating agent is formulated as a powder. In some embodiments, the modulating agent is formulated as a solvent. In some embodiments, the modulating agent is formulated as a concentrate. In some embodiments, the modulating agent is formulated as a diluent. In some embodiments, the modulating agent is prepared for delivery by combining any of the previous compositions with a carrier.

In another aspect, provided herein are methods of modulating a host-microbiota interaction that includes delivering any of the compositions described herein (e.g., a modulating agent (e.g., a polypeptide (e.g., antibody, bacteriocin, antimicrobial peptide, or bacteriocyte regulatory peptide), a nucleic acid (e.g., DNA, RNA (e.g., mRNA, gRNA, or inhibitory RNA (e.g., RNAi, shRNA, miRNA)), CRISPR nucleic acid), a small molecule (e.g., prostaglandin), or a combination thereof)) to the host, wherein the modulating agent modulates one or more interactions between the host and one or more microorganisms resident in the host.

In another aspect, provided herein are methods of modulating the fitness of an invertebrate host (e.g., insect (e.g., an aphid), mollusk, or nematode), wherein the method includes delivering any of the compositions described herein (e.g., a modulating agent (e.g., a polypeptide (e.g., antibody, bacteriocin, antimicrobial peptide, or bacteriocyte regulatory peptide), a nucleic acid (e.g., DNA, RNA (e.g., mRNA, gRNA, or inhibitory RNA (e.g., RNAi, shRNA, miRNA)), CRISPR nucleic acid), a small molecule (e.g., prostaglandin), or a combination thereof)) to the host and wherein the modulating agent alters interactions between the host and one or more microorganisms resident in the host.

In some embodiments of any of the above methods, the one or more microorganisms resident in the host may be a fungus or bacterium. In some embodiments, the one or more microorganisms is an endosymbiotic microorganism. In some embodiments, the one or more microorganisms is resident in the host's gut. In some embodiments, the one or more microorganisms is resident in a bacteriocyte in the host. In some embodiments, the one or more microorganisms are required for host fitness or host survival.

In some embodiments of any of the above methods, the modulating agent may target one or more host pathways that mediate interactions between the host and the one or more microorganisms. In some embodiments, the host pathway is a pathway that regulates insect (e.g., an aphid) bacteriocyte function or development. In some embodiments, the targeting of the host bacteriocyte function or development decreases the level, diversity, and/or function of one or more microorganisms resident in the bacteriocyte. Alternatively, the targeting of the host bacteriocyte function or development increases the level, diversity, and/or function of one or more microorganisms resident in the bacteriocyte. In some embodiments, the host pathway is a pathway that regulates the host's immune system.

In some embodiments, the modulating agent activates an immune response against the one or more microorganisms resident in the host, thereby decreasing the level, diversity, and/or function of the one or more microorganisms. In some embodiments, the modulating agent suppresses an immune response against the one or more microorganisms resident in the host, thereby increasing the level, diversity, and/or function of the one or more microorganisms.

In some embodiments, the modulating agent targets one or more microbial pathways that mediate interactions between the host and the one or more microorganisms.

In some embodiments, the delivering step includes providing the modulating agent at a dose and time sufficient to effect the one or more microorganisms, thereby modulating microbial diversity in the host. In some embodiments, the delivering step includes topical application of any of the previous compositions to a plant. In some embodiments, the delivering step includes providing the modulating agent through a genetically modified, engineered, or transgenic plant (e.g., any of the plants described herein). In other embodiments, the delivering step includes providing the modulating agent to the host as a comestible agent for invertebrates (e.g., insect, mollusk, or nematode). In further embodiments, the delivering step includes providing a host carrying the modulating agent. In some embodiments, the host carrying the modulating agent can transmit the modulating agent to one or more additional hosts.

Also provided herein are screening assays to identify a modulating agent that modulates (e.g., increases or decreases) the fitness of a host. The screening assay may include the steps of (a) exposing a microorganism that can be resident in the host to one or more candidate modulating agents and (b) identifying a modulating agent that increases or decreases the fitness of the host. In some embodiments, the modulating agent is a microorganism resident in the host. In some embodiments, the microorganism is a bacterium. In some embodiments, the bacterium, when resident in the host, increases host fitness. Alternatively, the bacterium, when resident in the host, decreases host fitness. In some embodiments, the modulating agent is any of the modulating agents described herein (e.g., a modulating agent (e.g., a polypeptide (e.g., antibody, bacteriocin, antimicrobial peptide, or bacteriocyte regulatory peptide (e.g., Coleoptericin A), a nucleic acid (e.g., DNA, RNA (e.g., mRNA, gRNA, or inhibitory RNA (e.g., RNAi, shRNA, miRNA)), CRISPR nucleic acid), a small molecule (e.g., prostaglandin), or a combination thereof)). In some embodiments, the modulating agent is provided by a genetically modified phage or bacteria. In some embodiments, the host's fitness is modulated by modulating the host microbiota.

Definitions

As used herein, the term "bacteriocyte" refers to a specialized cell found in invertebrates, e.g., insects, nematodes, or mollusks, where intracellular bacteria reside with symbiotic bacterial properties. In some instances, the bacteriocyte may be clustered with other bacteriocytes to form a bacteriome.

As used herein, the term "effective amount" refers to an amount of a modulating agent (e.g., a polypeptide, nucleic acid, small molecule, or combinations thereof) or composition including said agent sufficient to effect the recited result, e.g., to increase or decrease the fitness of a host organism (e.g., insect, nematode, or mollusk); to reach a target level (e.g., a predetermined or threshold level) of a modulating agent concentration inside a target host; to reach a target level (e.g., a predetermined or threshold level) of a modulating agent concentration inside a target host gut; to reach a target level (e.g., a predetermined or threshold level) of a modulating agent concentration inside a target host bacteriocyte; to modulate the level, or an activity, of one or more microorganisms (e.g., endosymbiont) in the target host.

As used herein, the term "fitness" refers to the ability of a host invertebrate (e.g., insect, mollusk, or nematode) to survive, and/or to produce surviving offspring. Fitness of a host (e.g., insect, mollusk, or nematode) may be measured by one or more parameters, including, but not limited to, life span, reproductive rate, mobility, body weight, or metabolic rate. Depending on the host, fitness may additionally be measured based on measures of activity (e.g., biting animals or humans, plant pollination), disease transmission (e.g., vector-vector transmission or vector-animal transmission), or production (e.g., honey or silk).

As used herein, the term "gut" refers to any portion of a host's gut, including, the foregut, midgut, or hindgut of the host.

As used herein, the term "host" refers to an organism, such as an invertebrate (e.g., insect, mollusk, or nematode) carrying resident microorganisms (e.g., endogenous microorganisms, endosymbiotic microorganisms (e.g., primary or secondary endosymbionts), commensal organisms, and/or pathogenic microorganisms).

As used herein "decreasing host fitness" or "reducing host fitness" refers to any disruption to host physiology, or any activity carried out by said host, as a consequence of administration of a modulating agent, including, but not limited to, any one or more of the following desired effects: (1) decreasing a population of a host (e.g., insect, mollusk, or nematode) by about 10%, 20%, 30%, 40%, 50%, 60%, 70%, 80%, 90%, 95%, 99%, 100% or more; (2) decreasing the reproductive rate of a host (e.g., insect, mollusk, or nematode) by about 10%, 20%, 30%, 40%, 50%, 60%, 70%, 80%, 90%, 95%, 99%, 100% or more; (3) decreasing the mobility of a host (e.g., insect, mollusk, or nematode) by about 10%, 20%, 30%, 40%, 50%, 60%, 70%, 80%, 90%, 95%, 99%, 100% or more; (4) decreasing the body weight of a host (e.g., insect, mollusk, or nematode) by about 10%, 20%, 30%, 40%, 50%, 60%, 70%, 80%, 90%, 95%, 99%, 100% or more; (5) decreasing the metabolic rate or activity of a host (e.g., insect, mollusk, or nematode) by about 10%, 20%, 30%, 40%, 50%, 60%, 70%, 80%, 90%, 95%, 99%, 100% or more; (6) decreasing plant infestation by a host (e.g., insect, mollusk, or nematode) by about 10%, 20%, 30%, 40%, 50%, 60%, 70%, 80%, 90%, 95%, 99%, 100% or more; (7) decrease disease transmission (e.g., of a plant, animal, or human pathogen) by a host (e.g., insect, mollusk, or nematode) by about 10%, 20%, 30%, 40%, 50%, 60%, 70%, 80%, 90%, 95%, 99%, 100% or more; or (8) decrease growth, increase nymphal mortality, and/or increase adult sterility of a host (e.g., insect, mollusk, or nematode) by about 10%, 20%, 30%, 40%, 50%, 60%, 70%, 80%, 90%, 95%, 99%, 100% or more. A decrease in host fitness can be determined in comparison to a host organism to which the modulating agent has not been administered.

As used herein "increasing host fitness" or "promoting host fitness" refers to any favorable alteration in host physiology, or any activity carried out by said host, as a consequence of administration of a modulating agent, including, but not limited to, any one or more of the following desired effects: (1) increasing a population of a host by about 10%, 20%, 30%, 40%, 50%, 60%, 70%, 80%, 90%, 95%, 99%, 100% or more; (2) increasing the reproductive rate of a host (e.g., insect, mollusk, or nematode) by about 10%, 20%, 30%, 40%, 50%, 60%, 70%, 80%, 90%, 95%, 99%, 100% or more; (3) increasing the mobility of a host (e.g., insect, mollusk, or nematode) by about 10%, 20%, 30%, 40%, 50%, 60%, 70%, 80%, 90%, 95%, 99%, 100% or more; (4) increasing the body weight of a host (e.g., insect, mollusk, or nematode) by about 10%, 20%, 30%, 40%, 50%, 60%, 70%, 80%, 90%, 95%, 99%, 100% or more; (5) increasing the metabolic rate or activity of a host (e.g., insect, mollusk, or nematode) by about 10%, 20%, 30%, 40%, 50%, 60%, 70%, 80%, 90%, 95%, 99%, 100% or more; (6) increasing pollination (e.g., number of plants pollinated in a given amount of time) by a host (e.g., insect, mollusk, or nematode) by about 10%, 20%, 30%, 40%, 50%, 60%, 70%, 80%, 90%, 95%, 99%, 100% or more; (7) increasing production of host (e.g., insect, mollusk, or nematode) byproducts (e.g., honey or silk) by about 10%, 20%, 30%, 40%, 50%, 60%, 70%, 80%, 90%, 95%, 99%, 100% or more; (8) increasing nutrient content of the host (e.g., insect, mollusk, or nematode) (e.g., protein, fatty acids, or amino acids) by about 10%, 20%, 30%, 40%, 50%, 60%, 70%, 80%, 90%, 95%, 99%, 100% or more; or (9) increasing host resistance to pesticides (e.g., insect, mollusk, or nematode) by about 10%, 20%, 30%, 40%, 50%, 60%, 70%, 80%, 90%, 95%, 99%, 100% or more. An increase in host fitness can be determined in comparison to a host organism to which the modulating agent has not been administered.

As used herein, "interactions between a host and microorganisms resident in the host" or "host-microbiota interactions" refer to (i) any pathways (e.g., metabolic, gene regulation, cell signaling, or immune-inflammatory pathways) in the host that directly or indirectly influences the survival, growth, or metabolism of microorganisms resident in the host (e.g., endosymbiotic microorganisms), (ii) any pathways (e.g., metabolic or cell signaling pathways) in a resident microorganism that directly or indirectly influences the fitness of the host invertebrate (e.g., insect, nematode, or mollusk), and/or (iii) any pathways (e.g., metabolic, cell signaling, or immune-inflammatory pathways) in a resident microorganism that directly or indirectly influences survival, growth or metabolism of the host, and/or (iv) any pathways (e.g., metabolic, gene regulation, cell signaling, or immune-inflammatory pathways) in the host that directly or indirectly influences the fitness of the resident microorganism.

The term "insect" includes any organism belonging to the phylum Arthropoda and to the class Insecta or the class Arachnida, in any stage of development, i.e., immature and adult insects.

The term "mollusk" includes any organism belonging to the phylum Mollusca, including organisms of the class Gastropoda (e.g., snails and slugs), in any stage of development, i.e., immature and adult mollusks.

The term "nematode" includes any organism belonging to the phylum Nematoda (e.g., nematodes) in any stage of development, i.e., immature and adult nematodes.

As used herein, the term "microorganism" or "microbiota" refers to bacteria or fungi. Microorganisms may refer to microorganisms resident in a host organism (e.g., endogenous microorganisms, endosymbiotic microorganisms (e.g., primary or secondary endosymbionts)) or microorganisms exogenous to the host, including those that may act as modulating agents. As used herein, the term "target microorganism" refers to a microorganism that is resident in the host and impacted by a modulating agent, either directly or indirectly.

As used herein, the term "modulating agent" or "agent" refers to an agent that is capable of altering the levels and/or functioning of microorganisms resident in a host organism (e.g., invertebrate, e.g., insect, mollusk, or nematode), and thereby modulate (e.g., increase or decrease) the fitness of the host organism.

As defined herein, the term "nucleic acid" and "polynucleotide" are interchangeable and refer to RNA or DNA that is linear or branched, single or double stranded, or a hybrid thereof, regardless of length (e.g., at least 2, 3, 4, 5, 6, 7, 8, 9, 10, 20, 30, 40, 50, 100, 150, 200, 250, 500, 1000, or more nucleic acids). The term also encompasses RNA/DNA hybrids. Nucleotides are typically linked in a nucleic acid by phosphodiester bonds, although the term "nucleic acid" also encompasses nucleic acid analogs having other types of linkages or backbones (e.g., phosphoramide, phosphorothioate, phosphorodithioate, O-methylphosphoroamidate, morpholino, locked nucleic acid (LNA), glycerol nucleic acid (GNA), threose nucleic acid (TNA), and peptide nucleic acid (PNA) linkages or backbones, among others). The nucleic acids may be single-stranded, double-stranded, or contain portions of both single-stranded and double-stranded sequence. A nucleic acid can contain any combination of deoxyribonucleotides and ribonucleotides, as well as any combination of bases, including, for example, adenine, thymine, cytosine, guanine, uracil, and modified or non-canonical bases (including, e.g., hypoxanthine, xanthine, 7-methylguanine, 5,6-dihydrouracil, 5-methylcytosine, and 5 hydroxymethylcytosine).

As used herein, the term "pest" refers to invertebrates (e.g., insects, nematodes, or mollusks) that cause damage to plants or other organisms, or otherwise are detrimental to humans, for example, human agricultural methods or products.

As used herein, the term "pesticide" or "pesticidal agent" refers to a substance that can be used in the control of agricultural, environmental, and domestic/household pests, such as insects, mollusks, nematodes, fungi, bacteria, and viruses. The term "pesticide" is understood to encompass naturally occurring or synthetic insecticides (larvicides or adulticides), insect growth regulators, nematicides, molluscicides, acaricides (miticides), nematicides, ectoparasiticides, bactericides, fungicides, or herbicides (substance which can be used in agriculture to control or modify plant growth). Further examples of pesticides or pesticidal agents are listed in Table 11. In some instances, the pesticide is an allelochemical. As used herein, "allelochemical" or "allelochemical agent" is a substance produced by an organism that can effect a physiological function (e.g., the germination, growth, survival, or reproduction) of another organism (e.g., an insect, mollusk, or nematode).

As used herein, the term "peptide," "protein," or "polypeptide" encompasses any chain of naturally or non-naturally occurring amino acids (either D- or L-amino acids), regardless of length (e.g., at least 2, 3, 4, 5, 6, 7, 10, 12, 14, 16, 18, 20, 25, 30, 40, 50, 100, or more amino acids), the presence or absence of post-translational modifications (e.g., glycosylation or phosphorylation), or the presence of, e.g., one or more non-amino acyl groups (for example, sugar, lipid, etc.) covalently linked to the peptide, and includes, for example, natural proteins, synthetic, or recombinant polypeptides and peptides, hybrid molecules, peptoids, or peptidomimetics.

As used herein, "percent identity" between two sequences is determined by the BLAST 2.0 algorithm, which is described in Altschul et al., *J. Mol. Biol.* 215:403-410, 1990. Software for performing BLAST analyses is publicly available through the National Center for Biotechnology Information.

As used herein, the term "plant" refers to whole plants, plant organs, plant tissues, seeds, plant cells, seeds, or progeny of the same. Plant cells include, without limitation, cells from seeds, suspension cultures, embryos, meristematic regions, callus tissue, leaves, roots, shoots, gametophytes, sporophytes, pollen, or microspores. Plant parts include differentiated and undifferentiated tissues including, but not limited to the following: roots, stems, shoots, leaves, pollen, seeds, tumor tissue, or various forms of cells and culture (e.g., single cells, protoplasts, embryos, and callus tissue). The plant tissue may be in a plant or in a plant organ, tissue, or cell culture.

As used herein a "transgenic plant," "genetically engineered plant," or "genetically modified plant" refers to a plant whose genome (e.g., chromosomal DNA, chloroplast DNA, or mitochondrial DNA) has been altered by the stable integration of recombinant DNA. A transgenic plant includes a plant regenerated from an originally-transformed plant cell and progeny transgenic plants from later generations or crosses of a transformed plant. For example, a transgenic plant may be genetically engineered to produce a heterologously (e.g., non-endogenous) or non-heterologously (e.g., endogenous) encoded protein or RNA, for example, of any of the modulating agents in the methods or compositions described herein. Any plant species may be transformed to create a transgenic plant. The transgenic plant may be a dicotyledonous plant or a monocotyledonous plant. For example and without limitation, transgenic plants of the compositions and methods described herein may be derived from any of the following diclotyledonous plant families: Leguminosae, including plants such as pea, alfalfa and soybean; Umbelliferae, including plants such as carrot and celery; Solanaceae, including the plants such as tomato, potato, aubergine, tobacco, and pepper; Cruciferae, particularly the genus *Brassica*, which includes plant such as oilseed rape, beet, cabbage, cauliflower and broccoli); and *Arabidopsis thaliana*; Compositae, which includes plants such as lettuce; Malvaceae, which includes cotton; Fabaceae, which includes plants such as peanut, and the like. Transgenic plants of the invention may be derived from monocotyle-donous plants, such as, for example, wheat, barley, sorghum, millet, rye, triticale, maize, rice, oats, switchgrass, *miscanthus*, and sugarcane. Transgenic plants of the invention are also embodied as trees such as apple, pear, quince, plum, cherry, peach, nectarine, apricot, *papaya*, mango, and other woody species including coniferous and deciduous trees such as poplar, pine, *sequoia*, cedar, oak, willow, and the like.

Other features and advantages of the invention will be apparent from the following Detailed Description and the Claims.

BRIEF DESCRIPTION OF THE FIGURES

The figures are meant to be illustrative of one or more features, aspects, or embodiments of the invention and are not intended to be limiting.

FIG. 16A: LSR-1 *A. pisum* aphids were injected with water or dsRNA-ApGLNT1 in water and life stages were monitored at the indicated time point after injection. Shown is the mean percent±of aphids that were dead or alive at each instar stage throughout the experiment. N=40 aphids/group. FIG. 16B: 4 days after offspring were collected, images were taken of each aphid to determine the area of each aphid. Shown is the mean area±SD of offspring taken from aphids injected with either water or dsRNA-ApGLNT1. Statistically significant differences were determined using a Student's t-test. Each data point represents one individual aphid.

DETAILED DESCRIPTION

Figure 1:
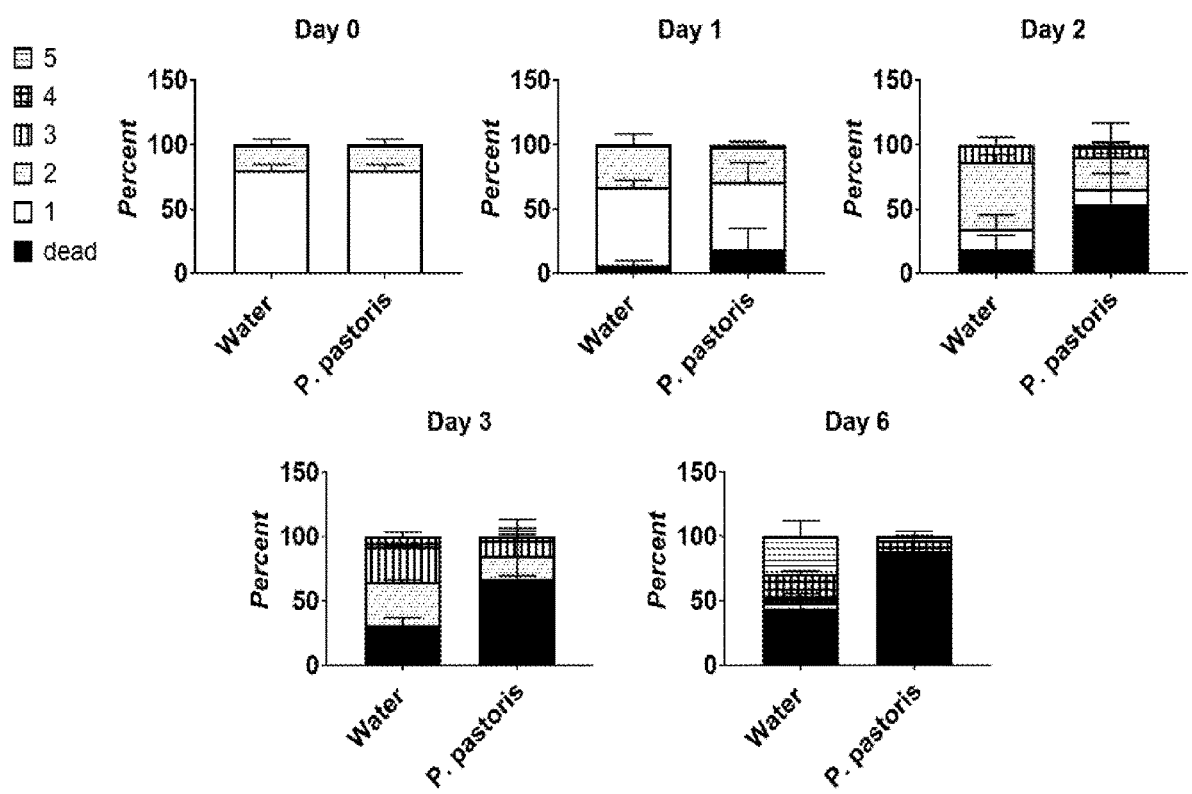
FIG. 1 is a panel of graphs showing that treatment with *P. pastoris* delayed aphid development. First and second instar LSR-1 aphids were placed on leaves perfused with water (negative control) or with a solution of *P. pastoris* in water and developmental stage was monitored at each indicated time point during the experiment. Shown are the mean percentages of aphids in each group±SD.

Provided herein are methods and compositions for modulating the fitness of a host invertebrate (e.g., insect, mollusk, or nematode) by altering interactions between the host and one or more microorganisms resident in the host. The invention features a composition including a modulating agent (e.g., a polypeptide, nucleic acid, small molecule, or combinations thereof) that can indirectly induce changes in the host's microbiota in a manner that modulates (e.g., increases or decreases) host fitness. For example, the modulating agent may target host pathways (e.g., immune system or bacteriocyte pathways) or microbial pathways that alter (e.g., increase or decrease) microbial levels, microbial activity, microbial metabolism, and/or microbial diversity, and in turn modulates (e.g., increase or decrease) the fitness of a variety of invertebrates (e.g., insect, mollusk, or nematode) that are important for agriculture, commerce, and/or public health.

The methods and compositions described herein are based, in part, on the examples which illustrate how different agents, for example, small compounds (e.g., prostaglandin), inhibitory RNA (e.g., dsRNA or PNAs), and microorganisms (fungi or bacteria) can be used to alter the host's immune system response towards microorganisms resident in the host. The methods and compositions described herein can also be used to alter the function of host organs or cells in which microorganisms typically reside. For example, RNA may be used to impair bacteriocyte function in an aphid, thereby disrupting endosymbiotic microorganism populations resident in the bacteriocyte of the aphid. Disruption of endosymbiotic populations of microorganisms (e.g., *Buchnera* spp.) in the aphid, in turn, decreases the fitness of the aphid. Nucleic acids, such as RNAs (e.g., dsRNA) or PNAs, or small molecules (e.g., prostaglandin) are representative of modulating agents useful in the invention, and other modulating agents of this type may be useful in the invention. On this basis, the present disclosure describes a variety of different approaches for the use of agents that modulates (e.g., increases or decreases) the fitness of an invertebrate host (e.g., insect, mollusk, or nematode), wherein the modulating agent alters interactions between the host and one or more microorganisms resident in the host.

I. Hosts
  i. Insect Hosts

In some instances, the host described herein is an organism belonging to the phylum Arthropoda. In some instances, the insect is considered a pest, e.g., an agricultural pest. In some instances, the insect carries a bacterium or virus that is considered a plant pest that causes disease in a plant (e.g., *Agrobacterium* or tomato yellow leaf curl virus (TYLCV)). The host may be at any stage developmentally. For instance, the host may be an embryo, a larva, a pupa, or an adult.

In some instances, the insect may belong to the following orders: Acari, Araneae, Anoplura, Coleoptera, Collembola, Dermaptera, Dictyoptera, Diplura, Diptera (e.g., spotted-wing *Drosophila*), Embioptera, Ephemeroptera, Grylloblatodea, Hemiptera (e.g., an aphid, Greenhous whitefly, or stinkbug), Homoptera, Hymenoptera, Isoptera, Lepidoptera, Mallophaga, Mecoptera, Neuroptera, Odonata, Orthoptera, Phasmida, Plecoptera, Protura, Psocoptera, Siphonaptera, Siphunculata, Thysanura, Strepsiptera, Thysanoptera, Trichoptera, or Zoraptera.

In some instances, the insect is from the class Arachnida, for example, *Acarus* spp., *Aceria sheldoni*, *Aculops* spp., *Aculus* spp., *Amblyomma* spp., *Amphitetranychus viennensis*, *Argas* spp., *Boophilus* spp., *Brevipalpus* spp., *Bryobia graminum*, *Bryobia praetiosa*, *Centruroides* spp., *Chorioptes* spp., *Dermanyssus gaffinae*, *Dermatophagoides pteronyssinus*, *Dermatophagoides farinae*, *Dermacentor* spp., *Eotetranychus* spp., *Epitrimerus gyri*, *Eutetranychus* spp., *Eriophyes* spp., *Glycyphagus domesticus*, *Halotydeus destructor*, *Hemitarsonemus* spp., *Hyalomma* spp., *Ixodes* spp., *Latrodectus* spp., *Loxosceles* spp., *Metatetranychus* spp., *Neutrombicula autumnalis*, *Nuphersa* spp., *Oligonychus* spp., *Ornithodorus* spp., *Ornithonyssus* spp., *Panonychus* spp., *Phyllocoptruta oleivora*, *Polyphagotarsonemus latus*, *Psoroptes* spp., *Rhipicephalus* spp., *Rhizoglyphus* spp., *Sarcoptes* spp., *Scorpio maurus*, *Steneotarsonemus* spp., *Steneotarsonemus spinki*, *Tarsonemus* spp., *Tetranychus* spp., *Trombicula alfreddugesi*, *Vaejovis* spp., *Vasates lycopersici*.

In some instances, the insect is from the class Chilopoda, for example, *Geophilus* spp., *Scutigera* spp.

In some instances, the insect is from the order Collembola, for example, *Onychiurus armatus*.

In some instances, the insect is from the class Diplopoda, for example, *Blaniulus guttulatus*.

In some instances, the insect is from the class Insecta, e.g. from the order Blattodea, for example, *Blattella asahinai*, *Blattella germanica*, *Blatta orientalis*, *Leucophaea maderae*, *Panchlora* spp., *Parcoblatta* spp., *Periplaneta* spp., *Supella longipalpa*.

In some instances, the insect is from the order Coleoptera, for example, *Acalymma vittatum*, *Acanthoscelides obtectus*, *Adoretus* spp., *Agelastica alni*, *Agriotes* spp., *Alphitobius diaperinus*, *Amphimallon solstitialis*, *Anobium punctatum*, *Anoplophora* spp., *Anthonomus* spp., *Anthrenus* spp., *Apion* spp., *Apogonia* spp., *Atomaria* spp., *Attagenus* spp., *Bruchidius obtectus*, *Bruchus* spp., *Cassida* spp., *Cerotoma trifurcata*, *Ceutorrhynchus* spp., *Chaetocnema* spp., *Cleonus mendicus*, *Conoderus* spp., *Cosmopolites* spp., *Costelytra zealandica*, *Ctenicera* spp., *Curculio* spp., *Cryptolestes ferrugineus*, *Cryptorhynchus lapathi*, *Cylindrocopturus* spp., *Dendroctonus* spp. (e.g., *Dendroctonus ponderosae*), *Dermestes* spp., *Diabrotica* spp. (e.g., corn rootworm), *Dichocrocis* spp., *Dicladispa armigera*, *Diloboderus* spp., *Epilachna* spp., *Epitrix* spp., *Faustinus* spp., *Gibbium psylloides*, *Gnathocerus cornutus*, *Hellula undalis*, *Heteronychus arator*, *Heteronyx* spp., *Hylamorpha elegans*, *Hylotrupes bajulus*, *Hypera postica*, *Hypomeces squamosus*, *Hypothenemus* spp. (*Hypothenemus hamper*), *Lachnosterna consanguinea*, *Lasioderma serricorne*, *Latheticus oryzae*, *Lathridius* spp., *Lema* spp., *Leptinotarsa decemlineata*, *Leucoptera* spp., *Lissorhoptrus oryzophilus*, *Lixus* spp., *Luperodes* spp., *Lyctus* spp., *Megascelis* spp., *Melanotus* spp., *Meligethes aeneus*, *Melolontha* spp., *Migdolus* spp., *Monochamus* spp., *Naupactus xanthographus*, *Necrobia* spp., *Niptus hololeucus*, *Oryctes rhinoceros*, *Oryzaephilus surinamensis*, *Oryzaphagus oryzae*, *Otiorrhynchus* spp.,

*Oxycetonia jucunda, Phaedon cochleariae, Phyllophaga* spp., *Phyllophaga helleri, Phyllotreta* spp., *Popillia japonica, Premnotrypes* spp., *Prostephanus truncatus, Psyffiodes* spp., *Ptinus* spp., *Rhizobius ventralis, Rhizopertha dominica, Sitophilus* spp., *Sitophilus oryzae, Sphenophorus* spp., *Stegobium paniceum, Sternechus* spp., *Symphyletes* spp., *Tanymecus* spp., *Tenebrio molitor, Tenebrioides mauretanicus, Tribolium* spp., *Trogoderma* spp., *Tychius* spp., *Xylotrechus* spp., *Zabrus* spp.;

from the order Diptera, for example, *Aedes* spp., *Agromyza* spp., *Anastrepha* spp., *Anopheles* spp., *Asphondylia* spp., *Bactrocera* spp., *Bibio hortulanus, Calliphora erythrocephala, Calliphora vicina, Ceratitis capitata, Chironomus* spp., *Chrysomyia* spp., *Chrysops* spp., *Chrysozona pluvialis, Cochliomyia* spp., *Contarinia* spp., *Cordylobia anthropophaga, Cricotopus sylvestris, Culex* spp., *Culicoides* spp., *Culiseta* spp., *Cuterebra* spp., *Dacus oleae, Dasyneura* spp., *Delia* spp., *Dermatobia hominis, Drosophila* spp., *Echinocnemus* spp., *Fannia* spp., *Gasterophilus* spp., *Glossina* spp., *Haematopota* spp., *Hydrellia* spp., *Hydrellia griseola, Hylemya* spp., *Hippobosca* spp., *Hypoderma* spp., *Liriomyza* spp., *Lucilia* spp., *Lutzomyia* spp., *Mansonia* spp., *Musca* spp. (e.g., *Musca domestica*), *Oestrus* spp., *Oscinella frit, Paratanytarsus* spp., *Paralauterborniella subcincta, Pegomyia* spp., *Phlebotomus* spp., *Phorbia* spp., *Phormia* spp., *Piophila casei, Prodiplosis* spp., *Psila rosae, Rhagoletis* spp., *Sarcophaga* spp., *Simulium* spp., *Stomoxys* spp., *Tabanus* spp., *Tetanops* spp., *Tipula* spp.

In some instances, the insect is from the order Heteroptera, for example, *Anasa tristis, Antestiopsis* spp., *Boisea* spp., *Blissus* spp., *Calocoris* spp., *Campylomma livida, Cavelerius* spp., *Cimex* spp., *Collaria* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptocorisa varicornis, Leptoglossus phyllopus, Lygus* spp., *Macropes excavatus, Miridae, Monalonion atratum, Nezara* spp., *Oebalus* spp., *Pentomidae, Piesma quadrata, Piezodorus* spp., *Psallus* spp., *Pseudacysta persea, Rhodnius* spp., *Sahlbergella singularis, Scaptocoris castanea, Scotinophora* spp., *Stephanitis nashi, Tibraca* spp., *Triatoma* spp.

In some instances, the insect is from the order Hemiptera or suborder Homoptera, for example, *Acizzia acaciaebaileyanae, Acizzia dodonaeae, Acizzia uncatoides, Acrida turrita, Acyrthosipon* spp., *Acrogonia* spp., *Aeneolamia* spp., *Agonoscena* spp., *Aleyrodes proletella, Aleurolobus barodensis, Aleurothrixus floccosus, Allocaridara malayensis, Amrasca* spp., *Anuraphis cardui, Aonidiella* spp., *Aphanostigma pini, Aphis* spp. (e.g., *Apis gossypii*), *Arboridia apicalis, Arytainilla* spp., *Aspidiella* spp., *Aspidiotus* spp., *Atanus* spp., *Aulacorthum solani, Bemisia tabaci, Blastopsylla occidentalis, Boreioglycaspis melaleucae, Brachycaudus helichrysi, Brachycolus* spp., *Brevicoryne brassicae, Cacopsylla* spp., *Calligypona marginata, Carneocephala fulgida, Ceratovacuna lanigera, Cercopidae, Ceroplastes* spp., *Chaetosiphon fragaefolii, Chionaspis tegalensis, Chlorita Chondracris rosea, Chromaphis juglandicola, Chrysomphalus ficus, Cicadulina mbila, Coccomytilus halli, Coccus* spp., *Cryptomyzus ribis, Cryptoneossa* spp., *Ctenarytaina* spp., *Dalbulus* spp., *Dialeurodes citri, Diaphorina citri, Diaspis* spp., *Drosicha* spp., *Dysaphis* spp., *Dysmicoccus* spp., *Empoasca* spp., *Eriosoma* spp., *Erythroneura* spp., *Eucalyptolyma* spp., *Euphyllura* spp., *Euscelis bilobatus, Ferrisia* spp., *Geococcus coffeae, Glycaspis* spp., *Heteropsylla cubana, Heteropsylla spinulosa, Homalodisca coagulata, Homalodisca vitripennis, Hyalopterus arundinis, Icerya* spp., *Idiocerus* spp., *Idioscopus* spp., *Laodelphax striatellus, Lecanium* spp., *Lepidosaphes* spp., *Lipaphis erysimi, Macrosiphum* spp., *Macrosteles facifrons, Mahanarva* spp., *Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nettigoniclla spectra, Nilaparvata lugens, Oncometopia* spp., *Orthezia praelonga, Oxya chinensis, Pachypsylla* spp., *Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Prosopidopsylla flava, Protopulvinaria pyriformis, Pseudaulacaspis pentagona, Pseudococcus* spp., *Psyllopsis* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoideus titanus, Schizaphis graminum, Selenaspidus articulatus, Sogata* spp., *Sogatella furcifera, Sogatodes* spp., *Stictocephala festina, Siphoninus phillyreae, Tenalaphara malayensis, Tetragonocephela* spp., *Tinocallis caryaefoliae, Tomaspis* spp., *Toxoptera* spp., *Trialeurodes vaporariorum, Trioza* spp., *Typhlocyba* spp., *Unaspis* spp., *Viteus vitifolii, Zygina* spp.; from the order Hymenoptera, for example, *Acromyrmex* spp., *Athalia* spp., *Atta* spp., *Diprion* spp., *Hoplocampa* spp., *Lasius* spp., *Monomorium pharaonis, Sirex* spp., *Solenopsis invicta, Tapinoma* spp., *Urocerus* spp., *Vespa* spp., *Xeris* spp. In certain instances, the insect is an aphid (e.g., *Rhopalosiphum maidis* or *Myzus persicae*).

In some instances, the insect is from the order Isopoda, for example, *Armadillidium vulgare, Oniscus asellus, Porcellio scaber.*

In some instances, the insect is from the order Isoptera, for example, *Coptotermes* spp., *Cornitermes cumulans, Cryptotermes* spp., *Incisitermes* spp., *Microtermes obesi, Odontotermes* spp., *Reticulitermes* spp.

In some instances, the insect is from the order Lepidoptera, for example, *Achroia grisella, Acronicta major, Adoxophyes* spp., *Aedia leucomelas, Agrotis* spp., *Alabama* spp., *Amyelois transitella, Anarsia* spp., *Anticarsia* spp., *Argyroploce* spp., *Barathra brassicae, Borbo cinnara, Bucculatrix thurberiella, Bupalus piniarius, Busseola* spp., *Cacoecia* spp., *Caloptilia theivora, Capua reticulana, Carpocapsa pomonella, Carposina niponensis, Cheimatobia brumata, Chilo* spp., *Choristoneura* spp., *Clysia ambiguella, Cnaphalocerus* spp., *Cnaphalocrocis medinalis, Cnephasia* spp., *Conopomorpha* spp., *Conotrachelus* spp., *Copitarsia* spp., *Cydia* spp., *Dalaca noctuides, Diaphania* spp., *Diatraea saccharalis, Earias* spp., *Ecdytolopha aurantium, Elasmopalpus lignosellus, Eldana saccharina, Ephestia* spp., *Epinotia* spp., *Epiphyas postvittana, Etiella* spp., *Eulia* spp., *Eupoecilia ambiguella, Euproctis* spp., *Euxoa* spp., *Feltia* spp., *Galleria mellonella, Gracillaria* spp., *Grapholitha* spp., *Hedylepta* spp., *Helicoverpa* spp., *Heliothis* spp., *Hofmannophila pseudospretella, Homoeosoma* spp., *Homona* spp., *Hyponomeuta padella, Kakivoria flavofasciata, Laphygma* spp., *Laspeyresia molesta, Leucinodes orbonalis, Leucoptera* spp., *Lithocolletis* spp., *Lithophane antennata, Lobesia* spp., *Loxagrotis albicosta, Lymantria* spp., *Lyonetia* spp., *Malacosoma neustria, Maruca testulalis, Mamstra brassicae, Melanitis leda, Mocis* spp., *Monopis obviella, Mythimna separata, Nemapogon cloacellus, Nymphula* spp., *Oiketicus* spp., *Oria* spp., *Orthaga* spp., *Ostrinia* spp., *Oulema oryzae, Panolis flammea, Parnara* spp., *Pectinophora* spp., *Perileucoptera* spp., *Phthorimaea* spp., *Phyllocnistis citrella, Phyllonorycter* spp., *Pieris* spp., *Platynota stultana, Plodia interpunctella, Plusia* spp., *Plutella xylostella, Prays* spp., *Prodenia* spp., *Protoparce* spp., *Pseuda-* letia spp., *Pseudaletia unipuncta*, *Pseudoplusia includens*, *Pyrausta nubilalis*, *Rachiplusia nu*, *Schoenobius* spp., *Scirpophaga* spp., *Scirpophaga innotata*, *Scotia segetum*, *Sesamia* spp., *Sesamia inferens*, *Sparganothis* spp., *Spodoptera* spp., *Spodoptera praefica*, *Stathmopoda* spp., *Stomopteryx subsecivella*, *Synanthedon* spp., *Tecia solanivora*, *Thermesia gemmatalis*, *Tinea cloacella*, *Tinea pellionella*, *Tineola bisselliella*, *Tortrix* spp., *Trichophaga tapetzella*, *Trichoplusia* spp., *Tryporyza incertulas*, *Tuta absoluta*, *Virachola* spp.

In some instances, the insect is from the order Orthoptera or Saltatoria, for example, *Acheta domesticus*, *Dichroplus* spp., *Gryllotalpa* spp., *Hieroglyphus* spp., *Locusta* spp., *Melanoplus* spp., *Schistocerca gregaria*.

In some instances, the insect is from the order Phthiraptera, for example, *Damalinia* spp., *Haematopinus* spp., *Linognathus* spp., *Pediculus* spp., *Ptirus pubis*, *Trichodectes* spp.

In some instances, the insect is from the order Psocoptera for example *Lepinatus* spp., *Liposcelis* spp.

In some instances, the insect is from the order Siphonaptera, for example, *Ceratophyllus* spp., *Ctenocephalides* spp., *Pulex irritans*, *Tunga penetrans*, *Xenopsylla cheopsis*.

In some instances, the insect is from the order Thysanoptera, for example, *Anaphothrips obscurus*, *Baliothrips biformis*, *Drepanothrips reuteri*, *Enneothrips flavens*, *Frankliniella* spp., *Heliothrips* spp., *Hercinothrips femoralis*, *Rhipiphorothrips cruentatus*, *Scirtothrips* spp., *Taeniothrips cardamomi*, *Thrips* spp.

In some instances, the insect is from the order Zygentoma (=Thysanura), for example, *Ctenolepisma* spp., *Lepisma saccharina*, *Lepismodes inquilinus*, *Thermobia domestica*.

In some instances, the insect is from the class Symphyla, for example, *Scutigerella* spp.

In some instances, the insect is a mite, including but not limited to, Tarsonemid mites, such as *Phytonemus pallidus*, *Polyphagotarsonemus latus*, Tarsonemus bilobatus, or the like; Eupodid mites, such as *Penthaleus erythrocephalus*, *Penthaleus major*, or the like; Spider mites, such as *Oligonychus shinkajii*, *Panonychus citri*, *Panonychus mors*, *Panonychus ulmi*, *Tetranychus kanzawai*, *Tetranychus urticae*, or the like; Eriophyid mites, such as *Acaphylla theavagrans*, *Aceria tulipae*, *Aculops lycopersici*, *Aculops pelekassi*, *Aculus schlechtendali*, *Eriophyes chibaensis*, *Phyllocoptruta oleivora*, or the like; Acarid mites, such as *Rhizoglyphus robini*, *Tyrophagus putrescentiae*, *Tyrophagus similis*, or the like; Bee brood mites, such as *Varroa jacobsoni*, *Varroa destructor* or the like; Ixodides, such as *Boophilus microplus*, *Rhipicephalus sanguineus*, *Haemaphysalis longicornis*, *Haemophysalis flava*, *Haemophysalis campanulata*, *Ixodes ovatus*, *Ixodes persulcatus*, *Amblyomma* spp., *Dermacentor* spp., or the like; Cheyletidae, such as *Cheyletiella yasguri*, *Cheyletiella blakei*, or the like; Demodicidae, such as *Demodex canis*, *Demodex cati*, or the like; Psoroptidae, such as *Psoroptes ovis*, or the like; Scarcoptidae, such as *Sarcoptes scabiei*, *Notoedres cati*, *Knemidocoptes* spp., or the like.

The methods and compositions provided herein may be used with any insect host that is considered a vector for a pathogen that is capable of causing disease in animals. For example, the insect host may include, but is not limited to those with piercing-sucking mouthparts, as found in Hemiptera and some Hymenoptera and Diptera such as mosquitoes, bees, wasps, midges, lice, tsetse fly, fleas and ants, as well as members of the Arachnidae such as ticks and mites; order, class or family of Acarina (ticks and mites) e.g. representatives of the families Argasidae, Dermanyssidae, Ixodidae, Psoroptidae or Sarcoptidae and representatives of the species *Amblyomma* spp., *Anocenton* spp., *Argas* spp., *Boophilus* spp., *Cheyletiella* spp., *Chorioptes* spp., *Demodex* spp., *Dermacentor* spp., *Denmanyssus* spp., *Haemophysalis* spp., *Hyalomma* spp., *Ixodes* spp., *Lynxacarus* spp., *Mesostigmata* spp., *Notoednes* spp., *Ornithodoros* spp., *Ornithonyssus* spp., *Otobius* spp., *otodectes* spp., *Pneumonyssus* spp., *Psoroptes* spp., *Rhipicephalus* spp., *Sancoptes* spp., or *Trombicula* spp.; Anoplura (sucking and biting lice) e.g. representatives of the species *Bovicola* spp., *Haematopinus* spp., *Linognathus* spp., *Menopon* spp., *Pediculus* spp., *Pemphigus* spp., *Phylloxera* spp., or *Solenopotes* spp.; Diptera (flies) e.g. representatives of the species *Aedes* spp., *Anopheles* spp., *Calliphora* spp., *Chrysomyia* spp., *Chrysops* spp., *Cochliomyia* spp., *Cw/ex* spp., *Culicoides* spp., *Cuterebra* spp., *Dermatobia* spp., *Gastrophilus* spp., *Glossina* spp., *Haematobia* spp., *Haematopota* spp., *Hippobosca* spp., *Hypoderma* spp., *Lucilia* spp., *Lyperosia* spp., *Melophagus* spp., *Oestrus* spp., *Phaenicia* spp., *Phlebotomus* spp., *Phormia* spp., *Sarcophaga* spp., *Simulium* spp., *Stomoxys* spp., *Tabanus* spp., *Tannia* spp. or *Zzpu/alpha* spp.; Mallophaga (biting lice) e.g. representatives of the species *Damalina* spp., *Felicola* spp., *Heterodoxus* spp. or *Trichodectes* spp.; or Siphonaptera (wingless insects) e.g. representatives of the species *Ceratophyllus* spp., *Xenopsylla* spp; Cimicidae (true bugs) e.g. representatives of the species *Cimex* spp., *Tritominae* spp., *Rhodinius* spp., or *Triatoma* spp. In some instances, the insect is a blood-sucking insect from the order Diptera (e.g., suborder Nematocera, e.g., family Colicidae). In some instances, the insect is from the subfamilies Culicinae, Corethrinae, Ceratopogonidae, or Simuliidae. In some instances, the insect is of a *Culex* spp., *Theobaldia* spp., *Aedes* spp., *Anopheles* spp., *Aedes* spp., *Forciponiyia* spp., *Culicoides* spp., or *Helea* spp.

ii. Mollusk Hosts

In some instances, the host described herein may be an organism belonging to the phylum Mollusca. In some instances, the mollusk is considered a pest, e.g., an agricultural pest. For example, the methods and compositions are suitable for controlling terrestrial Gastropods (e.g., slugs and snails) in agriculture and horticulture. They include all terrestrial slugs and snails which mostly occur as polyphagous pests on agricultural and horticultural crops.

In some instances, the mollusk belongs to the family Achatinidae, Agriolimacidae, Ampullariidae, Arionidae, Bradybaenidae, Helicidae, Hydromiidae, Lymnaeidae, Milacidae, Urocyclidae, or Veronicellidae.

For example, in some instances, the mollusk is *Achatina* spp., *Agriolimax* spp., *Arion* spp. (e.g., *A. ater*, *A. circumscriptus*, *A. distinctus*, *A. fasciatus*, *A. hortensis*, *A. intermedius*, *A. rufus*, *A. subfuscus*, *A. silvaticus*, *A. lusitanicus*), *Biomphalaria* spp., *Bradybaena* spp. (e.g., *B. fruticum*), *Bulinus* spp., *Cantareus* spp. (e.g., *C. asperses*), *Cepaea* spp. (e.g., *C. hortensis*, *C. nemoralis*), *Cernuella* spp., *Cochlicella* spp., *Cochlodina* spp. (e.g., *C. laminata*), *Deroceras* spp. (e.g., *D. agrestis*, *D. empiricorum*, *D. laeve*, *D. panornimatum*, *D. reticulatum*), *Discus* spp. (e.g., *D. rotundatus*), *Euomphalia* spp., *Galba* spp. (e.g., *G. trunculata*), *Helicella* spp. (e.g., *H. itala*, *H. obvia*), *Helicigona* spp. (e.g., *H. arbustorum*), *Helicodiscus* spp., *Helix* spp. (e.g., *H. aperta*, *H. aspersa*, *H. pomatia*), *Limax* spp. (e.g., *L. cinereoniger*, *L. flavus*, *L. marginatus*, *L. maximus*, *L. tenellus*), *Lymnaea* spp. (e.g., *L. stagnalis*), *Milax* spp. (e.g., *M. gagates*, *M. marginatus*, *M. sowerbyi*, *M. budapestensis*), *Oncomelania* spp., *Opeas* spp., *Oxyloma* spp. (e.g., *O. pfeifferi*), *Pomacea* spp. (e.g., *P. canaliculata*), *Succinea* spp., *Tandonia* spp. (e.g., *T. budapestensis, T. sowerbyi*), *Theba* spp., *Vallonia* spp., and *Zonitoides* spp. (e.g., *Z. nitidus*).

iii. Nematode Hosts

The host of any of the compositions or methods described herein may also be any organism belonging to the phylum Nematoda. In some instances, the nematode is considered a pest, e.g., an agricultural pest. For example, the nematode may be parasitic or cause health problems to plant or to fungi (for example species of the orders Aphelenchida, Meloidogyne, Tylenchida and others) or to humans and animals (for example species of the orders Trichinellida, Tylenchida, Rhabditina, and Spirurida).

Plant nematodes encompass plant parasitic nematodes and nematodes living in the soil. Plant parasitic nematodes include, but are not limited to, ectoparasites such as *Xiphinema* spp., *Longidorus* spp., and *Trichodorus* spp.; semiparasites such as *Tylenchulus* spp.; migratory endoparasites such as *Pratylenchus* spp., *Radopholus* spp., and *Scutellonema* spp.; sedentary parasites such as *Heterodera* spp., *Globodera* spp., and *Meloidogyne* spp., and stem and leaf endoparasites such as *Ditylenchus* spp., *Aphelenchoides* spp., and *Hirshmaniella* spp. Especially harmful root parasitic soil nematodes are such as cystforming nematodes of the genera *Heterodera* or *Globodera*, and/or root knot nematodes of the genus *Meloidogyne*. Harmful species of these genera are for example *Meloidogyne incognita, Heterodera glycines* (soybean cyst nematode), *Globodera paffida* and *Globodera rostochiensis* (potato cyst nematode), which species are effectively controlled with the modulating agents described herein. However, the use of the modulating agents described herein is in no way restricted to these genera or species, but also extends in the same manner to other nematodes.

Plant nematodes include but are not limited to e.g. *Aglenchus agricola, Anguina tritici, Aphelenchoides arachidis, Aphelenchoides fragaria* and the stem and leaf endoparasites *Aphelenchoides* spp. in general, *Belonolaimus gracilis, Belonolaimus longicaudatus, Belonolaimus nortoni, Bursaphelenchus cocophilus, Bursaphelenchus eremus, Bursaphelenchus xylophilus, Bursaphelenchus mucronatus*, and *Bursaphelenchus* spp. in general, *Cacopaurus pestis, Criconemella curvata, Criconemella onoensis, Criconemella ornata, Criconemella rusium, Criconemella xenoplax* (=Mesocriconema xenoplax) and *Criconemella* spp. in general, *Criconemoides femiae, Criconemoides onoense, Criconemoides ornatum* and *Criconemoides* spp. in general, *Ditylenchus destructor, Ditylenchus dipsaci, Ditylenchus myceliophagus* and the stem and leaf endoparasites *Ditylenchus* spp. in general, *Dolichodorus heterocephalus, Globodera paffida* (=*Heterodera pallida*), *Globodera rostochiensis* (potato cyst nematode), *Globodera solanacearum, Globodera tabacum, Globodera virginia* and the sedentary, cyst forming parasites *Globodera* spp. in general, *Helicotylenchus digonicus, Helicotylenchus dihystera, Helicotylenchus erythrine, Helicotylenchus multicinctus, Helicotylenchus nannus, Helicotylenchus pseudorobustus* and *Helicotylenchus* spp. in general, *Hemicriconemoides, Hemicycliophora arenaria, Hemicycliophora nudata, Hemicycliophora parvana, Heterodera avenae, Heterodera cruciferae, Heterodera glycines* (soybean cyst nematode), *Heterodera oryzae, Heterodera schachtii, Heterodera zeae* and the sedentary, cyst forming parasites *Heterodera* spp. in general, *Hirschmaniella gracilis, Hirshmaniella oryzae Hirschmaniella spinicaudata* and the stem and leaf *endoparasites Hirschmaniella* spp. in general, *Hoplolaimus aegyptii, Hoplolaimus califomicus, Hoplolaimus columbus, Hoplolaimus galeatus, Hoplolaimus indicus, Hoplolaimus magnistylus, Hoplolaimus pararobustus, Longidorus africanus, Longidorus breviannulatus, Longidorus elongatus, Longidorus laevicapitatus, Longidorus vineacola* and the ectoparasites *Longidorus* spp. in general, *Meloidogyne acronea, Meloidogyne africana, Meloidogyne arenaria, Meloidogyne arenaria thamesi, Meloidogyne artiella, Meloidogyne chitwoodi, Meloidogyne coffeicola, Meloidogyne ethiopica, Meloidogyne exigua, Meloidogyne fallax, Meloidogyne graminicola, Meloidogyne graminis, Meloidogyne hapla, Meloidogyne incognita, Meloidogyne incognita acrita, Meloidogyne javanica, Meloidogyne kikuyensis, Meloidogyne minor, Meloidogyne naasi, Meloidogyne paranaensis, Meloidogyne thamesi* and the sedentary parasites *Meloidogyne* spp. in general, *Meloinema* spp., *Nacobbus aberrans, Neotylenchus vigissi, Paraphelenchus pseudoparietinus, Paratrichodorus affius, Paratrichodorus lobatus, Paratrichodorus minor, Paratrichodorus nanus, Paratrichodorus porosus, Paratrichodorus teres* and *Paratrichodorus* spp. in general, *Paratylenchus hamatus, Paratylenchus minutus, Paratylenchus projectus* and *Paratylenchus* spp. in general, *Pratylenchus agilis, Pratylenchus alleni, Pratylenchus andinus, Pratylenchus brachyurus, Pratylenchus cerealis, Pratylenchus coffeae, Pratylenchus crenatus, Pratylenchus delattrei, Pratylenchus giibbicaudatus, Pratylenchus goodeyi, Pratylenchus hamatus, Pratylenchus hexincisus, Pratylenchus loosi, Pratylenchus neglectus, Pratylenchus penetrans, Pratylenchus pratensis, Pratylenchus scribneri, Pratylenchus teres, Pratylenchus thornei, Pratylenchus vulnus, Pratylenchus zeae* and the migratory endoparasites *Pratylenchus* spp. in general, *Pseudohalenchus minutus, Psilenchus magnidens, Psilenchus tumidus, Punctodera chalcoensis, Quinisulcius acutus, Radopholus citrophilus, Radopholus similis,* the migratory endoparasites *Radopholus* spp. in general, *Rotylenchulus borealis, Rotylenchulus parvus, Rotylenchulus reniformis* and *Rotylenchulus* spp. in general, *Rotylenchus laurentinus, Rotylenchus macrodoratus, Rotylenchus robustus, Rotylenchus uniformis* and *Rotylenchus* spp. in general, *Scutellonema brachyurum, Scutellonema bradys, Scutellonema clathricaudatum* and the migratory endoparasites *Scutellonema* spp. in general, *Subanguina radiciola, Tetylenchus nicotianae, Trichodorus cylindricus, Trichodorus minor, Trichodorus primitivus, Trichodorus proximus, Trichodorus similis, Trichodorus sparsus* and the ectoparasites *Trichodorus* spp. in general, *Tylenchorhynchus agri, Tylenchorhynchus brassicae, Tylenchorhynchus clarus, Tylenchorhynchus claytoni, Tylenchorhynchus digitatus, Tylenchorhynchus ebriensis, Tylenchorhynchus maximus, Tylenchorhynchus nudus, Tylenchorhynchus vulgaris* and *Tylenchorhynchus* spp. in general, *Tylenchulus semipenetrans* and the semiparasites *Tylenchulus* spp. in general, *Xiphinema americanum, Xiphinema brevicolle, Xiphinema dimorphicaudatum, Xiphinema index* and the ectoparasites *Xiphinema* spp. in general.

Other examples of nematode hosts include species belonging to the family Criconematidae, Belonolaimidae, Hoploaimidae, Heteroderidae, Longidoridae, Pratylenchidae, Trichodoridae, or Anguinidae.

iv. Beneficial Hosts

In some instances, the host described herein is a beneficial insect, mollusk, or nematode (e.g., a pollinator, a natural competitor of a pest, or a producer of useful substances for humans). The term "beneficial insect," "beneficial mollusk," or "beneficial nematode," as used herein, refers to an insect, mollusk, or nematode that confers a benefit (e.g., economical and/or ecological) to humans, animals, an ecosystem, and/or the environment. For example, the host may be an invertebrate (e.g., insect, mollusk, or nematode) that is involved in the production of a commercial product, including, but not limited to, invertebrates cultivated to produce food (e.g., honey from honey bees, e.g., *Apis mellifera*), materials (such as silk from *Bombyx mori*), and/or substances (e.g., lac from *Laccifer lacca* or pigments from *Dactylopius coccus* and *Cynipidae*). Additionally, the host may include invertebrates (e.g., insects, mollusks, or nematodes) that are used in agricultural applications, including invertebrates (e.g., insects, mollusks, or nematodes) that aid in the pollination of crops, spreading seeds, or pest control. Further, in some instances, the host may be an invertebrate (e.g., insect, mollusk, or nematode) that is useful for waste disposal and/or organic recycling (e.g., earthworms, termites, or Diptera larvae).

In some instances, the host produces a useable product (e.g., honey, silk, beeswax, or shellac). In some instances, the host is a bee. Exemplary bee genera include, but are not limited to *Apis, Bombus, Trigona*, and *Osmia*. In some instances, the bee is a honeybee (e.g., an insect belonging to the genus *Apis*). In some instances, the honeybee is the species *Apis mellifera* (the European or Western honey bee), *Apis cerana* (the Asiatic, Eastern, or Himalayan honey bee), *Apis dorsata* (the "giant" honey bee), *Apis florea* (the "red dwarf" honey bee), *Apis andreniformis* (the "black dwarf" honey bee), or *Apis nigrocincta*. In some instances, the host is a silkworm. The silkworm may be a species in the family Bombycidae or Saturniidae. In some instances, the silkworm is *Bombyx mori*. In some instances, the host is a lac bug. The lac bug may be a species in the family Kerriidae. In some instances, the lac bug is *Kerria lacca*.

In some instances, the host aids in pollination of a plant (e.g., bees, beetles, wasps, flies, butterflies, or moths). In some examples, the host aiding in pollination of a plant is beetle. In some instances, the beetle is a species in the family Buprestidae, Cantharidae, Cerambycidae, Chrysomelidae, Cleridae, Coccinellidae, Elateridae, Melandryidae, Meloidae, Melyridae, Mordellidae, Nitidulidae, Oedemeridae, Scarabaeidae, or Staphyllinidae. In some instances, the host aiding in pollination of a plant is a butterfly or moth (e.g., Lepidoptera). In some instances, the butterfly or moth is a species in the family Geometridae, Hesperiidae, Lycaenidae, Noctuidae, Nymphalidae, Papilionidae, Pieridae, or Sphingidae. In some instances, the host aiding in pollination of a plant is a fly (e.g., Diptera). In some instances, the fly is in the family Anthomyiidae, Bibionidae, Bombyliidae, Calliphoridae, Cecidomiidae, Certopogonidae, Chrionomidae, Conopidae, Culicidae, Dolichopodidae, Empididae, Ephydridae, Lonchopteridae, Muscidae, Mycetophilidae, Phoridae, Simuliidae, Stratiomyidae, or Syrphidae. In some instances, the host aiding in pollination is an ant (e.g., Formicidae), sawfly (e.g., Tenthredinidae), or wasp (e.g., Sphecidae or Vespidae). In some instances, the host aiding in pollination of a plant is a bee. In some instances, the bee is in the family Andrenidae, Apidae, Colletidae, Halictidae, or Megachilidae.

In some instances, the host aids in pest control. In some instances, the host aiding in pest control is a predatory nematode. In particular examples, the nematode is a species of Heterorhabditis or Steinernema. In some instances, the host aiding in pest control is an insect. For example, the host aiding in pest control may be a species belonging to the family Braconidae (e.g., parasitoid wasps), Carabidae (e.g., ground beetles), Chrysopidae (e.g., green lacewings), Coccinellidae (e.g., ladybugs), Hemerobiidae (e.g., brown lacewings), Ichneumonidae (e.g., ichneumon wasps), Lampyridae (e.g., fireflies), Mantidae (e.g., praying mantises), Myrmeleontidae (e.g., antlions), Odonata (e.g., dragonflies and damselflies), or Syrphidae (e.g., hoverfly). In other instances, the host aiding in pest control is an insect that competes with an insect that is considered a pest (e.g., an agricultural pest). For example, the Mediterranean fruit fly, *Ceratitis capitata* is a common pest of fruits and vegetables worldwide. One way to control *C. captitata* is to release the sterilized male insect into the environment to compete with wild males to mate the females. In these instances, the host may be a sterilized male belonging to a species that is typically considered a pest.

In some instances, the host aids in degradation of waste or organic material. In some examples, the host aiding in degradation of waste or organic material belongs to Coleoptera or Diptera. In some instances, the host belonging to Diptera is in the family Calliphoridae, Curtonotidae, Drosophilidae, Fanniidae, Heleomyzidae, Milichiidae, Muscidae, Phoridae, Psychodidae, Scatopsidae, Sepsidae, Sphaeroceridae, Stratiomyidae, Syrphidae, Tephritidae, or Ulidiidae. In some instances, the host belonging to Coleoptera is in the family Carabidae, Hydrophilidae, Phalacaridae, Ptiliidae, or Staphylinidae.

In some instances, the host may be an insect or an arachnid that may be cultivated for a consumable product (e.g., food or feed). For example, the host may be a moth, butterfly, fly, cricket, spider, or beetle. In some instances, the host is in the order Anoplura, Araneae, Blattodea, Coleoptera, Dermaptera, Dictyoptera, Diplura, Diptera, Embioptera, Ephemeroptera, Grylloblatodea, Hemiptera, Homoptera, Hymenoptera, Isoptera, Lepidoptera, Mantodea, Mecoptera, Neuroptera, Odonata, Orthoptera, Phasmida, Plecoptera, Protura, Psocoptera, Siphonaptera, Siphunculata, Thysanura, Strepsiptera, Thysanoptera, Trichoptera, or Zoraptera.

In some examples, the host is a black soldier fly (*Hermetia illucens*), a common house fly, a lesser mealworm, a weaver ant, a silkworm (*Bombyx mon*), a grasshopper, a Chinese grasshopper (*Acrida cinerea*), a yellow mealworm (*Clarias gariepinns*), a moth (*Anaphe infracta* or *Bombyx mori*), *Spodoptera littoralis*, a house cricket, a termite, a palm weevil (*Rhynchophorus ferruginens*), a giant water bug (*Lethocerus indicus*), a water beetle, a termite (*Macrotermes subhyalinus*), a drugstore beetle (*Stegobium paniceum*), *Imbrasia belina*, *Rhynchophorus phoenicis*, *Oryctes rhinoceros*, *Macrotermes bellicosus*, *Ruspolia differens*, *Oryctes Monoceros*, or *Oecophylla smaragdina*.

v. Decreasing Host Fitness

The methods and compositions provided herein may be used to decrease the fitness of any of the host invertebrates (e.g., insects, mollusks, or nematodes) described herein. The decrease in fitness arises from alterations in host pathways that mediate interactions between the host and microorganisms resident in the host, wherein the alterations are a consequence of administration of a modulating agent and have detrimental effects on the host.

In some instances, the decrease in host fitness may manifest as a deterioration or decline in the physiology of the host (e.g., reduced health or survival) as a consequence of administration of a modulating agent. In some instances, the fitness of an organism may be measured by one or more parameters, including, but not limited to, reproductive rate, fertility, lifespan, viability, mobility, fecundity, host development, body weight, metabolic rate or activity, or survival in comparison to a host organism to which the modulating agent has not been administered. For example, the methods or compositions provided herein may be effective to decrease the overall health of the host or to decrease the overall survival of the host. In some instances, the decreased survival of the host is about 2%, 5%, 10%, 20%, 30%, 40%, 50%, 60%, 70%, 80%, 90%, 100%, or greater than 100% greater relative to a reference level (e.g., a level found in a host that does not receive a modulating agent). In some instances, the methods and compositions are effective to decrease host reproduction (e.g., reproductive rate, fertility) in comparison to a host organism to which the modulating agent has not been administered. In some instances, the methods and compositions are effective to decrease other physiological parameters, such as mobility, body weight, life span, fecundity, or metabolic rate, by about 2%, 5%, 10%, 20%, 30%, 40%, 50%, 60%, 70%, 80%, 90%, 100%, or greater than 100% relative to a reference level (e.g., a level found in a host that does not receive a modulating agent).

In some instances, the decrease in host fitness may manifest as a decrease in the production of one or more nutrients in the host (e.g., vitamins, carbohydrates, amino acids, or polypeptides) in comparison to a host organism to which the modulating agent has not been administered. In some instances, the methods or compositions provided herein may be effective to decrease the production of nutrients in the host (e.g., vitamins, carbohydrates, amino acids, or polypeptides) by about 2%, 5%, 10%, 20%, 30%, 40%, 50%, 60%, 70%, 80%, 90%, 100%, or greater than 100% relative to a reference level (e.g., a level found in a host that does not receive a modulating agent). In some instances, the methods or compositions provided herein may decrease nutrients in the host by decreasing the production of nutrients by one or more microorganisms (e.g., endosymbiont) in the host in comparison to a host organism to which the modulating agent has not been administered.

In some instances, the decrease in host fitness may manifest as an increase in the host's sensitivity to a pesticidal agent (e.g., a pesticide listed in Table 11) and/or a decrease in the host's resistance to a pesticidal agent (e.g., a pesticide listed in Table 11) in comparison to a host organism to which the modulating agent has not been administered. In some instances, the methods or compositions provided herein may be effective to increase the host's sensitivity to a pesticidal agent (e.g., a pesticide listed in Table 11) by about 2%, 5%, 10%, 20%, 30%, 40%, 50%, 60%, 70%, 80%, 90%, 100%, or greater than 100% relative to a reference level (e.g., a level found in a host that does not receive a modulating agent). The pesticidal agent may be any pesticidal agent known in the art, including insecticidal agents. In some instances, the methods or compositions provided herein may increase the host's sensitivity to a pesticidal agent (e.g., a pesticide listed in Table 11) by decreasing the host's ability to metabolize or degrade the pesticidal agent into usable substrates in comparison to a host organism to which the modulating agent has not been administered.

In some instances, the decrease in host fitness may manifest as an increase in the host's sensitivity to an allelochemical agent and/or a decrease in the host's resistance to an allelochemical agent in comparison to a host organism to which the modulating agent has not been administered. In some instances, the methods or compositions provided herein may be effective to decrease the host's resistance to an allelochemical agent by about 2%, 5%, 10%, 20%, 30%, 40%, 50%, 60%, 70%, 80%, 90%, 100%, or greater than 100% relative to a reference level (e.g., a level found in a host that does not receive a modulating agent). In some instances, the allelochemical agent is caffeine, soyacystatin, fenitrothion, monoterpenes, diterpene acids, or phenolic compounds (e.g., tannins, flavonoids). In some instances, the methods or compositions provided herein may increase the host's sensitivity to an allelochemical agent by decreasing the host's ability to metabolize or degrade the allelochemical agent into usable substrates in comparison to a host organism to which the modulating agent has not been administered.

In some instances, the methods or compositions provided herein may be effective to decease the host's resistance to parasites or pathogens (e.g., fungal, bacterial, or viral pathogens or parasites) in comparison to a host organism to which the modulating agent has not been administered. In some instances, the methods or compositions provided herein may be effective to decrease the host's resistance to a pathogen or parasite (e.g., fungal, bacterial, or viral pathogens; or parasitic mites) by about 2%, 5%, 10%, 20%, 30%, 40%, 50%, 60%, 70%, 80%, 90%, 100%, or greater than 100% relative to a reference level (e.g., a level found in a host that does not receive a modulating agent).

In some instances, the methods or compositions provided herein may be effective to decrease the host's ability to carry or transmit a plant pathogen (e.g., plant virus (e.g., TYLCV) or a plant bacterium (e.g., *Agrobacterium* spp)) in comparison to a host organism to which the modulating agent has not been administered. For example, the methods or compositions provided herein may be effective to decrease the host's ability to carry or transmit a plant pathogen (e.g., a plant virus (e.g., TYLCV) or plant bacterium (e.g., *Agrobacterium* spp)) by about 2%, 5%, 10%, 20%, 30%, 40%, 50%, 60%, 70%, 80%, 90%, 100%, or greater than 100% relative to a reference level (e.g., a level found in a host that does not receive a modulating agent).

In some instances, the decrease in host fitness may manifest as other fitness disadvantages, such as a decreased tolerance to certain environmental factors (e.g., a high or low temperature tolerance), a decreased ability to survive in certain habitats, or a decreased ability to sustain a certain diet in comparison to a host organism to which the modulating agent has not been administered. In some instances, the methods or compositions provided herein may be effective to decrease host fitness in any plurality of ways described herein. Further, the modulating agent may decrease host fitness in any number of host classes, orders, families, genera, or species (e.g., 1 host species, 2, 3, 4, 5, 6, 7, 8, 9, 10, 15, 20, 30, 40, 50, 60, 70, 80, 90, 100, 150, 200, 200, 250, 500, or more host species). In some instances, the modulating agent acts on a single host class, order, family, genus, or species.

Host fitness may be evaluated using any standard methods in the art. In some instances, host fitness may be evaluated by assessing an individual host. Alternatively, host fitness may be evaluated by assessing a host population. For example, a decrease in host fitness may manifest as a decrease in successful competition against other insects, thereby leading to a decrease in the size of the host population.

vi. Increasing Host Fitness

The methods and compositions provided herein may be used to increase the fitness of any of the hosts described herein. The increase in fitness arises from alterations in host pathways that mediate interactions between the host and microorganisms resident in the host, wherein the alterations are a consequence of administration of a modulating agent and have beneficial effects on the host.

In some instances, the increase in host fitness may manifest as an improvement in the physiology of the host (e.g., improved health or survival) as a consequence of administration of a modulating agent. In some instances, the fitness of an organism may be measured by one or more parameters, including, but not limited to, reproductive rate, lifespan, mobility, fecundity, body weight, metabolic rate or activity, or survival in comparison to a host organism to which the modulating agent has not been administered. For example, the methods or compositions provided herein may be effective to improve the overall health of the host or to improve the overall survival of the host in comparison to a host organism to which the modulating agent has not been administered. In some instances, the improved survival of the host is about 2%, 5%, 10%, 20%, 30%, 40%, 50%, 60%, 70%, 80%, 90%, 100%, or greater than 100% greater relative to a reference level (e.g., a level found in a host that does not receive a modulating agent). In some instances, the methods and compositions are effective to increase host reproduction (e.g., reproductive rate) in comparison to a host organism to which the modulating agent has not been administered. In some instances, the methods and compositions are effective to increase other physiological parameters, such as mobility, body weight, life span, fecundity, or metabolic rate, by about 2%, 5%, 10%, 20%, 30%, 40%, 50%, 60%, 70%, 80%, 90%, 100%, or greater than 100% relative to a reference level (e.g., a level found in a host that does not receive a modulating agent).

In some instances, the increase in host fitness may manifest as an increased production of a product generated by said host in comparison to a host organism to which the modulating agent has not been administered. In some instances, the methods or compositions provided herein may be effective to increase the production of a product generated by the host, as described herein (e.g., honey, beeswax, beebread, propolis, silk, or lac), by about 2%, 5%, 10%, 20%, 30%, 40%, 50%, 60%, 70%, 80%, 90%, 100%, or greater than 100% relative to a reference level (e.g., a level found in a host that does not receive a modulating agent).

In some instances, the increase in host fitness may manifest as an increase in the frequency or efficacy of a desired activity carried out by the host (e.g., pollination, predation on pests, seed spreading, or breakdown of waste or organic material) in comparison to a host organism to which the modulating agent has not been administered. In some instances, the methods or compositions provided herein may be effective to increase the frequency or efficacy of a desired activity carried out by the host (e.g., pollination, predation on pests, seed spreading, or breakdown of waste or organic material) by about 2%, 5%, 10%, 20%, 30%, 40%, 50%, 60%, 70%, 80%, 90%, 100%, or greater than 100% relative to a reference level (e.g., a level found in a host that does not receive a modulating agent).

In some instances, the increase in host fitness may manifest as an increase in the production of one or more nutrients in the host (e.g., vitamins, carbohydrates, amino acids, or polypeptides) in comparison to a host organism to which the modulating agent has not been administered. In some instances, the methods or compositions provided herein may be effective to increase the production of nutrients in the host (e.g., vitamins, carbohydrates, amino acids, or polypeptides) by about 2%, 5%, 10%, 20%, 30%, 40%, 50%, 60%, 70%, 80%, 90%, 100%, or greater than 100% relative to a reference level (e.g., a level found in a host that does not receive a modulating agent). In some instances, the methods or compositions provided herein may increase nutrients in the host by increasing the production of nutrients by one or more microorganisms (e.g., endosymbiont) in the host in comparison to a host organism to which the modulating agent has not been administered.

In some instances, the increase in host fitness may manifest as a decrease in the host's sensitivity to a pesticidal agent (e.g., a pesticide listed in Table 11) and/or an increase in the host's resistance to a pesticidal agent (e.g., a pesticide listed in Table 11) in comparison to a host organism to which the modulating agent has not been administered. In some instances, the methods or compositions provided herein may be effective to decrease the host's sensitivity to a pesticidal agent (e.g., a pesticide listed in Table 11) by about 2%, 5%, 10%, 20%, 30%, 40%, 50%, 60%, 70%, 80%, 90%, 100%, or greater than 100% relative to a reference level (e.g., a level found in a host that does not receive a modulating agent). The pesticidal agent may be any pesticidal agent known in the art, including insecticidal agents. In some instances, the pesticidal agent is a neonicotinoid. In some instances, the methods or compositions provided herein may decrease the host's sensitivity to a pesticidal agent (e.g., a pesticide listed in Table 11) by increasing the host's ability to metabolize or degrade the pesticidal agent into usable substrates in comparison to a host organism to which the modulating agent has not been administered.

In some instances, the increase in host fitness may manifest as a decrease in the host's sensitivity to an allelochemical agent and/or an increase in the host's resistance to an allelochemical agent in comparison to a host organism to which the modulating agent has not been administered. In some instances, the methods or compositions provided herein may be effective to increase the host's resistance to an allelochemical agent by about 2%, 5%, 10%, 20%, 30%, 40%, 50%, 60%, 70%, 80%, 90%, 100%, or greater than 100% relative to a reference level (e.g., a level found in a host that does not receive a modulating agent). In some instances, the allelochemical agent is caffeine, soyacystatin, fenitrothion, monoterpenes, diterpene acids, or phenolic compounds (e.g., tannins, flavonoids). In some instances, the methods or compositions provided herein may decrease the host's sensitivity to an allelochemical agent by increasing the host's ability to metabolize or degrade the allelochemical agent into usable substrates in comparison to a host organism to which the modulating agent has not been administered.

In some instances, the methods or compositions provided herein may be effective to increase the host's resistance to parasites or pathogens (e.g., fungal, bacterial, or viral pathogens; or parasitic mites (e.g., *Varroa destructor* mite in honeybees)) in comparison to a host organism to which the modulating agent has not been administered. In some instances, the methods or compositions provided herein may be effective to increase the host's resistance to a pathogen or parasite (e.g., fungal, bacterial, or viral pathogens; or parasitic mites (e.g., *Varroa destructor* mite in honeybees)) by about 2%, 5%, 10%, 20%, 30%, 40%, 50%, 60%, 70%, 80%, 90%, 100%, or greater than 100% relative to a reference level (e.g., a level found in a host that does not receive a modulating agent).

In some instances, the increase in host fitness may manifest as other fitness advantages, such as improved tolerance to certain environmental factors (e.g., a high or low temperature tolerance), improved ability to survive in certain habitats, or an improved ability to sustain a certain diet (e.g., an improved ability to metabolize soy vs corn) in comparison to a host organism to which the modulating agent has not been administered. In some instances, the methods or compositions provided herein may be effective to increase host fitness in any plurality of ways described herein. Further, the modulating agent may increase host fitness in any number of host classes, orders, families, genera, or species (e.g., 1 host species, 2, 3, 4, 5, 6, 7, 8, 9, 10, 15, 20, 30, 40, 50, 60, 70, 80, 90, 100, 150, 200, 200, 250, 500, or more host species). In some instances, the modulating agent acts on a single host class, order, family, genus, or species.

Host fitness may be evaluated using any standard methods in the art. In some instances, host fitness may be evaluated by assessing an individual host. Alternatively, host fitness may be evaluated by assessing a host population. For example, an increase in host fitness may manifest as an increase in successful competition against other insects, thereby leading to an increase in the size of the host population.

vii. Hosts in Agriculture

The modulating agents described herein may be useful to promote the growth of plants. For example, by reducing the fitness of harmful invertebrates (e.g., insects, mollusks, or nematodes), the modulating agents provided herein may be effective to promote the growth of plants that are typically harmed by a host. Alternatively, by increasing the fitness of beneficial invertebrates (e.g., insects, mollusks, or nematodes), the modulating agents provided herein may be effective to promote the growth of plants that benefit from said hosts. The modulating agent may be delivered to the plant using any of the formulations and delivery methods described herein, in an amount and for a duration effective to modulate (e.g., increase or decrease) host fitness and thereby benefit the plant, e.g., increase crop growth, increase crop yield, decrease pest infestation, and/or decrease damage to plants. This may or may not involve direct application of the modulating agent to the plant. For example, in instances where the primary host habitat is different than the region of plant growth, the modulating agent may be applied to either the primary host habitat, the plants of interest, or a combination of both.

In some instances, the plant may be an agricultural food crop, such as a cereal, grain, legume, fruit, or vegetable crop, or a non-food crop, e.g., grasses, flowering plants, cotton, hay, hemp. The compositions described herein may be delivered to the crop any time prior to or after harvesting the cereal, grain, legume, fruit, vegetable, or other crop. Crop yield is a measurement often used for crop plants and is normally measured in metric tons per hectare (or kilograms per hectare). Crop yield can also refer to the actual seed generation from the plant. In some instances, the modulating agent may be effective to increase crop yield (e.g., increase metric tons of cereal, grain, legume, fruit, or vegetable per hectare and/or increase seed generation) by about 2%, 5%, 10%, 20%, 30%, 40%, 50%, 60%, 70%, 80%, 90%, 100%, or more in comparison to a reference level (e.g., a crop to which the modulating agent has not been administered).

In some instances, the plant (e.g., crop) may be at risk of developing a pest infestation (e.g., by an insect, mollusk, or nematode) or may have already developed a pest infestation. The methods and compositions described herein may be used to reduce or prevent pest infestation in such crops by reducing the fitness of invertebrates (e.g., insect, mollusk, or nematode) that infest the plants. In some instances, the modulating agent may be effective to reduce crop infestation (e.g., reduce the number of plants infested, reduce the pest population size, reduce damage to plants) by about 2%, 5%, 10%, 20%, 30%, 40%, 50%, 60%, 70%, 80%, 90%, 100%, or more in comparison to a reference level (e.g., a crop to which the modulating agent has not been administered). In other instances, the modulating agent may be effective to prevent or reduce the likelihood of crop infestation by about 2%, 5%, 10%, 20%, 30%, 40%, 50%, 60%, 70%, 80%, 90%, 100%, or more in comparison to a reference level (e.g., a crop to which the modulating agent has not been administered).

Any suitable plant tissues may benefit from the compositions and methods described herein, including, but not limited to, somatic embryos, pollen, leaves, stems, calli, stolons, microtubers, or shoots. The methods and compositions described herein may include treatment of angiosperm or gymnosperm plants such as acacia, alfalfa, apple, apricot, artichoke, ash tree, asparagus, avocado, banana, barley, beans, beet, birch, beech, blackberry, blueberry, broccoli, brussels sprouts, cabbage, canola, cantaloupe, carrot, cassaya, cauliflower, cedar, a cereal, celery, chestnut, cherry, Chinese cabbage, citrus, clementine, clover, coffee, corn, cotton, conifers, cowpea, cucumber, cypress, eggplant, elm, endive, *eucalyptus*, fava beans, fennel, forage crops, figs, fir, fruit and nut trees, geranium, grape, grapefruit, groundnuts, ground cherry, gum hemlock, hemp, hickory, kale, kiwifruit, kohlrabi, larch, lettuce, leek, lemon, lime, locust, pine, maidenhair, maize, mango, maple, melon, millet, mushroom, mustard, nuts, oak, oats, okra, onion, orange, an ornamental plant or flower or tree, *papaya*, palm, parsley, parsnip, pea, peach, peanut, pear, peat, pepper, persimmon, pigeon pea, pine, pineapple, plantain, plum, pomegranate, potato, pumpkin, radicchio, radish, rapeseed, raspberry, rice, rye, sorghum, sallow, soybean, spinach, spruce, squash, strawberry, sugarbeet, sugarcane, sunflower, sweet potato, sweet corn, tangerine, tea, tobacco, tomato, trees, triticale, turf grasses, turnips, a vine, walnut, watercress, watermelon, wheat, yams, yew, or zucchini.

viii. Host in Feed/Food Production

Upon reaching a desired life stage, the host may be harvested and, if desired, processed for use in the manufacture of a consumable product. In some instances, the harvested invertebrate host (e.g., insect, mollusk, or nematode) may be distributed in a whole form (e.g., as the whole, unprocessed host) as a consumable product. In some instances, the whole harvested host is processed (e.g., ground up) and distributed as a consumable product. Alternatively, one or more parts of the host (e.g., one or more body parts or one or more substances) may be extracted from the host for use in the manufacture of a consumable product.

The consumable product may be any product safe for human or animal consumption (e.g., ingestion). In some instances, the host may be used in the manufacture of a feed for an animal. In some instances, the animal is livestock or a farm animal (e.g., chicken, cow, horse, or pig). In some instances, the animal is a bird, reptile, amphibian, mammal, or fish. In some instances, the host may be used in the manufacture of a product that replaces the normal feed of an animal. Alternatively, the host may be used in the manufacture of a product that supplements the normal feed of an animal. The host may also be used in the manufacture of a food, food additive, or food ingredient for humans. In some instances, the host is used in the manufacture of a nutritional supplement (e.g., protein supplement) for humans.

The host may be a wild or domesticated host. Additionally, the host may be at any developmental stage at the time of delivering or applying the compositions described herein. Further, the host may be at any developmental stage at the time of harvesting the host for use in the manufacture of a consumable product. In some instances, the host is a larva, pupa, or adult insect at the time of harvesting, using, processing, or manufacturing. The delivery of the modulating agent and the harvesting steps may occur at the same time or different times.

In some instances, a host species is selected based upon their natural nutritional profile. In some instances, the modulating agent is used to improve the nutritional profile of the insect, wherein the modulating agent leads to an increased production of a nutrient in comparison to a host organism to which the modulating agent has not been administered. Examples of nutrients include vitamins, carbohydrates, amino acids, polypeptides, or fatty acids. In some instances, the increased production may arise from increased production of a nutrient by a microorganism resident in the host. Alternatively, the increased production may arise from increased production of a nutrient by the host insect itself, wherein the host has increased fitness following delivery or administration of a modulating agent.

In some instances, in final processing, a first insect species is combined with a second insect species whose nutritional profile provides a complementary benefit to the overall nutritional value of the food or feed product. For example, a species containing a high protein profile could be combined with a species containing a high omega 3/6 fatty acid profile. In this manner, host protein meal may be custom blended to suit the needs of humans or different species of animals.

ix. Host Insects in Disease Transmission

By decreasing the fitness of host insects that carry human and/or animal pathogens, the modulating agents provided herein may be effective to reduce the spread of vector-borne diseases. The modulating agent may be delivered to the hosts using any of the formulations and delivery methods described herein, in an amount and for a duration effective to reduce transmission of the disease, e.g., reduce vertical or horizontal transmission between vectors and/or reduce transmission to humans and/or animals. For example, the modulating agent described herein may reduce vertical or horizontal transmission of a vector-borne pathogen by about 2%, 5%, 10%, 20%, 30%, 40%, 50%, 60%, 70%, 80%, 90%, 100%, or more in comparison to a host organism to which the modulating agent has not been administered. As an another example, the modulating agent described herein may reduce vectorial competence of an host vector by about 2%, 5%, 10%, 20%, 30%, 40%, 50%, 60%, 70%, 80%, 90%, 100%, or more in comparison to a host organism to which the modulating agent has not been administered.

Non-limiting examples of diseases that may be controlled by the compositions and methods provided herein include diseases caused by Togaviridae viruses (e.g., Chikungunya, Ross River fever, Mayaro, Onyon-nyong fever, Sindbis fever, Eastern equine enchephalomyeltis, Wesetern equine encephalomyelitis, Venezualan equine encephalomyelitis, or Barmah forest); diseases caused by Flavivirdae viruses (e.g., Dengue fever, Yellow fever, Kyasanur Forest disease, Omsk haemorrhagic fever, Japaenese encephalitis, Murray Valley encephalitis, Rocio, St. Louis encephalitis, West Nile encephalitis, or Tick-borne encephalitis); diseases caused by Bunyaviridae viruses (e.g., Sandly fever, Rift Valley fever, La Crosse encephalitis, California encephalitis, Crimean-Congo haemorrhagic fever, or Oropouche fever); disease caused by Rhabdoviridae viruses (e.g., Vesicular stomatitis); disease caused by Orbiviridae (e.g., Bluetongue); diseases caused by bacteria (e.g., Plague, Tularaemia, Q fever, Rocky Mountain spotted fever, Murine typhus, Boutonneuse fever, Queensland tick typhus, Siberian tick typhus, Scrub typhus, Relapsing fever, or Lyme disease); or diseases caused by protozoa (e.g., Malaria, African trypanosomiasis, Nagana, Chagas disease, Leishmaniasis, Piroplasmosis, Bancroftian filariasis, or Brugian filariasis).

II. Target Microorganisms

The microorganisms targeted by the modulating agent described herein may include any microorganism resident in or on an invertebrate host (e.g., insect, mollusk, or nematode), including, but not limited to, any bacteria and/or fungi described herein. Microorganisms resident in the host may include, for example, symbiotic (e.g., endosymbiotic microorganisms that provide beneficial nutrients or enzymes to the host), commensal, pathogenic, or parasitic microorganisms. A symbiotic microorganism (e.g., bacteria or fungi) may be an obligate symbiont of the host or a facultative symbiont of the host. Microorganisms resident in the host may be acquired by any mode of transmission, including vertical, horizontal, or multiple origins of transmission.

i. Bacteria

Exemplary bacteria that may be targeted in accordance with the methods and compositions provided herein, include, but are not limited to, *Xenorhabdus* spp, *Photorhabdus* spp, *Candidatus* spp, *Buchnera* spp, *Blattabacterium* spp, *Baumania* spp, *Wigglesworthia* spp, *Wolbachia* spp, *Rickettsia* spp, *Orientia* spp, *Sodalis* spp, *Burkholderia* spp, *Cupriavidus* spp, *Frankia* spp, *Snirhizobium* spp, *Streptococcus* spp, *Wolinella* spp, *Xylella* spp (e.g., *Xylella fastidiosa*), *Erwinia* spp, *Agrobacterium* spp, *Bacillus* spp, *Commensalibacter* spp. (e.g., *Commensalibacter intestini*), *Paenibacillus* spp, *Streptomyces* spp, *Micrococcus* spp, *Corynebacterium* spp, *Acetobacter* spp (e.g., *Acetobacter pomorum*), *Cyanobacteria* spp, *Salmonella* spp, *Rhodococcus* spp, *Pseudomonas* spp (e.g., *Psuedomonas fulva* or *Pseudomonas mandelii*, *Pseudomonas migulae*), *Pantoea* spp. (e.g., *Pantoea vagans*), *Lactobacillus* spp (e.g., *Lactobacillus plantarum*), *Lysobacter* spp., *Herbaspirillum* spp., *Enterococcus* spp, *Gluconobacter* spp. (e.g., *Gluconobacter morbifer*), *Alcaligenes* spp., *Hamiltonella* spp., *Klebsiella* spp, *Paenibacillus* spp, *Serratia* spp. (e.g., *Serratia marcescens*), *Rahnella* spp. (e.g., *Rahnella aquatilis*), *Arthrobacter* spp, *Azotobacter* spp., *Corynebacterium* spp, *Brevibacterium* spp, *Regiella* spp. (e.g., *Regiella insecticola*), *Thermus* spp, *Pseudomonas* spp, *Clostridium* spp, *Mortierella* spp. (e.g., *Mortierella elongata*) and *Escherichia* spp. In some instances, the targeted bacteria are species in the genera *Xenorhabdus* spp., *Photorhabdus* spp., or *Wolbachia* spp. In some instances, the targeted bacteria are species in the order Streptomycetales, Rhizobiales, Pseudomonadales, Xanthomondadales, Sphingobacteriales, Chlorofelxales, Rhodospirllales, Enterobacteriales, Sphingomonadales, Gemmatimonadales, Micrococcales, Caulobacterales, Cytophagales, Firmicutes, Micromonosporales, Burkholderiales, Rickettsiales, Flavobacteriales, Acidimicroiales, Rhodocyclales, or Bdellovibrionales. In some instances, the targeted bacteria are Armatimonadetes, Firmicutes, TM7, Bacteroidetes, Proteobacteria, or Actinobacteria. In some instances, the targeted bacteria are bacteria in the genera *Lactococcus* spp., *Aeromonas* spp., *Pseudomonas* spp., *Enterobacter* spp., *Citrobacter* spp., *Sulfurospiffium* spp., *Phaeosphaeria* spp., or *Mycosphaerella* spp. In some instances, the bacteria targeted by the modulating agent may be ones that can be transmitted from the host (e.g., insect, mollusk, or nematode) to a plant, including, but not limited to, bacterial plant pathogens (e.g., *Agrobacterium* spp.). Non-limiting examples of bacteria that may be targeted by the methods and compositions provided herein are shown in Table 1. In some instances, the 16S rRNA sequence of the bacteria targeted by the modulating agent has at least 50%, 60%, 70%, 80%, 85%, 90%, 95%, 97%, 99%, 99.9%, or 100% identity with a sequence listed in Table 1.

TABLE 1

Examples of Target Bacteria and Host Insects

| Primary endosymbiont | Host | Location | 16S rRNA |
|---|---|---|---|
| *Gamma proteobacteria* | | | |
| *Carsonella ruddii* | Psyllids (*Psylloidea*) | bacteriocytes | TATCCAGCCACAGGTTCCC CTACAGCTACCTTGTTACGA CTTCACCCCAGTTACAAATC ATACCGTTGTAATAGTAAAA TTACTTATGATACAATTTAC TTCCATGGTGTGACGGGCG GTGTGTACAAGGCTCGAGA ACGTATTCACCGTAACATTC TGATTTACGATTACTAGCGA TTCCAACTTCATGAAATCGA GTTACAGATTTCAATCCGAA CTAAGAATATTTTTTAAGAT TAGCATTATGTTGCCATATA GCATATAACTTTTTGTAATA CTCATTGTAGCACGTGTGT AGCCCTACTTATAAGGGCC ATGATGACTTGACGTCGTC CTCACCTTCCTCCAATTTAT CATTGGCAGTTTCTTATTAG TTCTAATATATTTTTAGTAAA ATAAGATAAGGGTTGCGCT CGTTATAGGACTTAACCCAA CATTTCACAACACGAGCTG ACGACAGCCATGCAGCACC TGTCTCAAAGCTAAAAAAGC TTTATTATTTCTAATAAATTC TTTGGATGTCAAAAGTAGGT AAGATTTTTCGTGTTGTATC GAATTAAACCACATGCTCCA CCGCTTGTGCGAGCCCCCG TCAATTCATTTGAGTTTTAA CCTTGCGGTCGTAATCCCC AGGCGGTCAACTTAACGCG TTAGCTTTTTCACTAAAAAT ATATAACTTTTTTTCATAAAA CAAAATTACAATTATAATATT TAATAAATAGTTGACATCGT TTACTGCATGGACTACCAG GGTATCTAATCCTGTTTGCT CCCCATGCTTTCGTGTATTA GTGTCAGTATTAAAATAGAA ATACGCCTTCGCCACTAGT ATTCTTTCAGATATCTAAGC ATTTCACTGCTACTCCTGAA ATTCTAATTTCTTCTTTTATA CTCAAGTTTATAAGTATTAA TTTCAATATTAAATTACTTTA ATAAATTTAAAAATTAATTTT TAAAAACAACCTGCACACC CTTTACGCCCAATAATTCCG ATTAACGCTTGCACCCCTC GTATTACCGCGGCTGCTGG CACGAAGTTAGCCGGTGCT TCTTTTACAAATAACGTCAA AGATAATATTTTTTTATTATA AAATCTCTTCTTACTTTGTT GAAAGTGTTTTACAACCCTA AGGCCTTCTTCACACACGC GATATAGCTGGATCAAGCT TTCGCTCATTGTCCAATATC CCCCACTGCTGCCTTCCGT AAAAGTTTGGGCCGTGTCT CAGTCCCAATGTGGTTGTT CATCCTCTAAGATCAACTAC GAATCATAGTCTTGTTAAGC TTTTACTTTAACAACTAACT AATTCGATATAAGCTCTTCT ATTAGCGAACGACATTCTC GTTCTTTATCCATTAGGATA CATATTGAATTACTATACAT TTCTATATACTTTTCTAATAC TAATAGGTAGATTCTTATAT ATTACTCACCCGTTCGCTG |

TABLE 1-continued

Examples of Target Bacteria and Host Insects

| | | | |
|---|---|---|---|
| | | | CTAATTATTTTTTTAATAATT CGCACAACTTGCATGTGTT AAGCTTATCGCTAGCGTTC AATCTGAGCTATGATCAAAC TCA (SEQ ID NO: 1) |
| *Portiera aleyrodidarum* BT-B | whiteflyes (*Aleyrodoidea*) | bacteriocytes | AAGAGTTTGATCATGGCTC AGATTGAACGCTAGCGGCA GACATAACACATGCAAGTC GAGCGGCATCATACAGGTT GGCAAGCGGCGCACGGGT GAGTAATACATGTAAATATA CCTAAAAGTGGGGAATAAC GTACGGAAACGTACGCTAA TACCGCATAATTATTACGAG ATAAAGCAGGGGCTTGATA AAAAAAATCAACCTTGCGCT TTTAGAAAATTACATGCCGG ATTAGCTAGTTGGTAGAGTA AAAGCCTACCAAGGTAACG ATCCGTAGCTGGTCTGAGA GGATGATCAGCCACACTGG GACTGAGAAAAGGCCCAGA CTCCTACGGGAGGCAGCAG TGGGGAATATTGGACAATG GGGGGAACCCTGATCCAGT CATGCCGCGTGTGTGAAGA AGGCCTTTGGGTTGTAAAG CACTTTCAGCGAAGAAGAA AAGTTAGAAAATAAAAAGTT ATAACTATGACGGTACTCG CAGAAGAAGCACCGGCTAA CTCCGTGCCAGCAGCCGC GGTAAGACGGAGGGTGCAA GCGTTAATCAGAATTACTG GGCGTAAAGGGCATGTAGG TGGTTTGTTAAGCTTTATGT GAAAGCCCTATGCTTAACAT AGGAACGGAATAAAGAACT GACAAACTAGAGTGCAGAA GAGGAAGGTAGAATTCCCG GTGTAGCGGTGAAATGCGT AGATATCTGGAGGAATACC AGTTGCGAAGGCGACCTTC TGGGCTGACACTGACACTG AGATGCGAAAGCGTGGGA GCAAACAGGATTAGATACC CTGGTAGTCCACGCTGTAA ACGATATCAACTAGCCGTT GGATTCTTAAAGAATTTTGT GGCGTAGCTAACGCGATAA GTTGATCGCCTGGGGAGTA CGGTCGCAAGGCTAAAACT CAAATGAATTGACGGGGGC CCGCACAAGCGGTGGAGC ATGTGGTTTAATTCGATGCA ACGCGCAAAACCTTACCTA CTCTTGACATCCAAAGTACT TTCCAGAGATGGAAGGGTG CCTTAGGGAACTTTGAGAC AGGTGCTGCATGGCTGTCG TCAGCTCGTGTTGTGAAAT GTTGGGTTAAGTCCCGTAA CGAGCGCAACCCTTGTCCT TAGTTGCCAACGCATAAGG CGGGAACTTTAAGGAGACT GCTGGTGATAAACCGGAGG AAGGTGGGGACGACGTCAA GTCATCATGGCCCTTAAGA GTAGGGCAACACACGTGCT ACAATGGCAAAAACAAAGG GTCGCAAATGGTAACATG AAGCTAATCCCAAAAAAATT GTCTTAGTTCGGATTGGAG TCTGAAACTCGACTCCATAA AGTCGGAATCGCTAGTAAT CGTGAATCAGAATGTCACG |

TABLE 1-continued

Examples of Target Bacteria and Host Insects

| | | | |
|---|---|---|---|
| | | | GTGAATACGTTCTCGGGCC
TTGTACACACCGCCCGTCA
CACCATGGAAGTGAAATGC
ACCAGAAGTGGCAAGTTTA
ACCAAAAAACAGGAGAACA
GTCACTACGGTGTGGTTCA
TGACTGGGGTGAAGTCGTA
ACAAGGTAGCTGTAGGGGA
ACCTGTGGCTGGATCACCT
CCTTAA
(SEQ ID NO: 2) |
| Buchnera aphidicola str. APS (Acyrthosiphon pisum) | Aphids (Aphidoidea) | bacteriocytes | AGAGTTTGATCATGGCTCA
GATTGAACGCTGGCGGCAA
GCCTAACACATGCAAGTCG
AGCGGCAGCGAGAAGAGA
GCTTGCTCTCTTTGTCGGC
AAGCGGCAAACGGGTGAGT
AATATCTGGGGATCTACCC
AAAAGAGGGGGATAACTAC
TAGAAATGGTAGCTAATACC
GCATAATGTTGAAAAACCAA
AGTGGGGGACCTTTTGGCC
TCATGCTTTTGGATGAACCC
AGACGAGATTAGCTTGTTG
GTAGAGTAATAGCCTACCA
AGGCAACGATCTCTAGCTG
GTCTGAGAGGATAACCAGC
CACACTGGAACTGAGACAC
GGTCCAGACTCCTACGGGA
GGCAGCAGTGGGGAATATT
GCACAATGGGCGAAAGCCT
GATGCAGCTATGCCGCGTG
TATGAAGAAGGCCTTAGGG
TTGTAAAGTACTTTCAGCGG
GGAGGAAAAAAATAAAACT
AATAATTTTATTTCGTGACG
TTACCCGCAGAAGAAGCAC
CGGCTAACTCCGTGCCAGC
AGCCGCGGTAATACGGAGG
GTGCAAGCGTTAATCAGAA
TTACTGGGCGTAAAGAGCG
CGTAGGTGGTTTTTTAAGTC
AGGTGTGAAATCCCTAGGC
TCAACCTAGGAACTGCATTT
GAAACTGGAAAACTAGAGT
TTCGTAGAGGGAGGTAGAA
TTCTAGGTGTAGCGGTGAA
ATGCGTAGATATCTGGAGG
AATACCCGTGGCGAAAGCG
GCCTCCTAAACGAAAACTG
ACACTGAGGCGCGAAAGCG
TGGGGAGCAAACAGGATTA
GATACCCTGGTAGTCCATG
CCGTAAACGATGTCGACTT
GGAGGTTGTTTCCAAGAGA
AGTGACTTCCGAAGCTAAC
GCATTAAGTCGACCGCCTG
GGGAGTACGGCCGCAAGG
CTAAAACTCAAATGAATTGA
CGGGGGCCCGCACAAGCG
GTGGAGCATGTGGTTTAAT
TCGATGCAACGCGAAAAAC
CTTACCTGGTCTTGACATCC
ACAGAATTCTTTAGAAATAA
AGAAGTGCCTTCGGGAGCT
GTGAGACAGGTGCTGCATG
GCTGTCGTCAGCTCGTGTT
GTGAAATGTTGGGTTAAGT
CCCGCAACGAGCGCAACCC
TTATCCCCTGTTGCCAGCG
GTTCGGCCGGGAACTCAGA
GGAGACTGCCGGTTATAAA
CCGGAGGAAGGTGGGGAC
GACGTCAAGTCATCATGGC
CCTTACGACCAGGGCTACA
CACGTGCTACAATGGTTTAT
ACAAAGAGAAGCAAATCTG |

TABLE 1-continued

Examples of Target Bacteria and Host Insects

|  |  |  | CAAAGACAAGCAAACCTCA<br>TAAAGTAAATCGTAGTCCG<br>GACTGGAGTCTGCAACTCG<br>ACTCCACGAAGTCGGAATC<br>GCTAGTAATCGTGGATCAG<br>AATGCCACGGTGAATACGT<br>TCCCGGGCCTTGTACACAC<br>CGCCCGTCACACCATGGGA<br>GTGGGTTGCAAAAGAAGCA<br>GGTATCCTAACCCTTTAAAA<br>GGAAGGCGCTTACCACTTT<br>GTGATTCATGACTGGGGTG<br>AAGTCGTAACAAGGTAACC<br>GTAGGGGAACCTGCGGTTG<br>GATCACCTCCTT<br>(SEQ ID NO: 3) |
|---|---|---|---|
| *Buchnera aphidicola* str. Sg (*Schizaphis graminum*) | Aphids (*Aphidoidea*) | bacteriocytes | AAACTGAAGAGTTTGATCAT<br>GGCTCAGATTGAACGCTGG<br>CGGCAAGCCTAACACATGC<br>AAGTCGAGCGGCAGCGAAA<br>AGAAAGCTTGCTTTCTTGTC<br>GGCGAGCGGCAAACGGGT<br>GAGTAATATCTGGGGATCT<br>GCCCAAAAGAGGGGGATAA<br>CTACTAGAAATGGTAGCTAA<br>TACCGCATAAAGTTGAAAAA<br>CCAAAGTGGGGGACCTTTT<br>TTAAAGGCCTCATGCTTTTG<br>GATGAACCCAGACGAGATT<br>AGCTTGTTGGTAAGGTAAA<br>AGCTTACCAAGGCAACGAT<br>CTCTAGCTGGTCTGAGAGG<br>ATAACCAGCCACACTGGAA<br>CTGAGACACGGTCCAGACT<br>CCTACGGGAGGCAGCAGT<br>GGGGAATATTGCACAATGG<br>GCGAAAGCCTGATGCAGCT<br>ATGCCGCGTGTATGAAGAA<br>GGCCTTAGGGTTGTAAAGT<br>ACTTTCAGCGGGGAGGAAA<br>AAATTAAAACTAATAATTTTA<br>TTTTGTGACGTTACCCGCA<br>GAAGAAGCACCGGCTAACT<br>CCGTGCCAGCAGCCGCGG<br>TAATACGGAGGGTGCGAGC<br>GTTAATCAGAATTACTGGG<br>CGTAAAGAGCACGTAGGTG<br>GTTTTTTAAGTCAGATGTGA<br>AATCCCTAGGCTTAACCTA<br>GGAACTGCATTTGAAACTG<br>AAATGCTAGAGTATCGTAG<br>AGGGAGGTAGAATTCTAGG<br>TGTAGCGGTGAAATGCGTA<br>GATATCTGGAGGAATACCC<br>GTGGCGAAAGCGGCCTCCT<br>AAACGAATACTGACACTGA<br>GGTGCGAAAGCGTGGGGA<br>GCAAACAGGATTAGATACC<br>CTGGTAGTCCATGCCGTAA<br>ACGATGTCGACTTGGAGGT<br>TGTTTCCAAGAGAAGTGAC<br>TTCCGAAGCTAACGCGTTA<br>AGTCGACCGCCTGGGGAGT<br>ACGGCCGCAAGGCTAAAAC<br>TCAAATGAATTGACGGGGG<br>CCCGCACAAGCGGTGGAG<br>CATGTGGTTTAATTCGATGC<br>AACGCGAAAAACCTTACCT<br>GGTCTTGACATCCACAGAA<br>TTTTTTAGAAATAAAAAAGT<br>GCCTTCGGGAACTGTGAGA<br>CAGGTGCTGCATGGCTGTC<br>GTCAGCTCGTGTTGTGAAA<br>TGTTGGGTTAAGTCCCGCA<br>ACGAGCGCAACCCTTATCC<br>CCTGTTGCCAGCGGTTCGG<br>CCGGGAACTCAGAGGAGAC |

TABLE 1-continued

Examples of Target Bacteria and Host Insects

| | | | |
|---|---|---|---|
| | | | TGCCGGTTATAAACCGGAG
GAAGGTGGGGACGACGTC
AAGTCATCATGGCCCTTAC
GACCAGGGCTACACACGTG
CTACAATGGTTTATACAAAG
AGAAGCAAATCTGTAAAGA
CAAGCAAACCTCATAAAGTA
AATCGTAGTCCGGACTGGA
GTCTGCAACTCGACTCCAC
GAAGTCGGAATCGCTAGTA
ATCGTGGATCAGAATGCCA
CGGTGAATACGTTCCCGGG
CCTTGTACACACCGCCCGT
CACACCATGGGAGTGGGTT
GCAAAAGAAGCAGATTTCC
TAACCACGAAAGTGGAAGG
CGTCTACCACTTTGTGATTC
ATGACTGGGGTGAAGTCGT
AACAAGGTAACCGTAGGGG
AACCTGCGGTTGGATCACC
TCCTTA
(SEQ ID NO: 4) |
| Buchnera aphidicola str. Bp (Baizongia pistaciae) | Aphids (Aphidoidea) | bacteriocytes | ACTTAAAATTGAAGAGTTTG
ATCATGGCTCAGATTGAAC
GCTGGCGGCAAGCTTAACA
CATGCAAGTCGAGCGGCAT
CGAAGAAAAGTTTACTTTTC
TGGCGGCGAGCGGCAAAC
GGGTGAGTAACATCTGGGG
ATCTACCTAAAAGAGGGGG
ACAACCATTGGAAACGATG
GCTAATACCGCATAATGTTT
TTAAATAAACCAAAGTAGGG
GACTAAAATTTTTAGCCTTA
TGCTTTTAGATGAACCCAGA
CGAGATTAGCTTGATGGTA
AGGTAATGGCTTACCAAGG
CGACGATCTCTAGCTGGTC
TGAGAGGATAACCAGCCAC
ACTGGAACTGAGATACGGT
CCAGACTCCTACGGGAGGC
AGCAGTGGGGAATATTGCA
CAATGGGCTAAAGCCTGAT
GCAGCTATGCCGCGTGTAT
GAAGAAGGCCTTAGGGTTG
TAAAGTACTTTCAGCGGGG
AGGAAAGAATTATGTCTAAT
ATACATATTTTGTGACGTTA
CCCGAAGAAGAAGCACCGG
CTAACTCCGTGCCAGCAGC
CGCGGTAATACGGAGGGTG
CGAGCGTTAATCAGAATTA
CTGGGCGTAAAGAGCACGT
AGGCGGTTTATTAAGTCAG
ATGTGAAATCCCTAGGCTTA
ACTTAGGAACTGCATTTGAA
ACTAATAGACTAGAGTCTCA
TAGAGGGAGGTAGAATTCT
AGGTGTAGCGGTGAAATGC
GTAGATATCTAGAGGAATA
CCCGTGGCGAAAGCGACCT
CCTAAATGAAAACTGACGC
TGAGGTGCGAAAGCGTGG
GGAGCAAACAGGATTAGAT
ACCCTGGTAGTCCATGCTG
TAAACGATGTCGACTTGGA
GGTTGTTTCCTAGAGAAGT
GGCTTCCGAAGCTAACGCA
TTAAGTCGACCGCCTGGGG
AGTACGGTCGCAAGGCTAA
AACTCAAATGAATTGACGG
GGGCCCGCACAAGCGGTG
GAGCATGTGGTTTAATTCG
ATGCAACGCGAAGAACCTT
ACCTGGTCTTGACATCCATA
GAATTTTTAGAGATAAAAG
AGTGCCTTAGGGAACTATG |

TABLE 1-continued

Examples of Target Bacteria and Host Insects

| | | | |
|---|---|---|---|
| | | | AGACAGGTGCTGCATGGCT
GTCGTCAGCTCGTGTTGTG
AAATGTTGGGTTAAGTCCC
GCAACGAGCGCAACCCCTA
TCCTTTGTTGCCATCAGGTT
ATGCTGGGAACTCAGAGGA
GACTGCCGGTTATAAACCG
GAGGAAGGTGGGGATGAC
GTCAAGTCATCATGGCCCT
TACGACCAGGGCTACACAC
GTGCTACAATGGCATATAC
AAAGAGATGCAACTCTGCG
AAGATAAGCAAACCTCATAA
AGTATGTCGTAGTCCGGAC
TGGAGTCTGCAACTCGACT
CCACGAAGTAGGAATCGCT
AGTAATCGTGGATCAGAAT
GCCACGGTGAATACGTTCC
CGGGCCTTGTACACACCGC
CCGTCACACCATGGGAGTG
GGTTGCAAAAGAAGCAGGT
AGCTTAACCAGATTATTTTA
TTGGAGGGCGCTTACCACT
TTGTGATTCATGACTGGGG
TGAAGTCGTAACAAGGTAA
CCGTAGGGGAACCTGCGGT
TGGATCACCTCCTTA
(SEQ ID NO: 5) |
| *Buchnera aphidicola* BCc | Aphids (*Aphidoidea*) | bacteriocytes | ATGAGATCATTAATATATAA
AAATCATGTTCCAATTAAAA
AATTAGGACAAAATTTTTTA
CAGAATAAAGAAATTATTAA
TCAGATAATTAATTTAATAA
ATATTAATAAAAATGATAAT
ATTATTGAAATAGGATCAGG
ATTAGGAGCGTTAACTTTTC
CTATTTGTAGAATCATTAAA
AAAATGATAGTATTAGAAAT
TGATGAAGATCTTGTGTTTT
TTTTAACTCAAAGTTTATTTA
TTAAAAAATTACAAATTATAA
TTGCTGATATTATAAAATTT
GATTTTTGTTGTTTTTTTTCT
TTACAGAAATATAAAAAATA
TAGGTTTATTGGTAATTTAC
CATATAATATTGCTACTATA
TTTTTTTTAAAAACAATTAAA
TTTCTTTATAATATAATTGAT
ATGCATTTTATGTTTCAAAA
AGAAGTAGCAAAGAGATTA
TTAGCTACTCCTGGTACTAA
AGAATATGGTAGATTAAGTA
TTATTGCACAATATTTTTATA
AGATAGAAACTGTTATTAAT
GTTAATAAATTTAATTTTTTT
CCTACTCCTAAAGTAGATTC
TACTTTTTTACGATTTACTC
CTAAATATTTTAATAGTAAAT
ATAAAATAGATAAACATTTT
TCTGTTTTAGAATTAATTAC
TAGATTTTCTTTTCAACATA
GAAGAAAATTTTTAAATAAT
AATTTAATATCTTTATTTTCT
ACAAAAGAATTAATTTCTTT
AGATATTGATCCATATTCAA
GAGCAGAAAATGTTTCTTTA
ATTCAATATTGTAAATTAAT
GAAATATTATTTGAAAAGAA
AAATTTTATGTTTAGATTAA
(SEQ ID NO: 6) |
| *Buchnera aphidicola* (*Cinara tujafilina*) | Aphids (*Aphidoidea*) | bacteriocytes | TTATCTTATTTCACATATAC
GTAATATTGCGCTGCGTGC
ACGAGGATTTTTTTGAATTT
CAGATATATTTGGTTTAATA
CGTTTAATAAAACGTATTTT
TTTTTTTATTTTTCTTATTTG |

TABLE 1-continued

Examples of Target Bacteria and Host Insects

| | | | |
|---|---|---|---|
| | | | CAATTCAGTAATAGGAAGTT |
| | | | TTTTAGGTATATTTGGATAA |
| | | | TTACTGTAATTCTTAATAAA |
| | | | GTTTTTTACAATCCTATCTT |
| | | | CAATAGAATGAAAACTAATA |
| | | | ATAGCAATTTTTGATCCGGA |
| | | | ATGTAATATGTTAATAATAA |
| | | | TTTTTAATATTTTATGTAATT |
| | | | CATTTATTTCTTGGTTAATAT |
| | | | ATATTCGAAAAGCTTGAAAT |
| | | | GTTCTCGTAGCTGGATGTTT |
| | | | AAATTTGTCATATTTTGGGA |
| | | | TTGATTTTTTTATGATTTGAA |
| | | | CTAACTCTAACGTGCTTGTT |
| | | | ATGGTTTTTTTTTTATTTGT |
| | | | AATATGATGGCTCGGGATA |
| | | | TTTTTTTTGCGTATTTTCTT |
| | | | CGCCAAAATTTTTTATTACC |
| | | | TGTTCTATTGTTTTTTGGTTT |
| | | | GTTTTTTTTAACCATTGACT |
| | | | AACTGATATTCCAGATTTAG |
| | | | GGTTCATACGCATATCTAAA |
| | | | GGTCCATCATTCATAAATGA |
| | | | AAATCCTCGGATACTAGAAT |
| | | | TTAACTGTATTGAAGAAATA |
| | | | CCTAAATCTAATAATATTCC |
| | | | ATCTATTTTATCTCTATTTTT |
| | | | TTCTTTTTTTAATATTTTTTC |
| | | | AATATTAGAAAATTTACCTA |
| | | | AAAATATTTTAAATCGCGAA |
| | | | TCTTTTATTTTTTTTCCGATT |
| | | | TTTATAGATTGTGGGTCTTG |
| | | | ATCAATACTATATAACTTTC |
| | | | CATTAACCCCTAATTCTTGA |
| | | | AGAATTGCTTTTGAATGACC |
| | | | ACCACCTCCAAATGTACAAT |
| | | | CAACATATGTACCGTCTTTT |
| | | | TTTATTTTAAGTATTGTATG |
| | | | ATTTCTTTTGTTAAAACAGG |
| | | | TTTATGAATCAT |
| | | | (SEQ ID NO: 7) |
| Buchnera aphidicola str. G002 (Myzus persicae) | Aphids (Aphidoidea) | bacteriocytes | ATGAAAAGTATAAAAACTTT |
| | | | TAAAAAACACTTTCCTGTGA |
| | | | AAAAATATGGACAAAATTTT |
| | | | CTTATTAATAAAGAGATCAT |
| | | | AAAAAATATTGTTAAAAAAA |
| | | | TTAATCCAAATATAGAACAA |
| | | | ACATTAGTAGAAATCGGAC |
| | | | CAGGATTAGCTGCATTAACT |
| | | | GAGCCCATATCTCAGTTATT |
| | | | AAAAGAGTTAATAGTTATTG |
| | | | AAATAGACTGTAATCTATTA |
| | | | TATTTTTAAAAAAACAACC |
| | | | ATTTTATTCAAAATTAATAGT |
| | | | TTTTTGTCAAGATGCTTTAA |
| | | | ACTTTAATTATACAAATTTAT |
| | | | TTTATAAAAAAATAAATTAA |
| | | | TTCGTATTTTTGGTAATTTA |
| | | | CCATATAATATCTCTACATC |
| | | | TTTAATTATTTTTTATTTCA |
| | | | ACACATTAGAGTAATTCAAG |
| | | | ATATGAATTTATGCTTCAA |
| | | | AAAGAAGTTGCTGCAAGAT |
| | | | TAATTGCATTACCTGGAAAT |
| | | | AAATATTACGGTCGTTTGAG |
| | | | CATTATATCTCAATATTATT |
| | | | GTGATATCAAAATTTTATTA |
| | | | AATGTTGCTCCTGAAGATTT |
| | | | TTGGCCTATTCCGAGAGTT |
| | | | CATTCTATATTTGTAAATTTA |
| | | | ACACCTCATCATAATTCTCC |
| | | | TTATTTTGTTTATGATATTAA |
| | | | TATTTTAAGCCTTATTACAA |
| | | | ATAAGGCTTTCCAAAATAGA |
| | | | AGAAAAATATTACGTCATAG |
| | | | TTTAAAAAATTTATTTTCTGA |
| | | | AACAACTTTATTAAATTTAG |

TABLE 1-continued

Examples of Target Bacteria and Host Insects

| | | | |
|---|---|---|---|
| | | | ATATTAATCCCAGATTAAGA<br>GCTGAAAATATTTCTGTTTT<br>TCAGTATTGTCAATTAGCTA<br>ATTATTTGTATAAAAAAAATT<br>ATACTAAAAAAAATTAA<br>(SEQ ID NO: 8) |
| *Buchnera aphidicola* str. Ak (*Acyrthosiphon kondoi*) | Aphids (*Aphidoidea*) | bacteriocytes | ATTATAAAAATTTTAAAAAA<br>CATTTTCCTTTAAAAAGGTA<br>TGGACAAAATTTTCTTGTCA<br>ATACAAAAACTATTCAAAAG<br>ATAATTAATATAATTAATCCA<br>AACACCAAACAAACATTAGT<br>GGAAATTGGACCTGGATTA<br>GCTGCATTAACAAAACCAAT<br>TTGTCAATTATTAGAAGAAT<br>TAATTGTTATTGAAATAGAT<br>CCTAATTTATTGTTTTTATTA<br>AAAAAACGTTCATTTTATTC<br>AAAATTAACAGTTTTTTATC<br>AAGACGCTTTAAATTTCAAT<br>TATACAGATTTGTTTTATAA<br>GAAAAATCAATTAATTCGTG<br>TTTTTGGAAACTTGCCATAT<br>AATATTTCTACATCTTTAATT<br>ATTTCTTTATTCAATCATATT<br>AAAGTTATTCAAGATATGAA<br>TTTTATGTTACAGAAAGAGG<br>TTGCTGAAAGATTAATTTCT<br>ATTCCTGGAAATAAATCTTA<br>TGGCCGTTTAAGCATTATTT<br>CTCAGTATTATTGTAAAATT<br>AAAATATTATTAAATGTTGT<br>ACCTGAAGATTTTCGACCTA<br>TACCGAAAGTGCATTCTGTT<br>TTTATCAATTTAACTCCTCA<br>TACCAATTCTCCATATTTTG<br>TTTATGATACAAATATCCTC<br>AGTTCTATCACAAGAAATGC<br>TTTTCAAAATAGAAGGAAAA<br>TTTTGCGTCATAGTTTAAAA<br>AATTTATTTTCTGAAAAAGA<br>ACTAATTCAATTAGAAATTA<br>ATCCAAATTTACGAGCTGAA<br>AATATTTCTATCTTTCAGTAT<br>TGTCAATTAGCTGATTATTT<br>ATATAAAAAATTAAATAATCT<br>TGTAAAAATCAATTAA<br>(SEQ ID NO: 9) |
| *Buchnera aphidicola* str. Ua (*Uroleucon ambrosiae*) | Aphids (*Aphidoidea*) | bacteriocytes | ATGATACTAAATAAATATAA<br>AAAATTTATTCCTTTAAAAA<br>GATACGGACAAAATTTTCTT<br>GTAAATAGAGAAATAATCAA<br>AAATATTATCAAAATAATTAA<br>TCCTAAAAAAACGCAAACAT<br>TATTAGAAATTGGACCGGG<br>TTTAGGTGCGTTAACAAAAC<br>CTATTTGTGAATTTTTAAAT<br>GAACTTATCGTCATTGAAAT<br>AGATCCTAATATATTATCTT<br>TTTTAAAGAAATGTATATTTT<br>TTGATAAATTAAAAATATATT<br>GTCATAATGCTTTAGATTTT<br>AATTATAAAAATATATTCTAT<br>AAAAAAAGTCAATTAATTCG<br>TATTTTTGGAAATTTACCAT<br>ATAATATTTCTACATCTTTAA<br>TAATATATTTATTTCGGAAT<br>ATTGATATTATTCAAGATAT<br>GAATTTTATGTTACAACAAG<br>AAGTGGCTAAAAGATTAGTT<br>GCTATTCCTGGTGAAAAACT<br>TTATGGTCGTTTAAGTATTA<br>TATCTCAATATTATTGTAATA<br>TTAAAATATTATTACATATTC<br>GACCTGAAAATTTTCAACCT<br>ATTCCTAAAGTTAATTCAAT |

TABLE 1-continued

Examples of Target Bacteria and Host Insects

| | | | |
|---|---|---|---|
| | | | GTTTGTAAATTTAACTCCGC<br>ATATTCATTCTCCTTATTTTG<br>TTTATGATATTAATTTATTAA<br>CTAGTATTACAAAACATGCT<br>TTTCAACATAGAAGAAAAT<br>ATTGCGTCATAGTTTAAGAA<br>ATTTTTTTTCTGAGCAAGAT<br>TTAATTCATTTAGAAATTAAT<br>CCAAATTTAAGAGCTGAAAA<br>TGTTTCTATTATTCAATATTG<br>TCAATTGGCTAATAATTTAT<br>ATAAAAAACATAAACAGTTT<br>ATTAATAATTAA<br>(SEQ ID NO: 10) |
| *Buchnera aphidicola*<br>(*Aphis glycines*) | Aphids<br>(*Aphidoidea*) | bacteriocytes | ATGAAAAAGCATATTCCTAT<br>AAAAAAATTTAGTCAAAATT<br>TTCTTGTAGATTTGAGTGTG<br>ATTAAAAAAATAATTAAATTT<br>ATTAATCCGCAGTTAAATGA<br>AATATTGGTTGAAATTGGAC<br>CGGGATTAGCTGCTATCAC<br>TCGACCTATTTGTGATTTGA<br>TAGATCATTTAATTGTGATT<br>GAAATTGATAAAATTTTATT<br>AGATAGATTAAAACAGTTCT<br>CATTTTATTCAAAATTAACA<br>GTATATCATCAAGATGCTTT<br>AGCATTTGATTACATAAAGT<br>TATTTAATAAAAAAATAAAT<br>TAGTTCGAATTTTTGGTAAT<br>TTACCATATCATGTTTCTAC<br>GTCTTTAATATTGCATTTATT<br>TAAAAGAATTAATATTATTAA<br>AGATATGAATTTTATGCTAC<br>AAAAAGAAGTTGCTGAACG<br>TTTAATTGCAACTCCAGGTA<br>GTAAATTATATGGTCGTTTA<br>AGTATTATTTCTCAATATTAT<br>TGTAATATAAAAGTTTTATT<br>GCATGTGTCTTCAAAATGTT<br>TTAAACCAGTTCCTAAAGTA<br>GAATCAATTTTTCTTAATTT<br>GACACCTTATACTGATTATT<br>TCCCTTATTTTACTTATAAT<br>GTAAACGTTCTTAGTTATAT<br>TACAAATTTAGCTTTTCAAA<br>AAAGAAGAAAAATATTACGT<br>CATAGTTTAGGTAAAATATT<br>TTCTGAAAAGTTTTTATAA<br>AATTAAATATTAATCCCAAA<br>TTAAGACCTGAGAATATTTC<br>TATATTACAATATTGTCAGT<br>TATCTAATTATATGATAGAA<br>AATAATATTCATCAGGAACA<br>TGTTTGTATTTAA<br>(SEQ ID NO: 11) |
| *Annandia pinicola* | (*Phylloxeroidea*) | bacteriocytes | AGATTGAACGCTGGCGGCA<br>TGCCTTACACATGCAAGTC<br>GAACGGTAACAGGTCTTCG<br>GACGCTGACGAGTGGCGAA<br>CGGGTGAGTAATACATCGG<br>AACGTGCCCAGTCGTGGGG<br>GATAACTACTCGAAAGAGT<br>AGCTAATACCGCATACGAT<br>CTGAGGATGAAAGCGGGG<br>GACCTTCGGGCCTCGCGC<br>GATTGGAGCGGCCGATGG<br>CAGATTAGGTAGTTGGTGG<br>GATAAAAGCTTACCAAGCC<br>GACGATCTGTAGCTGGTCT<br>GAGAGGACGACCAGCCACA<br>CTGGAACTGAGATACGGTC<br>CAGACTCTTACGGGAGGCA<br>GCAGTGGGGAATATTGCAC<br>AATGGGCGCAAGCCTGATG<br>CAGCTATGTCGCGTGTATG |

TABLE 1-continued

Examples of Target Bacteria and Host Insects

| | | | |
|---|---|---|---|
| | | | AAGAAGACCTTAGGGTTGT
AAAGTACTTTCGATAGCATA
AGAAGATAATGAGACTAATA
ATTTTATTGTCTGACGTTAG
CTATAGAAGAAGCACCGGC
TAACTCCGTGCCAGCAGCC
GCGGTAATACGGGGGGTG
CTAGCGTTAATCGGAATTAC
TGGGCGTAAAGAGCATGTA
GGTGGTTTATTAAGTCAGAT
GTGAAATCCCTGGACTTAAT
CTAGGAACTGCATTTGAAA
CTAATAGGCTAGAGTTTCGT
AGAGGGAGGTAGAATTCTA
GGTGTAGCGGTGAAATGCA
TAGATATCTAGAGGAATATC
AGTGGCGAAGGCGACCTTC
TGGACGATAACTGACGCTA
AAATGCGAAAGCATGGGTA
GCAAACAGGATTAGATACC
CTGGTAGTCCATGCTGTAA
ACGATGTCGACTAAGAGGT
TGGAGGTATAACTTTTAATC
TCTGTAGCTAACGCGTTAA
GTCGACCGCCTGGGGAGTA
CGGTCGCAAGGCTAAAACT
CAAATGAATTGACGGGGGC
CTGCACAAGCGGTGGAGCA
TGTGGTTTAATTCGATGCAA
CGCGTAAAACCTTACCTGG
TCTTGACATCCACAGAATTT
TACAGAAATGTAGAAGTGC
AATTTGAACTGTGAGACAG
GTGCTGCATGGCTGTCGTC
AGCTCGTGTTGTGAAATGTT
GGGTTAAGTCCCGCAACGA
GCGCAACCCTTGTCCTTTG
TTACCATAAGATTTAAGGAA
CTCAAAGGAGACTGCCGGT
GATAAACTGGAGGAAGGCG
GGGACGACGTCAAGTCATC
ATGGCCCTTATGACCAGGG
CTACACACGTGCTACAATG
GCATATACAAAGAGATGCA
ATATTGCGAAATAAAGCCAA
TCTTATAAATATGTCCTAG
TTCGGACTGGAGTCTGCAA
CTCGACTCCACGAAGTCGG
AATCGCTAGTAATCGTGGA
TCAGCATGCCACGGTGAAT
ATGTTTCCAGGCCTTGTACA
CACCGCCCGTCACACCATG
GAAGTGGATTGCAAAAGAA
GTAAGAAAATTAACCTTCTT
AACAAGGAAATAACTTACCA
CTTTGTGACTCATAACTGG
GGTGA
(SEQ ID NO: 12) |
| *Moranella endobia* | (*Coccoidea*) | bacteriocytes | TCTTTTTGGTAAGGAGGTG
ATCCAACCGCAGGTTCCCC
TACGGTTACCTTGTTACGAC
TTCACCCCAGTCATGAATCA
CAAAGTGGTAAGCGCCCTC
CTAAAAGGTTAGGCTACCT
ACTTCTTTTGCAACCCACTT
CCATGGTGTGACGGGCGGT
GTGTACAAGGCCCGGGAAC
GTATTCACCGTGGCATTCT
GATCCACGATTACTAGCGA
TTCCTACTTCATGGAGTCGA
GTTGCAGACTCCAATCCGG
ACTACGACGCACTTTATGA
GGTCCGCTAACTCTCGCGA
GCTTGCTTCTCTTTGTATGC
GCCATTGTAGCACGTGTGT
AGCCCTACTCGTAAGGGCC
ATGATGACTTGACGTCATC |

TABLE 1-continued

Examples of Target Bacteria and Host Insects

|  |  |  | CCCACCTTCCTCCGGTTTAT<br>CACCGGCAGTCTCCTTTGA<br>GTTCCCGACCGAATCGCTG<br>GCAAAAAAGGATAAGGGTT<br>GCGCTCGTTGCGGGACTTA<br>ACCCAACATTTCACAACAC<br>GAGCTGACGACAGCCATGC<br>AGCACCTGTCTCAGAGTTC<br>CCGAAGGTACCAAAACATC<br>TCTGCTAAGTTCTCTGGATG<br>TCAAGAGTAGGTAAGGTTC<br>TTCGCGTTGCATCGAATTAA<br>ACCACATGCTCCACCGCTT<br>GTGCGGGCCCCCGTCAATT<br>CATTTGAGTTTTAACCTTGC<br>GGCCGTACTCCCCAGGCG<br>GTCGATTTAACGCGTTAACT<br>ACGAAAGCCACAGTTCAAG<br>ACCACAGCTTTCAAATCGA<br>CATAGTTTACGGCGTGGAC<br>TACCAGGGTATCTAATCCT<br>GTTTGCTCCCCACGCTTTC<br>GTACCTGAGCGTCAGTATT<br>CGTCCAGGGGGCCGCCTT<br>CGCCACTGGTATTCCTCCA<br>GATATCTACACATTTCACCG<br>CTACACCTGGAATTCTACC<br>CCCCTCTACGAGACTCTAG<br>CCTATCAGTTTCAAATGCAG<br>TTCCTAGGTTAAGCCCAGG<br>GATTTCACATCTGACTTAAT<br>AAACCGCCTACGTACTCTTT<br>ACGCCCAGTAATTCCGATT<br>AACGCTTGCACCCTCCGTA<br>TTACCGCGGCTGCTGGCAC<br>GGAGTTAGCCGGTGCTTCT<br>TCTGTAGGTAACGTCAATCA<br>ATAACCGTATTAAGGATATT<br>GCCTTCCTCCCTACTGAAA<br>GTGCTTTACAACCCGAAGG<br>CCTTCTTCACACACGCGGC<br>ATGGCTGCATCAGGGTTTC<br>CCCCATTGTGCAATATTCCC<br>CACTGCTGCCTCCCGTAGG<br>AGTCTGGACCGTGTCTCAG<br>TTCCAGTGTGGCTGGTCAT<br>CCTCTCAGACCAGCTAGGG<br>ATCGTCGCCTAGGTAAGCT<br>ATTACCTCACCTACTAGCTA<br>ATCCCATCTGGGTTCATCT<br>GAAGGTGTGAGGCCAAAAG<br>GTCCCCCACTTTGGTCTTA<br>CGACATTATGCGGTATTAG<br>CTACCGTTTCCAGCAGTTAT<br>CCCCCTCCATCAGGCAGAT<br>CCCCAGACTTTACTCACCC<br>GTTCGCTGCTCGCCGGCAA<br>AAAAGTAAACTTTTTTCCGT<br>TGCCGCTCAACTTGCATGT<br>GTTAGGCCTGCCGCCAGCG<br>TTCAATCTGAGCCATGATCA<br>AACTCTTCAATTAAA<br>(SEQ ID NO: 13) |
| Ishikawaella capsulata<br>Mpkobe | (Heteroptera) | bacteriocytes | AAATTGAAGAGTTTGATCAT<br>GGCTCAGATTGAACGCTAG<br>CGGCAAGCTTAACACATGC<br>AAGTCGAACGGTAACAGAA<br>AAAAGCTTGCTTTTTTGCTG<br>ACGAGTGGCGGACGGGTG<br>AGTAATGTCTGGGGATCTA<br>CCTAATGGCGGGGATAAC<br>TACTGGAAACGGTAGCTAA<br>TACCGCATAATGTTGTAAAA<br>CCAAAGTGGGGGACCTTAT<br>GGCCTCACACCATTAGATG<br>AACCTAGATGGGATTAGCT<br>TGTAGGTGGGGTAAAGGCT |

TABLE 1-continued

Examples of Target Bacteria and Host Insects

| | | | |
|---|---|---|---|
| | | | CACCTAGGCAACGATCCCT |
| | | | AGCTGGTCTGAGAGGATGA |
| | | | CCAGCCACACTGGAACTGA |
| | | | GATACGGTCCAGACTCCTA |
| | | | CGGGAGGCAGCAGTGGGG |
| | | | AATCTTGCACAATGGGCGC |
| | | | AAGCCTGATGCAGCTATGT |
| | | | CGCGTGTATGAAGAAGGCC |
| | | | TTAGGGTTGTAAAGTACTTT |
| | | | CATCGGGGAAGAAGGATAT |
| | | | GAGCCTAATATTCTCATATA |
| | | | TTGACGTTACCTGCAGAAG |
| | | | AAGCACCGGCTAACTCCGT |
| | | | GCCAGCAGCCGCGGTAACA |
| | | | CGGAGGGTGCGAGCGTTAA |
| | | | TCGGAATTACTGGGCGTAA |
| | | | AGAGCACGTAGGTGGTTTA |
| | | | TTAAGTCATATGTGAAATCC |
| | | | CTGGGCTTAACCTAGGAAC |
| | | | TGCATGTGAAACTGATAAAC |
| | | | TAGAGTTTCGTAGAGGGAG |
| | | | GTGGAATTCCAGGTGTAGC |
| | | | GGTGAAATGCGTAGATATC |
| | | | TGGAGGAATATCAGAGGCG |
| | | | AAGGCGACCTTCTGGACGA |
| | | | AAACTGACACTCAGGTGCG |
| | | | AAAGCGTGGGGAGCAAACA |
| | | | GGATTAGATACCCTGGTAG |
| | | | TCCACGCTGTAAACAATGT |
| | | | CGACTAAAAAACTGTGAGC |
| | | | TTGACTTGTGGTTTTTGTAG |
| | | | CTAACGCATTAAGTCGACC |
| | | | GCCTGGGGAGTACGGCCG |
| | | | CAAGGTTAAAACTCAAATGA |
| | | | ATTGACGGGGGTCCGCACA |
| | | | AGCGGTGGAGCATGTGGTT |
| | | | TAATTCGATGCAACGCGAA |
| | | | AAACCTTACCTGGTCTTGAC |
| | | | ATCCAGCGAATTATATAGAA |
| | | | ATATATAAGTGCCTTTCGGG |
| | | | GAACTCTGAGACGCTGCAT |
| | | | GGCTGTCGTCAGCTCGTGT |
| | | | TGTGAAATGTTGGGTTAAGT |
| | | | CCCGCAACGAGCGCCCTTA |
| | | | TCCTCTGTTGCCAGCGGCA |
| | | | TGGCCGGGAACTCAGAGGA |
| | | | GACTGCCAGTATTAAACTG |
| | | | GAGGAAGGTGGGGATGAC |
| | | | GTCAAGTCATCATGGCCCT |
| | | | TATGACCAGGGCTACACAC |
| | | | GTGCTACAATGGTGTATAC |
| | | | AAAGAGAAGCAATCTCGCA |
| | | | AGAGTAAGCAAAACTCAAA |
| | | | AAGTACATCGTAGTTCGGA |
| | | | TTAGAGTCTGCAACTCGAC |
| | | | TCTATGAAGTAGGAATCGC |
| | | | TAGTAATCGTGGATCAGAAT |
| | | | GCCACGGTGAATACGTTCT |
| | | | CTGGCCTTGTACACACCGC |
| | | | CCGTCACACCATGGGAGTA |
| | | | AGTTGCAAAAGAAGTAGGT |
| | | | AGCTTAACCTTTATAGGAG |
| | | | GGCGCTTACCACTTTGTGA |
| | | | TTTATGACTGGGGTGAAGT |
| | | | CGTAACAAGGTAACTGTAG |
| | | | GGGAACCTGTGGTTGGATT |
| | | | ACCTCCTTA |
| | | | (SEQ ID NO: 14) |
| *Baumannia cicadellinicola* | sharpshooter leafhoppers (*Cicadellinae*) | bacteriocytes | TTCAATTGAAGAGTTTGATC ATGGCTCAGATTGAACGCT GGCGGTAAGCTTAACACAT GCAAGTCGAGCGGCATCG GAAAGTAAATTAATTACTTT GCCGGCAAGCGGCGAACG GGTGAGTAATATCTGGGGA TCTACCTTATGGAGAGGGA TAACTATTGGAAACGATAGC |

TABLE 1-continued

Examples of Target Bacteria and Host Insects

| | | | |
|---|---|---|---|
| | | | TAACACCGCATAATGTCGT |
| | | | CAGACCAAAATGGGGGACC |
| | | | TAATTTAGGCCTCATGCCAT |
| | | | AAGATGAACCCAGATGAGA |
| | | | TTAGCTAGTAGGTGAGATA |
| | | | ATAGCTCACCTAGGCAACG |
| | | | ATCTCTAGTTGGTCTGAGA |
| | | | GGATGACCAGCCACACTGG |
| | | | AACTGAGACACGGTCCAGA |
| | | | CTCCTACGGGAGGCAGCAG |
| | | | TGGGGAATCTTGCACAATG |
| | | | GGGGAAACCCTGATGCAGC |
| | | | TATACCGCGTGTGTGAAGA |
| | | | AGGCCTTCGGGTTGTAAAG |
| | | | CACTTTCAGCGGGGAAGAA |
| | | | AATGAAGTTACTAATAATAA |
| | | | TTGTCAATTGACGTTACCCG |
| | | | CAAAAGAAGCACCGGCTAA |
| | | | CTCCGTGCCAGCAGCCGC |
| | | | GGTAAGACGGAGGGTGCAA |
| | | | GCGTTAATCGGAATTACTG |
| | | | GGCGTAAAGCGTATGTAGG |
| | | | CGGTTTATTTAGTCAGGTGT |
| | | | GAAAGCCCTAGGCTTAACC |
| | | | TAGGAATTGCATTTGAAACT |
| | | | GGTAAGCTAGAGTCTCGTA |
| | | | GAGGGGGGGAGAATTCCA |
| | | | GGTGTAGCGGTGAAATGCG |
| | | | TAGAGATCTGGAAGAATAC |
| | | | CAGTGGCGAAGGCGCCCC |
| | | | CCTGGACGAAAACTGACGC |
| | | | TCAAGTACGAAAGCGTGGG |
| | | | GAGCAAACAGGATTAGATA |
| | | | CCCTGGTAGTCCACGCTGT |
| | | | AAACGATGTCGATTTGAAG |
| | | | GTTGTAGCCTTGAGCTATA |
| | | | GCTTTCGAAGCTAACGCAT |
| | | | TAAATCGACCGCCTGGGGA |
| | | | GTACGACCGCAAGGTTAAA |
| | | | ACTCAAATGAATTGACGGG |
| | | | GGCCCGCACAAGCGGTGG |
| | | | AGCATGTGGTTTAATTCGAT |
| | | | ACAACGCGAAAAACCTTAC |
| | | | CTACTCTTGACATCCAGAGT |
| | | | ATAAAGCAGAAAAGCTTTAG |
| | | | TGCCTTCGGGAACTCTGAG |
| | | | ACAGGTGCTGCATGGCTGT |
| | | | CGTCAGCTCGTGTTGTGAA |
| | | | ATGTTGGGTTAAGTCCCGC |
| | | | AACGAGCGCAACCCTTATC |
| | | | CTTTGTTGCCAACGATTAAG |
| | | | TCGGGAACTCAAAGGAGAC |
| | | | TGCCGGTGATAAACCGGAG |
| | | | GAAGGTGAGGATAACGTCA |
| | | | AGTCATCATGGCCCTTACG |
| | | | AGTAGGGCTACACACGTGC |
| | | | TACAATGGTGCATACAAAG |
| | | | AGAAGCAATCTCGTAAGAG |
| | | | TTAGCAAACCTCATAAAGTG |
| | | | CATCGTAGTCCGGATTAGA |
| | | | GTCTGCAACTCGACTCTAT |
| | | | GAAGTCGGAATCGCTAGTA |
| | | | ATCGTGGATCAGAATGCCA |
| | | | CGGTGAATACGTTCCCGGG |
| | | | CCTTGTACACACCGCCCGT |
| | | | CACACCATGGGAGTGTATT |
| | | | GCAAAAGAAGTTAGTAGCT |
| | | | TAACTCATAATACGAGAGG |
| | | | GCGCTTACCACTTTGTGATT |
| | | | CATAACTGGGGTGAAGTCG |
| | | | TAACAAGGTAACCGTAGGG |
| | | | GAACCTGCGGTTGGATCAC |
| | | | CTCCTTACACTAAA |
| | | | (SEQ ID NO: 15) |
| *Sodalis* like | *Rhopalus sapporensis* | wider tissue tropism | ATTGAACGCTGGCGGCAGG CCTAACACATGCAAGTCGA GCGGCAGCGGGAAGAAGC |

TABLE 1-continued

Examples of Target Bacteria and Host Insects

TTGCTTCTTTGCCGGCGAG
CGGCGGACGGGTGAGTAAT
GTCTGGGGATCTGCCCGAT
GGAGGGGGATAACTACTGG
AAACGGTAGCTAATACCGC
ATAACGTCGCAAGACCAAA
GTGGGGGACCTTCGGGCC
TCACACCATCGGATGAACC
CAGGTGGGATTAGCTAGTA
GGTGGGGTAATGGCTCACC
TAGGCGACGATCCCTAGCT
GGTCTGAGAGGATGACCAG
TCACACTGGAACTGAGACA
CGGTCCAGACTCCTACGGG
AGGCAGCAGTGGGGAATAT
TGCACAATGGGGGAAACCC
TGATGCAGCCATGCCGCGT
GTGTGAAGAAGGCCTTCGG
GTTGTAAAGCACTTTCAGC
GGGGAGGAAGGCGATGGC
GTTAATAGCGCTATCGATTG
ACGTTACCCGCAGAAGAAG
CACCGGCTAACTCCGTGCC
AGCAGCCGCGGTAATACGG
AGGGTGCGAGCGTTAATCG
GAATTACTGGGCGTAAAGC
GTACGCAGGCGGTCTGTTA
AGTCAGATGTGAAATCCCC
GGGCTCAACCTGGGAACTG
CATTTGAAACTGGCAGGCT
AGAGTCTCGTAGAGGGGG
GTAGAATTCCAGGTGTAGC
GGTGAAATGCGTAGAGATC
TGGAGGAATACCGGTGGCG
AAGGCGGCCCCCTGGACG
AAGACTGACGCTCAGGTAC
GAAAGCGTGGGGAGCAAAC
AGGATTAGATACCCTGGTA
GTCCACGCTGTAAACGATG
TCGATTTGAAGGTTGTGGC
CTTGAGCCGTGGCTTTCGG
AGCTAACGTGTTAAATCGA
CCGCCTGGGGAGTACGGC
CGCAAGGTTAAAACTCAAAT
GAATTGACGGGGCCCGC
ACAAGCGGTGGAGCATGTG
GTTTAATTCGATGCAACGC
GAAGAACCTTACCTACTCTT
GACATCCAGAGAACTTGGC
AGAGATGCTTTGGTGCCTT
CGGGAACTCTGAGACAGGT
GCTGCATGGCTGTCGTCAG
CTCGTGTTGTGAAATGTTG
GGTTAAGTCCCGCAACGAG
CGCAACCCTTATCCTTTATT
GCCAGCGATTCGGTCGGGA
ACTCAAAGGAGACTGCCGG
TGATAAACCGGAGGAAGGT
GGGGATGACGTCAAGTCAT
CATGGCCCTTACGAGTAGG
GCTACACACGTGCTACAAT
GGCGCATACAAAGAGAAGC
GATCTCGCGAGAGTCAGCG
GACCTCATAAAGTGCGTCG
TAGTCCGGATTGGAGTCTG
CAACTCGACTCCATGAAGT
CGGAATCGCTAGTAATCGT
GGATCAGAATGCCACGGTG
AATACGTTCCCGGGCCTTG
TACACACCGCCCGTCACAC
CATGGGAGTGGGTTGCAAA
AGAAGTAGGTAGCTTAACC
TTCGGGAGGGCGCTTACCA
CTTTGTGATTCATGACTGG
GGTG
(SEQ ID NO: 16)

TABLE 1-continued

Examples of Target Bacteria and Host Insects

| *Hartigia pinicola* | The pine bark adelgid | bacteriocytes | AGATTTAACGCTGGCGGCA |
| | | | GGCCTAACACATGCAAGTC |
| | | | GAGCGGTACCAGAAGAAGC |
| | | | TTGCTTCTTGCTGACGAGC |
| | | | GGCGGACGGGTGAGTAAT |
| | | | GTATGGGATCTGCCCGAC |
| | | | AGAGGGGATAACTATTGG |
| | | | AAACGGTAGCTAATACCGC |
| | | | ATAATCTCTGAGGAGCAAA |
| | | | GCAGGGAACTTCGGTCCT |
| | | | TGCGCTATCGGATGAACCC |
| | | | ATATGGGATTAGCTAGTAG |
| | | | GTGAGGTAATGGCTCCCCT |
| | | | AGGCAACGATCCCTAGCTG |
| | | | GTCTGAGAGGATGATCAGC |
| | | | CACACTGGGACTGAGACAC |
| | | | GGCCCAGACTCCTACGGGA |
| | | | GGCAGCAGTGGGAATATT |
| | | | GCACAATGGGCGAAAGCCT |
| | | | GATGCAGCCATGCCGCGTG |
| | | | TATGAAGAAGGCTTTAGGG |
| | | | TTGTAAAGTACTTTCAGTCG |
| | | | AGAGGAAAACATTGATGCT |
| | | | AATATCATCAATTATTGACG |
| | | | TTTCCGACAGAAGAAGCAC |
| | | | CGGCTAACTCCGTGCCAGC |
| | | | AGCCGCGGTAATACGGAGG |
| | | | GTGCAAGCGTTAATCGGAA |
| | | | TTACTGGGCGTAAAGCGCA |
| | | | CGCAGGCGGTTAATTAAGT |
| | | | TAGATGTGAAAGCCCCGGG |
| | | | CTTAACCCAGGAATAGCAT |
| | | | ATAAAACTGGTCAACTAGA |
| | | | GTATTGTAGAGGGGGGTAG |
| | | | AATTCCATGTGTAGCGGTG |
| | | | AAATGCGTAGAGATGTGGA |
| | | | GGAATACCAGTGGCGAAGG |
| | | | CGGCCCCCTGGACAAAAAC |
| | | | TGACGCTCAAATGCGAAAG |
| | | | CGTGGGGAGCAAACAGGAT |
| | | | TAGATACCCTGGTAGTCCA |
| | | | TGCTGTAAACGATGTCGATT |
| | | | TGGAGGTTGTTCCCTTGAG |
| | | | GAGTAGCTTCCGTAGCTAA |
| | | | CGCGTTAAATCGACCGCCT |
| | | | GGGGGAGTACGACTGCAA |
| | | | GGTTAAAACTCAAATGAATT |
| | | | GACGGGGCCCGCACAAG |
| | | | CGGTGGAGCATGTGGTTTA |
| | | | ATTCGATGCAACGCGAAAA |
| | | | ACCTTACCTACTCTTGACAT |
| | | | CCAGATAATTTAGCAGAAAT |
| | | | GCTTTAGTACCTTCGGGAA |
| | | | ATCTGAGACAGGTGCTGCA |
| | | | TGGCTGTCGTCAGCTCGTG |
| | | | TTGTGAAATGTTGGGTTAAG |
| | | | TCCCGCAACGAGCGCAACC |
| | | | CTTATCCTTTGTTGCCAGCG |
| | | | ATTAGGTCGGGAACTCAAA |
| | | | GGAGACTGCCGGTGATAAA |
| | | | CCGGAGGAAGGTGGGGAT |
| | | | GACGTCAAGTCATCATGGC |
| | | | CCTTACGAGTAGGGCTACA |
| | | | CACGTGCTACAATGGCATA |
| | | | TACAAAGGGAAGCAACCTC |
| | | | GCGAGAGCAAGCGAAACTC |
| | | | ATAAATTATGTCGTAGTTCA |
| | | | GATTGGAGTCTGCAACTCG |
| | | | ACTCCATGAAGTCGGAATC |
| | | | GCTAGTAATCGTAGATCAG |
| | | | AATGCTACGGTGAATACGT |

TABLE 1-continued

Examples of Target Bacteria and Host Insects

|  |  |  | TCCCGGGCCTTGTACACAC<br>CGCCCGTCACACCATGGGA<br>GTGGGTTGCAAAAGAAGTA<br>GGTAACTTAACCTTATGGAA<br>AGCGCTTACCACTTTGTGAT<br>TCATAACTGGGGTG<br>(SEQ ID NO: 17) |
|---|---|---|---|
| *Wigglesworthia glossinidia* | tsetse fly (Diptera: Glossinidae) | bacteriocytes | |
| Beta proteobacteria | | | |
| *Tremblaya phenacola* | *Phenacoccus avenae* (TPPAVE). | bacteriomes | AGGTAATCCAGCCACACCT<br>TCCAGTACGGCTACCTTGT<br>TACGACTTCACCCCAGTCA<br>CAACCCTTACCTTCGGAAC<br>TGCCCTCCTCACAACTCAA<br>ACCACCAAACACTTTTAAAT<br>CAGGTTGAGAGAGGTTAGG<br>CCTGTTACTTCTGGCAAGA<br>ATTATTTCCATGGTGTGACG<br>GGCGGTGTGTACAAGACCC<br>GAGAACATATTCACCGTGG<br>CATGCTGATCCACGATTACT<br>AGCAATTCCAACTTCATGCA<br>CTCGAGTTTCAGAGTACAAT<br>CCGAACTGAGGCCGGCTTT<br>GTGAGATTAGCTCCCTTTTG<br>CAAGTTGGCAACTCTTTGG<br>TCCGGCCATTGTATGATGT<br>GTGAAGCCCCACCCATAAA<br>GGCCATGAGGACTTGACGT<br>CATCCCCACCTTCCTCCAA<br>CTTATCGCTGGCAGTCTCTT<br>TAAGGTAACTGACTAATCCA<br>GTAGCAATTAAAGACAGGG<br>GTTGCGCTCGTTACAGGAC<br>TTAACCCAACATCTCACGAC<br>ACGAGCTGACGACAGCCAT<br>GCAGCACCTGTGCACTAAT<br>TCTCTTTCAAGCACTCCCG<br>CTTCTCAACAGGATCTTAGC<br>CATATCAAAGGTAGGTAAG<br>GTTTTTCGCGTTGCATCGAA<br>TTAATCCACATCATCCACTG<br>CTTGTGCGGGTCCCCGTCA<br>ATTCCTTTGAGTTTTAACCT<br>TGCGGCCGTACTCCCCAGG<br>CGGTCGACTTGTGCGTTAG<br>CTGCACCACTGAAAAGGAA<br>AACTGCCCAATGGTTAGTC<br>AACATCGTTTAGGGCATGG<br>ACTACCAGGGTATCTAATC<br>CTGTTTGCTCCCCATGCTTT<br>AGTGTCTGAGCGTCAGTAA<br>CGAACCAGGAGGCTGCCTA<br>CGCTTTCGGTATTCCTCCA<br>CATCTCTACACATTTCACTG<br>CTACATGCGGAATTCTACCT<br>CCCCCTCTCGTACTCCAGC<br>CTGCCAGTAACTGCCGCAT<br>TCTGAGGTTAAGCCTCAGC<br>CTTTCACAGCAATCTTAACA<br>GGCAGCCTGCACACCCTTT<br>ACGCCCAATAAATCTGATTA<br>ACGCTCGCACCCTACGTAT<br>TACCGCGGCTGCTGGCACG<br>TAGTTTGCCGGTGCTTATTC<br>TTTCGGTACAGTCACACCA<br>CCAAATTGTTAGTTGGGTG<br>GCTTTCTTTCCGAACAAAAG<br>TGCTTTACAACCCAAAGGC<br>CTTCTTCACACACGCGGCA<br>TTGCTGGATCAGGCTTCCG<br>CCCATTGTCCAAGATTCCTC<br>ACTGCTGCCTTCCTCAGAA |

TABLE 1-continued

Examples of Target Bacteria and Host Insects

|  |  |  | GTCTGGGCCGTGTCTCAGT<br>CCCAGTGTGGCTGGCCGTC<br>CTCTCAGACCAGCTACCGA<br>TCATTGCCTTGGGAAGCCA<br>TTACCTTTCCAACAAGCTAA<br>TCAGACATCAGCCAATCTC<br>AGAGCGCAAGGCAATTGGT<br>CCCCTGCTTTCATTCTGCTT<br>GGTAGAGAACTTTATGCGG<br>TATTAATTAGGCTTTCACCT<br>AGCTGTCCCCCACTCTGAG<br>GCATGTTCTGATGCATTACT<br>CACCCGTTTGCCACTTGCC<br>ACCAAGCCTAAGCCCGTGT<br>TGCCGTTCGACTTGCATGT<br>GTAAGGCATGCCGCTAGCG<br>TTCAATCTGAGCCAGGATC<br>AAACTCT<br>(SEQ ID NO: 18) |
| --- | --- | --- | --- |
| *Tremblaya princeps* | citrus<br>mealybug<br>*Planococcus<br>citri* | bacteriomes | AGAGTTTGATCCTGGCTCA<br>GATTGAACGCTAGCGGCAT<br>GCATTACACATGCAAGTCG<br>TACGGCAGCACGGGCTTAG<br>GCCTGGTGGCGAGTGGCG<br>AACGGGTGAGTAACGCCTC<br>GGAACGTGCCTTGTAGTGG<br>GGGATAGCCTGGCGAAAGC<br>CAGATTAATACCGCATGAA<br>GCCGCACAGCATGCGCGG<br>TGAAAGTGGGGGATTCTAG<br>CCTCACGCTACTGGATCGG<br>CCGGGGTCTGATTAGCTAG<br>TTGGCGGGGTAATGGCCCA<br>CCAAGGCTTAGATCAGTAG<br>CTGGTCTGAGAGGACGATC<br>AGCCACACTGGGACTGAGA<br>CACGGCCCAGACTCCTACG<br>GGAGGCAGCAGTGGGGAA<br>TCTTGGACAATGGGCGCAA<br>GCCTGATCCAGCAATGCCG<br>CGTGTGTGAAGAAGGCCTT<br>CGGGTCGTAAAGCACTTTT<br>GTTCGGGATGAAGGGGGG<br>CGTGCAAACACCATGCCCT<br>CTTGACGATACCGAAAGAA<br>TAAGCACCGGCTAACTACG<br>TGCCAGCAGCCGCGGTAAT<br>ACGTAGGGTGCGAGCGTTA<br>ATCGGAATCACTGGGCGTA<br>AAGGGTGCGCGGGTGGTTT<br>GCCAAGACCCCTGTAAAAT<br>CCTACGGCCCAACCGTAGT<br>GCTGCGGAGGTTACTGGTA<br>AGCTTGAGTATGGCAGAGG<br>GGGGTAGAATTCCAGGTGT<br>AGCGGTGAAATGCGTAGAT<br>ATCTGGAGGAATACCGAAG<br>GCGAAGGCAACCCCCTGG<br>GCCATCACTGACACTGAGG<br>CACGAAAGCGTGGGGAGC<br>AAACAGGATTAGATACCCT<br>GGTAGTCCACGCCCTAAAC<br>CATGTCGACTAGTTGTCGG<br>GGGGAGCCCTTTTTCCTCG<br>GTGACGAAGCTAACGCATG<br>AAGTCGACCGCCTGGGGA<br>GTACGACCGCAAGGTTAAA<br>ACTCAAAGGAATTGACGGG<br>GACCCGCACAAGCGGTGG<br>ATGATGTGGATTAATTCGAT<br>GCAACGCGAAAAACCTTAC<br>CTACCCTTGACATGGCGGA<br>GATTCTGCCGAGAGGCGGA<br>AGTGCTCGAAAGAGAATCC<br>GTGCACAGGTGCTGCATGG<br>CTGTCGTCAGCTCGTGTCG<br>TGAGATGTTGGGTTAAGTC |

TABLE 1-continued

Examples of Target Bacteria and Host Insects

```
CCATAACGAGCGCAACCCC
CGTCTTTAGTTGCTACCACT
GGGGCACTCTATAGAGACT
GCCGGTGATAAACCGGAGG
AAGGTGGGGACGACGTCAA
GTCATCATGGCCTTTATGG
GTAGGGCTTCACACGTCAT
ACAATGGCTGGAGCAAAGG
GTCGCCAACTCGAGAGAGG
GAGCTAATCCCACAAACCC
AGCCCCAGTTCGGATTGCA
CTCTGCAACTCGAGTGCAT
GAAGTCGGAATCGCTAGTA
ATCGTGGATCAGCATGCCA
CGGTGAATACGTTCTCGGG
TCTTGTACACACCGCCCGT
CACACCATGGGAGTAAGCC
GCATCAGAAGCAGCCTCCC
TAACCCTATGCTGGGAAGG
AGGCTGCGAAGGTGGGGT
CTATGACTGGGGTGAAGTC
GTAACAAGGTAGCCGTACC
GGAAGGTGCGGCTGGATTA
CCT
(SEQ ID NO: 19)
```

| | | | |
|---|---|---|---|
| Vidania | | bacteriomes | |
| Nasuia deltocephalinicola | pestiferous insect host, Macrosteles quadripunctulatus (Hemiptera: Cicadellidae) | bacteriomes | AGTTTAATCCTGGCTCAGAT TTAACGCTTGCGACATGCC TAACACATGCAAGTTGAAC GTTGAAAATATTTCAAAGTA GCGTATAGGTGAGTATAAC ATTTAAACATACCTTAAAGT TCGGAATACCCCGATGAAA ATCGGTATAATACCGTATAA AAGTATTTAAGAATTAAAGC GGGGAAAACCTCGTGCTAT AAGATTGTTAAATGCCTGAT TAGTTTGTTGGTTTTTAAGG TAAAAGCTTACCAAGACTTT GATCAGTAGCTATTCTGTGA GGATGTATAGCCACATTGG GATTGAAATAATGCCCAAAC CTCTACGGAGGGCAGCAGT GGGGAATATTGGACAATGA GCGAAAGCTTGATCCAGCA ATGTCGCGTGTGCGATTAA GGGAAACTGTAAAGCACTT TTTTTTAAGAATAAGAAATTT TAATTAATAATTAAAATTTTT GAATGTATTAAAAGAATAAG TACCGACTAATCACGTGCC AGCAGTCGCGGTAATACGT GGGGTGCGAGCGTTAATCG GATTTATTGGGCGTAAAGT GTATTCAGGCTGCTTAAAAA GATTTATATTAAATATTTAAA TTAAATTTAAAAAATGTATAA ATTACTATTAAGCTAGAGTT TAGTATAAGAAAAAGAATT TTATGTGTAGCAGTGAAATG CGTTGATATATAAAGGAAC GCCGAAAGCGAAAGCATTT TTCTGTAATAGAACTGACGC TTATATACGAAAGCGTGGG TAGCAAACAGGATTAGATA CCCTGGTAGTCCACGCCCT AAACTATGTCAATTAACTAT TAGAATTTTTTTTAGTGGTG TAGCTAACGCGTTAAATTGA CCGCCTGGGTATTACGATC GCAAGATTAAAACTCAAAG GAATTGACGGGGACCAGCA CAAGCGGTGGATGATGTGG ATTAATTCGATGATACGCGA AAAACCTTACCTGCCCTTGA CATGGTTAGAATTTTATTGA AAAATAAAAGTGCTTGGAAA |

TABLE 1-continued

Examples of Target Bacteria and Host Insects

| | | | |
|---|---|---|---|
| | | | AGAGCTAACACACAGGTGC
TGCATGGCTGTCGTCAGCT
CGTGTCGTGAGATGTTGGG
TTAAGTCCCGCAACGAGCG
CAACCCCTACTCTTAGTTGC
TAATTAAAGAACTTTAAGAG
AACAGCTAACAATAAGTTTA
GAGGAAGGAGGGGATGAC
TTCAAGTCCTCATGGCCCTT
ATGGGCAGGGCTTCACACG
TCATACAATGGTTAATACAA
AAAGTTGCAATATCGTAAGA
TTGAGCTAATCTTTAAAATT
AATCTTAGTTCGGATTGTAC
TCTGCAACTCGAGTACATG
AAGTTGGAATCGCTAGTAAT
CGCGGATCAGCATGCCGC
GGTGAATAGTTTAACTGGT
CTTGTACACACCGCCCGTC
ACACCATGGAAATAAATCTT
GTTTTAAATGAAGTAATATA
TTTTATCAAAACAGGTTTTG
TAACCGGGGTGAAGTCGTA
ACA
(SEQ ID NO: 20) |
| *Zinderia insecticola* CARI | spittlebug *Clastoptera arizonana* | bacteriocytes | ATATAAATAAGAGTTTGATC
CTGGCTCAGATTGAACGCT
AGCGGTATGCTTTACACAT
GCAAGTCGAACGACAATAT
TAAAGCTTGCTTTAATATAA
AGTGGCGAACGGGTGAGTA
ATATATCAAAACGTACCTTA
AAGTGGGGGATAACTAATT
GAAAAATTAGATAATACCGC
ATATTAATCTTAGGATGAAA
ATAGGAATAATATCTTATGC
TTTTAGATCGGTTGATATCT
GATTAGCTAGTTGGTAGGG
TAAATGCTTACCAAGGCAAT
GATCAGTAGCTGGTTTTAG
CGAATGATCAGCCACACTG
GAACTGAGACACGGTCCAG
ACTTCTACGGAAGGCAGCA
GTGGGGAATATTGGACAAT
GGGAGAAATCCTGATCCAG
CAATACCGCGTGAGTGATG
AAGGCCTTAGGGTCGTAAA
ACTCTTTTGTTAGGAAAGAA
ATAATTTTAAATAATATTTAA
AATTGATGACGGTACCTAAA
GAATAAGCACCGGCTAACT
ACGTGCCAGCAGCCGCGG
TAATACGTAGGGTGCAAGC
GTTAATCGGAATTATTGGG
CGTAAAGAGTGCGTAGGCT
GTTATATAAGATAGATGTGA
AATACTTAAGCTTAACTTAA
GAACTGCATTTATTACTGTT
TAACTAGAGTTTATTAGAGA
GAAGTGGAATTTTATGTGTA
GCAGTGAAATGCGTAGATA
TATAAAGGAATATCGATGG
CGAAGGCAGCTTCTTGGAA
TAATACTGACGCTGAGGCA
CGAAAGCGTGGGGAGCAAA
CAGGATTAGATACCCTGGT
AGTCCACGCCCTAAACTAT
GTCTACTAGTTATTAAATTA
AAAATAAAATTTAGTAACGT
AGCTAACGCATTAAGTAGA
CCGCCTGGGGAGTACGATC
GCAAGATTAAAACTCAAAG
GAATTGACGGGACCCGCA
CAAGCGGTGGATGATGTGG
ATTAATTCGATGCAACACGA
AAAACCTTACCTACTCTTGA
CATGTTTGGAATTTTAAAGA |

TABLE 1-continued

Examples of Target Bacteria and Host Insects

| | | | |
|---|---|---|---|
| | | | AATTTAAAAGTGCTTGAAAA<br>AGAACCAAAACACAGGTGC<br>TGCATGGCTGTCGTCAGCT<br>CGTGTCGTGAGATGTTGGG<br>TTAAGTCCCGCAACGAGCG<br>CAACCCTTGTTATTATTTGC<br>TAATAAAAAGAACTTTAATA<br>AGACTGCCAATGACAAATT<br>GGAGGAAGGTGGGGATGA<br>CGTCAAGTCCTCATGGCCC<br>TTATGAGTAGGGCTTCACA<br>CGTCATACAATGATATATAC<br>AATGGGTAGCAAATTTGTG<br>AAAATGAGCCAATCCTTAAA<br>GTATATCTTAGTTCGGATTG<br>TAGTCTGCAACTCGACTAC<br>ATGAAGTTGGAATCGCTAG<br>TAATCGCGGATCAGCATGC<br>CGCGGTGAATACGTTCTCG<br>GGTCTTGTACACACCGCCC<br>GTCACACCATGGAAGTGAT<br>TTTTACCAGAAATTATTTGT<br>TTAACCTTTATTGGAAAAAA<br>ATAATTAAGGTAGAATTCAT<br>GACTGGGGTGAAGTCGTAA<br>CAAGGTAGCAGTATCGGAA<br>GGTGCGGCTGGATTACATT<br>TTAAAT<br>(SEQ ID NO: 21) |
| *Profftella armatura* | *Diaphorina citri*, the Asian citrus psyllid | bacteriomes | |

Alpha proteobacteria

| | | | |
|---|---|---|---|
| *Hodgkinia* | Cicada *Diceroprocta semicincta* | bacteriome | AATGCTGGCGGCAGGCCTA<br>ACACATGCAAGTCGAGCGG<br>ACAACGTTCAAACGTTGTTA<br>GCGGCGAACGGGTGAGTA<br>ATACGTGAGAATCTACCCAT<br>CCCAACGTGATAACATAGT<br>CAACACCATGTCAATAACGT<br>ATGATTCCTGCAACAGGTA<br>AAGATTTTATCGGGGATGG<br>ATGAGCTCACGCTAGATTA<br>GCTAGTTGGTGAGATAAAA<br>GCCCACCAAGGCCAAGATC<br>TATAGCTGGTCTGGAAGGA<br>TGGACAGCCACATTGGGAC<br>TGAGACAAGGCCCAACCCT<br>CTAAGGAGGGCAGCAGTGA<br>GGAATATTGGACAATGGGC<br>GTAAGCCTGATCCAGCCAT<br>GCCGCATGAGTGATTGAAG<br>GTCCAACGGACTGTAAAAC<br>TCTTTTCTCCAGAGATCATA<br>AATGATAGTATCTGGTGATA<br>TAAGCTCCGGCCAACTTCG<br>TGCCAGCAGCCGCGGTAAT<br>ACGAGGGGAGCGAGTATTG<br>TTCGGTTTTATTGGGCGTAA<br>AGGGTGTCCAGGTTGCTAA<br>GTAAGTTAACAACAAAATCT<br>TGAGATTCAACCTCATAACG<br>TTCGGTTAATACTACTAAGC<br>TCGAGCTTGGATAGAGACA<br>AACGGAATTCCGAGTGTAG<br>AGGTGAAATTCGTTGATACT<br>TGGAGGAACACCAGAGGC<br>GAAGGCGGTTTGTCATACC<br>AAGCTGACACTGAAGACAC<br>GAAAGCATGGGGAGCAAAC<br>AGGATTAGATACCCTGGTA<br>GTCCATGCCCTAAACGTTG<br>AGTGCTAACAGTTCGATCA<br>AGCCACATGCTATGATCCA |

TABLE 1-continued

Examples of Target Bacteria and Host Insects

| | | | |
|---|---|---|---|
| | | | GGATTGTACAGCTAACGCG
TTAAGCACTCCGCCTGGGT
ATTACGACCGCAAGGTTAA
AACTCAAAGGAATTGACGG
AGACCCGCACAAGCGGTG
GAGCATGTGGTTTAATTCG
AAGCTACACGAAGAACCTT
ACCAGCCCTTGACATACCA
TGGCCAACCATCCTGGAAA
CAGGATGTTGTTCAAGTTAA
ACCCTTGAAATGCCAGGAA
CAGGTGCTGCATGGCTGTT
GTCAGTTCGTGTCGTGAGA
TGTATGGTTAAGTCCCAAAA
CGAACACAACCCTCACCCA
TAGTTGCCATAAACACAATT
GGGTTCTCTATGGGTACTG
CTAACGTAAGTTAGAGGAA
GGTGAGGACCACAACAAGT
CATCATGGCCCTTATGGGC
TGGGCCACACACATGCTAC
AATGGTGGTTACAAAGAGC
CGCAACGTTGTGAGACCGA
GCAAATCTCCAAAGACCAT
CTCAGTCCGGATTGTACTC
TGCAACCCGAGTACATGAA
GTAGGAATCGCTAGTAATC
GTGGATCAGCATGCCACGG
TGAATACGTTCTCGGGTCTT
GTACACGCCGCCCGTCACA
CCATGGGAGCTTCGCTCCG
ATCGAAGTCAAGTTACCCTT
GACCACATCTTGGCAAGTG
ACCGA
(SEQ ID NO: 22) |
| *Wolbachia* sp. wPip | Mosquito
*Culex quinquefasciatus* | bacteriome | AAATTTGAGAGTTTGATCCT
GGCTCAGAATGAACGCTGG
CGGCAGGCCTAACACATGC
AAGTCGAACGGAGTTATATT
GTAGCTTGCTATGGTATAAC
TTAGTGGCAGACGGGTGAG
TAATGTATAGGAATCTACCT
AGTAGTACGGAATAATTGTT
GGAAACGACAACTAATACC
GTATACGCCCTACGGGGGA
AAAATTTATTGCTATTAGAT
GAGCCTATATTAGATTAGCT
AGTTGGTGGGTAATAGCC
TACCAAGGTAATGATCTATA
GCTGATCTGAGAGGATGAT
CAGCCACACTGGAACTGAG
ATACGGTCCAGACTCCTAC
GGGAGGCAGCAGTGGGGA
ATATTGGACAATGGGCGAA
AGCCTGATCCAGCCATGCC
GCATGAGTGAAGAAGGCCT
TTGGGTTGTAAAGCTCTTTT
AGTGAGGAAGATAATGACG
GTACTCACAGAAGAAGTCC
TGGCTAACTCCGTGCCAGC
AGCCGCGGTAATACGGAGA
GGGCTAGCGTTATTCGGAA
TTATTGGGCGTAAAGGGCG
CGTAGGCTGGTTAATAAGT
TAAAAGTGAAATCCCGAGG
CTTAACCTTGGAATTGCTTT
TAAAACTATTAATCTAGAGA
TTGAAAGAGGATAGAGGAA
TTCCTGATGTAGAGGTAAAA
TTCGTAAATATTAGGAGGAA
CACCAGTGGCGAAGGCGTC
TATCTGGTTCAAATCTGACG
CTGAAGCGCGAAGGCGTG
GGGAGCAAACAGGATTAGA
TACCCTGGTAGTCCACGCT
GTAAACGATGAATGTTAAAT
ATGGGAGTTTACTTTCTGT |

TABLE 1-continued

Examples of Target Bacteria and Host Insects

ATTACAGCTAACGCGTTAAA
CATTCCGCCTGGGGACTAC
GGTCGCAAGATTAAAACTC
AAAGGAATTGACGGGGACC
CGCACAAGCGGTGGAGCAT
GTGGTTTAATTCGATGCAAC
GCGAAAAACCTTACCACTT
CTTGACATGAAAATCATACC
TATTCGAAGGGATAGGGTC
GGTTCGGCCGGATTTTACA
CAAGTGTTGCATGGCTGTC
GTCAGCTCGTGTCGTGAGA
TGTTGGGTTAAGTCCCGCA
ACGAGCGCAACCCTCATCC
TTAGTTGCCATCAGGTAATG
CTGAGTACTTTAAGGAAACT
GCCAGTGATAAGCTGGAGG
AAGGTGGGATGATGTCAA
GTCATCATGGCCTTTATGG
AGTGGGCTACACACGTGCT
ACAATGGTGTCTACAATGG
GCTGCAAGGTGCGCAAGCC
TAAGCTAATCCCTAAAAGAC
ATCTCAGTTCGGATTGTACT
CTGCAACTCGAGTACATGA
AGTTGGAATCGCTAGTAAT
CGTGGATCAGCATGCCACG
GTGAATACGTTCTCGGGTC
TTGTACACACTGCCCGTCA
CGCCATGGGAATTGGTTTC
ACTCGAAGCTAATGGCCTA
ACCGCAAGGAAGGAGTTAT
TTAAAGTGGGATCAGTGAC
TGGGGTGAAGTCGTAACAA
GGTAGCAGTAGGGGAATCT
GCAGCTGGATTACCTCCTT
A
(SEQ ID NO: 23)

Bacteroidetes

| *Uzinura diaspidicola* | armoured scale insects | bacteriocytes | AAAGGAGATATTCCAACCA CACCTTCCGGTACGGTTAC CTTGTTACGACTTAGCCCTA GTCATCAAGTTTACCTTAGG CAGACCACTGAAGGATTAC TGACTTCAGGTACCCCCGA CTCCCATGGCTTGACGGGC GGTGTGTACAAGGTTCGAG AACATATTCACCGCGCCATT GCTGATGCGCGATTACTAG CGATTCCTGCTTCATAGAGT CGAATTGCAGACTCCAATC CGAACTGAGACTGGTTTTA GAGATTAGCTCCTGATCAC CCAGTGGCTGCCCTTTGTA ACCAGCCATTGTAGCACGT GTGTAGCCCAAGGCATAGA GGCCATGATGATTTGACAT CATCCCCACCTTCCTCACA GTTTACACCGGCAGTTTTGT TAGAGTCCCCGGCTTTACC CGATGGCAACTAACAATAG GGGTTGCGCTCGTTATAGG ACTTAACCAAACACTTCACA GCACGAACTGAAGACAACC ATGCAGCACCTTGTAATAC GTCGTATAGACTAAGCTGTT TCCAGCTTATTCGTAATACA TTTAAGCCTTGGTAAGGTTC CTCGCGTATCATCGAATTAA ACCACATGCTCCACCGCTT GTGCGAACCCCCGTCAATT CCTTTGAGTTTCAATCTTGC GACTGTACTTCCCAGGTGG ATCACTTATCGCTTTCGCTA AGCCACTGAATATCGTTTTT CCAATAGCTAGTGATCATC |
|---|---|---|---|

TABLE 1-continued

Examples of Target Bacteria and Host Insects

| | | | |
|---|---|---|---|
| | | | GTTTAGGGCGTGGACTACC
AGGGTATCTAATCCTGTTTG
CTCCCCACGCTTTCGTGCA
CTGAGCGTCAGTAAAGATT
TAGCAACCTGCCTTCGCTA
TCGGTGTTCTGTATGATATC
TATGCATTTCACCGCTACAC
CATACATTCCAGATGCTCCA
ATCTTACTCAAGTTTACCAG
TATCAATAGCAATTTTACAG
TTAAGCTGTAAGCTTTCACT
ACTGACTTAATAAACAGCCT
ACACACCCTTTAAACCCAAT
AAATCCGAATAACGCTTGT
GTCATCCGTATTGCCGCGG
CTGCTGGCACGGAATTAGC
CGACACTTATTCGTATAGTA
CCTTCAATCTCCTATCACGT
AAGATATTTATTTCTATACA
AAAGCAGTTTACAACCTAAA
AGACCTTCATCCTGCACGC
GACGTAGCTGGTTCAGAGT
TTCCTCCATTGACCAATATT
CCTCACTGCTGCCTCCCGT
AGGAGTCTGGTCCGTGTCT
CAGTACCAGTGTGGAGGTA
CACCCTCTTAGGCCCCCTA
CTGATCATAGTCTTGGTAGA
GCCATTACCTCACCAACTAA
CTAATCAAACGCAGGCTCA
TCTTTTGCCACCTAAGTTTT
AATAAAGGCTCCATGCAGA
AACTTTATATTATGGGGGAT
TAATCAGAATTTCTTCTGGC
TATACCCCAGCAAAAGGTA
GATTGCATACGTGTTACTCA
CCCATTCGCCGGTCGCCGA
CAAATTAAAAATTTTTCGAT
GCCCCTCGACTTGCATGTG
TTAAGCTCGCCGCTAGCGT
TAATTCTGAGCCAGGATCA
AACTCTTCGTTGTAG
(SEQ ID NO: 24) |
| *Sulcia muelleri* | Blue-Green Sharpshooter and several other leafhopper species | bacteriocytes | CTCAGGATAAACGCTAGCG
GAGGGCTTAACACATGCAA
GTCGAGGGGCAGCAAAAAT
AATTATTTTTGGCGACCGG
CAAACGGGTGAGTAATACA
TACGTAACTTTCCTTATGCT
GAGGAATAGCCTGAGGAAA
CTTGGATTAATACCTCATAA
TACAATTTTTTAGAAAGAAA
AATTGTTAAAGTTTTATTAT
GGCATAAGATAGGCGTATG
TCCAATTAGTTAGTTGGTAA
GGTAATGGCTTACCAAGAC
GATGATTGGTAGGGGGCCT
GAGAGGGGCGTTCCCCCA
CATTGGTACTGAGACACGG
ACCAAACTTCTACGGAAGG
CTGCAGTGAGGAATATTGG
TCAATGGAGGAAACTCTGA
ACCAGCCACTCCGCGTGCA
GGATGAAAGAAAGCCTTAT
TGGTTGTAAACTGCTTTTGT
ATATGAATAAAAAATTCTAA
TTATAGAAATAATTGAAGGT
AATATACGAATAAGTATCGA
CTAACTCTGTGCCAGCAGT
CGCGGTAAGACAGAGGATA
CAAGCGTTATCCGGATTTAT
TGGGTTTAAAGGGTGCGTA
GGCGGTTTTAAAGTCAGT
AGTGAAATCTTAAAGCTTAA
CTTTAAAAGTGCTATTGATA
CTGAAAAACTAGAGTAAGG
TTGGAGTAACTGGAATGTG |

TABLE 1-continued

Examples of Target Bacteria and Host Insects

| | | | |
|---|---|---|---|
| | | | TGGTGTAGCGGTGAAATGC
ATAGATATCACACAGAACAC
CGATAGCGAAAGCAAGTTA
CTAACCCTATACTGACGCT
GAGTCACGAAAGCATGGGG
AGCAAACAGGATTAGATAC
CCTGGTAGTCCATGCCGTA
AACGATGATCACTAACTATT
GGGTTTTATACGTTGTAATT
CAGTGGTGAAGCGAAAGTG
TTAAGTGATCCACCTGAGG
AGTACGACCGCAAGGTTGA
AACTCAAAGGAATTGACGG
GGGCCCGCACAATCGGTG
GAGCATGTGGTTTAATTCG
ATGATACACGAGGAACCTT
ACCAAGACTTAAATGTACTA
CGAATAAATTGGAAACAATT
TAGTCAAGCGACGGAGTAC
AAGGTGCTGCATGGTTGTC
GTCAGCTCGTGCCGTGAGG
TGTAAGGTTAAGTCCTTTAA
ACGAGCGCAACCCTTATTA
TTAGTTGCCATCGAGTAATG
TCAGGGGACTCTAATAAGA
CTGCCGGCGCAAGCCGAG
AGGAAGGTGGGGATGACGT
CAAATCATCACGGCCCTTA
CGTCTTGGGCCACACACGT
GCTACAATGATCGGTACAA
AAGGGAGCGACTGGGTGA
CCAGGAGCAAATCCAGAAA
GCCGATCTAAGTTCGGATT
GGAGTCTGAAACTCGACTC
CATGAAGCTGGAATCGCTA
GTAATCGTGCATCAGCCAT
GGCACGGTGAATATGTTCC
CGGGCCTTGTACACACCGC
CCGTCAAGCCATGGAAGTT
GGAAGTACCTAAAGTTGGT
TCGCTACCTAAGGTAAGTC
TAATAACTGGGGCTAAGTC
GTAACAAGGTA
(SEQ ID NO: 25) |

Yeast like

| | | | |
|---|---|---|---|
| *Symbiotaphrina buchneri* voucher JCM9740 | Anobiid beetles *Stegobium paniceum* | mycetome between the foregut and midgut | AGATTAAGCCATGCAAGTC
TAAGTATAAGNAATCTATAC
NGTGAAACTGCGAATGGCT
CATTAAATCAGTTATCGTTT
ATTTGATAGTACCTTACTAC
ATGGATAACCGTGGTAATT
CTAGAGCTAATACATGCTAA
AAACCCCGACTTCGGAAGG
GGTGTATTTATTAGATAAAA
AACCAATGCCCTTCGGGGC
TCCTTGGTGATTCATGATAA
CTTAACGAATCGCATGGCC
TTGCGCCGGCGATGGTTCA
TTCAAATTTCTGCCCTATCA
ACTTTCGATGGTAGGATAG
TGGCCTACCATGGTTTTAAC
GGGTAACGGGGAATTAGGG
TTCGATTCCGGAGAGGGAG
CCTGAGAAACGGCTACCAC
ATCCAAGGAAGGCAGCAGG
CGCGCAAATTACCCAATCC
CGACACGGGGAGGTAGTG
ACAATAAATACTGATACAGG
GCTCTTTTGGGTCTTGTAAT
TGGAATGAGTACAATTTAAA
TCCCTTAACGAGGAACAATT
GGAGGGCAAGTCTGGTGC
CAGCAGCCGCGGTAATTCC
AGCTCCAATAGCGTATATTA
AAGTTGTTGCAGTTAAAAAG
CTCGTAGTTGAACCTTGGG |

TABLE 1-continued

Examples of Target Bacteria and Host Insects

| | | | |
|---|---|---|---|
| | | | CCTGGCTGGCCGGTCCGC<br>CTAACCGCGTGTACTGGTC<br>CGGCCGGGCCTTTCCTTCT<br>GGGGAGCCGCATGCCCTTC<br>ACTGGGTGTGTCGGGAAC<br>CAGGACTTTTACTTTGAAAA<br>AATTAGAGTGTTCAAAGCA<br>GGCCTATGCTCGAATACAT<br>TAGCATGGAATAATAGAATA<br>GGACGTGCGGTTCTATTTT<br>GTTGGTTTCTAGGACCGCC<br>GTAATGATTAATAGGGATAG<br>TCGGGGGCATCAGTATTCA<br>ATTGTCAGAGGTGAAATTCT<br>TGGATTTATTGAAGACTAAC<br>TACTGCGAAAGCATTTGCC<br>AAGGATGTTTTCATTAATCA<br>GTGAACGAAAGTTAGGGGA<br>TCGAAGACGATCAGATACC<br>GTCGTAGTCTTAACCATAAA<br>CTATGCCGACTAGGGATCG<br>GGCGATGTTATTATTTTGAC<br>TCGCTCGGCACCTTACGAG<br>AAATCAAAGTCTTTGGGTTC<br>TGGGGGGAGTATGGTCGCA<br>AGGCTGAAACTTAAAGAAAT<br>TGACGGAAGGGCACCACCA<br>GGAGTGGAGCCTGCGGCTT<br>AATTTGACTCAACACGGGG<br>AAACTCACCAGGTCCAGAC<br>ACATTAAGGATTGACAGATT<br>GAGAGCTCTTTCTTGATTAT<br>GTGGGTGGTGGTGCATGG<br>CCGTTCTTAGTTGGTGGAG<br>TGATTTGTCTGCTTAATTGC<br>GATAACGAACGAGACCTTA<br>ACCTGCTAAATAGCCCGGT<br>CCGCTTTGGCGGGCCGCT<br>GGCTTCTTAGAGGGACTAT<br>CGGCTCAAGCCGATGGAAG<br>TTTGAGGCAATAACAGGTC<br>TGTGATGCCCTTAGATGTTC<br>TGGGCCGCACGCGCGCTA<br>CACTGACAGAGCCAACGAG<br>TAAATCACCTTGGCCGGAA<br>GGTCTGGGTAATCTTGTTAA<br>ACTCTGTCGTGCTGGGGAT<br>AGAGCATTGCAATTATTGCT<br>CTTCAACGAGGAATTCCTA<br>GTAAGCGCAAGTCATCAGC<br>TTGCGCTGATTACGTCCCT<br>GCCCTTTGTACACACCGCC<br>CGTCGCTACTACCGATTGA<br>ATGGCTCAGTGAGGCCTTC<br>GGACTGGCACAGGGACGTT<br>GGCAACGACGACCCAGTGC<br>CGGAAAGTTGGTCAAACTT<br>GGTCATTTAGAGGAAGTAA<br>AAGTCGTAACAAGGTTTCC<br>GTAGGTGAACCTGCGGAAG<br>GATCATTA<br>(SEQ ID NO: 26) |
| *Symbiotaphrina kochii* voucher CBS 589.63 | Anobiid beetles *Lasioderma serricorne* | mycetome | TACCTGGTTGATTCTGCCA<br>GTAGTCATATGCTTGTCTCA<br>AAGATTAAGCCATGCAAGT<br>CTAAGTATAAGCAATCTATA<br>CGGTGAAACTGCGAATGGC<br>TCATTAAATCAGTTATCGTT<br>TATTTGATAGTACCTTACTA<br>CATGGATAACCGTGGTAAT<br>TCTAGAGCTAATACATGCTA<br>AAAACCTCGACTTCGGAAG<br>GGGTGTATTTATTAGATAAA<br>AAACCAATGCCCTTCGGGG<br>CTCCTTGGTGATTCATGATA<br>ACTTAACGAATCGCATGGC<br>CTTGCGCCGGCGATGGTTC |

TABLE 1-continued

Examples of Target Bacteria and Host Insects

ATTCAAATTTCTGCCCTATC
AACTTTCGATGGTAGGATA
GTGGCCTACCATGGTTTCA
ACGGGTAACGGGGAATTAG
GGTTCGATTCCGGAGAGGG
AGCCTGAGAAACGGCTACC
ACATCCAAGGAAGGCAGCA
GGCGCGCAAATTACCCAAT
CCCGACACGGGGAGGTAG
TGACAATAAATACTGATACA
GGGCTCTTTTGGGTCTTGT
AATTGGAATGAGTACAATTT
AAATCCCTTAACGAGGAAC
AATTGGAGGGCAAGTCTGG
TGCCAGCAGCCGCGGTAAT
TCCAGCTCCAATAGCGTAT
ATTAAAGTTGTTGCAGTTAA
AAAGCTCGTAGTTGAACCTT
GGGCCTGGCTGGCCGGTC
CGCCTAACCGCGTGTACTG
GTCCGGCCGGGCCTTTCCT
TCTGGGGAGCCGCATGCCC
TTCACTGGGTGTGTCGGGG
AACCAGGACTTTTACTTTGA
AAAAATTAGAGTGTTCAAAG
CAGGCCTATGCTCGAATAC
ATTAGCATGGAATAATAGAA
TAGGACGTGTGGTTCTATTT
TGTTGGTTTCTAGGACCGC
CGTAATGATTAATAGGGATA
GTCGGGGCATCAGTATTC
AATTGTCAGAGGTGAAATTC
TTGGATTTATTGAAGACTAA
CTACTGCGAAAGCATTTGC
CAAGGATGTTTTCATTAATC
AGTGAACGAAAGTTAGGGG
ATCGAAGACGATCAGATAC
CGTCGTAGTCTTAACCATAA
ACTATGCCGACTAGGGATC
GGGCGATGTTATTATTTTGA
CTCGCTCGGCACCTTACGA
GAAATCAAAGTCTTTGGGTT
CTGGGGGAGTATGGTCG
CAAGGCTGAAACTTAAAGA
AATTGACGGAAGGGCACCA
CCAGGAGTGGAGCCTGCG
GCTTAATTTGACTCAACACG
GGGAAACTCACCAGGTCCA
GACACATTAAGGATTGACA
GATTGAGAGCTCTTTCTTGA
TTATGTGGGTGGTGGTGCA
TGGCCGTTCTTAGTTGGTG
GAGTGATTTGTCTGCTTAAT
TGCGATAACGAACGAGACC
TTAACCTGCTAAATAGCCC
GGTCCGCTTTGGCGGGCC
GCTGGCTTCTTAGAGGGAC
TATCGGCTCAAGCCGATGG
AAGTTTGAGGCAATAACAG
GTCTGTGATGCCCTTAGAT
GTTCTGGGCCGCACGCGC
GCTACACTGACAGAGCCAA
CGAGTACATCACCTTGGCC
GGAAGGTCTGGGTAATCTT
GTTAAACTCTGTCGTGCTG
GGGATAGAGCATTGCAATT
ATTGCTCTTCAACGAGGAAT
TCCTAGTAAGCGCAAGTCA
TCAGCTTGCGCTGATTACG
TCCCTGCCCTTTGTACACA

TABLE 1-continued

Examples of Target Bacteria and Host Insects

CCGCCCGTCGCTACTACCG
ATTGAATGGCTCAGTGAGG
CCTTCGGACTGGCACAGGG
ACGTTGGCAACGACGACCC
AGTGCCGGAAAGTTCGTCA
AACTTGGTCATTTAGAGGAA
GNNNAAGTCGTAACAAGGT
TTCCGTAGGTGAACCTGCG
GAAGGATCATTA
(SEQ ID NO: 27)

| Primary extracelullar symbiont | Host | location | 16 rRNA |
|---|---|---|---|
| fenitrothion-degrading bacteria | | | |
| Burkholderia sp. SFA1 | *Riptortus pedestris* | Gut | AGTTTGATCCTGGCTCAGA<br>TTGAACGCTGGCGGCATGC<br>CTTACACATGCAAGTCGAA<br>CGGCAGCACGGGGGCAAC<br>CCTGGTGGCGAGTGGCGA<br>ACGGGTGAGTAATACATCG<br>GAACGTGTCCTGTAGTGGG<br>GGATAGCCCGGCGAAAGC<br>CGGATTAATACCGCATACG<br>ACCTAAGGGAGAAAGCGGG<br>GGATCTTCGGACCTCGCGC<br>TATAGGGGCGGCCGATGG<br>CAGATTAGCTAGTTGGTGG<br>GGTAAAGGCCTACCAAGGC<br>GACGATCTGTAGCTGGTCT<br>GAGAGGACGACCAGCCACA<br>CTGGGACTGAGACACGGCC<br>CAGACTCCTACGGGAGGCA<br>GCAGTGGGGAATTTTGGAC<br>AATGGGGGCAACCCTGATC<br>CAGCAATGCCGCGTGTGTG<br>AAGAAGGCTTCGGGTTGTA<br>AAGCACTTTTGTCCGGAAA<br>GAAAACTTCGTCCCTAATAT<br>GGATGGAGGATGACGGTAC<br>CGGAAGAATAAGCACCGGC<br>TAACTACGTGCCAGCAGCC<br>GCGGTAATACGTAGGGTGC<br>GAGCGTTAATCGGAATTAC<br>TGGGCGTAAAGCGTGCGCA<br>GGCGGTCTGTTAAGACCGA<br>TGTGAAATCCCCGGGCTTA<br>ACCTGGGAACTGCATTGGT<br>GACTGGCAGGCTTTGAGTG<br>TGGCAGAGGGGGGTAGAAT<br>TCCACGTGTAGCAGTGAAA<br>TGCGTAGAGATGTGGAGGA<br>ATACCGATGGCGAAGGCAG<br>CCCCCTGGGCCAACTACTG<br>ACGCTCATGCACGAAAGCG<br>TGGGGAGCAAACAGGATTA<br>GATACCCTGGTAGTCCACG<br>CCCTAAACGATGTCAACTA<br>GTTGTTGGGGATTCATTTCC<br>TTAGTAACGTAGCTAACGC<br>GTGAAGTTGACCGCCTGGG<br>GAGTACGGTCGCAAGATTA<br>AAACTCAAAGGAATTGACG<br>GGGACCCGCACAAGCGGT<br>GGATGATGTGGATTAATTC<br>GATGCAACGCGAAAAACCT<br>TACCTACCCTTGACATGGT<br>CGGAACCCTGCTGAAAGGT<br>GGGGGTGCTCGAAAGAGAA<br>CCGGCGCACAGGTGCTGC<br>ATGGCTGTCGTCAGCTCGT<br>GTCGTGAGATGTTGGGTTA<br>AGTCCCGCAACGAGCGCAA<br>CCCTTGTCCTTAGTTGCTAC<br>GCAAGAGCACTCTAAGGAG<br>ACTGCCGGTGACAAACCGG |

TABLE 1-continued

Examples of Target Bacteria and Host Insects

| | | | |
|---|---|---|---|
| | | | AGGAAGGTGGGGATGACGT |
| | | | CAAGTCCTCATGGCCCTTA |
| | | | TGGGTAGGGCTTCACACGT |
| | | | CATACAATGGTCGGAACAG |
| | | | AGGGTTGCCAAGCCGCGA |
| | | | GGTGGAGCCAATCCCAGAA |
| | | | AACCGATCGTAGTCCGGAT |
| | | | CGCAGTCTGCAACTCGACT |
| | | | GCGTGAAGCTGGAATCGCT |
| | | | AGTAATCGCGGATCAGCAT |
| | | | GCCGCGGTGAATACGTTCC |
| | | | CGGGTCTTGTACACACCGC |
| | | | CCGTCACACCATGGGAGTG |
| | | | GGTTTCACCAGAAGTAGGT |
| | | | AGCCTAACCGCAAGGAGGG |
| | | | CGCTTACCACGGTGGGATT |
| | | | CATGACTGGGGTGAAGTCG |
| | | | TAACAAGGTAGC |
| | | | (SEQ ID NO: 28) |
| Burkholderia sp. KM-A | *Riptortus pedestris* | Gut | GCAACCCTGGTGGCGAGTG |
| | | | GCGAACGGGTGAGTAATAC |
| | | | ATCGGAACGTGTCCTGTAG |
| | | | TGGGGGATAGCCCGGCGA |
| | | | AAGCCGGATTAATACCGCA |
| | | | TACGATCTACGGAAGAAAG |
| | | | CGGGGGATCCTTCGGGAC |
| | | | CTCGCGCTATAGGGGCGG |
| | | | CCGATGGCAGATTAGCTAG |
| | | | TTGGTGGGGTAAAGGCCTA |
| | | | CCAAGGCGACGATCTGTAG |
| | | | CTGGTCTGAGAGGACGACC |
| | | | AGCCACACTGGGACTGAGA |
| | | | CACGGCCCAGACTCCTACG |
| | | | GGAGGCAGCAGTGGGGAA |
| | | | TTTTGGACAATGGGGGCAA |
| | | | CCCTGATCCAGCAATGCCG |
| | | | CGTGTGTGAAGAAGGCCTT |
| | | | CGGGTTGTAAAGCACTTTT |
| | | | GTCCGGAAAGAAAACGTCT |
| | | | TGGTTAATACCTGAGGCGG |
| | | | ATGACGGTACCGGAAGAAT |
| | | | AAGCACCGGCTAACTACGT |
| | | | GCCAGCAGCCGCGGTAATA |
| | | | CGTAGGGTGCGAGCGTTAA |
| | | | TCGGAATTACTGGGCGTAA |
| | | | AGCGTGCGCAGGCGGTCT |
| | | | GTTAAGACCGATGTGAAAT |
| | | | CCCCGGGCTTAACCTGGGA |
| | | | ACTGCATTGGTGACTGGCA |
| | | | GGCTTTGAGTGTGGCAGAG |
| | | | GGGGGTAGAATTCCACGTG |
| | | | TAGCAGTGAAATGCGTAGA |
| | | | GATGTGGAGGAATACCGAT |
| | | | GGCGAAGGCAGCCCCCTG |
| | | | GGCCAACACTGACGCTCAT |
| | | | GCACGAAAGCGTGGGGAG |
| | | | CAAACAGGATTAGATACCC |
| | | | TGGTAGTCCACGCCCTAAA |
| | | | CGATGTCAACTAGTTGTTG |
| | | | GGGATTCATTTCCTTAGTAA |
| | | | CGTAGCTAACGCGTGAAGT |
| | | | TGACCGCCTGGGGAGTACG |
| | | | GTCGCAAGATTAAAACTCAA |
| | | | AGGAATTGACGGGGACCCG |
| | | | CACAAGCGGTGGATGATGT |
| | | | GGATTAATTCGATGCAACG |
| | | | CGAAAAACCTTACCTACCCT |
| | | | TGACATGGTCGGAAGTCTG |
| | | | CTGAGAGGTGGACGTGCTC |
| | | | GAAAGAGAACCGGCGCACA |
| | | | GGTGCTGCATGGCTGTCGT |
| | | | CAGCTCGTGTCGTGAGATG |
| | | | TTGGGTTAAGTCCCGCAAC |
| | | | GAGCGCAACCCTTGTCCTT |
| | | | AGTTGCTACGCAAGAGCAC |
| | | | TCTAAGGAGACTGCCGGTG |
| | | | ACAAACCGGAGGAAGGTGG |

TABLE 1-continued

Examples of Target Bacteria and Host Insects

| | | | |
|---|---|---|---|
| | | | GGATGACGTCAAGTCCTCA |
| | | | TGGCCCTTATGGGTAGGGC |
| | | | TTCACACGTCATACAATGGT |
| | | | CGGAACAGAGGGTTGCCAA |
| | | | GCCGCGAGGTGGAGCCAA |
| | | | TCCCAGAAAACCGATCGTA |
| | | | GTCCGGATCGCAGTCTGCA |
| | | | ACTCGACTGCGTGAAGCTG |
| | | | GAATCGCTAGTAATCGCGG |
| | | | ATCAGCATGCCGCGGTGAA |
| | | | TACGTTCCCGGGTCTTGTA |
| | | | CACACCGCCCGTCACACCA |
| | | | TGGGAGTGGGTTTCACCAG |
| | | | AAGTAGGTAGCCTAACCGC |
| | | | AAGGAGGGCGCTTACCACG |
| | | | GTGGGATTCATGACTGGGG |
| | | | TGAAGT |
| | | | (SEQ ID NO: 29) |
| Burkholderia sp. KM-G | Riptortus pedestris | Gut | GCAACCCTGGTGGCGAGTG |
| | | | GCGAACGGGTGAGTAATAC |
| | | | ATCGGAACGTGTCCTGTAG |
| | | | TGGGGGATAGCCCGGCGA |
| | | | AAGCCGGATTAATACCGCA |
| | | | TACGACCTAAGGGAGAAAG |
| | | | CGGGGGATCTTCGGACCTC |
| | | | GCGCTATAGGGGCGGCCG |
| | | | ATGGCAGATTAGCTAGTTG |
| | | | GTGGGGTAAAGGCCTACCA |
| | | | AGGCGACGATCTGTAGCTG |
| | | | GTCTGAGAGGACGACCAGC |
| | | | CACACTGGGACTGAGACAC |
| | | | GGCCCAGACTCCTACGGGA |
| | | | GGCAGCAGTGGGGAATTTT |
| | | | GGACAATGGGGGCAACCCT |
| | | | GATCCAGCAATGCCGCGTG |
| | | | TGTGAAGAAGGCCTTCGGG |
| | | | TTGTAAAGCACTTTTGTCCG |
| | | | GAAAGAAAACTTCGAGGTT |
| | | | AATACCCTTGGAGGATGAC |
| | | | GGTACCGGAAGAATAAGCA |
| | | | CCGGCTAACTACGTGCCAG |
| | | | CAGCCGCGGTAATACGTAG |
| | | | GGTGCGAGCGTTAATCGGA |
| | | | ATTACTGGGCGTAAAGCGT |
| | | | GCGCAGGCGGTCTGTTAAG |
| | | | ACCGATGTGAAATCCCCGG |
| | | | GCTTAACCTGGGAACTGCA |
| | | | TTGGTGACTGGCAGGCTTT |
| | | | GAGTGTGGCAGAGGGGGG |
| | | | TAGAATTCCACGTGTAGCA |
| | | | GTGAAATGCGTAGAGATGT |
| | | | GGAGGAATACCGATGGCGA |
| | | | AGGCAGCCCCCTGGGCCA |
| | | | ACACTGACGCTCATGCACG |
| | | | AAAGCGTGGGGAGCAAACA |
| | | | GGATTAGATACCCTGGTAG |
| | | | TCCACGCCCTAAACGATGT |
| | | | CAACTAGTTGTTGGGGATT |
| | | | CATTTCCTTAGTAACGTAGC |
| | | | TAACGCGTGAAGTTGACCG |
| | | | CCTGGGGAGTACGGTCGCA |
| | | | AGATTAAAACTCAAAGGAAT |
| | | | TGACGGGACCCGCACAA |
| | | | GCGGTGGATGATGTGGATT |
| | | | AATTCGATGCAACGCGAAA |
| | | | AACCTTACCTACCCTTGACA |
| | | | TGGTCGGAAGTCTGCTGAG |
| | | | AGGTGGACGTGCTCGAAAG |
| | | | AGAACCGGCGCACAGGTG |
| | | | CTGCATGGCTGTCGTCAGC |
| | | | TCGTGTCGTGAGATGTTGG |
| | | | GTTAAGTCCCGCAACGAGC |
| | | | GCAACCCTTGTCCTTAGTT |
| | | | GCTACGCAAGAGCACTCTA |
| | | | AGGAGACTGCCGGTGACAA |
| | | | ACCGGAGGAAGGTGGGGA |
| | | | TGACGTCAAGTCCTCATGG |

TABLE 1-continued

Examples of Target Bacteria and Host Insects

|  |  |  |  |
|---|---|---|---|
|  |  |  | CCCTTATGGGTAGGGCTTC<br>ACACGTCATACAATGGTCG<br>GAACAGAGGGTTGCCAAGC<br>CGCGAGGTGGAGCCAATCC<br>CAGAAAACCGATCGTAGTC<br>CGGATCGCAGTCTGCAACT<br>CGACTGCGTGAAGCTGGAA<br>TCGCTAGTAATCGCGGATC<br>AGCATGCCGCGGTGAATAC<br>GTTCCCGGGTCTTGTACAC<br>ACCGCCCGTCACACCATGG<br>GAGTGGGTTTCACCAGAAG<br>TAGGTAGCCTAACCTGCAA<br>AGGAGGGCGCTTACCACG<br>(SEQ ID NO: 30) |

Nematodes

| Xiphinematobacter sp. | Xiphinema americanum | ovaries, developing eggs, and gut lining | GCAAGTCGAACGGAGTGGA<br>ACCTGCAGTAATGCAGATT<br>CGATTCAGTGGCGTACGGG<br>TGCGTAACACGTGAGTGAT<br>CTACCGGTAAGTGGGGGAT<br>AACCCGCCGAAAGGCGAAT<br>TAATACCGCATGTGGCTAG<br>GGATGCCTTCATCCTGTAG<br>CTAAAGTCGATTTTGACGCT<br>TTCTGATGAGCTCGCGGCC<br>TATCAGCTTGTTGGTGGAG<br>GTAATGGCCCACCAAGGCA<br>ATGACGGGTAGCTGGTCTG<br>AGAGGACGATCAGCCACAC<br>TGGAACTGAGACACGGTCC<br>AGACACCTACGGGTGGCAG<br>CAGTCGAGAATTTTTCACAA<br>TGGGGGAAACCCTGATGAA<br>GCAACGCCGCGTGGAGGA<br>TGAAGGGCTTCGCGCTCGT<br>AAACTCCTGTCAAGCGGGA<br>ACAAGAAAGTGATAGTACC<br>GCTAGAGGAAGAGACGGCT<br>AACTCTGTGCCAGCAGCCG<br>CGGTAATACAGAGGTCTCG<br>AGCGTTGTTCGGATTTATTG<br>GGCGTAAAGGGTGCGTAG<br>GCGGTGTGGCAAGTCAAGT<br>GTGAA<br>(SEQ ID NO: 31) |

Radopholus similis

| Wolbachia sp. wOo | Onchocerca ochengi | somatic hypodermal cords that run along the length of the worms and in the germinal zones of the female gonad | ATGCACACACATACCGGTTTT<br>ACTAAAAGAAATGCTATCGC<br>AACTTTCACCACAAAATGGT<br>AGTGTATATGTGGATGCCA<br>CATTTGGAGCTGGAGGATA<br>TAGTAAAGCAATATTGGAGT<br>CAGCTGATTGCAGAGTGTA<br>TGCAATCGACAGAGATGAA<br>ACGGTTATTAAATTTTATAA<br>TAGTTTGAATACCAAGTACC<br>ACGGTAAAATAAAACTATTT<br>ATTGAAAAGTTTAGCAATAT<br>TCAAACTATACTAAACAGTA<br>GTAATCTCAAACACTTTACA<br>GAACCTTCCGTCATTGTTTC<br>AGCTGGAATTCAGAAAAAA<br>AATGCAAGGTCAAGCACCG<br>AGATGATACAAAGTAATACC<br>GTAGATGGAGTTGTGTTCG<br>ATATAGGAGTATCGTCTATG<br>CAGCTTGATGAAGAAAATA<br>GAGGATTTTCATTTTTACAT<br>AACAGTCCGCTTGATATGC<br>GCATGGATACCTCTTCTCA<br>CATTAACGCTTCAATATTTG<br>TTAATGCCTTACGCGAAGA<br>AGAAATTGCAAACACTATAT |

TABLE 1-continued

Examples of Target Bacteria and Host Insects

|  |  |  | |
|---|---|---|---|
|  |  |  | ATAGCTATGGAGGTGAACG
TTATTCTCGCAAAATTGCAA
GAGCAATAGTGAACGTACG
TAAGAAAAAAACTATCGACA
CTACATTTGAGCTTGCAGA
CATTGTACGTTCCGTGGTAT
CTCGCGGAAAAAGCAAGAT
TGATCCTGCAACTAGGACA
TTTCAAGCAATCAGAATATG
GGTAAACGATGAGCTTAGA
GAGCTTGAAAAGGGTATTA
AAGCTGCATCCAAAATCTTA
AATAGGAATGGCAAGCTGA
TTGTCATTACTTTTCATTCC
TTGGAAGATCGTATAGTCAA
GACCTTTTTAAAGGCTTAT
GTGAGCCAAAATTCACCAA
CTGTAGAACGTTTTCTCTTC
TGAATAAAAAAGTAATCAAG
GCAAGCGCAGAAGAAATAA
GTGCAAATCCACGTGCGCG
TTCAGCAAAACTAAGAGCTA
TACAAAGGTTATTATGA
(SEQ ID NO: 32) |
| Snodgrassella alvi | Honeybee
(Apis
mellifera)
and Bombus
spp. | Ileum | GAGAGTTTGATCCTGGCTC
AGATTGAACGCTGGCGGCA
TGCCTTACACATGCAAGTC
GAACGGCAGCACGGAGAG
CTTGCTCTCTGGTGGCGAG
TGGCGAACGGGTGAGTAAT
GCATCGGAACGTACCGAGT
AATGGGGGATAACTGTCCG
AAAGGATGGCTAATACCGC
ATACGCCCTGAGGGGGAAA
GCGGGGATCGAAAGACCT
CGCGTTATTTGAGCGGCCG
ATGTTGGATTAGCTAGTTG
GTGGGGTAAAGGCCTACCA
AGGCGACGATCCATAGCGG
GTCTGAGAGGATGATCCGC
CACATTGGGACTGAGACAC
GGCCCAAACTCCTACGGGA
GGCAGCAGTGGGGAATTTT
GGACAATGGGGGGAACCCT
GATCCAGCCATGCCGCGTG
TCTGAAGAAGGCCTTCGGG
TTGTAAAGGACTTTTGTTAG
GGAAGAAAAGCCGGGTGTT
AATACCATCTGGTGCTGAC
GGTACCTAAAGAATAAGCA
CCGGCTAACTACGTGCCAG
CAGCCGCGGTAATACGTAG
GGTGCGAGCGTTAATCGGA
ATTACTGGGCGTAAAGCGA
GCGCAGACGGTTAATTAAG
TCAGATGTGAAATCCCCGA
GCTCAACTTGGGACGTGCA
TTTGAAACTGGTTAACTAGA
GTGTGTCAGAGGGAGGTAG
AATTCCACGTGTAGCAGTG
AAATGCGTAGAGATGTGGA
GGAATACCGATGGCGAAGG
CAGCCTCCTGGGATAACAC
TGACGTTCATGCTCGAAAG
CGTGGGTAGCAAACAGGAT
TAGATACCCTGGTAGTCCA
CGCCCTAAACGATGACAAT
TAGCTGTTGGGACACTAGA
TGTCTTAGTAGCGAAGCTA
ACGCGTGAAATTGTCCGCC
TGGGGAGTACGGTCGCAAG
ATTAAAACTCAAAGGAATTG
ACGGGGACCCGCACAAGC
GGTGGATGATGTGGATTAA
TTCGATGCAACGCGAAGAA
CCTTACCTGGTCTTGACAT
GTACGGAATCTCTTAGAGA |

TABLE 1-continued

Examples of Target Bacteria and Host Insects

| | | | |
|---|---|---|---|
| | | | TAGGAGAGTGCCTTCGGGA |
| | | | ACCGTAACACAGGTGCTGC |
| | | | ATGGCTGTCGTCAGCTCGT |
| | | | GTCGTGAGATGTTGGGTTA |
| | | | AGTCCCGCAACGAGCGCAA |
| | | | CCCTTGTCATTAGTTGCCAT |
| | | | CATTAAGTTGGGCACTCTAA |
| | | | TGAGACTGCCGGTGACAAA |
| | | | CCGGAGGAAGGTGGGGAT |
| | | | GACGTCAAGTCCTCATGGC |
| | | | CCTTATGACCAGGGCTTCA |
| | | | CACGTCATACAATGGTCGG |
| | | | TACAGAGGGTAGCGAAGCC |
| | | | GCGAGGTGAAGCCAATCTC |
| | | | AGAAAGCCGATCGTAGTCC |
| | | | GGATTGCACTCTGCAACTC |
| | | | GAGTGCATGAAGTCGGAAT |
| | | | CGCTAGTAATCGCAGGTCA |
| | | | GCATACTGCGGTGAATACG |
| | | | TTCCCGGGTCTTGTACACA |
| | | | CCGCCCGTCACACCATGGG |
| | | | AGTGGGGGATACCAGAATT |
| | | | GGGTAGACTAACCGCAAGG |
| | | | AGGTCGCTTAACACGGTAT |
| | | | GCTTCATGACTGGGGTGAA |
| | | | GTCGTAACAAGGTAGCCGT |
| | | | AG |
| | | | (SEQ ID NO: 33) |
| Gilliamella apicola | honeybee (Apis mellifera) and Bombus spp. | Ileum | TTAAATTGAAGAGTTTGATC |
| | | | ATGGCTCAGATTGAACGCT |
| | | | GGCGGCAGGCTTAACACAT |
| | | | GCAAGTCGAACGGTAACAT |
| | | | GAGTGCTTGCACTTGATGA |
| | | | CGAGTGGCGGACGGGTGA |
| | | | GTAAAGTATGGGGATCTGC |
| | | | CGAATGGAGGGGGACAACA |
| | | | GTTGGAAACGACTGCTAAT |
| | | | ACCGCATAAAGTTGAGAGA |
| | | | CCAAAGCATGGGACCTTCG |
| | | | GGCCATGCGCCATTTGATG |
| | | | AACCCATATGGGATTAGCT |
| | | | AGTTGGTAGGGTAATGGCT |
| | | | TACCAAGGCGACGATCTCT |
| | | | AGCTGGTCTGAGAGGATGA |
| | | | CCAGCCACACTGGAACTGA |
| | | | GACACGGTCCAGACTCCTA |
| | | | CGGGAGGCAGCAGTGGGG |
| | | | AATATTGCACAATGGGGGA |
| | | | AACCCTGATGCAGCCATGC |
| | | | CGCGTGTATGAAGAAGGCC |
| | | | TTCGGGTTGTAAAGTACTTT |
| | | | CGGTGATGAGGAAGGTGGT |
| | | | GTATCTAATAGGTGCATCAA |
| | | | TTGACGTTAATTACAGAAGA |
| | | | AGCACCGGCTAACTCCGTG |
| | | | CCAGCAGCCGCGGTAATAC |
| | | | GGAGGGTGCGAGCGTTAAT |
| | | | CGGAATGACTGGGCGTAAA |
| | | | GGGCATGTAGGCGGATAAT |
| | | | TAAGTTAGGTGTGAAAGCC |
| | | | CTGGGCTCAACCTAGGAAT |
| | | | TGCACTTAAAACTGGTTAAC |
| | | | TAGAGTATTGTAGAGGAAG |
| | | | GTAGAATTCCACGTGTAGC |
| | | | GGTGAAATGCGTAGAGATG |
| | | | TGGAGGAATACCGGTGGCG |
| | | | AAGGCGGCCTTCTGGACAG |
| | | | ATACTGACGCTGAGATGCG |
| | | | AAAGCGTGGGGAGCAAACA |
| | | | GGATTAGATACCCTGGTAG |
| | | | TCCACGCTGTAAACGATGT |
| | | | CGATTTGGAGTTTGTTGCCT |
| | | | AGAGTGATGGGCTCCGAAG |
| | | | CTAACGCGATAAATCGACC |
| | | | GCCTGGGGAGTACGGCCG |
| | | | CAAGGTTAAAACTCAAATGA |
| | | | ATTGACGGGGCCCGCACA |

TABLE 1-continued

Examples of Target Bacteria and Host Insects

| | | | |
|---|---|---|---|
| | | | AGCGGTGGAGCATGTGGTT<br>TAATTCGATGCAACGCGAA<br>GAACCTTACCTGGTCTTGA<br>CATCCACAGAATCTTGCAG<br>AGATGCGGGAGTGCCTTCG<br>GGAACTGTGAGACAGGTGC<br>TGCATGGCTGTCGTCAGCT<br>CGTGTTGTGAAATGTTGGG<br>TTAAGTCCCGCAACGAGCG<br>CAACCCTTATCCTTTGTTGC<br>CATCGGTTAGGCCGGGAAC<br>TCAAAGGAGACTGCCGTTG<br>ATAAAGCGGAGGAAGGTGG<br>GGACGACGTCAAGTCATCA<br>TGGCCCTTACGACCAGGGC<br>TACACACGTGCTACAATGG<br>CGTATACAAAGGGAGGCGA<br>CCTCGCGAGAGCAAGCGG<br>ACCTCATAAAGTACGTCTAA<br>GTCCGGATTGGAGTCTGCA<br>ACTCGACTCCATGAAGTCG<br>GAATCGCTAGTAATCGTGA<br>ATCAGAATGTCACGGTGAA<br>TACGTTCCCGGGCCTTGTA<br>CACACCGCCCGTCACACCA<br>TGGGAGTGGGTTGCACCAG<br>AAGTAGATAGCTTAACCTTC<br>GGGAGGGCGTTTACCACG<br>GTGTGGTCCATGACTGGGG<br>TGAAGTCGTAACAAGGTAA<br>CCGTAGGGGAACCTGCGGT<br>TGGATCACCTCCTTAC<br>(SEQ ID NO: 34) |
| *Bartonella apis* | honeybee<br>(*Apis mellifera*) | Gut | AAGCCAAAATCAAATTTTCA<br>ACTTGAGAGTTTGATCCTG<br>GCTCAGAACGAACGCTGGC<br>GGCAGGCTTAACACATGCA<br>AGTCGAACGCACTTTTCGG<br>AGTGAGTGGCAGACGGGT<br>GAGTAACGCGTGGGAATCT<br>ACCTATTTCTACGGAATAAC<br>GCAGAGAAATTTGTGCTAAT<br>ACCGTATACGTCCTTCGGG<br>AGAAAGATTTATCGGAGATA<br>GATGAGCCCGCGTTGGATT<br>AGCTAGTTGGTGAGGTAAT<br>GGCCCACCAAGGCGACGAT<br>CCATAGCTGGTCTGAGAGG<br>ATGACCAGCCACATTGGGA<br>CTGAGACACGGCCCAGACT<br>CCTACGGGAGGCAGCAGT<br>GGGGAATATTGGACAATGG<br>GCGCAAGCCTGATCCAGCC<br>ATGCCGCGTGAGTGATGAA<br>GGCCCTAGGGTTGTAAAGC<br>TCTTTCACCGGTGAAGATAA<br>TGACGGTAACCGGAGAAGA<br>AGCCCCGGCTAACTTCGTG<br>CCAGCAGCCGCGGTAATAC<br>GAAGGGGGCTAGCGTTGTT<br>CGGATTTACTGGGCGTAAA<br>GCGCACGTAGGCGGATATT<br>TAAGTCAGGGGTGAAATCC<br>CGGGGCTCAACCCCGGAA<br>CTGCCTTTGATACTGGATAT<br>CTTGAGTATGGAAGAGGTA<br>AGTGGAATTCCGAGTGTAG<br>AGGTGAAATTCGTAGATATT<br>CGGAGGAACACCAGTGGC<br>GAAGGCGGCTTACTGGTCC<br>ATTACTGACGCTGAGGTGC<br>GAAAGCGTGGGGAGCAAAC<br>AGGATTAGATACCCTGGTA<br>GTCCACGCTGTAAACGATG<br>AATGTTAGCCGTTGGACAG<br>TTTACTGTTCGGTGGCGCA<br>GCTAACGCATTAAACATTCC |

TABLE 1-continued

Examples of Target Bacteria and Host Insects

| | | | |
|---|---|---|---|
| | | | GCCTGGGGAGTACGGTCG
CAAGATTAAAACTCAAAGGA
ATTGACGGGGGCCCGCACA
AGCGGTGGAGCATGTGGTT
TAATTCGAAGCAACGCGCA
GAACCTTACCAGCCCTTGA
CATCCCGATCGCGGATGGT
GGAGACACCGTCTTTCAGT
TCGGCTGGATCGGTGACAG
GTGCTGCATGGCTGTCGTC
AGCTCGTGTCGTGAGATGT
TGGGTTAAGTCCCGCAACG
AGCGCAACCCTCGCCCTTA
GTTGCCATCATTTAGTTGG
GCACTCTAAGGGGACTGCC
GGTGATAAGCCGAGAGGAA
GGTGGGGATGACGTCAAGT
CCTCATGGCCCTTACGGGC
TGGGCTACACACGTGCTAC
AATGGTGGTGACAGTGGGC
AGCGAGACCGCGAGGTCG
AGCTAATCTCCAAAAGCCAT
CTCAGTTCGGATTGCACTC
TGCAACTCGAGTGCATGAA
GTTGGAATCGCTAGTAATC
GTGGATCAGCATGCCACGG
TGAATACGTTCCCGGGCCT
TGTACACACCGCCCGTCAC
ACCATGGGAGTTGGTTTTA
CCCGAAGGTGCTGTGCTAA
CCGCAAGGAGGCAGGCAA
CCACGGTAGGGTCAGCGAC
TGGGGTGAAGTCGTAACAA
GGTAGCCGTAGGGGAACCT
GCGGCTGGATCACCTCCTT
TCTAAGGAAGATGAAGAATT
GGAA
(SEQ ID NO: 35) |
| *Parasaccharibacter apium* | honeybee (*Apis mellifera*) | Gut | CTACCATGCAAGTCGCACG
AAACCTTTCGGGGTTAGTG
GCGGACGGGTGAGTAACG
CGTTAGGAACCTATCTGGA
GGTGGGGGATAACATCGG
GAAACTGGTGCTAATACCG
CATGATGCCTGAGGGCCAA
AGGAGAGATCCGCCATTGG
AGGGGCCTGCGTTCGATTA
GCTAGTTGGTTGGGTAAAG
GCTGACCAAGGCGATGATC
GATAGCTGGTTTGAGAGGA
TGATCAGCCACACTGGGAC
TGAGACACGCCCAGACTC
CTACGGGAGGCAGCAGTG
GGGAATATTGGACAATGGG
GGCAACCCTGATCCAGCAA
TGCCGCGTGTGTGAAGAAG
GTCTTCGGATTGTAAAGCA
CTTTCACTAGGGAAGATGA
TGACGGTACCTAGAGAAGA
AGCCCCGGCTAACTTCGTG
CCAGCAGCCGCGGTAATAC
GAAGGGGGCTAGCGTTGCT
CGGAATGACTGGGCGTAAA
GGGCGCGTAGGCTGTTTGT
ACAGTCAGATGTGAAATCC
CCGGGCTTAACCTGGGAAC
TGCATTTGATACGTGCAGA
CTAGAGTCCGAGAGAGGGT
TGTGGAATTCCCAGTGTAG
AGGTGAAATTCGTAGATATT
GGGAAGAACACCGGTTGCG
AAGGCGGCAACCTGGCTNN
NNNNNNNNNNNNNNNNNN
NNNNNNNNNNNNNNNNNN
NNNNNNNNNNNNNNNNNN
NNNNNNNNNNNNNNNNNN
NNNNNNNNNNNNNNNNNN |

TABLE 1-continued

Examples of Target Bacteria and Host Insects

| | | | |
|---|---|---|---|
| | | | NNNNNNNNNNNNNNNNN |
| | | | NNNNGAGCTAACGCGTTAA |
| | | | GCACACCGCCTGGGGAGTA |
| | | | CGGCCGCAAGGTTGAAACT |
| | | | CAAAGGAATTGACGGGGGC |
| | | | CCGCACAAGCGGTGGAGC |
| | | | ATGTGGTTTAATTCGAAGCA |
| | | | ACGCGCAGAACCTTACCAG |
| | | | GGCTTGCATGGGGAGGCT |
| | | | GTATTCAGAGATGGATATTT |
| | | | CTTCGGACCTCCCGCACAG |
| | | | GTGCTGCATGGCTGTCGTC |
| | | | AGCTCGTGTCGTGAGATGT |
| | | | TGGGTTAAGTCCCGCAACG |
| | | | AGCGCAACCCTTGTCTTTA |
| | | | GTTGCCATCACGTCTGGGT |
| | | | GGGCACTCTAGAGAGACTG |
| | | | CCGGTGACAAGCCGGAGG |
| | | | AAGGTGGGGATGACGTCAA |
| | | | GTCCTCATGGCCCTTATGT |
| | | | CCTGGGCTACACACGTGCT |
| | | | ACAATGGCGGTGACAGAGG |
| | | | GATGCTACATGGTGACATG |
| | | | GTGCTGATCTCAAAAAACC |
| | | | GTCTCAGTTCGGATTGTACT |
| | | | CTGCAACTCGAGTGCATGA |
| | | | AGGTGGAATCGCTAGTAAT |
| | | | CGCGGATCAGCATGCCGC |
| | | | GGTGAATACGTTCCCGGGC |
| | | | CTTGTACACACCGCCCGTC |
| | | | ACACCATGGGAGTTGGTTT |
| | | | GACCTTAAGCCGGTGAGCG |
| | | | AACCGCAAGGAACGCAGCC |
| | | | GACCACCGGTTCGGGTTCA |
| | | | GCGACTGGGGGA |
| | | | (SEQ ID NO: 36) |
| Lactobacillus kunkeei | honeybee (Apis mellifera) | Gut | TTCCTTAGAAAGGAGGTGA TCCAGCCGCAGGTTCTCCT ACGGCTACCTTGTTACGAC TTCACCCTAATCATCTGTCC CACCTTAGACGACTAGCTC CTAAAAGGTTACCCCATCG TCTTTGGGTGTTACAAACTC TCATGGTGTGACGGGCGGT GTGTACAAGGCCCGGGAAC GTATTCACCGTGGCATGCT GATCCACGATTACTAGTGAT TCCAACTTCATGCAGGCGA GTTGCAGCCTGCAATCCGA ACTGAGAATGGCTTTAAGA GATTAGCTTGACCTCGCGG TTTCGCGACTCGTTGTACC ATCCATTGTAGCACGTGTG TAGCCCAGCTCATAAGGGG CATGATGATTTGACGTCGT CCCCACCTTCCTCCGGTTT ATCACCGGCAGTCTCACTA GAGTGCCCAACTAAATGCT GGCAACTAATAATAAGGGT TGCGCTCGTTGCGGGACTT AACCCAACATCTCACGACA CGAGCTGACGACAACCATG CACCACCTGTCATTCTGTC CCCGAAGGGAACGCCCAAT CTCTTGGGTTGGCAGAAGA TGTCAAGAGCTGGTAAGGT TCTTCGCGTAGCATCGAATT AAACCACATGCTCCACCAC TTGTGCGGGCCCCCGTCAA TTCCTTTGAGTTTCAACCTT GCGGTCGTACTCCCCAGGC GGAATACTTAATGCGTTAG CTGCGGCACTGAAGGGCG GAAACCCTCCAACACCTAG TATTCATCGTTTACGGCATG GACTACCAGGGTATCTAAT CCTGTTCGCTACCCATGCT |

TABLE 1-continued

Examples of Target Bacteria and Host Insects

|  |  |  | TTCGAGCCTCAGCGTCAGT |
|---|---|---|---|
|  |  |  | AACAGACCAGAAAGCCGCC |
|  |  |  | TTCGCCACTGGTGTTCTTC |
|  |  |  | CATATATCTACGCATTTCAC |
|  |  |  | CGCTACACATGGAGTTCCA |
|  |  |  | CTTTCCTCTTCTGTACTCAA |
|  |  |  | GTTTTGTAGTTTCCACTGCA |
|  |  |  | CTTCCTCAGTTGAGCTGAG |
|  |  |  | GGCTTTCACAGCAGACTTA |
|  |  |  | CAAAACCGCCTGCGCTCGC |
|  |  |  | TTTACGCCCAATAAATCCG |
|  |  |  | GACAACGCTTGCCACCTAC |
|  |  |  | GTATTACCGCGGCTGCTGG |
|  |  |  | CACGTAGTTAGCCGTGGCT |
|  |  |  | TTCTGGTTAAATACCGTCAA |
|  |  |  | AGTGTTAACAGTTACTCTAA |
|  |  |  | CACTTGTTCTTCTTTAACAA |
|  |  |  | CAGAGTTTTACGATCCGAA |
|  |  |  | AACCTTCATCACTCACGCG |
|  |  |  | GCGTTGCTCCATCAGACTT |
|  |  |  | TCGTCCATTGTGGAAGATT |
|  |  |  | CCCTACTGCTGCCTCCCGT |
|  |  |  | AGGAGTCTGGGCCGTGTCT |
|  |  |  | CAGTCCCAATGTGGCCGAT |
|  |  |  | TACCCTCTCAGGTCGGCTA |
|  |  |  | CGTATCATCGTCTTGGTGG |
|  |  |  | GCTTTTATCTCACCAACTAA |
|  |  |  | CTAATACGGCGCGGGTCCA |
|  |  |  | TCCCAAAGTGATAGCAAAG |
|  |  |  | CCATCTTTCAAGTTGGAACC |
|  |  |  | ATGCGGTTCCAACTAATTAT |
|  |  |  | GCGGTATTAGCACTTGTTTC |
|  |  |  | CAAATGTTATCCCCCGCTTC |
|  |  |  | GGGGCAGGTTACCCACGTG |
|  |  |  | TTACTCACCAGTTCGCCACT |
|  |  |  | CGCTCCGAATCCAAAAATC |
|  |  |  | ATTTATGCAAGCATAAAATC |
|  |  |  | AATTTGGGAGAACTCGTTC |
|  |  |  | GACTTGCATGTATTAGGCA |
|  |  |  | CGCCGCCAGCGTTCGTCCT |
|  |  |  | GAGCCAGGATCAAACTCTC |
|  |  |  | ATCTTAA |
|  |  |  | (SEQ ID NO: 37) |
| Lactobacillus Firm-4 | honeybee (Apis mellifera) | Gut | ACGAACGCTGGCGGCGTG |
|  |  |  | CCTAATACATGCAAGTCGA |
|  |  |  | GCGCGGGAAGTCAGGGAA |
|  |  |  | GCCTTCGGGTGGAACTGGT |
|  |  |  | GGAACGAGCGGCGGATGG |
|  |  |  | GTGAGTAACACGTAGGTAA |
|  |  |  | CCTGCCCTAAAGCGGGGGA |
|  |  |  | TACCATCTGGAAACAGGTG |
|  |  |  | CTAATACCGCATAAACCCA |
|  |  |  | GCAGTCACATGAGTGCTGG |
|  |  |  | TTGAAAGACGGCTTCGGCT |
|  |  |  | GTCACTTTAGGATGGACCT |
|  |  |  | GCGGCGTATTAGCTAGTTG |
|  |  |  | GTGGAGTAACGGTTCACCA |
|  |  |  | AGGCAATGATACGTAGCCG |
|  |  |  | ACCTGAGAGGGTAATCGGC |
|  |  |  | CACATTGGGACTGAGACAC |
|  |  |  | GGCCCAAACTCCTACGGGA |
|  |  |  | GGCAGCAGTAGGGAATCTT |
|  |  |  | CCACAATGGACGCAAGTCT |
|  |  |  | GATGGAGCAACGCCGCGT |
|  |  |  | GGATGAAGAAGGTCTTCGG |
|  |  |  | ATCGTAAAATCCTGTTGTTG |
|  |  |  | AAGAAGAACGGTTGTGAGA |
|  |  |  | GTAACTGCTCATAACGTGA |
|  |  |  | CGGTAATCAACCAGAAAGT |
|  |  |  | CACGGCTAACTACGTGCCA |
|  |  |  | GCAGCCGCGGTAATACGTA |
|  |  |  | GGTGGCAAGCGTTGTCCGG |
|  |  |  | ATTTATTGGGCGTAAAGGG |
|  |  |  | AGCGCAGGCGGTCTTTTAA |
|  |  |  | GTCTGAATGTGAAAGCCCT |
|  |  |  | CAGCTTAACTGAGGAAGAG |
|  |  |  | CATCGGAAACTGAGAGACT |

TABLE 1-continued

Examples of Target Bacteria and Host Insects

TGAGTGCAGAAGAGGAGAG
TGGAACTCCATGTGTAGCG
GTGAAATGCGTAGATATAT
GGAAGAACACCAGTGGCGA
AGGCGGCTCTCTGGTCTGT
TACTGACGCTGAGGCTCGA
AAGCATGGGTAGCGAACAG
GATTAGATACCCTGGTAGT
CCATGCCGTAAACGATGAG
TGCTAAGTGTTGGGAGGTT
TCCGCCTCTCAGTGCTGCA
GCTAACGCATTAAGCACTC
CGCCTGGGGAGTACGACC
GCAAGGTTGAAACTCAAAG
GAATTGACGGGGGCCCGC
ACAAGCGGTGGAGCATGTG
GTTTAATTCGAAGCAACGC
GAAGAACCTTACCAGGTCT
TGACATCTCCTGCAAGCCT
AAGAGATTAGGGGTTCCCT
TCGGGGACAGGAAGACAG
GTGGTGCATGGTTGTCGTC
AGCTCGTGTCGTGAGATGT
TGGGTTAAGTCCCGCAACG
AGCGCAACCCTTGTTACTA
GTTGCCAGCATTAAGTTGG
GCACTCTAGTGAGACTGCC
GGTGACAAACCGGAGGAAG
GTGGGGACGACGTCAAATC
ATCATGCCCCTTATGACCT
GGGCTACACACGTGCTACA
ATGGATGGTACAATGAGAA
GCGAACTCGCGAGGGGAA
GCTGATCTCTGAAAACCATT
CTCAGTTCGGATTGCAGGC
TGCAACTCGCCTGCATGAA
GCTGGAATCGCTAGTAATC
GCGGATCAGCATGCCGCG
GTGAATACGTTCCCGGGCC
TTGTACACACCGCCC
(SEQ ID NO: 38)

Silk worm

| Enterococcus | Bombyx mori | Gut | AGGTGATCCAGCCGCACCT |
| | | | TCCGATACGGCTACCTTGT |
| | | | TACGACTTCACCCCAATCAT |
| | | | CTATCCCACCTTAGGCGGC |
| | | | TGGCTCCAAAAAGGTTACC |
| | | | TCACCGACTTCGGGTGTTA |
| | | | CAAACTCTCGTGGTGTGAC |
| | | | GGGCGGTGTGTACAAGGC |
| | | | CCGGGAACGTATTCACCGC |
| | | | GGCGTGCTGATCCGCGATT |
| | | | ACTAGCGATTCCGGCTTCA |
| | | | TGCAGGCGAGTTGCAGCCT |
| | | | GCAATCCGAACTGAGAGAA |
| | | | GCTTTAAGAGATTTGCATGA |
| | | | CCTCGCGGTCTAGCGACTC |
| | | | GTTGTACTTCCCATTGTAGC |
| | | | ACGTGTGTAGCCCAGGTCA |
| | | | TAAGGGGCATGATGATTTG |
| | | | ACGTCATCCCCACCTTCCT |
| | | | CCGGTTTGTCACCGGCAGT |
| | | | CTCGCTAGAGTGCCCAACT |
| | | | AAATGATGGCAACTAACAAT |
| | | | AAGGGTTGCGCTCGTTGCG |
| | | | GGACTTAACCCAACATCTC |
| | | | ACGACACGAGCTGACGACA |
| | | | ACCATGCACCACCTGTCAC |
| | | | TTTGTCCCCGAAGGGAAAG |
| | | | CTCTATCTCTAGAGTGGTCA |
| | | | AAGGATGTCAAGACCTGGT |
| | | | AAGGTTCTTCGCGTTGCTT |
| | | | CGAATTAAACCACATGCTC |
| | | | CACCGCTTGTGCGGGCCCC |
| | | | CGTCAATTCCTTTGAGTTTC |
| | | | AACCTTGCGGTCGTACTCC |

TABLE 1-continued

Examples of Target Bacteria and Host Insects

| | | | |
|---|---|---|---|
| | | | CCAGGCGGAGTGCTTAATG<br>CGTTTGCTGCAGCACTGAA<br>GGGCGGAAACCCTCCAACA<br>CTTAGCACTCATCGTTTACG<br>GCGTGGACTACCAGGGTAT<br>CTAATCCTGTTTGCTCCCCA<br>CGCTTTCGAGCCTCAGCGT<br>CAGTTACAGACCAGAGAGC<br>CGCCTTCGCCACTGGTGTT<br>CCTCCATATATCTACGCATT<br>TCACCGCTACACATGGAAT<br>TCCACTCTCCTCTTCTGCAC<br>TCAAGTCTCCCAGTTTCCAA<br>TGACCCTCCCCGGTTGAGC<br>CGGGGGCTTTCACATCAGA<br>CTTAAGAAACCGCCTGCGC<br>TCGCTTTACGCCCAATAAAT<br>CCGGACAACGCTTGCCACC<br>TACGTATTACCGCGGCTGC<br>TGGCACGTAGTTAGCCGTG<br>GCTTTCTGGTTAGATACCGT<br>CAGGGGACGTTCAGTTACT<br>AACGTCCTTGTTCTTCTCTA<br>ACAACAGAGTTTTACGATCC<br>GAAAACCTTCTTCACTCACG<br>CGGCGTTGCTCGGTCAGAC<br>TTTCGTCCATTGCCGAAGAT<br>TCCCTACTGCTGCCTCCCG<br>TAGGAGTCTGGGCCGTGTC<br>TCAGTCCCAGTGTGGCCGA<br>TCACCCTCTCAGGTCGGCT<br>ATGCATCGTGGCCTTGGTG<br>AGCCGTTACCTCACCAACT<br>AGCTAATGCACCGCGGGTC<br>CATCCATCAGCGACACCCG<br>AAAGCGCCTTTCACTCTTAT<br>GCCATGCGGCATAAACTGT<br>TATGCGGTATTAGCACCTG<br>TTTCCAAGTGTTATCCCCCT<br>CTGATGGGTAGGTTACCCA<br>CGTGTTACTCACCCGTCCG<br>CCACTCCTCTTTCCAATTGA<br>GTGCAAGCACTCGGGAGGA<br>AAGAAGCGTTCGACTTGCA<br>TGTATTAGGCACGCCGCCA<br>GCGTTCGTCCTGAGCCAGG<br>ATCAAACTCT<br>(SEQ ID NO: 39) |
| Delftia | Bombyx mori | Gut | CAGAAAGGAGGTGATCCAG<br>CCGCACCTTCCGATACGGC<br>TACCTTGTTACGACTTCACC<br>CCAGTCACGAACCCCGCCG<br>TGGTAAGCGCCCTCCTTGC<br>GGTTAGGCTACCTACTTCT<br>GGCGAGACCCGCTCCCATG<br>GTGTGACGGGCGGTGTGTA<br>CAAGACCCGGGAACGTATT<br>CACCGCGGCATGCTGATCC<br>GCGATTACTAGCGATTCCG<br>ACTTCACGCAGTCGAGTTG<br>CAGACTGCGATCCGGACTA<br>CGACTGGTTTTATGGGATTA<br>GCTCCCCCTCGCGGGTTGG<br>CAACCCTCTGTACCAGCCA<br>TTGTATGACGTGTGTAGCC<br>CCACCTATAAGGGCCATGA<br>GGACTTGACGTCATCCCCA<br>CCTTCCTCCGGTTTGTCAC<br>CGGCAGTCTCATTAGAGTG<br>CTCAACTGAATGTAGCAACT<br>AATGACAAGGGTTGCGCTC<br>GTTGCGGGACTTAACCCAA<br>CATCTCACGACACGAGCTG<br>ACGACAGCCATGCAGCACC<br>TGTGTGCAGGTTCTCTTTC<br>GAGCACGAATCCATCTCTG<br>GAAACTTCCTGCCATGTCA |

TABLE 1-continued

Examples of Target Bacteria and Host Insects

| | | | |
|---|---|---|---|
| | | | AAGGTGGGTAAGGTTTTTC<br>GCGTTGCATCGAATTAAAC<br>CACATCATCCACCGCTTGT<br>GCGGGTCCCCGTCAATTCC<br>TTTGAGTTTCAACCTTGCGG<br>CCGTACTCCCCAGGCGGTC<br>AACTTCACGCGTTAGCTTC<br>GTTACTGAGAAAACTAATTC<br>CCAACAACCAGTTGACATC<br>GTTTAGGGCGTGGACTACC<br>AGGGTATCTAATCCTGTTTG<br>CTCCCCACGCTTTCGTGCA<br>TGAGCGTCAGTACAGGTCC<br>AGGGGATTGCCTTCGCCAT<br>CGGTGTTCCTCCGCATATC<br>TACGCATTTCACTGCTACAC<br>GCGGAATTCCATCCCCCTC<br>TACCGTACTCTAGCCATGC<br>AGTCACAAATGCAGTTCCC<br>AGGTTGAGCCCGGGGATTT<br>CACATCTGTCTTACATAACC<br>GCCTGCGCACGCTTTACGC<br>CCAGTAATTCCGATTAACG<br>CTCGCACCCTACGTATTAC<br>CGCGGCTGCTGGCACGTA<br>GTTAGCCGGTGCTTATTCTT<br>ACGGTACCGTCATGGGCCC<br>CCTGTATTAGAAGGAGCTTT<br>TTCGTTCCGTACAAAAGCA<br>GTTTACAACCCGAAGGCCT<br>TCATCCTGCACGCGGCATT<br>GCTGGATCAGGCTTTCGCC<br>CATTGTCCAAAATTCCCCAC<br>TGCTGCCTCCCGTAGGAGT<br>CTGGGCCGTGTCTCAGTCC<br>CAGTGTGGCTGGTCGTCCT<br>CTCAGACCAGCTACAGATC<br>GTCGGCTTGGTAAGCTTTT<br>ATCCCACCAACTACCTAATC<br>TGCCATCGGCCGCTCCAAT<br>CGCGCGAGGCCCGAAGGG<br>CCCCCGCTTTCATCCTCAG<br>ATCGTATGCGGTATTAGCTA<br>CTCTTTCGAGTAGTTATCCC<br>CCACGACTGGGCACGTTCC<br>GATGTATTACTCACCCGTTC<br>GCCACTCGTCAGCGTCCGA<br>AGACCTGTTACCGTTCGAC<br>TTGCATGTGTAAGGCATGC<br>CGCCAGCGTTCAATCTGAG<br>CCAGGATCAAACTCTACAG<br>TTCGATCT<br>(SEQ ID NO: 40) |
| Pelomonas | Bombyx mori | Gut | ATCCTGGCTCAGATTGAAC<br>GCTGGCGGCATGCCTTACA<br>CATGCAAGTCGAACGGTAA<br>CAGGTTAAGCTGACGAGTG<br>GCGAACGGGTGAGTAATAT<br>ATCGGAACGTGCCCAGTCG<br>TGGGGGATAACTGCTCGAA<br>AGAGCAGCTAATACCGCAT<br>ACGACCTGAGGGTGAAAGC<br>GGGGGATCGCAAGACCTC<br>GCNNGATTGGAGCGGCCG<br>ATATCAGATTAGGTAGTTGG<br>TGGGGTAAAGGCCCACCAA<br>GCCAACGATCTGTAGCTGG<br>TCTGAGAGGACGACCAGCC<br>ACACTGGGACTGAGACACG<br>GCCCAGACTCCTACGGGAG<br>GCAGCAGTGGGGAATTTTG<br>GACAATGGGCGCAAGCCTG<br>ATCCAGCCATGCCGCGTGC<br>GGGAAGAAGGCCTTCGGGT<br>TGTAAACCGCTTTTGTCAG<br>GGAAGAAAAGGTTCTGGTT<br>AATACCTGGGACTCATGAC |

TABLE 1-continued

Examples of Target Bacteria and Host Insects

```
GGTACCTGAAGAATAAGCA
CCGGCTAACTACGTGCCAG
CAGCCGCGGTAATACGTAG
GGTGCAAGCGTTAATCGGA
ATTACTGGGCGTAAAGCGT
GCGCAGGCGGTTATGCAAG
ACAGAGGTGAAATCCCCGG
GCTCAACCTGGGAACTGCC
TTTGTGACTGCATAGCTAGA
GTACGGTAGAGGGGGATG
GAATTCCGCGTGTAGCAGT
GAAATGCGTAGATATGCGG
AGGAACACCGATGGCGAAG
GCAATCCCCTGGACCTGTA
CTGACGCTCATGCACGAAA
GCGTGGGGAGCAAACAGG
ATTAGATACCCTGGTAGTC
CACGCCCTAAACGATGTCA
ACTGGTTGTTGGGAGGGTT
TCTTCTCAGTAACGTANNTA
ACGCGTGAAGTTGACCGCC
TGGGGAGTACGGCCGCAA
GGTTGAAACTCAAAGGAAT
TGACGGGGACCCGCACAA
GCGGTGGATGATGTGGTTT
AATTCGATGCAACGCGAAA
AACCTTACCTACCCTTGACA
TGCCAGGAATCCTGAAGAG
ATTTGGGAGTGCTCGAAAG
AGAACCTGGACACAGGTGC
TGCATGGCCGTCGTCAGCT
CGTGTCGTGAGATGTTGGG
TTAAGTCCCGCAACGAGCG
CAACCCTTGTCATTAGTTGC
TACGAAAGGGCACTCTAAT
GAGACTGCCGGTGACAAAC
CGGAGGAAGGTGGGGATG
ACGTCAGGTCATCATGGCC
CTTATGGGTAGGGCTACAC
ACGTCATACAATGGCCGGG
ACAGAGGGCTGCCAACCCG
CGAGGGGGAGCTAATCCCA
GAAACCCGGTCGTAGTCCG
GATCGTAGTCTGCAACTCG
ACTGCGTGAAGTCGGAATC
GCTAGTAATCGCGGATCAG
CTTGCCGCGGTGAATACGT
TCCCGGGTCTTGTACACAC
CGCCCGTCACACCATGGGA
GCGGGTTCTGCCAGAAGTA
GTTAGCCTAACCGCAAGGA
GGGCGATTACCACGGCAG
GGTTCGTGACTGGGGTGAA
GTCGTAACAAGGTAGCCGT
ATCGGAAGGTGCGGCTGGA
TCAC
(SEQ ID NO: 41)
```

Any number of bacterial species may be targeted by the compositions or methods described herein. For example, in some instances, the modulating agent may target a single bacterial species. In some instances, the modulating agent may target at least about any of 1, 2, 3, 4, 5, 6, 7, 8, 9, 10, 15, 20, 30, 40, 50, 60, 70, 80, 90, 100, 150, 200, 250, 500, or more distinct bacterial species. In some instances, the modulating agent may target any one of about 1 to about 5, about 5 to about 10, about 10 to about 20, about 20 to about 50, about 50 to about 100, about 100 to about 200, about 200 to about 500, about 10 to about 50, about 5 to about 20, or about 10 to about 100 distinct bacterial species. In some instances, the modulating agent may target at least about any of 1, 2, 3, 4, 5, 6, 7, 8, 9, 10, 15, 20, 30, 40, 50, 60, 70, 80, 90, 100, or more phyla, classes, orders, families, or genera of bacteria.

In some instances, the modulating agent may increase a population of one or more bacteria by at least about any of 10%, 20%, 30%, 40%, 50%, 60%, 70%, 80%, 90% or more in the host. In some instances, the modulating agent may reduce the population of one or more bacteria by at least about any of 10%, 20%, 30%, 40%, 50%, 60%, 70%, 80%, 90%, or more in the host. In some instances, the modulating agent may eradicate the population of a bacterium in the host.

In some instances, the modulating agent may alter the bacterial diversity and/or bacterial composition of the host in comparison to a host organism to which the modulating agent has not been administered. In some instances, the modulating agent may increase the bacterial diversity in the host relative to a starting diversity by at least about any of 10%, 20%, 30%, 40%, 50%, 60%, 70%, 80%, 90%, or more in comparison to a host organism to which the modulating agent has not been administered. In some instances, the modulating agent may decrease the bacterial diversity in the host relative to a starting diversity by at least about any of 10%, 20%, 30%, 40%, 50%, 60%, 70%, 80%, 90%, or more in comparison to a host organism to which the modulating agent has not been administered.

In some instances, the modulating agent may alter the function, activity, growth, and/or division of one or more bacterial cells in comparison to a host organism to which the modulating agent has not been administered. For example, the modulating agent may alter the expression of one or genes in the bacteria. In some instances, the modulating agent may alter the function of one or more proteins in the bacteria. In some instances, the modulating agent may alter the function of one or more cellular structures (e.g., the cell wall, the outer or inner membrane) in the bacteria. In some instances, the modulating agent may kill (e.g., lyse) the bacteria.

The target bacterium may reside in one or more parts of the invertebrate host (e.g., insect, mollusk, or nematode). Further, the target bacteria may be intracellular or extracellular. In some instances, the bacteria reside in or on one or more parts of the host gut, including, e.g., the foregut, midgut, and/or hindgut. In some instances, the bacteria reside as an intracellular bacteria within a cell of the host. In some instances, the bacteria reside in a bacteriocyte of the host invertebrate (e.g., insect, mollusk, or nematode).

Changes to the populations of bacteria in the host invertebrate (e.g., insect, mollusk, or nematode) may be determined by any methods known in the art, such as standard culturing techniques, CFU counts, microarray, polymerase chain reaction (PCR), real-time PCR, flow cytometry, fluorescence microscopy, transmission electron microscopy, fluorescence in situ hybridization (e.g., FISH), spectrophotometry, matrix-assisted laser desorption ionization-mass spectrometry (MALDI-MS), or DNA sequencing. In some instances, a sample of the host treated with a modulating agent is sequenced (e.g., by metagenomics sequencing of 16S rRNA or rDNA) to determine the microbiome of the host after delivery or administration of the modulating agent. In some instances, a sample of a host that did not receive the modulating agent is also sequenced to provide a reference.

ii. Fungi and Yeast

Exemplary fungi that may be targeted in accordance with the methods and compositions provided herein, include, but are not limited to *Amylostereum areolatum*, Epichloe spp, *Pichia pinus, Hansenula capsulate, Daldinia decipien*, Ceratocytis spp, *Ophiostoma* spp, and *Attamyces bromatificus*. Non-limiting examples of yeast and yeast-like symbionts found in invertebrates (e.g., insect, mollusk, or nematode) include *Candida, Metschnikowia, Leucocoprinu* (e.g., *Leucocoprinus gongylophorus*), *Debaromyces, Scheffersomyces shehatae* and *Scheffersomyces stipites, Starmerella, Pichia, Trichosporon, Cryptococcus, Pseudozyma*, and yeast-like symbionts from the subphylum Pezizomycotina (e.g., *Symbiotaphrina bucneri* and *Symbiotaphrina kochii*). Non-limiting examples of yeast that may be targeted by the methods and compositions herein are listed in Table 2.

TABLE 2

Examples of Yeast in Insects

| Insect Species | Order: Family | Yeast Location (Species) |
| --- | --- | --- |
| *Stegobium paniceum* (=*Sitodrepa panicea*) | Coleoptera: Anobiidae | Mycetomes (*Saccharomyces*) Cecae (*Torulopsis buchnerii*) Mycetome between foregut and midgut Mycetomes (*Symbiotaphrina buchnerii*) Mycetomes and digestive tube (*Torulopsis buchnerii*) Gut cecae (*Symbiotaphrina buchnerii*) |
| *Lasioderma serricorne* | Coleoptera: Anobiidae | Mycetome between foregut and midgut (*Symbiotaphrina kochii*) |
| *Ernobius abietis* | Coleoptera: Anobiidae | Mycetomes (*Torulopsis karawaiewii*) (*Candida karawaiewii*) |
| *Ernobius mollis* | Coleoptera: Anobiidae | Mycetomes (*Torulopsis ernobii*) (*Candida ernobii*) |
| *Hemicoelus gibbicollis* | Coleoptera: Anobiidae | Larval mycetomes |
| *Xestobium plumbeum* | Coleoptera: Anobiidae | Mycetomes (*Torulopsis xestobii*) (*Candida xestobii*) |
| *Criocephalus rusticus* | Coleoptera: Cerambycidae | Mycetomes |
| *Phoracantha semipunctata* | Coleoptera: Cerambycidae | Alimentary canal (*Candida guilliermondii, C. tenuis*) Cecae around midgut (*Candida guilliermondii*) |
| *Harpium inquisitor* | Coleoptera: Cerambycidae | Mycetomes (*Candida rhagii*) |
| *Harpium mordax* *H. sycophanta* | Coleoptera: Cerambycidae | Cecae around midgut (*Candida tenuis*) |
| *Gaurotes virginea* | Coleoptera: Cerambycidae | Cecae around midgut (*Candida rhagii*) |
| *Leptura rubra* | Coleoptera: Cerambycidae | Cecae around midgut (*Candida tenuis*) Cecae around midgut (*Candida parapsilosis*) |

TABLE 2-continued

Examples of Yeast in Insects

| Insect Species | Order: Family | Yeast Location (Species) |
|---|---|---|
| *Leptura maculicornis* | Coleoptera: Cerambycidae | Cecae around midgut (*Candida parapsilosis*) |
| *L. cerambyciformis* | | |
| *Leptura sanguinolenta* | Coleoptera: Cerambycidae | Cecae around midgut (*Candida* sp.) |
| *Rhagium bifasciatum* | Coleoptera: Cerambycidae | Cecae around midgut (*Candida tenuis*) |
| *Rhagium inquisitor* | Coleoptera: Cerambycidae | Cecae around midgut (*Candida guilliermondii*) |
| *Rhagium mordax* | Coleoptera: Cerambycidae | Cecae around midgut (*Candida*) |
| *Carpophilus hemipterus* | Coleoptera: Nitidulidae | Intestinal tract (10 yeast species) |
| *Odontotaenius disjunctus* | Coleoptera: Passalidae | Hindgut (*Enteroramus dimorphus*) |
| *Odontotaenius disjunctus* | Coleoptera: Passalidae | Gut (*Pichia stipitis, P. segobiensis, Candida shehatae*) |
| *Verres sternbergianus* | | (*C. ergatensis*) |
| *Scarabaeus semipunctatus* | Coleoptera: Scarabaeidae | Digestive tract (10 yeast species) |
| *Chironitis furcifer* | | |
| Unknown species | Coleoptera: Scarabaeidae | Guts (*Trichosporon cutaneum*) |
| *Dendroctonus* and *Ips* spp. | Coleoptera: Scolytidae | Alimentary canal (13 yeast species) |
| *Dendroctonus frontalis* | Coleoptera: Scolytidae | Midgut (*Candida* sp.) |
| *Ips sexdentatus* | Coleoptera: Scolytidae | Digestive tract (*Pichia bovis, P. rhodanensis*) Hansenula holstii (*Candida rhagii*) Digestive tract (*Candida pulcherina*) |
| *Ips typographus* | Coleoptera: Scolytidae | Alimentary canal Alimentary tracts (*Hansenula capsulata, Candida parapsilosis*) Guts and beetle homogenates (*Hansenula holstii, H. capsulata, Candida diddensii, C. mohschtana, C. nitratophila, Cryptococcus albidus, C. laurentii*) |
| *Trypodendron lineatum* | Coleoptera: Scolytidae | Not specified |
| *Xyloterinus politus* | Coleoptera: Scolytidae | Head, thorax, abdomen (*Candida, Pichia*, Saccharomycopsis) |
| *Periplaneta americana* | Dictyoptera: Blattidae | Hemocoel (*Candida* sp. nov.) |
| *Blatta orientalis* | Dictyoptera: Blattidae | Intestinal tract (*Kluyveromyces blattae*) |
| *Blatella germanica* | Dictyoptera: Blattellidae | Hemocoel |
| *Cryptocercus punctulatus* | Dictyoptera: Cryptocercidae | Hindgut (1 yeast species) |
| *Philophylla heraclei* | Diptera: Tephritidae | Hemocoel |
| *Aedes* (4 species) | Diptera: Culicidae | Internal microflora (9 yeast genera) |
| *Drosophila pseudoobscura* | Diptera: Drosophilidae | Alimentary canal (24 yeast species) |
| *Drosophila* (5 spp.) | Diptera: Drosophilidae | Crop (42 yeast species) |
| *Drosophila melanogaster* | Diptera: Drosophilidae | Crop (8 yeast species) |
| *Drosophila* (4 spp.) | Diptera: Drosophilidae | Crop (7 yeast species) |
| *Drosophila* (6 spp.) | Diptera: Drosophilidae | Larval gut (17 yeast species) |
| *Drosophila* (20 spp.) | Diptera: Drosophilidae | Crop (20 yeast species) |
| *Drosophila* (8 species groups) | Diptera: Drosophilidae | Crop (*Kloeckera, Candida, Kluyveromyces*) |
| *Drosophila serido* | Diptera: Drosophilidae | Crop (18 yeast species) |
| *Drosophila* (6 spp.) | Diptera: Drosophilidae | Intestinal epithelium (*Coccidiascus legeri*) |
| *Protaxymia melanoptera* | Diptera | Unknown (*Candida, Cryptococcus, Sporoblomyces*) |
| *Astegopteryx styraci* | Homoptera: Aphididae | Hemocoel and fat body |
| *Tuberaphis* sp. | Homoptera: Aphididae | Tissue sections |
| *Hamiltonaphis styraci* | | |
| *Glyphinaphis bambusae* | | |
| *Cerataphis* sp. | | |
| *Hamiltonaphis styraci* | Homoptera: Aphididae | Abdominal hemocoel |
| *Cofana unimaculata* | Homoptera: Cicadellidae | Fat body |
| *Leofa unicolor* | Homoptera: Cicadellidae | Fat body |
| Lecaniines, etc. | Homoptera: Coccoidea d | Hemolymph, fatty tissue, etc. |

TABLE 2-continued

Examples of Yeast in Insects

| Insect Species | Order: Family | Yeast Location (Species) |
|---|---|---|
| *Lecanium* sp. | Homoptera: Coccidae | Hemolymph, adipose tissue |
| *Ceroplastes* (4 sp.) | Homoptera: Coccidae | Blood smears |
| *Laodelphax striatellus* | Homoptera: Delphacidae | Fat body |
| | | Eggs |
| | | Eggs (*Candida*) |
| *Nilaparvata lugens* | Homoptera: Delphacidae | Fat body |
| | | Eggs (2 unidentified yeast species) |
| | | Eggs, nymphs (*Candida*) |
| | | Eggs (7 unidentified yeast species) |
| | | Eggs (*Candida*) |
| *Nisia nervosa* | Homoptera: Delphacidae | Fat body |
| *Nisia grandiceps* | | |
| *Perkinsiella* spp. | | |
| *Sardia rostrata* | | |
| *Sogatella furcifera* | | |
| *Sogatodes orizicola* | Homoptera: Delphacidae | Fat body |
| *Amrasca devastans* | Homoptera: Jassidae | Eggs, mycetomes, hemolymph |
| *Tachardina lobata* | Homoptera: Kerriidae | Blood smears (*Torulopsis*) |
| *Laccifer* (=*Lakshadia*) sp. | Homoptera: Kerriidae | Blood smears (*Torula variabilis*) |
| *Comperia merceti* | Hymenoptera: Encyrtidae | Hemolymph, gut, poison gland |
| *Solenopsis invicta* | Hymenoptera: Formicidae | Hemolymph (*Myrmecomyces annellisae*) |
| *S. quinquecuspis* | | |
| *Solenopsis invicta* | Hymenoptera: Formicidae | Fourth instar larvae (*Candida parapsilosis, Yarrowia lipolytica*) |
| | | Gut and hemolymph (*Candida parapsilosis, C. lipolytica, C. guillermondii, C. rugosa, Debaryomyces hansenii*) |
| *Apis mellifera* | Hymenoptera: Apidae | Digestive tracts (*Torulopsis* sp.) |
| | | Intestinal tract (*Torulopsis apicola*) |
| | | Digestive tracts (8 yeast species) |
| | | Intestinal contents (12 yeast species) |
| | | Intestinal contents (7 yeast species) |
| | | Intestines (14 yeast species) |
| | | Intestinal tract (*Pichia melissophila*) |
| | | Intestinal tracts (7 yeast species) |
| | | Alimentary canal (*Hansenula silvicola*) |
| | | Crop and gut (13 yeast species) |
| *Apis mellifera* | Hymenoptera: Apidae | Midguts (9 yeast genera) |
| *Anthophora occidentalis* | Hymenoptera: Anthophoridae | |
| *Nomia melanderi* | Hymenoptera: Halictidae | |
| *Halictus rubicundus* | Hymenoptera: Halictidae | |
| *Megachile rotundata* | Hymenoptera: Megachilidae | |

Any number of fungal species may be targeted by the compositions or methods described herein. For example, in some instances, the modulating agent may target a single fungal species. In some instances, the modulating agent may target at least about any of 1, 2, 3, 4, 5, 6, 7, 8, 9, 10, 15, 20, 30, 40, 50, 60, 70, 80, 90, 100, 150, 200, 250, 500, or more distinct fungal species. In some instances, the modulating agent may target any one of about 1 to about 5, about 5 to about 10, about 10 to about 20, about 20 to about 50, about 50 to about 100, about 100 to about 200, about 200 to about 500, about 10 to about 50, about 5 to about 20, or about 10 to about 100 distinct fungal species. In some instances, the modulating agent may target at least about any of 1, 2, 3, 4, 5, 6, 7, 8, 9, 10, 15, 20, 30, 40, 50, 60, 70, 80, 90, 100, or more phyla, classes, orders, families, or genera of fungi.

In some instances, the modulating agent may increase a population of one or more fungi by at least about any of 10%, 20%, 30%, 40%, 50%, 60%, 70%, 80%, 90% or more in the host in comparison to a host organism to which the modulating agent has not been administered. In some instances, the modulating agent may reduce the population of one or more fungi by at least about any of 10%, 20%, 30%, 40%, 50%, 60%, 70%, 80%, 90% or more in the host in comparison to a host organism to which the modulating agent has not been administered. In some instances, the modulating agent may eradicate the population of a fungi in the host.

In some instances, the modulating agent may alter the fungal diversity and/or fungal composition of the host. In some instances, the modulating agent may increase the fungal diversity in the host relative to a starting diversity by at least about any of 10%, 20%, 30%, 40%, 50%, 60%, 70%, 80%, 90%, or more in comparison to a host organism to which the modulating agent has not been administered. In some instances, the modulating agent may decrease the fungal diversity in the host relative to a starting diversity by at least about any of 10%, 20%, 30%, 40%, 50%, 60%, 70%, 80%, 90%, or more in comparison to a host organism to which the modulating agent has not been administered.

In some instances, the modulating agent may alter the function, activity, growth, and/or division of one or more fungi. For example, the modulating agent may alter the expression of one or more genes in the fungus. In some instances, the modulating agent may alter the function of one or more proteins in the fungus. In some instances, the modulating agent may alter the function of one or more cellular components in the fungus. In some instances, the modulating agent may kill the fungus.

Further, the target fungus may reside in one or more parts of the insect. In some instances, the fungus resides in or on one or more parts of the insect gut, including, e.g., the foregut, midgut, and/or hindgut. In some instances, the fungus lives extracellularly in the hemolymph, fat bodies or in specialized structures in the host.

Changes to the population of fungi in the host may be determined by any methods known in the art, such as microarray, polymerase chain reaction (PCR), real-time PCR, flow cytometry, fluorescence microscopy, transmission electron microscopy, fluorescence in situ hybridization (e.g., FISH), spectrophotometry, matrix-assisted laser desorption ionization-mass spectrometry (MALDI-MS), and DNA sequencing. In some instances, a sample of the host treated with a modulating agent is sequenced (e.g., by metagenomics sequencing) to determine the microbiome of the host after delivery or administration of the modulating agent. In some instances, a sample of a host that did not receive the modulating agent is also sequenced to provide a reference.

III. Modulating Agents

The modulating agent of the methods and compositions provided herein may include a polypeptide, a nucleic acid, small molecule, or any combination thereof. In some instances, the modulating agent is a nucleic acid molecule (e.g., DNA molecule or RNA molecule, e.g., mRNA, guide RNA (gRNA), or inhibitory RNA molecule (e.g., siRNA, shRNA, or miRNA), or a hybrid DNA-RNA molecule), a small molecule, a peptide, or a polypeptide (e.g., an antibody molecule, e.g., an antibody or antigen binding fragment thereof). Any of these agents can be used to alter the microbiota of a host invertebrate (e.g., insect, mollusk, or nematode) by targeting pathways in the host and/or resident microorganisms (e.g., pathways that mediate host-microbiota interactions, e.g., host immune system pathways or bacteriocyte pathways). For example, any modulating agents described herein may be used to regulate (e.g., to induce or to inhibit) a gene or protein in the host or a microorganism resident in the host (e.g., a protein or a gene encoding a protein listed in Table 7, Table 8, or Table 9).

i. Polypeptides

The modulating agent described herein may include a polypeptide (e.g., antibody). In some instances, the modulating agent described herein includes a polypeptide or functional fragments or derivative thereof, which target pathways in the host invertebrate (e.g., insect, mollusk, or nematode) and/or resident microorganisms (e.g., pathways that mediate host-microbiota interactions, e.g., host immune system pathways or bacteriocyte pathways). In some instances, the agent is a polypeptide listed in Table 7, Table 8, or Table 9, wherein the primary sequence of the agent polypeptide is provided by reference to its accession number.

A modulating agent including a polypeptide as described herein can be contacted with the target host in an amount and for a time sufficient to: (a) reach a target level (e.g., a predetermined or threshold level) of concentration inside a target host; (b) reach a target level (e.g., a predetermined or threshold level) of concentration inside a target host gut; (c) reach a target level (e.g., a predetermined or threshold level) of concentration inside a target host bacteriocyte; (d) modulate the level, or an activity, of one or more microorganism (e.g., endosymbiont) in the target host; or/and (e) modulate fitness of the target host.

Polypeptides included herein may include naturally occurring polypeptides or recombinantly produced variants. In some instances, the polypeptide may be a functional fragments or variants thereof (e.g., an enzymatically active fragment or variant thereof of polypeptide listed in Table 7, Table 8, or Table 9). Such fragments or variants can be made and screened for similar activity as described herein and would be equivalent hereunder in the methods and compositions disclosed). For example, the polypeptide may be a functionally active variant of any of the polypeptides described herein with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity, e.g., over a specified region or over the entire sequence, to a sequence of a polypeptide described herein or a naturally occurring polypeptide. In some instances, the polypeptide may have at least 50% (e.g., at least 50%, 60%, 70%, 80%, 90%, 95%, 97%, 99%, or greater) identity to the amino acid sequence of a protein listed in Table 7, Table 8, or Table 9 with reference to the accession number provided.

Methods of making a therapeutic polypeptide are routine in the art. See, in general, *Smales & James (Eds.), Therapeutic Proteins: Methods and Protocols (Methods in Molecular Biology), Humana Press* (2005); *and Crommelin, Sindelar & Meibohm (Eds.), Pharmaceutical Biotechnology: Fundamentals and Applications, Springer* (2013).

Methods for producing a polypeptide involve expression in mammalian cells, although recombinant proteins can also be produced using insect cells, yeast, bacteria, or other cells under the control of appropriate promoters. Mammalian expression vectors may comprise nontranscribed elements such as an origin of replication, a suitable promoter and enhancer, and other 5' or 3' flanking nontranscribed sequences, and 5' or 3' nontranslated sequences such as necessary ribosome binding sites, a polyadenylation site, splice donor and acceptor sites, and termination sequences. DNA sequences derived from the SV40 viral genome, for example, SV40 origin, early promoter, enhancer, splice, and polyadenylation sites may be used to provide the other genetic elements required for expression of a heterologous DNA sequence. Appropriate cloning and expression vectors for use with bacterial, fungal, yeast, and mammalian cellular hosts are described in *Green & Sambrook, Molecular Cloning: A Laboratory Manual (Fourth Edition), Cold Spring Harbor Laboratory Press* (2012).

Various mammalian cell culture systems can be employed to express and manufacture a recombinant polypeptide agent (e.g., listed in Tables 4, 5, or 6). Examples of mammalian expression systems include CHO cells, COS cells, HeLA and BHK cell lines. Processes of host cell culture for production of protein therapeutics are described in, e.g., *Zhou and Kantardjieff (Eds.), Mammalian Cell Cultures for Biologics Manufacturing (Advances in Biochemical Engineering/Biotechnology), Springer* (2014). Purification of protein therapeutics is described in *Franks, Protein Biotechnology: Isolation, Characterization, and Stabilization, Humana Press* (2013); *and in Cutler, Protein Purification Protocols (Methods in Molecular Biology), Humana Press* (2010). Formulation of protein therapeutics is described in *Meyer (Ed.), Therapeutic Protein Drug Products: Practical*

*Approaches to formulation in the Laboratory, Manufacturing, and the Clinic,* Woodhead Publishing Series (2012).

The polypeptide modulating agents discussed hereinafter, namely antibodies, bacteriocins, antimicrobial peptides, and bacteriocyte regulatory peptides, can be used to alter pathways in the host that mediate interactions between the host and microorganisms resident in the host as indicated in the sections for increasing or decreasing the fitness of hosts.

(a) Antibodies

In some instances, the modulating agent includes an antibody or antigen binding fragment thereof. For example, an agent described herein may be an antibody that blocks or potentiates activity and/or function of a component of the host immune system pathway or bacteriocyte regulatory pathway listed in Table 8 or Table 9. The antibody may act as an antagonist or agonist of a polypeptide (e.g., enzyme or cell receptor) in the host or microorganisms resident in the host, including any proteins list in Table 7, Table 8, or Table 9.

The making and use of antibodies against a target antigen (e.g., proteins that mediate host-microbiota interactions, e.g., host immune system proteins or bacteriocyte proteins, e.g., proteins in Table 7, Table 8, or Table 9) is known in the art. See, for example, Zhiqiang An (Ed.), *Therapeutic Monoclonal Antibodies: From Bench to Clinic,* 1st Edition, Wiley, 2009 and also Greenfield (Ed.), *Antibodies: A Laboratory Manual,* 2nd Edition, Cold Spring Harbor Laboratory Press, 2013, for methods of making recombinant antibodies, including antibody engineering, use of degenerate oligonucleotides, 5'-RACE, phage display, and mutagenesis; antibody testing and characterization; antibody pharmacokinetics and pharmacodynamics; antibody purification and storage; and screening and labeling techniques.

(b) Bacteriocins

The modulating agent described herein may include a bacteriocin. In some instances, the bacteriocin is naturally produced by Gram-positive bacteria, such as *Pseudomonas, Streptomyces, Bacillus, Staphylococcus*, or lactic acid bacteria (LAB, such as *Lactococcus lactis*). In some instances, the bacteriocin is naturally produced by Gram-negative bacteria, such as *Hafnia alvei, Citrobacter freundii, Klebsiella oxytoca, Klebsiella pneumonia, Enterobacter cloacae, Serratia plymithicum, Xanthomonas campestris, Erwinia carotovora, Ralstonia solanacearum*, or *Escherichia coli*. Exemplary bacteriocins include, but are not limited to, Class I-IV LAB antibiotics (such as lantibiotics), colicins, microcins, and pyocins. Non-limiting examples of bacteriocins are listed in Table 3.

TABLE 3

Examples of Bacteriocins

| Class | Name | Producer | Targets | Sequence |
|---|---|---|---|---|
| Class I | Nisin | *Lactococcus lactis* | Active on Gram-positive bacteria: *Enterococcus, Lactobacillus, Lactococcus, Leuconostoc, Listeria, Clostridium* | ITSISLCTPGCKT GALMGCNMKTA TCHCSIHVSK (SEQ ID NO: 42) |
| | Epidermin | *Staphylococcus epidermis* | Gram-positive bacteria | IASKFICTPGCAK TGSFNSYCC (SEQ ID NO: 43) |
| Class II | | | | |
| Class II a | Pediocin PA-1 | *Pediococcus acidilactici* | *Pediococci, Lactobacilli, Leuconostoc, Brochothrix thermosphacta, Propionibacteria, Bacilli, Enterococci, Staphylococci, Listeria clostridia, Listeria monocytogenes, Listeria innocua* | KYYGNGVTCG KHSCSVDWGK ATTCIINNGAMA WATGGHQGNHK C (SEQ ID NO: 44) |
| Class II b | Enterocin P | *Enterococcus faecium* | *Lactobacillus sakei, Enterococcus faecium* | ATRSYGNGVYC NNSKCWVNWGE AKENIAGIVISGW ASGLAGMGH (SEQ ID NO: 45) |
| Class II c | Lactococcin G | *Streptococcus lactis* | Gram-positive bacteria | GTWDDIGQGIGR VAYWVGKAMGN MSDVNQASRINR KKKH (SEQ ID NO: 46) |
| Class II d | Lactacin-F | *Lactobacillus johnsonii* | *Lactobacilli, Enterococcus faecalis* | NRWGDTVLSAA SGAGTGIKACKS FGPWGMAICGV GGAAIGGYFGYT HN (SEQ ID NO: 47) |

TABLE 3-continued

Examples of Bacteriocins

| Class | Name | Producer | Targets | Sequence |
|---|---|---|---|---|
| Class III | | | | |
| Class III a | Enterocin AS-48 | Enterococcus faecalis | Broad spectrum: Gram positive and Gram negative bacteria. | MAKEFGIPAAVA GTVLNVVEAGG WVTTIVSILTAVG SGGLSLLAAAGR ESIKAYLKKEIKK KGKRAVIAW (SEQ ID NO: 48) |
| Class III b | Aureocin A70 | Staphylococcus aureus | Broad spectrum: Gram positive and Gram negative bacteria. | MSWLNFLKYIAK YGKKAVSAAWK YKGKVLEWLNV GPTLEWVWQKL KKIAGL (SEQ ID NO: 49) |
| Class IV | Garvicin A | Lactococcus garvieae | Broad spectrum: Gram positive and Gram negative bacteria. | IGGALGNALNGL GTWANMMNGG GFVNQWQVYAN KGKINQYRPY (SEQ ID NO: 50) |
| Unclassified | Colicin V | Escherichia coli | Active against Escherichia coli (also closely related bacteria), Enterobacteriaceae | MRTLTLNELDSV SGGASGRDIAMA IGTLSGQFVAGGI GAAAGGVAGGAI YDYASTHKPNPA MSPSGLGGTIKQ KPEGIPSEAWNY AAGRLCNWSPN NLSDVCL (SEQ ID NO: 51) |

In some instances, the bacteriocin is a colicin, a pyocin, or a microcin produced by Gram-negative bacteria. In some instances, the bacteriocin is a colicin. The colicin may be a group A colicin (e.g., uses the Tol system to penetrate the outer membrane of a target bacterium) or a group B colicin (e.g., uses the Ton system to penetrate the outer membrane of a target bacterium). In some instances, the bacteriocin is a microcin. The microcin may be a class I microcin (e.g., <5 kDa, has post-translational modifications) or a class II microcin (e.g., 5-10 kDa, with or without post-translational modifications). In some instances, the class II microcin is a class IIa microcin (e.g., requires more than one genes to synthesize and assemble functional peptides) or a class IIb microcin (e.g., linear peptides with or without post-translational modifications at C-terminus). In some instances, the bacteriocin is a pyocin. In some instances, the pyocin is an R-pyocin, F-pyocin, or S-pyocin.

In some instances, the bacteriocin is a class I, class II, class III, or class IV bacteriocin produced by Gram-positive bacteria. In some instances, the modulating agent includes a Class I bacteriocin (e.g., lanthionine-containing antibiotics (lantibiotics) produced by a Gram-positive bacteria). The class I bacteriocins or lantibiotic may be a low molecular weight peptide (e.g., less than about 5 kDa) and may possess post-translationally modified amino acid residues (e.g., lanthionine, β-methyllanthionine, or dehydrated amino acids).

In some instances, the bacteriocin is a Class II bacteriocin (e.g., non-lantibiotics produced by Gram-positive bacteria). Many are positively charged, non-lanthionine-containing peptides, which unlike lantibiotics, do not undergo extensive post-translational modification. The Class II bacteriocin may belong to one of the following subclasses: "pediocin-like" bacteriocins (e.g., pediocin PA-1 and carnobacteriocin X (Class IIa)); two-peptide bacteriocins (e.g., lactacin F and ABP-118 (Class IIb)); circular bacteriocins (e.g., carnocyclin A and and enterocin AS-48 (Class IIc)); or unmodified, linear, non-pediocin-like bacteriocins (e.g., epidermicin NI01 and lactococcin A (Class IId)).

In some instances, the bacteriocin is a Class III bacteriocin (e.g., produced by Gram-positive bacteria). Class III bacteriocins may have a molecular weight greater than 10 kDa and may be heat unstable proteins. The Class III bacteriocins can be further subdivided into Group IIIA and Group IIIB bacteriocins. The Group IIIA bacteriocins include bacteriolytic enzymes which kill sensitive strains by lysis of the cell well, such as Enterolisin A. Group IIIB bacteriocins include non-lytic proteins, such as Caseicin 80, Helveticin J, and lactacin B.

In some instances, the bacteriocin is a Class IV bacteriocin (e.g., produced by Gram-positive bacteria). Class IV bacteriocins are a group of complex proteins, associated with other lipid or carbohydrate moieties, which appear to be required for activity. They are relatively hydrophobic and heat stable. Examples of Class IV bacteriocins leuconocin S, lactocin 27, and lactocin S.

In some instances, the bacteriocin is an R-type bacteriocin. R-type bacteriocins are contractile bacteriocidal protein complexes. Some R-type bacteriocins have a contractile phage-tail-like structure. The C-terminal region of the phage tail fiber protein determines target-binding specificity. They may attach to target cells through a receptor-binding protein, e.g., a tail fiber. Attachment is followed by sheath contraction and insertion of the core through the envelope of the target bacterium. The core penetration results in a rapid depolarization of the cell membrane potential and prompt cell death. Contact with a single R-type bacteriocin particle can result in cell death. An R-type bacteriocin, for example, may be thermolabile, mild acid resistant, trypsin resistant, sedimentable by centrifugation, resolvable by electron microscopy, or a combination thereof. Other R-type bacteriocins may be complex molecules including multiple proteins, polypeptides, or subunits, and may resemble a tail structure of bacteriophages of the myoviridae family. In naturally occurring R-type bacteriocins, the subunit structures may be encoded by a bacterial genome, such as that of *C. difficile* or *P. aeruginosa* and form R-type bacteriocins to serve as natural defenses against other bacteria. In some instances, the R-type bacteriocin is a pyocin. In some instances, the pyocin is an R-pyocin, F-pyocin, or S-pyocin.

In some instances, the bacteriocin is a functionally active variant of the bacteriocins described herein. In some instances, the variant of the bacteriocin has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity, e.g., over a specified region or over the entire sequence, to a sequence of a bacteriocin described herein or a naturally occurring bacteriocin.

In some instances, the bacteriocin may be bioengineered, according to standard methods, to modulate their bioactivity, e.g., increase or decrease or regulate, or to specify their target microorganisms. In other instances, the bacteriocin is produced by the translational machinery (e.g. a ribosome, etc.) of a microbial cell. In some instances, the bacteriocin is chemically synthesized. Some bacteriocins can be derived from a polypeptide precursor. The polypeptide precursor can undergo cleavage (e.g., processing by a protease) to yield the polypeptide of the bacteriocin itself. As such, in some instances, the bacteriocin is produced from a precursor polypeptide. In some other instances, the bacteriocin includes a polypeptide that has undergone post-translational modifications, for example, cleavage, or the addition of one or more functional groups.

The bacteriocins described herein may be formulated in a composition for any of the uses described herein. The compositions disclosed herein may include any number or type (e.g., classes) of bacteriocins, such as at least about any one of 1 bacteriocin, 2, 3, 4, 5, 10, 15, 20, 30, 40, 50, 100, or more bacteriocins. Suitable concentrations of each bacteriocin in the compositions described herein depends on factors such as efficacy, stability of the bacteriocin, number of distinct bacteriocin types in the compositions, formulation, and methods of application of the composition. In some instances, each bacteriocin in a liquid composition is from about 0.01 ng/ml to about 100 mg/mL. In some instances, each bacteriocin in a solid composition is from about 0.01 ng/g to about 100 mg/g. In some instances, wherein the composition includes at least two types of bacteriocins, the concentration of each type of the bacteriocins may be the same or different. In some instances, the bacteriocin is provided in a composition including a bacterial cell that secretes the bacteriocin. In some instances, the bacteriocin is provided in a composition including a polypeptide (e.g., a polypeptide isolated from a bacterial cell).

Bacteriocins may neutralize (e.g., kill) at least one microorganism other than the individual bacterial cell in which the polypeptide is made, including cells clonally related to the bacterial cell and other microbial cells. As such, a bacterial cell may exert cytotoxic or growth-inhibiting effects on a plurality of microbial organisms by secreting bacteriocins. In some instances, the bacteriocin targets and kills one or more species of bacteria resident in the host via cytoplasmic membrane pore formation, cell wall interference (e.g., peptidoglycanase activity), or nuclease activity (e.g., DNase activity, 16S rRNase activity, or tRNase activity).

In some instances, the bacteriocin has a neutralizing activity. Neutralizing activity of bacteriocins may include, but is not limited to, arrest of microbial reproduction, or cytotoxicity. Some bacteriocins have cytotoxic activity, and thus can kill microbial organisms, for example bacteria, yeast, algae, and the like. Some bacteriocins can inhibit the reproduction of microbial organisms, for example bacteria, yeast, algae, and the like, for example by arresting the cell cycle.

In some instances, the bacteriocin has killing activity. The killing mechanism of bacteriocins is specific to each group of bacteriocins. In some instances, the bacteriocin has narrow-spectrum bioactivity. Bacteriocins are known for their very high potency against their target strains. Some bacteriocin activity is limited to strains that are closely related to the bacteriocin producer strain (narrow-spectrum bioactivity). In some instances, the bacteriocin has broad-spectrum bioactivity against a wide range of genera.

In some instances, bacteriocins interact with a receptor molecule or a docking molecule on the target bacterial cell membrane. For example, nisin is extremely potent against its target bacterial strains, showing antimicrobial activity even at a single-digit nanomolar concentration. The nisin molecule has been shown to bind to lipid II, which is the main transporter of peptidoglycan subunits from the cytoplasm to the cell wall In some instances, the bacteriocin has anti-fungal activity. A number of bacteriocins with anti-yeast or anti-fungal activity have been identified. For example, bacteriocins from *Bacillus* have been shown to have neutralizing activity against some yeast strains (see, for example, Adetunji and Olaoye, *Malaysian Journal of Microbiology* 9:130-13, 2013). In another example, an *Enterococcus faecalis* peptide has been shown to have neutralizing activity against *Candida* species (see, for example, Shekh and Roy, *BMC Microbiology* 12:132, 2012). In another example, bacteriocins from *Pseudomonas* have been shown to have neutralizing activity against fungi, such as *Curvularia lunata, Fusarium* species, *Helminthosporium* species, and *Biopolaris* species (see, for example, Shalani and Srivastava, *The Internet Journal of Microbiology* Volume 5 Number 2, 2008). In another example, botrycidin AJ1316 and alirin B1 from *B. subtilis* have been shown to have antifungal activities.

A modulating agent including a bacteriocin as described herein can be contacted with the target host in an amount and for a time sufficient to: (a) reach a target level (e.g., a predetermined or threshold level) of bacteriocin concentration inside a target host; (b) reach a target level (e.g., a predetermined or threshold level) of bacteriocin concentration inside a target host gut; (c) reach a target level (e.g., a predetermined or threshold level) of bacteriocin concentration inside a target host bacteriocyte; (d) modulate the level, or an activity, of one or more microorganism (e.g., endosymbiont) in the target host; or/and (e) modulate fitness of the target host.

As illustrated by Example 5, bacteriocins (e.g., colA produced by a transgenic plant) can be used as a modulating agent that targets a host pathway (e.g., an insect, e.g., an aphid) that alters the activity, levels, or metabolism of endosymbiotic bacteria resident in the host, such as a *Buchnera* spp., to modulate (e.g., decrease) the fitness of the host.

(c) Antimicrobial Peptides

The modulating agent described herein may include an antimicrobial peptide (AMP). Any AMP suitable for inhibiting a microorganism resident in the host may be used. AMPs are a diverse group of molecules, which are divided into subgroups on the basis of their amino acid composition and structure. The AMP may be derived or produced from any organism that naturally produces AMPs, including AMPs derived from plants (e.g., copsin), insects (e.g., mastoparan, poneratoxin, cecropin, moricin, melittin), frogs (e.g., magainin, dermaseptin, aurein), and mammals (e.g., cathelicidins, defensins and protegrins). Non-limiting examples of AMPs are listed in Table 4.

TABLE 4

Examples of Antimicrobial Peptides

| Type | Characteristic | Example AMP | Sequence |
|---|---|---|---|
| Anionic peptides | rich in glutamic and aspartic acid | dermcidin | SSLLEKGLDGAKKAVGGLGKL GKDAVEDLESVGKGAVHDVKD VLDSVL (SEQ ID NO: 52) |
| Linear cationic α-helical peptides | lack cysteine | cecropin A | KWKLFKKIEKVGQNIRDGIIKAG PAVAVVGQATQIAK (SEQ ID NO: 53) |
| | | andropin | MKYFSVLVVLTLILAIVDQSDAFI NLLDKVEDALHTGAQAGFKLIR PVERGATPKKSEKPEK (SEQ ID NO: 54) |
| | | moricin | MNILKFFFVPIVAMSLVSCSTAA PAKIPIKAIKTVGKAVGKGLRAI NIASTANDVFNFLKPKKRKH (SEQ ID NO: 55) |
| | | ceratotoxin | MANLKAVFLICIVAFIALQCVVA EPAAEDSVVVKRSIGSALKKAL PVAKKIGKIALPIAKAALPVAAG LVG (SEQ ID NO: 56) |
| Cationic peptide enriched for specific amino acid | rich in proline, arginine, phenylalanine, glycine, tryptophan | abaecin | MKVVIFIFALLATICAAFAYVPLP NVPQPGRRPFPTFPGQGPFNP KIKWPQGY (SEQ ID NO: 57) |
| | | apidaecins | KNFALAILVVTFVVAVFGNTNLD PPTRPTRLRREAKPEAEPGNN RPVYIPQPRPPHPRLRREAEPE AEPGNNRPVYIPQPRPPHPRL RREAELEAEPGNNRPVYISQP RPPHPRLRREAEPEAEPGNNR PVYIPQPRPPHPRLRREAELEA EPGNNRPVYISQPRPPHPRLR REAEPEAEPGNNRPVYIPQPR PPHPRLRREAEPEAEPGNNRP VYIPQPRPPHPRLRREAEPEAE PGNNRPVYIPQPRPPHPRLRR EAKPEAKPGNNRPVYIPQPRP PHPRI (SEQ ID NO: 58) |
| | | prophenin | METQRASLCLGRWSLWLLLLA LVVPSASAQALSYREAVLRAVD RLNEQSSEANLYRLLELDQPPK ADEDPGTPKPVSFTVKETVCP RPTRRPPELCDFKENGRVKQC VGTVTLDQIKDPLDITCNEGVR RFPWWWPFLRRPRLRRQAFP PPNVPGPRFPPPNVPGPRFPP PNFPGPRFPPPNFPGPRFPPP NFPGPPFPPPIFPGPWFPPPPP FRPPPFGPPRFPGRR (SEQ ID NO: 59) |
| | | indolicidin | MQTQRASLSLGRWSLWLLLLG LVVPSASAQALSYREAVLRAVD QLNELSSEANLYRLLELDPPPK DNEDLGTRKPVSFTVKETVCP RTIQQPAEQCDFKEKGRVKQC VGTVTLDPSNDQFDLNCNELQ SVILPWKWPWWPWRRG (SEQ ID NO: 60) |
| Anionic and cationic peptides that contain | contain 1-3 disulfide bond | protegrin | METQRASLCLGRWSLWLLLLA LVVPSASAQALSYREAVLRAVD RLNEQSSEANLYRLLELDQPPK ADEDPGTPKPVSFTVCP |

TABLE 4-continued

Examples of Antimicrobial Peptides

| Type | Characteristic | Example AMP | Sequence |
|---|---|---|---|
| | cysteine and form disulfide bonds | | RPTRQPPELCDFKENGRVKQC VGTVTLDQIKDPLDITCNEVQG VRGGRLCYCRRRFCVCVGRG (SEQ ID NO: 61) |
| | | tachyplesins | KWCFRVCYRGICYRRCR (SEQ ID NO: 62) |
| | | defensin | MKCATIVCTIAVVLAATLLNGSV QAAPQEEAALSGGANLNTLLD ELPEETHHAALENYRAKRATC DLASGFGVGSSLCAAHCIARR YRGGYCNSKAVCVCRN (SEQ ID NO: 63) |
| | | drosomycin | MMQIKYLFALFAVLMLVVLGAN EADADCLSGRYKGPCAVWDN ETCRRVCKEEGRSSGHCSPSL KCWCEGC (SEQ ID NO: 64) |

The AMP may be active against any number of target microorganisms. In some instances, the AMP may have antibacterial and/or antifungal activities. In some instances, the AMP may have a narrow-spectrum bioactivity or a broad-spectrum bioactivity. For example, some AMPs target and kill only a few species of bacteria or fungi, while others are active against both gram-negative and gram-positive bacteria as well as fungi.

Further, the AMP may function through a number of known mechanisms of action. For example, the cytoplasmic membrane is a frequent target of AMPs, but AMPs may also interfere with DNA and protein synthesis, protein folding, and cell wall synthesis. In some instances, AMPs with net cationic charge and amphipathic nature disrupt bacterial membranes leading to cell lysis. In some instances, AMPs may enter cells and interact with intracellular target to interfere with DNA, RNA, protein, or cell wall synthesis. In addition to killing microorganisms, AMPs have demonstrated a number of immunomodulatory functions that are involved in the clearance of infection, including the ability to alter host gene expression, act as chemokines and/or induce chemokine production, inhibit lipopolysaccharide induced pro-inflammatory cytokine production, promote wound healing, and modulating the responses of dendritic cells and cells of the adaptive immune response.

In some instances, the AMP is a functionally active variant of the AMPs described herein. In some instances, the variant of the AMP has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity, e.g., over a specified region or over the entire sequence, to a sequence of an AMP described herein or a naturally derived AMP.

In some instances, the AMP may be bioengineered to modulate its bioactivity, e.g., increase or decrease or regulate, or to specify a target microorganism. In some instances, the AMP is produced by the translational machinery (e.g. a ribosome, etc.) of a cell. In some instances, the AMP is chemically synthesized. In some instances, the AMP is derived from a polypeptide precursor. The polypeptide precursor can undergo cleavage (for example, processing by a protease) to yield the polypeptide of the AMP itself. As such, in some instances, the AMP is produced from a precursor polypeptide. In some instances, the AMP includes a polypeptide that has undergone post-translational modifications, for example, cleavage, or the addition of one or more functional groups.

The AMPs described herein may be formulated in a composition for any of the uses described herein. The compositions disclosed herein may include any number or type (e.g., classes) of AMPs, such as at least about any one of 1 AMP, 2, 3, 4, 5, 10, 15, 20, or more AMPs. A suitable concentration of each AMP in the composition depends on factors such as efficacy, stability of the AMP, number of distinct AMP in the composition, the formulation, and methods of application of the composition. In some instances, each AMP in a liquid composition is from about 0.1 ng/mL to about 100 mg/mL. In some instances, each AMP in a solid composition is from about 0.1 ng/g to about 100 mg/g. In some instances, wherein the composition includes at least two types of AMPs, the concentration of each type of AMP may be the same or different.

A modulating agent including an AMP as described herein can be contacted with the target host in an amount and for a time sufficient to: (a) reach a target level (e.g., a predetermined or threshold level) of AMP concentration inside a target host; (b) reach a target level (e.g., a predetermined or threshold level) of AMP concentration inside a target host gut; (c) reach a target level (e.g., a predetermined or threshold level) of AMP concentration inside a target host bacteriocyte; (d) modulate the level, or an activity, of one or more microorganism (e.g., endosymbiont) in the target host; or/and (e) modulate fitness of the target host.

(d) Bacteriocyte Regulatory Peptides

The modulating agent described herein may include a bacteriocyte regulatory peptide (BRP). BRPs are peptides expressed in the bacteriocytes of insects. These genes are expressed first at a developmental time point coincident with the incorporation of symbionts and their bacteriocyte-specific expression is maintained throughout the insect's life. In some instances, the BRP has a hydrophobic amino terminal domain, which is predicted to be a signal peptide. In addition, some BRPs have a cysteine-rich domain. In some instances, the bacteriocyte regulatory peptide is a bacteriocyte-specific cysteine rich (BCR) protein. Bacteriocyte regulatory peptides have a length between about 40 and 150 amino acids. In some instances, the bacteriocyte regulatory peptide has a length in the range of about 45 to about 145, about 50 to about 140, about 55 to about 135, about 60 to about 130, about 65 to about 125, about 70 to about 120, about 75 to about 115, about 80 to about 110, about 85 to about 105, or any range therebetween. Non-limiting examples of BRPs and their activities are listed in Table 5.

TABLE 5

Examples of Bacteriocyte Regulatory Peptides

| Name | Peptide Sequence |
|---|---|
| Bacteriocyte-specific cysteine rich proteins BCR family, peptide BCR1 | MKLLHGFLIIMLTMHLSIQYAYGGPFLTKYLCDRVCHKLC GDEFVCSCIQYKSLKGLWFPHCPTGKASVVLHNFLTSP (SEQ ID NO: 65) |
| Bacteriocyte-specific cysteine rich proteins BCR family, peptide BCR2 | MKLLYGFLIIMLTIHLSVQYFESPFETKYNCDTHCNKLCGK IDHCSCIQYHSMEGLWFPHCRTGSAAQMLHDFLSNP (SEQ ID NO: 66) |
| Bacteriocyte-specific cysteine rich proteins BCR family, peptide BCR3 | MSVRKNVLPTMFVVLLIMSPVTPTSVFISAVCYSGCGSLA LVCFVSNGITNGLDYFKSSAPLSTSETSCGEAFDTCTDH CLANFKF (SEQ ID NO: 67) |
| Bacteriocyte-specific cysteine rich proteins BCR family, peptide BCR4 | MRLLYGFLIIMLTIYLSVQDFDPTEFKGPFPTIEICSKYCAV VCNYTSRPCYCVEAAKERDQWFPYCYD (SEQ ID NO: 68) |
| Bacteriocyte-specific cysteine rich proteins BCR family, peptide BCR5 | MRLLYGFLIIMLTIHLSVQDIDPNTLRGPYPTKEICSKYCEY NVVCGASLPCICVQDARQLDHWFACCYDGGPEMLM (SEQ ID NO: 69) |
| Secreted proteins SP family, peptide SP1 | MKLFVVVLVAVGIMFVFASDTAAAPTDYEDTNDMISLSS LVGDNSPYVRVSSADSGGSSKTSSKNPILGLLKSVIKLLT KIFGTYSDAAPAMPPIPPALRKNRGMLA (SEQ ID NO: 70) |
| Secreted proteins SP family, peptide SP2 | MVACKVILAVAVVFVAAVQGRPGGEPEWAAPIFAELKSV SDNITNLVGLDNAGEYATAAKNNLNAFAESLKTEAAVFSK SFEGKASASDVFKESTKNFQAVVDTYIKNLPKDLTLKDFT EKSEQALKYMVEHGTEITKKAQGNTETEKEIKEFFKKQIE NLIGQGKALQAKIAEAKKA (SEQ ID NO: 71) |
| Secreted proteins SP family, peptide SP3 | MKTSSSKVFASCVAIVCLASVANALPVQKSVAATTENPIV EKHGCRAHKNLVRQNVVDLKTYDSMLITNEVVQKQSNE VQSSEQSNEGQNSEQSNEGQNSEQSNEVQSSEHSNEG QNSKQSNEGQNSEQSNEVQSSEHSNEGQNSEQSNEVQ SSEHSNEGQNSKQSNEGQNSKQSNEVQSSEHWNEGQ NSKQSNEDQNSEQSNEGQNSKQSNEGQNSKQSNEDQ NSEQSNEGQNSKQSNEVQSSEQSNEGQNSKQSNEGQS SEQSNEGQNSKQSNEVQSPEEHYDLPDPESSYESEETK GSHESGDDSEHR (SEQ ID NO: 72) |
| Secreted proteins SP family, peptide SP4 | MKTIILGLCLFGALFWSTQSMPVGEVAPAVPAVPSEAVP QKQVEAKPETNAASPVSDAKPESDSKPVDAEVKPTVSEV KAESEQKPSGEPKPESDAKPVVASESKPESDPKPAAVVE SKPENDAVAPETNNDAKPENAAAPVSENKPATDAKAETE LIAQAKPESKPASDLKAEPEAAKPNSEVPVALPLNPTETK ATQQSVETNQVEQAAPAAAQADPAAAPAADPAPAPAAA PVAAEEAKLSESAPSTENKAAEEPSKPAEQQSAKPVEDA VPAASEISETKVSPAVPAVPEVPASPSAPAVADPVSAPEA EKNAEPAKAANSAEPAVQSEAKPAEDIQKSGAVVSAENP KPVEEQKPAEVAKPAEQSKSEAPAEAPKPTEQSAAEEPK KPESANDEKKEQHSVNKRDATKEKKPTDSIMKKQKQKK AN (SEQ ID NO: 73) |
| Secreted proteins SP family, peptide SP5a | MNGKIVLCFAVVFIGQAMSAATGTTPEVEDIKKVAEQMS QTFMSVANHLVGITPNSADAQKSIEKIRTIMNKGFTDMET EANKMKDIVRKNADPKLVEKYDELEKELKKHLSTAKDMF EDKVVKPIGEKVELKKITENVIKTTKDMEATMNKAIDGFKK Q (SEQ ID NO: 74) |
| Secreted proteins SP family, peptide SP6 | MHLFLALGLFIVCGMVDATFYNPRSQTFNQLMERRQRSI PIPYSYGYHYNPIEPSINVLDSLSEGLDSRINTFKPIYQNV KMSTQDVNSVPRTQYQPKNSLYDSEYISAKDIPSLFPEE DSYDYKYLGSPLNKYLTRPSTQESGIAINLVAIKETSVFDY GFPTYKSPYSSDSVWNFGSKIPNTVFEDPQSVESDPNTF KVSSPTIKIVKLLPETPEQESIITTTKNYELNYKTTQETPTE AELYPITSEEFQTEDWHPMVPKENTTKDESSFITTEEPL TEDKSNSITIEKTQTEDESNSIEFNSIRTEEKSNSITTEENQ |

TABLE 5-continued

Examples of Bacteriocyte Regulatory Peptides

| Name | Peptide Sequence |
|---|---|
| | KEDDESMSTTSQETTTAFNLNDTFDTNRYSSSHESLMLR IRELMKNIADQQNKSQFRTVDNIPAKSQSNLSSDESTNQ QFEPQLVNGADTYK (SEQ ID NO: 75) |
| Coleoptericin A, ColA peptide | MTRTMLFLACVAALYVCISATAGKPEEFAKLSDEAPSND QAMYESIQRYRRFVDGNRYNGGQQQQQQPKQWEVRP DLSRDQRGNTKAQVEINKKGDNHDINAGWGKNINGPDS HKDTWHVGGSVRW (SEQ ID NO: 76) |
| RIpA Type I | MKETTVVWAKLFLILIILAKPLGLKAVNECKRLGNNSCRSH GECCSGFCFIEPGWALGVCKRLGTPKKSDDSNNGKNIEK NNGVHERIDDVFERGVCSYYKGPSITANGDVFDENEMTA AHRTLPFNTMVKVEGMGTSVVVKINDRKTAADGKVMLLS RAAAESLNIDENTGPVQCQLKFVLDGSGCTPDYGDTCVL HHECCSQNCFREMFSDKGFCLPK (SEQ ID NO: 77) |

In some instances, the BRP alters the growth and/or activity of one or more bacteria resident in the bacteriocyte of the host. In some instances, the BRP may be bioengineered to modulate its bioactivity (e.g., increase, decrease, or regulate) or to specify a target microorganism. In some instances, the BRP is produced by the translational machinery (e.g. a ribosome, etc.) of a cell. In some instances, the BRP is chemically synthesized. In some instances, the BRP is derived from a polypeptide precursor. The polypeptide precursor can undergo cleavage (for example, processing by a protease) to yield the polypeptide of the BRP itself. As such, in some instances, the BRP is produced from a precursor polypeptide. In some instances, the BRP includes a polypeptide that has undergone post-translational modifications, for example, cleavage, or the addition of one or more functional groups.

Functionally active variants of the BRPs as described herein are also useful in the compositions and methods described herein. In some instances, the variant of the BRP has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity, e.g., over a specified region or over the entire sequence, to a sequence of a BRP described herein or naturally derived BRP.

The BRP described herein may be formulated in a composition for any of the uses described herein. The compositions disclosed herein may include any number or type (e.g., classes) of BRPs, such as at least about any one of 1 BRP, 2, 3, 4, 5, 10, 15, 20, or more BRPs. A suitable concentration of each BRP in the composition depends on factors such as efficacy, stability of the BRP, number of distinct BRP, the formulation, and methods of application of the composition. In some instances, each BRP in a liquid composition is from about 0.1 ng/mL to about 100 mg/mL. In some instances, each BRP in a solid composition is from about 0.1 ng/g to about 100 mg/g. In some instances, wherein the composition includes at least two types of BRPs, the concentration of each type of BRP may be the same or different.

A modulating agent including a BRP as described herein can be contacted with the target host in an amount and for a time sufficient to: (a) reach a target level (e.g., a predetermined or threshold level) of BRP concentration inside a target host; (b) reach a target level (e.g., a predetermined or threshold level) of BRP concentration inside a target host gut; (c) reach a target level (e.g., a predetermined or threshold level) of BRP concentration inside a target host bacteriocyte; (d) modulate the level, or an activity, of one or more microorganism (e.g., endosymbiont) in the target host; or/and (e) modulate fitness of the target host.

ii. Small Molecules

In some instances, the modulating agent includes a small molecule. Numerous small molecule agents are useful in the methods and compositions described herein. The small molecules discussed hereinafter can be used to alter pathways in host that mediate interactions between the host and microorganisms resident in the host, as indicated in the sections for decreasing the fitness of insects, such as aphids. Additional small molecule agents can also be screened based on their ability to target components (e.g., polypeptides, e.g., enzymes or cell surface receptors) of pathways in the host invertebrate (e.g., insect, mollusk, or nematode) and/or resident microorganism (e.g., polypeptides that mediate host-microbiota interactions, e.g., host immune system pathways or bacteriocyte pathways). In some instances, the small molecule includes an agonist, antagonist, inhibitor, or an activator. For example, a small molecule described herein may be an agonist, antagonist, inhibitor, or an activator that blocks or potentiates activity and/or function of a component of the host immune system pathway or bacteriocyte regulatory pathway listed in Table 8 or Table 9. The small molecule may act as an antagonist or agonist of a polypeptide (e.g., enzyme or cell receptor) in the host or microorganisms resident in the host, including any proteins list in Table 7, Table 8, or Table 9.

Small molecules include, but are not limited to, small peptides, peptidomimetics (e.g., peptoids), amino acids, amino acid analogs, synthetic polynucleotides, polynucleotide analogs, nucleotides, nucleotide analogs, organic and inorganic compounds (including heterorganic and organometallic compounds) generally having a molecular weight less than about 5,000 grams per mole, e.g., organic or inorganic compounds having a molecular weight less than about 2,000 grams per mole, e.g., organic or inorganic compounds having a molecular weight less than about 1,000 grams per mole, e.g., organic or inorganic compounds having a molecular weight less than about 500 grams per mole, and salts, esters, and other pharmaceutically acceptable forms of such compounds.

The small molecule described herein may be formulated in a composition for any of the uses described herein. The compositions disclosed herein may include any number or type (e.g., classes) of small molecules, such as at least about any one of 1 small molecule, 2, 3, 4, 5, 10, 15, 20, or more small molecules. A suitable concentration of each small molecule in the composition depends on factors such as efficacy, stability of the small molecule, number of distinct small molecules, the formulation, and methods of application of the composition. In some instances, wherein the composition includes at least two types of small molecules, the concentration of each type of small molecule may be the same or different.

A modulating agent including a small molecule as described herein can be contacted with the target host in an amount and for a time sufficient to: (a) reach a target level (e.g., a predetermined or threshold level) of small molecule concentration inside a target host; (b) reach a target level (e.g., a predetermined or threshold level) of small molecule concentration inside a target host gut; (c) reach a target level (e.g., a predetermined or threshold level) of small molecule concentration inside a target host bacteriocyte; (d) modulate the level, or an activity, of one or more microorganism (e.g., endosymbiont) in the target host; or/and (e) modulate fitness of the target host.

In some instances, the small molecule triggers, stimulates, or increases a host's immune response in comparison to a host organism to which the small molecule has not been administered. For example, the small molecule may be peptidoglycan molecule that activates the ROS system in insects by binding to the epithelial cell surface, which in turns induces DUOX enzymatic activity by mobilizing intracellular calcium. In another example, the molecule dihydroxyphenylalanine (DOPA) is an essential component for cuticle synthesis. Once the cuticle is achieved, DOPA reaches high amounts in insects, which triggers apoptosis and autophagy activation. In another instance, the immune response is effective to reduce the level of an endosymbiont or kill an endosymbiont in comparison to a host organism to which the small molecule has not been administered. In some instances, the small molecule is effective to disrupt or decrease bacteriocyte function in comparison to a host organism to which the modulating agent has not been administered. For example, molecules that block transport of essential amino acid precursors inside the bacteriocyte also disrupt the production of essential amino acids, e.g., arginine. This alteration ultimately results in death of the endosymbiont, and, eventually, death of the host. Other examples of modulating agents that can be used to stimulate a host's immune system and thereby reduce the levels of endosymbionts resident in the host include lipopolysaccharides, rapamycin, and β-glucan.

In some instances, the small molecule decreases or increases gene expression of the resident microorganism by binding to non-coding RNA region. For example, the small molecule may be a riboswitch inhibitor, such as ribocil, that binds to a 'riboswitch' regulatory domain in a non-coding region of the messenger RNA that encodes a synthase enzyme involved in riboflavin synthesis, therefore inhibiting this pathway. In another instance, the small molecule is effective to increase or decrease gene expression that results in the killing of an endosymbiont. In some instances, the small molecule is effective to disrupt bacteriocyte function.

In some instances, the small molecule alters a host's homeostasis. For example, the small molecule may be an eicosanoid molecule, such as prostaglandin, that activates a fever response to infection as well as in protein exocytosis in salivary glands. Aside from ongoing actions in homeostasis, certain eicosanoid actions occur at crucial points in insect lite histories, such as during an infectious challenge and important events in reproduction. Eicosanoids mediate cellular defense reactions in insects. In one example, inhibition of prostaglandin synthesis severely impairs the insects' ability to clear bacteria from the hemolymph. In another instance, the small molecule is effective to increase or decrease an immune response in the host to an endosymbiont or increase or decrease a fever response in the host that results in the killing of an endosymbiont. In some instances, the small molecule is effective to disrupt bacteriocyte function.

As illustrated by Example 14, small molecules (e.g., prostaglandin) can be used as modulating agents that target host pathways that, in turn, alter the activity, levels, or metabolism of endosymbiotic bacteria in the host and thereby modulate (e.g., decrease) the fitness of the host.

iii. Nucleic Acids

Numerous nucleic acids are useful in the compositions and methods described herein. The compositions disclosed herein may include any number or type (e.g., classes) of nucleic acids (e.g., DNA molecule or RNA molecule, e.g., mRNA, guide RNA (gRNA), or inhibitory RNA molecule (e.g., siRNA, shRNA, or miRNA), or a hybrid DNA-RNA molecule), such as at least about 1 class or variant of a nucleic acid, 2, 3, 4, 5, 10, 15, 20, or more classes or variants of nucleic acids. A suitable concentration of each nucleic acid in the composition depends on factors such as efficacy, stability of the nucleic acid, number of distinct nucleic acids, the formulation, and methods of application of the composition. In some instances, wherein the composition includes at least two types of nucleic acid, the concentration of each type of nucleic acid may be the same or different.

A modulating agent including a nucleic acid as described herein can be contacted with the target host in an amount and for a time sufficient to: (a) reach a target level (e.g., a predetermined or threshold level) of nucleic acid concentration inside a target host; (b) reach a target level (e.g., a predetermined or threshold level) of nucleic acid concentration inside a target host gut; (c) reach a target level (e.g., a predetermined or threshold level) of nucleic acid concentration inside a target host bacteriocyte; (d) modulate the level, or an activity, of one or more microorganism (e.g., endosymbiont) in the target host; or/and (e) modulate fitness of the target host.

The nucleic acid modulating agents discussed hereinafter, including nucleic acids encoding polypeptides, synthetic RNA, inhibitory RNA, and gene editing systems, can be used to alter pathways in the host that mediate interactions between the host and microorganisms resident in the host as indicated in the sections for increasing or decreasing the fitness of hosts (e.g., aphids).

(a) Nucleic Acids Encoding a Polypeptide

In some instances, a composition includes a nucleic acid encoding any one of the polypeptides described herein. Nucleic acids encoding a polypeptide may have a length from about 10 to about 50,000 nucleotides (nts), about 25 to about 100 nts, about 50 to about 150 nts, about 100 to about 200 nts, about 150 to about 250 nts, about 200 to about 300 nts, about 250 to about 350 nts, about 300 to about 500 nts, about 10 to about 1000 nts, about 50 to about 1000 nts, about 100 to about 1000 nts, about 1000 to about 2000 nts, about 2000 to about 3000 nts, about 3000 to about 4000 nts, about 4000 to about 5000 nts, about 5000 to about 6000 nts, about 6000 to about 7000 nts, about 7000 to about 8000 nts, about 8000 to about 9000 nts, about 9000 to about 10,000 nts, about 10,000 to about 15,000 nts, about 10,000 to about 20,000 nts, about 10,000 to about 25,000 nts, about 10,000 to about 30,000 nts, about 10,000 to about 40,000 nts, about 10,000 to about 45,000 nts, about 10,000 to about 50,000 nts, or any range therebetween.

The modulating agent may also include functionally active variants of the nucleic acids described herein. In some instances, the variant of the nucleic acids has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity, e.g., over a specified region or over the entire sequence, to a sequence of a nucleic acids described herein. In some instances, the invention includes a functionally active polypeptide encoded by a nucleic acid variant as described herein. In some instances, the functionally active polypeptide encoded by the nucleic acid variant has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity, e.g., over a specified region or over the entire amino acid sequence, to a sequence of a polypeptide described herein or the naturally derived polypeptide sequence.

Some methods for expressing a nucleic acid encoding a protein may involve expression in cells, including host cells (e.g., insect cells, mollusk cells, or nematode cells), yeast, bacteria, or other cells under the control of appropriate promoters. Expression vectors may include nontranscribed elements, such as an origin of replication, a suitable promoter and enhancer, and other 5' or 3' flanking nontranscribed sequences, and 5' or 3' nontranslated sequences such as necessary ribosome binding sites, a polyadenylation site, splice donor and acceptor sites, and termination sequences. DNA sequences derived from the SV40 viral genome, for example, SV40 origin, early promoter, enhancer, splice, and polyadenylation sites may be used to provide the other genetic elements required for expression of a heterologous DNA sequence. Appropriate cloning and expression vectors for use with bacterial, fungal, yeast, and mammalian cellular hosts are described in Green et al., *Molecular Cloning: A Laboratory Manual*, Fourth Edition, Cold Spring Harbor Laboratory Press, 2012.

Genetic modification using recombinant methods is generally known in the art. A nucleic acid sequence coding for a desired gene can be obtained using recombinant methods known in the art, such as, for example by screening libraries from cells expressing the gene, by deriving the gene from a vector known to include the same, or by isolating directly from cells and tissues containing the same, using standard techniques. Alternatively, a gene of interest can be produced synthetically, rather than cloned.

Expression of natural or synthetic nucleic acids is typically achieved by operably linking a nucleic acid encoding the gene of interest to a promoter, and incorporating the construct into an expression vector. Expression vectors can be suitable for replication and expression in bacteria. Expression vectors can also be suitable for replication and integration in eukaryotes. Typical cloning vectors contain transcription and translation terminators, initiation sequences, and promoters useful for expression of the desired nucleic acid sequence.

Additional promoter elements, e.g., enhancers, regulate the frequency of transcriptional initiation. Typically, these are located in the region 30-110 basepairs (bp) upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter.

Alternatively, the promoter may be an inducible promoter. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

The expression vector to be introduced can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes may be used for identifying potentially transformed cells and for evaluating the functionality of regulatory sequences. In general, a reporter gene is a gene that is not present in or expressed by the recipient source and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., *FEBS Letters* 479:79-82, 2000). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

In some instances, an organism may be genetically modified to alter expression of one or more proteins. Expression of the one or more proteins may be modified for a specific time, e.g., development or differentiation state of the organism. In one instances, the invention includes a composition to alter expression of one or more proteins, e.g., proteins that affect activity, structure, or function. Expression of the one or more proteins may be restricted to a specific location(s) or widespread throughout the organism.

(b) Synthetic mRNA

The modulating agent may include an mRNA molecule, e.g., a synthetic mRNA molecule encoding a polypeptide. In some instances, the mRNA molecule increases the level (e.g., protein and/or mRNA level) and/or activity of an agent, e.g., a positive regulator of function, e.g., a gene or gene product listed in Table 7, Table 8, or Table 9. In some instances, the mRNA molecule encodes a polypeptide agent or a fragment thereof. For example, the mRNA molecule may encode a polypeptide having at least 50% (e.g., at least 50%, 60%, 70%, 80%, 90%, 95%, 97%, 99%, or greater) identity to the amino acid sequence of an agent listed in Table 7, Table 8, or Table 9 all with reference to accession number provided. In other examples, the mRNA molecule has at least 50% (e.g., at least 50%, 60%, 70%, 80%, 90%, 95%, 97%, 99%, or greater) identity to the nucleic acid sequence encoding an agent listed in Table 7, Table 8, or Table 9. In some instances, the mRNA molecule encodes an amino acid sequence differing by no more than 30 (e.g., no more than 30, 20, 10, 5, 4, 3, 2, or 1) amino acids to the amino acid sequence of an agent listed in Table 7, Table 8, or Table 9 all with reference to accession number provided. In some instances, the mRNA molecule includes a sequence encoding a fragment of a gene or gene product listed in Table 7, Table 8, or Table 9 all with reference to accession number provided. For example, the fragment includes 10-20, 20-40, 40-60, 60-80, 80-100, 100-120, 120-140, 140-160, 160-180, 180-200, 200-250, 250-300, 300-400, 400-500, 500-600, or more amino acids in length. In some instances, the fragment is a functional fragment, e.g., having at least 20%, e.g., at least 20%, 30%, 40%, 50%, 60%, 70%, 80%, 90%, or greater, of an activity of a full length gene or gene product listed in Table 7, Table 8, or Table 9 all with reference to accession numbers provided. In some instances, the mRNA molecule increases the level and/or activity of or encodes an agent (or fragment thereof).

An exemplary mRNA molecule includes an RNA encoding any polypeptide selected from Table 7, Table 8, or Table 9.

The synthetic mRNA molecule can be modified, e.g., chemically. The mRNA molecule can be chemically synthesized or transcribed in vitro. The mRNA molecule can be disposed on a plasmid, e.g., a viral vector, bacterial vector, or eukaryotic expression vector. In some examples, the mRNA molecule can be delivered to cells by transfection, electroporation, or transduction (e.g., adenoviral or lentiviral transduction).

In some instances, the modified RNA agent of interest described herein has modified nucleosides or nucleotides. Such modifications are known and are described, e.g., in WO 2012/019168. Additional modifications are described, e.g., in WO 2015/038892; WO 2015/038892; WO 2015/089511; WO 2015/196130; WO 2015/196118 and WO 2015/196128 A2.

In some instances, the modified RNA encoding a polypeptide of interest described herein has one or more terminal modification, e.g., a 5' cap structure and/or a poly-A tail (e.g., of between 100-200 nucleotides in length). The 5' cap structure may be selected from the group consisting of Cap0, Cap1, ARCA, inosine, N1-methyl-guanosine, 2'fluoro-guanosine, 7-deaza-guanosine, 8-oxo-guanosine, 2-amino-guanosine, LNA-guanosine, and 2-azido-guanosine. In some cases, the modified RNAs also contain a 5' UTR including at least one Kozak sequence, and a 3' UTR. Such modifications are known and are described, e.g., in WO 2012/135805 and WO 2013/052523. Additional terminal modifications are described, e.g., in WO 2014/164253 and WO 2016/011306, WO 2012/045075, and WO 2014/093924.

Chimeric enzymes for synthesizing capped RNA molecules (e.g., modified mRNA) which may include at least one chemical modification are described in WO 2014/028429.

In some instances, a modified mRNA may be cyclized, or concatemerized, to generate a translation competent molecule to assist interactions between poly-A binding proteins and 5'-end binding proteins. The mechanism of cyclization or concatemerization may occur through at least 3 different routes: 1) chemical, 2) enzymatic, and 3) ribozyme catalyzed. The newly formed 5'-3'-linkage may be intramolecular or intermolecular. Such modifications are described, e.g., in WO 2013/151736.

Methods of making and purifying modified RNAs are known and disclosed in the art. For example, modified RNAs are made using only in vitro transcription (IVT) enzymatic synthesis. Methods of making IVT polynucleotides are known in the art and are described in WO 2013/151666, WO 2013/151668, WO 2013/151663, WO 2013/151669, WO 2013/151670, WO 2013/151664, WO 2013/151665, WO 2013/151671, WO 2013/151672, WO 2013/151667 and WO 2013/151736.S Methods of purification include purifying an RNA transcript including a polyA tail by contacting the sample with a surface linked to a plurality of thymidines or derivatives thereof and/or a plurality of uracils or derivatives thereof (polyT/U) under conditions such that the RNA transcript binds to the surface and eluting the purified RNA transcript from the surface (WO 2014/152031); using ion (e.g., anion) exchange chromatography that allows for separation of longer RNAs up to 10,000 nucleotides in length via a scalable method (WO 2014/144767); and subjecting a modified mRNA sample to DNAse treatment (WO 2014/152030).

Formulations of modified RNAs are known and are described, e.g., in WO 2013/090648. For example, the formulation may be, but is not limited to, nanoparticles, poly(lactic-co-glycolic acid)(PLGA) microspheres, lipidoids, lipoplex, liposome, polymers, carbohydrates (including simple sugars), cationic lipids, fibrin gel, fibrin hydrogel, fibrin glue, fibrin sealant, fibrinogen, thrombin, rapidly eliminated lipid nanoparticles (reLNPs) and combinations thereof.

Modified RNAs encoding polypeptides in the fields of human disease, antibodies, viruses, and a variety of in vivo settings are known and are disclosed in for example, Table 6 of International Publication Nos. WO 2013/151666, WO 2013/151668, WO 2013/151663, WO 2013/151669, WO 2013/151670, WO 2013/151664, WO 2013/151665, WO 2013/151736; Tables 6 and 7 International Publication No. WO 2013/151672; Tables 6, 178 and 179 of International Publication No. WO 2013/151671; Tables 6, 185 and 186 of International Publication No WO 2013/151667. Any of the foregoing may be synthesized as an IVT polynucleotide, chimeric polynucleotide or a circular polynucleotide, and each may include one or more modified nucleotides or terminal modifications.

(c) Inhibitory RNA

In some instances, the modulating agent includes an inhibitory RNA molecule, e.g., that acts via the RNA interference (RNAi) pathway. For example, an inhibitory RNA molecule may include a short interfering RNA, short hairpin RNA, and/or a microRNA that targets host pathways (e.g., pathways that mediate host-microbiota interactions, e.g., host immune system pathways or bacteriocyte pathways, e.g., proteins or genes encoding proteins listed in Table 8 or Table 9, all with reference to accession number provided) in the host invertebrate (e.g., insect, mollusk, or nematode) and/or pathways in the resident microorganisms (e.g., proteins or genes encoding proteins listed in Table 7, all with reference to accession number provided). Certain RNA molecules can inhibit gene expression through the biological process of RNA interference (RNAi). RNAi molecules include RNA or RNA-like structures typically containing 15-50 base pairs (such as about 18-25 base pairs) and having a nucleobase sequence identical (complementary) or nearly identical (substantially complementary) to a coding sequence in an expressed target gene within the cell. RNAi molecules include, but are not limited to: short interfering RNAs (siRNAs), double-strand RNAs (dsRNA), short hairpin RNAs (shRNA), meroduplexes, dicer substrates, and multivalent RNA interference (U.S. Pat. Nos. 8,084,599 8,349,809, 8,513,207 and 9,200,276). A shRNA is a RNA molecule comprising a hairpin turn that decreases expression of target genes via RNAi. shRNAs can be delivered to cells in the form of plasmids, e.g., viral or bacterial vectors, e.g., by transfection, electroporation, or transduction). A microRNA is a non-coding RNA molecule that typically has a length of about 22 nucleotides. MiRNAs bind to target sites on mRNA molecules and silence the mRNA, e.g., by causing cleavage of the mRNA, destabilization of the mRNA, or inhibition of translation of the mRNA. In some instances, the inhibitory RNA molecule decreases the level and/or activity of a negative regulator of function. In other embodiments, the inhibitor RNA molecule decreases the level and/or activity of an inhibitor of a positive regulator of function.

RNAi molecules include a sequence substantially complementary, or fully complementary, to all or a fragment of a target gene. RNAi molecules may complement sequences at the boundary between introns and exons to prevent the maturation of newly-generated nuclear RNA transcripts of specific genes into mRNA for transcription. RNAi molecules complementary to specific genes can hybridize with the mRNA for a target gene and prevent its translation. The antisense molecule can be DNA, RNA, or a derivative or hybrid thereof. Examples of such derivative molecules include, but are not limited to, peptide nucleic acid (PNA) and phosphorothioate-based molecules such as deoxyribonucleic guanidine (DNG) or ribonucleic guanidine (RNG).

RNAi molecules can be provided as "ready-to-use" RNA synthesized in vitro or as an antisense gene transfected into cells which will yield RNAi molecules upon transcription. Hybridization with mRNA results in degradation of the hybridized molecule by RNAse H and/or inhibition of the formation of translation complexes. Both result in a failure to produce the product of the original gene.

The length of the RNAi molecule that hybridizes to the transcript of interest may be around 10 nucleotides, between about 15 or 30 nucleotides, or about 15, 16, 17, 18, 19, 20, 21, 22, 23, 24, 25, 26, 27, 28, 29, 30 or more nucleotides. The degree of identity of the antisense sequence to the targeted transcript may be at least 75%, at least 80%, at least 85%, at least 90%, or at least 95.

RNAi molecules may also include overhangs, i.e., typically unpaired, overhanging nucleotides which are not directly involved in the double helical structure normally formed by the core sequences of the herein defined pair of sense strand and antisense strand. RNAi molecules may contain 3' and/or 5' overhangs of about 1-5 bases independently on each of the sense strands and antisense strands. In some instances, both the sense strand and the antisense strand contain 3' and 5' overhangs. In some instances, one or more of the 3' overhang nucleotides of one strand base pairs with one or more 5' overhang nucleotides of the other strand. In other instances, the one or more of the 3' overhang nucleotides of one strand base do not pair with the one or more 5' overhang nucleotides of the other strand. The sense and antisense strands of an RNAi molecule may or may not contain the same number of nucleotide bases. The antisense and sense strands may form a duplex wherein the 5' end only has a blunt end, the 3' end only has a blunt end, both the 5' and 3' ends are blunt ended, or neither the 5' end nor the 3' end are blunt ended. In another instance, one or more of the nucleotides in the overhang contains a thiophosphate, phosphorothioate, deoxynucleotide inverted (3' to 3' linked) nucleotide or is a modified ribonucleotide or deoxynucleotide.

Small interfering RNA (siRNA) molecules include a nucleotide sequence that is identical to about 15 to about 25 contiguous nucleotides of the target mRNA. In some instances, the siRNA sequence commences with the dinucleotide AA, includes a GC-content of about 30-70% (about 30-60%, about 40-60%, or about 45%-55%), and does not have a high percentage identity to any nucleotide sequence other than the target in the genome in which it is to be introduced, for example as determined by standard BLAST search.

siRNAs and shRNAs resemble intermediates in the processing pathway of the endogenous microRNA (miRNA) genes (Bartel, *Cell* 116:281-297, 2004). In some instances, siRNAs can function as miRNAs and vice versa (Zeng et al., *Mol. Cell* 9:1327-1333, 2002; Doench et al., *Genes Dev.* 17:438-442, 2003). Exogenous siRNAs downregulate mRNAs with seed complementarity to the siRNA (Birmingham et al., *Nat. Methods* 3:199-204, 2006). Multiple target sites within a 3' UTR give stronger downregulation (Doench et al., *Genes Dev.* 17:438-442, 2003).

Known effective siRNA sequences and cognate binding sites are also well represented in the relevant literature. RNAi molecules are readily designed and produced by technologies known in the art. In addition, there are computational tools that increase the chance of finding effective and specific sequence motifs (Pei et al., *Nat. Methods* 3(9):670-676, 2006; Reynolds et al., *Nat. Biotechnol.* 22(3): 326-330, 2004; Khvorova et al., *Nat. Struct. Biol.* 10(9): 708-712, 2003; Schwarz et al., *Cell* 115(2):199-208, 2003; Ui-Tei et al., *Nucleic Acids Res.* 32(3):936-948, 2004; Heale et al., *Nucleic Acids Res.* 33(3):e30, 2005; Chalk et al., *Biochem. Biophys. Res. Commun.* 319(1):264-274, 2004; and Amarzguioui et al., *Biochem. Biophys. Res. Commun.* 316(4):1050-1058, 2004).

The RNAi molecule modulates expression of RNA encoded by a gene. Because multiple genes can share some degree of sequence homology with each other, in some instances, the RNAi molecule can be designed to target a class of genes with sufficient sequence homology. In some instances, the RNAi molecule can contain a sequence that has complementarity to sequences that are shared amongst different gene targets or are unique for a specific gene target. In some instances, the RNAi molecule can be designed to target conserved regions of an RNA sequence having homology between several genes thereby targeting several genes in a gene family (e.g., different gene isoforms, splice variants, mutant genes, etc.). In some instances, the RNAi molecule can be designed to target a sequence that is unique to a specific RNA sequence of a single gene.

In some instances, the inhibitory RNA molecule decreases the level and/or activity of a host component (e.g., component in pathways that mediate host-microbiota interactions, e.g., host immune system pathways or bacteriocyte pathways) and/or microbial component, including genes encoding proteins listed in Table 7, Table 8, or Table 9, all with reference to accession number provided. In some instances, the inhibitory RNA molecule inhibits expression of a host component (e.g., component in pathways that mediate host-microbiota interactions, e.g., host immune system pathways or bacteriocyte pathways) or microbial component, e.g., genes encoding proteins listed in Table 7, Table 8, or Table 9 (e.g., inhibits translation to protein). In other instances, the inhibitor RNA molecule increases degradation of a host component (e.g., component in pathways that mediate host-microbiota interactions, e.g., host immune system pathways or bacteriocyte pathways) and/or microbial component, e.g., genes encoding proteins listed in Table 7, Table 8, or Table 9 and/or decreases the stability (i.e., half-life) of the pathway component. The inhibitory RNA molecule can be chemically synthesized or transcribed in vitro.

In some instances, the compositions described herein include an RNAi, e.g., siRNA, to regulate (e.g., inhibit) expression of a gene encoding any of the components described herein that regulate a host's immune system. In some instances, a composition includes an RNAi, e.g., siRNA, to inhibit expression of any one of the genes described herein that regulate (e.g., inhibit) the development or function of a bacteriocyte in the host. In some instances, regulation of the host immune system leads to a reduction or killing of an endosymbiotic microorganism in the host, and in turn, reduces the fitness of the host. In some instances, regulation of bacteriocyte development and/or function leads to a reduction or killing of an endosymbiotic microorganism in the host, and in turn, reduces the fitness of the host. In some instances, the RNAi (e.g., siRNA) may inhibit expression of Ubx to disrupt symbiont localization of bacteriocytes. In some instances, the RNAi (e.g., siRNA) inhibits expression of abd-A and Antp to disrupt bacteriome integrity and positioning.

In some instances, one or more RNAi molecules target any gene encoding any protein described herein, e.g., see Table 7, Table 8, or Table 9. In some instances, one or more RNAi molecules target a bacterial gene as described herein. In some instances, one or more RNAi molecules target an endosymbiont gene as described herein. In some instances, one or more RNAi molecules target a bacteriocyte gene as described herein. In some instances, one or more RNAi molecules target a host gene as described herein. In some instances, one or more RNAi molecules target an immune system gene in a host as described herein.

An inhibitory RNA molecule can be modified, e.g., to contain modified nucleotides, e.g., 2'-fluoro, 2'-o-methyl, 2'-deoxy, unlocked nucleic acid, 2'-hydroxy, phosphorothioate, 2'-thiouridine, 4'-thiouridine, 2'-deoxyuridine. Without being bound by theory, it is believed that such modifications can increase nuclease resistance and/or serum stability, or decrease immunogenicity.

In some instances, the RNAi molecule is linked to a delivery polymer via a physiologically labile bond or linker. The physiologically labile linker is selected such that it undergoes a chemical transformation (e.g., cleavage) when present in certain physiological conditions, (e.g., disulfide bond cleaved in the reducing environment of the cell cytoplasm). Release of the molecule from the polymer, by cleavage of the physiologically labile linkage, facilitates interaction of the molecule with the appropriate cellular components for activity.

The RNAi molecule-polymer conjugate may be formed by covalently linking the molecule to the polymer. The polymer is polymerized or modified such that it contains a reactive group A. The RNAi molecule is also polymerized or modified such that it contains a reactive group B. Reactive groups A and B are chosen such that they can be linked via a reversible covalent linkage using methods known in the art.

Conjugation of the RNAi molecule to the polymer can be performed in the presence of an excess of polymer. Because the RNAi molecule and the polymer may be of opposite charge during conjugation, the presence of excess polymer can reduce or eliminate aggregation of the conjugate. Alternatively, an excess of a carrier polymer, such as a polycation, can be used. The excess polymer can be removed from the conjugated polymer prior to administration of the conjugate. Alternatively, the excess polymer can be co-administered with the conjugate.

Injection of double-stranded RNA (dsRNA) into mother insects efficiently suppresses their offspring's gene expression during embryogenesis, see for example, Khila et al., *PLoS Genet.* 5(7):e1000583, 2009; and Liu et al., *Development* 131(7):1515-1527, 2004. Matsuura et al. (*PNAS* 112 (30):9376-9381, 2015) has shown that suppression of Ubx eliminates bacteriocytes and the symbiont localization of bacteriocytes.

The making and use of inhibitory agents based on non-coding RNA such as ribozymes, RNAse P, siRNAs, and miRNAs are also known in the art, for example, as described in Sioud, *RNA Therapeutics: Function, Design, and Delivery (Methods in Molecular Biology).* Humana Press (2010).

Other examples of nucleic acid modulating agents that can be used herein include dsRNAs having at least 50% (e.g., at least 50%, 60%, 70%, 80%, 90%, 95%, 97%, 99%, or greater) identity to the sequence of any one of SEQ ID NOs: 148-150.

As illustrated by Examples 1-4 and 7-9, inhibitory RNA (e.g., dsRNA or PNA) can be used as a modulating agent that targets a host pathway (e.g., an insect, e.g., an aphid) that, in turn, alters the activity, levels, or metabolism of endosymbiotic bacteria, such as a *Buchnera* spp., resident in the host and thereby modulates (e.g., decreases) the fitness of the host.

(d) Gene Editing

The modulating agents described herein may include a component of a gene editing system. For example, the agent may introduce an alteration (e.g., insertion, deletion (e.g., knockout), translocation, inversion, single point mutation, or other mutation) in a gene related to the immune system or bacteriocyte of a host invertebrate (e.g., insect, mollusk, or nematode) or in a gene in a microorganism resident in the host invertebrate, e.g., an enzyme or receptor gene described in Table 7, Table 8, or Table 9 all with reference to accession number provided. Exemplary gene editing systems include the zinc finger nucleases (ZFNs), Transcription Activator-Like Effector-based Nucleases (TALEN), and the clustered regulatory interspaced short palindromic repeat (CRISPR) system. ZFNs, TALENs, and CRISPR-based methods are described, e.g., in Gaj et al., *Trends Biotechnol.* 31(7):397-405, 2013.

In a typical CRISPR/Cas system, an endonuclease is directed to a target nucleotide sequence (e.g., a site in the genome that is to be sequence-edited) by sequence-specific, non-coding "guide RNAs" that target single- or double-stranded DNA sequences. Three classes (I-III) of CRISPR systems have been identified. The class II CRISPR systems use a single Cas endonuclease (rather than multiple Cas proteins). One class II CRISPR system includes a type II Cas endonuclease such as Cas9, a CRISPR RNA ("crRNA"), and a trans-activating crRNA ("tracrRNA"). The crRNA contains a "guide RNA," i.e., typically an about 20-nucleotide RNA sequence that corresponds to a target DNA sequence. The crRNA also contains a region that binds to the tracrRNA to form a partially double-stranded structure which is cleaved by RNase III, resulting in a crRNA/tracrRNA hybrid. The RNAs serve as guides to direct Cas proteins to silence specific DNA/RNA sequences, depending on the spacer sequence. See, e.g., Horvath et al., *Science* 327:167-170, 2010; Makarova et al., *Biology Direct* 1:7, 2006; Pennisi, *Science* 341:833-836, 2013. The target DNA sequence must generally be adjacent to a "protospacer adjacent motif" ("PAM") that is specific for a given Cas endonuclease; however, PAM sequences appear throughout a given genome. CRISPR endonucleases identified from various prokaryotic species have unique PAM sequence requirements; examples of PAM sequences include 5'-NGG (SEQ ID NO: 78) (*Streptococcus pyogenes*), 5'-NNAGAA (SEQ ID NO: 79) (*Streptococcus thermophilus* CRISPR1), 5'-NGGNG (SEQ ID NO: 80) (*Streptococcus thermophilus* CRISPR3), and 5'-NNNGATT (SEQ ID NO: 81) (*Neisseria meningiditis*). Some endonucleases, e.g., Cas9 endonucleases, are associated with G-rich PAM sites, e.g., 5'-NGG (SEQ ID NO: 78), and perform blunt-end cleaving of the target DNA at a location 3 nucleotides upstream from (5' from) the PAM site. Another class II CRISPR system includes the type V endonuclease Cpf1, which is smaller than Cas9; examples include AsCpf1 (from *Acidaminococcus* sp.) and LbCpf1 (from *Lachnospiraceae* sp.). Cpf1-associated CRISPR arrays are processed into mature crRNAs without the requirement of a tracrRNA; in other words a Cpf1 system requires only the Cpf1 nuclease and a crRNA to cleave the target DNA sequence. Cpf1 endonucleases, are associated with T-rich PAM sites, e.g., 5'-TTN. Cpf1 can also recognize a 5'-CTA PAM motif. Cpf1 cleaves the target DNA by introducing an offset or staggered double-strand break with a 4- or 5-nucleotide 5' overhang, for example, cleaving a target DNA with a 5-nucleotide offset or staggered cut located 18 nucleotides downstream from (3' from) from the PAM site on the coding strand and 23 nucleotides downstream from the PAM site on the complimentary strand; the 5-nucleotide overhang that results from such offset cleavage allows more precise genome editing by DNA insertion by homologous recombination than by insertion at blunt-end cleaved DNA. See, e.g., Zetsche et al., *Cell* 163:759-771, 2015.

For the purposes of gene editing, CRISPR arrays can be designed to contain one or multiple guide RNA sequences corresponding to a desired target DNA sequence; see, for example, Cong et al., *Science* 339:819-823, 2013; Ran et al., *Nature Protocols* 8:2281-2308, 2013. At least about 16 or 17 nucleotides of gRNA sequence are required by Cas9 for DNA cleavage to occur; for Cpf1 at least about 16 nucleotides of gRNA sequence is needed to achieve detectable DNA cleavage. In practice, guide RNA sequences are generally designed to have a length of between 17-24 nucleotides (e.g., 19, 20, or 21 nucleotides) and complementarity to the targeted gene or nucleic acid sequence. Custom gRNA generators and algorithms are available commercially for use in the design of effective guide RNAs. Gene editing has also been achieved using a chimeric "single guide RNA" ("sgRNA"), an engineered (synthetic) single RNA molecule that mimics a naturally occurring crRNA-tracrRNA complex and contains both a tracrRNA (for binding the nuclease) and at least one crRNA (to guide the nuclease to the sequence targeted for editing). Chemically modified sgRNAs have also been demonstrated to be effective in genome editing; see, for example, Hendel et al., *Nature Biotechnol.* 985-991, 2015.

Whereas wild-type Cas9 generates double-strand breaks (DSBs) at specific DNA sequences targeted by a gRNA, a number of CRISPR endonucleases having modified functionalities are available, for example: a "nickase" version of Cas9 generates only a single-strand break; a catalytically inactive Cas9 ("dCas9") does not cut the target DNA but interferes with transcription by steric hindrance. dCas9 can further be fused with an effector to repress (CRISPRi) or activate (CRISPRa) expression of a target gene. For example, Cas9 can be fused to a transcriptional repressor (e.g., a KRAB domain) or a transcriptional activator (e.g., a dCas9-VP64 fusion). A catalytically inactive Cas9 (dCas9) fused to FokI nuclease ("dCas9-FokI") can be used to generate DSBs at target sequences homologous to two gRNAs. See, e.g., the numerous CRISPR/Cas9 plasmids disclosed in and publicly available from the Addgene repository (Addgene, 75 Sidney St., Suite 550A, Cambridge, MA 02139; addgene.org/crispr/). A "double nickase" Cas9 that introduces two separate double-strand breaks, each directed by a separate guide RNA, is described as achieving more accurate genome editing by Ran et al., *Cell* 154:1380-1389, 2013.

CRISPR technology for editing the genes of eukaryotes is disclosed in US Patent Application Publications US 2016/0138008 A1 and US 2015/0344912 A1, and in U.S. Pat. Nos. 8,697,359, 8,771,945, 8,945,839, 8,999,641, 8,993,233, 8,895,308, 8,865,406, 8,889,418, 8,871,445, 8,889,356, 8,932,814, 8,795,965, and 8,906,616. Cpf1 endonuclease and corresponding guide RNAs and PAM sites are disclosed in US Patent Application Publication 2016/0208243 A1.

In some instances, the desired genome modification involves homologous recombination, wherein one or more double-stranded DNA breaks in the target nucleotide sequence is generated by the RNA-guided nuclease and guide RNA(s), followed by repair of the break(s) using a homologous recombination mechanism ("homology-directed repair"). In such instances, a donor template that encodes the desired nucleotide sequence to be inserted or knocked-in at the double-stranded break is provided to the cell or subject; examples of suitable templates include single-stranded DNA templates and double-stranded DNA templates (e.g., linked to the polypeptide described herein). In general, a donor template encoding a nucleotide change over a region of less than about 50 nucleotides is provided in the form of single-stranded DNA; larger donor templates (e.g., more than 100 nucleotides) are often provided as double-stranded DNA plasmids. In some instances, the donor template is provided to the cell or subject in a quantity that is sufficient to achieve the desired homology-directed repair but that does not persist in the cell or subject after a given period of time (e.g., after one or more cell division cycles). In some instances, a donor template has a core nucleotide sequence that differs from the target nucleotide sequence (e.g., a homologous endogenous genomic region) by at least 1, at least 5, at least 10, at least 20, at least 30, at least 40, at least 50, or more nucleotides. This core sequence is flanked by "homology arms" or regions of high sequence identity with the targeted nucleotide sequence; in some instances, the regions of high identity include at least 10, at least 50, at least 100, at least 150, at least 200, at least 300, at least 400, at least 500, at least 600, at least 750, or at least 1000 nucleotides on each side of the core sequence. In some instances where the donor template is in the form of a single-stranded DNA, the core sequence is flanked by homology arms including at least 10, at least 20, at least 30, at least 40, at least 50, at least 60, at least 70, at least 80, or at least 100 nucleotides on each side of the core sequence. In instances, where the donor template is in the form of a double-stranded DNA, the core sequence is flanked by homology arms including at least 500, at least 600, at least 700, at least 800, at least 900, or at least 1000 nucleotides on each side of the core sequence. In one instance, two separate double-strand breaks are introduced into the cell or subject's target nucleotide sequence with a "double nickase" Cas9 (see Ran et al., *Cell* 154:1380-1389, 2013), followed by delivery of the donor template.

In some instances, the composition includes a gRNA and a targeted nuclease, e.g., a Cas9, e.g., a wild type Cas9, a nickase Cas9 (e.g., Cas9 D10A), a dead Cas9 (dCas9), eSpCas9, Cpf1, C2C1, or C2C3, or a nucleic acid encoding such a nuclease. The choice of nuclease and gRNA(s) is determined by whether the targeted mutation is a deletion, substitution, or addition of nucleotides, e.g., a deletion, substitution, or addition of nucleotides to a targeted sequence. Fusions of a catalytically inactive endonuclease e.g., a dead Cas9 (dCas9, e.g., D10A; H840A) tethered with all or a portion of (e.g., biologically active portion of) an (one or more) effector domain create chimeric proteins that can be linked to the polypeptide to guide the composition to specific DNA sites by one or more RNA sequences (sgRNA) to modulate activity and/or expression of one or more target nucleic acids sequences.

In instances, the agent includes a guide RNA (gRNA) for use in a CRISPR system for gene editing. In some instances, the agent includes a zinc finger nuclease (ZFN), or a mRNA encoding a ZFN, that targets (e.g., cleaves) a nucleic acid sequence (e.g., DNA sequence) of a gene related to pathways in the host invertebrate (e.g., insect, mollusk, or nematode) and/or resident microorganisms (e.g., pathways that mediate host-microbiota interactions, e.g., host immune system pathways or bacteriocyte pathways, e.g., a gene encoding a protein listed in Table 7, Table 8, or Table 9, all with reference to accession number provided). In some instances, the agent includes a TALEN, or an mRNA encoding a TALEN, that targets (e.g., cleaves) a nucleic acid sequence (e.g., DNA sequence) in a gene related to pathways in the host invertebrate (e.g., insect, mollusk, or nematode) and/or resident microorganisms (e.g., pathways that mediate host-microbiota interactions, e.g., host immune system pathways or bacteriocyte pathways, e.g., a gene encoding a protein listed in Table 7, Table 8, or Table 9, all with reference to accession number provided).

For example, the gRNA can be used in a CRISPR system to engineer an alteration in a gene related to pathways in the host invertebrate (e.g., insect, mollusk, or nematode) and/or resident microorganisms (e.g., pathways that mediate host-microbiota interactions, e.g., host immune system pathways or bacteriocyte pathways, e.g., a gene encoding a protein listed in Table 7, Table 8, or Table 9, all with reference to accession number provided). In other examples, the ZFN and/or TALEN can be used to engineer an alteration in a gene related to pathways in the host invertebrate (e.g., insect, mollusk, or nematode) and/or resident microorganisms (e.g., pathways that mediate host-microbiota interactions, e.g., host immune system pathways or bacteriocyte pathways, e.g., a gene encoding a protein listed in Table 7, Table 8, or Table 9, all with reference to accession number provided). Exemplary alterations include insertions, deletions (e.g., knockouts), translocations, inversions, single point mutations, or other mutations. The alteration can be introduced in the gene in a cell, e.g., in vitro, ex vivo, or in vivo. In some examples, the alteration increases the level and/or activity of a gene related to pathways in the host invertebrate (e.g., insect, mollusk, or nematode) and/or resident microorganisms (e.g., pathways that mediate host-microbiota interactions, e.g., host immune system pathways or bacteriocyte pathways, e.g., a gene encoding a protein listed in Table 7, Table 8, or Table 9, all with reference to accession number provided). In other examples, the alteration decreases the level and/or activity of (e.g., knocks down or knocks out) a gene related to pathways in the host invertebrate (e.g., insect, mollusk, or nematode) and/or resident microorganisms (e.g., pathways that mediate host-microbiota interactions, e.g., host immune system pathways or bacteriocyte pathways, e.g., a gene encoding a protein listed in Table 7, Table 8, or Table 9, all with reference to accession number provided). In yet another example, the alteration corrects a defect (e.g., a mutation causing a defect), in a gene related to pathways in the host invertebrate (e.g., insect, mollusk, or nematode) and/or resident microorganisms (e.g., pathways that mediate host-microbiota interactions, e.g., host immune system pathways or bacteriocyte pathways, e.g., a gene encoding protein listed in Table 7, Table 8, or Table 9, all with reference to accession number provided).

In some instances, the CRISPR system is used to edit (e.g., to add or delete a base pair) a target gene (e.g., a gene related to pathways in the host invertebrate (e.g., insect, mollusk, or nematode) and/or resident microorganisms, e.g., pathways that mediate host-microbiota interactions, e.g., host immune system pathways or bacteriocyte pathways, e.g., a gene encoding a protein listed in Table 7, Table 8, or Table 9, all with reference to accession number provided). In other instances, the CRISPR system is used to introduce a premature stop codon, e.g., thereby decreasing the expression of a target gene. In yet other instances, the CRISPR system is used to turn off a target gene in a reversible manner, e.g., similarly to RNA interference. In some instances, the CRISPR system is used to direct Cas to a promoter of a gene, thereby blocking an RNA polymerase sterically.

In some instances, a CRISPR system can be generated to edit a gene related to pathways in the host invertebrate (e.g., insect, mollusk, or nematode) and/or resident microorganisms (e.g., pathways that mediate host-microbiota interactions, e.g., host immune system pathways or bacteriocyte pathways, e.g., genes that encode a protein listed in Table 7, Table 8, or Table 9, all with reference to accession number provided), using technology described in, e.g., U.S. Publication No. 20140068797, Cong, *Science* 339: 819-823, 2013; Tsai, *Nature Biotechnol.* 32:6 569-576, 2014; U.S. Pat. Nos. 8,871,445; 8,865,406; 8,795,965; 8,771,945; and 8,697,359.

In some instances, the CRISPR interference (CRISPRi) technique can be used for transcriptional repression of specific genes, e.g., a gene encoding a host immune system or bacteriocyte component (e.g., an enzyme or receptor described herein). In CRISPRi, an engineered Cas9 protein (e.g., nuclease-null dCas9, or dCas9 fusion protein, e.g., dCas9-KRAB or dCas9-SID4X fusion) can pair with a sequence specific guide RNA (sgRNA). The Cas9-gRNA complex can block RNA polymerase, thereby interfering with transcription elongation. The complex can also block transcription initiation by interfering with transcription factor binding. The CRISPRi method is specific with minimal off-target effects and is multiplexable, e.g., can simultaneously repress more than one gene (e.g., using multiple gRNAs). Also, the CRISPRi method permits reversible gene repression.

In some instances, CRISPR-mediated gene activation (CRISPRa) can be used for transcriptional activation, e.g., of one or more genes described herein (e.g., a gene encoding any of the proteins listed in Table 7, Table 8, or Table 9). In the CRISPRa technique, dCas9 fusion proteins recruit transcriptional activators. For example, dCas9 can be fused to polypeptides (e.g., activation domains) such as VP64 or the p65 activation domain (p65D) and used with sgRNA (e.g., a single sgRNA or multiple sgRNAs), to activate a gene or genes, e.g., endogenous gene(s) in the host or microorganism resident in the host. Multiple activators can be recruited by using multiple sgRNAs—this can increase activation efficiency. A variety of activation domains and single or multiple activation domains can be used. In addition to engineering dCas9 to recruit activators, sgRNAs can also be engineered to recruit activators. For example, RNA aptamers can be incorporated into a sgRNA to recruit proteins (e.g., activation domains) such as VP64. In some examples, the synergistic activation mediator (SAM) system can be used for transcriptional activation. In SAM, MS2 aptamers are added to the sgRNA. MS2 recruits the MS2 coat protein (MCP) fused to p65AD and heat shock factor 1 (HSF1).

The CRISPRi and CRISPRa techniques are described in greater detail, e.g., in Dominguez et al., *Nat. Rev. Mol. Cell Biol.* 17:5-15, 2016, incorporated herein by reference. In addition, dCas9-mediated epigenetic modifications and simultaneous activation and repression using CRISPR systems, as described in Dominguez et al., can be used to modulate a component of a host or microbial pathway described herein (e.g., pathways that mediate host-microbiota interactions, e.g., host immune system pathways or bacteriocyte pathways, e.g., a gene encoding a protein listed in Table 7, Table 8, or Table 9, all with reference to accession number provided).

iv. Target Genes and Proteins

Any of the modulating agents described herein can be used to alter (e.g., increase or decrease) gene expression, alter (e.g., increase or decrease) a target protein activity, and/or alter function in the host or a microorganism resident in the host. Proteins or genes that are involved in a variety of processes may be targeted, including any of the functional classes listed in Table 6.

TABLE 6

Functional classes of target genes

| Functional class | Effect |
| --- | --- |
| Homeostasis | Downregulation or knockout of these genes will disrupt inner target microorganism homeostatic balance generating in the host a cellular malfunction and therefore a decrease in their fitness. |
| Information | Downregulation or knockout of these genes will stop or slow protein synthesis therefore affecting proliferation of the microorganism. This in turn will generate in the host a cellular malfunction and therefore a decrease in their fitness. |
| Metabolism | Downregulation or knockout of these genes will stop the catabolism and anabolism of nutrients affecting proliferation of the microorganism. This in turn will generate in the host a cellular malfunction and therefore a decrease in their fitness. |
| Transport | Downregulation or knockout of these genes will stop or decrease the transport of amino acids or their precursors therefore affecting microorganism survival. This in turn will generate in the host a cellular malfunction and therefore a decrease in their fitness. |

(a) Target Microbial Genes and Proteins

Any of the modulating agents described herein can be used to alter gene expression or target proteins in a microorganism resident in the host. In some instances, the modulating agent (e.g., an antibody) directly targets a protein in a microorganism resident in the host, including any one of the proteins listed in Table 7. In other instances, the modulating agent (e.g., nucleic acid, e.g., RNAi) alters gene expression (e.g., increases or decreases gene expression) in a microorganism resident in the host, including genes that encode any of the proteins listed in Table 7, in comparison to a host organism to which the modulating agent has not been administered.

TABLE 7

Target bacterial proteins

| Functional class | Protein name | Sequence Accession No. | Organism |
| --- | --- | --- | --- |
| Homeostasis | chaperonin GroEL | NP_239860.1 | *Buchnera aphidicola* str. APS (*Acyrthosiphon pisum*) |
| Homeostasis | DnaK protein | NP_239985.1 | *Buchnera aphidicola* str. APS (*Acyrthosiphon pisum*) |
| Homeostasis | heat shock protein GrpE1 | NP_240076.1 | *Buchnera aphidicola* str. APS (*Acyrthosiphon pisum*) |

TABLE 7-continued

Target bacterial proteins

| Functional class | Protein name | Sequence Accession No. | Organism |
|---|---|---|---|
| Homeostasis | ATP-dependent protease ATP-binding subunit | NP_240382.1 | Buchnera aphidicola str. APS (Acyrthosiphon pisum) |
| Homeostasis | heat shock protein GrpE2 | NP_240015.1 | Buchnera aphidicola str. APS (Acyrthosiphon pisum) |
| Information | methionine aminopeptidase | NP_240059.1 | Buchnera aphidicola str. APS (Acyrthosiphon pisum) |
| Information | 30S ribosomal protein S1 | NP_240132.1 | Buchnera aphidicola str. APS (Acyrthosiphon pisum) |
| Information | DnaJ protein | NP_239984.1 | Buchnera aphidicola str. APS (Acyrthosiphon pisum) |
| Information | polynucleotide phosphorylase/polyadenylase | NP_240191.1 | Buchnera aphidicola str. APS (Acyrthosiphon pisum) |
| Information | DNA gyrase subunit B | NP_239852.1 | Buchnera aphidicola str. APS (Acyrthosiphon pisum) |
| Information | tryptophanyl-tRNA synthetase | NP_240343.1 | Buchnera aphidicola str. APS (Acyrthosiphon pisum) |
| Information | threonyl-tRNA synthetase | NP_239957.1 | Buchnera aphidicola str. APS (Acyrthosiphon pisum) |
| Information | alanyl-tRNA synthetase | NP_240220.1 | Buchnera aphidicola str. APS (Acyrthosiphon pisum) |
| Information | asparaginyl-tRNA synthetase | NP_240178.1 | Buchnera aphidicola str. APS (Acyrthosiphon pisum) |
| Information | tRNA (guanine-N1)-methyltransferase | NP_240213.1 | Buchnera aphidicola str. APS (Acyrthosiphon pisum) |
| Information | 50S ribosomal protein L30 | NP_240313.1 | Buchnera aphidicola str. APS (Acyrthosiphon pisum) |
| Information | replicative DNA helicase | NP_240352.2 | Buchnera aphidicola str. APS (Acyrthosiphon pisum) |
| Information | glycyl-tRNA synthetase subunit alpha | NP_239968.2 | Buchnera aphidicola str. APS (Acyrthosiphon pisum) |

TABLE 7-continued

| Target bacterial proteins | | | |
|---|---|---|---|
| Functional class | Protein name | Sequence Accession No. | Organism |
| Information | A/G-specific adenine glycosylase | NP_240358.1 | *Buchnera aphidicola* str. APS (*Acyrthosiphon pisum*) |
| Information | tRNA pseudouridine 55 synthase | NP_240193.1 | *Buchnera aphidicola* str. APS (*Acyrthosiphon pisum*) |
| Information | methionyl-tRNA synthetase | NP_239942.1 | *Buchnera aphidicola* str. APS (*Acyrthosiphon pisum*) |
| Information | lysyl-tRNA synthetase | NP_240385.1 | *Buchnera aphidicola* str. APS (*Acyrthosiphon pisum*) |
| Information | glutaminyl-tRNA synthetase | NP_240227.1 | *Buchnera aphidicola* str. APS (*Acyrthosiphon pisum*) |
| Information | DNA polymerase I | NP_240243.1 | *Buchnera aphidicola* str. APS (*Acyrthosiphon pisum*) |
| Information | ribosomal large subunit pseudouridine synthase C | NP_240167.1 | *Buchnera aphidicola* str. APS (*Acyrthosiphon pisum*) |
| Information | histidyl-tRNA synthetase | NP_240112.1 | *Buchnera aphidicola* str. APS (*Acyrthosiphon pisum*) |
| Information | DNA polymerase III subunits gamma and tau | NP_240292.1 | *Buchnera aphidicola* str. APS (*Acyrthosiphon pisum*) |
| Information | tRNA modification GTPase TrmE | NP_239858.2 | *Buchnera aphidicola* str. APS (*Acyrthosiphon pisum*) |
| Information | DNA polymerase III beta chain | NP_239853.1 | *Buchnera aphidicola* str. APS (*Acyrthosiphon pisum*) |
| Information | RNA polymerase sigma factor RpoD | NP_239892.1 | *Buchnera aphidicola* str. APS (*Acyrthosiphon pisum*) |
| Information | arginyl-tRNA synthetase | NP_240071.1 | *Buchnera aphidicola* str. APS (*Acyrthosiphon pisum*) |
| Information | seryl-tRNA synthetase | NP_240135.1 | *Buchnera aphidicola* str. APS (*Acyrthosiphon pisum*) |
| Information | DNA polymerase III alpha chain | NP_240067.1 | *Buchnera aphidicola* str. APS (*Acyrthosiphon pisum*) |

TABLE 7-continued

| | Target bacterial proteins | | |
|---|---|---|---|
| Functional class | Protein name | Sequence Accession No. | Organism |
| Information | aspartyl-tRNA synthetase | NP_240138.1 | *Buchnera aphidicola* str. APS (*Acyrthosiphon pisum*) |
| Information | leucyl-tRNA synthetase | NP_240256.1 | *Buchnera aphidicola* str. APS (*Acyrthosiphon pisum*) |
| Information | phenylalanyl-tRNA synthetase beta chain | NP_239962.1 | *Buchnera aphidicola* str. APS (*Acyrthosiphon pisum*) |
| Metabolism | 5-methyltetrahydropteroyltriglutamate--homocysteine methyltransferase | NP_239871.1 | *Buchnera aphidicola* str. APS (*Acyrthosiphon pisum*) |
| Metabolism | bifunctional aspartokinase I/homeserine dehydrogenase I | NP_240025.1 | *Buchnera aphidicola* str. APS (*Acyrthosiphon pisum*) |
| Metabolism | sulfate adenylate transferase subunit 1 | NP_240235.1 | *Buchnera aphidicola* str. APS (*Acyrthosiphon pisum*) |
| Metabolism | adenylosuccinate synthetase | NP_240370.1 | *Buchnera aphidicola* str. APS (*Acyrthosiphon pisum*) |
| Metabolism | phosphoadenosine phosphosulfate reductase | NP_240238.1 | *Buchnera aphidicola* str. APS (*Acyrthosiphon pisum*) |
| Metabolism | phosphoserine aminotransferase | NP_240134.1 | *Buchnera aphidicola* str. APS (*Acyrthosiphon pisum*) |
| Metabolism | F0F1 ATP synthase subunit gamma | NP_239849.1 | *Buchnera aphidicola* str. APS (*Acyrthosiphon pisum*) |
| Transport | cell division inhibitor MinC | NP_240149.1 | *Buchnera aphidicola* str. APS (*Acyrthosiphon pisum*) |
| Transport | 23S rRNA m(2)G2445 methyltransferase | NP_240181.1 | *Buchnera aphidicola* str. APS (*Acyrthosiphon pisum*) |
| Transport | tRNA uridine 5-carboxymethylaminomethyl modification enzyme GidA | NP_239843.1 | *Buchnera aphidicola* str. APS (*Acyrthosiphon pisum*) |

(b) Target Genes and Proteins in Hosts

Any of the modulating agents described herein can be used to alter gene expression or target proteins in the host. In some instances, the modulating agent (e.g., an antibody) directly targets a protein in the host, including any one of the proteins listed in Table 8 or Table 9. In other instances, the modulating agent (e.g., nucleic acid, e.g., RNAi) targets a gene in the host, including genes that encode any of the proteins listed in Table 8 or Table 9. For example, the nucleic acids described herein can be used to alter (e.g., increase or decrease) gene expression in a host (e.g., genes that regulate bacteriocyte function or development (e.g., bacteriocyte regulatory peptides) or genes that regulate the immune system) including, but not limited to, any of the genes listed in Table 8 and Table 9, in comparison to a host organism to which the modulating agent has not been administered.

TABLE 8

Proteins that regulate bacteriocyte function

| Functional class | Protein name | Sequence accession number | Organism |
| --- | --- | --- | --- |
| Homeostasis | ns1 binding protein | ACYPI000701-PA | *Acyrthosiphon pisum* |
| Homeostasis | Ubx transcription factor | ACYPI001856-RA | *Acyrthosiphon pisum* |
| Metabolism | ATPase | ACYPI002584-PA | *Acyrthosiphon pisum* |
| Metabolism | Succinic semialdehyde dehydrogenase isoform 1 | ACYPI002063-PA | *Acyrthosiphon pisum* |
| Metabolism | Vacuolar proton atpases isoform 1 | ACYPI007445-PA | *Acyrthosiphon pisum* |
| Metabolism | Membrane alanyl aminopeptidase N | ACYPI006675-PA | *Acyrthosiphon pisum* |
| Metabolism | Protease m1 zinc metalloprotease | ACYPI009427-PA | *Acyrthosiphon pisum* |
| Metabolism | Zinc metalloprotease | ACYPI000580-PA | *Acyrthosiphon pisum* |
| Metabolism | Purine biosynthesis protein 6, pur6 | ACYPI010114-PA | *Acyrthosiphon pisum* |
| Metabolism | Myo inositol monophosphatase | ACYPI009018-PA | *Acyrthosiphon pisum* |
| Metabolism | Phenylalanine hydroxylase | ACYPI007803-PA | *Acyrthosiphon pisum* |
| Metabolism | 4-nitrophenylphosphatase isoform 1 | ACYPI005939-PA | *Acyrthosiphon pisum* |
| Metabolism | Cytosolic purine 5-nucleotidase | ACYPI007730-PA | *Acyrthosiphon pisum* |
| Metabolism | Amine oxidase | ACYPI006507-PA | *Acyrthosiphon pisum* |
| Metabolism | Phosphoserine aminotransferase | ACYPI004666-PA | *Acyrthosiphon pisum* |
| Metabolism | 4-Hydroxybutyrate CoA-transferase | ACYPI001782-PA | *Acyrthosiphon pisum* |
| Metabolism | Dihydropyrimidine dehydrogenase | ACYPI004747-PA | *Acyrthosiphon pisum* |
| Metabolism | Glycine dehydrogenase, mitochondrial | ACYPI005060-PA | *Acyrthosiphon pisum* |
| Metabolism | Ribose-phosphate pyrophosphokinase 1, putative | ACYPI006288-PA | *Acyrthosiphon pisum* |
| Metabolism | Phosphoserine phosphatase isoform 1 | ACYPI000304-PA | *Acyrthosiphon pisum* |
| Metabolism | Adenine phosphoribosyltransferase | ACYPI003436-PA | *Acyrthosiphon pisum* |
| Metabolism | Pantothenate kinase 4 (Pantothenic acid kinase 4) (hPanK4) | ACYPI003518-PA | *Acyrthosiphon pisum* |
| Metabolism | Phosphoenolpyruvate carboxykinase | ACYPI001978-PA | *Acyrthosiphon pisum* |
| Metabolism | Cystathionine beta-lyase, partial | ACYPI000593-PA | *Acyrthosiphon pisum* |
| Metabolism | Putative 5-nucleotidase, partial | ACYPI002452-PA | *Acyrthosiphon pisum* |
| Metabolism | Zipper CG15792-PD | ACYPI004129-PA | *Acyrthosiphon pisum* |
| Metabolism | Aconitase | ACYPI008211-PA | *Acyrthosiphon pisum* |
| Metabolism | Prophenoloxidase | ACYPI001367-PA | *Acyrthosiphon pisum* |
| Metabolism | Glycinamide ribonucleotide synthetase-aminoimidazole ribonucleotide synthetase-glycinamide ribonucleotide transformylase, partial | ACYPI009448-PA | *Acyrthosiphon pisum* |
| Metabolism | Aldehyde dehydrogenase | ACYPI003925-PA | *Acyrthosiphon pisum* |

TABLE 8-continued

Proteins that regulate bacteriocyte function

| Functional class | Protein name | Sequence accession number | Organism |
|---|---|---|---|
| Metabolism | Metalloprotease | ACYPI008675-PA | *Acyrthosiphon pisum* |
| Metabolism | Prophenoloxidase | ACYPI004484-PA | *Acyrthosiphon pisum* |
| Metabolism | 5-aminoimidazole-4-carboxamide ribonucleotide formyltransferase/IMP cyclohydrolase | ACYPI008919-PA | *Acyrthosiphon pisum* |
| Metabolism | Sec24B protein, putative | ACYPI005848-PA | *Acyrthosiphon pisum* |
| Metabolism | Gmp synthase | ACYPI006177-PA | *Acyrthosiphon pisum* |
| Metabolism | mCG117402 | ACYPI000180-PA | *Acyrthosiphon pisum* |
| Metabolism | Lambda-crystallin | ACYPI001738-PA | *Acyrthosiphon pisum* |
| Metabolism | Glyoxylate/hydroxypyruvate reductase | ACYPI001693-PA | *Acyrthosiphon pisum* |
| Metabolism | Fructose-1,6-bisphosphatase | ACYPI002694-PA | *Acyrthosiphon pisum* |
| Metabolism | Imaginal disk growth factor | ACYPI001365-PA | *Acyrthosiphon pisum* |
| Metabolism | Lysosomal alpha-mannosidase (mannosidase alpha class 2b member 1) | ACYPI000371-PA | *Acyrthosiphon pisum* |
| Metabolism | 5-oxoprolinase (ATP-hydrolysing) | ACYPI004211-PA | *Acyrthosiphon pisum* |
| Metabolism | Aspartate ammonia lyase | ACYPI006003-PA | *Acyrthosiphon pisum* |
| Metabolism | Aldo-keto reductase | ACYPI005685-PA | *Acyrthosiphon pisum* |
| Metabolism | Aminomethyltransferase | ACYPI002795-PA | *Acyrthosiphon pisum* |
| Regulatory | Bacteriocyte-specific cysteine rich proteins BCR family, peptide BCR1 | ACYPI32128 | *Acyrthosiphon pisum* |
| Regulatory | Bacteriocyte-specific cysteine rich proteins BCR family, peptide BCR2 | ACYPI38738 | *Acyrthosiphon pisum* |
| Regulatory | Bacteriocyte-specific cysteine rich proteins BCR family, peptide BCR3 | ACYPI44142 | *Acyrthosiphon pisum* |
| Regulatory | Bacteriocyte-specific cysteine rich proteins BCR family, peptide BCR6 | ACYPI49532 | *Acyrthosiphon pisum* |
| Regulatory | Bacteriocyte-specific cysteine rich proteins BCR family, peptide BCR8 | ACYPI45157 | *Acyrthosiphon pisum* |
| Regulatory | Secreted proteins SP family, peptide SP1 | ACYPI008389 | *Acyrthosiphon pisum* |
| Regulatory | Secreted proteins SP family, peptide SP2 | ACYPI000294 | *Acyrthosiphon pisum* |
| Regulatory | Secreted proteins SP family, peptide SP3 | ACYPI005168 | *Acyrthosiphon pisum* |
| Regulatory | Secreted proteins SP family, peptide SP4 | ACYPI009984 | *Acyrthosiphon pisum* |
| Regulatory | Secreted proteins SP family, peptide SP5a | ACYPI004796 | *Acyrthosiphon pisum* |
| Regulatory | Secreted proteins SP family, peptide SP6 | ACYPI001839 | *Acyrthosiphon pisum* |
| Signaling | Glean peptide GLEAN_28598 | ACYPI48598-PA | *Acyrthosiphon pisum* |
| Signaling | Glean peptide GLEAN_33885 | ACYPI53885-PA | *Acyrthosiphon pisum* |
| Signaling | past-1 | ACYPI007266-PA | *Acyrthosiphon pisum* |
| Transport | Putative vacuolar ATP synthase subunit E isoform 1 | ACYPI006090-PA | *Acyrthosiphon pisum* |
| Transport | Vacuolar ATP synthase subunit H | ACYPI002312-PA | *Acyrthosiphon pisum* |
| Transport | Vacuolar ATPase subunit C | ACYPI006545-PA | *Acyrthosiphon pisum* |
| Transport | Vacuolar ATP synthase 16 kDa proteolipid subunit (Ductin) (VHA16K) | ACYPI003545-PA | *Acyrthosiphon pisum* |
| Transport | Potassium/chloride symporter, putative, partial | ACYPI000507-PA | *Acyrthosiphon pisum* |
| Transport | Cationic amino acid transporter | ACYPI008904-PA | *Acyrthosiphon pisum* |

In some instances, the methods or compositions provided herein may be effective to decrease the host's resistance to parasites or pathogens (e.g., fungal, bacterial, or viral pathogens or parasites) in comparison to a host organism to which the modulating agent has not been administered. In some instances, the methods or compositions provided herein may be effective to decrease the host's resistance to a pathogen or parasite (e.g., fungal, bacterial, or viral pathogens; or parasitic mites) by about 2%, 5%, 10%, 20%, 30%, 40%, 50%, 60%, 70%, 80%, 90%, 100%, or greater than 100% relative to a reference level (e.g., a level found in a host that does not receive a modulating agent).

In some instances, the modulating agent is effective to alter the innate immune system of a host to indirectly change microbial diversity in the host relative to a host organism to which the modulating agent has not been administered. Invertebrates exhibit multiple immune reactions, some of which are homologous to immune mechanisms found in mammals. General principles of innate immunity in insects have been summarized by other reviews (Lemaitre et al., Annu. Rev. Immunol. 25:697-743, 2007; Charroux et al., Fly 4:40-47, 2010; Ganesan et al., Curr. Top. Microbiol. Immunol. 349:25-60, 2011; Chambers et al., Curr. Opin. Immunol. 24:10-14, 2012). For example, in D. melanogaster, there are two major inducible responses enabling local immunity at the intestinal epithelial cell layer: production of AMPs and synthesis of reactive oxygen species (ROS). While both of these induced responses might be seen as classical resistance mechanisms, they both include negative feedback loops and modulatory components, which can confer host tolerance toward the commensal gut microbiota.

Colonization of the gut by commensal bacteria could induce immune priming events resulting in the activation or alteration of the immune response not only toward recurrent colonization of commensal bacteria, but also against pathogens. Gut microbiota is essential not only for priming the immune system of the host to bacteria, e.g., mosquitoes to *Plasmodium*, but also for eliciting the priming response upon rechallenging the hosts with the bacteria. The bacteria-dependent priming response in mosquitoes is characterized by differentiation of prohemocytes into granulocytes and the presence of increased numbers of circulating granulocytes with changed morphology and binding properties. In another example, tsetse fly bacterial symbionts, including the gut-inhabiting Gammaproteobacterium *S. glossinidius*, are essential during larval development in order that the adult flies could present a trypanosome-refractory phenotype. In this case, the bacteria seem to influence the formation and integrity of the adult peritrophic matrix, thereby indirectly regulating the fly's ability to detect and respond to the presence of trypanosomes.

In some instances, an immune response is modulated by production of a modulating agent. For example, in the systemic immune response of *D. melanogaster*, Toll and IMD are the two major signaling pathways inducing antimicrobial peptide (AMP) production. Upon pathogen exposure, only the IMD pathway is active and triggers a local AMP response. Activation occurs by binding different variants of bacterial peptidoglycan (PGN) to extra- or intracellular epithelial receptors belonging to the peptidoglycan recognition protein (PGRP) family. The protein Pirk sequesters specific PGN-binding receptors (PGRP-LC) in the cytoplasm, thereby reducing the number of these receptors localizing to the cell surface and retarding IMD pathway signaling. PGRP-LE ensures immune tolerance to the commensal microbiota via the up-regulation of amidases and Pirk. Downstream signaling via the IMD pathway results in activation of the transcription factor Relish, which in turn induces expression of several AMPs and other immunity-related genes. PGRP-LE induces a Relish-dependent immune response to pathogenic bacteria. PGRP-LE also ensures immune tolerance to the commensal microbiota via the up-regulation of amidases and Pirk.

The homeobox transcription factor Caudal specifically represses AMP gene transcription in the gut by binding to promoter regions. Caudal-deficiency causes a constitutive AMP production to occur and a shift in the gut microbiota. In one embodiment, an IMD pathway is inactivated to restrict expression of one or more AMPs and/or other immunity-related genes, e.g., caudal deficiency, thereby activating an immune response to a gut microbiota.

In some instances, exposure to pathogens in the gut triggers the generation of ROS via the membrane-associated dual oxidase (DUOX) system. For example, in *D. melanogaster*, PGN-dependent and PGN-independent signaling pathways produce ROS that causes oxidative stress not only on the bacteria but also on the host's epithelial cells. *D. melanogaster* eliminates excessive ROS by activating immune responsive catalases. This catalase production results in increased tolerance, due to a decrease in self-harm caused by the bacteria-induced immune response, possibly through locally restricted catalase activity, e.g., to the proximity of the epithelial surface. In one embodiment, immune responsive catalases are inactivated or repressed to maintain ROS production via the DUOX system and oxidative stress via PGN-dependent and PGN-independent signaling pathways to activate an immune response to a gut microbiota.

In some instances, the modulating agent is effective to alter (e.g., increase or decrease) gene expression in a host to increase or decrease the host's immune system response or immunoregulatory signaling, e.g., immune system response to microorganisms resident in the host (e.g., microorganisms resident in host bacteriocytes) in comparison to a host organism to which the modulating agent has not been administered. Nonlimiting examples of immune system related genes/proteins in bacteriocytes are shown in Table 9.

TABLE 9

Immunoregulatory proteins that modulate bacteriocytes

| Functional class | Protein name | Sequence accession number | Organism |
|---|---|---|---|
| Regulatory | BicD (Protein bicaudal D) | CG6605 | D. melanogaster |
| Regulatory | PGRP SA (Peptidoglycan recognition protein) | CG11709 | D. melanogaster |
| Regulatory | Relish (transcription factor) | CG11992 | D. melanogaster |
| Regulatory | Pirk (poor Imd response upon knock-in) | CG15678 | D. melanogaster |
| Regulatory | DUOX (Dual oxidase) | CG3131 | D. melanogaster |
| Regulatory | p38c (p38c MAP kinase) | CG33338 | D. melanogaster |
| Regulatory | MKP3 (Dual phosphatase) | CG14080 | D. melanogaster |
| Regulatory | CanB (calcineurin B) | CG4209 | D. melanogaster |
| Regulatory | Plad (phospholipase D) | CG12110 | D. melanogaster |
| Regulatory | Cact (cactus) | CG5848 | D. melanogaster |
| Regulatory | DIF (Dorsal related immunity factor) | CG6794 | D. melanogaster |
| Regulatory | dIAP2 (*Drosophila* Inhibitor of APoptosis2) | CG8293 | D. melanogaster |
| Regulatory | Toll (Toll Interacting Protein) | CG5490 | D. melanogaster |
| Regulatory | gnbp1 (Gram Negative Binding Protein1) | CG6895 | D. melanogaster |

TABLE 9-continued

Immunoregulatory proteins that modulate bacteriocytes

| Functional class | Protein name | Sequence accession number | Organism |
| --- | --- | --- | --- |
| Regulatory | LysC (c-type lysozyme) | CR9111 | D. melanogaster |
| Regulatory | imd (immune deficiency) | CG5576 | D. melanogaster |
| Regulatory | Diap2 (Death-associated inhibitor of apoptosis 2) | CG8293 | D. melanogaster |
| Regulatory | ecsit | CG10610 | D. melanogaster | v. Bacteria as Modulating Agents

In some instances, the modulating agent described herein includes one or more bacteria. Numerous bacteria are useful in the compositions and methods described herein. In some instances, the agent is a bacterial species endogenously found in the host. In some instances, the bacterial modulating agent is an endosymbiotic bacterial species. In some instances, the bacterial modulating agent is a pathogen in the host. Non-limiting examples of bacteria that may be used as modulating agents include all bacterial species described herein in Section II of the detailed description and those listed in Table 1. For example, the modulating agent may be a bacterial species from any bacterial phyla present in host (e.g., insect, mollusk, or nematode) guts, including *Gammaproteobacteria, Alphaproteobacteria, Betaproteobacteria, Bacteroidetes, Firmicutes* (e.g., *Lactobacillus* and *Bacillus* spp.), Clostridia, Actinomycetes, Spirochetes, Verrucomicrobia, and Actinobacteria.

In some instances, the bacteria may be used as a modulating agent to stimulate an immune response in the host that leads to a decrease in the level, diversity, or metabolism of one or more microorganisms resident in the host. In some instances, the bacteria are delivered as live bacterial cells (e.g., *E. coli* cells). Alternatively, the bacteria may be delivered as heat-killed bacterial cells (e.g., heat-killed *E. coli* cells). In other instances, the bacteria may be delivered as lysates (e.g., prepared from lysed whole cells), or fractions thereof.

In some instances, the modulating agent includes genetically modified or transformed bacteria as described herein. In some instances, the bacteria are genetically modified. For example, the bacteria may be modified via the introduction of genetic material into a bacterium using standard methods in the art (e.g., transduction, transformation, or conjugation), thereby modifying or altering the cellular physiology, and/or biochemistry of the bacterium. Through the introduction of genetic material, the modified bacteria may acquire new functions or properties. In some instances, the genetically modified bacteria may produce and secrete a modulating agent described herein. For example, genetically modified bacteria may produce polypeptides, small molecules, or nucleic acids that target specific host endosymbionts or other microorganisms resident in the host. In some instances, the genetically modified bacteria may be used to produce a product that stimulates a host immune response.

In some instances, the genetically engineered or transformed bacteria are provided to impart new functionalities to the host. New functionalities may include, for example, the ability to degrade pesticides (e.g., insecticides, molluscicides, or nematicides; e.g., a pesticide listed in Table 11), plant allelochemicals, or produce nutrients. For example, genetically modified bacteria may be generated from naturally occurring bacteria isolated from pesticide (e.g., insecticide, molluscicide, or nematicides; e.g., a pesticide listed in Table 11) resistant pests, e.g. *Burkholderia* strains from the insect *R. pedestris*. When bacteria from insecticide resistant pests are cultured with commensal bacteria isolated from a host of interest, e.g., bees, genes imparting insecticide resistance (e.g., the ability to use the insecticide as a carbon source) may be transferred to the commensal bacteria of the host of interest, e.g., bees. The genetically modified bacteria are then reintroduced into the host, e.g., bees, and insecticide resistant insects are selected by breeding them in an environment rich in the insecticide. Any bacterial phyla that are commonly present in a host may be modified to have a new functionality, including, but not limited to, *Gammaproteobacteria, Alphaproteobacteria, Betaproteobacteria, Bacteroidetes, Firmicutes* including *Lactobacillus* and *Bacillus* species, Clostridia, Actinomycetes, Spirochetes, Verrucomicrobia, Actinobacteria, and others.

The bacterium may be genetically modified to decrease the fitness of the host or to kill the host. In some instances, a bacterium may be genetically modified to improve its survival in host cells, to increase its toxicity to the host cell, and/or to provide a function that decreases the fitness of the host (e.g., decreased resistance to a pesticide, e.g., a pesticide listed in Table 11). In some instances, the bacterium is modified to no longer synthesize an essential molecule that it typically provides to the host cell. In some instances, the bacterium is genetically modified so that the population of the bacteria is increased to a level that negatively impacts the host, e.g., by excessive utilization of essential materials or machinery or by competing with beneficial microorganisms resident in the host. In some instances, the bacteria only kill the host following further human intervention.

The genetically modified bacteria described herein can be generated using any methods known in the art. For example, methods for the delivery of nucleic acids to bacteria include, but are not limited to, different chemical, electrochemical and biological approaches, for example, heat shock transformation, electroporation, transfection, for example liposome-mediated transfection, DEAE-Dextran-mediated transfection or calcium phosphate transfection. In some instances, a nucleic acid construct, for example, an expression construct including at least one nucleic acid sequence is introduced into the bacteria using a vehicle, or vector, for transferring genetic material. Vectors for transferring genetic material to bacteria are well known to those of skill in the art and include, for example, plasmids, artificial chromosomes, and viral vectors. Methods for the construction of nucleic acid constructs, including expression constructs including constitutive or inducible heterologous promoters, knockout and knockdown constructs, as well as methods and vectors for the delivery of a nucleic acid or nucleic acid construct to bacteria are well known to those of skill in the art, and are described, for example, in Sambrook et al., *Molecular Cloning: A Laboratory Manual,* 3rd edition, Cold Spring Harbor Laboratory Press, Cold Spring Harbor, New York, 2001; Amberg et al., *Methods in Yeast Genetics: A Cold Spring Harbor Laboratory Course Manual*, Cold Spring Harbor Laboratory Press, 2005; Abelson et al., *Guide to Yeast Genetics and Molecular Biology*, Part A, Volume 194 (Methods in Enzymology Series, 194), Academic Press, 2004; Guthrie et al., *Guide to Yeast Genetics and Molecular and Cell Biology,* 1st edition, Part B, Volume 350 (Methods in Enzymology, Vol 350), Academic Press, 2002; Stephanopoulos et al., *Metabolic Engineering: Principles and Methodologies,* 1st edition, Academic Press, 1998; and Smolke, *The Metabolic Pathway Engineering Handbook: Fundamentals,* 1st edition, CRC Press, 2009, all of which are incorporated by reference herein in their entireties.

vi. Fungi as Modulating Agents In some instances, the modulating agent described herein includes one or more fungi. Numerous fungi are useful in the compositions and methods. For example, the fungal modulating agent may be yeast such as *Saccharomyces cerevisiae* or *Pichia pastoris*.

In some instances, the fungi (e.g., *S. cerevisiae* or *P. pastoris*) may be used as modulating agents to stimulate an immune response in the host that leads to a decrease in the levels, diversity, or metabolism of one or more microorganisms (e.g., bacteria or fungi) resident in the host. In some instances, the fungi are delivered as live fungal cells (e.g., *P. pastoris* cells, see Example 15). Alternatively, the fungi may be delivered as heat-killed fungal cells (e.g., heat-killed *S. cerevisiae* cells). In other instances, the fungi may be delivered as lysates (e.g., prepared from lysed whole cells), or fractions thereof.

In some instances, the modulating agent includes a genetically modified or transformed fungus as described herein. In some instances, the fungus is genetically modified. For example, the fungus may be modified via the introduction of genetic material into a fungus using standard methods in the art, thereby modifying or altering the cellular physiology and/or biochemistry of the fungus. Through the introduction of genetic material, the modified fungus may acquire new functions or properties. In some instances, the genetically modified fungus may produce and secrete a modulating agent described herein. In some instances, the genetically modified fungus may be used to produce a product that stimulates a host immune response.

In some instances, the genetically engineered or transformed fungus is provided to impart new functionalities to the host. New functionalities may include, for example, the ability to degrade pesticides (e.g., insecticides), plant allelochemicals, or produce nutrients. Any fungal phyla that are commonly present in a host may be genetically modified to have a new functionality, including, but not limited to, *Candida*, *Metschnikowia*, *Debaromyces*, *Scheffersomyces shehatae* and *Scheffersomyces stipites*, *Starmerella*, *Pichia*, *Trichosporon*, *Cryptococcus*, *Pseudozyma*, and yeast-like symbionts from the subphylum Pezizomycotina (e.g., *Symbiotaphrina bucneri* and *Symbiotaphrina kochii*).

As illustrated by Example 15, yeast, such as *P. pastoris*, can be used as a modulating agent that stimulates a host immune response (e.g., in an insect, e.g., an aphid) that, in turn, alters the activity, levels, or metabolism of endosymbiotic bacteria, such as a *Buchnera* spp., resident in the host and thereby modulates (e.g., decreases) the fitness of the host.

vii. Modifications to Modulating Agents

In some instances, the nucleic acid molecule, peptide, polypeptide, or antibody molecule can be modified. For example, the modification can be a chemical modification, e.g., conjugation to a marker, e.g., fluorescent marker or a radioactive marker. In other examples, the modification can include conjugation or operational linkage to a moiety that enhances the stability, delivery, targeting, bioavailability, or half-life of the agent, e.g., a lipid, a glycan, a polymer (e.g., PEG), a cation moiety.

(a) Fusions

Any of the modulating agents described herein may be fused or linked to an additional moiety. In some instances, the modulating agent includes a fusion of one or more additional moieties (e.g., 1 additional moiety, 2, 3, 4, 5, 6, 7, 8, 9, 10, or more additional moieties). In some instances, the additional moiety is any one of the modulating agents described herein (e.g., a peptide, polypeptide, small molecule, or antibiotic). Alternatively, the additional moiety may not act as modulating agent itself but may instead serve a secondary function. For example, the additional moiety may to help the modulating agent access, bind, or become activated at a target site in the host (e.g., at a host gut or a host bacteriocyte) or at a target microorganism resident in the host.

In some instances, the additional moiety may help the modulating agent penetrate a target host cell or target microorganism resident in the host. For example, the additional moiety may include a cell penetrating peptide. Cell penetrating peptides (CPPs) may be natural sequences derived from proteins; chimeric peptides that are formed by the fusion of two natural sequences; or synthetic CPPs, which are synthetically designed sequences based on structure—activity studies. In some instances, CPPs have the capacity to ubiquitously cross cellular membranes (e.g., prokaryotic and eukaryotic cellular membranes) with limited toxicity. Further, CPPs may have the capacity to cross cellular membranes via energy-dependent and/or independent mechanisms, without the necessity of a chiral recognition by specific receptors. Non-limiting examples of CPPs are listed in Table 10.

TABLE 10

Examples of Cell Penetrating Peptides (CPPs)

| Peptide | Origin | Sequence |
|---|---|---|
| Protein-derived | | |
| Penetratin | Antennapedia | RQIKIWFQNRRMKWKK (SEQ ID NO: 82) |
| Tat peptide | Tat | GRKKRRQRRRPPQ (SEQ ID NO: 83) |
| pVEC | Cadherin | LLIILRRRIRKQAHAHSK (SEQ ID NO: 84) |
| Chimeric | | |
| Transportan | Galanine/ Mastoparan | GWTLNSAGYLLGKIN LKALAALAKKIL (SEQ ID NO: 85) |
| MPG | HIV-gp41/ SV40 T-antigen | GALFLGFLGAAGSTM GAWSQPKKKRKV (SEQ ID NO: 86) |
| Pep-1 | HIV-reverse transcriptase/ SV40 T-antigen | KETWWETWWTEWSQ PKKKRKV (SEQ ID NO: 87) |
| Synthetic | | |
| Polyarginines | Based on Tat peptide | $(R)_n$; $6 < n < 12$ |
| MAP | de novo | KLALKLALKALKAALKLA (SEQ ID NO: 88) |
| $R_6W_3$ | Based on penetratin | RRWWRRWRR (SEQ ID NO: 89) |

In some instances, the additional moiety is a peptide nucleic acid (PNAs). Peptide nucleic acids (PNAs) include one or more nucleic acid side chains linked to an amide backbone. One or more amino acid units in the PNA have an amide containing backbone, e.g., aminoethyl-glycine, similar to a peptide backbone, with a nucleic acid side chain in place of the amino acid side chain. PNAs are known to hybridize complementary DNA and RNA with higher affinity than their oligonucleotide counterparts. This character of PNA not only makes the polypeptide of the invention a stable hybrid with the nucleic acid side chains, but at the same time, the neutral backbone and hydrophobic side chains result in a hydrophobic unit within the polypeptide. Examples of PNA moieties include a molecule that includes a peptide, such as a CPP (e.g., an amino acid sequence having at least at least 80% (e.g., 80%, 90%, 95%, 97%, 99%, or greater) identity to SEQ ID NO: 106) and a nucleotide sequence having at least 80% (e.g., 80%, 90%, 95%, 97%, 99%, or greater) identity to the sequence of any one of SEQ ID NOs: 105 or 151-153.

The nucleic acid side chain includes, but is not limited to, a purine or a pyrimidine side chain such as adenine, cytosine, guanine, thymine, and uracil. In one instances, the nucleic acid side chain includes a nucleoside analog, such as 5-fluorouracil; 5-bromouracil, 5-chlorouracil, 5-iodouracil, hypoxanthine, xanthine, 4-acetylcytosine, 4-methylbenzimidazole, 5-(carboxyhydroxylmethyl) uracil, 5-carboxymethylaminomethyl-2-thiouridine, 5-carboxymethylaminomethyluracil, dihydrouracil, dihydrouridine, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil (acp$^3$ U), 2,6-diaminopurine, 3-nitropyrrole, inosine, thiouridine, queuosine, wyosine, diaminopurine, isoguanine, isocytosine, diaminopyrimidine, 2,4-difluorotoluene, isoquinoline, pyrrolo[2,3-β]pyridine, and any others that can base pair with a purine or a pyrimidine side chain.

In other instances, the additional moiety helps the modulating agent bind a target microorganism (e.g., a fungi or bacterium) resident in the host. The additional moiety may include one or more targeting domains. In some instances, the targeting domain may target the modulating agent to one or more microorganisms (e.g., bacterium or fungus) resident in the gut of the host. In some instances, the targeting domain may target the modulating agent to a specific region of the host (e.g., host gut or bacteriocyte) to access microorganisms that are generally present in said region of the host. For example, the targeting domain may target the modulating agent to the foregut, midgut, or hindgut of the host. In other instances, the targeting domain may target the modulating agent to a bacteriocyte in the host and/or one or more specific bacteria resident in a host bacteriocyte.

(b) Pre- or Pro-Domains

In some instances, the modulating agent may include a pre- or pro-amino acid sequence. For example, the modulating agent may be an inactive protein or peptide that can be activated by cleavage or post-translational modification of a pre- or pro-sequence. In some instances, the modulating agent is engineered with an inactivating pre- or pro-sequence. For example, the pre- or pro-sequence may obscure an activation site on the modulating agent, e.g., a receptor binding site, or may induce a conformational change in the modulating agent. Thus, upon cleavage of the pre- or pro-sequence, the modulating agent is activated.

Alternatively, the modulating agent may include a pre- or pro-small molecule, e.g., an antibiotic. The modulating agent may be an inactive small molecule described herein that can be activated in a target environment inside the host. For example, the small molecule may be activated upon reaching a certain pH in the host gut.

(c) Linkers

In instances where the modulating agent is connected to an additional moiety, the modulating agent may further include a linker. For example, the linker may be a chemical bond, e.g., one or more covalent bonds or non-covalent bonds. In some instances, the linker may be a peptide linker (e.g., 2, 3, 4, 5, 6, 8, 10, 12, 14, 16, 20, 25, 30, 35, 40, or more amino acids longer). The linker maybe include any flexible, rigid, or cleavable linkers described herein.

A flexible peptide linker may include any of those commonly used in the art, including linkers having sequences having primarily Gly and Ser residues ("GS" linker). Flexible linkers may be useful for joining domains that require a certain degree of movement or interaction and may include small, non-polar (e.g. Gly) or polar (e.g. Ser or Thr) amino acids.

Alternatively, a peptide linker may be a rigid linker. Rigid linkers are useful to keep a fixed distance between moieties and to maintain their independent functions. Rigid linkers may also be useful when a spatial separation of the domains is critical to preserve the stability or bioactivity of one or more components in the fusion. Rigid linkers may, for example, have an alpha helix-structure or Pro-rich sequence, (XP)n, with X designating any amino acid, preferably Ala, Lys, or Glu.

In yet other instances, a peptide linker may be a cleavable linker. In some instances, linkers may be cleaved under specific conditions, such as the presence of reducing reagents or proteases. In vivo cleavable linkers may utilize the reversible nature of a disulfide bond. One example includes a thrombin-sensitive sequence (e.g., PRS) between two Cys residues. In vitro thrombin treatment of CPRSC results in the cleavage of the thrombin-sensitive sequence, while the reversible disulfide linkage remains intact. Such linkers are known and described, e.g., in Chen et al., *Adv. Drug Deliv. Rev.* 65(10):1357-1369, 2013. Cleavage of linkers in fusions may also be carried out by proteases that are expressed in vivo under conditions in specific cells or tissues of the host or microorganisms resident in the host. In some instances, cleavage of the linker may release a free functional, modulating agent upon reaching a target site or cell.

Fusions described herein may alternatively be linked by a linking molecule, including a hydrophobic linker, such as a negatively charged sulfonate group; lipids, such as a poly (—CH2-) hydrocarbon chains, such as polyethylene glycol (PEG) group, unsaturated variants thereof, hydroxylated variants thereof, amidated or otherwise N-containing variants thereof, non-carbon linkers; carbohydrate linkers; phosphodiester linkers, or other molecule capable of covalently linking two or more molecules, e.g., two modulating agents. Non-covalent linkers may be used, such as hydrophobic lipid globules to which the modulating agent is linked, for example, through a hydrophobic region of the modulating agent or a hydrophobic extension of the modulating agent, such as a series of residues rich in leucine, isoleucine, valine, or perhaps also alanine, phenylalanine, or even tyrosine, methionine, glycine, or other hydrophobic residue. The modulating agent may be linked using charge-based chemistry, such that a positively charged moiety of the modulating agent is linked to a negative charge of another modulating agent or an additional moiety.

IV. Formulations and Compositions

The compositions described herein may be formulated either in pure form (e.g., the composition contains only the modulating agent) or together with one or more additional agents (such as excipient, delivery vehicle, carrier, diluent, stabilizer, etc.) to facilitate application or delivery of the compositions. Examples of suitable excipients and diluents include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline solution, syrup, methylcellulose, methyl- and propylhydroxybenzoates, talc, magnesium stearate, and mineral oil.

In some instances, the composition includes a delivery vehicle or carrier. In some instances, the delivery vehicle includes an excipient. Exemplary excipients include, but are not limited to, solid or liquid carrier materials, solvents, stabilizers, slow-release excipients, colorings, and surface-active substances (surfactants). In some instances, the delivery vehicle is a stabilizing vehicle. In some instances, the stabilizing vehicle includes a stabilizing excipient. Exemplary stabilizing excipients include, but are not limited to, epoxidized vegetable oils, antifoaming agents, e.g. silicone oil, preservatives, viscosity regulators, binding agents and tackifiers. In some instances, the stabilizing vehicle is a buffer suitable for the modulating agent. In some instances, the composition is microencapsulated in a polymer bead delivery vehicle. In some instances, the stabilizing vehicle protects the modulating agent against UV and/or acidic conditions. In some instances, the delivery vehicle contains a pH buffer. In some instances, the composition is formulated to have a pH in the range of about 4.5 to about 9.0, including for example pH ranges of about any one of 5.0 to about 8.0, about 6.5 to about 7.5, or about 6.5 to about 7.0.

Depending on the intended objectives and prevailing circumstances, the composition may be formulated into emulsifiable concentrates, suspension concentrates, directly sprayable or dilutable solutions, coatable pastes, diluted emulsions, spray powders, soluble powders, dispersible powders, wettable powders, dusts, granules, encapsulations in polymeric substances, microcapsules, foams, aerosols, carbon dioxide gas preparations, tablets, resin preparations, paper preparations, nonwoven fabric preparations, or knitted or woven fabric preparations. In some instances, the composition is a liquid. In some instances, the composition is a solid. In some instances, the composition is an aerosol, such as in a pressurized aerosol can. In some instances, the composition is present in the waste (such as feces) of the pest. In some instances, the composition is present in or on a live pest.

In some instances, the delivery vehicle is the food or water of the host. In other instances, the delivery vehicle is a food source for the host. In some instances, the delivery vehicle is a food bait for the host. In some instances, the composition is a comestible agent consumed by the host. In some instances, the composition is delivered by the host to a second host, and consumed by the second host. In some instances, the composition is consumed by the host or a second host, and the composition is released to the surrounding of the host or the second host via the waste (such as feces) of the host or the second host. In some instances, the modulating agent is included in food bait intended to be consumed by a host or carried back to its colony.

In some instances, the delivery vehicle is a bacterial vector. The modulating agent can be incorporated in a bacterial vector using any suitable cloning methods and reagents known in the art, such as described in Sambrook et al., *Molecular Cloning: A Laboratory Manual*, Cold Spring Harbor Laboratory Press, Cold Spring Harbor, New York, 1989. "Bacterial vector" as used herein refers to any genetic element, such as plasmids, bacteriophage vectors, transposons, cosmids, and chromosomes, which is capable of replication inside bacterial cells and which is capable of transferring genes between cells. Exemplary bacterial vectors include, but are not limited to, lambda vector system gt1 1, gt WES.tB, Charon 4, and plasmid vectors such as pBR322, pBR325, pACYC177, pACYC184, pUC8, pUC9, pUC18, pUC19, pLG339, pR290, pKC37, pKCIOI, SV 40, pBluescript II SK+/− or KS+/−(see "Stratagene Cloning Systems" Catalog, Stratagene, La Jolla, California, 1993), pQE, pIH821, pGEX, pET series (see Studier et al., "Use of T7 RNA Polymerase to Direct Expression of Cloned Genes," *Gene Expression Technology*, Vol. 185, 1990), and any derivatives thereof.

Each bacterial vector may encode one or more modulating agents. In some instances, the bacterial vector includes a nucleic acid molecule encoding a polypeptide to be expressed in the target symbiotic bacterium or a host bacterium. In some instances, the bacterial vector includes a nucleic acid molecule encoding a bacteriocin to be expressed in the target bacterium. In some instances, the bacterial vector further includes one or more regulatory elements, such as promoters, termination signals, and transcription and translation elements. In some instances, the regulatory sequence is operably linked to a nucleic acid encoding a gene (e.g., any of the nucleic acids described herein) to be expressed in the target symbiotic bacterium.

In some instances, the bacterial vector is introduced into a bacterium to be consumed by the host or a member in the colony of the host. In some instances, the bacterium is the target symbiotic bacterium. In some instances, the bacterium is a naturally occurring bacterium of the gut of the host, or a genetically modified derivative thereof, which can be easily introduced to the host through ingestion. Exemplary bacteria for use in carrying the bacterial vector include, but are not limited to, *Proteobacter*, including the genus *Pseudomonas; Actinobacter*, including *Priopionibacterium* and *Corynebacterium*; Firmicutes, including the any species of the genera *Mycoplasma, Bacillus, Streptococcus, Staphylococcus; Fibrobacteres; Spirochaetes*, including *Treponema* and *Borrelia; Bacteroides*, including the genera *Bacteroides* and *Flavobacterium*. Also suitable are any bacteria of the Enterobacteriaceae, including the genus *Serratia*, including, but not limited to *S. marcescens, S. entomophila, S. proteamaculans*; any species of *Enterobacter*, including, but not limited to, *E. cloacae, E. aerogenes, E. dissolvens, E. agglomerans, E. hafiiiae*; and any species belonging to the following genera: *Citrobacter, Escherichia, Klebsiella, Kluyvera, Panotea, Proteus, Salmonella, Xenorhabdus*, and *Yokenella*.

In some instances, the modulating agent may make up about 0.1% to about 100% of the composition, such as any one of about 0.01% to about 100%, about 1% to about 99.9%, about 0.1% to about 10%, about 1% to about 25%, about 10% to about 50%, about 50% to about 99%, or about 0.1% to about 90% of active ingredients (e.g., a polypeptide, nucleic acid, small molecule, or combinations thereof). In some instances, the composition includes at least any of 0.1%, 0.5%, 1%, 5%, 10%, 20%, 30%, 40%, 50%, 60%, 70%, 80%, 90%, 95%, or more active ingredients (e.g., a polypeptide, nucleic acid, small molecule, or combinations thereof). In some instances, the concentrated agents are preferred as commercial products, the final user normally uses diluted agents, which have a substantially lower concentration of active ingredient.

Any of the formulations described herein may be used in the form of a bait, a coil, an electric mat, a smoking preparation, a fumigant, or a sheet.

i. Liquid Formulations

The compositions provided herein may be in a liquid formulation. Liquid formulations are generally mixed with water, but in some instances may be used with crop oil, diesel fuel, kerosene or other light oil as a carrier. The amount of active ingredient often ranges from about 0.5 to about 80 percent by weight.

An emulsifiable concentrate formulation may contain a liquid active ingredient, one or more petroleum-based solvents, and an agent that allows the formulation to be mixed with water to form an emulsion. Such concentrates may be used in agricultural, ornamental and turf, forestry, structural, food processing, livestock, and public health pest formulations. These may be adaptable to application equipment from small portable sprayers to hydraulic sprayers, low-volume ground sprayers, mist blowers, and low-volume aircraft sprayers. Some active ingredients are readily dissolve in a liquid carrier. When mixed with a carrier, they form a solution that does not settle out or separate, e.g., a homogenous solution. Formulations of these types may include an active ingredient, a carrier, and one or more other ingredients. Solutions may be used in any type of sprayer, indoors and outdoors.

In some instances, the composition may be formulated as an invert emulsion. An invert emulsion is a water-soluble active ingredient dispersed in an oil carrier. Invert emulsions require an emulsifier that allows the active ingredient to be mixed with a large volume of petroleum-based carrier, usually fuel oil. Invert emulsions aid in reducing drift. With other formulations, some spray drift results when water droplets begin to evaporate before reaching target surfaces; as a result the droplets become very small and lightweight. Because oil evaporates more slowly than water, invert emulsion droplets shrink less and more active ingredient reaches the target. Oil further helps to reduce runoff and improve rain resistance. It further serves as a sticker-spreader by improving surface coverage and absorption. Because droplets are relatively large and heavy, it is difficult to get thorough coverage on the undersides of foliage. Invert emulsions are most commonly used along rights-of-way where drift to susceptible non-target areas can be a problem.

A flowable or liquid formulation combines many of the characteristics of emulsifiable concentrates and wettable powders. Manufacturers use these formulations when the active ingredient is a solid that does not dissolve in either water or oil. The active ingredient, impregnated on a substance such as clay, is ground to a very fine powder. The powder is then suspended in a small amount of liquid. The resulting liquid product is quite thick. Flowables and liquids share many of the features of emulsifiable concentrates, and they have similar disadvantages. They require moderate agitation to keep them in suspension and leave visible residues, similar to those of wettable powders.

Flowables/liquids are easy to handle and apply. Because they are liquids, they are subject to spilling and splashing. They contain solid particles, so they contribute to abrasive wear of nozzles and pumps. Flowable and liquid suspensions settle out in their containers. Because flowable and liquid formulations tend to settle, packaging in containers of five gallons or less makes remixing easier.

Aerosol formulations contain one or more active ingredients and a solvent. Most aerosols contain a low percentage of active ingredients. There are two types of aerosol formulations—the ready-to-use type commonly available in pressurized sealed containers and those products used in electrical or gasoline-powered aerosol generators that release the formulation as a smoke or fog.

Ready to use aerosol formulations are usually small, self-contained units that release the formulation when the nozzle valve is triggered. The formulation is driven through a fine opening by an inert gas under pressure, creating fine droplets. These products are used in greenhouses, in small areas inside buildings, or in localized outdoor areas. Commercial models, which hold five to 5 pounds of active ingredient, are usually refillable.

Smoke or fog aerosol formulations are not under pressure. They are used in machines that break the liquid formulation into a fine mist or fog (aerosol) using a rapidly whirling disk or heated surface.

ii. Dry or Solid Formulations

Dry formulations can be divided into two types: ready-to-use and concentrates that must be mixed with water to be applied as a spray. Most dust formulations are ready to use and contain a low percentage of active ingredients (less than about 10 percent by weight), plus a very fine, dry inert carrier made from talc, chalk, clay, nut hulls, or volcanic ash. The size of individual dust particles varies. A few dust formulations are concentrates and contain a high percentage of active ingredients. Mix these with dry inert carriers before applying. Dusts are always used dry and can easily drift to non-target sites.

iii. Granule or Pellet Formulations

In some instances, the composition is formulated as granules. Granular formulations are similar to dust formulations, except granular particles are larger and heavier. The coarse particles may be made from materials such as clay, corncobs, or walnut shells. The active ingredient either coats the outside of the granules or is absorbed into them. The amount of active ingredient may be relatively low, usually ranging from about 0.5 to about 15 percent by weight. Granular formulations are most often used to apply to the soil, insects, mollusks, or nematodes living in the soil, or absorption into plants through the roots. Granular formulations are sometimes applied by airplane or helicopter to minimize drift or to penetrate dense vegetation. Once applied, granules may release the active ingredient slowly. Some granules require soil moisture to release the active ingredient. Granular formulations also are used to control larval mosquitoes and other aquatic pests. Granules are used in agricultural, structural, ornamental, turf, aquatic, right-of-way, and public health (biting insect) pest-control operations.

In some instances, the composition is formulated as pellets. Most pellet formulations are very similar to granular formulations; the terms are used interchangeably. In a pellet formulation, however, all the particles are the same weight and shape. The uniformity of the particles allows use with precision application equipment.

iv. Powders

In some instances, the composition is formulated as a powder. In some instances, the composition is formulated as a wettable powder. Wettable powders are dry, finely ground formulations that look like dusts. They usually must be mixed with water for application as a spray. A few products, however, may be applied either as a dust or as a wettable powder—the choice is left to the applicator. Wettable powders have about 1 to about 95 percent active ingredient by weight; in some cases more than about 50 percent. The particles do not dissolve in water. They settle out quickly unless constantly agitated to keep them suspended. They can be used for most pest problems and in most types of spray equipment where agitation is possible. Wettable powders have excellent residual activity. Because of their physical properties, most of the formulation remains on the surface of treated porous materials such as concrete, plaster, and untreated wood. In such cases, only the water penetrates the material.

In some instances, the composition is formulated as a soluble powder. Soluble powder formulations look like wettable powders. However, when mixed with water, soluble powders dissolve readily and form a true solution. After they are mixed thoroughly, no additional agitation is necessary. The amount of active ingredient in soluble powders ranges from about 15 to about 95 percent by weight; in some cases more than about 50 percent. Soluble powders have all the advantages of wettable powders and none of the disadvantages, except the inhalation hazard during mixing.

In some instances, the composition is formulated as a water-dispersible granule. Water-dispersible granules, also known as dry flowables, are like wettable powders, except instead of being dust-like, they are formulated as small, easily measured granules. Water-dispersible granules must be mixed with water to be applied. Once in water, the granules break apart into fine particles similar to wettable powders. The formulation requires constant agitation to keep it suspended in water. The percentage of active ingredient is high, often as much as 90 percent by weight. Water-dispersible granules share many of the same advantages and disadvantages of wettable powders, except they are more easily measured and mixed. Because of low dust, they cause less inhalation hazard to the applicator during handling v. Bait In some instances, the composition includes a bait. The bait can be in any suitable form, such as a solid, paste, pellet or powdered form. The bait can also be carried away by the host back to a population of said host (e.g., a colony or hive). The bait can then act as a food source for other members of the colony, thus providing an effective modulating agent for a large number of hosts and potentially an entire host colony.

The baits can be provided in a suitable "housing" or "trap." Such housings and traps are commercially available and existing traps can be adapted to include the compositions described herein. The housing or trap can be box-shaped for example, and can be provided in pre-formed condition or can be formed of foldable cardboard for example. Suitable materials for a housing or trap include plastics and cardboard, particularly corrugated cardboard. The inside surfaces of the traps can be lined with a sticky substance in order to restrict movement of the host once inside the trap. The housing or trap can contain a suitable trough inside which can hold the bait in place. A trap is distinguished from a housing because the host cannot readily leave a trap following entry, whereas a housing acts as a "feeding station" which provides the host with a preferred environment in which they can feed and feel safe from predators.

vi. Attractants

In some instances, the composition includes an attractant (e.g., a chemoattractant). The attractant may attract an adult host or immature host (e.g., larva) to the vicinity of the composition. Attractants include pheromones, a chemical that is secreted by an animal, especially a host (e.g., insect, mollusk, or nematode), which influences the behavior or development of others of the same species. Other attractants include sugar and protein hydrolysate syrups, yeasts, and rotting meat. Attractants also can be combined with an active ingredient and sprayed onto foliage or other items in the treatment area.

Various attractants are known which influence host behavior as a host's search for food, oviposition or mating sites, or mates. Attractants useful in the methods and compositions described herein include, for example, eugenol, phenethyl propionate, ethyl dimethylisobutyl-cyclopropane carboxylate, propyl benszodioxancarboxylate, cis-7,8-epoxy-2-methyloctadecane, trans-8,trans-0-dodecadienol, cis-9-tetradecenal (with cis-11-hexadecenal), trans-11-tetradecenal, cis-11-hexadecenal, (Z)-11,12-hexadecadienal, cis-7-dodecenyl acetate, cis-8-dodecenyul acetate, cis-9-dodecenyl acetate, cis-9-tetradecenyl acetate, cis-11-tetradecenyl acetate, trans-11-tetradecenyl acetate (with cis-11), cis-9,trans-11-tetradecadienyl acetate (with cis-9,trans-12), cis-9,trans-1 2-tetradecadienyl acetate, cis-7,cis-11-hexadecadienyl acetate (with cis-7,trans-11), cis-3,cis-13-octadecadienyl acetate, trans-3,cis-13-octadecadienyl acetate, anethole and isoamyl salicylate.

Means other than chemoattractants may also be used to attract a host (e.g., insect, mollusk, or nematode), including lights in various wavelengths or colors.

vii. Nanocapsules/Microencapsulation/Liposomes

In some instances, the composition is provided in a microencapsulated formulation. Microencapsulated formulations are mixed with water and sprayed in the same manner as other sprayable formulations. After spraying, the plastic coating breaks down and slowly releases the active ingredient.

viii. Carriers

Any of the compositions described herein may be formulated to include the modulating agent described herein and an inert carrier. Such carrier can be a solid carrier, a liquid carrier, a gel carrier, and/or a gaseous carrier. In certain instances, the carrier can be a seed coating. The seed coating is any non-naturally occurring formulation that adheres, in whole or part, to the surface of the seed. The formulation may further include an adjuvant or surfactant. The formulation can also include one or more modulating agents to enlarge the action spectrum.

A solid carrier used for formulation includes finely-divided powder or granules of clay (e.g. kaolin clay, diatomaceous earth, bentonite, Fubasami clay, acid clay, etc.), synthetic hydrated silicon oxide, talc, ceramics, other inorganic minerals (e.g., sericite, quartz, sulfur, activated carbon, calcium carbonate, hydrated silica, etc.), a substance which can be sublimated and is in the solid form at room temperature (e.g., 2,4,6-triisopropyl-1,3,5-trioxane, naphthalene, p-dichlorobenzene, camphor, adamantan, etc.); wool; silk; cotton; hemp; pulp; synthetic resins (e.g., polyethylene resins such as low-density polyethylene, straight low-density polyethylene and high-density polyethylene; ethylene-vinyl ester copolymers such as ethylene-vinyl acetate copolymers; ethylene-methacrylic acid ester copolymers such as ethylene-methyl methacrylate copolymers and ethylene-ethyl methacrylate copolymers; ethylene-acrylic acid ester copolymers such as ethylene-methyl acrylate copolymers and ethylene-ethyl acrylate copolymers; ethylene-vinylcarboxylic acid copolymers such as ethylene-acrylic acid copolymers; ethylene-tetracyclododecene copolymers; polypropylene resins such as propylene homopolymers and propylene-ethylene copolymers; poly-4-methylpentene-1, polybutene-1, polybutadiene, polystyrene; acrylonitrile-styrene resins; styrene elastomers such as acrylonitrile-butadiene-styrene resins, styrene-conjugated diene block copolymers, and styrene-conjugated diene block copolymer hydrides; fluororesins; acrylic resins such as poly(methyl methacrylate); polyamide resins such as nylon 6 and nylon 66; polyester resins such as polyethylene terephthalate, polyethylene naphthalate, polybutylene terephthalate, and polycyclohexylenedimethylene terephthalate; polycarbonates, polyacetals, polyacrylsulfones, polyarylates, hydroxybenzoic acid polyesters, polyetherimides, polyester carbonates, polyphenylene ether resins, polyvinyl chloride, polyvinylidene chloride, polyurethane, and porous resins such as foamed polyurethane, foamed polypropylene, or foamed ethylene, etc.), glasses, metals, ceramics, fibers, cloths, knitted fabrics, sheets, papers, yarn, foam, porous substances, and multifilaments.

A liquid carrier may include, for example, aromatic or aliphatic hydrocarbons (e.g., xylene, toluene, alkylnaphthalene, phenylxylylethane, kerosine, gas oil, hexane, cyclohexane, etc.), halogenated hydrocarbons (e.g., chlorobenzene, dichloromethane, dichloroethane, trichloroethane, etc.), alcohols (e.g., methanol, ethanol, isopropyl alcohol, butanol, hexanol, benzyl alcohol, ethylene glycol, etc.), ethers (e.g., diethyl ether, ethylene glycol dimethyl ether, diethylene glycol monomethyl ether, diethylene glycol monoethyl ether, propylene glycol monomethyl ether, tetrahydrofuran, dioxane, etc.), esters (e.g., ethyl acetate, butyl acetate, etc.), ketones (e.g., acetone, methyl ethyl ketone, methyl isobutyl ketone, cyclohexanone, etc.), nitriles (e.g., acetonitrile, isobutyronitrile, etc.), sulfoxides (e.g., dimethyl sulfoxide, etc.), amides (e.g., N,N-dimethylformamide, N,N-dimethylacetamide, cyclic imides (e.g. N-methylpyrrolidone) alkylidene carbonates (e.g., propylene carbonate, etc.), vegetable oil (e.g., soybean oil, cottonseed oil, etc.), vegetable essential oils (e.g., orange oil, hyssop oil, lemon oil, etc.), or water.

A gaseous carrier may include, for example, butane gas, flon gas, liquefied petroleum gas (LPG), dimethyl ether, and carbon dioxide gas.

ix. Adjuvants

In some instances, the composition provided herein may include an adjuvant. Adjuvants are chemicals that do not possess activity. Adjuvants are either pre-mixed in the formulation or added to the spray tank to improve mixing or application or to enhance performance. They are used extensively in products designed for foliar applications. Adjuvants can be used to customize the formulation to specific needs and compensate for local conditions. Adjuvants may be designed to perform specific functions, including wetting, spreading, sticking, reducing evaporation, reducing volatilization, buffering, emulsifying, dispersing, reducing spray drift, and reducing foaming. No single adjuvant can perform all these functions, but compatible adjuvants often can be combined to perform multiple functions simultaneously.

Among nonlimiting examples of adjuvants included in the formulation are binders, dispersants and stabilizers, specifically, for example, casein, gelatin, polysaccharides (e.g., starch, gum arabic, cellulose derivatives, alginic acid, etc.), lignin derivatives, bentonite, sugars, synthetic water-soluble polymers (e.g., polyvinyl alcohol, polyvinylpyrrolidone, polyacrylic acid, etc.), PAP (acidic isopropyl phosphate), BHT (2,6-di-t-butyl-4-methylphenol), BHA (a mixture of 2-t-butyl-4-methoxyphenol and 3-t-butyl-4-methoxyphenol), vegetable oils, mineral oils, fatty acids and fatty acid esters.

x. Surfactants

In some instances, the composition provided herein includes a surfactant. Surfactants, also called wetting agents and spreaders, physically alter the surface tension of a spray droplet. For a formulation to perform its function properly, a spray droplet must be able to wet the foliage and spread out evenly over a leaf. Surfactants enlarge the area of formulation coverage, thereby increasing the pest's exposure to the chemical. Surfactants are particularly important when applying a formulation to waxy or hairy leaves. Without proper wetting and spreading, spray droplets often run off or fail to cover leaf surfaces adequately. Too much surfactant, however, can cause excessive runoff and reduce efficacy.

Surfactants are classified by the way they ionize or split apart into electrically charged atoms or molecules called ions. A surfactant with a negative charge is anionic. One with a positive charge is cationic, and one with no electrical charge is nonionic. Formulation activity in the presence of a nonionic surfactant can be quite different from activity in the presence of a cationic or anionic surfactant. Selecting the wrong surfactant can reduce the efficacy of a pesticide product and injure the target plant. Anionic surfactants are most effective when used with contact pesticides (pesticides that control the pest by direct contact rather than being absorbed systemically). Cationic surfactants should never be used as stand-alone surfactants because they usually are phytotoxic.

Nonionic surfactants, often used with systemic pesticides, help pesticide sprays penetrate plant cuticles. Nonionic surfactants are compatible with most pesticides, and most EPA-registered pesticides that require a surfactant recommend a nonionic type. Adjuvants include, but are not limited to, stickers, extenders, plant penetrants, compatibility agents, buffers or pH modifiers, drift control additives, defoaming agents, and thickeners.

Among nonlimiting examples of surfactants included in the compositions described herein are alkyl sulfate ester salts, alkyl sulfonates, alkyl aryl sulfonates, alkyl aryl ethers and polyoxyethylenated products thereof, polyethylene glycol ethers, polyvalent alcohol esters and sugar alcohol derivatives.

xi. Combinations

In formulations and in the use forms prepared from these formulations, the modulating agent may be in a mixture with other active compounds, such as pesticidal agents (e.g., insecticides, sterilants, acaricides, nematicides, molluscicides, or fungicides; e.g., a pesticide listed in Table 11), attractants, growth-regulating substances, or herbicides. As used herein, the term "pesticidal agent" refers to any substance or mixture of substances intended for preventing, destroying, repelling, or mitigating any pest. A pesticide can be a chemical substance or biological agent used against pests including insects, mollusks, pathogens, weeds, nematodes, and microbes that compete with humans for food, destroy property, spread disease, or are a nuisance. The term "pesticidal agent" may further encompass other bioactive molecules such as antibiotics, antivirals pesticides, antifungals, antihelminthics, nutrients, pollen, sucrose, and/or agents that stun or slow insect movement.

In instances where the modulating agent is applied to plants, a mixture with other known compounds, such as herbicides, fertilizers, growth regulators, safeners, semiochemicals, or else with agents for improving plant properties is also possible.

V. Delivery

A host described herein can be exposed to any of the compositions described herein in any suitable manner that permits delivering or administering the composition to the host invertebrate (e.g., insect, mollusk, or nematode). The modulating agent may be delivered either alone or in combination with other active or inactive substances and may be applied by, for example, spraying, microinjection, through plants, pouring, dipping, in the form of concentrated liquids, gels, solutions, suspensions, sprays, powders, pellets, briquettes, bricks and the like, formulated to deliver an effective concentration of the modulating agent. Amounts and locations for application of the compositions described herein are generally determined by the habits of the host, the lifecycle stage at which the microorganisms of the host can be targeted by the modulating agent, the site where the application is to be made, and the physical and functional characteristics of the modulating agent. The modulating agents described herein may be administered to the host invertebrate (e.g., insect, mollusk, or nematode) by oral ingestion, but may also be administered by means which permit penetration through the cuticle or penetration of the host (e.g., insect, mollusk, or nematode) respiratory system.

In some instances, the invertebrate host (e.g., insect, mollusk, or nematode) can be simply "soaked" or "sprayed" with a solution including the modulating agent. Alternatively, the modulating agent can be linked to a food component (e.g., comestible) of the invertebrate host (e.g., insect, mollusk, or nematode) for ease of delivery and/or in order to increase uptake of the modulating agent by the host. Methods for oral introduction include, for example, directly mixing a modulating agent with the host's food, spraying the modulating agent in the host's habitat or field, as well as engineered approaches in which a species that is used as food is engineered to express a modulating agent, then fed to the host to be affected. In some instances, for example, the modulating agent composition can be incorporated into, or overlaid on the top of, the host's diet. For example, the modulating agent composition can be sprayed onto a field of crops which a host inhabits.

In some instances, the composition is sprayed directly onto a plant e.g., crops, by e.g., backpack spraying, aerial spraying, crop spraying/dusting etc. In instances where the modulating agent is delivered to a plant, the plant receiving the modulating agent may be at any stage of plant growth. For example, formulated modulating agents can be applied as a seed-coating or root treatment in early stages of plant growth or as a total plant treatment at later stages of the crop cycle. In some instances, the modulating agent may be applied as a topical agent to a plant, such that the host invertebrate (e.g., insect, mollusk, or nematode) ingests or otherwise comes in contact with the plant upon interacting with the plant.

Further, the modulating agent may be applied (e.g., in the soil in which a plant grows, or in the water that is used to water the plant) as a systemic agent that is absorbed and distributed through the tissues of a plant or animal host, such that a host invertebrate (e.g., insect, mollusk, or nematode) feeding thereon will obtain an effective dose of the modulating agent. In some instances, plants or food organisms may be genetically transformed to express the modulating agent such that a host feeding upon the plant or food organism will ingest the modulating agent.

Delayed or continuous release can also be accomplished by coating the modulating agent or a composition with the modulating agent(s) with a dissolvable or bioerodible coating layer, such as gelatin, which coating dissolves or erodes in the environment of use, to then make the modulating agent available, or by dispersing the agent in a dissolvable or erodible matrix. Such continuous release and/or dispensing means devices may be advantageously employed to consistently maintain an effective concentration of one or more of the modulating agents described herein in a specific host habitat.

Alternatively, the modulating agent is expressed in a bacterial or fungal cell and the bacterial or fungal cell is taken up or eaten by the host invertebrate (e.g., insect, mollusk, or nematode) species. Bacteria or fungi can be engineered to produce any of the modulating agents described herein. In other instances, a virus such as a baculovirus which specifically infects host invertebrates (e.g., insect, mollusk, or nematode) may also be used. This ensures safety for mammals, especially humans and animals, since the virus will not infect mammals.

The modulating agent can also be incorporated into the medium in which the host invertebrate (e.g., insect, mollusk, or nematode) grows, lives, reproduces, feeds, or infests. For example, a modulating agent can be incorporated into a food container, feeding station, protective wrapping, or a hive. For some applications the modulating agent may be bound to a solid support for application in powder form or in a "trap" or "feeding station." As an example, for applications where the composition is to be used in a trap or as bait for a particular host invertebrate (e.g., insect, mollusk, or nematode), the compositions may also be bound to a solid support or encapsulated in a time-release material. For example, the compositions described herein can be administered by delivering the composition to at least one habitat where an agricultural pest (e.g., aphid) grows, lives, reproduces, or feeds.

i. Engineered Plants

The terms "genetically engineered plant" or "transgenic plant" refer to a plant cell or a plant that expresses a modulating agent. The transgenic plants are also meant to include progeny (decedent, offspring, etc.) of any generation of such a transgenic plant or a seed of any generation of all such transgenic plants wherein said progeny or seed includes a modulating agent.

The skilled artisan will recognize that a wide variety of transformation techniques exist in the art, and new techniques are continually becoming available. Any technique that is suitable for the target host plant can be employed. For example, the constructs can be introduced in a variety of forms including, but not limited to as a strand of DNA, in a plasmid, or in an artificial chromosome. The introduction of the constructs into the target plant cells can be accomplished by a variety of techniques, including, but not limited to *Agrobacterium*-mediated transformation, electroporation, microinjection, microprojectile bombardment calcium-phosphate-DNA co-precipitation or liposome-mediated transformation of a heterologous nucleic acid. The transformation of the plant is preferably permanent, i.e. by integration of the introduced expression constructs into the host plant genome, so that the introduced constructs are passed onto successive plant generations.

Any plant species may be transformed to create a transgenic plant. The transgenic plant may be a dicotyledonous plant or a mono-cotyledonous plant. For example and without limitation, transgenic plants of the compositions and methods described herein may be derived from any of the following diclotyledonous plant families: Leguminosae, including plants such as pea, alfalfa and soybean; Umbelliferae, including plants such as carrot and celery; Solanaceae, including the plants such as tomato, potato, aubergine, tobacco, and pepper; Cruciferae, particularly the genus *Brassica*, which includes plant such as oilseed rape, beet, cabbage, cauliflower and broccoli; and *Arabidopsis thaliana*; Compositae, which includes plants such as lettuce;

Malvaceae, which includes cotton; Fabaceae, which includes plants such as peanut, and the like. Transgenic plants of the invention may be derived from monocotyledonous plants, such as, for example, wheat, barley, sorghum, millet, rye, triticale, maize, rice, oats, switchgrass, *miscanthus*, and sugarcane. Transgenic plants of the invention are also embodied as trees such as apple, pear, quince, plum, cherry, peach, nectarine, apricot, *papaya*, mango, and other woody species including coniferous and deciduous trees such as poplar, pine, *sequoia*, cedar, oak, willow, and the like.

Any promoter capable of driving expression in the plant of interest may be used. The promoter may be native or analogous or foreign or heterologous to the plant host. The choice of promoters to be included depends upon several factors, including, but not limited to, efficiency, selectability, inducibility, desired expression level, and cell- or tissue-preferential expression. It is a routine matter for one of skill in the art to modulate the expression of a sequence by appropriately selecting and positioning promoters and other regulatory regions relative to that sequence.

Promoters active in photosynthetic tissue in order to drive transcription in green tissues such as leaves and stems are of particular interest. Most suitable are promoters that drive expression only or predominantly in such tissues. The promoter may confer expression constitutively throughout the plant, or differentially with respect to the green tissues, or differentially with respect to the developmental stage of the green tissue in which expression occurs, or in response to external stimuli.

Examples of such promoters include the ribulose-1,5-bisphosphate carboxylase (RbcS) promoters such as the RbcS promoter from eastern larch (*Larix laricina*), the pine cab6 promoter (Yamamoto et al., *Plant Cell Physiol.* 35:773-778, 1994), the Cab-1 gene promoter from wheat (Fejes et al., *Plant Mol. Biol.* 15:921-932, 1990), the CAB-1 promoter from spinach (Lubberstedt et al., *Plant Physiol.* 104:997-1006, 1994), the cab1 R promoter from rice (Luan et al., *Plant Cell* 4:971-981, 1992), the pyruvate orthophosphate dikinase (PPDK) promoter from corn (Matsuoka et al., *Proc. Natl. Acad. Sci. USA* 90:9586-9590, 1993), the tobacco Lhcb1*2 promoter (Cerdan et al. (1997) *Plant Mol. Biol.* 33:245-255), the *Arabidopsis thaliana* SUC2 sucrose-H+ symporter promoter (Truernit et al. *Planta* 196:564-570, 1995), and thylakoid membrane protein promoters from spinach (psaD, psaF, psaE, PC, FNR, atpC, atpD, cab, rbcS. Other promoters that drive transcription in stems, leafs and green tissue are described in U.S. Patent Publication No. 2007/0006346. The TrpA promoter is a pith preferred promoter and has been described in U.S. Pat. No. 6,018,104.

A maize gene encoding phosphoenol carboxylase (PEPC) has been described by Hudspeth et al. (*Plant Molec. Biol.* 12:579-589, 1989). Using standard molecular biological techniques the promoter for this gene can be used to drive the expression of any gene in a green tissue-specific manner in transgenic plants.

In some other instances, inducible promoters may be desired. Inducible promoters drive transcription in response to external stimuli such as chemical agents or environmental stimuli. For example, inducible promoters can confer transcription in response to hormones such as giberellic acid or ethylene, or in response to light or drought.

VI. Screening

Any of the modulating agents described herein may be isolated from a screening assay, wherein a library of modulating agents (e.g., a mixture of variants of a starting modulating agent) is screened for modulating agents (e.g., modulating agent variants) that are effective to alter the microbiota of a host (e.g., insect/mollusk/nematode) and thereby modulate (e.g., increase or decrease) host fitness.

For example, the screening assays provided herein may be effective to identify one or more modulating agents (e.g., a polypeptide, nucleic acid, small molecule, or combinations thereof) that target symbiotic microorganisms resident in the host and thereby decrease the fitness of the host. For example, the identified modulating agent (e.g., a polypeptide, nucleic acid, small molecule, or combinations thereof) may be effective to decrease the viability of pesticide- or allelochemical-degrading microorganisms (e.g., bacteria e.g., a bacterium that degrades a pesticide listed in Table 11), thereby increasing the host's sensitivity to a pesticide (e.g., sensitivity to a pesticide listed in Table 11) or allelochemical agent.

Alternatively, a screening assay may be used to identify a modulating agent effective to increase host fitness (e.g., insect, mollusk, or nematode fitness). For example, the screening assay may be used to identify one or more modulating agents that target specific microorganisms and/or specific hosts. Further, the screening assays may be used to identify modulating agents that provide one or more microorganisms with enhanced functionalities. For example, the screening assay may be effective to isolate modulating agents that provide one or more microorganisms with an enhanced ability to metabolize (e.g., degrade) a pesticide (e.g., insecticide, e.g., neonicotinoid) or plant allelochemical (e.g., caffeine, soyacystatin, fenitrothion, monoterpenes, diterpene acids, or phenolic compounds (e.g., tannins, flavonoids)). Delivery and colonization of an isolated microorganism in the host may increase the host's resistance to the pesticide or plant allelochemical, thereby increasing host fitness. The methods may also be useful for the isolation of modulating agents that provide microorganisms with an enhanced ability to colonize any of the hosts described herein.

TABLE 11

| Pesticides |
|---|
| Aclonifen |
| Acetamiprid |
| Alanycarb |
| Amidosulfuron |
| Aminocyclopyrachlor |
| Amisulbrom |
| Anthraquinone |
| Asulam, sodium salt |
| Benfuracarb |
| Bensulide |
| beta-HCH; beta-BCH |
| Bioresmethrin |
| Blasticidin-S |
| Borax; disodium tetraborate |
| Boric acid |
| Bromoxynil heptanoate |
| Bromoxynil octanoate |
| Carbosulfan |
| Chlorantraniliprole |
| Chlordimeform |
| Chlorfluazuron |
| Chlorphropham |
| Climbazole |
| Clopyralid |
| Copper (II) hydroxide |
| Cyflufenamid |
| Cyhalothrin |
| Cyhalothrin, gamma |
| Decahydrate |
| Diafenthiuron |

TABLE 11-continued

Pesticides

Dimefuron
Dimoxystrobin
Dinotefuran
Diquat dichloride
Dithianon
E-Phosphamidon
EPTC
Ethaboxam
Ethirimol
Fenchlorazole-ethyl
Fenothiocarb
Fentirothion
Fenpropidin
Fluazolate
Flufenoxuron
Flumetralin
Fluxapyroxad
Fuberidazole
Glufosinate-ammonium
Glyphosate
Group: Borax, borate salts (see
Group: Paraffin oils, Mineral
Halfenprox
Imiprothrin
Imidacloprid
Ipconazole
Isopyrazam
Isopyrazam
Lenacil
Magnesium phosphide
Metaflumizone
Metazachlor
Metazachlor
Metobromuron
Metoxuron
Metsulfuron-methyl
Milbemectin
Naled
Napropamide
Nicosulfuron
Nitenpyram
Nitrobenzene
o-phenylphenol
oils
Oxadiargyl
Oxycarboxin
Paraffin oil
Penconazole
Pendimethalin
Penflufen
Penflufen
Pentachlorbenzene
Penthiopyrad
Penthiopyrad
Pirimiphos-methyl
Prallethrin
Profenofos
Proquinazid
Prothiofos
Pyraclofos
Pyrazachlor
Pyrazophos
Pyridaben
Pyridalyl
Pyridiphenthion
Pyrifenox
Quinmerac
Rotenone
Sedaxane
Sedaxane
Silafluofen
Sintofen
Spinetoram
Sulfoxaflor
Temephos
thiocloprid
Thiamethoxam

TABLE 11-continued

Pesticides

Tolfenpyrad
Tralomethrin
Tributyltin compounds
Tridiphane
Triflumizole
Validamycin
Zinc phosphide

EXAMPLES

The following is an example of the methods of the invention. It is understood that various other embodiments may be practiced, given the general description provided above.

Example 1: Generation of a cDNA Library from Corn Leaf Aphid Larvae (*Rhopalosiphum maidis*)

This Example demonstrates the production of a cDNA library from corn leaf aphid larvae (*Rhopalosiphum maidis*).
Experimental Design:

To generate the library, RNA from 0.9 g whole first-instar larvae (4 to 5 days post-hatch; held at 16° C.) is purified using the following phenol/TRI REAGENT®-based method (MOLECULAR RESEARCH CENTER, Cincinnati, Ohio). Larvae are homogenized at room temperature in a 15 mL homogenizer with 10 mL of TRI REAGENT® until a homogenous suspension is obtained. Following 5 min incubation at room temperature, the homogenate is dispensed into 1.5 mL microfuge tubes (1 mL per tube), 200 µL of chloroform is added, and the mixture is vigorously shaken for 15 seconds. After allowing the extraction to sit at room temperature for 10 min, the phases are separated by centrifugation at 12,000×g at 4° C. The upper phase (including about 0.6 mL) is carefully transferred into another sterile 1.5 mL tube, and an equal volume of room temperature isopropanol is added. After incubation at room temperature for 5 to 10 min, the mixture is centrifuged 8 min at 12,000×g (4° C. or 25° C.).

The supernatant is carefully removed and discarded, and the RNA pellet is washed twice by vortexing with 75% ethanol, with recovery by centrifugation for 5 min at 7,500×g (4° C. or 25° C.) after each wash. The ethanol is carefully removed, the pellet is allowed to air-dry for 3 to 5 min, and then is dissolved in nuclease-free sterile water. RNA concentration is determined by measuring the absorbance (A) at 260 nm and 280 nm. The RNA extracted is stored at −80° C. until further processed, and RNA quality is determined by running an aliquot through a 1% agarose gel.

The larval total RNA is converted into a cDNA library using random priming. The larval cDNA library is sequenced at ½ plate scale by GS FLX 454 Titanium™ series chemistry at EUROFINS MWG Operon, which results in over 600,000 reads with an average read length of 348 bp. 350,000 reads are assembled into over 50,000 contigs. Both the unassembled reads and the contigs are converted into BLASTable databases using the publicly available program, FORMATDB (available from NCBI).

Example 2: Production and Purification of Bcr1 dsRNA

This Example demonstrates the production and purification of a synthetic dsRNA from a cDNA library.

Experimental Design:

Bcr1 gene (ACYP132128) is an essential gene for bacteriocyte regulation and function in insects. Bcr1 cDNA is prepared from the larval total RNA described in Example 1 and for Bcr1 dsRNA synthesis prepared by PCR using the primer pairs: Forward 5'-aaactgctgcatggctttct-3' (SEQ ID NO: 90) and reverse 5'-acaggcctttcaggctttta-3' (SEQ ID NO: 91). For the target gene region, two separate PCR amplifications are performed. The first PCR amplification introduces a T7 promoter sequence at the 5' end ((TTAATACGACTCACTATAGGGAGA; SEQ ID NO: 92) of the amplified sense strands. The second reaction incorporates the T7 promoter sequence at the 5' ends of the antisense strands. The two PCR amplified fragments for each region of the target Bcr1 gene are then mixed in equal amounts, and the mixture is used as a transcription template for dsRNA production. Double-stranded RNA for insect bioassay is synthesized and purified using an AMBION® MEGASCRIPT® RNAi kit following the manufacturer's instructions (INVITROGEN) or HiScribe® T7 In Vitro Transcription Kit following the manufacturer's instructions (New England Biolabs, Ipswich, Mass.). The concentration of Bcr1 dsRNA is measured using a NANODROP™ 8000 spectrophotometer (THERMO SCIENTIFIC, Wilmington, Del.) and the purified Bcr1 dsRNA is prepared in TE buffer.

```
Bcr1 dsRNA hairpin sequence of one strand:
                                  (SEQ ID NO: 93)
AUGAAACUGCUGCAUGGCUUUCUGAUUAUUAUGCUGACCAUGCAUCUG

AGCAUUCAGUAUGCGUAUGGCGGCCCGUUUCUGACCAAAUAUCUGUGC

GAUCGCGUGUGCCAUAAACUGUGCGGCGAUGAAUUUGUGUGCAGCUGC

AUUCAGUAUAAAAGCCUGAAAGGCCUGUGGUUUCCGCAUUGCCCGACC

GGCAAAGCGAGCGUGGUGCUGCAUAACUUUCUGACCAGCCCGUUUUUU

UUUUCGGGCUGGUCAGAAAGUUAUGCAGCACCACGCUCGCUUUGCCGG

UCGGGCAAUGCGGAAACCACAGGCCUUUCAGGCUUUUAUACUGAAUGC

AGCUGCACACAAAUUCAUCGCCGCACAGUUUAUGGCACACGCGAUCGC

ACAGAUAUUUGGUCAGAAACGGGCCGCCAUACGCAUACUGAAUGCUCA

GAUGCAUGGUCAGCAUAAUAAUCAGAAAGCCAUGCAGCAGUUUCAU
```

Example 3: Treatment of Aphids (*Rhopalosiphum maidis*) with Bcr1 dsRNA

This Example demonstrates the ability to kill or decrease the fitness of aphids, *Rhopalosiphum maidis*, through treatment with a dsRNA solution by targeting expression of the Bcr1 gene (ACYP132128), which is an essential gene for bacteriocyte regulation and function in insects.

Aphids are one of the most important agricultural insect pests. They cause direct feeding damage to crops and serve as vectors of plant viruses. In addition, aphid honeydew promotes the growth of sooty mold and attracts nuisance ants. The use of chemical treatments, unfortunately still widespread, leads to the selection of resistant individuals whose eradication becomes increasingly difficult. Therapeutic design: dsRNA solutions are formulated with 0 (negative control), 0.5, 1, or 5 μg/ml of Bcr1 dsRNA from Example 2 in 10 mL of TE buffer with 0.5% sucrose and essential amino acids.

Experimental Design:

To prepare for the treatment, aphids are grown in a lab environment and medium. In a climate-controlled room (16 h light photoperiod; 60±5% RH; 20±2° C.), fava bean plants are grown in a mixture of vermiculite and perlite and are infested with aphids. To limit maternal effects or health differences between plants, 5-10 adults from different plants are distributed among 10 two-week-old plants, and allowed to multiply to high density for 5-7 days. For experiments, second and third instar aphids are collected from healthy plants and divided into treatments so that each treatment receives approximately the same number of individuals from each of the collection plants.

Wells of a 96-well plate are filled with 200 μl of artificial aphid diet (Febvay et al., *Canadian Journal of Zoology* 66(11):2449-2453, 1988) and the plate is covered with parafilm to make a feeding sachet. Artificial diet is either mixed with the solution of TE buffer (Tris HCl (1 mM) plus EDTA (0.1 mM) buffer, pH 7.2.) with 0.5% sucrose and essential amino acids only as a negative control, or mixed with dsRNA solutions diluted in TE buffer containing varying concentrations of dsRNA. dsRNA solutions are mixed with artificial diet to obtain final concentrations between 0.5 to 5 μg/ml.

For each replicate treatment, 30-50 second and third instar aphids are placed individually in wells of a 96-well plate and a feeding sachet plate is inverted above them, allowing the insects to feed through the parafilm and keeping them restricted to individual wells. Experimental aphids are kept under the same environmental conditions as aphid colonies. After the aphids are fed for 24 hr, the feeding sachet is replaced with a new one containing sterile artificial diet and a new sterile sachet is provided every 24 h for 4 days. At the time that the sachet is replaced, aphids are also checked for mortality. An aphid is counted as dead if it had turned brown or is at the bottom of the well and does not move during the observation. If an aphid is on the parafilm of the feeding sachet but not moving, it is assumed to be feeding and alive.

The survival rates of aphids treated with Bcr1 dsRNA are compared to the aphids treated with the negative control. The survival rate of aphids treated with Bcr1 dsRNA is decreased as compared to the control treated aphids.

Example 4: Production of Transgenic Grass Expressing Bcr1 dsRNAs

This Example demonstrates genetic modification and production of Bcr1 dsRNA in a transgenic grass for delivery to aphids.

Transgenic forage grass blue grama, Bouteloua gracilis, that produces the Bcr1 dsRNA molecules, through expression of a chimeric gene stably-integrated into the plant genome, is produced by microprojectile bombardment, using a system based on the highly chlorophyllous and embryogenic cell line 'TIANSJ98' (Aguado-Santacruz et al., *Theoretical and Applied Genetics* 104(5):763-771, 2002).

'TIANSJ98' cell line establishment and maintenance: The embryogenic, highly chlorophyllous 'TIANSJ98' cell line is obtained from culturing shoot apice-derived green calli in liquid MPC medium as described in (Aguado-Santacruz et al., *Plant Cell Rep.* 20:131-136, 2001). This cell line is subcultured every 20 days, transferring 1 ml of the cell suspension into 24 ml of fresh MPC medium. The reasons for utilizing the finely dispersed condition of the embryogenic calli are 1) to synchronize the physiological stage of the target cells, 2) to maximize the distribution of the totipotent material on the paper filters (optimizing the shoot cover of the bombarded plasmids), and 3) to facilitate the identification of independent transformation events (green spots) within the dispersed cell clusters under selection.

Microprojectile Bombardment of Embryogenic Cells:

A binary transformation vector is used with the template fragment for Bcr1 dsRNA expression. This plasmid contains the inverted repeat of the target Bcr1 gene under the control of a double 35S Cauliflower Mosaic Virus promoter, and a leader sequence from Alfalfa Mosaic Virus (Aguado-Santacruz et al., *Theoretical and Applied Genetics* 104(5):763-771, 2002).

The highly chlorophyllous embryogenic cell line 'TIANSJ98' is used as the target for the microprojectile delivery experiments. The cells are distributed onto 2.0-cm diameter paper-filter disks (approximately 2 g FW cells). Bombardment mixtures are as follows: 50 µL of M10 tungsten particles (15 mg/ml), 10 µL of DNA (1 µg/ml), 50 µL of 2.5 M CaCl$_2$) and 20 µL of 0.1 M espermidine are mixed in sequential order, vortexed for 5 min and then briefly sonicated. The mixture is centrifuged at 10,000 rpm for 10 s. 60 µL of the supernatant are removed and the rest is dispensed into 5-µL aliquots for individual shoots. Bombardments are performed using the Particle Inflow Gun (Finer et al., *Plant Cell Rep.* 11:323-328, 1992). The particle/DNA mixture is placed in the center of the syringe filter unit. Embryogenic cells are covered with a 500-µm baffle, placed at a distance of 10 cm from the screen filter unit containing the particles, and bombarded once in the vacuum chamber at 60 mmHg. Two different osmotic media for pre- and post-bombardment treatments (0.4 and 1 M mannitol supplied in solidified MPC medium) and three bombardment pressures (60, 80 and 100 PSI) are tested. Pre-bombardment treatment is applied 24 hr before shooting. After discharge, the paper filters supporting the embryogenic cells are maintained for 3-days more on the same osmotic medium used in the pre-bombardment treatment. Thus, a total of nine treatments are evaluated with ten dishes bombarded per treatment. As a control, filters with suspension material are bombarded using particles without DNA.

Selection of Stable Transformed Clones and Recovery of Plants:

After the 3-day post-bombardment osmotic treatment on MPC medium containing 0.4 or 1 M manitol, but lacking antibiotic, the paper filter disks supporting the bombarded cells are transferred onto MPC medium containing 140 mg/l of kanamycin and incubated at 30±1° C. in white light provided by cold fluorescent lamps. The same procedure is followed for cells bombarded but not subjected to osmotic treatment. The kanamycin concentration is raised 2-months later to 150 or 160 mg/l. The cells are sub cultured every 3 weeks and maintained for 8 months in selection. After this period, kanamycin-resistant clones are transferred to regeneration medium containing full-strength MS medium, 3% sucrose, 2.5% phytagel (Sigma, St. Louis, Missouri) but no antibiotic. The regenerated shoots are transferred for rooting to ½ MS containing 3.0 µM (0.56 mg/l) α-naphthaleneacetic acid, 2.5 µM (0.51 mg/l) indole-3-butyric acid and 2.5% phytagel, and incubated at 30±1° C. under continuous fluorescent light. Later, rooted plantlets are transferred to pots, hardened off, and grown to maturity in a greenhouse.

PCR Analysis for Transformation Verification:

Total genomic DNA is prepared from kanamycin-resistant and untransformed control plants using the following protocol: Approximately 250 mg of cells are collected in 2-ml Eppendorf tubes and ground to a fine powder in liquid N2 using a glass pestle attached to a homogenizer (Caframo, Stirrer type RZR). Powdered cells are re-suspended with 500 µL of extraction buffer (7.0 M urea, 0.35 M NaCl, 0.05 M Tris-HCl, pH 8.0, 0.02 M EDTA, 1% sarcosine) for at least 45 min. The cell homogenate is extracted with 1 vol of phenol/chloroform. The aqueous phase is separated by centrifugation and then precipitated using an equal volume of isopropyl alcohol. The precipitated DNA is washed once with 70% ethanol and resuspended in TE buffer (0.01 M Tris-HCl, 0.01 M EDTA, pH 8.0).

For PCR analysis, 100 to 150 ng, are used for genomic DNA amplifications, in 25-µL reactions. Primers forward 5'-aaactgctgcatggctttct-3' (SEQ ID NO: 91) and reverse 5'-acaggcctttcaggctttta-3' (SEQ ID NO: 92) are designed for amplifying an internal 169-bp fragment of the Bcr1 sense anti sense inserted fragment. PCR reactions are carried out using a Perkin Elmer thermocycler for 30 cycles. Reaction temperatures are denaturation 95° C. (2 min), annealing 56° C. (30 s), and extension 72° C. (30 s). The 25-reaction volumes contain: 1×PCR buffer, 0.25 mM of dNTPs, 2 mM MgCl2, 0.2 µM of primers and 2.5 u of Taq. The amplification products are analyzed by electrophoreses in 1% agarose/SYBR green gels.

Example 5: Production of Transgenic Grass Producing colA Bacteriocin

This Example demonstrates genetic modification and production of the bacteriocyte regulatory peptide Coleoptericin A (colA) in a transgenic grass for delivery to aphids.

Transgenic forage grass blue grama, Bouteloua gracilis, that produces Coleoptericin A, through expression of a chimeric gene stably-integrated into the plant genome, is produced by microprojectile bombardment, using a system described in Example 4.

The embryogenic, highly chlorophyllous 'TIANSJ98' cell line is subcultured every 20 days, transferring 1 ml of the cell suspension into 24 ml of fresh MPC medium.

```
Coleoptericin A (colA)
                                       (SEQ ID NO: 94)
atgacccgcaccatgctgtttctggcgtgcgtggcggcgctgtatgtg tgcattagcgcgaccgcgggcaaaccggaagaatttgcgaaactgagc gatgaagcgccgagcaacgatcaggcgatgtatgaaagcattcagcgc tatcgccgctttgtggatggcaaccgctataacggcggccagcagcag cagcagcagccgaaacagtgggaagtgcgcccggatctgagccgcgat cagcgcggcaacaccaaagcgcaggtggaaattaacaaaaaaggcgat aaccatgatattaacgcgggctggggcaaaaacattaacggcccggat agccataaagatacctggcatgtgggcggcagcgtgcgctgg
```

A transformation plasmid is constructed for Coleoptericin A (colA) expression. The plasmid contains the nucleic acid for colA under the control of a double 35S Cauliflower Mosaic Virus promoter, and a leader sequence from Alfalfa Mosaic Virus (Aguado-Santacruz et al., *Theoretical and Applied Genetics* 104(5):763-771, 2002).

The highly chlorophyllous embryogenic cell line 'TIANSJ98' is used as the target for the microprojectile delivery experiments. The cells are distributed onto 2.0-cm diameter paper-filter disks (approximately 2 g FW cells). Bombardment mixtures are as follows: 50 µL of M10 tungsten particles (15 mg/ml), 10 µL of DNA (1 µg/ml), 50 µL of 2.5 M CaCl$_2$) and 20 µL of 0.1 M espermidine are mixed in sequential order, vortexed for 5 min and then briefly sonicated. The mixture is centrifuged at 10,000 rpm for 10 s. 60 µL of the supernatant are removed and the rest is dispensed into 5-µL aliquots for individual shoots. Bombardments are performed using the Particle Inflow Gun (Finer et al., *Plant Cell Rep.* 11:323-328, 1992). The particle/DNA mixture is placed in the center of the syringe filter unit. Embryogenic cells are covered with a 500-µm baffle, placed at a distance of 10 cm from the screen filter unit containing the particles, and bombarded once in the vacuum chamber at 60 mmHg. Two different osmotic media for pre- and post-bombardment treatments (0.4 and 1 M mannitol supplied in solidified MPC medium) and three bombardment pressures (60, 80 and 100 PSI) are tested. Pre-bombardment treatment is applied 24 hr before shooting. After discharge, the paper filters supporting the embryogenic cells are maintained for 3-days more on the same osmotic medium used in the pre-bombardment treatment. Thus, a total of nine treatments are evaluated with ten dishes bombarded per treatment. As a control, filters with suspension material are bombarded using particles without DNA.

Selection of Stable Transformed Clones and Recovery of Plants:

After the 3-day post-bombardment osmotic treatment on MPC medium containing 0.4 or 1 M manitol, but lacking antibiotic, the paper filter disks supporting the bombarded cells are transferred onto MPC medium containing 140 mg/l of kanamycin and incubated at 30±1° C. in white light provided by cold fluorescent lamps. The same procedure is followed for cells bombarded but not subjected to osmotic treatment. The kanamycin concentration is raised 2-months later to 150 or 160 mg/l. The cells are sub cultured every 3 weeks and maintained for 8 months in selection. After this period, kanamycin-resistant clones are transferred to regeneration medium containing full-strength MS medium, 3% sucrose, 2.5% phytagel (Sigma, St. Louis, Missouri) but no antibiotic. The regenerated shoots are transferred for rooting to ½ MS containing 3.0 µM (0.56 mg/l) α-naphthaleneacetic acid, 2.5 µM (0.51 mg/l) indole-3-butyric acid and 2.5% phytagel, and incubated at 30±1° C. under continuous fluorescent light. Later, rooted plantlets are transferred to pots, hardened off, and grown to maturity in a greenhouse.

PCR Analysis for Transformation Verification:

Total genomic DNA is prepared from kanamycin-resistant and untransformed control plants using the following protocol: Approximately 250 mg of cells are collected in 2-ml Eppendorf tubes and ground to a fine powder in liquid N2 using a glass pestle attached to a homogenizer (Caframo, Stirrer type RZR). Powdered cells are re-suspended with 500 µL of extraction buffer (7.0 M urea, 0.35 M NaCl, 0.05 M Tris-HCl, pH 8.0, 0.02 M EDTA, 1% sarcosine) for at least 45 min. The cell homogenate is extracted with 1 vol of phenol/chloroform. The aqueous phase is separated by centrifugation and then precipitated using an equal volume of isopropyl alcohol. The precipitated DNA is washed once with 70% ethanol and resuspended in TE buffer (0.01 M Tris-HCl, 0.01 M EDTA, pH 8.0).

For PCR analysis, 100 to 150 ng, are used for genomic DNA amplifications, in 25-µL reactions. Primers forward 5'-caacgatcaggcgatgtatg-3' (SEQ ID NO: 95) and reverse 5'-ttaatttccacctgcgcttt-3' (SEQ ID NO: 96) are designed for amplifying an internal 165-bp fragment of the colA gene inserted fragment. PCR reactions are carried out using a Perkin Elmer thermocycler for 30 cycles. Reaction temperatures are denaturation 95° C. (2 min), annealing 56° C. (30 s), and extension 72° C. (30 s). The 25-µL reaction volumes contain: 1×PCR buffer, 0.25 mM of dNTPs, 2 mM MgCl2, 0.2 µM of primers and 2.5 u of Taq. The amplification products are analyzed by electrophoreses in 1% agarose/SYBR green gels.

Example 6: Production of Transgenic Grass Producing colA Bacteriocin

This example demonstrates genetic modification and production of colA bacteriocin in a transgenic grass for delivery to aphids.

Transgenic forage grass blue grama, Bouteloua gracilis, that produces colA bacteriocin, through expression of a chimeric gene stably-integrated into the plant genome, is produced by microprojectile bombardment, using a system based on the highly chlorophyllous and embryogenic cell line 'TIANSJ98' (Aguado-Santacruz et al., 2002. Theoretical and Applied Genetics, 104(5), 763-771).

'TIANSJ98' cell line establishment and maintenance: The embryogenic, highly chlorophyllous 'TIANSJ98' cell line is obtained from culturing shoot apice-derived green calli in liquid MPC medium as described in (Aguado-Santacruz et al., 2001. ex Steud. Plant Cell Rep 20:131-136). This cell line is subcultured every 20 days, transferring 1 ml of the cell suspension into 24 ml of fresh MPC medium. The reasons for utilizing the finely dispersed condition of the embryogenic calli are 1) to synchronize the physiological stage of the target cells, 2) to maximize the distribution of the totipotent material on the paper filters (optimizing the shoot cover of the bombarded plasmids), and 3) to facilitate the identification of independent transformation events (green spots) within the dispersed cell clusters under selection.

Microprojectile Bombardment of Embryogenic Cells

A transformation vector is used with the template fragment for colA bacteriocin expression.

colA bacteriocin
(SEQ ID NO: 94)
atgacccgcaccatgctgtttctggcgtgcgtggcggcgctgtatgtg tgcattagcgcgaccgcgggcaaaccggaagaatttgcgaaactgagc gatgaagcgccgagcaacgatcaggcgatgtatgaaagcattcagcgc tatcgccgctttgtggatggcaaccgctataacggcggccagcagcag cagcagcagccgaaacagtgggaagtgcgcccggatctgagccgcgat cagcgcggcaacaccaaagcgcaggtggaaattaacaaaaaaggcgat aaccatgatattaacgcgggctggggcaaaaacattaacggcccggat agccataaagatacctggcatgtgggcggcagcgtgcgctgg This plasmid contains the nucleic acid for colA bacteriocin under the control of a double 35S Cauliflower Mosaic Virus promoter, and a leader sequence from Alfalfa Mosaic Virus (Aguado-Santacruz et al., 2002. Theoretical and Applied Genetics, 104(5), 763-771).

The highly chlorophyllous embryogenic cell line 'TIANSJ98' is used as the target for the microprojectile delivery experiments. The cells are distributed onto 2.0-cm diameter paper-filter disks (approximately 2 g FW cells). Bombardment mixtures are as follows: 50 µL of M10 tungsten particles (15 mg/ml), 10 µL of DNA (1 µg/ml), 50 µL of 2.5 M CaCl$_2$) and 20 µL of 0.1 M espermidine are mixed in sequential order, vortexed for 5 min and then briefly sonicated. The mixture is centrifuged at 10,000 rpm for 10 s. 60 µL of the supernatant are removed and the rest is dispensed into 5-µL aliquots for individual shoots.

Bombardments are performed using the Particle Inflow Gun (Finer et al., 1992. Plant Cell Rep 11:323-328). The particle/DNA mixture is placed in the center of the syringe filter unit. Embryogenic cells are covered with a 500-µm baffle, placed at a distance of 10 cm from the screen filter unit containing the particles, and bombarded once in the vacuum chamber at 60 mmHg. Two different osmotic media for pre- and post-bombardment treatments (0.4 and 1 M mannitol supplied in solidified MPC medium) and three bombardment pressures (60, 80 and 100 PSI) are tested. Pre-bombardment treatment is applied 24 hr before shooting.

After discharge, the paper filters supporting the embryogenic cells are maintained for 3-days more on the same osmotic medium used in the pre-bombardment treatment. Thus, a total of nine treatments are evaluated with ten dishes bombarded per treatment. As a control, filters with suspension material are bombarded using particles without DNA.
Selection of Stable Transformed Clones and Recovery of Plants After the 3-day post-bombardment osmotic treatment on MPC medium with 0.4 or 1 M manitol, but lacking antibiotic, the paper filter disks supporting the bombarded cells are transferred onto MPC medium containing 140 mg/l of kanamycin and incubated at 30±1° C. in white light provided by cold fluorescent lamps. The same procedure is followed for cells bombarded but not subjected to osmotic treatment. The kanamycin concentration is raised 2-months later to 150 or 160 mg/l. The cells are subcultured every 3 weeks and maintained for 8 months in selection. After this period, kanamycin-resistant clones are transferred to regeneration medium with full-strength MS medium, 3% sucrose, 2.5% phytagel (Sigma, St. Louis, Missouri) but no antibiotic. The regenerated shoots are transferred for rooting to ½ MS with 3.0 µM (0.56 mg/l) α-naphthaleneacetic acid, 2.5 µM (0.51 mg/l) indole-3-butyric acid and 2.5% phytagel, and incubated at 30±1° C. under continuous fluorescent light. Later, rooted plantlets are transferred to pots, hardened off, and grown to maturity in a greenhouse.
PCR Analysis for Transformation Verification Total genomic DNA is prepared from kanamycin-resistant and untransformed control plants using the following protocol: Approximately 250 mg of cells are collected in 2-ml Eppendorf tubes and ground to a fine powder in liquid N2 using a glass pestle attached to a homogenizer (Caframo, Stirrer type RZR). Powdered cells are re-suspended with 500 µL of extraction buffer (7.0 M urea, 0.35 M NaCl, 0.05 M Tris-HCl, pH 8.0, 0.02 M EDTA, 1% sarcosine) for at least 45 min. The cell homogenate is extracted with 1 vol of phenol/chloroform. The aqueous phase is separated by centrifugation and then precipitated using an equal volume of isopropyl alcohol. The precipitated DNA is washed once with 70% ethanol and resuspended in TE buffer (0.01 M Tris-HCl, 0.01 M EDTA, pH 8.0).

For PCR analysis, 100 to 150 ng, are used for genomic DNA amplifications, in 25-µL reactions. Primers forward 5'-caacgatcaggcgatgtatg-3' and reverse 5'-ttaatttc-cacctgcgcttt-3' are designed for amplifying an internal 165-bp fragment of the ColA gene inserted fragment. PCR reactions are carried out using a Perkin Elmer thermocycler for 30 cycles. Reaction temperatures are denaturation 95° C. (2 min), annealing 56° C. (30 s), and extension 72° C. (30 s). The 25-µL reaction volumes contain: 1×PCR buffer, 0.25 mM of dNTPs, 2 mM MgCl2, 0.2 µM of primers and 2.5 u of Taq. The amplification products are analyzed by electrophoreses in 1% agarose/SYBR green gels.

Example 7: Production of a cDNA Library from Green Peach Aphid (*Myzus persicae*)

This Example demonstrates the production of a cDNA library from green peach aphid larvae (*Myzus persicae*).
Total RNA Isolation from Aphid Larvae and cDNA Library Preparation:

Total RNA from 0.9 g of whole first-instar larvae (4 to 5 days post-hatch; held at 16° C.) is extracted using the following phenol/TRI REAGENT®-based method (MOLECULAR RESEARCH CENTER, Cincinnati, Ohio). Larvae are homogenized at room temperature in a 15 mL homogenizer with 10 mL of TRI REAGENT® until a homogenous suspension is obtained. Following 5 min. incubation at room temperature, the homogenate is dispensed into 1.5 mL microfuge tubes (1 mL per tube), 200 µL of chloroform is added, and the mixture is vigorously shaken for 15 seconds. After allowing the extraction to sit at room temperature for 10 min, the phases are separated by centrifugation at 12,000×g at 4° C. The upper phase (including about 0.6 mL) is carefully transferred into another sterile 1.5 mL tube, and an equal volume of room temperature isopropanol is added. After incubation at room temperature for 5 to 10 min, the mixture is centrifuged 8 min at 12,000×g (4° C. or 25° C.).

The supernatant is carefully removed and discarded, and the RNA pellet is washed twice by vortexing with 75% ethanol, with recovery by centrifugation for 5 min at 7,500×g (4° C. or 25° C.) after each wash. The ethanol is carefully removed, the pellet is allowed to air-dry for 3 to 5 min, and then is dissolved in nuclease-free sterile water. The RNA concentration is determined by measuring the absorbance (A) at 260 nm and 280 nm. The RNA is stored at −80° C., and the RNA quality is determined by running an aliquot through a 1% agarose gel.

The larval total RNA is converted into a cDNA library using random priming. The larval cDNA library is sequenced at ½ plate scale by GS FLX 454 Titanium™ series chemistry at EUROFINS MWG Operon, which results in over 600,000 reads with an average read length of 348 bp. 350,000 reads are assembled into over 50,000 contigs. Both the unassembled reads and the contigs are converted into BLASTable databases using the publicly available program, FORMATDB (available from NCBI).

Example 8: Production of Bcr1 dsRNA

This Example demonstrates the production and purification of a synthetic dsRNA from a cDNA library.
Experimental Design:

Bcr1 gene (ACYP132128) is an essential gene for bacteriocyte regulation and function in insects. The cDNA described in the Example 6 is used for Bcr1 dsRNA synthesis prepared by PCR using the primer pairs: Forward 5'-aaactgctgcatggctttct-3' (SEQ ID NO: 90) and reverse 5'-acaggcctttcaggctttta-3' (SEQ ID NO: 91). For the target gene region, two separate PCR amplifications are performed. The first PCR amplification introduces a T7 promoter sequence at the 5' end ((TTAATACGACTCAC-TATAGGGAGA; SEQ ID NO: 92) of the amplified sense strands. The second reaction incorporates the T7 promoter sequence at the 5' ends of the antisense strands. The two PCR amplified fragments for each region of the target gene Bcr1 are then mixed in equal amounts, and the mixture is used as a transcription template for dsRNA production. Double-stranded RNA for insect bioassay is synthesized and purified using an AMBION® MEGASCRIPT® RNAi kit following the manufacturer's instructions (INVITROGEN) or HiScribe® T7 In Vitro Transcription Kit following the manufacturer's instructions (New England Biolabs, Ipswich, Mass.). The concentration of dsRNAs against Bcr1 is measured using a NANODROP™ 8000 spectrophotometer (THERMO SCIENTIFIC, Wilmington, Del.) and the purified dsRNA molecules are prepared in TE buffer.

```
Bcr1 dsRNA hairpin sequence of one strand:
                                          (SEQ ID NO: 93)
AUGAAACUGCUGCAUGGCUUUCUGAUUAUUAUGCUGACCAUGCAUCUG

AGCAUUCAGUAUGCGUAUGGCGGCCCGUUUCUGACCAAAUAUCUGUGC

GAUCGCGUGUGCCAUAAACUGUGCGGCGAUGAAUUUGUGUGCAGCUGC

AUUCAGUAUAAAAGCCUGAAAGGCCUGUGGUUUCCGCAUUGCCCGACC

GGCAAAGCGAGCGUGGUGCUGCAUAACUUUCUGACCAGCCCGUUUUUU

UUUUCGGGCUGGUCAGAAAGUUAUGCAGCACCACGCUCGCUUUGCCGG

UCGGGCAAUGCGGAAACCACAGGCCUUUCAGGCUUUUAUACUGAAUGC

AGCUGCACACAAAUUCAUCGCCGCACAGUUUAUGGCACACGCGAUCGC

ACAGAUAUUUGGUCAGAAACGGGCCGCCAUACGCAUACUGAAUGCUCA

GAUGCAUGGUCAGCAUAAUAAUCAGAAAGCCAUGCAGCAGUUUCAU
```

Example 9: Treatment of Aphids (*Myzus persicae*) with a Solution of Bcr1 dsRNA This Example demonstrates the ability to kill or decrease the fitness of aphids, *Myzus persicae*, by treating them with a dsRNA solution by targeting expression of the Bcr1 gene (ACYP132128), which is an essential gene for bacteriocyte regulation and function in insects.

Aphids are one of the most important agricultural insect pests. They cause direct feeding damage to crops and serve as vectors of plant viruses. In addition, aphid honeydew promotes the growth of sooty mold and attracts nuisance ants. The use of chemical treatments, unfortunately still widespread, leads to the selection of resistant individuals whose eradication becomes increasingly difficult. Therapeutic design: dsRNA solutions are formulated with 0 (negative control), 0.5, 1, or 5 µg/mL of Bcr1 dsRNA from Example 7 in 10 mL of TE buffer with 0.5% sucrose and essential amino acids.

Experimental Design:

To prepare for the treatment, aphids are grown in a lab environment and medium. In a climate-controlled room (16 hr light photoperiod; 60±5% RH; 20±2° C.), plants are grown in a mixture of vermiculite and perlite and are infested with aphids. To limit maternal effects or health differences between plants, 5-10 adults from different plants are distributed among 10 two-week-old plants, and allowed to multiply to high density for 5-7 days. For experiments, second and third instar aphids are collected from healthy plants and divided into treatments so that each treatment receives approximately the same number of individuals from each of the collection plants.

Wells of a 96-well plate are filled with 200 µl of artificial aphid diet (Febvay et al., *Canadian Journal of Zoology* 66(11):2449-2453, 1988) and the plate is covered with parafilm to make a feeding sachet. Artificial diet is either mixed with the solution of TE buffer (Tris HCl (1 mM) plus EDTA (0.1 mM) buffer, pH 7.2.) with 0.5% sucrose and essential amino acids only as a negative control, or mixed with dsRNA solutions diluted in TE buffer containing varying concentrations of dsRNA. dsRNA solutions are mixed with artificial diet to obtain final concentrations between 0.5 to 5 µg/ml.

For each replicate treatment, 30-50 second and third instar aphids are placed individually in wells of a 96-well plate and a feeding sachet plate is inverted above them, allowing the insects to feed through the parafilm and keeping them restricted to individual wells. Experimental aphids are kept under the same environmental conditions as aphid colonies. After the aphids are fed for 24 hr, the feeding sachet is replaced with a new one containing sterile artificial diet and a new sterile sachet is provided every 24 h for 4 days. At the time that the sachet is replaced, aphids are also checked for mortality. An aphid is counted as dead if it had turned brown or is at the bottom of the well and does not move during the observation. If an aphid is on the parafilm of the feeding sachet but not moving, it is assumed to be feeding and alive.

The survival rates of aphids treated with Bcr1 dsRNA are compared to the aphids treated with the negative control. The survival rate of aphids treated with Bcr1 dsRNA is decreased as compared to the control treated aphids.

Example 10: Topical-Plant Delivery of Bacteriocyte Specific dsRNA for Crop Protection This Example demonstrates the ability to deliver bacteriocyte specific dsRNA by topical application on tobacco plant leaves. dsRNA targets the expression of the Bcr1 gene (ACYPI32128), which is an essential gene for bacteriocyte regulation and function in insects. Therapeutic design: dsRNA-LDH spray solutions are formulated with Bcr1 dsRNA produced in Example 7 at 1:0 (negative control), 1:1, 1:2, or 1:3 ratio of dsRNA:LDH at 125 uL/$cm^2$ of leave surface.

Preparation and Characterization of LDH Nanosheets:

Sheet-like clay nanoparticles, specifically positively charged LDH, are excellent nanocarrier systems for dsRNA, to deliver RNAi as stable spray formulations for crop protection (Mitter et al., *Nature Plants* 1-10, 2017). LDH conjugates strongly adhere to the leaf surface even after vigorous rinsing, and enhance the stability of dsRNA for a longer period under environmental conditions. The sustained release of dsRNA is facilitated through the formation of carbonic acid on the leaf surface from atmospheric $CO_2$ and humidity, which helps degrade the LDH nanosheets.

LDH nanosheets are prepared according to (Mitter et al., *Nature Plants* 1-10, 2017) by modified non-aqueous precipitation, followed by heat treatment, purification and dispersion in water to get an average particle size of 45 nm. The particles (five repeated LDH samples) are characterized by the Nanosizer Nano ZS instrument (Malvern Instruments) to obtain the Z average size and Pdl and imaged using JEOL JSM-2010 TEM22. The chemical composition and crystal structure are verified by powder XRD with five LDH samples and Fourier transform infrared spectroscopy with attenuated total reflection mode, using a Rigaku Miniflex X-Ray diffractometer and a Nicolet 6700 FT-IR (Thermo Electron Corporation), respectively.

dsRNA Loading on LDH:

To define optimal and complete loading of the dsRNA hairpin construct obtained in Example 7 into LDH nanosheets, the ratio of in vitro transcribed dsRNA (500 ng) to LDH (dsRNA-LDH (w/w)) is assayed at 1:1, 1:2, 1:3, 1:4, 1:5 and 1:10 multiple times. dsRNA and LDH are incubated in a total volume of 10 µL at room temperature for 30 min with gentle orbital agitation. Complete dsRNA loading is assessed by retention of dsRNA-LDH complexes in the well of a 1% agarose gel. Appropriate loading ratios are consistent, irrespective of the scale-up volume required.

Release of dsRNA from dsRNA-LDH complexes and stability of the released dsRNA are tested as described in (Mitter et al., *Nature Plants* 1-10, 2017).

Northern Blot Analysis for dsRNA Detection within the Leaves:

To detect dsRNA uptake, *N. tabacum* plants (three replicates) are sprayed with either LDH, Bcr1-dsRNA or Bcr1-dsRNA-LDH at day 0. The ratios of the complex tested are: 1:1, 1:2, or 1:3 ratios of dsRNA-LDH. Plants are grown in UQ23 soil in 10 cm wide pots under glasshouse conditions (average temperature 25° C. with natural light). The apex of these plants is covered using a masking tape at the time of the spray. New leaves that emerge 20 days after the spray are collected. Total RNA is extracted by TRIzol extraction and enriched for small RNAs (Mitter et al., *Am. Phytopathological Soc.* 16:936-944, 2003). Small RNAs (20 µg) for each treatment are run on a 15% (wt/vol) denaturing urea polyacrylamide gel (PAGE). ZR Small-RNA ladder (Zymo Research) labelled with DIG at the 3' end is used as a marker. The blots are transferred by trans-blot SD semi-dry transfer unit (Bio-Rad) on a Hybond-N membrane (Roche). Blots are processed as per manufacture's recommendation using DIG-labelled Bcr1 24 nt probe (5-atgctgaccatgcatctgagcatt), proprietary buffer set (Roche). Following hybridization, filters are detected using the CSPD chemiluminescent alkaline phosphatase substrate. The quantification analysis is performed using the NIH Image 1.6 software.

Example 11: Solid Phase Synthesis of a PNA

This Example demonstrates solid phase synthesis of a PNA.
Therapeutic Design:
Complementary antisense PNA constructs against the bacteriocyte target gene Bcr1 gaatgcagctgc
Experimental Design:
The PNA antisense is synthesized automatically (Milli-Gen 9050 peptide synthesizer) by the solid-phase method using standard Fmoc (N-(9-fluorenyl)methoxycarbonyl) chemistry in a continuous flow mode.

PNA antisense purification is performed by reversed-phase high-performance liquid chromatography (RP-HPLC) with UV detection at 260 nm using a semi-prep column C18 (10 µm, 300×7.7 mm, Xterra Waters, 300 Å), eluting with water containing 0.1% TFA (eluent A) and acetonitrile containing 0.1% TFA (eluent B); elution gradient: from 100% A to 50% B in 30 min, flow: 4 ml/min. The purity and identity of the purified PNA antisense is examined by ultra-performance liquid chromatography tandem mass-spectrometry (UPLC-MS; Waters Acquity equipped with ESI-Q analizer) using an Acquity UPLC BEH C18; 2.1×50 MM, 1.7 µm column. The expected mass peaks are observed for the correct amino and nucleic acid sequence.

Example 12: Production of Cy3 Labeled PNA

This Example demonstrates joining the PNA described in Example 10 to Cy3 dye as a marker to tag the PNA through click chemistry.

Therapeutic Design: PNA with Dibenzylcyclooctyne (DBCO) Modification and Cy3 Dye with Azide Modification: Cy3-Gaatgcagctgc.
Experimental Design:
To prepare for the click reaction the PNA synthesized in Example 10 is labeled with DBCO (Glen Research, Sterling, VA). DBCO-sulfo-NHS ester is dissolved at a concentration of 5.2 mg per 60 µL in water or anhydrous DMSO. This stock solution is used to conjugate the amino-modified PNA in sodium carbonate/bicarbonate conjugation buffer, pH=~9.

For a 0.2 µmol synthesis of PNA, PNA is dissolved in 500 µL of conjugation buffer. Approx. a 6 fold excess (6 µL) of DBCO-sulfo-NHS ester solution is added to the dissolved PNA. The mixture is vortexed and incubated at room temperature for 2-4 hours up to about overnight. The conjugated PNA is desalted on a desalting column (Glen Research, Sterling, VA) to remove salts and organics.

Cy3-azide modified dye is obtained from Sigma Aldrich (777315). For the click reaction, 1 mg of Cy3-azide is dissolved in 150 µL of DMSO. The Cy3-azide solution is added to 10 OD of DBCO conjugated PNA in 100 µL of water. The mixture is incubated at room temperature overnight. The ligated PNAs are desalted on a desalting column (Glen Research, Sterling, VA) to remove salts and organics.

Example 13: Treatment of Aphids (*Myzus persicae*) with a Solution of Cy3-PNA

This Example demonstrates the ability to kill or decrease the fitness of aphids, *Myzus persicae*, by treating them with a Cy3-PNA constructs that targets expression of the Bcr1 gene (ACYPI32128), which is an essential gene for bacteriocyte regulation and function in insects.

Aphids are one of the most important agricultural insect pests. They cause direct feeding damage to crops and serve as vectors of plant viruses. In addition, aphid honeydew promotes the growth of sooty mold and attracts nuisance ants. The use of chemical treatments, unfortunately still widespread, leads to the selection of resistant individuals whose eradication becomes increasingly difficult.

Therapeutic Design: Cy3-PNA Solutions are Formulated with 0, 0.5, 1, 5 or 10 mg/L of Cy3-PNA from Example 11 in 10 mL of 0.5% Sucrose and Essential Amino Acids.
Experimental Design:
To prepare for the treatment, aphids are grown in a lab environment and medium. In a climate-controlled room (16 h light photoperiod; 60±5% RH; 20±2° C.), plants are grown in a mixture of vermiculite and perlite and are infested with aphids. To limit maternal effects or health differences between plants, 5-10 adults from different plants are distributed among 10 two-week-old plants, and allowed to multiply to high density for 5-7 days. For experiments, second and third instar aphids are collected from healthy plants and divided into treatments so that each treatment receives approximately the same number of individuals from each of the collection plants.

Wells of a 96-well plate are filled with 200 µl of artificial aphid diet (Febvay et al., *Canadian Journal of Zoology* 66(11):2449-2453, 1988) and the plate is covered with parafilm to make a feeding sachet. Artificial diet is either mixed with the solution of sterile water with 0.5% sucrose and essential amino acids only as a negative control, or mixed with Cy3-PNA solutions. Cy3-PNA solutions are mixed with artificial diet to obtain final concentrations between 0.5 to 10 mg/L.

For each replicate treatment, 30-50 second and third instar aphids are placed individually in wells of a 96-well plate and a feeding sachet plate is inverted above them, allowing the insects to feed through the parafilm and keeping them restricted to individual wells. Experimental aphids are kept under the same environmental conditions as aphid colonies. After the aphids are fed for 24 hr, the feeding sachet is replaced with a new one containing sterile artificial diet and a new sterile sachet is provided every 24 h for 4 days. At the time that the sachet is replaced, aphids are also checked for mortality. An aphid is counted as dead if it had turned brown or is at the bottom of the well and does not move during the observation. If an aphid is on the parafilm of the feeding sachet but not moving, it is assumed to be feeding and alive.

The survival rates of aphids treated with Bcr1 specific Cy3-PNA are compared to the aphids treated with the negative control. The survival rate of aphids treated with Bcr1 specific Cy3-PNA is decreased as compared to the control treated aphids.

Example 14: Topical-Plant Delivery of Cy3-PNA for Crop Protection

This Example demonstrates the ability to deliver Cy3-PNA by topical application on tobacco plant leaves. Cy3-PNA targets the expression of the Bcr1 gene (ACYPI32128), which is an essential gene for bacteriocyte regulation and function in insects.
Therapeutic Design:
Cy3-PNA-LDH spray solutions are formulated with Cy3-PNA synthesized in Example 11 at 1:0 (negative control), 1:1, 1:2, or 1:3 ratio of Cy3-PNA:LDH at 125 uL/cm$^2$ of leave surface.
Preparation and Characterization of LDH Nanosheets:
Sheet-like clay nanoparticles, specifically positively charged LDH, are excellent nanocarrier systems to deliver nucleic acids as stable spray formulations for crop protection (Mitter et al., *Nature Plants* 1-10, 2017). LDH conjugates strongly adhere to the leaf surface even after vigorous rinsing, and enhance the stability of PNAs for a longer period under environmental conditions. The sustained release of PNAs is facilitated through the formation of carbonic acid on the leaf surface from atmospheric $CO_2$ and humidity, which helps degrade the LDH nanosheets.

LDH nanosheets are prepared according to (Mitter et al., *Nature Plants* 1-10, 2017) by modified non-aqueous precipitation, followed by heat treatment, purification, and dispersion in water to get an average particle size of 45 nm. The particles (five repeated LDH samples) are characterized by the Nanosizer Nano ZS instrument (Malvern Instruments) to obtain the Z average size and Pdl and imaged using JEOL JSM-2010 TEM22. The chemical composition and crystal structure are verified by powder XRD with five LDH samples and Fourier transform infrared spectroscopy with attenuated total reflection mode, using a Rigaku Miniflex X-Ray diffractometer and a Nicolet 6700 FT-IR (Thermo Electron Corporation), respectively.

Cy3-PNA Loading on LDH:

To define optimal and complete loading of the Cy3-PNAs obtained in Example 11 into LDH nanosheets, the ratio of Cy3-PNA (0.5 μg) to LDH (Cy3-PNA-LDH (w/w)) is assayed at 1:1, 1:2, 1:3, 1:4, 1:5 and 1:10 multiple times. Cy3-PNA and LDH are incubated in a total volume of 10 μL at room temperature for 30 min with gentle orbital agitation. Complete Cy3-PNA loading is assessed by retention of Cy3-PNA-LDH complexes in a well of a 1% agarose gel. Appropriate loading ratios are consistent, irrespective of the scale-up volume required.

Confocal Imaging for Cy3-PNA Detection within Plant Leaves:

Surface-sterilized seeds of *Arabidopsis thaliana* Col-0 are vernalized, plated and vertically grown at 21° C. (16 h/8 h day/night) for 11 days on solid MS media.

To detect uptake of Cy3-PNA, 11-day-old *A. thaliana* seedlings in replicates of three are treated with 3 μL droplets of Cy3 only, Cy3-PNA (1 μg) and Cy3-PNA-LDH (1:3). Droplets are applied onto individual leaves. After 48 h the leaves are rinsed twice for 2 min in 3 ml of water with vigorous pipetting and visualized below the epidermis as florescence remained on the surface in case of LDH treatments. Natural chlorophyll florescence is detected with 650-800 nm bandpath filter. Z-stacks are used to verify that the florescence observed in the spongy mesophyll and xylem are internalized. The leaves are viewed under a Zeiss LSM510 META (Carl Zeiss) confocal laser scanning microscope. Cy3 florescence is visualized by excitation with a HeNe laser at 543 nm and detected with a 560-615 nm bandpath filter.

Example 15: Treatment of Aphids with a Solution that Increases Body Temperature This Example demonstrates the ability to kill or decrease the fitness of aphids by treating them with prostaglandin. Prostaglandins are eicosanoids associated with immune function that rapidly induce fever in vertebrates and invertebrates. This example demonstrates that the effect of prostaglandin on aphids is mediated through the modulation of bacterial populations endogenous to the aphid that are sensitive to an increase in temperature generated by prostaglandin. One targeted bacterial strain is *Buchnera.*

Therapeutic Design:

The prostaglandin solution E2 (PGE2) was formulated with 0 (negative control), 10, 20 or 50 μg/μl of prostaglandin formulated in a solution of ethanol and sterile water with 0.5% sucrose and essential aminoacids.

Experimental Design:

To prepare for the treatment, aphids are grown in a lab environment and medium. In a climate-controlled room (16 h light photoperiod; 60±5% RH; 20±2° C.), fava bean plants are grown in a mixture of vermiculite and perlite at 24° C. with 16 h of light and 8 h of darkness. To limit maternal effects or health differences between plants, 5-10 adults from different plants are distributed among 10 two-week-old plants, and allowed to multiply to high density for 5-7 days. For experiments, second and third instar aphids are collected from healthy plants and divided into treatments so that each treatment receives approximately the same number of individuals from each of the collection plants.

Prostaglandin solutions are made by dissolving prostaglandin (SIGMA-ALDRICH, P5640) in sterile water and ethanol (1:1) with 0.5% sucrose and essential aminoacids. Wells of a 96-well plate are filled with 200 μl of artificial aphid diet (Febvay, et al., *Canadian Journal of Zoology;* 1988, 66 (11): 2449-2453) and the plate is covered with parafilm to make a feeding sachet. Artificial diet is either mixed with sterile water and with 0.5% sucrose and essential aminoacids as a negative control or a prostaglandin solution containing one of the concentrations of prostaglandin. Prostaglandin solutions are mixed with artificial diet to get final concentrations between 10 and 50 μg/μL.

For each replicate treatment, 30-50 second and third instar aphids are placed individually in wells of a 96-well plate and a feeding sachet plate is inverted above them, allowing the insects to feed through the parafilm and keeping them restricted to individual wells. Experimental aphids are kept under the same environmental conditions as aphid colonies. After the aphids are fed for 24 hr, the feeding sachet is replaced with a new one containing sterile artificial diet and a new sterile sachet is provided every 24 h for four days. At the time that the sachet is replaced, aphids are also checked for mortality. An aphid is counted as dead if it had turned brown or is at the bottom of the well and does not move during the observation. If an aphid is on the parafilm of the feeding sachet but not moving, it is assumed to be feeding and alive.

The status of Buchnera in aphid samples is assessed by PCR. Total DNA is isolated from control (non-prostaglandin treated) and prostaglandin treated individuals using an Insect DNA Kit (OMEGA, Bio-tek) according to the manufacturer's protocol. The primers for Buchnera, forward primer 5'-GTCGGCTCATCACATCC-3' (SEQ ID NO: 97) and reverse primer 5'-TTCCGTCTGTATTATCTCCT-3' (SEQ ID NO: 98), are designed based on 23S-5S rRNA sequences obtained from the Buchnera genome (Accession Number: GCA_000009605.1) (Shigenobu, et al., Nature 200.407, 81-86) using Primer 5.0 software (Primer-E Ltd., Plymouth, UK). The PCR amplification cycles included an initial denaturation step at 95° C. for 5 min, 35 cycles of 95° C. for 30 s, 55° C. for 30 s, and 72° C. for 60 s, and a final extension step of 10 min at 72° C. Amplification products from prostaglandin treated and control samples are analyzed on 1% agarose gels, stained with SYBR safe, and visualized using an imaging System. Prostaglandin treated aphids show a reduction of Buchnera specific genes.

The survival rates of aphids treated with prostaglandin solution are compared to the aphids treated with the negative control. The survival rate of aphids treated with prostaglandin solution is decreased compared to the control.

Example 16: Treatment of Aphids with dsRNA to Stimulate an Insect Immune Response to Decrease Fitness This Example demonstrates that the treatment of aphids with double-stranded RNA (dsRNA) resulted in the knockdown of immunoregulatory genes to induce an immune response and decrease aphid fitness. By inducing an immune response by inhibiting an immunoregulatory gene, specifically, Cact a negative regulator of the Toll pathway, which is the primary immunity pathway in aphids, to induce Toll pathway activation to express and secrete antimicrobial peptides, lysozymes, and prophenoloxidase that ultimately affect bacterial populations endogenous to the aphid. This Example demonstrates that the effect of lowering the levels of Cact in aphids to upregulate the systemic immune responses leading to the dysregulation of bacterial populations endogenous to the aphid that are sensitive to the increase in Aphid immune responses generated by Toll pathway activation. One targeted bacterial strain is Buchnera.

Therapeutic Design:
5th instar LSR-1 aphids are microinjected. The injection solutions will be either dd-water (negative control) or dsRNA diluted in dd-water at various concentrations (8 or 60 ng/aphid; see below).
Experimental Design:
Aphids LSR-1 (which harbor only Buchnera), A. pisum will be grown on fava bean plants (Vroma Vicia faba from Johnny's Selected Seeds) in a climate-controlled incubator (16 h light/8 h dark photoperiod; 60±5% RH; 25±2° C.). Prior to being used for aphid rearing, fava bean plants will be grown in potting soil at 24° C. with 16 h of light and 8 h of darkness. To limit maternal effects or health differences between plants, 5-10 adults from different plants will be distributed among 10 two-week-old plants, and allowed to multiply to high density for 5-7 days. For experiments, fifth instar aphids will be collected from healthy plants and divided into 2 different treatment groups: 1) water (negative control) or 2) dsRNA against ApGLNT1 (at the concentrations indicated herein).
Microinjection Delivery Experimental Design
Microinjection will be performed using NanoJet III Auto-Nanoliter Injector with an in-house pulled borosilicate needle (Drummond Scientific; Cat #3-000-203-G/XL). Aphids will be transferred using a paint brush to a tubing system connected to vacuum which held the aphid in place during the microinjection. The injection site will be at the ventral thorax of the aphid. The injection volume will be 20 nl for adult aphids at a rate of 2 nl/sec. Each treatment group will have approximately the same number of individuals injected from each of the collection plants.

After injection, aphids will be released into a petri dish onto a fava bean leaves that have stems in an Eppendorf tube filled with 1 ml water. Aphid survival will be monitored daily, and dead aphids will be removed when they are found. The number of offspring from each group will be counted and fecundity will be measured as the number of offspring (F1's) produced per aphid at each time point.

In select experiments, development will be measured in groups of offspring from each treatment group by noting the developmental stage of offspring each day ($1^{st}$, $2^{nd}$, $3^{rd}$, $4^{th}$, and $5^{th}$ instar). Development will be also measured by imaging aphids at 4 days post-collection and determining their area. The template for synthesizing dsRNAs will be the cDNA reverse-transcribed from the mRNA. RNA will be extracted from one 5th instar A. pisum (LSR-1 strain) and is quantified by Nanodrop (Thermo fisher scientific). ~100 µg of total RNA will be added as template into the reverse-transcription reaction using Superscript IV kit (Thermo Fisher Scientific) following manufacturer's protocol.

To amplify the templates for the dsRNAs, the cDNA will be diluted 100-fold and used in the following PCRs. The PCR reactions (25 µl final volume) contain 12.5 µL of Go Taq Green 2× mix (Promega), 0.2 µl of forward primer (Table 12), 0.2 µl of reverse primer (Table 12), and 12.1 µl of 100-fold diluted cDNA. PCR reactions are performed using following conditions: 1) 95° C. for 2 minutes, 2) 95° C. for 20 seconds, 3) 55° C. for 15 seconds, 4) 72° C. for 30 seconds, 5) repeat steps 2-4 35×, 6) 72° C. for 5 minutes. The sizes of PCR amplified products are verified by electrophoresis on 1.5% agarose and the expected-size bands are cut and purified by QIAquick DNA purification kit (Qiagen). The dsRNAs will be synthesized in vitro using T7 MEGAscript kit (Ambion, Thermo Fisher Scientific; Cat #AM1334) following manufacturer's protocol. The concentration of dsRNA is measured by Nanodrop (Thermo Fisher Scientific).

TABLE 12

Cact dsRNA sequences:

| Target gene | Forward primer | Reverse primer | product size |
|---|---|---|---|
| Mpcactus | taatacgactcact atagggTACACCCA TTGTGTGCACCT (SEQ ID NO: 99) | taatacgactcact atagggCCACTGTC CAAGGCAATTTT (SEQ ID NO: 100) | 487 |

The status of *Buchnera* in aphid samples will be assessed by PCR. Aphids adults from the negative control and phage treated will be first surface-sterilized with 70% ethanol for 1 min, 10% bleach for 1 min and three washes of ultrapure water for 1 min. Total DNA will be extracted from each individual (whole body) using an Insect DNA Kit (OMEGA, Bio-tek) according to the manufacturer's protocol. The primers for *Buchnera*, forward primer 5'-GTCGGCTCAT-CACATCC-3' (SEQ ID NO: 97) and reverse primer 5'-TTCCGTCTGTATTATCTCCT-3' (SEQ ID NO: 98), are designed based on 23S-5S rRNA sequences obtained from the *Buchnera* genome (Accession Number: GCA_000009605.1) (Shigenobu, et al., *Nature* 200.407, 81-86) using Primer 5.0 software (Primer-E Ltd., Plymouth, UK). The PCR amplification cycles include an initial denaturation step at 95° C. for 5 min, 35 cycles of 95° C. for 30 s, 55° C. for 30 s, and 72° C. for 60 s, and a final extension step of 10 min at 72° C. Amplification products from rifampicin treated and control samples will be analyzed on 1% agarose gels, stained with SYBR safe, and visualized using an imaging System. dsRNA treated aphids are expected to show a reduction of *Buchnera* specific genes.

The expression of Cact and survival rates of aphids treated with Cactus are compared to the aphids treated with the negative control. The expression of Cact and survival rate of aphids treated with dsRNA to Cact are expected to decrease as compared to the control treated aphids.

Example 17: Aphids Treated with a Fungi Solution that Stimulated an Insect Immune Response to Decrease Fitness This Example demonstrates the treatment of aphids with a solution of *Pichia pastoris*, a yeast strain that resulted in decreased aphid fitness. Although many of the innate immune system pathways present in insects are absent in aphids, the key players that recognize and induce immune responses to fungi remain intact. Specifically, the presence of fungi induces the cleavage of the aphid serine protease, Persephone, which then activates the Toll pathway. Next, Cactus is phosphorylated and Dorsal is released and translocated to the nucleus which activates the expression and secretion of antimicrobial peptides, lysozymes, and prophenoloxidase that ultimately affect bacterial populations endogenous to the aphid. This Example demonstrates that the effect of the solution of *Pichia pastoris* on aphids was mediated through the modulation of bacterial populations endogenous to the aphid that were sensitive to the increase in the Aphid immune response generated by the presence of the yeast. One targeted bacterial strain was *Buchnera*.

Aphids are agricultural insect pests causing direct feeding damage to the plant and serving as vectors of plant viruses. In addition, aphid honeydew promotes the growth of sooty mold and attracts nuisance ants. The use of chemical treatments, unfortunately still widespread, leads to the selection of resistant individuals whose eradication becomes increasingly difficult.

Therapeutic Design

*P. pastoris* was delivered using two different methods: Fava bean leaf perfusion and air brush spraying onto fava bean leaves. For each experiment, there were two experimental groups: 1) treatment with water as a negative control; and 2) treatment with *P. pastoris* in water. Treatment methods and doses are described herein in the Experimental Design section.

Leaf Perfusion Experimental Design

Aphids (LSR-1 strain, *Acyrthosiphon pisum*) were grown on fava bean plants (Vroma *Vicia faba* from Johnny's Selected Seeds) in a climate-controlled incubator (16 h light/8 h dark photoperiod; 60±5% RH; 25±2° C.). Prior to being used for aphid rearing, fava bean plants were grown in potting soil at 24° C. with 16 h of light and 8 h of darkness. To limit maternal effects or health differences between plants, 5-10 adults from different plants were distributed among 10 two-week-old plants, and allowed to multiply to high density for 5-7 days. For experiments, first and second instar aphids were collected from healthy plants and divided into two different treatment groups: 1) those allowed to feed on leaves perfused with water; and 2) those allowed to feed on leaves perfused with a *P. pastoris* solution in water.

The "protease wild-type" ade2 knockout strain (Strain 1) from the *Pichia* Pink System (Thermo Fisher Scientific) was used for experiments. *P. pastoris* was grown in YPD overnight at 30° C., and the following day, the culture was washed once with water and resuspended in water to a final $OD_{600}$ of 0.918 for the first leaf perfusion on day 0 or $OD_{600}$ of 5.58 for the second leaf perfusion on day 3 of the experiment. For each leaf perfusion, approximately 1 ml of the *P. pastoris* solution or water (negative control) was injected into a fava bean leaf. The stem of the leaf was then placed in a 1.5 ml Eppendorf that was sealed with parafilm. The leaf stem was then placed into a deep petri dish (Fisher Scientific, Cat #FB0875711) and aphids were applied to the leaves of the plant and allowed to feed. Leaves were changed on day 3 of the experiment and old leaves were replaced with new leaves perfused with *P. pastoris* (at the indicated $OD_{600}$) or water.

For each treatment, 62-63 aphids were placed onto each leaf. Aphids were monitored daily for survival and dead aphids were removed when they were discovered. In addition, the developmental stage ($1^{st}$, $2^{nd}$, $3^{rd}$, $4^{th}$, and $5^{th}$ instar) was determined daily throughout the experiment.

After 6 days of treatment, DNA was extracted from multiple aphids from each treatment group. Briefly, the aphid body surface was sterilized by dipping the aphid into a 6% bleach solution for approximately 5 seconds. Aphids were then rinsed in sterile water and DNA was extracted from each individual aphid using a DNA extraction kit (Qiagen, DNeasy kit) according to manufacturer's instructions. DNA concentration was measured using a nanodrop nucleic acid quantification, and *Buchnera* and aphid DNA copy numbers were measured by qPCR. The primers used for *Buchnera* were Buch_groES_18F (CAT-GATCGTGTGCTTGTTAAG; SEQ ID NO: 101) and Buch_groES_98R (CTGTTCCTCGAGTCGATTTCC; SEQ ID NO: 102) (Chong and Moran, 2016 PNAS). The primers used for aphid were ApEF1a 107F (CTGAT-TGTGCCGTGCTTATTG; SEQ ID NO: 103) and ApEF1a 246R (TATGGTGGTTCAGTAGAGTCC; SEQ ID NO: 104) (Chong and Moran, 2016 PNAS). qPCR was performed using a qPCR amplification ramp of 1.6 degrees C./s and the following conditions: 1) 95° C. for 10 minutes, 2) 95° C. for 15 seconds, 3) 55° C. for 30 seconds, 4) repeat steps 2-3 40×, 5) 95° C. for 15 seconds, 6) 55° C. for 1 minute, 7) ramp change to 0.15 degrees C./s, 8) 95° C. for 1 second. qPCR data was analyzed using analytic (Thermo Fisher Scientific, QuantStudio Design and Analysis) software.

Treatment with a Yeast Solution Delayed Progression of Aphid Development

LSR-1 first and second instar aphids were divided into two treatment groups as defined in Leaf Perfusion Experimental Design. Aphids were monitored daily and the number of aphids at each developmental stage was determined. By day 6 of the experiment, approximately 30% of aphids feeding on leaves perfused with water reached the fifth instar stage (FIG. 1). In contrast, only approximately 3% of aphids feeding on leaves perfused with *P. pastoris* reached the fifth instar stage by day 6 of the experiment (FIG. 1). The majority of aphids feeding on the leaves perfused with *P. pastoris* that survived to day 6 were at the 4th instar stage (~5%) (FIG. 1). These data indicated that *P. pastoris* treatment slowed aphid development.

Treatment with a Yeast Solution Increased Aphid Mortality

Figure 2:
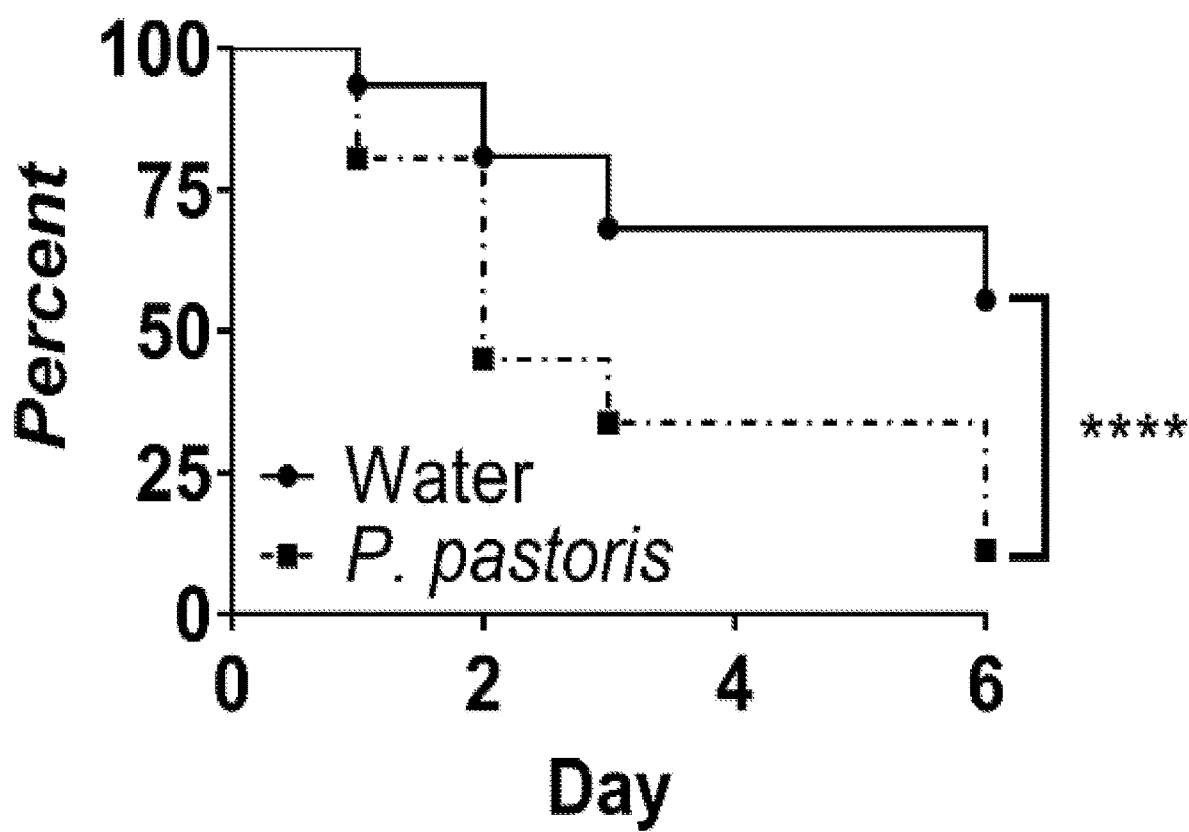
FIG. 2 is a graph showing that *P. pastoris* treatment resulted in aphid death. First and second instar LSR-1 aphids were treated with water (control) or with *P. pastoris* via leaf perfusion and survival was monitored daily during the experiment. N=62-63 aphids/group. Statistically significant differences were determined using Log-Rank (Mantel Cox) test. ****, p<0.0001.

Survival of aphids was also measured during the treatments. Approximately 55.5% of aphids feeding on leaves perfused with water survived to day 6 of the experiment (FIG. 2). In contrast, aphids feeding on leaves perfused with *P. pastoris* rapidly began to die at day 2 post-treatment and by day 6, only 11% of aphids were alive (FIG. 2). These data indicated that *P. pastoris* treatment delivered through leaf perfusion resulted in a significant ($p<0.0001$) increase in aphid mortality.

To test whether *P. pastoris* treatment specifically resulted in loss of *Buchnera* in aphids, and that this loss impacted aphid fitness, DNA was extracted from aphids in each treatment group after 6 days of treatment and qPCR was performed to determine the *Buchnera*/aphid copy numbers. Results were inconclusive due to the low number of aphids remaining in the *P. pastoris* treatment group at day 6 and the lack of extractable *Buchnera* DNA.

Airbrush Spraying Experimental Design:

Aphids (LSR-1 strain, *Acyrthosiphon pisum*) were grown on fava bean plants as described herein. For experiments, first and second instar aphids were collected from healthy plants and divided into 2 different treatment groups: 1) aphids placed on leaves sprayed with water (negative control), and 2) aphids placed on leaves sprayed with *P. pastoris*.

The "protease wild-type" ade2 knockout strain (Strain 1) from the *Pichia* Pink System (Thermo Fisher Scientific) was used for experiments. *P. pastoris* was grown in YPD overnight at 30° C. and the following day, the culture was washed once with water and resuspended in water to a final OD600 of 0.918 for the first and second leaf spraying (on day 0 and 3) and OD600 of 5.58 for the final leaf spraying on day 6 of the experiment. For the treatments, fava bean leaves were cut and the stems were placed into a 1.5 ml Eppendorf tube with sterile water and sprayed on both sides using an airbrush with water or *P. pastoris* at the concentration indicated above. The leaves were then placed in a deep petri dish (Fisher Scientific, Cat #FB0875711) and aphids were applied to the leaves of the plant and allowed to feed. On day 3 and 6 of the experiment, old leaves were replaced with new, freshly sprayed leaves.

Each treatment group received approximately the same number of individuals from each of the collection plant. For each treatment, 30 aphids were placed onto each leaf. Each treatment was performed in duplicate for a total of 60 aphids/treatment group. Aphids were monitored daily for survival, and dead aphids were removed when they were discovered. In addition, the developmental stage (1st, 2nd, 3rd, 4th, and 5th instar) was determined daily throughout the experiment.

After 6 and 9 days of treatment, DNA was extracted from multiple aphids from each treatment group and qPCR for quantifying *Buchnera* levels was done as described herein.

Treatment with a Yeast Solution Did not Greatly Impact Aphid Development

Figure 3:
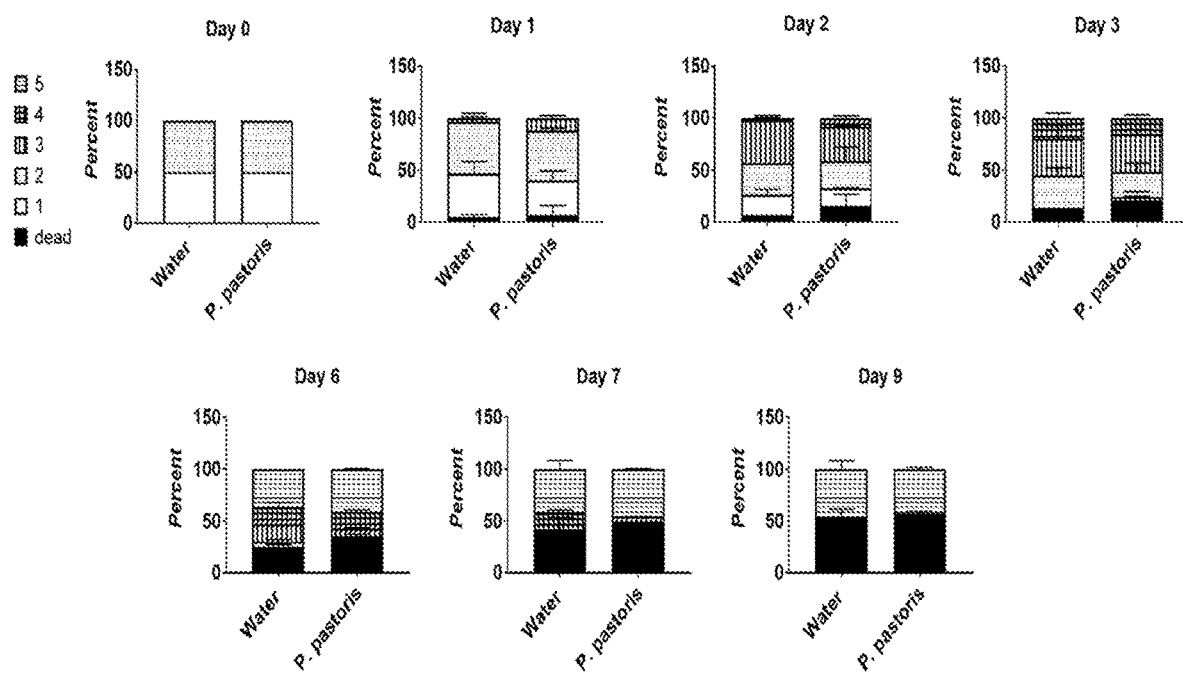
FIG. 3 is a panel of graphs showing that *P. pastoris* treatment via leaf spraying did not affect aphid development. First and second instar LSR-1 aphids were treated with water (control) or *P. pastoris* via airbrush spraying and developmental stage was monitored over time. Shown are the mean percentages±SD of dead or live aphids in each developmental stage (1st, 2nd, 3rd, 4th, or 5th instar) at each time point. N=two replicates of 30 aphids/group.

LSR-1 first and second instar aphids were divided into two treatment groups as defined in the Airbrush Spraying Experimental Design described herein. Aphids were monitored daily and the number of aphids at each developmental stage was determined. By 6 days post-treatment, aphids from both treatment groups began reaching the 5th instar stage (FIG. 3). By day 9 post-treatment, nearly all remaining aphids in each group reached maturity (FIG. 3). These data indicated that there was little difference in development between aphids treated with water or *P. pastoris*.

A Yeast Solution Treatment Via Spraying Resulted in Increased Aphid Mortality

Figure 4:
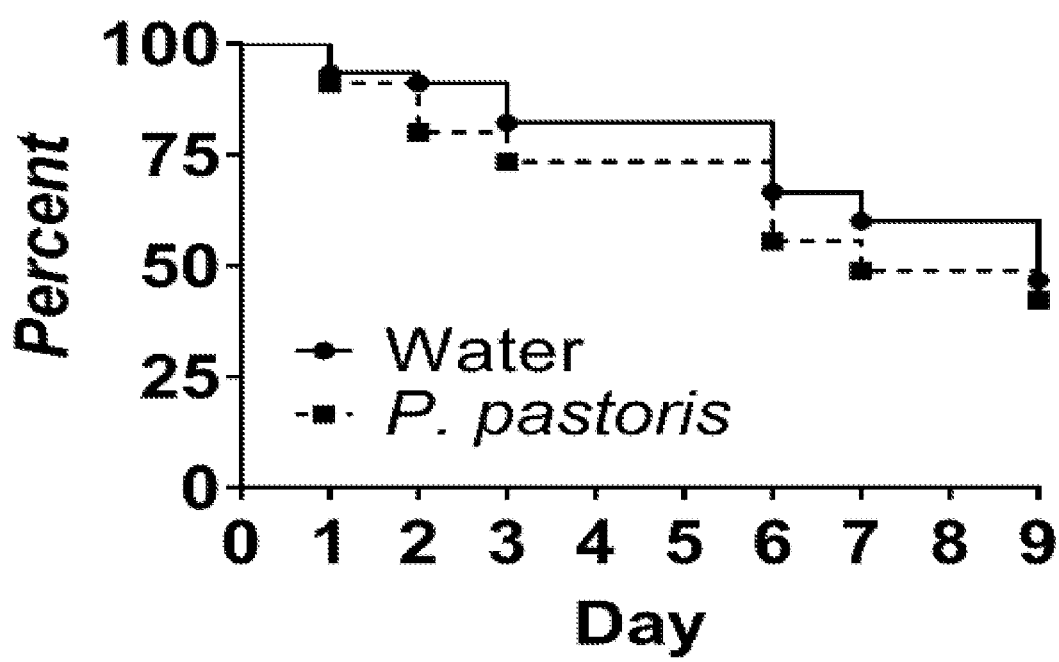
FIG. 4 is a graph showing that *P. pastoris* treatment increased aphid mortality. First and second instar LSR-1 aphids were placed on leaves sprayed with water (control) or *P. pastoris* and survival was monitored over time. N=60 aphids/treatment group.

Survival of aphids was also measured during the leaf spraying experiments. Throughout the course of the experiment, only a few aphids feeding on leaves sprayed with water died, whereas a greater number of aphids died at each time point in the *P. pastoris* treatment group (FIG. 4). Specifically, on day 2 post-treatment 91% of water-treated aphids remained alive, while only 80% of *P. pastoris*-treated aphids remained alive. This trend continued through days 3, 6, and 7 of the experiment where 82%, 66%, and 60% of water-treated aphids were alive at each time point, respectively, in contrast to only 73%, 55%, and 49% of *P. pastoris*-treated aphids were alive at each time point, respectively (FIG. 4). These data indicated that *P. pastoris* treatment delivered by airbrush spraying resulted in higher mortality compared to treatment with water alone.

A Yeast Solution Treatment Reduced *Buchnera* Titers in Aphids

Figures 5A, 5B:
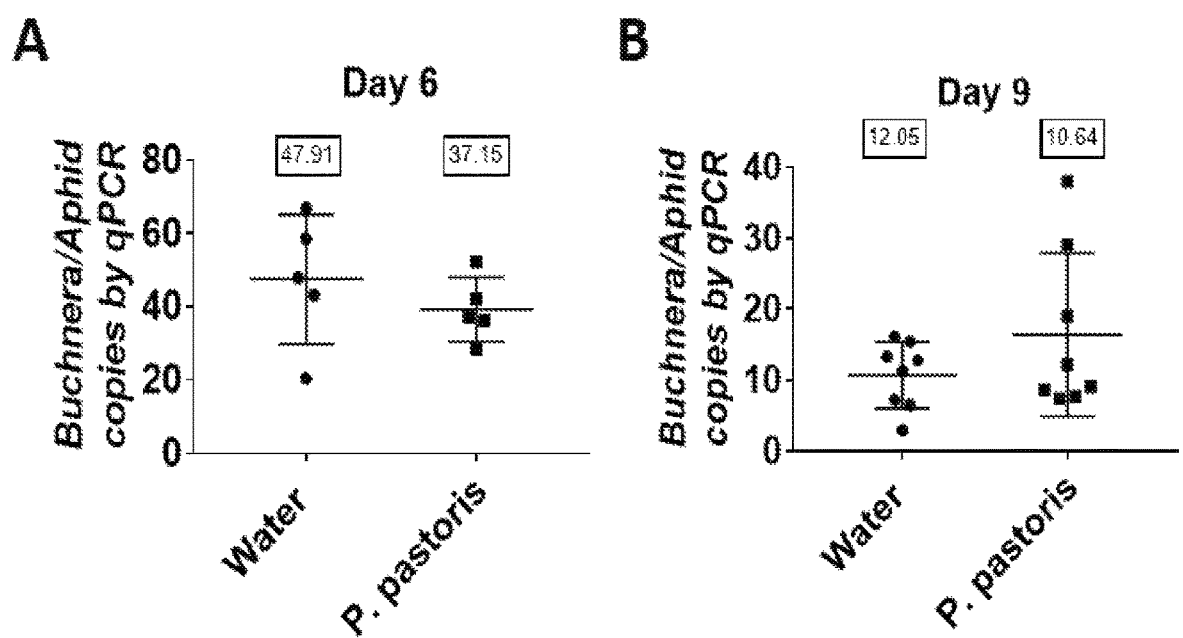
FIGS. 5A and 5B are graphs showing that spraying *P. pastoris* on fava bean leaves reduced endosymbiotic *Buchnera* in aphids feeding on the leaves. Symbiont titer was determined at 6 (A) and 9 (B) days post-treatment with *P. pastoris*. Shown are the mean *Buchnera*/aphid copies±SD. The number in the box above the indicated dataset represents the median value of that group. Each dot represents a single aphid.

To test whether *P. pastoris* delivered through airbrush spraying, specifically resulted in loss of *Buchnera* in aphids, and that this loss impacted aphid fitness, DNA was extracted from aphids in each treatment group after 6 and 9 days of treatment and qPCR was performed to determine the *Buchnera*/aphid copy numbers. At 6 days post-treatment the mean *Buchnera*/aphid ratios were 47.5 in aphids feeding on leaves sprayed with water (FIG. 5). In contrast, mean *Buchnera*/aphid ratios were approximately 1.2-fold lower (~39) in aphids feeding on leaves sprayed with *P. pastoris* (FIG. 5). At 9 days post-treatment however, the ratios of *Buchnera*/aphid DNA copies were similar in both treatment groups (FIG. 5).

These data indicated that spraying *P. pastoris* onto fava bean leaves decreased endosymbiotic *Buchnera* in aphids after 6 days post-treatment. It was possible that *P. pastoris*-treated aphids that survived to 9 days post-treatment were able to overcome the detrimental effects of the increased immune response and could explain why these aphids had similar *Buchnera* titers to the water treated controls. Nonetheless, examination of the median *Buchnera*/aphid copies on day 9, revealed a trend for decreased *Buchnera* in the *P. pastoris* treatment group.

Confirmation of that *P. pastoris* Upregulates the Immune Response in Aphids

Given that treatment with *P. pastoris* resulted in decreased aphid fitness and lower titers of the aphid endosymbiont, *Buchnera*, the next experiment is to confirm that *P. pastoris* is upregulating the immune response. To test this, RNA has been isolated from aphids in each of the experiments described herein (Leaf Perfusion Experimental Design and Airbrush Spraying Experimental Design) and the expression of genes involved in the fungal immune response pathway will be measured (Persephone, Cactus, and Dorsal) as described in Gerardo et al., 2010, Genome Biology, 11:R21, https://doi.org/10.1186/gb-2010-11-2-r21. It is expected to see upregulation of the genes involved in this pathway.

Together, the data described in these Examples demonstrated the ability to kill and decrease the development, longevity, and endogenous bacterial populations, e.g., fitness, of aphids by treating them with *P. pastoris* which likely resulted in activation of the aphid immune response.

Example 18: Aphids Treated with a Solution of a Peptide Nucleic Acid

This Example demonstrates that the treatment of aphids with a peptide nucleic acid (PNA) to BCR-4 fused to a cell penetrating peptide (CPP) (Cermenati et al., 2011; Zhou et al., 2015), herein referred to as PNA to BCR-4 or BCR-4 PNA, resulted in knock-down of BCR-4 gene expression and reduction of aphid fitness.

BCR-4 is one of several cysteine-rich secreted peptides expressed in bacteriocytes of the pea aphid, *Acyrthosiphon pisum*. The obligate aphid bacterial symbiont, *Buchnera*, is housed inside of the bacteriocytes. BCR-4 has sequence homology to many of the nodule cysteine rich (NCRs) peptides involved in keeping plant bacterial symbiont numbers in check (Pan and Wang, 2017 Nature Plants and Durgo et al., 2015 Proteomics). Given the sequence similarity of BCR-4 and the NCRs, this Example demonstrates that BCR-4 played a similar role in maintaining endosymbiont homeostasis inside the bacteriocyte by disrupting BCR-4 though gene knockdown to dysregulate *Buchnera*, thereby negatively affecting aphid fitness.

Therapeutic Design

The BCR-4 PNA was delivered either by microinjection or through fava bean leaf perfusion. For microinjection experiments, injection solutions were either water (negative control) or BCR-4 PNA in water. For leaf perfusion studies, fava bean leaves were perfused with water (negative control) or with BCR-4 PNA in water. Each experimental delivery design is explained in detail below.

Microinjection Delivery Experimental Design

Microinjection was performed using NanoJet III Auto-Nanoliter Injector with an in-house pulled borosilicate needle (Drummond Scientific; Cat #3-000-203-G/XL). Aphids were transferred using a paint brush to a tubing system connected to vacuum which held them in place during the injection. The injection site was at the ventral thorax of the aphid. The injection solutions were water (negative control) or 321 ng/µl of BCR-4 PNA in water. The injection volume was 20 nl for adult (4th and 5th instar) aphids at a rate of 2 nl/sec. Each treatment group had approximately the same number of individuals injected from each of the collection plants. After injection, aphids were released into a petri dish onto fava bean leaves that had stems in an Eppendorf tube filled with 1 ml water. Survival and fecundity were monitored over the course of the experiment.

Aphid Rearing and Maintenance:

Aphids LSR-1 (which harbor only *Buchnera*), *A. pisum* were grown on fava bean plants (Vroma *Vicia faba* from Johnny's Selected Seeds) in a climate-controlled incubator (16 h light/8 h dark photoperiod; 60±5% RH; 25±2° C.). Prior to being used for aphid rearing, fava bean plants were grown in potting soil at 24° C. with 16 h of light and 8 h of darkness. To limit maternal effects or health differences between plants, 5-10 adults from different plants were distributed among 10 two-week-old plants, and allowed to multiply to high density for 5-7 days. For experiments, fourth and fifth instar aphids were collected from healthy plants and divided into two treatment groups: 1) water (negative control) or 2) BCR-4 PNA in water.

BCR-4 PNA Synthesis

BCR-4-CPP was synthesized by PNA bio and the sequence is YGRKKRRQRRR-CGTACAATAATCT-CATGG; SEQ ID NOs: 105 and 106. The sequence of the CPP (Tat) is YGRKKRRQRRR; SEQ ID NO: 106. The PNA was dissolved in 80% Acetonitrile and 20% Water supplemented with 0.1% Trifluoroacetic acid (TFA). Once dissolved, the PNA was aliquoted [32.1 µg/5 nmol per aliquot], air dried, and stored at −20° C. Working solutions of the PNA were made in water at 50 uM.

After 7 days of treatment, RNA was extracted from the remaining aphids in each treatment group. Briefly, the aphid body surface was sterilized by dipping the aphid into a 6% bleach solution for approximately 5 seconds. Aphids were then rinsed in sterile water and total RNA was extracted from each individual aphid using the RNA extraction kit (Qiagen miRNeasy kit) according to manufacturer's instructions. RNA concentrations were measured using a nanodrop nucleic acid quantification. BCR-4 relative expression was measured by RT-qPCR. The primers used were ApBCR-4F (CTCTGTCAACCACCATGAGATTA; SEQ ID NO: 107) and ApBCR-4R (TGCAGACTACAGCACAATACTT; SEQ ID NO: 108). The internal reference gene primers were for Actin (housekeeping gene). The forward sequence was GATCAGCAGCCACACACAAG; SEQ ID NO: 109 and the reverse sequence was TTTGAACCGGTTTACGACGA; SEQ ID NO: 110. RT-qPCR was performed using a qPCR amplification ramp of 1.6 degrees C./s and the following conditions: 1) 48° C. for 30 min, 2) 95° C. for 10 minutes, 3) 95° C. for 15 seconds, 4) 60° C. for 1 minute, 5) repeat steps 3-4 40×, 6) 95° C. for 15 seconds, 7) 60° C. for 1 minute, 8) ramp change to 0.15 degrees C./s, 9) 95° C. for 1 second. RT-qPCR data was analyzed using analytic (Thermo Fisher Scientific, QuantStudio Design and Analysis) software.

Microinjection with a PNA Against the BCR-4 Gene Resulted in Decreased Expression of BCR-4

Figure 6:
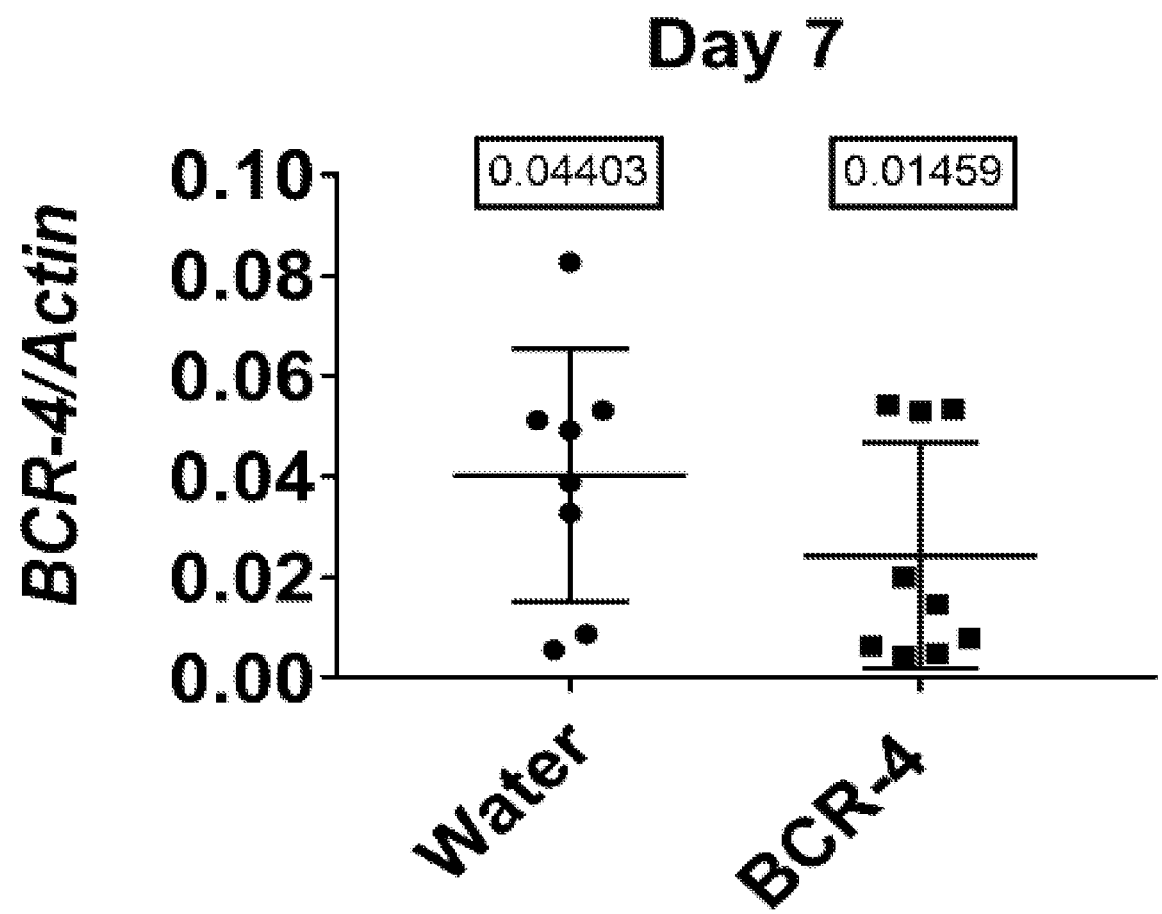
FIG. 6 is a graph showing microinjection of BCR-4 PNA reduced BCR-4 expression. Fourth and fifth instar *A. pisum* aphids were injected with 20 nl water or 321 ng/ul of BCR-4 PNA, RNA was extracted from aphids after 7 days, and RT-qPCR was performed to measure expression of BCR-4. Shown are the mean BCR-4/Actin copies±SD. Each data point represents a single aphid. The number in the box above each dataset represents the median of the data.

To test whether a PNA against BCR-4 delivered by microinjection results in decreased BCR-4 gene expression in aphids, aphids were injected with water (control) or BCR-4 PNA. After 7 days of treatment, RNA was extracted from aphids in each treatment group and RT-qPCR was performed. Aphids microinjected with water had approximately 2-fold higher expression of BCR-4 compared to aphids injected with BCR-4 PNA (FIG. 6), indicating that injection of BCR-4 PNA resulted in knockdown of BCR-4.

Treatment with a PNA to BCR-4 Increased Aphid Mortality

Figure 7:
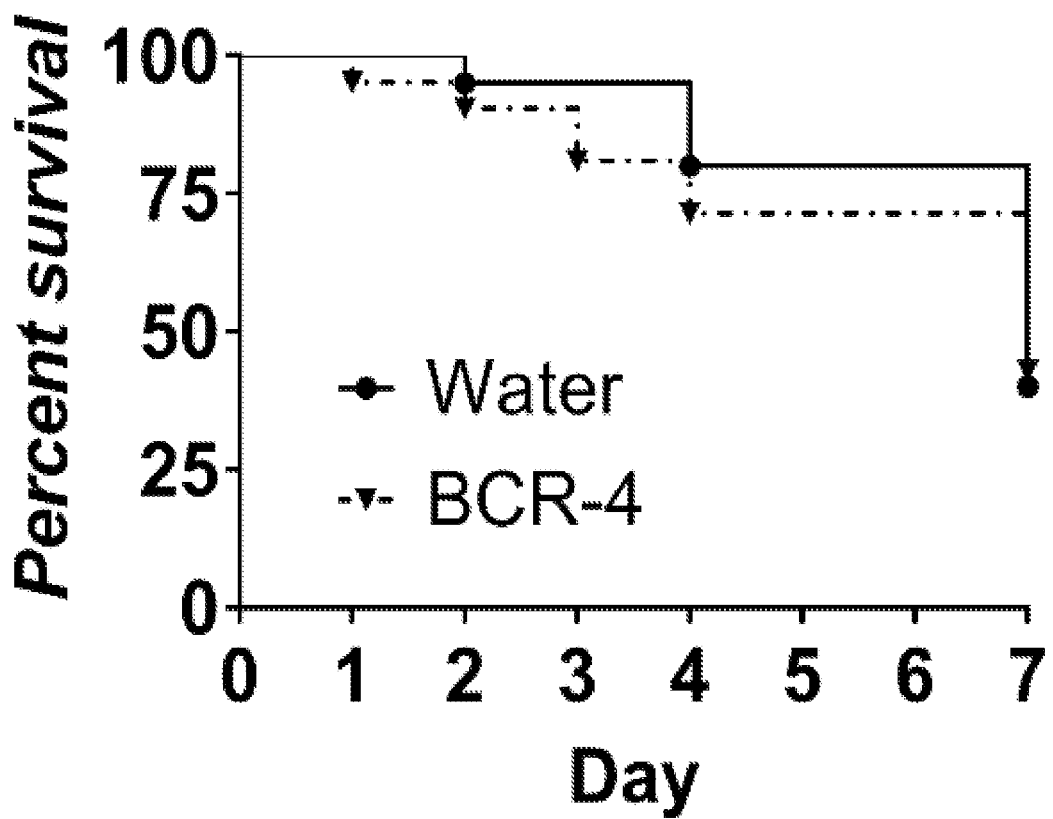
FIG. 7 is a graph showing the decrease in insect survival after treatment with a PNA to BCR-4. Fourth and fifth instar *A. pisum* aphids were injected with water or with a PNA to BCR-4. Survival was monitored daily over the course of the experiment. N=20 aphids per treatment group.

Survival rate of aphids was also measured during the treatments. At most time points during the experiment, there were more control (water injected) aphids alive compared to aphids injected with the PNA to BCR-4 (FIG. 7). These data indicated that there was a slight decrease in survival upon injection with a PNA to BCR-4.

Treatment with a PNA to BCR-4 Reduced Aphid Fecundity

Figure 8:
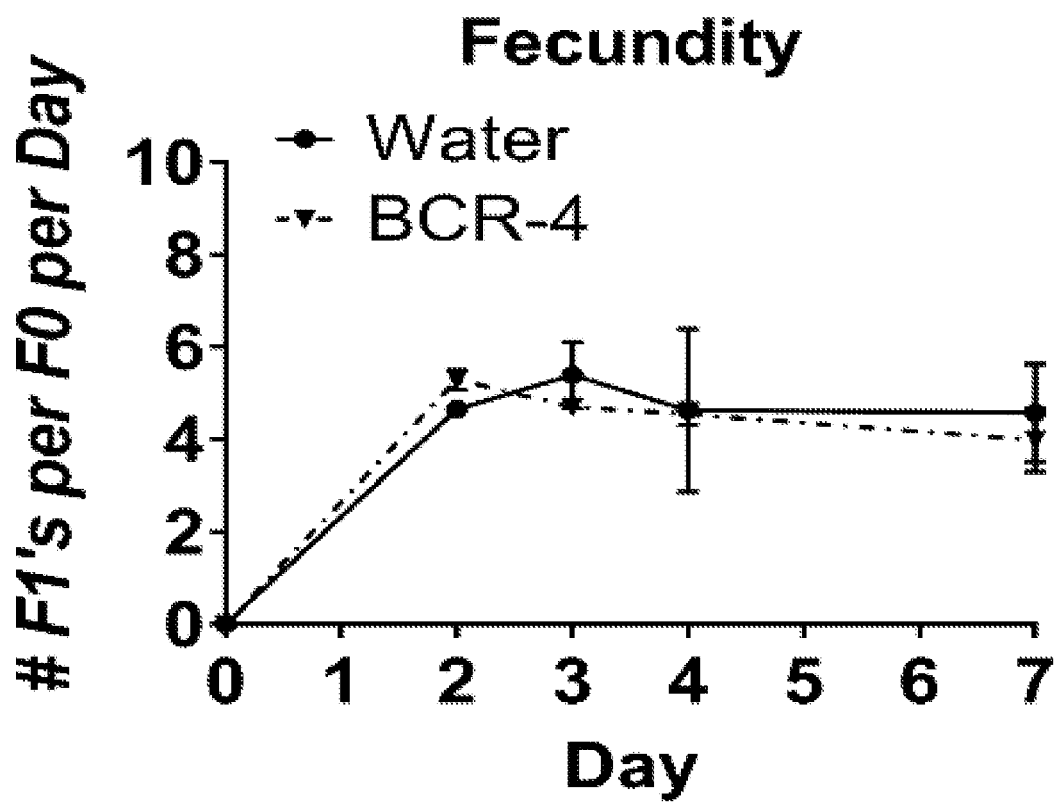
FIG. 8 is a graph showing injection of aphids with a PNA to BCR-4 resulted in decreased fecundity. Fourth and fifth instar *A. pisum* aphids were injected with water or with a PNA to BCR-4. Fecundity was measured by counting the number of offspring produced by each group at each time point and is represented as the number of F1's (first generation offspring) produced by F0 (adults) per day. N=20 aphids per treatment group.

The number of offspring produced from aphids in each treatment group was also assessed during the experiment and fecundity was represented as the number of offspring produced per adult at each time point assessed. Overall, there was a trend for control (water-injected) aphids producing more offspring compared to those injected with the PNA to BCR-4. Specifically, at 3 and 7 days post-treatment, aphids in the water treated group produced an average of 5 offspring/adult whereas aphids in the BCR-4 PNA treatment group only produced 4 offspring/adult (FIG. 8). These data indicated that treatment with BCR-4 PNA resulted in a slight decrease in aphid fecundity.

Leaf Perfusion Experimental Design

Aphids (LSR-1 strain, *Acyrthosiphon pisum*) were grown on fava bean plants (Vroma *Vicia faba* from Johnny's Selected Seeds) in a climate-controlled incubator (16 h light/8 h dark photoperiod; 60±5% RH; 25±2° C.). Prior to being used for aphid rearing, fava bean plants were grown in potting soil at 24° C. with 16 h of light and 8 h of darkness. To limit maternal effects or health differences between plants, 5-10 adults from different plants were distributed among 10 two-week-old plants and allowed to multiply to high density for 5-7 days. For experiments, first and second instar aphids were collected from healthy plants and divided into two different treatment groups: 1) those allowed to feed on leaves perfused with water, and, 2) those allowed to feed on leaves perfused with a BCR-4 PNA solution in water.

The BCR-4 PNA fused to a CPP was synthesized as described herein (see Microinjection Delivery Experimental Design BCR-4 PNA synthesis).

For each leaf perfusion, approximately 1 ml of water (negative control) or a 1 uM BCR-4 PNA solution was injected into a fava bean leaf. The stem of the leaf was then placed in a 1.5 ml Eppendorf that was sealed with parafilm. The leaf stem was then placed into a deep petri dish (Fisher Scientific, Cat #FB0875711) and aphids were applied to the leaves of the plant and allowed to feed. Old leaves were replaced with new, freshly injected leaves every 2-3 days throughout the experiment. For each treatment, 60 aphids were placed onto each leaf. Aphids were monitored daily for survival and dead aphids were removed when they were discovered. In addition, the developmental stage (1st, 2nd, 3rd, 4th, and 5th instar) was determined daily throughout the experiment.

After 5 and 6 days of treatment, DNA was extracted from dead aphids from each treatment group. Briefly, the aphid body surface was sterilized by dipping the aphid into a 6% bleach solution for approximately 5 seconds. Aphids were then rinsed in sterile water and DNA was extracted from each individual aphid using a DNA extraction kit (Qiagen, DNeasy kit) according to manufacturer's instructions. DNA concentration was measured using a nanodrop nucleic acid quantification, and *Buchnera* and aphid DNA copy numbers were measured by qPCR. The primers used for *Buchnera* were Buch_groES_18F (CATGATCGTGTGCTTGTTAAG; SEQ ID NO: 101) and Buch_groES_98R (CTGTTCCTCGAGTCGATTTCC; SEQ ID NO: 102) (Chong and Moran, 2016 PNAS). The primers used for aphid were ApEF1a 107F (CTGATTGTGCCGTGCTT-ATTG; SEQ ID NO: 103) and ApEF1a 246R (TATGGTGGTTCAGTAGAGTCC; SEQ ID NO: 104) (Chong and Moran, 2016 PNAS). qPCR was performed using a qPCR amplification ramp of 1.6 degrees C./s and the following conditions: 1) 95° C. for 10 minutes, 2) 95° C. for 15 seconds, 3) 55° C. for 30 seconds, 4) repeat steps 2-3 40×, 5) 95° C. for 15 seconds, 6) 55° C. for 1 minute, 7) ramp change to 0.15 degrees C./s, 8) 95° C. for 1 second. qPCR data was analyzed using analytic (Thermo Fisher Scientific, QuantStudio Design and Analysis) software.

At 7 post-treatment, RNA was extracted from live aphids and RT-pPCR was done as described above (see Microinjection Delivery Experimental Design) to quantify expression of BCR-4.

Figure 9:
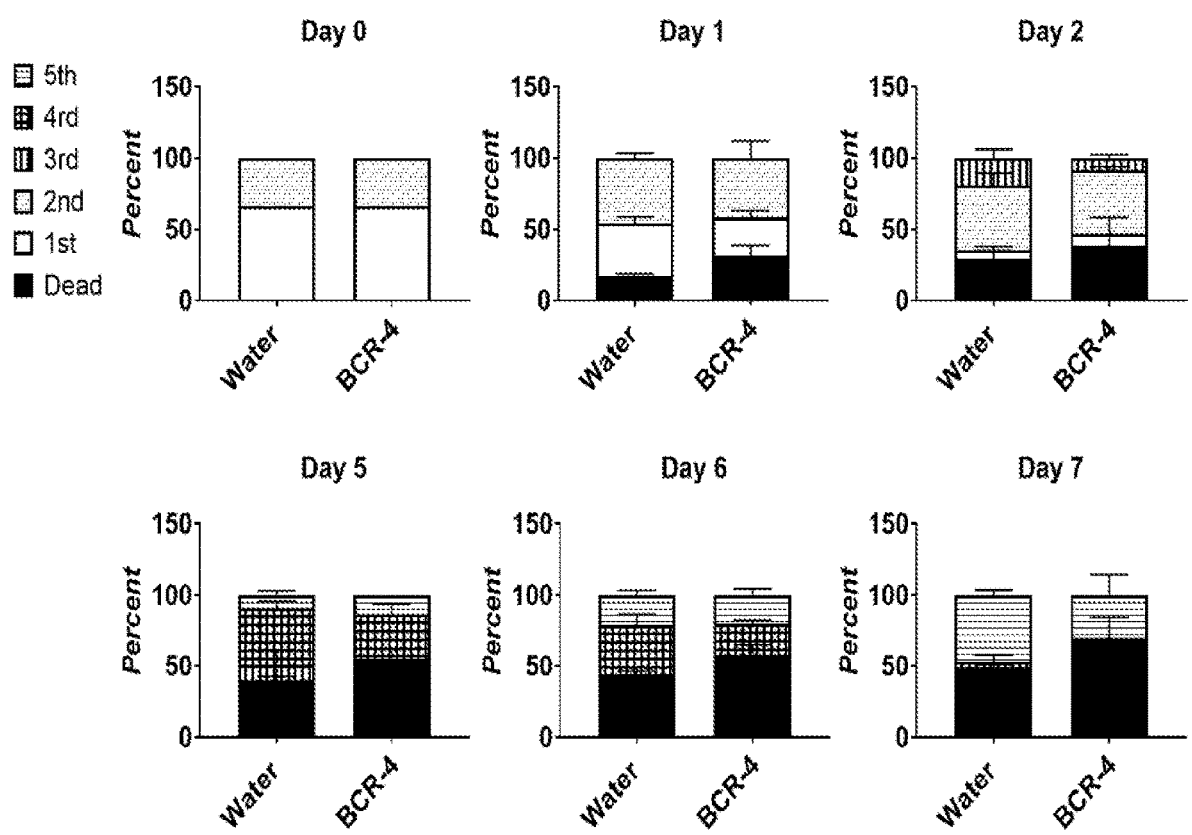
FIG. 9 is a panel of graphs showing treatment with BCR-4 PNA delayed aphid development. First and second instar LSR-1 aphids were placed on leaves perfused with water (negative control) or with a solution of BCR-4 PNA in water and developmental stage was monitored at each indicated time point during the experiment. Shown are the mean percentages of aphids in each group±SD.

Leaf Perfusion Treatment with BCR-4 PNA Delayed Progression of Aphid Development LSR-1 first and second instar aphids were divided into two groups as defined in Leaf Perfusion Experimental Design. Aphids were monitored daily and the number of aphids at each developmental stage was determined. At several time points during the experiment, development was delayed in aphids treated with the BCR-4 PNA. For example, on day 2 post-treatment, approximately 19% of aphids feeding on leaves perfused with water were in the 3rd instar stage (FIG. 9). In contrast, only 8% of aphids feeding on leaves perfused with the PNA to BCR-4 were in the 3rd instar stage. These data indicated that treatment with a PNA to BCR-4 slowed aphid development.

Figure 10:
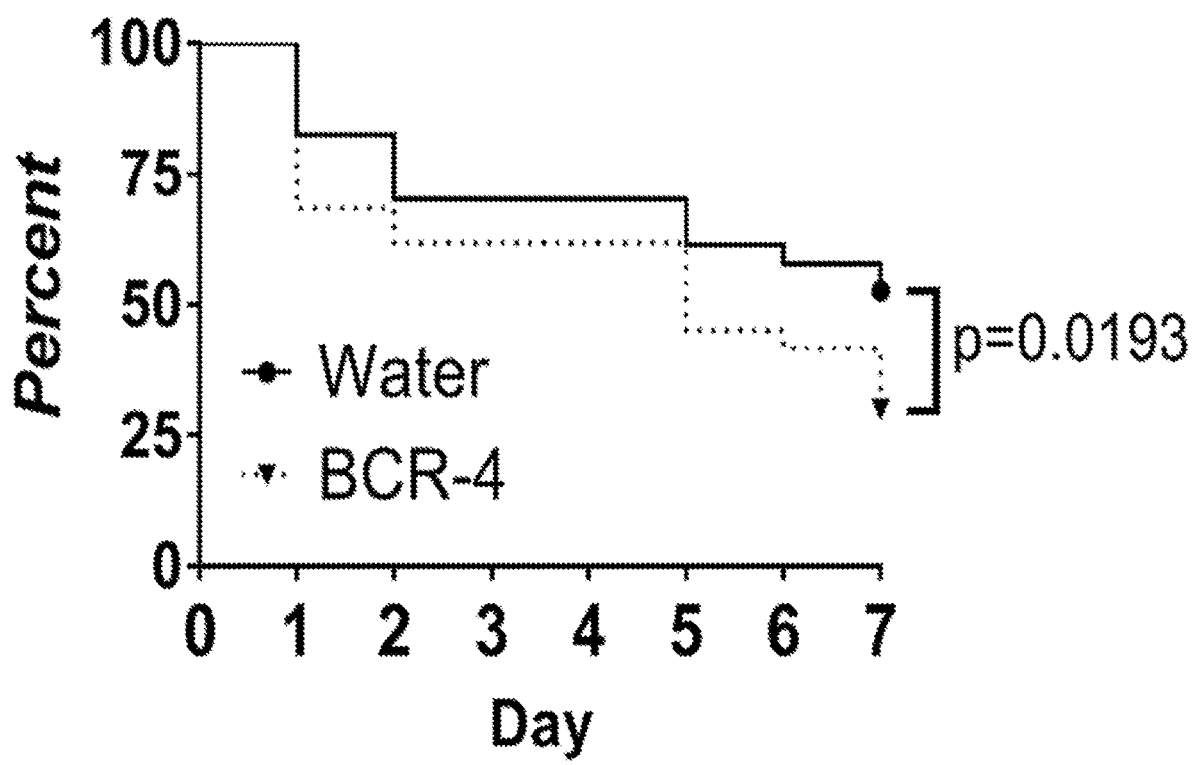
FIG. 10 is a graph showing BCR-4 treatment resulted in increased aphid death. First and second instar LSR-1 aphids were treated with water (control) or with BCR-4 PNA via leaf perfusion and survival was monitored daily during the experiment. N=60 aphids/group. Statistically significant differences were determined using Log-Rank (Mantel Cox) test.

Leaf Perfusion Treatment with BCR-4 PNA Increased Aphid Mortality Survival was also monitored throughout the course of treatment. By 7 days post-treatment, 53% of aphids in the water (control) treatment group remained alive (FIG. 10). In contrast, only 30% of aphids in the PNA BCR-4 treatment group were alive on day 7 (FIG. 10). These data showed that treatment with a PNA to BCR-4 resulted in increased aphid mortality.

Leaf Perfusion Treatment with BCR-4 PNA Increased *Buchnera* Titers in Aphids

Figure 11:
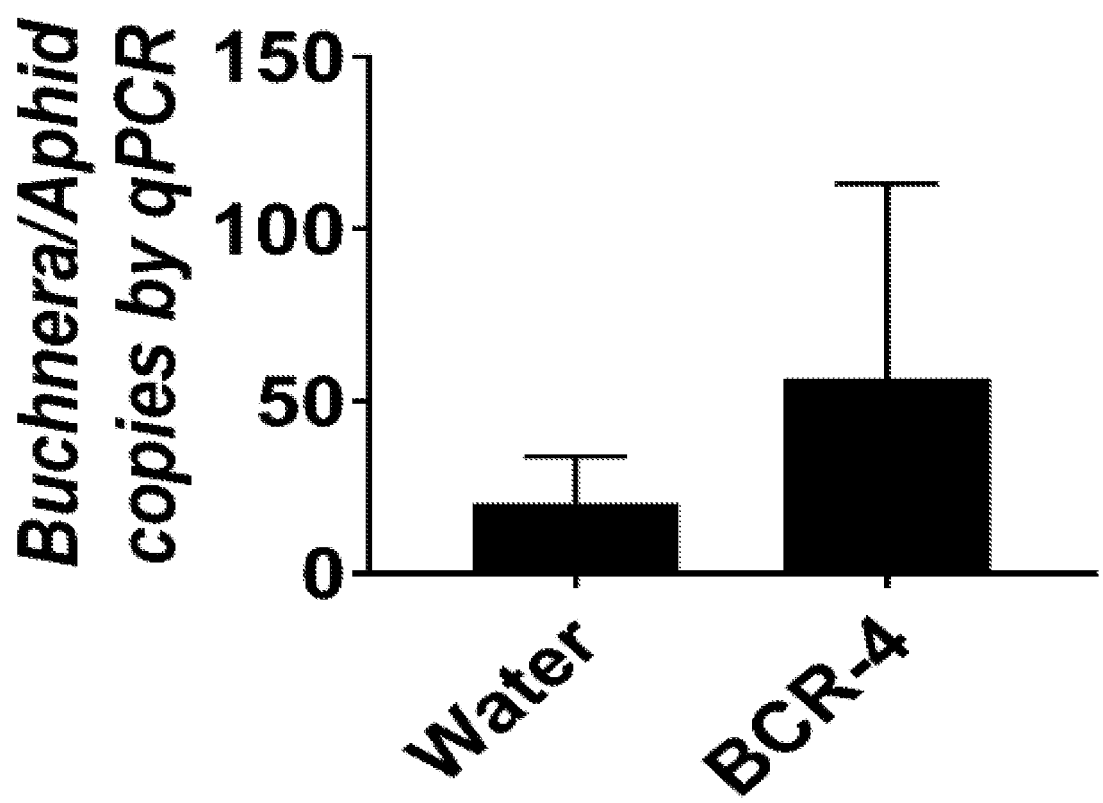
FIG. 11 is a graph showing treatment with BCR-4 PNA delivered via leaf perfusion increased *Buchnera* titers. First and second instar LSR-1 aphids were treated with water (control) or BCR4 PNA via leaf perfusion and dead aphids were collected on days 5 and 6 after treatment. DNA was extracted, and qPCR was performed to determine the number of *Buchnera*/aphid DNA copies. Shown are the mean number of *Buchnera*/aphid DNA copies±SD of 6-7 aphids/group.

To test whether BCR-4 PNA delivered through leaf perfusion, specifically resulted affecting *Buchnera* in aphids, and that this impacted aphid fitness, DNA was extracted from dead aphids in each treatment group after 5 and 6 days post-treatment, and qPCR was performed to determine *Buchnera* tiers in each treatment group. While aphids feeding on leaves perfused with water had a mean ratio of approximately 20 *Buchnera*/aphid copies, aphids feeding on leaves perfused with the PNA to BCR-4 had substantially higher *Buchnera*/aphid copies (approximately 57), see FIG. 11. These data indicate that treatment with a PNA to BCR-4 leads to a misbalance in *Buchnera* titers.

Treatment with a PNA Against BCR-4 Via Leaf Perfusion Knocked Down BCR-4

Figure 12:
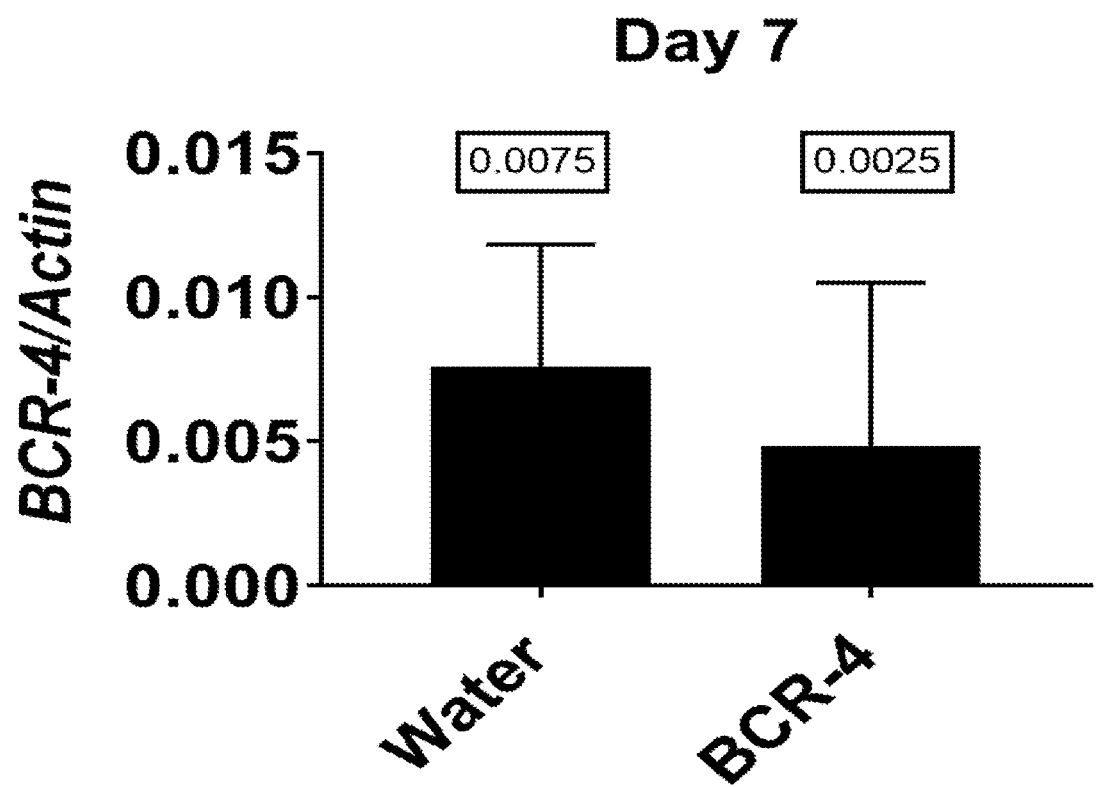
FIG. 12 is a graph showing treatment of aphids with a PNA against BCR-4 via leaf perfusion resulted in a reduction of BCR-4 expression. First and second instar LSR-1 aphids were treated with water (control) or BCR-4 PNA via leaf perfusion and on day 7, RNA was extracted from living aphids and RT-qPCR was performed to quantify expression of BCR-4 relative to actin expression. The number in the box represents the median of the dataset.

To assess whether BCR-4 expression was reduced in aphids feeding on leaves perfused with a PNA to BCR-4, RNA was isolated from living aphids after 7 days of treatment and RT-qPCR was performed. The median transcript levels of BCR-4 in aphids treated with a PNA to BCR-4 were approximately 3-fold lower compared to aphids treated with water alone (FIG. 12), confirming that the PNA to BCR-4 knocked down BCR-4 expression.

Together, these data demonstrated the ability to kill and decrease the development, fecundity, and longevity, (e.g., fitness), of aphids by treating them with a PNA targeting a gene expressed in bacteriocytes (BCR-4) to control the population of endosymbiont *Buchnera*.

Example 19: Aphids Treated with a Solution of dsRNA Against Bacteriocyte Transporters This Example demonstrates that the treatment of aphids with double-stranded RNA (dsRNA) resulted in the knockdown of some essential genes, including glutamine transporter 1 gene (ApGLNT1), which has been identified in the bacteriocytes in the aphid, *Acyrthosiphon pisum*. The glutamine transporter is responsible for glutamine uptake from the aphid hemolymph into the bacteriocytes where the obligate endosymbiont, *Buchnera aphidicola*, is located. The combined biosynthetic capability of the holobiont (*A. pisum* and *Buchnera*) is sufficient for biosynthesis of all twenty protein coding amino acids, including amino acids that aphids alone cannot synthesize. Blocking the glutamine uptake by deactivating or silencing (e.g. RNAi by dsRNA) the glutamine transporter negatively affected amino acid and protein synthesis in the bacteriocytes and in the entire aphid, thereby negatively affecting their fitness.

Therapeutic Design

5th instar LSR-1 aphids were microinjected. The injection solutions were either dd-water (negative control) or dsRNA diluted in dd-water at various concentrations (8 or 60 ng/aphid; see below).

Aphid Rearing and Maintenance

Aphids LSR-1 (which harbor only *Buchnera*), *A. pisum* were grown on fava bean plants (Vroma *Vicia faba* from Johnny's Selected Seeds) in a climate-controlled incubator (16 h light/8 h dark photoperiod; 60±5% RH; 25±2° C.). Prior to being used for aphid rearing, fava bean plants were grown in potting soil at 24° C. with 16 h of light and 8 h of darkness. To limit maternal effects or health differences between plants, 5-10 adults from different plants were distributed among 10 two-week-old plants, and allowed to multiply to high density for 5-7 days. For experiments, fifth instar aphids were collected from healthy plants and divided into 2 different treatment groups: 1) water (negative control) or 2) dsRNA against ApGLNT1 (at the concentrations indicated herein).

Microinjection Delivery Experimental Design

Microinjection was performed using NanoJet III Auto-Nanoliter Injector with an in-house pulled borosilicate needle (Drummond Scientific; Cat #3-000-203-G/XL). Aphids were transferred using a paint brush to a tubing system connected to vacuum which held the aphid in place during the microinjection. The injection site was at the ventral thorax of the aphid. The injection volume was 20 nl for adult aphids at a rate of 2 nl/sec. Each treatment group had approximately the same number of individuals injected from each of the collection plants.

After injection, aphids were released into a petri dish onto a fava bean leaves that had stems in an Eppendorf tube filled with 1 ml water. Aphid survival was monitored daily, and dead aphids were removed when they were found. The number of offspring from each group was counted and fecundity was measured as the number of offspring (F1's) produced per aphid at each time point.

In select experiments, development was measured in groups of offspring from each treatment group by noting the developmental stage of offspring each day ($1^{st}$, $2^{nd}$, $3^{rd}$, $4^{th}$, and $5^{th}$ instar). Development was also measured by imaging aphids at 4 days post-collection and determining their area. The template for synthesizing dsRNAs was the cDNA reverse-transcribed from the mRNA. RNA was extracted from one 5th instar *A. pisum* (LSR-1 strain) and was quantified by Nanodrop (Thermo fisher scientific). ~100 μg of total RNA was added as template into the reverse-transcription reaction using Superscript IV kit (Thermo Fisher Scientific) following manufacturer's protocol.

To amplify the templates for the dsRNAs, the cDNA was diluted 100-fold and used in the following PCRs. The PCR reactions (25 μl final volume) contain 12.5 μL of Go Taq Green 2× mix (Promega), 0.2 μl of forward primer (Table 12), 0.2 μl of reverse primer (Table 12), and 12.1 μl of 100-fold diluted cDNA. PCR reactions were performed using following conditions: 1) 95° C. for 2 minutes, 2) 95° C. for 20 seconds, 3) 55° C. for 15 seconds, 4) 72° C. for 30 seconds, 5) repeat steps 2-4 35×, 6) 72° C. for 5 minutes. The sizes of PCR amplified products were verified by electrophoresis on 1.5% agarose and the expected-size bands were cut and purified by QIAquick DNA purification kit (Qiagen). The dsRNAs were synthesized in vitro using T7 MEGA-script kit (Ambion, Thermo Fisher Scientific; Cat #AM1334) following manufacturer's protocol. The concentration of dsRNA was measured by Nanodrop (Thermo Fisher Scientific).

TABLE 12

Accession numbers and primers for dsRNA syntheses.

| Gene | gene ID | Forward primer | Reverse primer |
|---|---|---|---|
| ApGLNT1 | ACYPI001018 | TAATACGACTCACTATAGGGCAATTACAAAGGACGGCAG (SEQ ID NO: 111) | TAATACGACTCACTATAGGGCCGCTCTAGGAACACCGTAT (SEQ ID NO: 112) |

At the indicated time point post-treatment, DNA and/or RNA was extracted from aphids in each treatment group. Briefly, the aphid body surface was sterilized by dipping the aphid into a 6% bleach solution for approximately 5 seconds. Aphids were then rinsed in sterile water and total DNA or RNA was extracted from each individual aphid using either the DNA or RNA extraction kit (Qiagen, DNeasy or miRNeasy kit, respectively) according to manufacturer's instructions. DNA and RNA concentrations were measured using a nanodrop nucleic acid quantification. *Buchnera* and aphid DNA copy numbers were measured by qPCR. The primers used for *Buchnera* were Buch_groES_18F (CATGATCGTGTGCTTGTTAAG; SEQ ID NO: 101) and Buch_groES_98R (CTGTTCCTCGAGTCGATTTCC; SEQ ID NO: 102) (Chong and Moran, 2016 PNAS). The primers used for aphid were ApEF1a 107F (CTGATTGTGCCGTGCTTATTG; SEQ ID NO: 103) and ApEF1a 246R (TATGGTGGTTCAGTAGAGTCC; SEQ ID NO: 104) (Chong and Moran, 2016 PNAS). qPCR was performed using a qPCR amplification ramp of 1.6 degrees C./s and the following conditions: 1) 95° C. for 10 minutes, 2) 95° C. for 15 seconds, 3) 55° C. for 30 seconds, 4) repeat steps 2-3 40×, 5) 95° C. for 15 seconds, 6) 55° C. for 1 minute, 7) ramp change to 0.15 degrees C./s, 8) 95° C. for 1 second. qPCR data was analyzed using analytic (Thermo Fisher Scientific, QuantStudio Design and Analysis) software. ApGLNT1 relative expression was measured by RT-qPCR. The primers used for ApGLNT1 were ACYPI001018-fwd (CCTGAAATCGACGGGGTCC; SEQ ID NO: 113) and ACYPI001018-rev (AGATCGGCAACATCTGTTCGT; SEQ ID NO: 114) (both designed by NCBI pick primers). The internal reference gene was Actin (housekeeping gene). The primers used for Actin were Actin-F (GATCAGCAGCCACACACAAG; SEQ ID NO: 109) and Actin-R (TTTGAACCGGTTTACGACGA; SEQ ID NO: 110) RT-qPCR was performed using a qPCR amplification ramp of 1.6 degrees C./s and the following conditions: 1) 48° C. for 30 min, 2) 95° C. for 10 minutes, 3) 95° C. for 15 seconds, 4) 60° C. for 1 minute, 5) repeat steps 3-4 40×, 6) 95° C. for 15 seconds, 7) 60° C. for 1 minute, 8) ramp change to 0.15 degrees C./s, 9) 95° C. for 1 second. RT-qPCR data was analyzed using analytic (Thermo Fisher Scientific, QuantStudio Design and Analysis) software.

Figure 13:
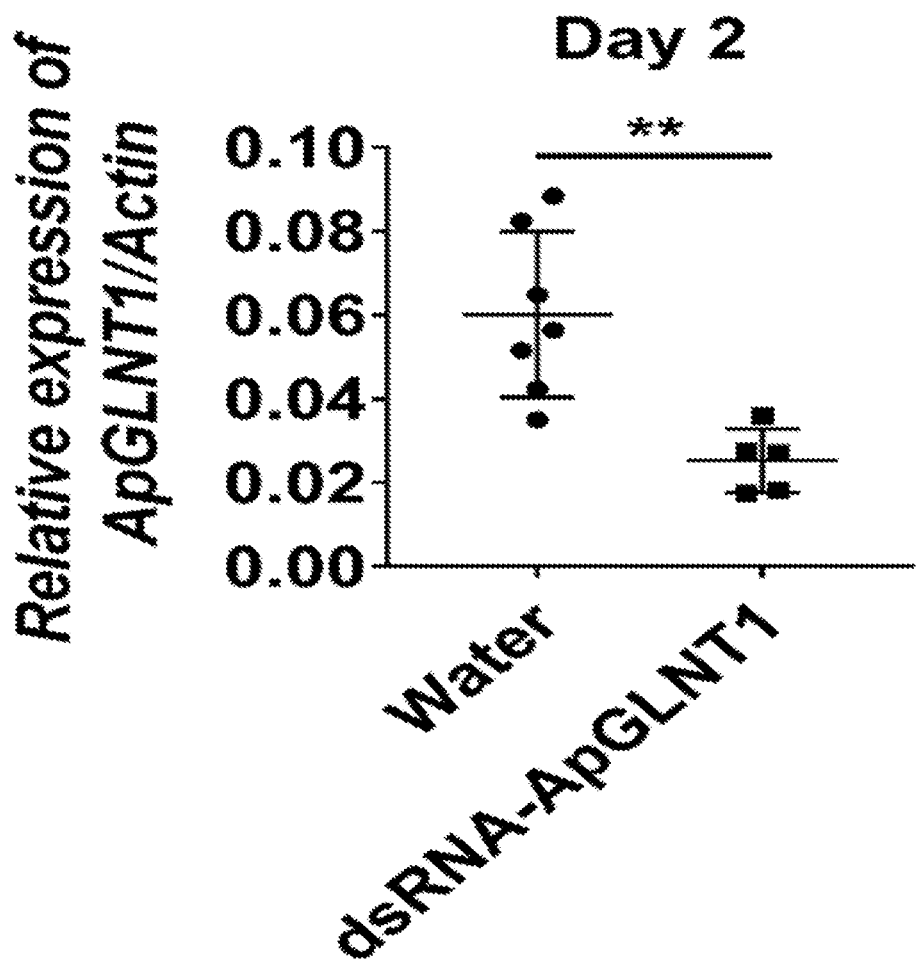
FIG. 13 is a graph showing treatment with dsRNA-ApGLNT1 knocked down the expression of ApGLNT1. Fifth instar *A. pisum* aphids were injected with water or dsRNA-ApGLNT1 in water. At 2 days post-treatment, total RNA was extracted and RT-qPCR was performed to determine ApGLNT1 gene relative expression (Actin as internal reference gene). Shown is the mean ratio of relative expression of ApGLNT1/Actin±SD of 5-7 aphids/group. Statistically significant differences were determined by Student's T-test (**, p<0.01).

Microinjection with dsRNA Knocked-Down the Bacteriocyte Transporter Gene Expression in Aphids The preliminary experiment assessed whether injecting dsRNA into aphids would result in decreased gene expression. Adult aphids were injected with 8 ng dsRNA or water (as a negative control). On two days post-injection, RNA was extracted from the remaining aphids in each treatment group and RT-qPCR was performed to quantify expression of ApGLNT1. Aphids microinjected with the negative control solution (water) had high relative expression of the ApGLNT1 gene. In contrast, aphid adults microinjected with the dsRNA of ApGLNT1 had a drastic, and significant, reduction of ApGLNT1 gene expression (FIG. 13), indicating that dsRNA microinjection treatment decreased expression of ApGLNT1 gene.

Microinjection of dsRNA-ApGLNT1 Resulted in Increased Aphid Mortality

Figure 14:
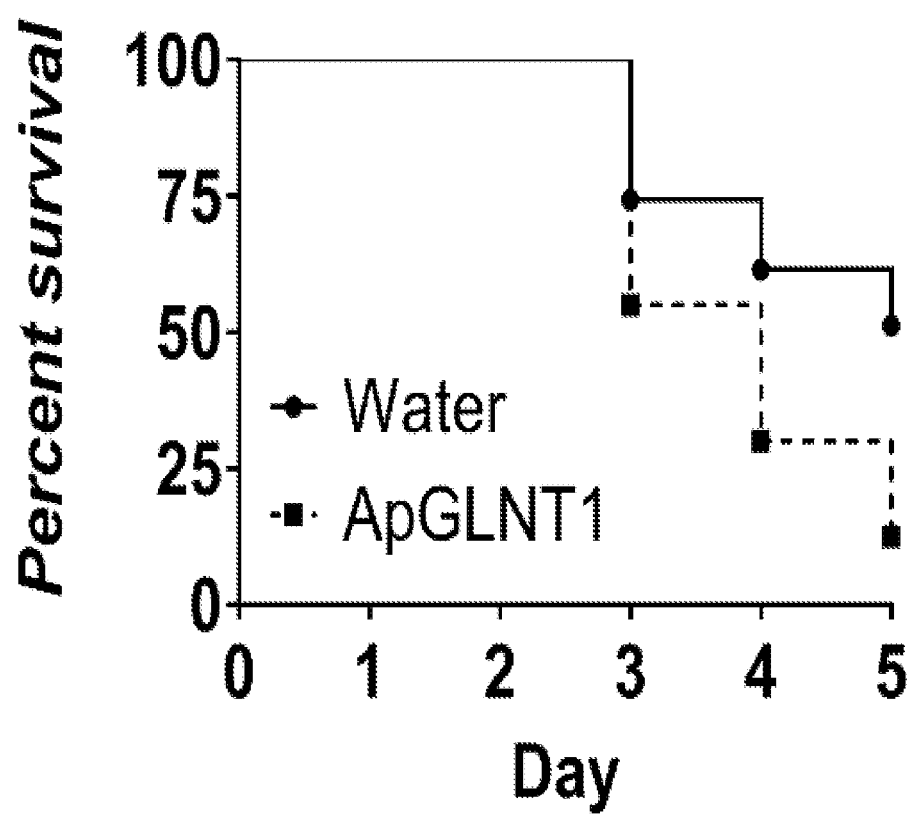
FIG. 14 is a graph showing treatment with dsRNA-ApGLNT1 increased aphid mortality. LSR-1 *A. pisum* aphids were injected with water or dsRNA-ApGLNT1 in water and survival was monitored over the course of the experiment. N=40 aphids/group. A statistically significant difference was identified between the two groups as determined using a Log-Rank (Mantel Cox) test.

To assess the effect of dsRNA-ApGLNT1 microinjection on insect fitness, LSR-1 fifth instar aphids were injected with 60 ng dsRNA and survival was monitored for 5 days. At 3 days post-injection, approximately 72% of water-injected aphids were alive (FIG. 14). In contrast, only 52% of dsRNA-injected aphids were alive (FIG. 14). At days 4 and 5 post-injection, there were significantly more aphids alive in the water-injected group compared to the dsRNA-injected group. Approximately 62% and 51% of water-injected aphids were alive on days 4 and 5, respectively, whereas only 30% and 12.5% of dsRNA-injected aphids were alive on day 4 and 5, respectively (FIG. 14). These data indicated that dsRNA against ApGLNT1 significantly (p=0.0004) increased aphid mortality compared to water-injected controls.

Microinjection of dsRNA-ApGLNT1 Resulted in Decreased Buchnera Titers

Figure 15:
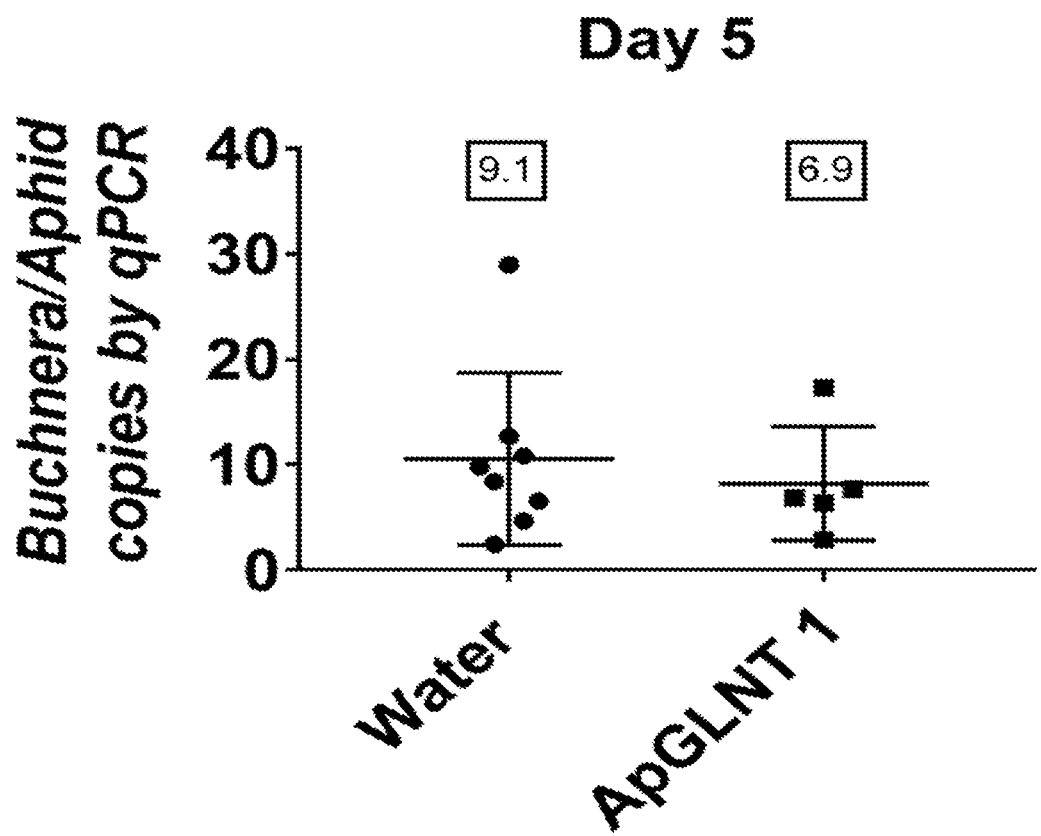
FIG. 15 is a graph showing treatment with dsRNA-ApGLNT1 resulted in decreased *Buchnera* titers. LSR-1 *A. pisum* aphids were injected with water or dsRNA-ApGLNT1 in water, DNA was extracted from aphids at 5 days post-injection, and qPCR was performed to quantify *Buchnera*. Shown are the mean copies of *Buchnera*/aphid DNA±SD. Each dot represents an individual aphid. The number in the box above each data set represents the median of the group.

To test whether the decrease in survival and fitness was due to decreased number of endosymbionts, DNA was extracted from living aphids at 5 days post-injection and qPCR was performed to quantify the amount of Buchnera present in the aphid. Aphids microinjected with water had mean ratios of approximately 11 Buchnera/aphid copies (FIG. 15). In contrast, Buchnera/aphid copies was approximately 1.28 times lower in aphids injected with the dsRNA against the ApGLNT1 (FIG. 15). These data showed that microinjection of dsRNA-ApGLNT1 resulted in decreased Buchnera titers which led to decreased aphid fitness.

Development was Delayed in Offspring of Aphids Microinjected with dsRNA-ApGLNT1

Figure 16A:
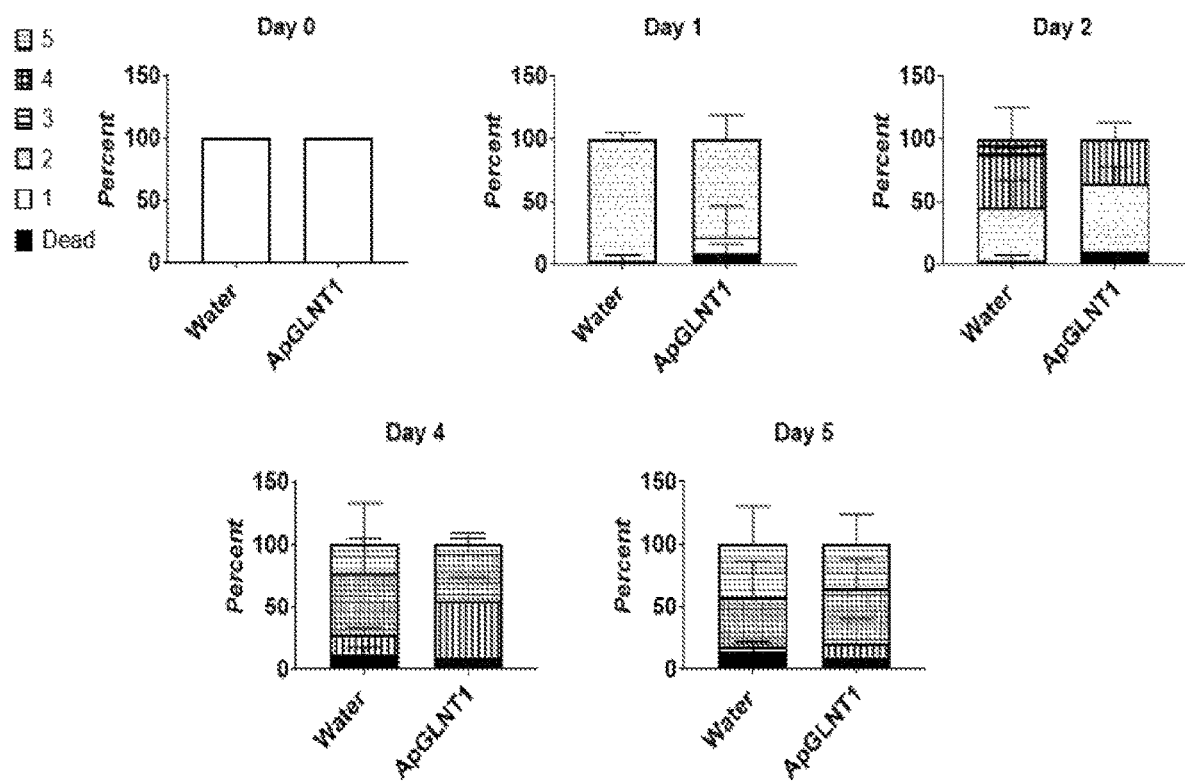
FIGS. 16A and 16B are a panel of graphs showing offspring from aphids microinjected with dsRNA-ApGLNT1 displayed delayed development.
Figure 16B:
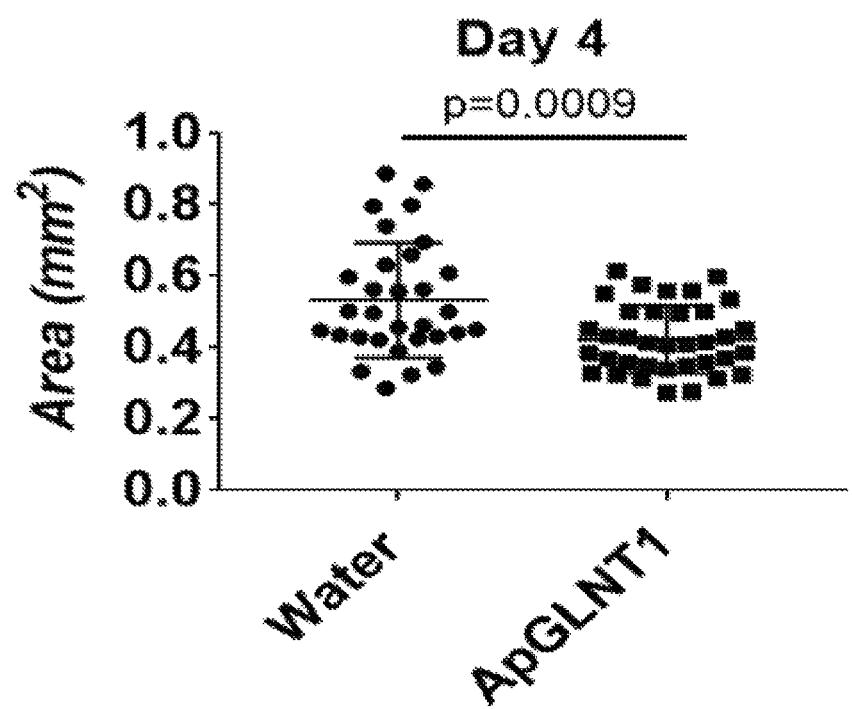

On day 3 post-injection, 40 offspring (first instars) from each treatment group were transferred to their own artificial feeding system (a petri dish containing a fava bean leaf stem put into a 1.5 ml Eppendorf tube sealed with parafilm) and development was monitored over time. Overall, development was delayed in offspring taken from adults injected with dsRNA-ApGLNT1. By day 4 post offspring transfer, approximately 22.5% of offspring from water-injected aphids began reaching the 5th instar stage (FIG. 4A). In contrast, on day 4, only 7.5% of offspring from adults injected with dsRNA-ApGLNT1 reached the 5th instar stage (FIG. 16A). Additionally, aphid areas were measured on day 4 by imaging each aphid in each group. While the average size of offspring from water-injected adults was 0.55 mm$^2$, offspring dsRNA-ApGLNT1-injected adults were significantly smaller (p=0.009) and averaged 0.4 mm$^2$ (FIG. 16B). These data indicated that treatment of adults with dsRNA-ApGLNT1 resulted in offspring with severely delayed development.

Example 20: Production of Transgenic Plants Expressing dsRNAs that Target Multiple Pathways to Destabilize Insect-Symbiont Homeostasis Through Treatment of Aphids with the Transgenic Plants This Example demonstrates the ability to genetically modify Nicotiana tabacum to produce dsRNA for delivery to aphids to affect insect-symbiont homeostasis. Genetic constructs that stably express dsRNA in Nicotiana tabacum are delivered to the plant using transgenic Agrobacterium tumefaciens that will carry the plasmid to the plant.

Experimental Design

Several genes will be targeted for knockdown in multiple pathways that are critical for the symbiotic relationship between the aphids and their obligate endosymbiotic bacteria, Buchnera. Specifically, the glutamine transporter of the bacteriocytes (GlnT1), ultrabithorax (Ubx), beta alanine synthase (bAS), and cactus (Cact) are targeted. GlnT1 is a glutamine transporter that is used for the import of glutamine into the bacteriocytes, and the downstream products of glutamine are essential for the synthesis of essential amino acids by Buchnera. Ubx is a gene involved in both the general development of the aphids, as well as the formation of the bacteriocytes which will house Buchnera. bAS is an aphid gene required to synthesize beta Alanine which is a precursor for the synthesis of vitamin B5 by Buchnera. Cact is the negative regulator of the Toll pathway, which is the primary immunity pathway in aphids. Lowering the levels of Cact could upregulate the systemic immune responses leading to the dysregulation of the Buchnera levels.

Figure 17:
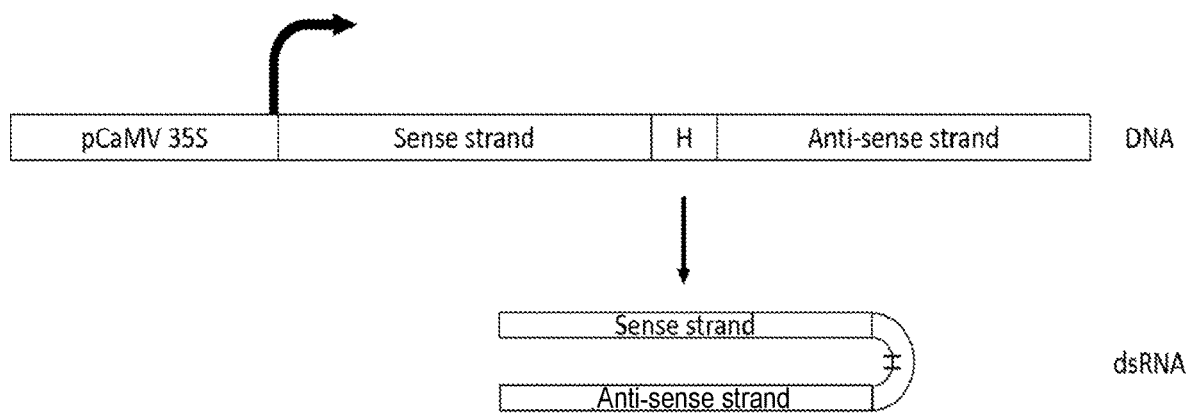
FIG. 17 is an illustration showing the dsRNA expression cassette. pCaMV 35S promoter is placed upstream of the dsRNA expressing sequence. The sense and the antisense strands of a region of the target aphid gene are placed in tandem with a small spacer which will act as the hairpin loop. Once expressed, the RNA formed will assume a double stranded configuration due to the complementarity of the sequence.

Generating a Plasmid Containing dsRNA Expression Cassette:

A shuttle vector between E. coli and A. tumefaciens will be used to carry the dsRNA expression cassette, which includes the cauliflower mosaic virus 35S promoter (pCaMV 35S) upstream of the dsRNA expressing sequence. The dsRNA expressing sequence includes the sense sequence followed by the antisense sequence of a region of the target aphid gene connected by a small hairpin loop sequence (FIG. 17).

Figure 18:
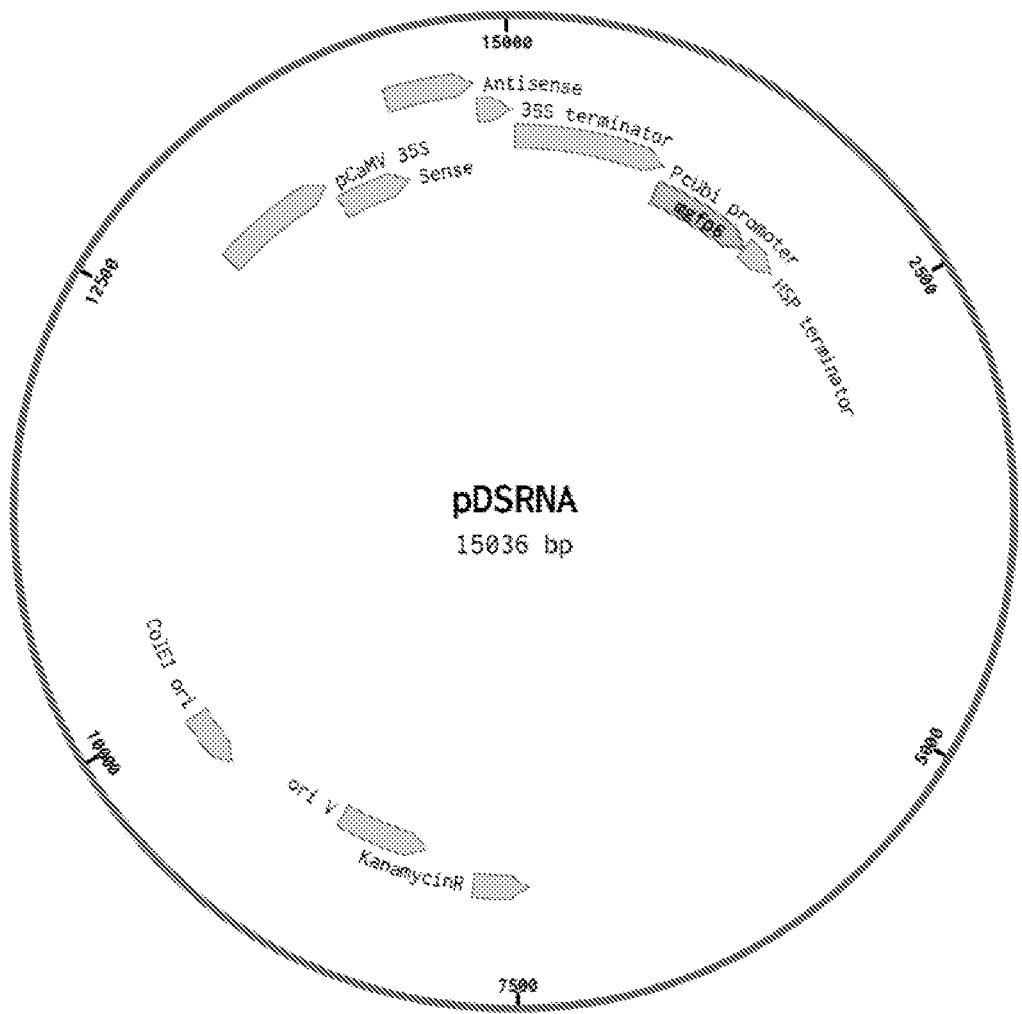
FIG. 18 is an illustration of the shuttle vector for the constructs for expressing dsRNA in *N. tabacum*. The plasmid includes origins of replications compatible with *E. coli* and *A. tumefaciens*, kanamycin and gentamycin resistance markers, green fluorescence expression cassette under a parsley ubiquitin promoter, and finally the dsRNA expression cassette driven by the pCaMV 35S.

The dsRNA expression cassette will then be placed in a shuttle vector for E. coli and A. tumefaciens (FIG. 18). The plasmid will also contain both Kanamycin and Gentamycin resistance cassettes which can be used as selection markers. A transcription terminator will be placed after the dsRNA expression transcript to eliminate runaway transcription.

The dsRNA expressing sequences for various genes (GlnT1, Ubx, bAS, and Cact) can be introduced into the vector via Gibson assembly. First, the sense and the antisense amplicons with overhangs that match the neighboring regions in the plasmid will be generated using the appropriate primers in a PCR. Specifically, the left overhang of the sense strand will have region of homology (~30 bp) to the pCaMV 35S, and the right overhang of the antisense strand will have region of homology (~30 bp) to the 35S terminator region. The right overhang of the sense strand and the left overhang of the antisense strands will have overlapping pieces of each other with the inclusion of a small hairpin region (acacgt, SEQ ID NO: 115). The primer sequences to produce the amplicons are shown in Table 13.

TABLE 13

List of primers to generate amplicons for the Gibson assembly to generate hairpin dsRNA sequences against A. pisum genes. Each target gene's region will be amplified as either sense or antisense with flanking regions that are homologous to the plasmid backbone for Gibson assembly.

| Primer name | Primer sequence |
| --- | --- |
| ApGlnT1 sense fwd | ctacaaatctatctctcctaggCAATTACA AAAGGACGGCAG (SEQ ID NO: 116) |
| ApGlnT1 sense rev | ttacaaactgggaagaacctggagacgtgC CGCTCTAGGAACACCGTAT (SEQ ID NO: 117) |
| ApGlnT1 antisense fwd | ttacaaactgggaagaacctggaacacgtc CCGCTCTAGGAACACCGTAT (SEQ ID NO: 118) |
| ApGlnT1 antisense rev | agaaactagagcttgtcgatcgttaattaa CAATTACAAAAGGACGGCAG (SEQ ID NO: 119) |
| ApUbx sense fwd | ctacaaatctatctctcctaggTTTTACCG TCACAGGCATCA (SEQ ID NO: 120) |
| ApUbx sense rev | acgagtgctgaagtccctagccagacgtgt TCGTGCTCGTTACCAAATGT (SEQ ID NO: 121) |
| ApUbx antisense fwd | acgagtgctgaagtccctagccaacacgtc TCGTGCTCGTTACCAAATGT (SEQ ID NO: 122) |
| ApUbx antisense rev | agaaactagagcttgtcgatcgttaattaa TTTTACCGTCACAGGCATCA (SEQ ID NO: 123) |
| ApbAs sense fwd | ctacaaatctatctctcctaggGGTGTCAC CATCGAGACGTT (SEQ ID NO: 124) |
| ApbAs sense rev | aaaaaccacatacctcgagtggggacgtgt CATGACTCTGGCAGTTGAAGTT (SEQ ID NO: 125) |
| ApbAs antisense fwd | aaaaaccacatacctcgagtgggacacgtc CATGACTCTGGCAGTTGAAGTT (SEQ ID NO: 126) |
| ApbAs antisense rev | agaaactagagcttgtcgatcgttaattaa GGTGTCACCATCGAGACGTT (SEQ ID NO: 127) |
| Apcactus sense fwd | ctacaaatctatctctcctaggGTCGTCGT CGTCGTCGTAGT (SEQ ID NO: 128) |
| Apcactus sense rev | accaaaattgccttggacagtgggacgtgt GCACGCACGGAAAACATTTA (SEQ ID NO: 129) |
| Apcactus antisense fwd | accaaaattgccttggacagtggacacgtc GCACGCACGGAAAACATTTA (SEQ ID NO: 130) |
| Apcactus antisense rev | agaaactagagcttgtcgatcgttaattaa GTCGTCGTCGTCGTCGTAGT (SEQ ID NO: 131) |

TABLE 14

List of primers to generate amplicons for the Gibson assembly to generate hairpin dsRNA sequences against Myzus persicae genes. Each target gene's region will be amplified as either sense or antisense with flanking regions that are homologous to the plasmid backbone for Gibson assembly.

| Primer name | Primer sequence |
| --- | --- |
| MpGlnT1 sense fwd | ctacaaatctatctctcctaggTTGGAA GGGATTGGTGTTGTAATGCC (SEQ ID NO: 132) |
| MpGlnT1 sense rev | ttacaaactgggaagaacctggagacgt gTTCCAGGTTCTTCCCAGTTTGTAACTA GATCG (SEQ ID NO: 133) |
| MpGlnT1 antisense fwd | ttacaaactgggaagaacctggaacacg tcTCCAGGTTCTTCCCAGTTTGTAACTA GATCG (SEQ ID NO: 134) |
| MpGlnT1 antisense rev | agaaactagagcttgtcgatcgttaatt aaTTGGAAGGGATTGGTGTTGTAATGCC (SEQ ID NO: 135) |
| MpUbx sense fwd | ctacaaatctatctctcctaggTCGTGT GGAGCAAGTACAGCG (SEQ ID NO: 136) |
| MpUbx sense rev | acgagtgctgaagtccctagccagacgt gtTGGCTAGGGACTTCAGCACTCG (SEQ ID NO: 137) |
| MpUbx antisense fwd | acgagtgctgaagtccctagccaacacg tcTGGCTAGGGACTTCAGCACTCG (SEQ ID NO: 138) |
| MpUbx antisense rev | agaaactagagcttgtcgatcgttaatt aaTCGTGTGGAGCAAGTACAGCGG (SEQ ID NO: 139) |
| MpbAs sense fwd | ctacaaatctatctctcctaggGAGGAA CTCCAACTGCCAGAGTCATG (SEQ ID NO: 140) |
| MpbAs sense rev | aaaaaccacatacctcgagtggggacgt gtCCCACTCGAGGTATGTGGTTTTTCCT ATG (SEQ ID NO: 141) |
| MpbAs antisense fwd | aaaaaccacatacctcgagtgggacacg tcCCCACTCGAGGTATGTGGTTTTTCC (SEQ ID NO: 142) |
| MpbAs antisense rev | agaaactagagcttgtcgatcgttaatt aaGAGGAACTCCAACTGCCAGAGTCATG (SEQ ID NO: 143) |
| Mpcactus sense fwd | ctacaaatctatctctcctaggTACACC CATTGTGTGCACCTGAGTAC (SEQ ID NO: 144) |
| Mpcactus sense rev | accaaaattgccttggacagtgggacgt gtCCACTGTCCAAGGCAATTTTGGTTG (SEQ ID NO: 145) |
| Mpcactus antisense fwd | accaaaattgccttggacagtggacacg tcCCACTGTCCAAGGCAATTTTGGTTG (SEQ ID NO: 146) |
| Mpcactus antisense rev | agaaactagagcttgtcgatcgttaatt aaTACACCCATTGTGTGCACCTGAGTAC (SEQ ID NO: 147) |

Once the sense and the antisense amplicons are generated, the plasmid will be double digested to generate overhangs at the end of the pCaMV 35S and the start of the 35S terminator. The digested plasmid, sense, and the antisense amplicons will be assembled together in a Gibson assembly using Gibson assembly kits (such as SGI Gibson Assembly kit). *E. coli* (DH5α, electrocompetent cells) will then be transformed with the plasmid and grown on LB plates containing 50 mg/ml kanamycin. Resistant colonies will be used to harvest the plasmid containing the dsRNA expression cassette. The plasmids will be named pGlnT1dsRNA, pUbxdsRNA, pbASdsRNA, and pCactdsRNA for each of the four different inserts. These plasmids will be used to transform *A. tumefaciens* via electroporation. Upon selection on LB medium containing Kanamycin (50 mg/ml) and Gentamycin (50 mg/ml), resistant colonies will be isolated and maintained on selection plates.

Transformed *A. tumefaciens* Infiltrated into *N. tabacum*:

Transformed *A. tumefaciens* were grown overnight in LB medium with the selection antibiotics until the OD 600 was 0.6. The cells were pelleted down, resuspended in infiltration medium (10 mM MES, 150 μM acetosyringone, and 10 mM MgCl2, pH 5.5), and adjusted to an OD600 of 0.6. The cells were incubated at room temperature for 2-4 hours. The cell suspension was infiltrated into healthy *N. tabacum* leaves. The infiltration process was achieved by placing the blunt open end of a 1 ml syringe on the underside of the leaf and forcing the cell suspension into the leaf. The infiltrated areas were easily distinguished from the untreated areas and were clearly demarcated using a marker. The plants were then covered to created high moisture environment for 24 h.

Figure 19:
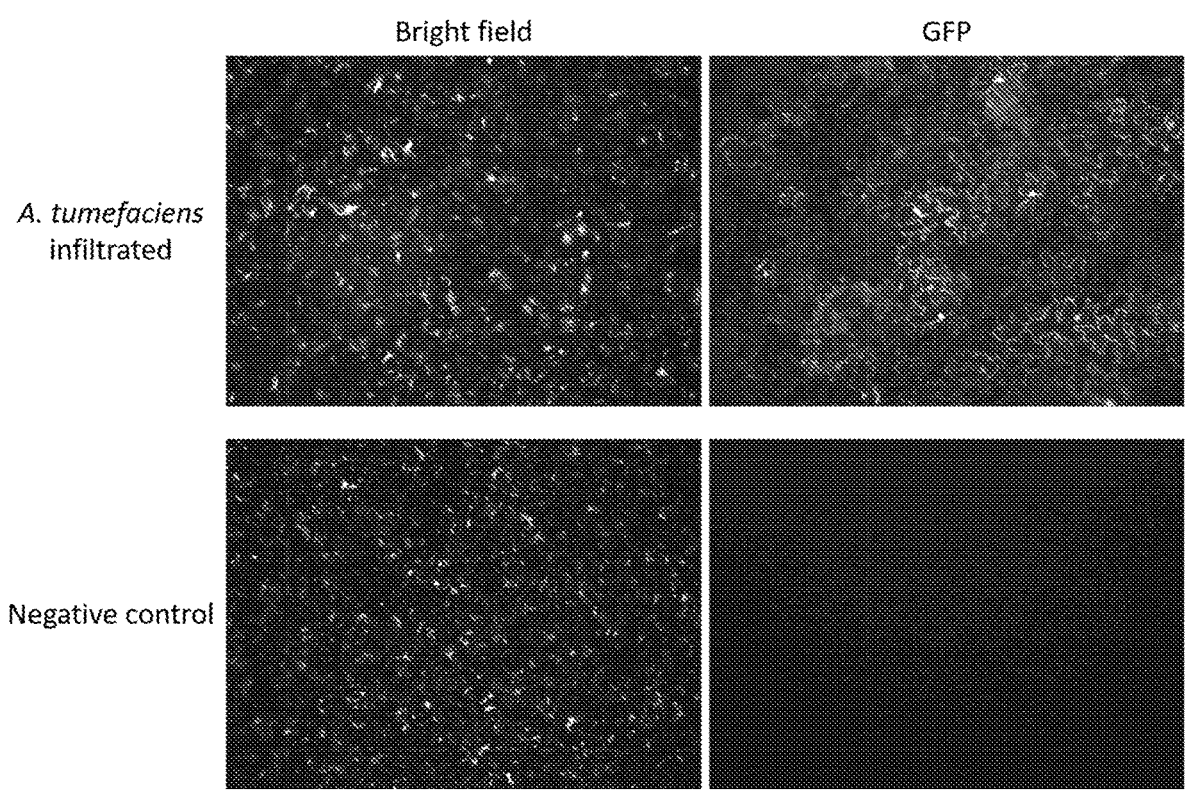
FIG. 19 is a panel of images showing GFP expression in *N. tabacum* plant infiltrated by *A. tumefaciens*. The top panels are *N. tabacum* infiltrated with *A. tumefaciens* containing a plasmid that can constitutively drive the expression of GFP in *N. tabacum* (Top left is brightfield, and top right is green channel). The bottom panels are negative control leaves not infiltrated by *A. tumefaciens*.

The leaves expressed green fluorescent protein and were visualized under an epi fluorescence microscope after 1-2 days, see FIG. 19. The genetic material that was transferred to the plant by the *A. tumefaciens* contained a green fluorescence (GFP) expression cassette that was driven by an ubiquitin promoter that was active in *N. tabacum*. The expression of GFP will be used a proxy for the expression of dsRNA.

Generating a Stable Clone of *N. tabacum* Expressing dsRNA

The infiltrated leaves that show expression of GFP will be isolated, and the regions of the leaf near the midrib that express GFP very strongly will be cutout. The leaf disks will then be thoroughly sterilized using a sterilization solution (2% hypochlorite, 0.01% tween 20) for 10 min by agitation. The sterile leaf disks will be placed on petri dishes containing shooting medium (2.15 g/l Murashige and Skoog salts (without IAA, kinetin or sucrose), 0.8% (w/v) agar, 3.0% (w/v) sucrose, 0.1 mg/l indole butyric acid, 0.8 mg/l 6-benzylaminopurine, 0.1 mg/l Carbenicillin, 0.2 mg/l Ticarcillin/Clavulanic acid and suitable selection for the binary vector carrying your FP fusion construct) at 25° C., 16 h:8 h light:dark cycle till shoots appear. The new shoots will then be transplanted into plates containing rooting medium (2.15 g/l Murashige and Skoog salts, 0.8% (w/v) agar, 3.0% (w/v) sucrose, 0.5 mg/l indole butyric acid, 0.1 mg/l carbenicillin, 0.2 mg/l Ticarcillin/Clavulanic acid) at 25° C., 16 h:8 h light:dark cycle till roots appear. These new plants will be transferred to phytatrays to develop larger roots so that they can be transferred to soil. The expression of the GFP will be tested in all new clones to ensure stable expression.

Treating Aphids with dsRNA by Rearing them on *N. tabacum* Expressing dsRNA

Aphids will be grown on 10-week-old *N. tabacum* plants in a climate controlled incubator (16 h:8 h light:dark cycle, 60% humidity, 25° C.). To limit maternal effects or health differences between plants, 5-10 adults from different plants will be distributed among 10 two-week-old plants and allowed to multiply to high density for 5-7 days. For experiments, first and second instar aphids will be collected from healthy plants and divided into two different treatment groups: 1) those allowed to feed on leaves that express the dsRNA, and 2) those allowed to feed on control leaves that do no express the dsRNA.

For each feeding experiment, leaves will be taken from the plant and placed in a 1.5 ml Eppendorf sealed with parafilm. The leaf stem will be placed into a deep petri dish (Fisher Scientific, Cat #FB0875711) and aphids will be applied to the leaves of the plant and allowed to feed. Old leaves will be replaced with new, freshly injected leaves every 2-3 days throughout the experiment. For each treatment, 60 aphids will be placed onto each leaf. Aphids will be monitored daily for survival and dead aphids will be removed when they were discovered. In addition, the developmental stage (1st, 2nd, 3rd, 4th, and 5th instar) will be determined daily throughout the experiment.

After 5 and 6 days of treatment, DNA will be extracted from dead aphids from each treatment group. Briefly, the aphid body surface will be sterilized by dipping the aphid into a 6% bleach solution for approximately 5 seconds. Aphids will then be rinsed in sterile water and DNA will be extracted from each individual aphid using a DNA extraction kit (Qiagen, DNeasy kit) according to manufacturer's instructions. DNA concentration will be measured using a nanodrop nucleic acid quantification, and *Buchnera* and aphid DNA copy numbers will be measured by qPCR. The primers that will be used for *Buchnera* are Buch_groES_18F (CATGATCGTGTGCTTGTTAAG; SEQ ID NO: 101) and Buch_groES_98R (CTGTTCCTCGAGTCGATTTCC; SEQ ID NO: 102) (Chong and Moran, 2016 PNAS). The primers that will be used for aphid are ApEF1a 107F (CTGATTGTGCCGTGCTTATTG; SEQ ID NO: 103) and ApEF1a 246R (TATGGTGGTTCAGTAGAGTCC; SEQ ID NO: 104) (Chong and Moran, 2016 PNAS). qPCR will be performed using a qPCR amplification ramp of 1.6 degrees C./s and the following conditions: 1) 95° C. for 10 minutes, 2) 95° C. for 15 seconds, 3) 55° C. for 30 seconds, 4) repeat steps 2-3 40×, 5) 95° C. for 15 seconds, 6) 55° C. for 1 minute, 7) ramp change to 0.15 degrees C./s, 8) 95° C. for 1 second. qPCR data will be analyzed using analytic (Thermo Fisher Scientific, QuantStudio Design and Analysis) software.

At 7 post-treatment, RNA will be extracted from live aphids and RT-pPCR will be performed to quantify expression of BCR-4. Briefly, the aphid body surface will be sterilized by dipping the aphid into a 6% bleach solution for approximately 5 seconds. Aphids will then be rinsed in sterile water and total RNA will be extracted from each individual aphid using the RNA extraction kit (Qiagen miRNeasy kit) according to manufacturer's instructions. RNA concentrations will be measured using a nanodrop nucleic acid quantification. BCR-4 relative expression will be measured by RT-qPCR. The primers used will be ApBCR-4F (CTCTGTCAACCACCATGAGATTA; SEQ ID NO: 107) and ApBCR-4R (TGCAGACTACAGCACAATACTT; SEQ ID NO: 108). The internal reference gene primers were for Actin (housekeeping gene). The forward sequence is GATCAGCAGCCACACACAAG; SEQ ID NO: 109 and the reverse sequence is TTTGAACCGGTTTACGACGA; SEQ ID NO: 110. RT-qPCR will be performed using a qPCR amplification ramp of 1.6 degrees C./s and the following conditions: 1) 48° C. for 30 min, 2) 95° C. for 10 minutes, 3) 95° C. for 15 seconds, 4) 60° C. for 1 minute, 5) repeat steps 3-4 40×, 6) 95° C. for 15 seconds, 7) 60° C. for 1 minute, 8) ramp change to 0.15 degrees C./s, 9) 95° C. for 1 second. RT-qPCR data was analyzed using analytic (Thermo Fisher Scientific, QuantStudio Design and Analysis) software.

As shown in previous Examples, the aphids fed on the leaves expressing the dsRNA against the aphid target genes are expected to have lower survival, develop slower, contain fewer *Buchnera*, and have reduced target gene expression compared to the aphids reared on the control leaves.

Together this data described herein demonstrate the ability to kill and decrease the development and longevity (e.g., fitness) of aphids by treating them with plants expressing dsRNA targeting the essential gene(s) (e.g. glutamine transporter ApGLNT1) of bacteriocytes in the aphids.

OTHER EMBODIMENTS

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

The invention claimed is:

1. A method for decreasing the fitness of an insect, the method comprising:
   delivering to the insect an effective amount of a polynucleotide comprising a dsRNA that targets and decreases expression of an ApGLNT1 gene encoded by SEQ ID NO: 149 in the insect relative to an insect that has not been administered the dsRNA,
   wherein the dsRNA is fully complementary to 23 to 30 nucleotides of SEQ ID NO: 149, and
   wherein the delivery comprises spraying the polynucleotide on an agricultural crop or wherein the polynucleotide is delivered as an insect comestible composition for ingestion by the insect, and wherein the insect is *Acyrthosiphon pisum*.

2. The method of claim 1, wherein the method is effective to inhibit expression of a protein expressed by SEQ ID NO: 149.

3. The method of claim 1, wherein the method is effective to decrease the level, diversity, or metabolism of one or more microorganisms resident in the insect relative to an insect that has not been delivered the polynucleotide.

4. The method of claim 3, wherein the one or more microorganisms is a *Buchnera* spp.

5. The method of claim 1, wherein the method is effective to decrease the fitness of the insect relative to an insect that has not been delivered the polynucleotide, wherein decreased fitness includes an increased rate of mortality.

6. The method of claim 1, wherein the polynucleotide is delivered in a composition formulated for delivery to *Acyrthosiphon pisum*.

7. The method of claim 1, wherein the delivery comprises delivering the polynucleotide to at least one habitat where the insect pest grows, lives, reproduces, feeds, or infests.

8. The method of claim 1, wherein the polynucleotide is formulated with an agriculturally acceptable carrier as a liquid, a solid, an aerosol, a paste, a gel, or a gas composition.

9. A composition comprising a polynucleotide comprising a dsRNA formulated for delivery to *Acyrthosiphon pisum*, wherein the dsRNA is fully complementary to 23 to 30 nucleotides of an ApGLNT1 gene encoded by SEQ ID NO: 149.

10. A recombinant DNA construct, wherein the recombinant DNA construct comprises a heterologous promoter operably linked to a DNA encoding a RNA comprising at least one double-stranded RNA region, at least one strand of which comprises a nucleotide sequence that is fully complementary to 23 to 30 nucleotides of an ApGLNT1 gene encoded by SEQ ID NO: 149.

* * * * *

SEQUENCE LISTING

```
<160> NUMBER OF SEQ ID NOS: 153

<210> SEQ ID NO 1
<211> LENGTH: 1526
<212> TYPE: DNA
<213> ORGANISM: Carsonella ruddii

<400> SEQUENCE: 1
tatccagcca caggttcccc tacagctacc ttgttacgac ttcacccccag ttacaaatca      60 taccgttgta atagtaaaat tacttatgat acaatttact tccatggtgt gacgggcggt     120
gtgtacaagg ctcgagaacg tattcaccgt aacattctga tttacgatta ctagcgattc     180
caacttcatg aaatcgagtt acagatttca atccgaacta agaatatttt ttaagattag     240
cattatgttg ccatatagca tataactttt tgtaatactc attgtagcac gtgtgtagcc     300
ctacttataa gggccatgat gacttgacgt cgtcctcacc ttcctccaat ttatcattgg     360
cagtttctta ttagttctaa tatattttta gtaaaataag ataagggttg cgctcgttat     420
aggacttaac ccaacatttc acaacacgag ctgacgacag ccatgcagca cctgtctcaa     480
agctaaaaaa gctttattat ttctaataaa ttctttggat gtcaaaagta ggtaagattt     540
ttcgtgttgt atcgaattaa accacatgct ccaccgcttg tgcgagcccc cgtcaattca     600
tttgagtttt aaccttgcgg tcgtaatccc caggcggtca acttaacgcg ttagcttttt     660
cactaaaaat ataaactttt ttttcataaa acaaaattac aattataata tttaataaat     720
agttgacatc gtttactgca tggactacca gggtatctaa tcctgtttgc tccccatgct     780
ttcgtgtatt agtgtcagta ttaaaataga aatacgcctt cgccactagt attctttcag     840
atatctaagc atttcactgc tactcctgaa attctaattt cttctttat actcaagttt     900 ataagtatta atttcaatat taaattactt taataaattt aaaaattaat tttaaaaac     960 aacctgcaca cccttttacgc ccaataattc cgattaacgc ttgcaccccct cgtattaccg    1020 cggctgctgg cacgaagtta gccggtgctt cttttacaaa taacgtcaaa gataatattt    1080
ttttattata aaatctcttc ttactttgtt gaaagtgttt tacaaccccta aggccttctt    1140 cacacacgcg atatagctgg atcaagcttt cgctcattgt ccaatatccc ccactgctgc    1200
cttccgtaaa agtttgggcc gtgtctcagt cccaatgtgg ttgttcatcc tctaagatca    1260
actacgaatc atagtcttgt taagcttta ctttaacaac taactaattc gatataagct    1320
cttctattag cgaacgacat tctcgttctt tatccattag gatacatatt gaattactat    1380
acatttctat atactttct aatactaata ggtagattct tatatattac tcacccgttc    1440
gctgctaatt atttttttaa taattcgcac aacttgcatg tgttaagctt atcgctagcg    1500
ttcaatctga gctatgatca aactca                                        1526

<210> SEQ ID NO 2
<211> LENGTH: 1536
<212> TYPE: DNA
```

<213> ORGANISM: Portiera aleyrodidarum BT-B

<400> SEQUENCE: 2

```
aagagtttga tcatggctca gattgaacgc tagcggcaga cataacacat gcaagtcgag      60
cggcatcata caggttggca agcggcgcac gggtgagtaa tacatgtaaa tatacctaaa     120
agtggggaat aacgtacgga aacgtacgct aataccgcat aattattacg agataaagca     180
ggggcttgat aaaaaaatc aaccttgcgc ttttagaaaa ttacatgccg gattagctag     240
ttggtagagt aaaagcctac caaggtaacg atccgtagct ggtctgagag gatgatcagc     300
cacactggga ctgagaaaag gcccagactc ctacggagg cagcagtggg gaatattgga      360
caatggggg aaccctgatc cagtcatgcc gcgtgtgtga agaaggcctt tgggttgtaa      420
agcactttca gcgaagaaga aaagttagaa aataaaaagt tataactatg acggtactcg     480
cagaagaagc accggctaac tccgtgccag cagccgcggt aagacggagg gtgcaagcgt     540
taatcagaat tactgggcgt aaagggcatg taggtggttt gttaagcttt atgtgaaagc     600
cctatgctta acataggaac ggaataaaga actgacaaac tagagtgcag aagaggaagg     660
tagaattccc ggtgtagcgg tgaaatgcgt agatatctgg aggaatacca gttgcgaagg     720
cgaccttctg gctgacact gacactgaga tgcgaaagcg tggggagcaa acaggattag      780
atacccctggt agtccacgct gtaaacgata tcaactagcc gttggattct taaagaattt     840
tgtggcgtag ctaacgcgat aagttgatcg cctggggagt acggtcgcaa ggctaaaact     900
caaatgaatt gacgggggcc cgcacaagcg gtggagcatg tggtttaatt cgatgcaacg     960
cgcaaaacct tacctactct tgacatccaa agtactttcc agagatggaa gggtgcctta    1020
gggaactttg agacaggtgc tgcatggctg tcgtcagctc gtgttgtgaa atgttgggtt    1080
aagtcccgta acgagcgcaa cccttgtcct tagttgccaa cgcataaggc gggaacttta    1140
aggagactgc tggtgataaa ccggaggaag gtggggacga cgtcaagtca tcatggccct    1200
taagagtagg gcaacacacg tgctacaatg gcaaaaacaa agggtcgcaa aatggtaaca    1260
tgaagctaat cccaaaaaaa ttgtcttagt tcggattgga gtctgaaact cgactccata    1320
aagtcggaat cgctagtaat cgtgaatcag aatgtcacgg tgaatacgtt ctcgggcctt    1380
gtacacaccg cccgtcacac catggaagtg aaatgcacca gaagtggcaa gtttaaccaa    1440
aaaacaggag aacagtcact acggtgtggt tcatgactgg ggtgaagtcg taacaaggta    1500
gctgtagggg aacctgtggc tggatcacct ccttaa                              1536
```

<210> SEQ ID NO 3
<211> LENGTH: 1540
<212> TYPE: DNA
<213> ORGANISM: Buchnera aphidicola str. APS (Acyrthosiphon pisum)

<400> SEQUENCE: 3

```
agagtttgat catggctcag attgaacgct ggcggcaagc ctaacacatg caagtcgagc      60
ggcagcgaga agagagcttg ctctctttgt cggcaagcgg caaacgggtg agtaatatct     120
ggggatctac ccaaaagagg gggataacta ctagaaatgg tagctaatac cgcataatgt     180
tgaaaaacca aagtgggga cctttttggcc tcatgctttt ggatgaaccc agacgagatt      240
agcttgttgg tagagtaata gcctaccaag gcaacgatct ctagctggtc tgagaggata     300
accagccaca ctggaactga gacacggtcc agactcctac gggaggcagc agtggggaat     360
attgcacaat gggcgaaagc ctgatgcagc tatgccgcgt gtatgaagaa ggccttaggg     420
ttgtaaagta ctttcagcgg ggaggaaaaa aataaaacta ataattttat tcgtgacgt      480
```

```
tacccgcaga agaagcaccg gctaactccg tgccagcagc cgcggtaata cggagggtgc      540
aagcgttaat cagaattact gggcgtaaag agcgcgtagg tggttttta agtcaggtgt      600 gaaatcccta ggctcaacct aggaactgca tttgaaactg gaaaactaga gtttcgtaga     660
gggaggtaga attctaggtg tagcggtgaa atgcgtagat atctggagga atacccgtgg     720
cgaaagcggc ctcctaaacg aaaactgaca ctgaggcgcg aaagcgtggg gagcaaacag     780
gattagatac cctggtagtc catgccgtaa acgatgtcga cttggaggtt gttttccaaga    840 gaagtgactt ccgaagctaa cgcattaagt cgaccgcctg ggagtacgg ccgcaaggct      900 aaaactcaaa tgaattgacg ggggcccgca caagcggtgg agcatgtggt ttaattcgat    960
gcaacgcgaa aaaccttacc tggtcttgac atccacagaa ttctttagaa ataaagaagt    1020
gccttcggga gctgtgagac aggtgctgca tggctgtcgt cagctcgtgt tgtgaaatgt    1080
tgggttaagt cccgcaacga gcgcaaccct tatcccctgt tgccagcggt tcggccggga    1140
actcagagga gactgccggt tataaaccgg aggaaggtgg ggacgacgtc aagtcatcat    1200
ggcccttacg accagggcta cacacgtgct acaatggttt atacaaagag aagcaaatct    1260
gcaaagacaa gcaaacctca taagtaaat cgtagtccgg actggagtct gcaactcgac     1320
tccacgaagt cggaatcgct agtaatcgtg gatcagaatg ccacggtgaa tacgttcccg    1380
ggccttgtac acaccgcccg tcacaccatg ggagtgggtt gcaaagaag caggtatcct     1440 aacccttaa aaggaaggcg cttaccactt tgtgattcat gactggggtg aagtcgtaac     1500
aaggtaaccg taggggaacc tgcggttgga tcacctcctt                          1540
```

<210> SEQ ID NO 4
<211> LENGTH: 1552
<212> TYPE: DNA
<213> ORGANISM: Buchnera aphidicola str. Sg (Schizaphis graminum)

<400> SEQUENCE: 4

```
aaactgaaga gtttgatcat ggctcagatt gaacgctggc ggcaagccta acacatgcaa      60
gtcgagcggc agcgaaaaga aagcttgctt tcttgtcggc gagcggcaaa cgggtgagta     120
atatctgggg atctgcccaa aagagggga taactactag aaatggtagc taataccgca     180
taaagttgaa aaaccaaagt gggggacctt ttttaaaggc ctcatgcttt tggatgaacc    240
cagacgagat tagcttgttg gtaaggtaaa agcttaccaa ggcaacgatc tctagctggt    300
ctgagaggat aaccagccac actggaactg agacacggtc cagactccta cgggaggcag    360
cagtggggaa tattgcacaa tgggcgaaag cctgatgcag ctatgccgcg tgtatgaaga    420
aggccttagg gttgtaaagt actttcagcg gggaggaaaa aattaaaact aataatttta    480
ttttgtgacg ttaccgcag aagaagcacc ggctaactcc gtgccagcag ccgcggtaat     540
acggagggtg cgagcgttaa tcagaattac tgggcgtaaa gagcacgtag gtggttttt     600 aagtcagatg tgaaatccct aggcttaacc taggaactgc atttgaaact gaatgctag    660 agtatcgtag agggaggtag aattctaggt gtagcggtga aatgcgtaga tatctggagg    720
aatacccgtg gcgaaagcgg cctcctaaac gaatactgac actgaggtgc gaaagcgtgg    780
ggagcaaaca ggattagata ccctggtagt ccatgccgta acgatgtcg acttggaggt    840 tgtttccaag agaagtgact tccgaagcta acgcgttaag tcgaccgcct ggggagtacg    900
gccgcaaggc taaaactcaa atgaattgac ggggcccgc acaagcggtg gagcatgtgg    960
tttaattcga tgcaacgcga aaaaccttac ctggtcttga catccacaga attttttaga   1020
```

```
aataaaaaag tgccttcggg aactgtgaga caggtgctgc atggctgtcg tcagctcgtg    1080
ttgtgaaatg ttggggttaag tcccgcaacg agcgcaaccc ttatccctg ttgccagcgg    1140 ttcggccggg aactcagagg agactgccgg ttataaaccg gaggaaggtg gggacgacgt    1200
caagtcatca tggcccttac gaccagggct acacacgtgc tacaatggtt tatacaaaga    1260
gaagcaaatc tgtaaagaca agcaaacctc ataaagtaaa tcgtagtccg gactggagtc    1320
tgcaactcga ctccacgaag tcggaatcgc tagtaatcgt ggatcagaat gccacggtga    1380
atacgttccc gggccttgta cacaccgccc gtcacaccat gggagtgggt tgcaaaagaa    1440
gcagatttcc taaccacgaa agtggaaggc gtctaccact ttgtgattca tgactggggt    1500
gaagtcgtaa caaggtaacc gtagggaac ctgcggttgg atcacctcct ta             1552
```

<210> SEQ ID NO 5
<211> LENGTH: 1566
<212> TYPE: DNA
<213> ORGANISM: Buchnera aphidicola str. Bp (Baizongia pistaciae)

<400> SEQUENCE: 5

```
acttaaaatt gaagagtttg atcatggctc agattgaacg ctggcggcaa gcttaacaca     60
tgcaagtcga gcggcatcga agaaaagttt acttttctgg cggcgagcgg caaacgggtg    120
agtaacatct ggggatctac ctaaagagg gggacaacca ttggaaacga tggctaatac    180
cgcataatgt ttttaaataa accaaagtag gggactaaaa tttttagcct tatgcttta    240 gatgaaccca gacgagatta gcttgatggt aaggtaatgg cttaccaagg cgacgatctc    300
tagctggtct gagaggataa ccagccacac tggaactgag atacggtcca gactcctacg    360
ggaggcagca gtggggaata ttgcacaatg gctaaagcc tgatgcagct atgccgcgtg    420
tatgaagaag gccttagggt tgtaaagtac tttcagcggg gaggaaagaa ttatgtctaa    480
tatacatatt ttgtgacgtt acccgaagaa gaagcaccgg ctaactccgt gccagcagcc    540
gcggtaatac ggagggtgcg agcgttaatc agaattactg ggcgtaaaga gcacgtaggc    600
ggtttattaa gtcagatgtg aaatccctag gcttaactta ggaactgcat ttgaaactaa    660
tagactagag tctcatagag ggaggtagaa ttcaggtgt agcggtgaaa tgcgtagata    720
tctagaggaa tacccgtggc gaaagcgacc tcctaaatga aaactgacgc tgaggtgcga    780
aagcgtgggg agcaaacagg attagatacc ctggtagtcc atgctgtaaa cgatgtcgac    840
ttggaggttg tttcctagag aagtggcttc cgaagctaac gcattaagtc gaccgcctgg    900
ggagtacggt cgcaaggcta aaactcaaat gaattgacgg gggcccgcac aagcggtgga    960
gcatgtggtt taattcgatg caacgcgaag aaccttacct ggtcttgaca tccatagaat   1020
tttttagaga taaagagtg ccttaggaa ctatgagaca ggtgctgcat ggctgtcgtc    1080
agctcgtgtt gtgaaatgtt gggttaagtc ccgcaacgag cgcaaccct atcctttgtt    1140 gccatcaggt tatgctggga actcagagga gactgccggt tataaaccgg aggaaggtgg   1200
ggatgacgtc aagtcatcat ggcccttacg accagggcta cacacgtgct acaatggcat   1260
atacaaagag atgcaactct gcgaagataa gcaaacctca taagtatgt cgtagtccgg   1320 actggagtct gcaactcgac tccacgaagt aggaatcgct agtaatcgtg gatcagaatg   1380
ccacggtgaa tacgttcccg ggccttgtac acaccgcccg tcacaccatg ggagtgggtt   1440
gcaaaagaag caggtagctt aaccagatta tttattgga gggcgcttac cactttgtga   1500
ttcatgactg gggtgaagtc gtaacaaggt aaccgtaggg gaacctgcgg ttggatcacc   1560
tcctta                                                              1566
```

<210> SEQ ID NO 6
<211> LENGTH: 828
<212> TYPE: DNA
<213> ORGANISM: Buchnera aphidicola BCc

<400> SEQUENCE: 6

```
atgagatcat taatatataa aaatcatgtt ccaattaaaa aattaggaca aaattttta        60
cagaataaag aaattattaa tcagataatt aatttaataa atattaataa aaatgataat      120
attattgaaa taggatcagg attaggagcg ttaactttc ctatttgtag aatcattaaa      180
aaaatgatag tattagaaat tgatgaagat cttgtgtttt ttttaactca agtttattt      240
attaaaaaat tacaaattat aattgctgat attataaaat ttgattttg ttgtttttt      300
tctttacaga aatataaaaa ataggttt attggtaatt taccatataa tattgctact      360
ataatttttt taaaaacaat taaatttctt tataatataa ttgatatgca ttttatgttt      420
caaaaagaag tagcaaagag attattagct actcctggta ctaaagaata tggtagatta      480
agtattattg cacaatattt ttataagata gaaactgtta ttaatgttaa taaatttaat      540
ttttttccta ctcctaaagt agattctact ttttacgat ttactcctaa atattttaat      600
agtaaatata aaatagataa acatttttct gttttagaat taattactag attttctttt      660
caacatagaa gaaattttt aaataataat ttaatatctt tattttctac aaaagaatta      720
atttctttag atattgatcc atattcaaga gcagaaaatg tttcttaat tcaatattgt      780
aaattaatga atatattttt gaaagaaaa atttttatgtt tagattaa                   828
```

<210> SEQ ID NO 7
<211> LENGTH: 921
<212> TYPE: DNA
<213> ORGANISM: Buchnera aphidicola (Cinara tujafilina)

<400> SEQUENCE: 7

```
ttatcttatt tcacatatac gtaatattgc gctgcgtgca cgaggatttt tttgaatttc        60
agatatattt ggtttaatac gttaataaaa acgtatttt tttttttattt ttcttatttg      120
caattcagta ataggaagtt ttttaggtat atttggataa ttactgtaat tcttaataaa      180
gttttttaca atcctatctt caatagaatg aaaactaata atagcaattt ttgatccgga      240
atgtaatatg ttaataataa ttttaatat tttatgtaat tcatttattt cttggttaat      300
atatattcga aaagcttgaa atgttctcgt agctggatgt taaatttgt catattttgg      360
gattgatttt tttatgattt gaactaactc taacgtgctt gttatggttt tttttttat      420
ttgtaatatg atggctcggg atatttttt tgcgtatttt tcttcgccaa aattttttat      480
tacctgttct attgtttttt ggtttgtttt ttttaaccat tgactaactg atattccaga      540
tttagggttc atacgcatat ctaaaggtcc atcattcata aatgaaaatc ctcggatact      600
agaatttaac tgtattgaag aaataccta atctaataat attccatcta ttttatctct      660
atttttttct tttttttaata tttttcaat attagaaaat ttacctaaaa atattttaa     720
tcgcgaatct tttattttt ttccgatttt tatagattgt gggtcttgat caatactata      780
taactttca ttaaccccta attcttgaag aattgctttt gaatgaccac cacctccaaa      840
tgtacaatca acatatgtac cgtcttttt tatttttaag tattgtatga tttcttttgt      900
taaaacaggt ttatgaatca t                                                921
```

<210> SEQ ID NO 8

```
<211> LENGTH: 822
<212> TYPE: DNA
<213> ORGANISM: Buchnera aphidicola str. G002 (Myzus persicae)

<400> SEQUENCE: 8
atgaaaagta taaaaacttt taaaaaacac tttcctgtga aaaatatgg acaaaatttt      60 cttattaata aagagatcat aaaaaatatt gttaaaaaaa ttaatccaaa tatagaacaa     120
acattagtag aaatcggacc aggattagct gcattaactg agcccatatc tcagttatta    180
aaagagttaa tagttattga aatagactgt aatctattat attttttaaa aaaacaacca    240
ttttattcaa aattaatagt tttttgtcaa gatgctttaa actttaatta tacaaattta    300
ttttataaaa aaataaatt aattcgtatt tttggtaatt taccatataa tatctctaca    360
tctttaatta ttttttttatt tcaacacatt agagtaattc aagatatgaa ttttatgctt    420 caaaagaag ttgctgcaag attaattgca ttacctggaa ataaatatta cggtcgtttg    480
agcattatat ctcaatatta ttgtgatatc aaaattttat aaatgttgc tcctgaagat    540 ttttggccta ttccgagagt tcattctata tttgtaaatt taacacctca tcataattct    600
ccttattttg tttatgatat taatatttta agccttatta caaataaggc tttccaaaat    660
agaagaaaaa tattacgtca tagtttaaaa aatttattt ctgaaacaac tttattaaat    720
ttagatatta atcccagatt aagagctgaa aatatttctg tttttcagta ttgtcaatta    780
gctaattatt tgtataaaaa aaattatact aaaaaaaatt aa                      822

<210> SEQ ID NO 9
<211> LENGTH: 822
<212> TYPE: DNA
<213> ORGANISM: Buchnera aphidicola str. Ak (Acyrthosiphon kondoi)

<400> SEQUENCE: 9
attataaaaa attttaaaaa acattttcct ttaaaaaggt atggacaaaa ttttcttgtc      60
aatacaaaaa ctattcaaaa gataattaat ataattaatc aaacaccaa acaaacatta    120 gtggaaattg gacctggatt agctgcatta acaaaaccaa tttgtcaatt attagaagaa    180
ttaattgtta ttgaaataga tcctaattta ttgtttttat taaaaaaacg ttcattttat    240
tcaaaattaa cagttttttta tcaagacgct ttaaatttca attatacaga tttgtttat    300 aagaaaatc aattaattcg tgttttggga aacttgccat ataatatttc tacatcttta    360
attatttctt tattcaatca tattaaagtt attcaagata tgaatttttat gttacagaaa    420 gaggttgctg aaagattaat ttctattcct ggaaataaat cttatggccg tttaagcatt    480
atttctcagt attattgtaa aattaaaata ttattaaatg ttgtacctga agattttcga    540
cctataccga aagtgcattc tgttttattc aatttaactc ctcataccaa ttctccatat    600
tttgtttatg atacaaatat cctcagttct atcacaagaa atgcttttca aaatagaagg    660
aaaattttgc gtcatagttt aaaaaattta ttttctgaaa aagaactaat tcaattagaa    720
attaatccaa atttacgagc tgaaaatatt tctatctttc agtattgtca attagctgat    780
tatttatata aaaattaaa taatcttgta aaaatcaatt aa                       822

<210> SEQ ID NO 10
<211> LENGTH: 822
<212> TYPE: DNA
<213> ORGANISM: Buchnera aphidicola str. Ua (Uroleucon ambrosiae)

<400> SEQUENCE: 10
atgatactaa ataaatataa aaaatttatt cctttaaaaa gatacggaca aaattttctt      60
```

```
gtaaatagag aaataatcaa aaatattatc aaaataatta atcctaaaaa aacgcaaaca    120
ttattagaaa ttggaccggg tttaggtgcg ttaacaaaac ctatttgtga atttttaaat    180
gaacttatcg tcattgaaat agatcctaat atattatctt ttttaaagaa atgtatattt    240
tttgataaat taaaaatata ttgtcataat gctttagatt ttaattataa aaatatattc    300
tataaaaaaa gtcaattaat tcgtattttt ggaaatttac catataatat ttctacatct    360
ttaataatat atttatttcg gaatattgat attattcaag atatgaattt tatgttacaa    420
caagaagtgg ctaaaagatt agttgctatt cctggtgaaa actttatgg tcgtttaagt     480 attatatctc aatattattg taatattaaa atattattac atattcgacc tgaaaatttt    540
caacctattc ctaaagttaa ttcaatgttt gtaaatttaa ctccgcatat tcattctcct    600
tattttgttt atgatattaa tttattaact agtattacaa aacatgcttt tcaacataga    660
agaaaaatat tgcgtcatag tttaagaaat tttttttctg agcaagattt aattcattta    720
gaaattaatc caaatttaag agctgaaaat gtttctatta ttcaatattg tcaattggct    780
aataatttat ataaaaaaca taaacagttt attaataatt aa                      822

<210> SEQ ID NO 11
<211> LENGTH: 816
<212> TYPE: DNA
<213> ORGANISM: Buchnera aphidicola (Aphis glycines)

<400> SEQUENCE: 11
atgaaaaagc atattcctat aaaaaaattt agtcaaaatt ttcttgtaga tttgagtgtg     60
attaaaaaaa taattaaatt tattaatccg cagttaaatg aaatattggt tgaaattgga    120
ccgggattag ctgctatcac tcgaccatt tgtgatttga tagatcattt aattgtgatt     180
gaaattgata aatttttatt agatagatta aaacagttct catttattc aaaattaaca     240 gtatatcatc aagatgcttt agcatttgat tacataaagt tatttaataa aaaaaataaa    300
ttagttcgaa tttttggtaa tttaccatat catgtttcta cgtctttaat attgcattta    360
tttaaaagaa ttaatattat taagatatg aatttatgc tacaaaaaga agttgctgaa     420
cgtttaattg caactccagg tagtaaatta tatggtcgtt taagtattat ttctcaatat    480
tattgtaata taaaagtttt attgcatgtg tcttcaaaat gttttaaacc agttcctaaa    540
gtagaatcaa ttttttcttaa tttgacacct tatactgatt atttcccta ttttacttat    600 aatgtaaacg ttcttagtta tattacaaat ttagcttttc aaaaagaag aaaaatatta    660 cgtcatagtt taggtaaaat attttctgaa aaagtttta taaaattaaa tattaatccc    720
aaattaagac ctgagaatat ttctatatta caatattgtc agttatctaa ttatatgata    780
gaaaataata ttcatcagga acatgtttgt atttaa                              816

<210> SEQ ID NO 12
<211> LENGTH: 1463
<212> TYPE: DNA
<213> ORGANISM: Annandia pinicola

<400> SEQUENCE: 12
agattgaacg ctggcggcat gccttacaca tgcaagtcga acggtaacag gtcttcggac     60
gctgacgagt ggcgaacggg tgagtaatac atcggaacgt gcccagtcgt ggggataac    120 tactcgaaag agtagctaat accgcatacg atctgaggat gaaagcgggg gaccttcggg    180
cctcgcgcga ttggagcggc cgatggcaga ttaggtagtt ggtgggataa aagcttacca    240
```

-continued

```
agccgacgat ctgtagctgg tctgagagga cgaccagcca cactggaact gagatacggt     300
ccagactctt acgggaggca gcagtgggga atattgcaca atgggcgcaa gcctgatgca     360
gctatgtcgc gtgtatgaag aagaccttag ggttgtaaag tactttcgat agcataagaa     420
gataatgaga ctaataattt tattgtctga cgttagctat agaagaagca ccggctaact     480
ccgtgccagc agccgcggta atacgggggg tgctagcgtt aatcggaatt actgggcgta     540
aagagcatgt aggtggttta ttaagtcaga tgtgaaatcc ctggacttaa tctaggaact     600
gcatttgaaa ctaataggct agagtttcgt agagggaggt agaattctag gtgtagcggt     660
gaaatgcata gatatctaga ggaatatcag tggcgaaggc gaccttctgg acgataactg     720
acgctaaaat gcgaaagcat gggtagcaaa caggattaga taccctggta gtccatgctg     780
taaacgatgt cgactaagag gttggaggta aacttttaa tctctgtagc taacgcgtta     840
agtcgaccgc ctggggagta cggtcgcaag gctaaaactc aaatgaattg acggggggcct     900 gcacaagcgg tggagcatgt ggtttaattc gatgcaacgc gtaaaacctt acctggtctt     960
gacatccaca gaattttaca gaaatgtaga agtgcaattt gaactgtgag acaggtgctg    1020
catggctgtc gtcagctcgt gttgtgaaat gttgggttaa gtcccgcaac gagcgcaacc    1080
cttgtccttt gttaccataa gatttaagga actcaaagga gactgccggt gataaactgg    1140
aggaaggcgg ggacgacgtc aagtcatcat ggcccttatg accagggcta cacacgtgct    1200
acaatggcat atacaaagag atgcaatatt gcgaaataaa gccaatctta taaatatgt    1260 cctagttcgg actggagtct gcaactcgac tccacgaagt cggaatcgct agtaatcgtg    1320
gatcagcatg ccacggtgaa tatgttcca ggccttgtac acaccgcccg tcacaccatg    1380
gaagtggatt gcaaaagaag taagaaaatt aaccttctta caaggaaat aacttaccac    1440 tttgtgactc ataactgggg tga                                            1463

<210> SEQ ID NO 13
<211> LENGTH: 1554
<212> TYPE: DNA
<213> ORGANISM: Moranella endobia

<400> SEQUENCE: 13 tcttttggt aaggaggtga tccaaccgca ggttccccta cggttacctt gttacgactt      60 cacccccagtc atgaatcaca aagtggtaag cgccctccta aaaggttagg ctacctactt    120
cttttgcaac ccacttccat ggtgtgacgg gcggtgtgta caaggcccgg gaacgtattc    180
accgtggcat tctgatccac gattactagc gattcctact tcatggagtc gagttgcaga    240
ctccaatccg gactacgacg cactttatga ggtccgctaa ctctcgcgag cttgcttctc    300
tttgtatgcg ccattgtagc acgtgtgtag ccctactcgt aagggccatg atgacttgac    360
gtcatcccca ccttcctccg gtttatcacc ggcagtctcc tttgagttcc cgaccgaatc    420
gctggcaaaa aaggataagg gttgcgctcg ttgcgggact aacccaaca tttcacaaca     480 cgagctgacg acagccatgc agcacctgtc tcagagttcc cgaaggtacc aaaacatctc    540
tgctaagttc tctggatgtc aagagtaggt aaggttcttc gcgttgcatc gaattaaacc    600
acatgctcca ccgcttgtgc gggccccgt caattcattt gagttttaac cttgcggccg     660
tactccccag gcggtcgatt taacgcgtta actacgaaag ccacagttca agaccacagc    720
tttcaaatcg acatagttta cggcgtggac taccagggta tctaatcctg tttgctcccc    780
acgctttcgt acctgagcgt cagtattcgt ccagggggcc gccttcgcca ctggtattcc    840
tccagatatc tacacatttc accgctacac ctggaattct accccctct acgagactct    900
```

-continued

```
agcctatcag tttcaaatgc agttcctagg ttaagcccag ggatttcaca tctgacttaa      960
taaaccgcct acgtactctt tacgcccagt aattccgatt aacgcttgca ccctccgtat     1020
taccgcggct gctggcacgg agttagccgg tgcttcttct gtaggtaacg tcaatcaata     1080
accgtattaa ggatattgcc ttcctcccta ctgaaagtgc tttacaaccc gaaggccttc     1140
ttcacacacg cggcatggct gcatcagggt ttcccccatt gtgcaatatt ccccactgct     1200
gcctcccgta ggagtctgga ccgtgtctca gttccagtgt ggctggtcat cctctcagac     1260
cagctaggga tcgtcgccta ggtaagctat tacctcacct actagctaat cccatctggg     1320
ttcatctgaa ggtgtgaggc caaaaggtcc cccactttgg tcttacgaca ttatgcggta     1380
ttagctaccg tttccagcag ttatccccct ccatcaggca gatccccaga ctttactcac     1440
ccgttcgctg ctcgccggca aaaagtaaa cttttttccg ttgccgctca acttgcatgt     1500
gttaggcctg ccgccagcgt tcaatctgag ccatgatcaa actcttcaat taaa          1554
```

<210> SEQ ID NO 14
<211> LENGTH: 1539
<212> TYPE: DNA
<213> ORGANISM: Ishikawaella capsulata Mpkobe

<400> SEQUENCE: 14

```
aaattgaaga gtttgatcat ggctcagatt gaacgctagc ggcaagctta acacatgcaa       60
gtcgaacggt aacagaaaaa agcttgcttt tttgctgacg agtggcggac gggtgagtaa      120
tgtctgggga tctacctaat ggcgggggat aactactgga aacggtagct aataccgcat      180
aatgttgtaa aaccaaagtg ggggacctta tggcctcaca ccattagatg aacctagatg      240
ggattagctt gtaggtgggg taaaggctca cctaggcaac gatccctagc tggtctgaga      300
ggatgaccag ccacactgga actgagatac ggtccagact cctacgggag gcagcagtgg      360
ggaatcttgc acaatgggcg caagcctgat gcagctatgt cgcgtgtatg aagaaggcct      420
tagggttgta aagtactttc atcggggaag aaggatatga gcctaatatt ctcatatatt      480
gacgttacct gcagaagaag caccggctaa ctccgtgcca gcagccgcgg taacacggag      540
ggtgcgagcg ttaatcggaa ttactgggcg taaagagcac gtaggtggtt tattaagtca      600
tatgtgaaat ccctgggctt aacctaggaa ctgcatgtga aactgataaa ctagagtttc      660
gtagagggag gtggaattcc aggtgtagcg gtgaaatgcg tagatatctg gaggaatatc      720
agaggcgaag gcgaccttct ggacgaaaac tgacactcag gtgcgaaagc gtgggagca      780 aacaggatta gatacctgg tagtccacgc tgtaaacaat gtcgactaaa aaactgtgag      840
cttgacttgt ggttttttgta gctaacgcat taagtcgacc gcctggggag tacggccgca      900
aggttaaaac tcaaatgaat tgacgggggt ccgcacaagc ggtggagcat gtggtttaat      960
tcgatgcaac gcgaaaaacc ttacctggtc ttgacatcca gcgaattata gaaatata      1020 taagtgcctt tcggggaact ctgagacgct gcatggctgt cgtcagctcg tgttgtgaaa     1080
tgttgggtta agtcccgcaa cgagcgccct tatcctctgt tgccagcggc atggccggga     1140
actcagagga gactgccagt attaaactgg aggaaggtgg ggatgacgtc aagtcatcat     1200
ggcccttatg accagggcta cacacgtgct acaatggtgt atacaaagag aagcaatctc     1260
gcaagagtaa gcaaaactca aaaagtacat cgtagttcgg attagagtct gcaactcgac     1320
tctatgaagt aggaatcgct agtaatcgtg gatcagaatg ccacggtgaa tacgttctct     1380
ggccttgtac acaccgcccg tcacaccatg ggagtaagtt gcaaagaag taggtagctt     1440
```

```
aacctttata ggagggcgct taccactttg tgatttatga ctggggtgaa gtcgtaacaa      1500
ggtaactgta ggggaacctg tggttggatt acctcctta                             1539
```

<210> SEQ ID NO 15
<211> LENGTH: 1561
<212> TYPE: DNA
<213> ORGANISM: Baumannia cicadellinicola

<400> SEQUENCE: 15

```
ttcaattgaa gagtttgatc atggctcaga ttgaacgctg gcggtaagct taacacatgc        60
aagtcgagcg gcatcggaaa gtaaattaat tactttgccg gcaagcggcg aacgggtgag       120
taatatctgg ggatctacct tatggagagg gataactatt ggaaacgata gctaacaccg       180
cataatgtcg tcagaccaaa tgggggacc  taatttaggc ctcatgccat aagatgaacc       240
cagatgagat tagctagtag gtgagataat agctcaccta gcaacgatc  tctagttggt       300 ctgagaggat gaccagccac actggaactg agacacggtc cagactccta cgggaggcag       360
cagtggggaa tcttgcacaa tgggggaaac cctgatgcag ctataccgcg tgtgtgaaga       420
aggccttcgg gttgtaaagc actttcagcg gggaagaaaa tgaagttact aataataatt       480
gtcaattgac gttacccgca aaagaagcac cggctaactc cgtgccagca gccgcggtaa       540
gacggagggt gcaagcgtta atcggaatta ctgggcgtaa agcgtatgta ggcggtttat       600
ttagtcaggt gtgaaagccc taggcttaac ctaggaattg catttgaaac tggtaagcta       660
gagtctcgta gagggggga  gaattccagg tgtagcggtg aaatgcgtag agatctggaa       720
gaataccagt ggcgaaggcg ccccccctgga cgaaaactga cgctcaagta cgaaagcgtg       780
gggagcaaac aggattagat accctggtag tccacgctgt aaacgatgtc gatttgaagg       840
ttgtagcctt gagctatagc tttcgaagct aacgcattaa atcgaccgcc tggggagtac       900
gaccgcaagg ttaaaactca aatgaattga cgggggcccg cacaagcggt ggagcatgtg       960
gtttaattcg atacaacgcg aaaaacctta cctactcttg acatccagag tataaagcag      1020
aaaagcttta gtgccttcgg gaactctgag acaggtgctg catggctgtc gtcagctcgt      1080
gttgtgaaat gttgggttaa gtcccgcaac gagcgcaacc cttatccttt gttgccaacg      1140
attaagtcgg gaactcaaag gagactgccg gtgataaacc ggaggaaggt gaggataacg      1200
tcaagtcatc atggccctta cgagtagggc tacacacgtg ctacaatggt gcatacaaag      1260
agaagcaatc tcgtaagagt tagcaaacct cataaagtgc atcgtagtcc ggattagagt      1320
ctgcaactcg actctatgaa gtcggaatcg ctagtaatcg tggatcagaa tgccacggtg      1380
aatacgttcc cgggccttgt acacaccgcc cgtcacacca tgggagtgta ttgcaaaaga      1440
agttagtagc ttaactcata atacgagagg gcgcttacca ctttgtgatt cataactggg      1500
gtgaagtcgt aacaaggtaa ccgtagggga acctgcggtt ggatcacctc cttacactaa      1560
a                                                                      1561
```

<210> SEQ ID NO 16
<211> LENGTH: 1464
<212> TYPE: DNA
<213> ORGANISM: Sodalis like

<400> SEQUENCE: 16

```
attgaacgct ggcggcaggc ctaacacatg caagtcgagc ggcagcggga agaagcttgc        60
ttctttgccg gcgagcggcg gacgggtgag taatgtctgg ggatctgccc gatgaggggg       120
gataactact ggaaacggta gctaataccg cataacgtcg caagaccaaa gtggggggacc      180
```

```
ttcgggcctc acaccatcgg atgaacccag gtgggattag ctagtaggtg gggtaatggc        240
tcacctaggc gacgatccct agctggtctg agaggatgac cagtcacact ggaactgaga        300
cacggtccag actcctacgg gaggcagcag tggggaatat tgcacaatgg gggaaaccct       360
gatgcagcca tgccgcgtgt gtgaagaagg ccttcgggtt gtaaagcact ttcagcgggg        420
aggaaggcga tggcgttaat agcgctatcg attgacgtta cccgcagaag aagcaccggc       480
taactccgtg ccagcagccg cggtaatacg gagggtgcga gcgttaatcg gaattactgg       540
gcgtaaagcg tacgcaggcg gtctgttaag tcagatgtga aatccccggg ctcaacctgg       600
gaactgcatt tgaaactggc aggctagagt ctcgtagagg gggtagaat tccaggtgta       660 gcggtgaaat gcgtagagat ctggaggaat accggtggcg aaggcggccc cctggacgaa       720
gactgacgct caggtacgaa agcgtgggga gcaaacagga ttagataccc tggtagtcca       780
cgctgtaaac gatgtcgatt tgaaggttgt ggccttgagc cgtggctttc ggagctaacg       840
tgttaaatcg accgcctggg gagtacggcc gcaaggttaa aactcaaatg aattgacggg       900
ggcccgcaca agcggtggag catgtggttt aattcgatgc aacgcgaaga accttaccta       960
ctcttgacat ccagagaact tggcagagat gctttggtgc cttcgggaac tctgagacag      1020
gtgctgcatg gctgtcgtca gctcgtgttg tgaaatgttg ggttaagtcc cgcaacgagc      1080
gcaaccctta tcctttattg ccagcgattc ggtcgggaac tcaaaggaga ctgccggtga      1140
taaaccggag gaaggtgggg atgacgtcaa gtcatcatgg cccttacgag tagggctaca      1200
cacgtgctac aatggcgcat acaaagagaa gcgatctcgc gagagtcagc ggacctcata      1260
aagtgcgtcg tagtccggat tggagtctgc aactcgactc catgaagtcg gaatcgctag      1320
taatcgtgga tcagaatgcc acggtgaata cgttcccggg ccttgtacac accgcccgtc      1380
acaccatggg agtgggttgc aaaagaagta ggtagcttaa ccttcgggag ggcgcttacc      1440
actttgtgat tcatgactgg ggtg                                              1464
```

<210> SEQ ID NO 17
<211> LENGTH: 1465
<212> TYPE: DNA
<213> ORGANISM: Hartigia pinicola

<400> SEQUENCE: 17

```
agatttaacg ctggcggcag gcctaacaca tgcaagtcga gcggtaccag aagaagcttg         60
cttcttgctg acgagcggcg gacgggtgag taatgtatgg ggatctgccc gacagagggg       120
gataactatt ggaaacggta gctaataccg cataatctct gaggagcaaa gcagggggaac     180 ttcggtcctt gcgctatcgg atgaacccat atgggattag ctagtaggtg aggtaatggc       240 tccctaggc aacgatccct agctggtctg agaggatgat cagccacact gggactgaga         300
cacggcccag actcctacgg gaggcagcag tggggaatat tgcacaatgg gcgaaagcct       360
gatgcagcca tgccgcgtgt atgaagaagg ctttagggtt gtaaagtact ttcagtcgag       420
aggaaaacat tgatgctaat atcatcaatt attgacgttt ccgacagaag aagcaccggc       480
taactccgtg ccagcagccg cggtaatacg gagggtgcaa gcgttaatcg gaattactgg       540
gcgtaaagcg cacgcaggcg gttaattaag ttagatgtga agccccggg cttaacccag       600 gaatagcata taaaactggt caactagagt attgtagagg gggtagaat tccatgtgta       660 gcggtgaaat gcgtagagat gtggaggaat accagtggcg aaggcggccc cctggacaaa       720
aactgacgct caaatgcgaa agcgtgggga gcaaacagga ttagataccc tggtagtcca       780
```

```
tgctgtaaac gatgtcgatt tggaggttgt tcccttgagg agtagcttcc gtagctaacg    840
cgttaaatcg accgcctggg ggagtacgac tgcaaggtta aaactcaaat gaattgacgg    900
gggcccgcac aagcggtgga gcatgtggtt taattcgatg caacgcgaaa aaccttacct    960
actcttgaca tccagataat ttagcagaaa tgctttagta ccttcgggaa atctgagaca   1020
ggtgctgcat ggctgtcgtc agctcgtgtt gtgaaatgtt gggttaagtc ccgcaacgag   1080
cgcaaccctt atcctttgtt gccagcgatt aggtcgggaa ctcaaaggag actgccggtg   1140
ataaaccgga ggaaggtggg gatgacgtca agtcatcatg gcccttacga gtagggctac   1200
acacgtgcta caatggcata tacaaaggga agcaacctcg cgagagcaag cgaaactcat   1260
aaattatgtc gtagttcaga ttggagtctg caactcgact ccatgaagtc ggaatcgcta   1320
gtaatcgtag atcagaatgc tacggtgaat acgttcccgg gccttgtaca caccgcccgt   1380
cacaccatgg gagtgggttg caaaagaagt aggtaactta accttatgga aagcgcttac   1440
cactttgtga ttcataactg gggtg                                         1465

<210> SEQ ID NO 18
<211> LENGTH: 1571
<212> TYPE: DNA
<213> ORGANISM: Tremblaya phenacola

<400> SEQUENCE: 18
aggtaatcca gccacacctt ccagtacggc taccttgtta cgacttcacc ccagtcacaa     60
cccttacctt cggaactgcc ctcctcacaa ctcaaaccac caaacacttt taaatcaggt    120
tgagagaggt taggcctgtt acttctggca agaattattt ccatggtgtg acgggcggtg    180
tgtacaagac ccgagaacat attcaccgtg gcatgctgat ccacgattac tagcaattcc    240
aacttcatgc actcgagttt cagagtacaa tccgaactga ggccggcttt gtgagattag    300
ctcccttttg caagttggca actctttggt ccggccattg tatgatgtgt gaagccccac    360
ccataaaggc catgaggact tgacgtcatc cccaccttcc tccaacttat cgctggcagt    420
ctctttaagg taactgacta atccagtagc aattaaagac aggggttgcg ctcgttacag    480
gacttaaccc aacatctcac gacacgagct gacgacagcc atgcagcacc tgtgcactaa    540
ttctctttca agcactcccg cttctcaaca ggatcttagc catatcaaag gtaggtaagg    600 ttttttcgcgt tgcatcgaat taatccacat catccactgc ttgtgcgggt ccccgtcaat    660
tcctttgagt tttaaccttg cggccgtact ccccaggcgg tcgacttgtg cgttagctgc    720
accactgaaa aggaaaactg cccaatggtt agtcaacatc gtttagggca tggactacca    780
gggtatctaa tcctgtttgc tccccatgct ttagtgtctg agcgtcagta acgaaccagg    840
aggctgccta cgctttcggt attcctccac atctctacac atttcactgc tacatgcgga    900
attctacctc cccctctcgt actccagcct gccagtaact gccgcattct gaggttaagc    960
ctcagccttt cacagcaatc ttaacaggca gcctgcacac cctttacgcc aataaatct   1020 gattaacgct cgcaccctac gtattaccgc ggctgctggc acgtagtttg ccggtgctta   1080
ttcttccggt acagtcacac caccaaattg ttagttgggt ggctttctttt ccgaacaaaa   1140 gtgcttaca acccaaaggc cttcttcaca cacgcggcat tgctggatca ggcttccgcc   1200
cattgtccaa gattcctcac tgctgccttc ctcagaagtc tgggccgtgt ctcagtccca   1260
gtgtggctgg ccgtcctctc agaccagcta ccgatcattg ccttgggaag ccattacctt   1320
tccaacaagc taatcagaca tcagccaatc tcagagcgca aggcaattgg tcccctgctt   1380
tcattctgct tggtagagaa ctttatgcgg tattaattag gctttcacct agctgtcccc   1440
```

```
cactctgagg catgttctga tgcattactc acccgtttgc cacttgccac caagcctaag    1500
cccgtgttgc cgttcgactt gcatgtgtaa ggcatgccgc tagcgttcaa tctgagccag    1560
gatcaaactc t                                                         1571
```

<210> SEQ ID NO 19
<211> LENGTH: 1535
<212> TYPE: DNA
<213> ORGANISM: Tremblaya princeps

<400> SEQUENCE: 19

```
agagtttgat cctggctcag attgaacgct agcggcatgc attacacatg caagtcgtac      60
ggcagcacgg gcttaggcct ggtggcgagt ggcgaacggg tgagtaacgc ctcggaacgt     120
gccttgtagt gggggatagc ctggcgaaag ccagattaat accgcatgaa gccgcacagc     180
atgcgcggtg aaagtggggg attctagcct cacgctactg gatcggccgg ggtctgatta     240
gctagttggc ggggtaatgg cccaccaagg cttagatcag tagctggtct gagaggacga     300
tcagccacac tgggactgag acacggccca gactcctacg ggaggcagca gtggggaatc     360
ttggacaatg ggcgcaagcc tgatccagca atgccgcgtg tgtgaagaag gccttcgggt     420
cgtaaagcac ttttgttcgg gatgaagggg ggcgtgcaaa caccatgccc tcttgacgat     480
accgaaagaa taagcaccgg ctaactacgt gccagcagcc gcggtaatac gtagggtgcg     540
agcgttaatc ggaatcactg ggcgtaaagg gtgcgcgggt ggtttgccaa gaccctgta     600 aaatcctacg gcccaaccgt agtgctgcgg aggttactgg taagcttgag tatggcagag     660
gggggtagaa ttccaggtgt agcggtgaaa tgcgtagata tctggaggaa taccgaaggc     720
gaaggcaacc ccctgggcca tcactgacac tgaggcacga aagcgtgggg agcaaacagg     780
attagatacc ctggtagtcc acgccctaaa ccatgtcgac tagttgtcgg ggggagccct     840
ttttcctcgg tgacgaagct aacgcatgaa gtcgaccgcc tggggagtac gaccgcaagg     900
ttaaaactca aggaattga cggggacccg cacaagcggt ggatgatgtg gattaattcg     960
atgcaacgcg aaaaacctta cctacccttg acatggcgga gattctgccg agaggcggaa    1020
gtgctcgaaa gagaatccgt gcacaggtgc tgcatggctg tcgtcagctc gtgtcgtgag    1080
atgttgggtt aagtcccata acgagcgcaa ccccgtctt tagttgctac cactggggca    1140
ctctatagag actgccggtg ataaaccgga ggaaggtggg gacgacgtca agtcatcatg    1200
gcctttatgg gtagggcttc acacgtcata caatggctgg agcaaagggt cgccaactcg    1260
agagagggag ctaatcccac aaacccagcc ccagttcgga ttgcactctg caactcgagt    1320
gcatgaagtc ggaatcgcta gtaatcgtgg atcagcatgc cacggtgaat acgttctcgg    1380
gtcttgtaca caccgcccgt cacaccatgg gagtaagccg catcagaagc agcctcccta    1440 acccctatgct gggaaggagg ctgcgaaggt ggggtctatg actggggtga agtcgtaaca    1500
aggtagccgt accggaaggt gcggctggat tacct                              1535
```

<210> SEQ ID NO 20
<211> LENGTH: 1450
<212> TYPE: DNA
<213> ORGANISM: Nasuia deltocephalinicola

<400> SEQUENCE: 20

```
agtttaatcc tggctcagat ttaacgcttg cgacatgcct aacacatgca agttgaacgt      60
tgaaaatatt tcaaagtagc gtataggtga gtataacatt taaacatacc ttaaagttcg     120
```

```
gaatacccog atgaaaatcg gtataatacc gtataaaagt atttaagaat taaagcgggg    180
aaaacctcgt gctataagat tgttaaatgc ctgattagtt tgttggtttt taaggtaaaa    240
gcttaccaag actttgatca gtagctattc tgtgaggatg tatagccaca ttgggattga    300
aataatgccc aaacctctac ggagggcagc agtggggaat attggacaat gagcgaaagc    360
ttgatccagc aatgtcgcgt gtgcgattaa gggaaactgt aaagcacttt tttttaagaa    420
taagaaattt taattaataa ttaaaatttt tgaatgtatt aaaagaataa gtaccgacta    480
atcacgtgcc agcagtcgcg gtaatacgtg gggtgcgagc gttaatcgga tttattgggc    540
gtaaagtgta ttcaggctgc ttaaaaagat ttatattaaa tatttaaatt aaatttaaaa    600
aatgtataaa ttactattaa gctagagttt agtataagaa aaagaatttt tatgtgtagc    660
agtgaaatgc gttgatatat aaaggaacgc cgaaagcgaa agcattttc tgtaatagaa     720 ctgacgctta tatacgaaag cgtgggtagc aaacaggatt agataccctg gtagtccacg    780
ccctaaacta tgtcaattaa ctattagaat ttttttagt ggtgtagcta acgcgttaaa     840
ttgaccgcct gggtattacg atcgcaagat taaaactcaa aggaattgac ggggaccagc    900
acaagcggtg gatgatgtgg attaattcga tgatacgcga aaaaccttac ctgcccttga    960
catggttaga attttattga aaaataaaag tgcttggaaa agagctaaca cacaggtgct    1020
gcatggctgt cgtcagctcg tgtcgtgaga tgttgggtta agtcccgcaa cgagcgcaac    1080
ccctactctt agttgctaat taagaacttt aagagaaca gctaacaata agtttagagg     1140 aaggaggggga tgacttcaag tcctcatggc ccttatgggc agggcttcac acgtcataca    1200
atggttaata caaaaagttg caatatcgta agattgagct aatctttaaa attaatctta    1260
gttcggattg tactctgcaa ctcgagtaca tgaagttgga atcgctagta atcgcggatc    1320
agcatgccgc ggtgaatagt ttaactggtc ttgtacacac cgcccgtcac accatggaaa    1380
taaatcttgt tttaaatgaa gtaatatatt ttatcaaaac aggttttgta accggggtga    1440
agtcgtaaca                                                         1450
```

<210> SEQ ID NO 21
<211> LENGTH: 1536
<212> TYPE: DNA
<213> ORGANISM: Zinderia insecticola CARI

<400> SEQUENCE: 21

```
atataaataa gagtttgatc ctggctcaga ttgaacgcta gcggtatgct ttacacatgc     60
aagtcgaacg acaatattaa agcttgcttt aatataaagt ggcgaacggg tgagtaatat    120
atcaaaacgt acctttaaagt gggggataac taattgaaaa attagataat accgcatatt    180
aatcttagga tgaaaatagg aataatatct tatgctttta gatcggttga tatctgatta    240
gctagttggt agggtaaatg cttaccaagg caatgatcag tagctggttt tagcgaatga    300
tcagccacac tggaactgag acacggtcca gacttctacg gaaggcagca gtggggaata    360
ttggacaatg ggagaaatcc tgatccagca ataccgcgtg agtgatgaag gccttagggt    420
cgtaaaactc ttttgttagg aaagaaataa ttttaaataa tatttaaaat tgatgacggt    480
acctaaagaa taagcaccgg ctaactacgt gccagcagcc gcggtaatac gtagggtgca    540
agcgttaatc ggaattattg ggcgtaaaga gtgcgtaggc tgttatataa gatagatgtg    600
aaatacttaa gcttaactta agaactgcat ttattactgt ttaactagag tttattagag    660
agaagtggaa tttatgtgt agcagtgaaa tgcgtagata tataaggaa tatcgatggc      720 gaaggcagct tcttggaata atactgacgc tgaggcacga aagcgtgggg agcaaacagg    780
```

```
attagatacc ctggtagtcc acgccctaaa ctatgtctac tagttattaa attaaaaata    840
aaatttagta acgtagctaa cgcattaagt agaccgcctg gggagtacga tcgcaagatt    900
aaaactcaaa ggaattgacg gggacccgca caagcggtgg atgatgtgga ttaattcgat    960
gcaacacgaa aaaccttacc tactcttgac atgtttggaa ttttaaagaa atttaaaagt    1020
gcttgaaaaa gaaccaaaac acaggtgctg catggctgtc gtcagctcgt gtcgtgagat    1080
gttgggttaa gtcccgcaac gagcgcaacc cttgttatta tttgctaata aaagaacatt    1140
taataagact gccaatgaca aattggagga aggtggggat gacgtcaagt cctcatggcc    1200
cttatgagta gggcttcaca cgtcatacaa tgatatatac aatgggtagc aaatttgtga    1260
aaatgagcca atccttaaag tatatcttag ttcggattgt agtctgcaac tcgactacat    1320
gaagttggaa tcgctagtaa tcgcggatca gcatgccgcg gtgaatacgt tctcgggtct    1380
tgtacacacc gcccgtcaca ccatggaagt gattttttacc agaaattatt tgtttaacct    1440
ttattggaaa aaataatta aggtagaatt catgactggg gtgaagtcgt aacaaggtag    1500
cagtatcgga aggtgcggct ggattacatt ttaaat                              1536

<210> SEQ ID NO 22
<211> LENGTH: 1423
<212> TYPE: DNA
<213> ORGANISM: Hodgkinia

<400> SEQUENCE: 22
aatgctggcg gcaggcctaa cacatgcaag tcgagcggac aacgttcaaa cgttgttagc     60
ggcgaacggg tgagtaatac gtgagaatct acccatccca acgtgataac atagtcaaca    120
ccatgtcaat aacgtatgat tcctgcaaca ggtaaagatt ttatcgggga tggatgagct    180
cacgctagat tagctagttg gtgagataaa agccccaccaa ggccaagatc tatagctggt    240
ctggaaggat ggacagccac attgggactg agacaaggcc caaccctcta aggagggcag    300
cagtgaggaa tattggacaa tgggcgtaag cctgatccag ccatgccgca tgagtgattg    360
aaggtccaac ggactgtaaa actcttttct ccagagatca taaatgatag tatctggtga    420
tataagctcc ggccaacttc gtgccagcag ccgcggtaat acgaggggag cgagtattgt    480
tcggttttat tgggcgtaaa gggtgtccag gttgctaagt aagttaacaa caaaatcttg    540
agattcaacc tcataacgtt cggttaatac tactaagctc gagcttggat agagacaaac    600
ggaattccga gtgtagaggt gaaattcgtt gatacttgga ggaacaccag aggcgaaggc    660
ggtttgtcat accaagctga cactgaagac acgaaagcat ggggagcaaa caggattaga    720
taccctggta gtccatgccc taaacgttga gtgctaacag ttcgatcaag ccacatgcta    780
tgatccagga ttgtacagct aacgcgttaa gcactccgcc tgggtattac gaccgcaagg    840
ttaaaactca aggaattga cggagacccg cacaagcggt ggagcatgtg gtttaattcg    900
aagctacacg aagaacctta ccagcccttg acataccatg ccaaccatc ctggaaacag    960 gatgttgttc aagttaaacc cttgaaatgc caggaacagg tgctgcatgg ctgttgtcag   1020
ttcgtgtcgt gagatgtatg gttaagtccc aaaacgaaca caaccctcac ccatagttgc   1080
cataaacaca attgggttct ctatgggtac tgctaacgta agttagagga aggtgaggac   1140
cacaacaagt catcatggcc cttatgggct gggccacaca catgctacaa tggtggttac   1200
aaagagccgc aacgttgtga gaccgagcaa atctccaaag accatctcag tccgattgt    1260 actctgcaac ccgagtacat gaagtaggaa tcgctagtaa tcgtggatca gcatgccacg   1320
```

```
gtgaatacgt tctcgggtct tgtacacgcc gcccgtcaca ccatgggagc ttcgctccga    1380
tcgaagtcaa gttacccttg accacatctt ggcaagtgac cga                      1423
```

<210> SEQ ID NO 23
<211> LENGTH: 1504
<212> TYPE: DNA
<213> ORGANISM: Wolbachia sp. wPip

<400> SEQUENCE: 23

```
aaatttgaga gtttgatcct ggctcagaat gaacgctggc ggcaggccta acacatgcaa      60
gtcgaacgga gttatattgt agcttgctat ggtataactt agtggcagac gggtgagtaa     120
tgtataggaa tctacctagt agtacggaat aattgttgga aacgacaact aataccgtat     180
acgccctacg ggggaaaaat ttattgctat tagatgagcc tatattagat tagctagttg     240
gtggggtaat agcctaccaa ggtaatgatc tatagctgat ctgagaggat gatcagccac     300
actggaactg agatacggtc cagactccta cgggaggcag cagtggggaa tattggacaa     360
tgggcgaaag cctgatccag ccatgccgca tgagtgaaga aggcctttgg gttgtaaagc     420
tcttttagtg aggaagataa tgacggtact cacagaagaa gtcctggcta actccgtgcc     480
agcagccgcg gtaatacgga gagggctagc gttattcgga attattgggc gtaaagggcg     540
cgtaggctgg ttaataagtt aaaagtgaaa tcccgaggct taaccttgga attgctttta     600
aaactattaa tctagagatt gaagaggat agaggaattc ctgatgtaga ggtaaaattc     660
gtaaatatta ggaggaacac cagtggcgaa ggcgtctatc tggttcaaat ctgacgctga     720
agcgcgaagg cgtgggagc aaacaggatt agatacctg gtagtccacg ctgtaaacga     780
tgaatgttaa atatggggag tttactttct gtattacagc taacgcgtta acattccgc     840 ctggggacta cggtcgcaag attaaaactc aaaggaattg acggggaccc gcacaagcgg     900
tggagcatgt ggtttaattc gatgcaacgc gaaaaacctt accacttctt gacatgaaaa     960
tcatacctat tcgaagggat agggtcggtt cggccggatt ttacacaagt gttgcatggc    1020
tgtcgtcagc tcgtgtcgtg agatgttggg ttaagtcccg caacgagcgc aaccctcatc    1080
cttagttgcc atcaggtaat gctgagtact ttaaggaaac tgccagtgat aagctggagg    1140
aaggtgggga tgatgtcaag tcatcatggc ctttatggag tgggctacac acgtgctaca    1200
atggtgtcta caatgggctg caaggtgcgc aagcctaagc taatccctaa agacatctc    1260 agttcggatt gtactctgca actcgagtac atgaagttgg aatcgctagt aatcgtggat    1320
cagcatgcca cggtgaatac gttctcgggt cttgtacaca ctgcccgtca cgccatggga    1380
attggtttca ctcgaagcta atggcctaac cgcaaggaag gagttattta agtgggatc    1440 agtgactggg gtgaagtcgt aacaaggtag cagtagggga atctgcagct ggattacctc    1500
ctta                                                                 1504
```

<210> SEQ ID NO 24
<211> LENGTH: 1532
<212> TYPE: DNA
<213> ORGANISM: Uzinura diaspidicola

<400> SEQUENCE: 24

```
aaaggagata ttccaaccac accttccggt acggttacct tgttacgact tagccctagt     60
catcaagttt accttaggca gaccactgaa ggattactga cttcaggtac ccccgactcc    120
catggcttga cgggcggtgt gtacaaggtt cgagaacata ttcaccgcgc cattgctgat    180
gcgcgattac tagcgattcc tgcttcatag agtcgaattg cagactccaa tccgaactga    240
```

```
gactggtttt agagattagc tcctgatcac ccagtggctg ccctttgtaa ccagccattg    300
tagcacgtgt gtagcccaag gcatagaggc catgatgatt tgacatcatc cccaccttcc    360
tcacagttta caccggcagt tttgttagag tccccggctt tacccgatgg caactaacaa    420
taggggttgc gctcgttata ggacttaacc aaacacttca cagcacgaac tgaagacaac    480
catgcagcac cttgtaatac gtcgtataga ctaagctgtt tccagcttat tcgtaataca    540
tttaagcctt ggtaaggttc ctcgcgtatc atcgaattaa accacatgct ccaccgcttg    600
tgcgaacccc cgtcaattcc tttgagtttc aatcttgcga ctgtacttcc caggtggatc    660
acttatcgct ttcgctaagc cactgaatat cgttttttcca atagctagtg atcatcgttt    720
agggcgtgga ctaccagggt atctaatcct gtttgctccc cacgctttcg tgcactgagc    780
gtcagtaaag atttagcaac ctgccttcgc tatcggtgtt ctgtatgata tctatgcatt    840
tcaccgctac accatacatt ccagatgctc caatcttact caagtttacc agtatcaata    900
gcaattttac agtaagctg taagctttca ctactgactt aataaacagc ctacacaccc    960
tttaaaccca ataaatccga ataacgcttg tgtcatccgt attgccgcgg ctgctggcac   1020
ggaattagcc gacacttatt cgtatagtac cttcaatctc ctatcacgta agatatttta   1080
tttctataca aaagcagttt acaacctaaa agaccttcat cctgcacgcg acgtagctgg   1140
ttcagagttt cctccattga ccaatattcc tcactgctgc ctcccgtagg agtctggtcc   1200
gtgtctcagt accagtgtgg aggtacaccc tcttaggccc cctactgatc atagtcttgg   1260
tagagccatt acctcaccaa ctaactaatc aaacgcaggc tcatcttttg ccacctaagt   1320
tttaataaag gctccatgca gaaactttat attatggggg attaatcaga atttcttctg   1380 gctataccc agcaaaaggt agattgcata cgtgttactc acccattcgc cggtcgccga   1440
caaattaaaa atttttcgat gccctcgac ttgcatgtgt taagctcgcc gctagcgtta   1500
attctgagcc aggatcaaac tcttcgttgt ag                                  1532
```

<210> SEQ ID NO 25
<211> LENGTH: 1470
<212> TYPE: DNA
<213> ORGANISM: Sulcia muelleri

<400> SEQUENCE: 25

```
ctcaggataa acgctagcgg agggcttaac acatgcaagt cgaggggcag caaaaataat     60 tattttggc gaccggcaaa cgggtgagta atacatacgt aactttcctt atgctgagga    120
atagcctgag gaaacttgga ttaataccttc ataatacaat ttttagaaa gaaaaattgt    180 taaagtttta ttatggcata agataggcgt atgtccaatt agttagttgg taaggtaatg    240
gcttaccaag acgatgattg gtaggggcc tgagaggggc gttcccccac attggtactg    300
agacacggac caaacttcta cggaaggctg cagtgaggaa tattggtcaa tggaggaaac    360
tctgaaccag ccactccgcg tgcaggatga agaaagcct tattggttgt aaactgcttt    420
tgtatatgaa taaaaattc taattataga ataattgaa ggtaatatac gataagtat     480 cgactaactc tgtgccagca gtcgcggtaa gacagaggac acaagcgtta tccggattta    540
ttgggtttaa agggtgcgta ggcggttttt aaagtcagta gtgaaatctt aaagcttaac    600
tttaaaagtg ctattgatac tgaaaaacta gagtaaggtt ggagtaactg gaatgtgtgg    660
tgtagcggtg aaatgcatag atatcacaca gaacaccgat agcgaaagca agttactaac    720
cctatactga cgctgagtca cgaaagcatg gggagcaaac aggattagat accctggtag    780
```

```
tccatgccgt aaacgatgat cactaactat tgggttttat acgttgtaat tcagtggtga    840
agcgaaagtg ttaagtgatc cacctgagga gtacgaccgc aaggttgaaa ctcaaaggaa    900 ttgacgggg cccgcacaat cggtggagca tgtggtttaa ttcgatgata cacgaggaac     960
cttaccaaga cttaaatgta ctacgaataa attggaaaca atttagtcaa gcgacggagt   1020
acaaggtgct gcatggttgt cgtcagctcg tgccgtgagg tgtaaggtta agtcctttaa   1080
acgagcgcaa cccttattat tagttgccat cgagtaatgt caggggactc taataagact   1140
gccggcgcaa gccgagagga aggtggggat gacgtcaaat catcacggcc cttacgtctt   1200
gggccacaca cgtgctacaa tgatcggtac aaaagggagc gactgggtga ccaggagcaa   1260
atccagaaag ccgatctaag ttcggattgg agtctgaaac tcgactccat gaagctggaa   1320
tcgctagtaa tcgtgcatca gccatggcac ggtgaatatg ttcccgggcc ttgtacacac   1380
cgcccgtcaa gccatggaag ttggaagtac ctaaagttgg ttcgctacct aaggtaagtc   1440
taataactgg ggctaagtcg taacaaggta                                    1470

<210> SEQ ID NO 26
<211> LENGTH: 1761
<212> TYPE: DNA
<213> ORGANISM: Symbiotaphrina buchneri
<220> FEATURE:
<221> NAME/KEY: misc_feature
<222> LOCATION: (30)..(30)
<223> OTHER INFORMATION: n is a, g, c, or t
<220> FEATURE:
<221> NAME/KEY: misc_feature
<222> LOCATION: (40)..(40)
<223> OTHER INFORMATION: n is a, g, c, or t

<400> SEQUENCE: 26
agattaagcc atgcaagtct aagtataagn aatctatacn gtgaaactgc gaatggctca     60
ttaaatcagt tatcgtttat ttgatagtac cttactacat ggataaccgt ggtaattcta    120
gagctaatac atgctaaaaa ccccgacttc ggaaggggtg tatttattag ataaaaaacc    180
aatgcccttc ggggctcctt ggtgattcat gataacttaa cgaatcgcat ggccttgcgc    240
cggcgatggt tcattcaaat ttctgcccta tcaactttcg atggtaggat agtggcctac    300
catggtttta acgggtaacg gggaattagg gttcgattcc ggagagggag cctgagaaac    360
ggctaccaca tccaaggaag gcagcaggcg cgcaaattac ccaatcccga cacggggagg    420
tagtgacaat aaatactgat acagggctct tttgggtctt gtaattggaa tgagtacaat    480
ttaaatccct taacgaggaa caattggagg gcaagtctgg tgccagcagc cgcggtaatt    540
ccagctccaa tagcgtatat taaagttgtt gcagttaaaa agctcgtagt tgaaccttgg    600
gcctggctgg ccggtccgcc taaccgcgtg tactggtccg gccgggcctt tccttctggg    660
gagccgcatg cccttcactg ggtgtgtcgg ggaaccagga cttttacttt gaaaaaatta    720
gagtgttcaa agcaggccta tgctcgaata cattagcatg gaataataga ataggacgtg    780
cggttctatt ttgttggttt ctaggaccgc cgtaatgatt aatagggata gtcggggca    840 tcagtattca attgtcagag gtgaaattct tggatttatt gaagactaac tactgcgaaa    900
gcatttgcca aggatgtttt cattaatcag tgaacgaaag ttaggggatc gaagacgatc    960
agataccgtc gtagtcttaa ccataaacta tgccgactag ggatcgggcg atgttattat   1020
tttgactcgc tcggcacctt acgagaaatc aaagtctttg ggttctgggg ggagtatggt   1080
cgcaaggctg aaacttaaag aaattgacgg aagggcacca ccaggagtgg agcctgcggc   1140
ttaatttgac tcaacacggg gaaactcacc aggtccagac acattaagga ttgacagatt   1200
```

-continued

```
gagagctctt tcttgattat gtgggtggtg gtgcatggcc gttcttagtt ggtggagtga      1260
tttgtctgct taattgcgat aacgaacgag accttaacct gctaaatagc ccggtccgct      1320
ttggcgggcc gctggcttct tagagggact atcggctcaa gccgatggaa gtttgaggca      1380
ataacaggtc tgtgatgccc ttagatgttc tgggccgcac gcgcgctaca ctgacagagc      1440
caacgagtaa atcaccttgg ccggaaggtc tgggtaatct tgttaaactc tgtcgtgctg      1500
gggatagagc attgcaatta ttgctcttca acgaggaatt cctagtaagc gcaagtcatc      1560
agcttgcgct gattacgtcc ctgcccttg tacacaccgc ccgtcgctac taccgattga      1620
atggctcagt gaggccttcg gactggcaca gggacgttgg caacgacgac ccagtgccgg      1680
aaagttggtc aaacttggtc atttagagga agtaaaagtc gtaacaaggt ttccgtaggt      1740
gaacctgcgg aaggatcatt a                                               1761
```

<210> SEQ ID NO 27
<211> LENGTH: 1801
<212> TYPE: DNA
<213> ORGANISM: Symbiotaphrina kochii
<220> FEATURE:
<221> NAME/KEY: misc_feature
<222> LOCATION: (1753)..(1755)
<223> OTHER INFORMATION: n is a, g, c, or t

<400> SEQUENCE: 27

```
tacctggttg attctgccag tagtcatatg cttgtctcaa agattaagcc atgcaagtct        60
aagtataagc aatctatacg gtgaaactgc gaatggctca ttaaatcagt tatcgtttat       120
ttgatagtac cttactacat ggataaccgt ggtaattcta gagctaatac atgctaaaaa       180
cctcgacttc ggaaggggtg tatttattag ataaaaaacc aatgcccttc ggggctcctt       240
ggtgattcat gataacttaa cgaatcgcat ggccttgcgc cggcgatggt tcattcaaat       300
ttctgcccta tcaactttcg atggtaggat agtggcctac catggtttca acgggtaacg       360
gggaattagg gttcgattcc ggagagggag cctgagaaac ggctaccaca tccaaggaag       420
gcagcaggcg cgcaaattac ccaatcccga cacggggagg tagtgacaat aaatactgat       480
acagggctct tttgggtctt gtaattggaa tgagtacaat ttaaatccct aacgaggaa       540 caattggagg gcaagtctgg tgccagcagc cgcggtaatt ccagctccaa tagcgtatat       600
taaagttgtt gcagttaaaa agctcgtagt tgaaccttgg gcctggctgg ccggtccgcc       660
taaccgcgtg tactggtccg gccgggcctt tccttctggg gagccgcatg cccttcactg       720
ggtgtgtcgg ggaaccagga cttttacttt gaaaaaatta gagtgttcaa gcaggccta       780 tgctcgaata cattagcatg gaataataga ataggacgtg tggttctatt ttgttggttt       840
ctaggaccgc cgtaatgatt aatagggata gtcggggca tcagtattca attgtcagag       900
gtgaaattct tggatttatt gaagactaac tactgcgaaa gcatttgcca aggatgtttt       960
cattaatcag tgaacgaaag ttaggggatc gaagacgatc agataccgtc gtagtcttaa      1020
ccataaacta tgccgactag ggatcgggcg atgttattat tttgactcgc tcggcaccct      1080
acgagaaatc aaagtctttg ggttctgggg ggagtatggt cgcaaggctg aaacttaaag      1140
aaattgacgg aagggcacca ccaggagtgg agcctgcggc ttaatttgac tcaacacggg      1200
gaaactcacc aggtccagac acattaagga ttgacagatt gagagctctt tcttgattat      1260
gtgggtggtg gtgcatggcc gttcttagtt ggtggagtga tttgtctgct taattgcgat      1320
aacgaacgag accttaacct gctaaatagc ccggtccgct ttggcgggcc gctggcttct      1380
```

| | |
|---|---|
| tagagggact atcggctcaa gccgatggaa gtttgaggca ataacaggtc tgtgatgccc | 1440 |
| ttagatgttc tgggccgcac gcgcgctaca ctgacagagc caacgagtac atcaccttgg | 1500 |
| ccggaaggtc tgggtaatct tgttaaactc tgtcgtgctg gggatagagc attgcaatta | 1560 |
| ttgctcttca acgaggaatt cctagtaagc gcaagtcatc agcttgcgct gattacgtcc | 1620 |
| ctgccctttg tacacaccgc ccgtcgctac taccgattga atggctcagt gaggccttcg | 1680 |
| gactggcaca gggacgttgg caacgacgac ccagtgccgg aaagttcgtc aaacttggtc | 1740 |
| atttagagga agnnnaagtc gtaacaaggt ttccgtaggt gaacctgcgg aaggatcatt | 1800 |
| a | 1801 |

<210> SEQ ID NO 28
<211> LENGTH: 1490
<212> TYPE: DNA
<213> ORGANISM: Burkholderia sp. SFA1

<400> SEQUENCE: 28

| | |
|---|---|
| agtttgatcc tggctcagat tgaacgctgg cggcatgcct tacacatgca agtcgaacgg | 60 |
| cagcacgggg gcaaccctgg tggcgagtgg cgaacgggtg agtaatacat cggaacgtgt | 120 |
| cctgtagtgg gggatagccc ggcgaaagcc ggattaatac cgcatacgac ctaagggaga | 180 |
| aagcggggga tcttcggacc tcgcgctata ggggcggccg atggcagatt agctagttgg | 240 |
| tggggtaaag gcctaccaag cgacgatct gtagctggtc tgagaggacg accagccaca | 300 |
| ctgggactga gacacggccc agactcctac gggaggcagc agtggggaat tttggacaat | 360 |
| gggggcaacc ctgatccagc aatgccgcgt gtgtgaagaa ggcttcgggt tgtaaagcac | 420 |
| ttttgtccgg aaagaaaact cgtccctaa tatggatgga ggatgacggt accggaagaa | 480 |
| taagcaccgg ctaactacgt gccagcagcc gcggtaatac gtagggtgcg agcgttaatc | 540 |
| ggaattactg ggcgtaaagc gtgcgcaggc ggtctgttaa gaccgatgtg aaatccccgg | 600 |
| gcttaacctg gaactgcat tggtgactgg caggctttga gtgtggcaga ggggggtaga | 660 |
| attccacgtg tagcagtgaa atgcgtagag atgtggagga ataccgatgg cgaaggcagc | 720 |
| cccctgggcc aactactgac gctcatgcac gaaagcgtgg ggagcaaaca ggattagata | 780 |
| ccctggtagt ccacgcccta acgatgtca actagttgtt ggggattcat ttccttagta | 840 |
| acgtagctaa cgcgtgaagt tgaccgcctg gggagtacgg tcgcaagatt aaaactcaaa | 900 |
| ggaattgacg gggacccgca caagcggtgg atgatgtgga ttaattcgat gcaacgcgaa | 960 |
| aaaccttacc taccttgac atggtcgaa ccctgctgaa aggtggggt gctcgaaaga | 1020 |
| gaaccggcgc acaggtgctg catggctgtc gtcagctcgt gtcgtgagat gttgggttaa | 1080 |
| gtcccgcaac gagcgcaacc cttgtcctta gttgctacgc aagagcactc taaggagact | 1140 |
| gccggtgaca aaccggagga aggtggggat gacgtcaagt cctcatggcc cttatgggta | 1200 |
| gggcttcaca cgtcatacaa tggtcggaac agagggttgc caagccgcga ggtggagcca | 1260 |
| atcccagaaa accgatcgta gtccggatcg cagtctgcaa ctcgactgcg tgaagctgga | 1320 |
| atcgctagta atcgcggatc agcatgccgc ggtgaatacg ttcccgggtc ttgtacacac | 1380 |
| cgcccgtcac accatgggag tgggtttcac cagaagtagg tagcctaacc gcaaggaggg | 1440 |
| cgcttaccac ggtgggattc atgactgggg tgaagtcgta acaaggtagc | 1490 |

<210> SEQ ID NO 29
<211> LENGTH: 1408
<212> TYPE: DNA
<213> ORGANISM: Burkholderia sp. KM-A

<400> SEQUENCE: 29

```
gcaaccctgg tggcgagtgg cgaacgggtg agtaatacat cggaacgtgt cctgtagtgg      60
gggatagccc ggcgaaagcc ggattaatac cgcatacgat ctacggaaga aagcggggga     120
tccttcggga cctcgcgcta tagggcggc cgatggcaga ttagctagtt ggtggggtaa      180
aggcctacca aggcgacgat ctgtagctgg tctgagagga cgaccagcca cactgggact     240
gagacacggc ccagactcct acgggaggca gcagtgggga attttggaca atggggcaa     300
ccctgatcca gcaatgccgc gtgtgtgaag aaggccttcg ggttgtaaag cacttttgtc     360
cggaaagaaa acgtcttggt taatacctga ggcggatgac ggtaccggaa gaataagcac     420
cggctaacta cgtgccagca gccgcggtaa tacgtagggt gcgagcgtta atcggaatta     480
ctgggcgtaa agcgtgcgca ggcggtctgt taagaccgat gtgaaatccc cgggcttaac     540
ctgggaactg cattggtgac tggcaggctt tgagtgtggc agagggggt agaattccac      600
gtgtagcagt gaaatgcgta gagatgtgga ggaataccga tggcgaaggc agccccctgg     660
gccaacactg acgctcatgc acgaaagcgt ggggagcaaa caggattaga taccctggta     720
gtccacgccc taaacgatgt caactagttg ttggggattc atttccttag taacgtagct     780
aacgcgtgaa gttgaccgcc tggggagtac ggtcgcaaga ttaaaactca aaggaattga     840
cggggacccg cacaagcggt ggatgatgtg gattaattcg atgcaacgcg aaaaaccta     900
cctaccttg acatggtcgg aagtctgctg agaggtggac gtgctcgaaa gagaaccggc     960
gcacaggtgc tgcatggctg tcgtcagctc gtgtcgtgag atgttgggtt aagtcccgca    1020
acgagcgcaa cccttgtcct tagttgctac gcaagagcac tctaaggaga ctgccggtga    1080
caaaccggag gaaggtgggg atgacgtcaa gtcctcatgg cccttatggg tagggcttca    1140
cacgtcatac aatggtcgga acagagggtt gccaagccgc gaggtggagc caatcccaga    1200
aaaccgatcg tagtccggat cgcagtctgc aactcgactg cgtgaagctg gaatcgctag    1260
taatcgcgga tcagcatgcc gcggtgaata cgttcccggg tcttgtacac accgcccgtc    1320
acaccatggg agtgggtttc accagaagta ggtagcctaa ccgcaaggag ggcgcttacc    1380
acggtgggat tcatgactgg ggtgaagt                                        1408
```

<210> SEQ ID NO 30
<211> LENGTH: 1383
<212> TYPE: DNA
<213> ORGANISM: Burkholderia sp. KM-G

<400> SEQUENCE: 30

```
gcaaccctgg tggcgagtgg cgaacgggtg agtaatacat cggaacgtgt cctgtagtgg      60
gggatagccc ggcgaaagcc ggattaatac cgcatacgac ctaagggaga aagcggggga     120
tcttcggacc tcgcgctata ggggcggccg atggcagatt agctagttgg tggggtaaag     180
gcctaccaag gcgacgatct gtagctggtc tgagaggacg accagccaca ctgggactga     240
gacacggccc agactcctac gggaggcagc agtggggaat tttggacaat ggggcaacc     300
ctgatccagc aatgccgcgt gtgtgaagaa ggccttcggg ttgtaaagca cttttgtccg     360
gaaagaaaac ttcgaggtta taccctggg aggatgacgg taccggaaga ataagcaccg     420
gctaactacg tgccagcagc cgcggtaata cgtagggtgc gagcgttaat cggaattact     480
gggcgtaaag cgtgcgcagg cggtctgtta agaccgatgt gaaatcccg ggcttaacct     540
gggaactgca ttggtgactg gcaggctttg agtgtggcag agggggtag aattccacgt     600
```

```
gtagcagtga aatgcgtaga gatgtggagg aataccgatg gcgaaggcag ccccctgggc      660
caacactgac gctcatgcac gaaagcgtgg ggagcaaaca ggattagata ccctggtagt      720
ccacgcccta aacgatgtca actagttgtt ggggattcat ttccttagta acgtagctaa      780
cgcgtgaagt tgaccgcctg gggagtacgg tcgcaagatt aaaactcaaa ggaattgacg      840
gggacccgca caagcggtgg atgatgtgga ttaattcgat gcaacgcgaa aaaccttacc      900 taccccttgac atggtcggaa gtctgctgag aggtggacgt gctcgaaaga gaaccggcgc      960
acaggtgctg catggctgtc gtcagctcgt gtcgtgagat gttgggttaa gtcccgcaac     1020
gagcgcaacc cttgtcctta gttgctacgc aagagcactc taaggagact gccggtgaca     1080
aaccggagga aggtggggat gacgtcaagt cctcatggcc cttatgggta gggcttcaca     1140
cgtcatacaa tggtcggaac agagggttgc caagccgcga ggtggagcca atcccagaaa     1200
accgatcgta gtccggatcg cagtctgcaa ctcgactgcg tgaagctgga atcgctagta     1260
atcgcggatc agcatgccgc ggtgaatacg ttcccgggtc ttgtacacac cgcccgtcac     1320
accatgggag tgggtttcac cagaagtagg tagcctaacc tgcaaggagg gcgcttacc     1380 acg                                                                  1383

<210> SEQ ID NO 31
<211> LENGTH: 538
<212> TYPE: DNA
<213> ORGANISM: Xiphinematobacter sp.

<400> SEQUENCE: 31
gcaagtcgaa cggagtggaa cctgcagtaa tgcagattcg attcagtggc gtacgggtgc       60
gtaacacgtg agtgatctac cggtaagtgg gggataaccc gccgaaaggc gaattaatac      120
cgcatgtggc tagggatgcc ttcatcctgt agctaaagtc gattttgacg cttctctgatg     180 agctcgcggc ctatcagctt gttggtggag gtaatggccc accaaggcaa tgacgggtag      240
ctggtctgag aggacgatca gccacactgg aactgagaca cggtccagac acctacgggt      300
ggcagcagtc gagaattttt cacaatgggg gaaaccctga tgaagcaacg ccgcgtggag      360
gatgaagggc ttcgcgctcg taaactcctg tcaagcggga acaagaaagt gatagtaccg      420
ctagaggaag agacggctaa ctctgtgcca gcagccgcgg taatacagag gtctcgagcg      480
ttgttcggat ttattgggcg taaagggtgc gtaggcggtg tggcaagtca agtgtgaa        538

<210> SEQ ID NO 32
<211> LENGTH: 975
<212> TYPE: DNA
<213> ORGANISM: Wolbachia sp. wOo

<400> SEQUENCE: 32
atgacacaca taccggtttt actaaaagaa atgctatcgc aactttcacc acaaaatggt       60
agtgtatatg tggatgccac atttggagct ggaggatata gtaaagcaat attggagtca      120
gctgattgca gagtgtatgc aatcgacaga gatgaaacgg ttattaaatt ttataatagt      180
ttgaatacca agtaccacgg taaaataaaa ctatttattg aaaagtttag caatattcaa      240
actatactaa acagtagtaa tctcaaacac tttacagaac cttccgtcat tgtttcagct      300
ggaattcaga aaaaaaatgc aaggtcaagc accgagatga tacaaagtaa taccgtagat      360
ggagttgtgt tcgatatagg agtatcgtct atgcagcttg atgaagaaaa tagaggattt      420
tcatttttac ataacagtcc gcttgatatg cgcatggata cctcttctca cattaacgct      480
tcaatatttg ttaatgcctt acgcgaagaa gaaattgcaa acactatata tagctatgga      540
```

```
ggtgaacgtt attctcgcaa aattgcaaga gcaatagtga acgtacgtaa gaaaaaaact    600
atcgacacta catttgagct tgcagacatt gtacgttccg tggtatctcg cggaaaaagc    660
aagattgatc ctgcaactag gacatttcaa gcaatcagaa tatgggtaaa cgatgagctt    720
agagagcttg aaaagggtat taaagctgca tccaaaatct taaataggaa tggcaagctg    780
attgtcatta cttttcattc cttggaagat cgtatagtca agacctttt taaaggctta    840 tgtgagccaa aattcaccaa ctgtagaacg ttttctcttc tgaataaaaa agtaatcaag    900
gcaagcgcag aagaaataag tgcaaatcca cgtgcgcgtt cagcaaaact aagagctata    960
caaaggttat tatga                                                    975

<210> SEQ ID NO 33
<211> LENGTH: 1505
<212> TYPE: DNA
<213> ORGANISM: Snodgrassella alvi

<400> SEQUENCE: 33
gagagtttga tcctggctca gattgaacgc tggcggcatg ccttacacat gcaagtcgaa     60
cggcagcacg gagagcttgc tctctggtgg cgagtggcga acgggtgagt aatgcatcgg    120
aacgtaccga gtaatggggg ataactgtcc gaaaggatgg ctaataccgc atacgccctg    180 aggggggaaag cggggatcg aaagacctcg cgttatttga gcggccgatg ttggattagc    240
tagttggtgg ggtaaaggcc taccaaggcg acgatccata gcgggtctga gaggatgatc    300
cgccacattg ggactgagac acggcccaaa ctcctacggg aggcagcagt ggggaatttt    360
ggacaatggg gggaaccctg atccagccat gccgcgtgtc tgaagaaggc cttcgggttg    420 taaggactt tgttaggga agaaaagccg ggtgttaata ccatctgtg ctgacggtac     480 ctaaagaata agcaccggct aactacgtgc cagcagccgc ggtaatacgt agggtgcgag    540
cgttaatcgg aattactggg cgtaaagcga gcgcagacgg ttaattaagt cagatgtgaa    600
atccccgagc tcaacttggg acgtgcattt gaaactggtt aactagagtg tgtcagaggg    660
aggtagaatt ccacgtgtag cagtgaaatg cgtagagatg tggaggaata ccgatggcga    720
aggcagcctc ctgggataac actgacgttc atgctcgaaa gcgtgggtag caaacaggat    780 tagatacccct ggtagtccac gccctaaacg atgacaatta gctgttggga cactagatgt    840
cttagtagcg aagctaacgc gtgaaattgt ccgcctgggg agtacggtcg caagattaaa    900
actcaaagga attgacgggg acccgcacaa gcggtggatg atgtggatta attcgatgca    960
acgcgaagaa ccttacctgg tcttgacatg tacggaatct cttagagata ggagagtgcc   1020
ttcgggaacc gtaacacagg tgctgcatgg ctgtcgtcag ctcgtgtcgt gagatgttgg   1080
gttaagtccc gcaacgagcg caaccttgt cattagttgc catcattaag ttgggcactc   1140
taatgagact gccggtgaca aaccggagga aggtgggat gacgtcaagt cctcatggcc   1200
cttatgacca gggcttcaca cgtcatacaa tggtcggtac agagggtagc gaagccgcga   1260
ggtgaagcca atctcagaaa gccgatcgta gtccggattg cactctgcaa ctcgagtgca   1320
tgaagtcgga atcgctagta atcgcaggtc agcatactgc ggtgaatacg ttcccgggtc   1380
ttgtacacac cgcccgtcac accatgggag tgggggatac cagaattggg tagactaacc   1440
gcaaggaggt cgcttaacac ggtatgcttc atgactgggg tgaagtcgta acaaggtagc   1500
cgtag                                                              1505

<210> SEQ ID NO 34
```

```
<211> LENGTH: 1541
<212> TYPE: DNA
<213> ORGANISM: Gilliamella apicola

<400> SEQUENCE: 34
ttaaattgaa gagtttgatc atggctcaga ttgaacgctg gcggcaggct taacacatgc      60
aagtcgaacg gtaacatgag tgcttgcact tgatgacgag tggcggacgg gtgagtaaag     120
tatggggatc tgccgaatgg agggggacaa cagttggaaa cgactgctaa taccgcataa     180
agttgagaga ccaaagcatg ggaccttcgg gccatgcgcc atttgatgaa cccatatggg     240
attagctagt tggtagggta atggcttacc aaggcgacga tctctagctg gtctgagagg     300
atgaccagcc acactggaac tgagacacgg tccagactcc tacgggaggc agcagtgggg     360
aatattgcac aatgggggaa accctgatgc agccatgccg cgtgtatgaa gaaggccttc     420
gggttgtaaa gtactttcgg tgatgaggaa ggtggtgtat ctaataggtg catcaattga     480
cgttaattac agaagaagca ccggctaact ccgtgccagc agccgcggta atacggaggg     540
tgcgagcgtt aatcggaatg actgggcgta aagggcatgt aggcggataa ttaagttagg     600
tgtgaaagcc ctgggctcaa cctaggaatt gcacttaaaa ctggttaact agagtattgt     660
agaggaaggt agaattccac gtgtagcggt gaaatgcgta gagatgtgga ggaataccgg     720
tggcgaaggc ggccttctgg acagatactg acgctgagat gcgaaagcgt ggggagcaaa     780
caggattaga taccctggta gtccacgctg taaacgatgt cgatttggag tttgttgcct     840
agagtgatgg gctccgaagc taacgcgata aatcgaccgc ctggggagta cggccgcaag     900
gttaaaactc aaatgaattg acgggggccc gcacaagcgg tggagcatgt ggtttaattc     960
gatgcaacgc gaagaacctt acctggtctt gacatccaca gaatcttgca gagatgcggg    1020
agtgccttcg ggaactgtga cacaggtgct gcatggctgt cgtcagctcg tgttgtgaaa    1080
tgttgggtta agtcccgcaa cgagcgcaac ccttatcctt gttgccatcg gttaggccg     1140
ggaactcaaa ggagactgcc gttgataaag cggaggaagg tggggacgac gtcaagtcat    1200
catggccctt acgaccaggg ctacacacgt gctacaatgg cgtatacaaa gggaggcgac    1260
ctcgcgagag caagcggacc tcataaagta cgtctaagtc cggattggag tctgcaactc    1320
gactccatga agtcggaatc gctagtaatc gtgaatcaga atgtcacggt gaatacgttc    1380
ccgggccttg tacaccgcc cgtcacacc atgggagtgg gttgcaccag aagtagatag      1440
cttaaccttc ggagggcgt ttaccacggt gtggtccatg actgggtga agtcgtaaca       1500
aggtaaccgt agggggaacct gcggttggat cacctcctta c                       1541

<210> SEQ ID NO 35
<211> LENGTH: 1528
<212> TYPE: DNA
<213> ORGANISM: Bartonella apis

<400> SEQUENCE: 35
aagccaaaat caaattttca acttgagagt ttgatcctgg ctcagaacga acgctggcgg      60
caggcttaac acatgcaagt cgaacgcact tttcggagtg agtggcagac gggtgagtaa     120
cgcgtgggaa tctacctatt tctacggaat aacgcagaga aatttgtgct aataccgtat     180
acgtccttcg ggagaaagat ttatcggaga tagatgagcc cgcgttggat tagctagttg     240
gtgaggtaat ggcccaccaa ggcgacgatc catagctggt ctgagaggat gaccagccac     300
attgggactg agacacggcc cagactccta cgggaggcag cagtgggaa tattggacaa      360
tgggcgcaag cctgatccag ccatgccgcg tgagtgatga aggccctagg gttgtaaagc     420
```

```
tctttcaccg gtgaagataa tgacggtaac cggagaagaa gccccggcta acttcgtgcc    480
agcagccgcg gtaatacgaa gggggctagc gttgttcgga tttactgggc gtaaagcgca    540
cgtaggcgga tatttaagtc aggggtgaaa tcccggggct caaccccgga actgcctttg    600
atactggata tcttgagtat ggaagaggta agtggaattc cgagtgtaga ggtgaaattc    660
gtagatattc ggaggaacac cagtggcgaa ggcggcttac tggtccatta ctgacgctga    720
ggtgcgaaag cgtggggagc aaacaggatt agataccctg gtagtccacg ctgtaaacga    780
tgaatgttag ccgttggaca gtttactgtt cggtggcgca gctaacgcat taaacattcc    840
gcctggggag tacggtcgca agattaaaac tcaaaggaat tgacggggc ccgcacaagc    900 ggtggagcat gtggtttaat tcgaagcaac gcgcagaacc ttaccagccc ttgacatccc    960
gatcgcggat ggtggagaca ccgtctttca gttcggctgg atcggtgaca ggtgctgcat   1020
ggctgtcgtc agctcgtgtc gtgagatgtt gggttaagtc ccgcaacgag cgcaaccctc   1080
gcccttagtt gccatcattt agttgggcac tctaagggga ctgccggtga taagccgaga   1140
ggaaggtggg gatgacgtca agtcctcatg gcccttacgg gctgggctac acacgtgcta   1200
caatggtggt gacagtgggc agcgagaccg cgaggtcgag ctaatctcca aaagccatct   1260
cagttcggat tgcactctgc aactcgagtg catgaagttg gaatcgctag taatcgtgga   1320
tcagcatgcc acggtgaata cgttcccggg ccttgtacac accgcccgtc acaccatggg   1380
agttggtttt acccgaaggt gctgtgctaa ccgcaaggag gcaggcaacc acggtagggt   1440
cagcgactgg ggtgaagtcg taacaaggta gccgtagggg aacctgcggc tggatcacct   1500
cctttctaag gaagatgaag aattggaa                                      1528

<210> SEQ ID NO 36
<211> LENGTH: 1390
<212> TYPE: DNA
<213> ORGANISM: Parasaccharibacter apium
<220> FEATURE:
<221> NAME/KEY: misc_feature
<222> LOCATION: (643)..(756)
<223> OTHER INFORMATION: n is a, g, c, or t

<400> SEQUENCE: 36
ctaccatgca agtcgcacga aacctttcgg ggttagtggc ggacgggtga gtaacgcgtt    60
aggaacctat ctggaggtgg gggataacat cgggaaactg gtgctaatac cgcatgatgc   120
ctgagggcca aaggagagat ccgccattgg aggggcctgc gttcgattag ctagttggtt   180
gggtaaaggc tgaccaaggc gatgatcgat agctggtttg agaggatgat cagccacact   240
gggactgaga cacggcccag actcctacgg gaggcagcag tggggaatat tggacaatgg   300
gggcaaccct gatccagcaa tgccgcgtgt gtgaagaagg tcttcggatt gtaaagcact   360
ttcactaggg aagatgatga cggtacctag agaagaagcc ccggctaact tcgtgccagc   420
agccgcggta atacgaaggg gctagcgtt gctcggaatg actgggcgta aagggcgcgt   480
aggctgtttg tacagtcaga tgtgaaatcc ccgggcttaa cctgggaact gcatttgata   540
cgtgcagact agagtccgag agagggttgt ggaattccca gtgtagaggt gaaattcgta   600
gatattggga agaacaccgg ttgcgaaggc ggcaacctgg ctnnnnnnnn nnnnnnnnnn    660
nnnnnnnnnn nnnnnnnnnn nnnnnnnnnn nnnnnnnnnn nnnnnnnnnn nnnnnnnnnn    720
nnnnnnnnnn nnnnnnnnnn nnnnnnnnnn nnnnnngagc taacgcgtta agcacaccgc    780
ctggggagta cggccgcaag gttgaaactc aaaggaattg acggggcccc gcacaagcgg    840
```

| | |
|---|---|
| tggagcatgt ggtttaattc gaagcaacgc gcagaacctt accagggctt gcatggggag | 900 |
| gctgtattca gagatggata tttcttcgga cctcccgcac aggtgctgca tggctgtcgt | 960 |
| cagctcgtgt cgtgagatgt tgggttaagt cccgcaacga gcgcaaccct tgtctttagt | 1020 |
| tgccatcacg tctgggtggg cactctagag agactgccgg tgacaagccg aggaaggtg | 1080 |
| gggatgacgt caagtcctca tggcccttat gtcctgggct acacacgtgc tacaatggcg | 1140 |
| gtgacagagg gatgctacat ggtgacatgg tgctgatctc aaaaaaccgt ctcagttcgg | 1200 |
| attgtactct gcaactcgag tgcatgaagg tggaatcgct agtaatcgcg gatcagcatg | 1260 |
| ccgcggtgaa tacgttcccg ggccttgtac acaccgcccg tcacaccatg ggagttggtt | 1320 |
| tgaccttaag ccggtgagcg aaccgcaagg aacgcagccg accaccggtt cgggttcagc | 1380 |
| gactggggga | 1390 |

<210> SEQ ID NO 37
<211> LENGTH: 1583
<212> TYPE: DNA
<213> ORGANISM: Lactobacillus kunkeei

<400> SEQUENCE: 37

| | |
|---|---|
| ttccttagaa aggaggtgat ccagccgcag gttctcctac ggctaccttg ttacgacttc | 60 |
| accctaatca tctgtcccac cttagacgac tagctcctaa aaggttaccc catcgtcttt | 120 |
| gggtgttaca aactctcatg gtgtgacggg cggtgtgtac aaggcccggg aacgtattca | 180 |
| ccgtggcatg ctgatccacg attactagtg attccaactt catgcaggcg agttgcagcc | 240 |
| tgcaatccga actgagaatg gctttaagag attagcttga cctcgcggtt tcgcgactcg | 300 |
| ttgtaccatc cattgtagca cgtgtgtagc ccagctcata aggggcatga tgatttgacg | 360 |
| tcgtccccac cttcctccgg tttatcaccg gcagtctcac tagagtgccc aactaaatgc | 420 |
| tggcaactaa taataagggt tgcgctcgtt gcgggactta acccaacatc tcacgacacg | 480 |
| agctgacgac aaccatgcac cacctgtcat tctgtccccg aagggaacgc caatctctt | 540 |
| gggttggcag aagatgtcaa gagctggtaa ggttcttcgc gtagcatcga attaaaccac | 600 |
| atgctccacc acttgtgcgg gccccgtca attcctttga gtttcaacct gcggtcgta | 660 |
| ctccccaggc ggaatactta atgcgttagc tgcggcactg aagggcggaa accctccaac | 720 |
| acctagtatt catcgtttac ggcatggact accagggtat ctaatcctgt tcgctaccca | 780 |
| tgctttcgag cctcagcgtc agtaacagac cagaaagccg ccttcgccac tggtgttctt | 840 |
| ccatatatct acgcatttca ccgctacaca tggagttcca cttcctcttt ctgtactcaa | 900 |
| gttttgtagt ttccactgca cttcctcagt tgagctgagg gctttcacag cagacttaca | 960 |
| aaaccgcctg cgctcgcttt acgcccaata aatccggaca acgcttgcca cctacgtatt | 1020 |
| accgcggctg ctggcacgta gttagccgtg gctttctggt taaataccgt caaagtgtta | 1080 |
| acagttactc taaacttgt tcttctttaa caacagagtt ttacgatccg aaaaccttca | 1140 |
| tcactcacgc ggcgttgctc catcagactt tcgtccattg tggaagattc cctactgctg | 1200 |
| cctcccgtag gagtctgggc cgtgtctcag tcccaatgtg gccgattacc ctctcaggtc | 1260 |
| ggctacgtat catcgtcttg gtgggctttt atctcaccaa ctaactaata cggcgcgggt | 1320 |
| ccatcccaaa gtgatagcaa agccatcttt caagttggaa ccatgcggtt ccaactaatt | 1380 |
| atgcggtatt agcacttgtt tccaaatgtt atccccgct tcgggcagg ttacccacgt | 1440 |
| gttactcacc agttcgccac tcgctccgaa tccaaaaatc atttatgcaa gcataaaatc | 1500 |
| aatttgggag aactcgttcg acttgcatgt attaggcacg ccgccagcgt tcgtcctgag | 1560 | ccaggatcaa actctcatct taa                                              1583

<210> SEQ ID NO 38
<211> LENGTH: 1395
<212> TYPE: DNA
<213> ORGANISM: Lactobacillus Firm-4

<400> SEQUENCE: 38
acgaacgctg gcggcgtgcc taatacatgc aagtcgagcg cgggaagtca gggaagcctt      60
cgggtggaac tggtggaacg agcggcggat gggtgagtaa cacgtaggta acctgcccta     120
aagcggggga taccatctgg aaacaggtgc taataccgca taaacccagc agtcacatga     180
gtgctggttg aaagacggct tcggctgtca ctttaggatg gacctgcggc gtattagcta     240
gttggtggag taacggttca ccaaggcaat gatacgtagc cgacctgaga gggtaatcgg     300
ccacattggg actgagacac ggcccaaact cctacgggag gcagcagtag ggaatcttcc     360
acaatggacg caagtctgat ggagcaacgc cgcgtggatg aagaaggtct tcggatcgta     420
aaatcctgtt gttgaagaag aacggttgtg agagtaactg ctcataacgt gacggtaatc     480
aaccagaaag tcacggctaa ctacgtgcca gcagccgcgg taatacgtag gtggcaagcg     540
ttgtccggat ttattgggcg taaagggagc gcaggcggtc ttttaagtct gaatgtgaaa     600
gccctcagct taactgagga agagcatcgg aaactgagag acttgagtgc agaagaggag     660
agtggaactc catgtgtagc ggtgaaatgc gtagatatat ggaagaacac cagtggcgaa     720
ggcggctctc tggtctgtta ctgacgctga ggctcgaaag catgggtagc gaacaggatt     780
agataccctg gtagtccatg ccgtaaacga tgagtgctaa gtgttgggag gtttccgcct     840
ctcagtgctg cagctaacgc attaagcact ccgcctgggg agtacgaccg caaggttgaa     900
actcaaagga attgacgggg gcccgcacaa gcggtggagc atgtggttta attcgaagca     960
acgcgaagaa ccttaccagg tcttgacatc tcctgcaagc ctaagagatt aggggttccc    1020
ttcggggaca ggaagacagg tggtgcatgg ttgtcgtcag ctcgtgtcgt gagatgttgg    1080
gttaagtccc gcaacgagcg caaccccttgt tactagttgc cagcattaag ttgggcactc    1140
tagtgagact gccggtgaca aaccggagga aggtgggac gacgtcaaat catcatgccc     1200
cttatgacct gggctacaca cgtgctacaa tggatggtac aatgagaagc gaactcgcga    1260
ggggaagctg atctctgaaa accattctca gttcggattg caggctgcaa ctcgcctgca    1320
tgaagctgga atcgctagta atcgcggatc agcatgccgc ggtgaatacg ttcccgggcc    1380
ttgtacacac cgccc                                                    1395

<210> SEQ ID NO 39
<211> LENGTH: 1549
<212> TYPE: DNA
<213> ORGANISM: Enterococcus

<400> SEQUENCE: 39
aggtgatcca gccgcacctt ccgatacggc taccttgtta cgacttcacc ccaatcatct      60
atcccacctt aggcggctgg ctccaaaaag gttacctcac cgacttcggg tgttacaaac     120
tctcgtggtg tgacgggcgg tgtgtacaag gcccgggaac gtattcaccg cggcgtgctg     180
atccgcgatt actagcgatt ccggcttcat gcaggcgagt tgcagcctgc aatccgaact     240
gagagaagct ttaagagatt tgcatgacct cgcggtctag cgactcgttg tacttcccat     300
tgtagcacgt gtgtagccca ggtcataagg ggcatgatga tttgacgtca tccccacctt     360

```
cctccggttt gtcaccggca gtctcgctag agtgcccaac taaatgatgg caactaacaa      420
taagggttgc gctcgttgcg ggacttaacc caacatctca cgacacgagc tgacgacaac      480
catgcaccac ctgtcacttt gtccccgaag ggaaagctct atctctagag tggtcaaagg      540
atgtcaagac ctggtaaggt tcttcgcgtt gcttcgaatt aaaccacatg ctccaccgct      600
tgtgcgggcc cccgtcaatt cctttgagtt tcaaccttgc ggtcgtactc cccaggcgga      660
gtgcttaatg cgtttgctgc agcactgaag ggcggaaacc ctccaacact tagcactcat      720
cgtttacggc gtggactacc agggtatcta atcctgtttg ctccccacgc tttcgagcct      780
cagcgtcagt tacagaccag agagccgcct tcgccactgg tgttcctcca tatatctacg      840
catttcaccg ctacacatgg aattccactc tcctcttctg cactcaagtc tcccagtttc      900
caatgaccct ccccggttga ccgggggct ttcacatcag acttaagaaa ccgcctgcgc       960
tcgctttacg cccaataaat ccggacaacg cttgccacct acgtattacc gcggctgctg      1020
gcacgtagtt agccgtggct ttctggttag ataccgtcag gggacgttca gttactaacg      1080
tccttgttct tctctaacaa cagagtttta cgatccgaaa accttcttca ctcacgcggc      1140
gttgctcggt cagactttcg tccattgccg aagattccct actgctgcct cccgtaggag      1200
tctgggccgt gtctcagtcc cagtgtggcc gatcaccctc tcaggtcggc tatgcatcgt      1260
ggccttggtg agccgttacc tcaccaacta gctaatgcac cgcgggtcca tccatcagcg      1320
acacccgaaa gcgcctttca ctcttatgcc atgcggcata aactgttatg cggtattagc      1380
acctgtttcc aagtgttatc cccctctgat gggtaggtta cccacgtgtt actcacccgt      1440
ccgccactcc tctttccaat tgagtgcaag cactcgggag gaaagaagcg ttcgacttgc      1500
atgtattagg cacgccgcca gcgttcgtcc tgagccagga tcaaactct                 1549

<210> SEQ ID NO 40
<211> LENGTH: 1541
<212> TYPE: DNA
<213> ORGANISM: Delftia

<400> SEQUENCE: 40
cagaaaggag gtgatccagc cgcaccttcc gatacggcta ccttgttacg acttcacccc       60
agtcacgaac cccgccgtgg taagcgccct ccttgcggtt aggctaccta cttctggcga      120
gacccgctcc catggtgtga cgggcggtgt gtacaagacc cgggaacgta ttcaccgcgg      180
catgctgatc cgcgattact agcgattccg acttcacgca gtcgagttgc agactgcgat      240
ccggactacg actggtttta tgggattagc tccccctcgc gggttggcaa ccctctgtac      300
cagccattgt atgacgtgtg tagccccacc tataagggcc atgaggactt gacgtcatcc      360
ccaccttcct ccggtttgtc accggcagtc tcattagagt gctcaactga atgtagcaac      420
taatgacaag ggttgcgctc gttgcgggac ttaacccaac atctcacgac acgagctgac      480
gacagccatg cagcacctgt gtgcaggttc tctttcgagc acgaatccat ctctggaaac      540
ttcctgccat gtcaaaggtg ggtaaggttt ttcgcgttgc atcgaattaa accacatcat      600
ccaccgcttg tgcgggtccc cgtcaattcc tttgagtttc aaccttgcgg ccgtactccc      660
caggcggtca acttcacgcg ttagcttcgt tactgagaaa actaattccc aacaaccagt      720
tgacatcgtt tagggcgtgg actaccaggg tatctaatcc tgtttgctcc ccacgctttc      780
gtgcatgagc gtcagtacag gtccagggga ttgccttcgc catcggtgtt cctccgcata      840
tctacgcatt tcactgctac acgcggaatt ccatcccct ctaccgtact ctagccatgc      900
agtcacaaat gcagttccca ggttgagccc ggggatttca catctgtctt acataaccgc      960
```

-continued

```
ctgcgcacgc tttacgccca gtaattccga ttaacgctcg caccctacgt attaccgcgg     1020
ctgctggcac gtagttagcc ggtgcttatt cttacggtac cgtcatgggc ccctgtatt     1080 agaaggagct ttttcgttcc gtacaaaagc agtttacaac ccgaaggcct tcatcctgca    1140
cgcggcattg ctggatcagg ctttcgccca ttgtccaaaa ttccccactg ctgcctcccg    1200
taggagtctg ggccgtgtct cagtcccagt gtggctggtc gtcctctcag accagctaca   1260
gatcgtcggc ttggtaagct tttatcccac caactaccta atctgccatc ggccgctcca   1320
atcgcgcgag gcccgaaggg ccccgctttt catcctcaga tcgtatgcgg tattagctac   1380
tctttcgagt agttatcccc cacgactggg cacgttccga tgtattactc acccgttcgc   1440
cactcgtcag cgtccgaaga cctgttaccg ttcgacttgc atgtgtaagg catgccgcca   1500
gcgttcaatc tgagccagga tcaaactcta cagttcgatc t                       1541
```

<210> SEQ ID NO 41
<211> LENGTH: 1502
<212> TYPE: DNA
<213> ORGANISM: Pelomonas
<220> FEATURE:
<221> NAME/KEY: misc_feature
<222> LOCATION: (192)..(193)
<223> OTHER INFORMATION: n is a, g, c, or t
<220> FEATURE:
<221> NAME/KEY: misc_feature
<222> LOCATION: (832)..(833)
<223> OTHER INFORMATION: n is a, g, c, or t

<400> SEQUENCE: 41

```
atcctggctc agattgaacg ctggcggcat gccttacaca tgcaagtcga acggtaacag     60
gttaagctga cgagtggcga acgggtgagt aatatatcgg aacgtgccca gtcgtggggg    120
ataactgctc gaaagagcag ctaataccgc atacgacctg agggtgaaag cggggatcg    180 caagacctcg cnngattgga gcggccgata tcagattagg tagttggtgg ggtaaaggcc   240
caccaagcca acgatctgta gctggtctga gaggacgacc agccacactg ggactgagac   300
acggcccaga ctcctacggg aggcagcagt ggggaatttt ggacaatggg cgcaagcctg   360
atccagccat gccgcgtgcg ggaagaaggc cttcgggttg taaaccgctt ttgtcaggga   420
agaaaaggtt ctggttaata cctgggactc atgacggtac ctgaagaata agcaccggct   480
aactacgtgc cagcagccgc ggtaatacgt agggtgcaag cgttaatcgg aattactggg   540
cgtaaagcgt gcgcaggcgg ttatgcaaga cagaggtgaa atccccgggc tcaacctggg   600
aactgccttt gtgactgcat agctagagta cggtagaggg ggatggaatt ccgcgtgtag   660
cagtgaaatg cgtagatatg cggaggaaca ccgatggcga aggcaatccc ctggacctgt   720
actgacgctc atgcacgaaa gcgtggggag caaacaggat tagataccct ggtagtccac   780
gccctaaacg atgtcaactg gttgttggga gggtttcttc tcagtaacgt anntaacgcg   840
tgaagttgac cgcctgggga gtacggccgc aaggttgaaa ctcaaaggaa ttgacgggga   900
cccgcacaag cggtggatga tgtggtttaa ttcgatgcaa cgcgaaaaac cttacctacc   960
cttgacatgc caggaatcct gaagagattt gggagtgctc gaaagagaac ctggacacag   1020
gtgctgcatg gccgtcgtca gctcgtgtcg tgagatgttg ggttaagtcc cgcaacgagc   1080
gcaacccttg tcattagttg ctacgaaagg gcactctaat gagactgccg gtgacaaacc   1140
ggaggaaggt ggggatgacg tcaggtcatc atggccctta tgggtagggc tacacacgtc   1200
atacaatggc cgggacagag ggctgccaac ccgcgagggg gagctaatcc cagaaacccg   1260
```

```
gtcgtagtcc ggatcgtagt ctgcaactcg actgcgtgaa gtcggaatcg ctagtaatcg    1320
cggatcagct tgccgcggtg aatacgttcc cgggtcttgt acacaccgcc cgtcacacca    1380
tgggagcggg ttctgccaga agtagttagc ctaaccgcaa ggagggcgat taccacggca    1440
gggttcgtga ctggggtgaa gtcgtaacaa ggtagccgta tcggaaggtg cggctggatc    1500
ac                                                                   1502

<210> SEQ ID NO 42
<211> LENGTH: 34
<212> TYPE: PRT
<213> ORGANISM: Lactococcus lactis

<400> SEQUENCE: 42

Ile Thr Ser Ile Ser Leu Cys Thr Pro Gly Cys Lys Thr Gly Ala Leu
1               5                   10                  15

Met Gly Cys Asn Met Lys Thr Ala Thr Cys His Cys Ser Ile His Val
            20                  25                  30

Ser Lys

<210> SEQ ID NO 43
<211> LENGTH: 22
<212> TYPE: PRT
<213> ORGANISM: Staphylococcus epidermis

<400> SEQUENCE: 43

Ile Ala Ser Lys Phe Ile Cys Thr Pro Gly Cys Ala Lys Thr Gly Ser
1               5                   10                  15

Phe Asn Ser Tyr Cys Cys
            20

<210> SEQ ID NO 44
<211> LENGTH: 44
<212> TYPE: PRT
<213> ORGANISM: Pediococcus acidilactici

<400> SEQUENCE: 44

Lys Tyr Tyr Gly Asn Gly Val Thr Cys Gly Lys His Ser Cys Ser Val
1               5                   10                  15

Asp Trp Gly Lys Ala Thr Thr Cys Ile Ile Asn Asn Gly Ala Met Ala
            20                  25                  30

Trp Ala Thr Gly Gly His Gln Gly Asn His Lys Cys
            35                  40

<210> SEQ ID NO 45
<211> LENGTH: 44
<212> TYPE: PRT
<213> ORGANISM: Enterococcus faecium

<400> SEQUENCE: 45

Ala Thr Arg Ser Tyr Gly Asn Gly Val Tyr Cys Asn Asn Ser Lys Cys
1               5                   10                  15

Trp Val Asn Trp Gly Glu Ala Lys Glu Asn Ile Ala Gly Ile Val Ile
            20                  25                  30

Ser Gly Trp Ala Ser Gly Leu Ala Gly Met Gly His
            35                  40

<210> SEQ ID NO 46
<211> LENGTH: 39
<212> TYPE: PRT
<213> ORGANISM: Streptococcus lactis
```

<400> SEQUENCE: 46

Gly Thr Trp Asp Asp Ile Gly Gln Gly Ile Gly Arg Val Ala Tyr Trp
1               5                   10                  15

Val Gly Lys Ala Met Gly Asn Met Ser Asp Val Asn Gln Ala Ser Arg
            20                  25                  30

Ile Asn Arg Lys Lys Lys His
        35

<210> SEQ ID NO 47
<211> LENGTH: 48
<212> TYPE: PRT
<213> ORGANISM: Lactobacillus johnsonii

<400> SEQUENCE: 47

Asn Arg Trp Gly Asp Thr Val Leu Ser Ala Ala Ser Gly Ala Gly Thr
1               5                   10                  15

Gly Ile Lys Ala Cys Lys Ser Phe Gly Pro Trp Gly Met Ala Ile Cys
            20                  25                  30

Gly Val Gly Gly Ala Ala Ile Gly Gly Tyr Phe Gly Tyr Thr His Asn
        35                  40                  45

<210> SEQ ID NO 48
<211> LENGTH: 70
<212> TYPE: PRT
<213> ORGANISM: Enterococcus faecalis

<400> SEQUENCE: 48

Met Ala Lys Glu Phe Gly Ile Pro Ala Ala Val Ala Gly Thr Val Leu
1               5                   10                  15

Asn Val Val Glu Ala Gly Gly Trp Val Thr Thr Ile Val Ser Ile Leu
            20                  25                  30

Thr Ala Val Gly Ser Gly Gly Leu Ser Leu Leu Ala Ala Ala Gly Arg
        35                  40                  45

Glu Ser Ile Lys Ala Tyr Leu Lys Lys Glu Ile Lys Lys Lys Gly Lys
    50                  55                  60

Arg Ala Val Ile Ala Trp
65                  70

<210> SEQ ID NO 49
<211> LENGTH: 51
<212> TYPE: PRT
<213> ORGANISM: Staphylococcus aureus

<400> SEQUENCE: 49

Met Ser Trp Leu Asn Phe Leu Lys Tyr Ile Ala Lys Tyr Gly Lys Lys
1               5                   10                  15

Ala Val Ser Ala Ala Trp Lys Tyr Lys Gly Lys Val Leu Glu Trp Leu
            20                  25                  30

Asn Val Gly Pro Thr Leu Glu Trp Val Trp Gln Lys Leu Lys Lys Ile
        35                  40                  45

Ala Gly Leu
    50

<210> SEQ ID NO 50
<211> LENGTH: 43
<212> TYPE: PRT
<213> ORGANISM: Lactococcus garvieae

<400> SEQUENCE: 50

```
Ile Gly Gly Ala Leu Gly Asn Ala Leu Asn Gly Leu Gly Thr Trp Ala
1               5                   10                  15

Asn Met Met Asn Gly Gly Phe Val Asn Gln Trp Gln Val Tyr Ala
            20                  25                  30

Asn Lys Gly Lys Ile Asn Gln Tyr Arg Pro Tyr
            35                  40
```

<210> SEQ ID NO 51
<211> LENGTH: 103
<212> TYPE: PRT
<213> ORGANISM: Escherichia coli

<400> SEQUENCE: 51

```
Met Arg Thr Leu Thr Leu Asn Glu Leu Asp Ser Val Ser Gly Gly Ala
1               5                   10                  15

Ser Gly Arg Asp Ile Ala Met Ala Ile Gly Thr Leu Ser Gly Gln Phe
            20                  25                  30

Val Ala Gly Gly Ile Gly Ala Ala Gly Gly Val Ala Gly Gly Ala
        35                  40                  45

Ile Tyr Asp Tyr Ala Ser Thr His Lys Pro Asn Pro Ala Met Ser Pro
50                  55                  60

Ser Gly Leu Gly Gly Thr Ile Lys Gln Lys Pro Glu Gly Ile Pro Ser
65                  70                  75                  80

Glu Ala Trp Asn Tyr Ala Ala Gly Arg Leu Cys Asn Trp Ser Pro Asn
                85                  90                  95

Asn Leu Ser Asp Val Cys Leu
            100
```

<210> SEQ ID NO 52
<211> LENGTH: 48
<212> TYPE: PRT
<213> ORGANISM: Homo sapiens

<400> SEQUENCE: 52

```
Ser Ser Leu Leu Glu Lys Gly Leu Asp Gly Ala Lys Lys Ala Val Gly
1               5                   10                  15

Gly Leu Gly Lys Leu Gly Lys Asp Ala Val Glu Asp Leu Glu Ser Val
            20                  25                  30

Gly Lys Gly Ala Val His Asp Val Lys Asp Val Leu Asp Ser Val Leu
        35                  40                  45
```

<210> SEQ ID NO 53
<211> LENGTH: 37
<212> TYPE: PRT
<213> ORGANISM: Hyalophora cecropia

<400> SEQUENCE: 53

```
Lys Trp Lys Leu Phe Lys Lys Ile Glu Lys Val Gly Gln Asn Ile Arg
1               5                   10                  15

Asp Gly Ile Ile Lys Ala Gly Pro Ala Val Ala Val Val Gly Gln Ala
            20                  25                  30

Thr Gln Ile Ala Lys
        35
```

<210> SEQ ID NO 54
<211> LENGTH: 62
<212> TYPE: PRT
<213> ORGANISM: Drosophila teissieri

```
<400> SEQUENCE: 54

Met Lys Tyr Phe Ser Val Leu Val Leu Thr Leu Ile Leu Ala Ile
1               5                   10                  15

Val Asp Gln Ser Asp Ala Phe Ile Asn Leu Leu Asp Lys Val Glu Asp
            20                  25                  30

Ala Leu His Thr Gly Ala Gln Ala Gly Phe Lys Leu Ile Arg Pro Val
        35                  40                  45

Glu Arg Gly Ala Thr Pro Lys Lys Ser Glu Lys Pro Glu Lys
    50                  55                  60

<210> SEQ ID NO 55
<211> LENGTH: 66
<212> TYPE: PRT
<213> ORGANISM: Bombyx mori

<400> SEQUENCE: 55

Met Asn Ile Leu Lys Phe Phe Val Phe Ile Val Ala Met Ser Leu
1               5                   10                  15

Val Ser Cys Ser Thr Ala Ala Pro Ala Lys Ile Pro Ile Lys Ala Ile
            20                  25                  30

Lys Thr Val Gly Lys Ala Val Gly Lys Gly Leu Arg Ala Ile Asn Ile
        35                  40                  45

Ala Ser Thr Ala Asn Asp Val Phe Asn Phe Leu Lys Pro Lys Lys Arg
    50                  55                  60

Lys His
65

<210> SEQ ID NO 56
<211> LENGTH: 71
<212> TYPE: PRT
<213> ORGANISM: Ceratitis capitata

<400> SEQUENCE: 56

Met Ala Asn Leu Lys Ala Val Phe Leu Ile Cys Ile Val Ala Phe Ile
1               5                   10                  15

Ala Leu Gln Cys Val Val Ala Glu Pro Ala Ala Glu Asp Ser Val Val
            20                  25                  30

Val Lys Arg Ser Ile Gly Ser Ala Leu Lys Lys Ala Leu Pro Val Ala
        35                  40                  45

Lys Lys Ile Gly Lys Ile Ala Leu Pro Ile Ala Lys Ala Ala Leu Pro
    50                  55                  60

Val Ala Ala Gly Leu Val Gly
65                  70

<210> SEQ ID NO 57
<211> LENGTH: 53
<212> TYPE: PRT
<213> ORGANISM: Apis mellifera

<400> SEQUENCE: 57

Met Lys Val Val Ile Phe Ile Phe Ala Leu Leu Ala Thr Ile Cys Ala
1               5                   10                  15

Ala Phe Ala Tyr Val Pro Leu Pro Asn Val Pro Gln Pro Gly Arg Arg
            20                  25                  30

Pro Phe Pro Thr Phe Pro Gly Gln Gly Pro Phe Asn Pro Lys Ile Lys
        35                  40                  45

Trp Pro Gln Gly Tyr
    50
```

<210> SEQ ID NO 58
<211> LENGTH: 283
<212> TYPE: PRT
<213> ORGANISM: Apis mellifera

<400> SEQUENCE: 58

Lys Asn Phe Ala Leu Ala Ile Leu Val Val Thr Phe Val Ala Val
1               5                   10                  15

Phe Gly Asn Thr Asn Leu Asp Pro Pro Thr Arg Pro Thr Arg Leu Arg
            20                  25                  30

Arg Glu Ala Lys Pro Glu Ala Glu Pro Gly Asn Asn Arg Pro Val Tyr
            35                  40                  45

Ile Pro Gln Pro Arg Pro Pro His Pro Arg Leu Arg Arg Glu Ala Glu
            50                  55                  60

Pro Glu Ala Glu Pro Gly Asn Asn Arg Pro Val Tyr Ile Pro Gln Pro
65                  70                  75                  80

Arg Pro Pro His Pro Arg Leu Arg Arg Glu Ala Glu Leu Glu Ala Glu
                85                  90                  95

Pro Gly Asn Asn Arg Pro Val Tyr Ile Ser Gln Pro Arg Pro Pro His
            100                 105                 110

Pro Arg Leu Arg Arg Glu Ala Glu Pro Glu Ala Glu Pro Gly Asn Asn
            115                 120                 125

Arg Pro Val Tyr Ile Pro Gln Pro Arg Pro Pro His Pro Arg Leu Arg
            130                 135                 140

Arg Glu Ala Glu Leu Glu Ala Glu Pro Gly Asn Asn Arg Pro Val Tyr
145                 150                 155                 160

Ile Ser Gln Pro Arg Pro Pro His Pro Arg Leu Arg Arg Glu Ala Glu
                165                 170                 175

Pro Glu Ala Glu Pro Gly Asn Asn Arg Pro Val Tyr Ile Pro Gln Pro
            180                 185                 190

Arg Pro Pro His Pro Arg Leu Arg Arg Glu Ala Glu Pro Glu Ala Glu
            195                 200                 205

Pro Gly Asn Asn Arg Pro Val Tyr Ile Pro Gln Pro Arg Pro Pro His
            210                 215                 220

Pro Arg Leu Arg Arg Glu Ala Glu Pro Glu Ala Glu Pro Gly Asn Asn
225                 230                 235                 240

Arg Pro Val Tyr Ile Pro Gln Pro Arg Pro Pro His Pro Arg Leu Arg
                245                 250                 255

Arg Glu Ala Lys Pro Glu Ala Lys Pro Gly Asn Asn Arg Pro Val Tyr
            260                 265                 270

Ile Pro Gln Pro Arg Pro Pro His Pro Arg Ile
            275                 280

<210> SEQ ID NO 59
<211> LENGTH: 228
<212> TYPE: PRT
<213> ORGANISM: Sus scrofa

<400> SEQUENCE: 59

Met Glu Thr Gln Arg Ala Ser Leu Cys Leu Gly Arg Trp Ser Leu Trp
1               5                   10                  15

Leu Leu Leu Leu Ala Leu Val Val Pro Ser Ala Ser Ala Gln Ala Leu
            20                  25                  30

Ser Tyr Arg Glu Ala Val Leu Arg Ala Val Asp Arg Leu Asn Glu Gln
            35                  40                  45

```
Ser Ser Glu Ala Asn Leu Tyr Arg Leu Leu Glu Leu Asp Gln Pro Pro
    50                  55                  60

Lys Ala Asp Glu Asp Pro Gly Thr Pro Lys Pro Val Ser Phe Thr Val
65                  70                  75                  80

Lys Glu Thr Val Cys Pro Arg Pro Thr Arg Arg Pro Pro Glu Leu Cys
                85                  90                  95

Asp Phe Lys Glu Asn Gly Arg Val Lys Gln Cys Val Gly Thr Val Thr
                100                 105                 110

Leu Asp Gln Ile Lys Asp Pro Leu Asp Ile Thr Cys Asn Glu Gly Val
            115                 120                 125

Arg Arg Phe Pro Trp Trp Pro Phe Leu Arg Arg Pro Arg Leu Arg
        130                 135                 140

Arg Gln Ala Phe Pro Pro Asn Val Pro Gly Pro Arg Phe Pro Pro
145                 150                 155                 160

Pro Asn Val Pro Gly Pro Arg Phe Pro Pro Asn Phe Pro Gly Pro
                165                 170                 175

Arg Phe Pro Pro Pro Asn Phe Pro Gly Pro Arg Phe Pro Pro Pro Asn
                180                 185                 190

Phe Pro Gly Pro Pro Phe Pro Pro Pro Ile Phe Pro Gly Pro Trp Phe
                195                 200                 205

Pro Pro Pro Pro Pro Phe Arg Pro Pro Pro Phe Gly Pro Pro Arg Phe
210                 215                 220

Pro Gly Arg Arg
225

<210> SEQ ID NO 60
<211> LENGTH: 144
<212> TYPE: PRT
<213> ORGANISM: Bos taurus

<400> SEQUENCE: 60

Met Gln Thr Gln Arg Ala Ser Leu Ser Leu Gly Arg Trp Ser Leu Trp
1               5                   10                  15

Leu Leu Leu Leu Gly Leu Val Val Pro Ser Ala Ser Ala Gln Ala Leu
            20                  25                  30

Ser Tyr Arg Glu Ala Val Leu Arg Ala Val Asp Gln Leu Asn Glu Leu
        35                  40                  45

Ser Ser Glu Ala Asn Leu Tyr Arg Leu Leu Glu Leu Asp Pro Pro Pro
    50                  55                  60

Lys Asp Asn Glu Asp Leu Gly Thr Arg Lys Pro Val Ser Phe Thr Val
65                  70                  75                  80

Lys Glu Thr Val Cys Pro Arg Thr Ile Gln Gln Pro Ala Glu Gln Cys
                85                  90                  95

Asp Phe Lys Glu Lys Gly Arg Val Lys Gln Cys Val Gly Thr Val Thr
                100                 105                 110

Leu Asp Pro Ser Asn Asp Gln Phe Asp Leu Asn Cys Asn Glu Leu Gln
            115                 120                 125

Ser Val Ile Leu Pro Trp Lys Trp Pro Trp Trp Pro Trp Arg Arg Gly
        130                 135                 140

<210> SEQ ID NO 61
<211> LENGTH: 149
<212> TYPE: PRT
<213> ORGANISM: Sus scrofa

<400> SEQUENCE: 61
```

```
Met Glu Thr Gln Arg Ala Ser Leu Cys Leu Gly Arg Trp Ser Leu Trp
1               5                   10                  15

Leu Leu Leu Leu Ala Leu Val Val Pro Ser Ala Ser Ala Gln Ala Leu
            20                  25                  30

Ser Tyr Arg Glu Ala Val Leu Arg Ala Val Asp Arg Leu Asn Glu Gln
        35                  40                  45

Ser Ser Glu Ala Asn Leu Tyr Arg Leu Leu Glu Leu Asp Gln Pro Pro
50                  55                  60

Lys Ala Asp Glu Asp Pro Gly Thr Pro Lys Pro Val Ser Phe Thr Val
65                  70                  75                  80

Lys Glu Thr Val Cys Pro Arg Pro Thr Arg Gln Pro Pro Glu Leu Cys
                85                  90                  95

Asp Phe Lys Glu Asn Gly Arg Val Lys Gln Cys Val Gly Thr Val Thr
            100                 105                 110

Leu Asp Gln Ile Lys Asp Pro Leu Asp Ile Thr Cys Asn Glu Val Gln
            115                 120                 125

Gly Val Arg Gly Gly Arg Leu Cys Tyr Cys Arg Arg Phe Cys Val
130                 135                 140

Cys Val Gly Arg Gly
145

<210> SEQ ID NO 62
<211> LENGTH: 17
<212> TYPE: PRT
<213> ORGANISM: Tachypleus gigas

<400> SEQUENCE: 62

Lys Trp Cys Phe Arg Val Cys Tyr Arg Gly Ile Cys Tyr Arg Arg Cys
1               5                   10                  15

Arg

<210> SEQ ID NO 63
<211> LENGTH: 102
<212> TYPE: PRT
<213> ORGANISM: Anopheles gambiae

<400> SEQUENCE: 63

Met Lys Cys Ala Thr Ile Val Cys Thr Ile Ala Val Val Leu Ala Ala
1               5                   10                  15

Thr Leu Leu Asn Gly Ser Val Gln Ala Ala Pro Gln Glu Glu Ala Ala
            20                  25                  30

Leu Ser Gly Gly Ala Asn Leu Asn Thr Leu Leu Asp Glu Leu Pro Glu
        35                  40                  45

Glu Thr His His Ala Ala Leu Glu Asn Tyr Arg Ala Lys Arg Ala Thr
50                  55                  60

Cys Asp Leu Ala Ser Gly Phe Gly Val Gly Ser Ser Leu Cys Ala Ala
65                  70                  75                  80

His Cys Ile Ala Arg Arg Tyr Arg Gly Gly Tyr Cys Asn Ser Lys Ala
                85                  90                  95

Val Cys Val Cys Arg Asn
            100

<210> SEQ ID NO 64
<211> LENGTH: 70
<212> TYPE: PRT
<213> ORGANISM: Drosophila melanogaster
```

<400> SEQUENCE: 64

Met Met Gln Ile Lys Tyr Leu Phe Ala Leu Phe Ala Val Leu Met Leu
1               5                   10                  15

Val Val Leu Gly Ala Asn Glu Ala Asp Ala Asp Cys Leu Ser Gly Arg
            20                  25                  30

Tyr Lys Gly Pro Cys Ala Val Trp Asp Asn Glu Thr Cys Arg Arg Val
        35                  40                  45

Cys Lys Glu Glu Gly Arg Ser Ser Gly His Cys Ser Pro Ser Leu Lys
    50                  55                  60

Cys Trp Cys Glu Gly Cys
65                  70

<210> SEQ ID NO 65
<211> LENGTH: 78
<212> TYPE: PRT
<213> ORGANISM: Buchnera aphidicola

<400> SEQUENCE: 65

Met Lys Leu Leu His Gly Phe Leu Ile Ile Met Leu Thr Met His Leu
1               5                   10                  15

Ser Ile Gln Tyr Ala Tyr Gly Gly Pro Phe Leu Thr Lys Tyr Leu Cys
            20                  25                  30

Asp Arg Val Cys His Lys Leu Cys Gly Asp Glu Phe Val Cys Ser Cys
        35                  40                  45

Ile Gln Tyr Lys Ser Leu Lys Gly Leu Trp Phe Pro His Cys Pro Thr
    50                  55                  60

Gly Lys Ala Ser Val Val Leu His Asn Phe Leu Thr Ser Pro
65                  70                  75

<210> SEQ ID NO 66
<211> LENGTH: 77
<212> TYPE: PRT
<213> ORGANISM: Buchnera aphidicola

<400> SEQUENCE: 66

Met Lys Leu Leu Tyr Gly Phe Leu Ile Ile Met Leu Thr Ile His Leu
1               5                   10                  15

Ser Val Gln Tyr Phe Glu Ser Pro Phe Glu Thr Lys Tyr Asn Cys Asp
            20                  25                  30

Thr His Cys Asn Lys Leu Cys Gly Lys Ile Asp His Cys Ser Cys Ile
        35                  40                  45

Gln Tyr His Ser Met Glu Gly Leu Trp Phe Pro His Cys Arg Thr Gly
    50                  55                  60

Ser Ala Ala Gln Met Leu His Asp Phe Leu Ser Asn Pro
65                  70                  75

<210> SEQ ID NO 67
<211> LENGTH: 86
<212> TYPE: PRT
<213> ORGANISM: Buchnera aphidicola

<400> SEQUENCE: 67

Met Ser Val Arg Lys Asn Val Leu Pro Thr Met Phe Val Leu Leu
1               5                   10                  15

Ile Met Ser Pro Val Thr Pro Thr Ser Val Phe Ile Ser Ala Val Cys
            20                  25                  30

Tyr Ser Gly Cys Gly Ser Leu Ala Leu Val Cys Phe Val Ser Asn Gly
        35                  40                  45

Ile Thr Asn Gly Leu Asp Tyr Phe Lys Ser Ser Ala Pro Leu Ser Thr
 50                  55                  60

Ser Glu Thr Ser Cys Gly Glu Ala Phe Asp Thr Cys Thr Asp His Cys
 65                  70                  75                  80

Leu Ala Asn Phe Lys Phe
                 85

<210> SEQ ID NO 68
<211> LENGTH: 69
<212> TYPE: PRT
<213> ORGANISM: Buchnera aphidicola

<400> SEQUENCE: 68

Met Arg Leu Leu Tyr Gly Phe Leu Ile Ile Met Leu Thr Ile Tyr Leu
 1               5                  10                  15

Ser Val Gln Asp Phe Asp Pro Thr Glu Phe Lys Gly Pro Phe Pro Thr
                 20                  25                  30

Ile Glu Ile Cys Ser Lys Tyr Cys Ala Val Val Cys Asn Tyr Thr Ser
             35                  40                  45

Arg Pro Cys Tyr Cys Val Glu Ala Ala Lys Glu Arg Asp Gln Trp Phe
 50                  55                  60

Pro Tyr Cys Tyr Asp
 65

<210> SEQ ID NO 69
<211> LENGTH: 77
<212> TYPE: PRT
<213> ORGANISM: Buchnera aphidicola

<400> SEQUENCE: 69

Met Arg Leu Leu Tyr Gly Phe Leu Ile Ile Met Leu Thr Ile His Leu
 1               5                  10                  15

Ser Val Gln Asp Ile Asp Pro Asn Thr Leu Arg Gly Pro Tyr Pro Thr
                 20                  25                  30

Lys Glu Ile Cys Ser Lys Tyr Cys Glu Tyr Asn Val Val Cys Gly Ala
             35                  40                  45

Ser Leu Pro Cys Ile Cys Val Gln Asp Ala Arg Gln Leu Asp His Trp
 50                  55                  60

Phe Ala Cys Cys Tyr Asp Gly Gly Pro Glu Met Leu Met
 65                  70                  75

<210> SEQ ID NO 70
<211> LENGTH: 108
<212> TYPE: PRT
<213> ORGANISM: Buchnera aphidicola

<400> SEQUENCE: 70

Met Lys Leu Phe Val Val Val Leu Val Ala Val Gly Ile Met Phe
 1               5                  10                  15

Val Phe Ala Ser Asp Thr Ala Ala Pro Thr Asp Tyr Glu Asp Thr
                 20                  25                  30

Asn Asp Met Ile Ser Leu Ser Ser Leu Val Gly Asp Asn Ser Pro Tyr
             35                  40                  45

Val Arg Val Ser Ser Ala Asp Ser Gly Gly Ser Ser Lys Thr Ser Ser
 50                  55                  60

Lys Asn Pro Ile Leu Gly Leu Leu Lys Ser Val Ile Lys Leu Leu Thr
 65                  70                  75                  80

```
Lys Ile Phe Gly Thr Tyr Ser Asp Ala Ala Pro Ala Met Pro Pro Ile
                85                  90                  95

Pro Pro Ala Leu Arg Lys Asn Arg Gly Met Leu Ala
            100                 105

<210> SEQ ID NO 71
<211> LENGTH: 178
<212> TYPE: PRT
<213> ORGANISM: Buchnera aphidicola

<400> SEQUENCE: 71

Met Val Ala Cys Lys Val Ile Leu Ala Val Ala Val Val Phe Val Ala
1               5                   10                  15

Ala Val Gln Gly Arg Pro Gly Gly Glu Pro Glu Trp Ala Ala Pro Ile
            20                  25                  30

Phe Ala Glu Leu Lys Ser Val Ser Asp Asn Ile Thr Asn Leu Val Gly
        35                  40                  45

Leu Asp Asn Ala Gly Glu Tyr Ala Thr Ala Ala Lys Asn Asn Leu Asn
    50                  55                  60

Ala Phe Ala Glu Ser Leu Lys Thr Glu Ala Ala Val Phe Ser Lys Ser
65                  70                  75                  80

Phe Glu Gly Lys Ala Ser Ala Ser Asp Val Phe Lys Glu Ser Thr Lys
                85                  90                  95

Asn Phe Gln Ala Val Val Asp Thr Tyr Ile Lys Asn Leu Pro Lys Asp
            100                 105                 110

Leu Thr Leu Lys Asp Phe Thr Glu Lys Ser Glu Gln Ala Leu Lys Tyr
        115                 120                 125

Met Val Glu His Gly Thr Glu Ile Thr Lys Lys Ala Gln Gly Asn Thr
    130                 135                 140

Glu Thr Glu Lys Glu Ile Lys Glu Phe Phe Lys Lys Gln Ile Glu Asn
145                 150                 155                 160

Leu Ile Gly Gln Gly Lys Ala Leu Gln Ala Lys Ile Ala Glu Ala Lys
                165                 170                 175

Lys Ala

<210> SEQ ID NO 72
<211> LENGTH: 311
<212> TYPE: PRT
<213> ORGANISM: Buchnera aphidicola

<400> SEQUENCE: 72

Met Lys Thr Ser Ser Ser Lys Val Phe Ala Ser Cys Val Ala Ile Val
1               5                   10                  15

Cys Leu Ala Ser Val Ala Asn Ala Leu Pro Val Gln Lys Ser Val Ala
            20                  25                  30

Ala Thr Thr Glu Asn Pro Ile Val Glu Lys His Gly Cys Arg Ala His
        35                  40                  45

Lys Asn Leu Val Arg Gln Asn Val Val Asp Leu Lys Thr Tyr Asp Ser
    50                  55                  60

Met Leu Ile Thr Asn Glu Val Val Gln Lys Gln Ser Asn Glu Val Gln
65                  70                  75                  80

Ser Ser Glu Gln Ser Asn Glu Gly Gln Asn Ser Glu Gln Ser Asn Glu
                85                  90                  95

Gly Gln Asn Ser Glu Gln Ser Asn Glu Val Gln Ser Ser Glu His Ser
            100                 105                 110

Asn Glu Gly Gln Asn Ser Lys Gln Ser Asn Glu Gly Gln Asn Ser Glu
```

-continued

```
            115                 120                 125
Gln Ser Asn Glu Val Gln Ser Ser Glu His Ser Asn Glu Gly Gln Asn
130                 135                 140

Ser Glu Gln Ser Asn Glu Val Gln Ser Ser Glu His Ser Asn Glu Gly
145                 150                 155                 160

Gln Asn Ser Lys Gln Ser Asn Glu Gly Gln Asn Ser Lys Gln Ser Asn
                165                 170                 175

Glu Val Gln Ser Ser Glu His Trp Asn Glu Gly Gln Asn Ser Lys Gln
                180                 185                 190

Ser Asn Glu Asp Gln Asn Ser Glu Gln Ser Asn Glu Gly Gln Asn Ser
                195                 200                 205

Lys Gln Ser Asn Glu Gly Gln Asn Ser Lys Gln Ser Asn Glu Asp Gln
            210                 215                 220

Asn Ser Glu Gln Ser Asn Glu Gly Gln Asn Ser Lys Gln Ser Asn Glu
225                 230                 235                 240

Val Gln Ser Ser Glu Gln Ser Asn Glu Gly Gln Asn Ser Lys Gln Ser
                245                 250                 255

Asn Glu Gly Gln Ser Ser Glu Gln Ser Asn Glu Gly Gln Asn Ser Lys
                260                 265                 270

Gln Ser Asn Glu Val Gln Ser Pro Glu Glu His Tyr Asp Leu Pro Asp
            275                 280                 285

Pro Glu Ser Ser Tyr Glu Ser Glu Glu Thr Lys Gly Ser His Glu Ser
            290                 295                 300

Gly Asp Asp Ser Glu His Arg
305                 310

<210> SEQ ID NO 73
<211> LENGTH: 431
<212> TYPE: PRT
<213> ORGANISM: Buchnera aphidicola

<400> SEQUENCE: 73

Met Lys Thr Ile Ile Leu Gly Leu Cys Leu Phe Gly Ala Leu Phe Trp
1               5                   10                  15

Ser Thr Gln Ser Met Pro Val Gly Glu Val Ala Pro Ala Val Pro Ala
                20                  25                  30

Val Pro Ser Glu Ala Val Pro Gln Lys Gln Val Glu Ala Lys Pro Glu
            35                  40                  45

Thr Asn Ala Ala Ser Pro Val Ser Asp Ala Lys Pro Glu Ser Asp Ser
    50                  55                  60

Lys Pro Val Asp Ala Glu Val Lys Pro Thr Val Ser Glu Val Lys Ala
65                  70                  75                  80

Glu Ser Glu Gln Lys Pro Ser Gly Glu Pro Lys Pro Glu Ser Asp Ala
                85                  90                  95

Lys Pro Val Val Ala Ser Glu Ser Lys Pro Glu Ser Asp Pro Lys Pro
            100                 105                 110

Ala Ala Val Val Glu Ser Lys Pro Glu Asn Asp Ala Val Ala Pro Glu
        115                 120                 125

Thr Asn Asn Asp Ala Lys Pro Glu Asn Ala Ala Pro Val Ser Glu
130                 135                 140

Asn Lys Pro Ala Thr Asp Ala Lys Ala Glu Thr Glu Leu Ile Ala Gln
145                 150                 155                 160

Ala Lys Pro Glu Ser Lys Pro Ala Ser Asp Leu Lys Ala Glu Pro Glu
                165                 170                 175
```

```
Ala Ala Lys Pro Asn Ser Glu Val Pro Val Ala Leu Pro Leu Asn Pro
            180                 185                 190

Thr Glu Thr Lys Ala Thr Gln Gln Ser Val Glu Thr Asn Gln Val Glu
            195                 200                 205

Gln Ala Ala Pro Ala Ala Gln Ala Asp Pro Ala Ala Pro Ala
    210                 215                 220

Ala Asp Pro Ala Pro Ala Pro Ala Ala Pro Val Ala Ala Glu Glu
225                 230                 235                 240

Ala Lys Leu Ser Glu Ser Ala Pro Ser Thr Glu Asn Lys Ala Ala Glu
            245                 250                 255

Glu Pro Ser Lys Pro Ala Glu Gln Gln Ser Ala Lys Pro Val Glu Asp
            260                 265                 270

Ala Val Pro Ala Ala Ser Glu Ile Ser Glu Thr Lys Val Ser Pro Ala
            275                 280                 285

Val Pro Ala Val Pro Glu Val Pro Ala Ser Pro Ser Ala Pro Ala Val
            290                 295                 300

Ala Asp Pro Val Ser Ala Pro Glu Ala Glu Lys Asn Ala Glu Pro Ala
305                 310                 315                 320

Lys Ala Ala Asn Ser Ala Glu Pro Ala Val Gln Ser Glu Ala Lys Pro
            325                 330                 335

Ala Glu Asp Ile Gln Lys Ser Gly Ala Val Val Ser Ala Glu Asn Pro
            340                 345                 350

Lys Pro Val Glu Gln Lys Pro Ala Glu Val Ala Lys Pro Ala Glu
            355                 360                 365

Gln Ser Lys Ser Glu Ala Pro Ala Glu Ala Pro Lys Pro Thr Glu Gln
            370                 375                 380

Ser Ala Glu Glu Pro Lys Lys Pro Glu Ser Ala Asn Asp Glu Lys
385                 390                 395                 400

Lys Glu Gln His Ser Val Asn Lys Arg Asp Ala Thr Lys Glu Lys Lys
                405                 410                 415

Pro Thr Asp Ser Ile Met Lys Lys Gln Lys Gly Lys Lys Ala Asn
            420                 425                 430

<210> SEQ ID NO 74
<211> LENGTH: 160
<212> TYPE: PRT
<213> ORGANISM: Buchnera aphidicola

<400> SEQUENCE: 74

Met Asn Gly Lys Ile Val Leu Cys Phe Ala Val Val Phe Ile Gly Gln
1               5                   10                  15

Ala Met Ser Ala Ala Thr Gly Thr Thr Pro Glu Val Glu Asp Ile Lys
            20                  25                  30

Lys Val Ala Glu Gln Met Ser Gln Thr Phe Met Ser Val Ala Asn His
        35                  40                  45

Leu Val Gly Ile Thr Pro Asn Ser Ala Asp Ala Gln Lys Ser Ile Glu
    50                  55                  60

Lys Ile Arg Thr Ile Met Asn Lys Gly Phe Thr Asp Met Glu Thr Glu
65                  70                  75                  80

Ala Asn Lys Met Lys Asp Ile Val Arg Lys Asn Ala Asp Pro Lys Leu
                85                  90                  95

Val Glu Lys Tyr Asp Glu Leu Glu Lys Glu Leu Lys Lys His Leu Ser
            100                 105                 110

Thr Ala Lys Asp Met Phe Glu Asp Lys Val Val Lys Pro Ile Gly Glu
        115                 120                 125
```

```
Lys Val Glu Leu Lys Lys Ile Thr Glu Asn Val Ile Lys Thr Thr Lys
        130                 135                 140

Asp Met Glu Ala Thr Met Asn Lys Ala Ile Asp Gly Phe Lys Lys Gln
145                 150                 155                 160

<210> SEQ ID NO 75
<211> LENGTH: 415
<212> TYPE: PRT
<213> ORGANISM: Buchnera aphidicola

<400> SEQUENCE: 75

Met His Leu Phe Leu Ala Leu Gly Leu Phe Ile Val Cys Gly Met Val
1               5                   10                  15

Asp Ala Thr Phe Tyr Asn Pro Arg Ser Gln Thr Phe Asn Gln Leu Met
                20                  25                  30

Glu Arg Arg Gln Arg Ser Ile Pro Ile Pro Tyr Ser Tyr Gly Tyr His
            35                  40                  45

Tyr Asn Pro Ile Glu Pro Ser Ile Asn Val Leu Asp Ser Leu Ser Glu
        50                  55                  60

Gly Leu Asp Ser Arg Ile Asn Thr Phe Lys Pro Ile Tyr Gln Asn Val
65                  70                  75                  80

Lys Met Ser Thr Gln Asp Val Asn Ser Val Pro Arg Thr Gln Tyr Gln
                85                  90                  95

Pro Lys Asn Ser Leu Tyr Asp Ser Glu Tyr Ile Ser Ala Lys Asp Ile
            100                 105                 110

Pro Ser Leu Phe Pro Glu Glu Asp Ser Tyr Asp Tyr Lys Tyr Leu Gly
        115                 120                 125

Ser Pro Leu Asn Lys Tyr Leu Thr Arg Pro Ser Thr Gln Glu Ser Gly
130                 135                 140

Ile Ala Ile Asn Leu Val Ala Ile Lys Glu Thr Ser Val Phe Asp Tyr
145                 150                 155                 160

Gly Phe Pro Thr Tyr Lys Ser Pro Tyr Ser Ser Asp Ser Val Trp Asn
                165                 170                 175

Phe Gly Ser Lys Ile Pro Asn Thr Val Phe Glu Asp Pro Gln Ser Val
            180                 185                 190

Glu Ser Asp Pro Asn Thr Phe Lys Val Ser Ser Pro Thr Ile Lys Ile
        195                 200                 205

Val Lys Leu Leu Pro Glu Thr Pro Glu Gln Glu Ser Ile Ile Thr Thr
210                 215                 220

Thr Lys Asn Tyr Glu Leu Asn Tyr Lys Thr Thr Gln Glu Thr Pro Thr
225                 230                 235                 240

Glu Ala Glu Leu Tyr Pro Ile Thr Ser Glu Glu Phe Gln Thr Glu Asp
                245                 250                 255

Glu Trp His Pro Met Val Pro Lys Glu Asn Thr Thr Lys Asp Glu Ser
            260                 265                 270

Ser Phe Ile Thr Thr Glu Glu Pro Leu Thr Glu Asp Lys Ser Asn Ser
        275                 280                 285

Ile Thr Ile Glu Lys Thr Gln Thr Glu Asp Glu Ser Asn Ser Ile Glu
        290                 295                 300

Phe Asn Ser Ile Arg Thr Glu Glu Lys Ser Asn Ser Ile Thr Thr Glu
305                 310                 315                 320

Glu Asn Gln Lys Glu Asp Asp Glu Ser Met Ser Thr Thr Ser Gln Glu
                325                 330                 335

Thr Thr Thr Ala Phe Asn Leu Asn Asp Thr Phe Asp Thr Asn Arg Tyr
```

340                 345                 350
Ser Ser Ser His Glu Ser Leu Met Leu Arg Ile Arg Glu Leu Met Lys
            355                 360                 365

Asn Ile Ala Asp Gln Gln Asn Lys Ser Gln Phe Arg Thr Val Asp Asn
370                 375                 380

Ile Pro Ala Lys Ser Gln Ser Asn Leu Ser Ser Asp Glu Ser Thr Asn
385                 390                 395                 400

Gln Gln Phe Glu Pro Gln Leu Val Asn Gly Ala Asp Thr Tyr Lys
                405                 410                 415

<210> SEQ ID NO 76
<211> LENGTH: 126
<212> TYPE: PRT
<213> ORGANISM: Sitophilus zeamais

<400> SEQUENCE: 76

Met Thr Arg Thr Met Leu Phe Leu Ala Cys Val Ala Ala Leu Tyr Val
1               5                   10                  15

Cys Ile Ser Ala Thr Ala Gly Lys Pro Glu Glu Phe Ala Lys Leu Ser
            20                  25                  30

Asp Glu Ala Pro Ser Asn Asp Gln Ala Met Tyr Glu Ser Ile Gln Arg
        35                  40                  45

Tyr Arg Arg Phe Val Asp Gly Asn Arg Tyr Asn Gly Gly Gln Gln Gln
    50                  55                  60

Gln Gln Gln Pro Lys Gln Trp Glu Val Arg Pro Asp Leu Ser Arg Asp
65                  70                  75                  80

Gln Arg Gly Asn Thr Lys Ala Gln Val Glu Ile Asn Lys Lys Gly Asp
                85                  90                  95

Asn His Asp Ile Asn Ala Gly Trp Gly Lys Asn Ile Asn Gly Pro Asp
            100                 105                 110

Ser His Lys Asp Thr Trp His Val Gly Gly Ser Val Arg Trp
        115                 120                 125

<210> SEQ ID NO 77
<211> LENGTH: 220
<212> TYPE: PRT
<213> ORGANISM: Acyrthosiphon pisum

<400> SEQUENCE: 77

Met Lys Glu Thr Thr Val Val Trp Ala Lys Leu Phe Leu Ile Leu Ile
1               5                   10                  15

Ile Leu Ala Lys Pro Leu Gly Leu Lys Ala Val Asn Glu Cys Lys Arg
            20                  25                  30

Leu Gly Asn Asn Ser Cys Arg Ser His Gly Glu Cys Cys Ser Gly Phe
        35                  40                  45

Cys Phe Ile Glu Pro Gly Trp Ala Leu Gly Val Cys Lys Arg Leu Gly
    50                  55                  60

Thr Pro Lys Lys Ser Asp Asp Ser Asn Asn Gly Lys Asn Ile Glu Lys
65                  70                  75                  80

Asn Asn Gly Val His Glu Arg Ile Asp Asp Val Phe Glu Arg Gly Val
                85                  90                  95

Cys Ser Tyr Tyr Lys Gly Pro Ser Ile Thr Ala Asn Gly Asp Val Phe
            100                 105                 110

Asp Glu Asn Glu Met Thr Ala Ala His Arg Thr Leu Pro Phe Asn Thr
        115                 120                 125

Met Val Lys Val Glu Gly Met Gly Thr Ser Val Val Val Lys Ile Asn

```
                130                 135                 140
Asp Arg Lys Thr Ala Ala Asp Gly Lys Val Met Leu Leu Ser Arg Ala
145                 150                 155                 160

Ala Ala Glu Ser Leu Asn Ile Asp Glu Asn Thr Gly Pro Val Gln Cys
                165                 170                 175

Gln Leu Lys Phe Val Leu Asp Gly Ser Gly Cys Thr Pro Asp Tyr Gly
                180                 185                 190

Asp Thr Cys Val Leu His His Glu Cys Cys Ser Gln Asn Cys Phe Arg
                195                 200                 205

Glu Met Phe Ser Asp Lys Gly Phe Cys Leu Pro Lys
    210                 215                 220

<210> SEQ ID NO 78
<211> LENGTH: 3
<212> TYPE: DNA
<213> ORGANISM: Streptococcus pyogenes
<220> FEATURE:
<221> NAME/KEY: misc_feature
<222> LOCATION: (1)..(1)
<223> OTHER INFORMATION: n is a, g, c, or t

<400> SEQUENCE: 78 ngg                                                                        3

<210> SEQ ID NO 79
<211> LENGTH: 6
<212> TYPE: DNA
<213> ORGANISM: Streptococcus thermophilus
<220> FEATURE:
<221> NAME/KEY: misc_feature
<222> LOCATION: (1)..(2)
<223> OTHER INFORMATION: n is a, g, c, or t

<400> SEQUENCE: 79 nnagaa                                                                     6

<210> SEQ ID NO 80
<211> LENGTH: 5
<212> TYPE: DNA
<213> ORGANISM: Streptococcus thermophilus
<220> FEATURE:
<221> NAME/KEY: misc_feature
<222> LOCATION: (1)..(1)
<223> OTHER INFORMATION: n is a, g, c, or t
<220> FEATURE:
<221> NAME/KEY: misc_feature
<222> LOCATION: (4)..(4)
<223> OTHER INFORMATION: n is a, g, c, or t

<400> SEQUENCE: 80 nggng                                                                      5

<210> SEQ ID NO 81
<211> LENGTH: 7
<212> TYPE: DNA
<213> ORGANISM: Neisseria meningitidis
<220> FEATURE:
<221> NAME/KEY: misc_feature
<222> LOCATION: (1)..(3)
<223> OTHER INFORMATION: n is a, g, c, or t

<400> SEQUENCE: 81 nnngatt                                                                    7

<210> SEQ ID NO 82
```

```
<211> LENGTH: 16
<212> TYPE: PRT
<213> ORGANISM: Artificial Sequence
<220> FEATURE:
<223> OTHER INFORMATION: Penetratin

<400> SEQUENCE: 82

Arg Gln Ile Lys Ile Trp Phe Gln Asn Arg Arg Met Lys Trp Lys Lys
1               5                   10                  15

<210> SEQ ID NO 83
<211> LENGTH: 13
<212> TYPE: PRT
<213> ORGANISM: Human immunodeficiency virus type 1

<400> SEQUENCE: 83

Gly Arg Lys Lys Arg Arg Gln Arg Arg Arg Pro Pro Gln
1               5                   10

<210> SEQ ID NO 84
<211> LENGTH: 18
<212> TYPE: PRT
<213> ORGANISM: Artificial Sequence
<220> FEATURE:
<223> OTHER INFORMATION: pVEC

<400> SEQUENCE: 84

Leu Leu Ile Ile Leu Arg Arg Arg Ile Arg Lys Gln Ala His Ala His
1               5                   10                  15

Ser Lys

<210> SEQ ID NO 85
<211> LENGTH: 27
<212> TYPE: PRT
<213> ORGANISM: Artificial Sequence
<220> FEATURE:
<223> OTHER INFORMATION: Transportan

<400> SEQUENCE: 85

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 86
<211> LENGTH: 27
<212> TYPE: PRT
<213> ORGANISM: Artificial Sequence
<220> FEATURE:
<223> OTHER INFORMATION: MPG

<400> SEQUENCE: 86

Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 87
<211> LENGTH: 21
<212> TYPE: PRT
<213> ORGANISM: Artificial Sequence
<220> FEATURE:
<223> OTHER INFORMATION: Pep-1

<400> SEQUENCE: 87
```

```
Lys Glu Thr Trp Trp Glu Thr Trp Trp Thr Glu Trp Ser Gln Pro Lys
1               5                   10                  15

Lys Lys Arg Lys Val
            20

<210> SEQ ID NO 88
<211> LENGTH: 18
<212> TYPE: PRT
<213> ORGANISM: Artificial Sequence
<220> FEATURE:
<223> OTHER INFORMATION: MAP

<400> SEQUENCE: 88

Lys Leu Ala Leu Lys Leu Ala Leu Lys Ala Leu Lys Ala Ala Leu Lys
1               5                   10                  15

Leu Ala

<210> SEQ ID NO 89
<211> LENGTH: 9
<212> TYPE: PRT
<213> ORGANISM: Artificial Sequence
<220> FEATURE:
<223> OTHER INFORMATION: R6W3

<400> SEQUENCE: 89

Arg Arg Trp Trp Arg Arg Trp Arg Arg
1               5

<210> SEQ ID NO 90
<211> LENGTH: 20
<212> TYPE: DNA
<213> ORGANISM: Artificial Sequence
<220> FEATURE:
<223> OTHER INFORMATION: Bcr1 forward primer

<400> SEQUENCE: 90
aaactgctgc atggctttct                                              20

<210> SEQ ID NO 91
<211> LENGTH: 20
<212> TYPE: DNA
<213> ORGANISM: Artificial Sequence
<220> FEATURE:
<223> OTHER INFORMATION: Bcr1 reverse primer

<400> SEQUENCE: 91
acaggccttt caggctttta                                              20

<210> SEQ ID NO 92
<211> LENGTH: 24
<212> TYPE: DNA
<213> ORGANISM: Artificial Sequence
<220> FEATURE:
<223> OTHER INFORMATION: T7 promoter sequence

<400> SEQUENCE: 92
ttaatacgac tcactatagg gaga                                         24

<210> SEQ ID NO 93
<211> LENGTH: 478
<212> TYPE: RNA
<213> ORGANISM: Acyrthosiphon pisum

<400> SEQUENCE: 93
augaaacugc ugcauggcuu ucugauuauu augcugacca ugcaucugag cauucaguau    60
```

```
gcguauggcg gcccguuucu gaccaaauau cugugcgauc gcgugugcca uaaacugugc    120
ggcgaugaau uugugugcag cugcauucag uauaaaagcc ugaaaggccu gugguuuccg    180
cauugcccga ccggcaaagc gagcguggug cugcauaacu uucugaccag cccguuuuuu    240
uuuucgggcu ggucagaaag uuaugcagca ccacgcucgc uuugccgguc gggcaaugcg    300
gaaaccacag gccuuucagg cuuuuauacu gaaugcagcu gcacacaaau ucaucgccgc    360
acaguuuaug gcacacgcga ucgcacagau auuuggucag aaacgggccg ccauacgcau    420
acugaaugcu cagaugcaug gucagcauaa uaaucagaaa gccaugcagc aguuucau     478

<210> SEQ ID NO 94
<211> LENGTH: 378
<212> TYPE: DNA
<213> ORGANISM: Artificial Sequence
<220> FEATURE:
<223> OTHER INFORMATION: Coleoptericin A (colA) gene

<400> SEQUENCE: 94
atgacccgca ccatgctgtt tctggcgtgc gtggcggcgc tgtatgtgtg cattagcgcg     60
accgcgggca aaccggaaga atttgcgaaa ctgagcgatg aagcgccgag caacgatcag    120
gcgatgtatg aaagcattca cgctatcgc cgctttgtgg atggcaaccg ctataacggc    180
ggccagcagc agcagcagca gccgaaacag tgggaagtgc gcccggatct gagccgcgat    240
cagcgcggca acaccaaagc gcaggtggaa attaacaaaa aaggcgataa ccatgatatt    300
aacgcgggct ggggcaaaaa cattaacggc ccggatagcc ataaagatac ctggcatgtg    360
ggcggcagcg tgcgctgg                                                378

<210> SEQ ID NO 95
<211> LENGTH: 20
<212> TYPE: DNA
<213> ORGANISM: Artificial Sequence
<220> FEATURE:
<223> OTHER INFORMATION: ColA forward primer

<400> SEQUENCE: 95
caacgatcag gcgatgtatg                                                20

<210> SEQ ID NO 96
<211> LENGTH: 20
<212> TYPE: DNA
<213> ORGANISM: Artificial Sequence
<220> FEATURE:
<223> OTHER INFORMATION: ColA reverse primer

<400> SEQUENCE: 96
ttaatttcca cctgcgcttt                                                20

<210> SEQ ID NO 97
<211> LENGTH: 17
<212> TYPE: DNA
<213> ORGANISM: Artificial Sequence
<220> FEATURE:
<223> OTHER INFORMATION: Buchnera forward primer

<400> SEQUENCE: 97
gtcggctcat cacatcc                                                   17

<210> SEQ ID NO 98
<211> LENGTH: 20
<212> TYPE: DNA
```

<213> ORGANISM: Artificial Sequence
<220> FEATURE:
<223> OTHER INFORMATION: Buchnera reverse primer

<400> SEQUENCE: 98
ttccgtctgt attatctcct    20

<210> SEQ ID NO 99
<211> LENGTH: 40
<212> TYPE: DNA
<213> ORGANISM: Artificial Sequence
<220> FEATURE:
<223> OTHER INFORMATION: Mpcactus fwd

<400> SEQUENCE: 99
taatacgact cactataggg tacacccatt gtgtgcacct    40

<210> SEQ ID NO 100
<211> LENGTH: 40
<212> TYPE: DNA
<213> ORGANISM: Artificial Sequence
<220> FEATURE:
<223> OTHER INFORMATION: Mpcactus rev

<400> SEQUENCE: 100
taatacgact cactataggg ccactgtcca aggcaatttt    40

<210> SEQ ID NO 101
<211> LENGTH: 21
<212> TYPE: DNA
<213> ORGANISM: Artificial Sequence
<220> FEATURE:
<223> OTHER INFORMATION: Buch_groES_18F

<400> SEQUENCE: 101
catgatcgtg tgcttgttaa g    21

<210> SEQ ID NO 102
<211> LENGTH: 21
<212> TYPE: DNA
<213> ORGANISM: Artificial Sequence
<220> FEATURE:
<223> OTHER INFORMATION: Buch_groES_98R

<400> SEQUENCE: 102
ctgttcctcg agtcgatttc c    21

<210> SEQ ID NO 103
<211> LENGTH: 21
<212> TYPE: DNA
<213> ORGANISM: Artificial Sequence
<220> FEATURE:
<223> OTHER INFORMATION: ApEF1a 107F

<400> SEQUENCE: 103
ctgattgtgc cgtgcttatt g    21

<210> SEQ ID NO 104
<211> LENGTH: 21
<212> TYPE: DNA
<213> ORGANISM: Artificial Sequence
<220> FEATURE:
<223> OTHER INFORMATION: ApEF1a 246R

<400> SEQUENCE: 104
tatggtggtt cagtagagtc c    21

<210> SEQ ID NO 105
<211> LENGTH: 18
<212> TYPE: DNA
<213> ORGANISM: Artificial Sequence
<220> FEATURE:
<223> OTHER INFORMATION: BCR4 (from BCR4-CPP)

<400> SEQUENCE: 105
cgtacaataa tctcatgg                                                  18

<210> SEQ ID NO 106
<211> LENGTH: 11
<212> TYPE: PRT
<213> ORGANISM: Artificial Sequence
<220> FEATURE:
<223> OTHER INFORMATION: Tat

<400> SEQUENCE: 106

Tyr Gly Arg Lys Lys Arg Arg Gln Arg Arg
1               5                   10

<210> SEQ ID NO 107
<211> LENGTH: 23
<212> TYPE: DNA
<213> ORGANISM: Artificial Sequence
<220> FEATURE:
<223> OTHER INFORMATION: ApBCR-4F

<400> SEQUENCE: 107
ctctgtcaac caccatgaga tta                                            23

<210> SEQ ID NO 108
<211> LENGTH: 22
<212> TYPE: DNA
<213> ORGANISM: Artificial Sequence
<220> FEATURE:
<223> OTHER INFORMATION: ApBCR-4R

<400> SEQUENCE: 108
tgcagactac agcacaatac tt                                             22

<210> SEQ ID NO 109
<211> LENGTH: 20
<212> TYPE: DNA
<213> ORGANISM: Artificial Sequence
<220> FEATURE:
<223> OTHER INFORMATION: Actin forward

<400> SEQUENCE: 109
gatcagcagc cacacacaag                                                20

<210> SEQ ID NO 110
<211> LENGTH: 20
<212> TYPE: DNA
<213> ORGANISM: Artificial Sequence
<220> FEATURE:
<223> OTHER INFORMATION: Actin reverse

<400> SEQUENCE: 110
tttgaaccgg tttacgacga                                                20

<210> SEQ ID NO 111
<211> LENGTH: 40
<212> TYPE: DNA
<213> ORGANISM: Artificial Sequence
<220> FEATURE:
<223> OTHER INFORMATION: ApGLNT1 forward

<400> SEQUENCE: 111
taatacgact cactataggg caattacaaa aggacggcag                    40

<210> SEQ ID NO 112
<211> LENGTH: 40
<212> TYPE: DNA
<213> ORGANISM: Artificial Sequence
<220> FEATURE:
<223> OTHER INFORMATION: ApGLNT1 reverse

<400> SEQUENCE: 112
taatacgact cactataggg ccgctctagg aacaccgtat                    40

<210> SEQ ID NO 113
<211> LENGTH: 19
<212> TYPE: DNA
<213> ORGANISM: Artificial Sequence
<220> FEATURE:
<223> OTHER INFORMATION: ACYPI001018-fwd

<400> SEQUENCE: 113
cctgaaatcg acggggtcc                                          19

<210> SEQ ID NO 114
<211> LENGTH: 21
<212> TYPE: DNA
<213> ORGANISM: Artificial Sequence
<220> FEATURE:
<223> OTHER INFORMATION: ACYPI001018-rev

<400> SEQUENCE: 114
agatcggcaa catctgttcg t                                       21

<210> SEQ ID NO 115
<211> LENGTH: 6
<212> TYPE: DNA
<213> ORGANISM: Artificial Sequence
<220> FEATURE:
<223> OTHER INFORMATION: Small hairpin

<400> SEQUENCE: 115 acacgt                                                         6

<210> SEQ ID NO 116
<211> LENGTH: 42
<212> TYPE: DNA
<213> ORGANISM: Artificial Sequence
<220> FEATURE:
<223> OTHER INFORMATION: ApGlnT1 sense fwd

<400> SEQUENCE: 116
ctacaaatct atctctccta ggcaattaca aaaggacggc ag                 42

<210> SEQ ID NO 117
<211> LENGTH: 49
<212> TYPE: DNA
<213> ORGANISM: Artificial Sequence
<220> FEATURE:
<223> OTHER INFORMATION: ApGlnT1 sense rev

<400> SEQUENCE: 117
ttacaaactg ggaagaacct ggagacgtgc cgctctagga acaccgtat          49

<210> SEQ ID NO 118
<211> LENGTH: 50
<212> TYPE: DNA
<213> ORGANISM: Artificial Sequence
<220> FEATURE:
<223> OTHER INFORMATION: ApGlnT1 antisense fwd

<400> SEQUENCE: 118
ttacaaactg ggaagaacct ggaacacgtc ccgctctagg aacaccgtat            50

<210> SEQ ID NO 119
<211> LENGTH: 50
<212> TYPE: DNA
<213> ORGANISM: Artificial Sequence
<220> FEATURE:
<223> OTHER INFORMATION: ApGlnT1 antisense rev

<400> SEQUENCE: 119
agaaactaga gcttgtcgat cgttaattaa caattacaaa aggacggcag            50

<210> SEQ ID NO 120
<211> LENGTH: 42
<212> TYPE: DNA
<213> ORGANISM: Artificial Sequence
<220> FEATURE:
<223> OTHER INFORMATION: ApUbx sense fwd

<400> SEQUENCE: 120
ctacaaatct atctctccta ggttttaccg tcacaggcat ca                    42

<210> SEQ ID NO 121
<211> LENGTH: 50
<212> TYPE: DNA
<213> ORGANISM: Artificial Sequence
<220> FEATURE:
<223> OTHER INFORMATION: ApUbx sense rev

<400> SEQUENCE: 121
acgagtgctg aagtccctag ccagacgtgt tcgtgctcgt taccaaatgt            50

<210> SEQ ID NO 122
<211> LENGTH: 50
<212> TYPE: DNA
<213> ORGANISM: Artificial Sequence
<220> FEATURE:
<223> OTHER INFORMATION: ApUbx antisense fwd

<400> SEQUENCE: 122
acgagtgctg aagtccctag ccaacacgtc tcgtgctcgt taccaaatgt            50

<210> SEQ ID NO 123
<211> LENGTH: 50
<212> TYPE: DNA
<213> ORGANISM: Artificial Sequence
<220> FEATURE:
<223> OTHER INFORMATION: ApUbx antisense rev

<400> SEQUENCE: 123
agaaactaga gcttgtcgat cgttaattaa ttttaccgtc acaggcatca            50

<210> SEQ ID NO 124
<211> LENGTH: 42
<212> TYPE: DNA
<213> ORGANISM: Artificial Sequence
<220> FEATURE:
<223> OTHER INFORMATION: ApbAs sense fwd

```
<400> SEQUENCE: 124
ctacaaatct atctctccta ggggtgtcac catcgagacg tt                    42

<210> SEQ ID NO 125
<211> LENGTH: 52
<212> TYPE: DNA
<213> ORGANISM: Artificial Sequence
<220> FEATURE:
<223> OTHER INFORMATION: ApbAs sense rev

<400> SEQUENCE: 125
aaaaaccaca tacctcgagt ggggacgtgt catgactctg gcagttgaag tt         52

<210> SEQ ID NO 126
<211> LENGTH: 52
<212> TYPE: DNA
<213> ORGANISM: Artificial Sequence
<220> FEATURE:
<223> OTHER INFORMATION: ApbAs antisense fwd

<400> SEQUENCE: 126
aaaaaccaca tacctcgagt gggacacgtc catgactctg gcagttgaag tt         52

<210> SEQ ID NO 127
<211> LENGTH: 50
<212> TYPE: DNA
<213> ORGANISM: Artificial Sequence
<220> FEATURE:
<223> OTHER INFORMATION: ApbAs antisense rev

<400> SEQUENCE: 127
agaaactaga gcttgtcgat cgttaattaa ggtgtcacca tcgagacgtt            50

<210> SEQ ID NO 128
<211> LENGTH: 42
<212> TYPE: DNA
<213> ORGANISM: Artificial Sequence
<220> FEATURE:
<223> OTHER INFORMATION: Apcactus sense fwd

<400> SEQUENCE: 128
ctacaaatct atctctccta gggtcgtcgt cgtcgtcgta gt                    42

<210> SEQ ID NO 129
<211> LENGTH: 50
<212> TYPE: DNA
<213> ORGANISM: Artificial Sequence
<220> FEATURE:
<223> OTHER INFORMATION: Apcactus sense rev

<400> SEQUENCE: 129
accaaaattg ccttggacag tgggacgtgt gcacgcacgg aaaacattta            50

<210> SEQ ID NO 130
<211> LENGTH: 50
<212> TYPE: DNA
<213> ORGANISM: Artificial Sequence
<220> FEATURE:
<223> OTHER INFORMATION: Apcactus antisense fwd

<400> SEQUENCE: 130
accaaaattg ccttggacag tggacacgtc gcacgcacgg aaaacattta            50

<210> SEQ ID NO 131
```

```
<211> LENGTH: 50
<212> TYPE: DNA
<213> ORGANISM: Artificial Sequence
<220> FEATURE:
<223> OTHER INFORMATION: Apcactus antisense rev

<400> SEQUENCE: 131
agaaactaga gcttgtcgat cgttaattaa gtcgtcgtcg tcgtcgtagt          50

<210> SEQ ID NO 132
<211> LENGTH: 48
<212> TYPE: DNA
<213> ORGANISM: Artificial Sequence
<220> FEATURE:
<223> OTHER INFORMATION: MpGlnT1 sense fwd

<400> SEQUENCE: 132
ctacaaatct atctctccta ggttggaagg gattggtgtt gtaatgcc            48

<210> SEQ ID NO 133
<211> LENGTH: 61
<212> TYPE: DNA
<213> ORGANISM: Artificial Sequence
<220> FEATURE:
<223> OTHER INFORMATION: MpGlnT1 sense rev

<400> SEQUENCE: 133
ttacaaactg ggaagaacct ggagacgtgt tccaggttct tcccagtttg taactagatc   60
g                                                                  61

<210> SEQ ID NO 134
<211> LENGTH: 61
<212> TYPE: DNA
<213> ORGANISM: Artificial Sequence
<220> FEATURE:
<223> OTHER INFORMATION: MpGlnT1 antisense fwd

<400> SEQUENCE: 134
ttacaaactg ggaagaacct ggaacacgtc tccaggttct tcccagtttg taactagatc   60
g                                                                  61

<210> SEQ ID NO 135
<211> LENGTH: 56
<212> TYPE: DNA
<213> ORGANISM: Artificial Sequence
<220> FEATURE:
<223> OTHER INFORMATION: MpGlnT1 antisense rev

<400> SEQUENCE: 135
agaaactaga gcttgtcgat cgttaattaa ttggaaggga ttggtgttgt aatgcc      56

<210> SEQ ID NO 136
<211> LENGTH: 43
<212> TYPE: DNA
<213> ORGANISM: Artificial Sequence
<220> FEATURE:
<223> OTHER INFORMATION: MpUbx sense fwd

<400> SEQUENCE: 136
ctacaaatct atctctccta ggtcgtgtgg agcaagtaca gcg                 43

<210> SEQ ID NO 137
<211> LENGTH: 52
<212> TYPE: DNA
<213> ORGANISM: Artificial Sequence
```

```
<220> FEATURE:
<223> OTHER INFORMATION: MpUbx sense rev

<400> SEQUENCE: 137
acgagtgctg aagtccctag ccagacgtgt tggctaggga cttcagcact cg          52

<210> SEQ ID NO 138
<211> LENGTH: 52
<212> TYPE: DNA
<213> ORGANISM: Artificial Sequence
<220> FEATURE:
<223> OTHER INFORMATION: MpUbx antisense fwd

<400> SEQUENCE: 138
acgagtgctg aagtccctag ccaacacgtc tggctaggga cttcagcact cg          52

<210> SEQ ID NO 139
<211> LENGTH: 52
<212> TYPE: DNA
<213> ORGANISM: Artificial Sequence
<220> FEATURE:
<223> OTHER INFORMATION: MpUbx antisense rev

<400> SEQUENCE: 139
agaaactaga gcttgtcgat cgttaattaa tcgtgtggag caagtacagc gg          52

<210> SEQ ID NO 140
<211> LENGTH: 48
<212> TYPE: DNA
<213> ORGANISM: Artificial Sequence
<220> FEATURE:
<223> OTHER INFORMATION: MpbAs sense fwd

<400> SEQUENCE: 140
ctacaaatct atctctccta gggaggaact ccaactgcca gagtcatg               48

<210> SEQ ID NO 141
<211> LENGTH: 59
<212> TYPE: DNA
<213> ORGANISM: Artificial Sequence
<220> FEATURE:
<223> OTHER INFORMATION: MpbAs sense rev

<400> SEQUENCE: 141
aaaaaccaca tacctcgagt ggggacgtgt cccactcgag gtatgtggtt tttcctatg   59

<210> SEQ ID NO 142
<211> LENGTH: 55
<212> TYPE: DNA
<213> ORGANISM: Artificial Sequence
<220> FEATURE:
<223> OTHER INFORMATION: MpbAs antisense fwd

<400> SEQUENCE: 142
aaaaaccaca tacctcgagt gggacacgtc cccactcgag gtatgtggtt tttcc       55

<210> SEQ ID NO 143
<211> LENGTH: 56
<212> TYPE: DNA
<213> ORGANISM: Artificial Sequence
<220> FEATURE:
<223> OTHER INFORMATION: MpbAs antisense rev

<400> SEQUENCE: 143
agaaactaga gcttgtcgat cgttaattaa gaggaactcc aactgccaga gtcatg      56
```

<210> SEQ ID NO 144
<211> LENGTH: 48
<212> TYPE: DNA
<213> ORGANISM: Artificial Sequence
<220> FEATURE:
<223> OTHER INFORMATION: Mpcactus sense fwd

<400> SEQUENCE: 144
ctacaaatct atctctccta ggtacaccca ttgtgtgcac ctgagtac         48

<210> SEQ ID NO 145
<211> LENGTH: 55
<212> TYPE: DNA
<213> ORGANISM: Artificial Sequence
<220> FEATURE:
<223> OTHER INFORMATION: Mpcactus sense rev

<400> SEQUENCE: 145
accaaaattg ccttggacag tgggacgtgt ccactgtcca aggcaattttt ggttg    55

<210> SEQ ID NO 146
<211> LENGTH: 55
<212> TYPE: DNA
<213> ORGANISM: Artificial Sequence
<220> FEATURE:
<223> OTHER INFORMATION: Mpcactus antisense fwd

<400> SEQUENCE: 146
accaaaattg ccttggacag tggacacgtc ccactgtcca aggcaattttt ggttg    55

<210> SEQ ID NO 147
<211> LENGTH: 56
<212> TYPE: DNA
<213> ORGANISM: Artificial Sequence
<220> FEATURE:
<223> OTHER INFORMATION: Mpcactus antisense rev

<400> SEQUENCE: 147
agaaactaga gcttgtcgat cgttaattaa tacacccatt gtgtgcacct gagtac    56

<210> SEQ ID NO 148
<211> LENGTH: 172
<212> TYPE: DNA
<213> ORGANISM: Artificial Sequence
<220> FEATURE:
<223> OTHER INFORMATION: C002

<400> SEQUENCE: 148
ctgaaccgta cgatgagcag gaagaagcgt ctgtcgaatt accgatggag caccgtcagt    60
gcgatgaata caaatcgaag atctgggaca agcatttag caaccaggag gctatgcagc   120
tgatggaact aacgtttaat acaggtaagg aattaggctc ccacgaagtg tg          172

<210> SEQ ID NO 149
<211> LENGTH: 266
<212> TYPE: DNA
<213> ORGANISM: Artificial Sequence
<220> FEATURE:
<223> OTHER INFORMATION: ApGLNT1

<400> SEQUENCE: 149
caattacaaa aggacggcag cgatacaact ctcatacaga cagaacagca atattagcgt    60
tgtcaattac agctattagt gtccagtaaa attgttttta acaaaaaaa cgacaataaa   120 tattttgtac tgattaacta gggtgcaaca gtgaatttg aaaaaaatat aaaaacaaaa   180

```
tcatggattt tagatattag tcttttatct ttggtcatca gtttttgagt attatattat      240
tatattatac ggtgttccta gagcgg                                            266

<210> SEQ ID NO 150
<211> LENGTH: 191
<212> TYPE: DNA
<213> ORGANISM: Artificial Sequence
<220> FEATURE:
<223> OTHER INFORMATION: Rnase

<400> SEQUENCE: 150
attgcaccga gcagaagact acctataccc ataataatat tacaaggaag aaacctgagg       60
actgtactta gacgtgttat atcataagac ctaataacgt acatgctcga aaatgcattc      120
aactgcatta attactgcag tatgtttagt catttgttcg tgtcttcttc cgaccatcaa      180
tgccaagaaa a                                                           191

<210> SEQ ID NO 151
<211> LENGTH: 14
<212> TYPE: DNA
<213> ORGANISM: Artificial Sequence
<220> FEATURE:
<223> OTHER INFORMATION: ApGLNT1 (from ApGLNT1-CPP)

<400> SEQUENCE: 151
tgatgcgaca tagc                                                         14

<210> SEQ ID NO 152
<211> LENGTH: 15
<212> TYPE: DNA
<213> ORGANISM: Artificial Sequence
<220> FEATURE:
<223> OTHER INFORMATION: ApC002 (from ApC002-CPP)

<400> SEQUENCE: 152
taacttccca tgttg                                                        15

<210> SEQ ID NO 153
<211> LENGTH: 16
<212> TYPE: DNA
<213> ORGANISM: Artificial Sequence
<220> FEATURE:
<223> OTHER INFORMATION: BCR-4 (from BCR-4-CPP)

<400> SEQUENCE: 153
tacaataatc tcatgg                                                       16
```

UNITED STATES PATENT AND TRADEMARK OFFICE
CERTIFICATE OF CORRECTION

| | |
|---|---|
| PATENT NO. | : 11,974,574 B2 |
| APPLICATION NO. | : 16/487661 |
| DATED | : May 7, 2024 |
| INVENTOR(S) | : Martinez et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 663 days.

Signed and Sealed this
Seventh Day of January, 2025

Derrick Brent
*Acting Director of the United States Patent and Trademark Office*